(12) United States Patent
Zhang et al.

(10) Patent No.: US 12,371,429 B2
(45) Date of Patent: Jul. 29, 2025

(54) ANTIBIOTIC RESISTANCE-MODIFYING TRICYCLIC HETEROARYL COMPOUNDS AND USES THEREOF

(71) Applicant: Recreo Pharmaceuticals LLC, Superior, CO (US)

(72) Inventors: Jing Zhang, Lexington, MA (US); Xiang Wang, Superior, CO (US); Jessica D. Podoll, Boulder, CO (US)

(73) Assignee: Recreo Pharmaceuticals LLC, Superior, CO (US)

( * ) Notice: Subject to any disclaimer, the term of this patent is extended or adjusted under 35 U.S.C. 154(b) by 672 days.

(21) Appl. No.: 17/265,794

(22) PCT Filed: Aug. 15, 2019

(86) PCT No.: PCT/US2019/046712
§ 371 (c)(1),
(2) Date: Feb. 3, 2021

(87) PCT Pub. No.: WO2020/037155
PCT Pub. Date: Feb. 20, 2020

(65) Prior Publication Data
US 2021/0163479 A1     Jun. 3, 2021

Related U.S. Application Data

(60) Provisional application No. 62/719,048, filed on Aug. 16, 2018.

(51) Int. Cl.
*C07D 471/04*     (2006.01)
*A61K 31/407*     (2006.01)
(Continued)

(52) U.S. Cl.
CPC .......... *C07D 471/04* (2013.01); *A61K 31/407* (2013.01); *A61K 31/437* (2013.01);
(Continued)

(58) Field of Classification Search
CPC .................................................. A61K 9/0048
See application file for complete search history.

(56) References Cited

U.S. PATENT DOCUMENTS 3,652,574 A   *   3/1972   Garmaise ............. C07D 471/04
                                                      546/85
2003/0232850 A1    12/2003   Miller et al.
(Continued)

FOREIGN PATENT DOCUMENTS

CN           1365280 A          8/2002
CN        102424681   *   10/2011   .............. A61P 11/00
(Continued)

OTHER PUBLICATIONS

Fujita et al., "Stabilization by meglumine of an amine compound degraded by formaldehyde in tablets" International Journal of Pharmaceutics vol. 386 pp. 195-200 doi:10.1016/j.ijpharm.2009.11.017 (Year: 2010).*

(Continued)

*Primary Examiner* — Eric Olson
(74) *Attorney, Agent, or Firm* — Don D. Cha; HDC Intellectual Property Law, LLP

(57) ABSTRACT

The present invention provides 1,3,4,9-tetrahydro-2H-pyrido[3,4-b]indole derivative compounds and uses thereof. In particular, compounds of the invention are of the formula

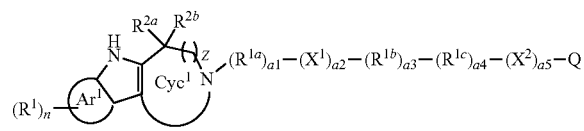

where n is an integer from 0-4; each of z, a1, a2, a3, a4, and a5 is independently 0 or 1, provided at least one of a1-a5 is 1; $Ar^1$ is phenyl or a nitrogen atom containing 6-membered heteroaryl; $Cyc^1$ is 5, 6, or 7-membered nitrogen atom containing heterocyclyl optionally containing one to three additional substituents in addition to $R^{2a}$ and $R^{2b}$; $X^1$ is —C(═O)—, —C(═O)—$NR^6$—, or —$SO_2$—NH—; each of $R^{1a}$ and $R^{1c}$ is independently $C_1$-$C_6$ alkylene; $R^{1b}$ is optionally substituted $C_1$-$C_6$ alkylene; $X^2$ is O or $NR^6$; each $R^1$ is independently halogen, optionally substituted $C_1$-$C_6$ alkyl, optionally substituted $C_1$-$C_6$ haloalkyl, optionally substituted cycloalkyl, optionally substituted heterocyclyl, —$OR^a$, or $NR^bR^c$, where $R^a$ hydrogen, $C_1$-$C_6$ alkyl, $C_1$-$C_6$ haloalkyl, or a hydroxyl protecting group, and wherein each of $R^b$ and $R^c$ is independently hydrogen, $C_1$-$C_6$ alkyl, $C_1$-$C_6$ haloalkyl, optionally substituted cycloalkyl, optionally substituted heterocyclyl, or a nitrogen protecting group; each of $R^{2a}$ and $R^{2b}$ is independently hydrogen, halogen, optionally substituted $C_1$-$C_6$ alkyl, optionally substituted $C_1$-$C_6$ haloalkyl, optionally substituted cycloalkyl, optionally substituted heterocyclyl, —$OR^a$, or —$NR^bR^c$, where $R^a$ hydrogen, $C_1$-$C_6$ alkyl, $C_1$-$C_6$ haloalkyl, or a hydroxyl protecting group, and wherein each of $R^b$ and $R^c$ is independently hydrogen, $C_1$-$C_6$ alkyl, $C_1$-$C_6$ haloalkyl, optionally substituted cycloalkyl, optionally substituted heterocyclyl, or a nitrogen protecting group, or $R^{2a}$ and $R^{2b}$ together with the carbon atom to which they are attached to form a cycloalkyl group; and Q is an optionally substituted aryl, optionally substituted heteroaryl, or optionally substituted $C_3$-$C_8$ cycloalkyl.

5 Claims, No Drawings

(51) Int. Cl.
    *A61K 31/437*     (2006.01)
    *A61K 31/55*     (2006.01)
    *A61K 45/06*     (2006.01)
    *A61P 31/04*     (2006.01)

(52) U.S. Cl.
    CPC .............. *A61K 31/55* (2013.01); *A61K 45/06* (2013.01); *A61P 31/04* (2018.01)

(56) References Cited

U.S. PATENT DOCUMENTS

| | | | |
|---|---|---|---|
| 2011/0046368 A1* | 2/2011 | Ivashchenko | A61P 25/14 546/85 |
| 2015/0038437 A1 | 2/2015 | Branstrom et al. | |
| 2015/0157563 A1* | 6/2015 | Wirostko | A61K 31/5575 424/428 |

FOREIGN PATENT DOCUMENTS

| | | | | |
|---|---|---|---|---|
| WO | WO 02062339 A1 | 8/2002 | | |
| WO | WO 2004/113300 A1 | 12/2004 | | |
| WO | WO 2006/105971 A1 | 10/2006 | | |
| WO | WO 2010/051501 A1 | 5/2010 | | |
| WO | WO 2010/080253 A1 | 7/2010 | | |
| WO | WO-2013067409 A1 * | 5/2013 | ........... | A61K 31/165 |

OTHER PUBLICATIONS

Rai et al., "Temozolomide analogs with improved brain/plasma ratios—Exploring the possibility of enhancing the therapeutic index of temozolomide" Bioorganic and Medicinal Chemistry Letters vol. 26 pp. 5103-5109 DOI:10.1016/j.bmcl.2016.08.064 (Year: 2016).*

English translation of CN102424681B, downloaded form worldwide.espacenet.com (Year: 2011).*

Kelemen et al., "Spiro[pyrrolidine-3,3'-oxindoles] as 5-HT7 receptor ligands" Bioorganic and Medicinal Chemistry Letters vol. 28 pp. 2418-2421, DOI:10.1016/j.bmcl.2018.06.019 (Year: 2018).*

International Search Report of PCT Patent Application No. PCT/US2019/046712 dated Dec. 18, 2019.

Written Opinion of PCT Patent Application No. PCT/US2019/046712 dated Dec. 18, 2019.

1st Office Action of Chinese Patent Application No. 201980052062.8 dated Aug. 30, 2023.

2nd Office Action of Chinese Patent Application No. 201980052062.8 dated Jun. 14, 2024.

1st Office Action of Japanese Patent Application No. JP2021-532276 dated Sep. 4, 2023.

2nd Office Action of Japanese Patent Application No. JP2021-532276 dated Apr. 2, 2024.

Nagatake Tsuyoshi, 2. Resistant infections, Nihon's Pharmaceutical Society, Oct. 10, 2002, vol. 91, No. 10, pp. 2916-2921, DOI https://doi.org/10.2169/naika.91.2916.

Extended European Search Report of EP Application No. 19849557.4 dated Apr. 22, 2022.

Lee R. Swem et al., A Quorum / Sensing Antagonist Targets Both Membrane , e-Bound and Cytoplasmic Receptors and Controls Bacterial Pathogenicity, Molecular Cell, Jul. 31, 2009, vol. 35, No. 2, pp. 143-153, DOI: 10.1016/j.molcel.2009.05.029.

* cited by examiner

ANTIBIOTIC RESISTANCE-MODIFYING TRICYCLIC HETEROARYL COMPOUNDS AND USES THEREOF

CROSS-REFERENCE TO RELATED APPLICATIONS

This application is a U.S. National Stage Patent Application of PCT Patent Application No. PCT/US19/46712, filed Aug. 15, 2019, which claims the priority benefit of U.S. Provisional Application No. 62/719,048, filed Aug. 16, 2018, which are incorporated herein by reference in their entirety.

FIELD OF THE INVENTION

The present invention relates to 1,3,4,9-tetrahydro-2H-pyrido[3,4-b]indole derivative compounds and uses thereof. In particular, compounds of the invention have antibacterial activity and/or are capable of re-sensitizing methicillin-resistant *Staphylococcus aureus* to a β-lactam antibiotic or a combination of a β-lactam antibiotic and a β-lactamase inhibitor. The present invention also relates to a method for producing and using said compounds.

BACKGROUND OF THE INVENTION

Antibiotics are one of the most important and widely used medicines. Their extensive use has led to the resistance development by their pathogenic bacterial targets. The emergence of multi-drug resistant bacteria has become a global public health threat. Serious infection of multi-drug resistant microorganisms often causes considerable patient mortality and modality. For example, more people died from methicillin-resistant *Staphylococcus aureus* (MRSA) infection than those from HIV/AIDS, Parkinson's disease and homicide combined. The development of structural analogs of existing antibiotics had kept up with the emergence of new resistance until 20 years ago. Currently, there are not enough analogs in the antibiotic pipeline to combat imminent and future resistance emergence. In addition, the search for new structural classes of antibiotics has yielded only two new classes of antibacterial since 1960. The Pharmaceutical industry has devoted significant resources to high-throughput screening of large compound libraries against targets identified from genetic methods in recent years. However, these efforts have made limited progress.

Resistance-modifying agents (RMAs) are a highly favorable alternative. These target non-essential resistance-conferring genes and can further expand the life span of antibiotics that are currently used in the clinics, which have already been optimized for toxicity and large-scale production. For example, clavulanic acid is a β-lactamase inhibitor. Its use in combination with amoxicillin restores the efficacy of amoxicillin against many β-lactamase-producing bacteria.

Despite current efforts in identification and synthesis of RMAs, there is a continuing and urgent need for RMAs that can extend the usefulness of antibiotics for the treatment of drug-resistant bacteria.

SUMMARY OF THE INVENTION

Some aspects of the invention provide a compound of the formula

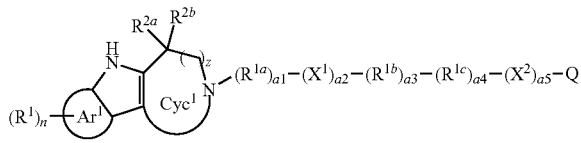

where n is an integer from 0-4; each of z, a1, a2, a3, a4, and a5 is independently 0 or 1, provided at least one of a1-a5 is 1; $Ar^1$ is phenyl or a nitrogen atom containing 6-membered heteroaryl; $Cyc^1$ is 5, 6, or 7-membered nitrogen atom containing heterocyclyl optionally containing one to three additional substituents in addition to $R^{2a}$ and $R^{2b}$; $X^1$ is —C(=O)—, —C(=O)NR$^6$—, or —SO$_2$—NH—; each of $R^{1a}$ and $R^{1c}$ is independently $C_1$-$C_6$ alkylene; $R^{1b}$ is optionally substituted $C_1$-$C_6$ alkylene; $X^2$ is O or NR$^6$; each $R^1$ is independently halogen, optionally substituted $C_1$-$C_6$ alkyl, optionally substituted $C_1$-$C_6$ haloalkyl, optionally substituted cycloalkyl, optionally substituted heterocyclyl, —OR$^a$, or —NR$^b$R$^c$, where R$^a$ hydrogen, $C_1$-$C_6$ alkyl, $C_1$-$C_6$ haloalkyl, or a hydroxyl protecting group, and wherein each of R$^b$ and R$^c$ is independently hydrogen, $C_1$-$C_6$ alkyl, $C_1$-$C_6$ haloalkyl, optionally substituted cycloalkyl, optionally substituted heterocyclyl, or a nitrogen protecting group; each of $R^{2a}$ and $R^{2b}$ is independently hydrogen, halogen, optionally substituted $C_1$-$C_6$ alkyl, optionally substituted $C_1$-$C_6$ haloalkyl, optionally substituted cycloalkyl, optionally substituted heterocyclyl, —OR$^a$, or NR$^b$R$^c$, where R$^a$ hydrogen, $C_1$-$C_6$ alkyl, $C_1$-$C_6$ haloalkyl, or a hydroxyl protecting group, and wherein each of R$^b$ and R$^c$ is independently hydrogen, $C_1$-$C_6$ alkyl, $C_1$-$C_6$ haloalkyl, optionally substituted cycloalkyl, optionally substituted heterocyclyl, or a nitrogen protecting group, or $R^{2a}$ and $R^{2b}$ together with the carbon atom to which they are attached to form a cycloalkyl group; and Q is an optionally substituted aryl, optionally substituted heteroaryl, or optionally substituted $C_3$-$C_8$ cycloalkyl.

Some of the compounds of Formula I are resistance-modifying agent ("RMA"). Without being bound by any theory, it is believed that RMAs target non-essential, resistance-conferring genes and restore antibiotic sensitivity of a bacteria. A notable advantage of RMAs is that they are capable of extending the market lifespan of known antibiotics that have already been optimized for large-scale production with well-studied toxicity profiles. In one particular aspect of the invention, some compounds of formula I selectively re-sensitizes methicillin-resistant *S. aureus* to β-lactam antibiotics or combinations of a β-lactam antibiotic and a β-lactamase inhibitor, such as a penicillin, a cephalosporin, a penem, a monobactam, Amoxicillin/clavulanic acid, Imipenem/cilastatin, Ampicillin/flucloxacillin, Piperacillin/tazobactam, Piperacillin/sulbactam, Amoxicillin/sulbactam, Ampicillin/sulbactam (Sultamicillin), Amoxicillin/pivsulbactam, Ceftolozane/tazobactam, Cefoperazone/sulbactam, Cefoperazone/tazobactam, Ceftriaxone/tazobactam, Meropenem/vaborbactam, and Ceftazidime/avibactam, or a combination thereof.

Still in other embodiments, compounds of the invention have antibiotic activity without a need for an additional antibiotic compound, such as a β-lactam antibiotic compound. Therefore, some compounds of the invention can be used alone or in combination with a β-lactam antibiotic to treat bacterial infections. Some compounds of Formula I are effective antibiotics in and of themselves for methicillin-sensitive *S. aureus* and methicillin-resistant *S. aureus*, *E. faecium*, *E. coli*, *K pneumoniae*, *A. baumannii*, *Enterococcus*, *S. enterica*, among others.

Another aspect of the invention provides an antibiotic composition comprising a compound of Formula I. In some embodiments, the antibiotic composition further comprises a β-lactam antibiotic. Still in other embodiments, the antibiotic composition further comprises a β-lactamase inhibitor, or other resistance-modifying agent or a combination thereof. Exemplary β-lactamase inhibitors that are useful in compositions of the invention include, but are not limited to, clavulanic acid, sulbactam, tazobactam, avibactam, relebactam (MK-7655), tebipenem, 6-methylidene penem2 and boron-based transition state inhibitors (BATSIs).

Yet another aspect of the invention provides a method for treating bacterial infection in a subject comprising administering to the subject in need of such a treatment a therapeutically effective amount of a compound of Formula I or a composition comprising a compound of Formula I as disclosed herein.

Still other aspects of the invention provide methods for producing various compounds and/or intermediate compounds disclosed herein.

While some of the specific substituents at various positions for the compound of Formula I are disclosed in specific compounds disclosed herein, it should be noted that combinations of various substituents in various positions can be combined to form other embodiments. In this manner, a variety of compounds are embodied within the present invention.

DETAILED DESCRIPTION OF THE INVENTION

As used herein, the terms "halide," "halogen" and "halo" are used interchangeably herein and refer to fluoro, chloro, bromo, or iodo.

The term "alkyl" refers to a saturated linear monovalent hydrocarbon moiety of one to twenty, typically one to fifteen, and often one to ten carbon atoms or a saturated branched monovalent hydrocarbon moiety of three to twenty, typically three to fifteen, and often three to ten carbon atoms. Exemplary alkyl groups include, but are not limited to, methyl, ethyl, n-propyl, 2-propyl, tert-butyl, pentyl, iso-pentyl, hexyl, and the like. Each alkyl can also be optionally substituted with one or more substituents such as halogen, a heteroatom (e.g., alkoxy, hydroxy, amino, alkylamino, thiol, alkylthiol, carbonyl, etc.). Sometime, heteroatom substituted alkyl may be referred to as heteroalkyl.

"Alkylene" refers to a saturated linear divalent hydrocarbon moiety of one to twenty, typically one to fifteen and often one to ten carbon atoms or a branched saturated divalent hydrocarbon moiety of three to twenty, typically three to fifteen and often three to ten carbon atoms. Exemplary alkylene groups include, but are not limited to, methylene, ethylene, propylene, butylene, pentylene, and the like.

"Alkoxide" or "alkoxy" refers to a moiety of the formula —$OR^x$, where $R^x$ is alkyl as defined herein. "Alkoxycarbonyl" refers to a moiety of the formula —$C(=O)OR^z$, where $R^z$ is alkyl, aralkyl, aryl, haloalkyl or the like as defined herein.

"Haloalkyl" refers to an alkyl group as defined herein in which one or more hydrogen atom is replaced by same or different halide atoms. The term "haloalkyl" also includes perhalogenated alkyl groups in which all alkyl hydrogen atoms are replaced by halogen atoms. Exemplary haloalkyl groups include, but are not limited to, —$CH_2Cl$, $CF_3$, $CH_2CF_3$, $CH_2CCl_3$, and the like.

"Cycloalkyl" refers to a non-aromatic, typically saturated, monovalent mono- or bicyclic hydrocarbon moiety of three to ten ring carbons. The cycloalkyl can be optionally substituted with one or more, typically one, two, or three, substituents within the ring structure. When two or more substituents are present in a cycloalkyl group, each substituent is independently selected.

The terms "(cycloalkyl)alkyl" and "cycloalkylalkyl" are used interchangeably herein and refer to a moiety of the formula —$R^dR^e$ where $R^d$ is an alkylene group and $R^e$ is a cycloalkyl group as defined herein. Exemplary cycloalkylalkyl groups include, but are not limited to, cyclopropylmethyl, cyclohexylpropyl, 3-cyclohexyl-2-methylpropyl, and the like.

"Aryl" refers to a monovalent mono-, bi- or tricyclic aromatic hydrocarbon moiety of 6 to 15 ring atoms such as phenyl, naphthyl, etc. "Optionally substituted aryl" refers to an aryl group that is optionally substituted with one or more, typically one, two, or three substituents within the aryl ring structure. When two or more substituents are present in an aryl group, each substituent is independently selected.

The terms "aralkyl" and "(aryl)alkyl" are used interchangeably herein and refer to a moiety of the formula —$R^dR^e$ where $R^d$ is alkylene and W is aryl as defined herein. Exemplary aralkyl or arylalkyl groups include, but are not limited to, phenylmethyl (i.e., benzyl), naphthylmethyl, phenylethyl, phenylpropyl, and the like. "Aralkoxy" refers to a moiety of the formula —$OR^bAr^b$, where $R^b$ is alkylene and $Ar^b$ is optionally substituted aryl as defined herein.

"Alkenyl" means a linear monovalent hydrocarbon moiety of two to ten carbon atoms or a branched monovalent hydrocarbon moiety of three to ten carbon atoms, containing at least one carbon-carbon double bond, e.g., ethenyl, propenyl, and the like.

"Alkynyl" means a linear monovalent hydrocarbon moiety of two to ten carbon atoms or a branched monovalent hydrocarbon moiety of three to ten carbon atoms, containing at least one carbon-carbon triple bond, e.g., ethenyl, propenyl, and the like.

"Acyl" refers to a moiety of the formula —C(O)R', where R' is alkyl, haloalkyl, aryl, or aralkyl.

Terms "heterocyclyl" and "heterocycloalkyl" are used interchangeably herein and refer to a non-aromatic mono- or bicyclic moiety of three to eight ring atoms in which one or two ring atoms are heteroatoms selected from N, O, or $S(O)_n$ (where n is an integer from 0 to 2), the remaining ring atoms being C, where one or two C atoms can optionally be a carbonyl group. The heterocyclyl ring can be optionally substituted independently with one or more, preferably one, two, or three, substituents. When two or more substituents are present in a heterocyclyl group, each substituent is independently selected. Exemplary substituents for heterocyclyl group include, but are not limited to, alkyl, haloalkyl, heteroalkyl, halo, nitro, cyano, optionally substituted phenyl, optionally substituted heteroaryl, optionally substituted phenyalkyl, optionally substituted heteroaralkyl, acyl, -(alkylene)$_n$-COOR (n is 0 or 1 and R is hydrogen, alkyl, optionally substituted phenyl, optionally substituted phenyalkyl, or optionally substituted heteroaralkyl), or -(alkylene)$_n$-CONR$^a$R$^b$ (where n is 0 or 1, and R$^a$ and R$^b$ are, independently of each other, hydrogen, alkyl, cycloalkyl, cycloalkylalkyl, hydroxyalkyl, aryl, or R and R' together with the nitrogen atom to which they are attached form a heterocyclyl ring). More specifically the term heterocyclyl includes, but is not limited to, oxetane, azetidine, aziridine, tetrahydropyranyl, piperidino, piperazino, diazepine, morpholino and thiomorpholino, thiomorpholino-1-oxide, thiomorpholino-1,1-dioxide, and the derivatives thereof.

"Sulfonyl" refers to a moiety of the formula —S(O)$_2$R$^y$, where R$^y$ is alkyl, haloalkyl, optionally substitute aryl, optionally substituted aralkyl, or (cycloalkyl)alkyl.

"Enantiomeric excess" refers to the difference between the amount of enantiomers. The percentage of enantiomeric excess (% ee) can be calculated by subtracting the percentage of one enantiomer from the percentage of the other enantiomer. For example, if the percent of (R)-enantiomer is 99% and the percent of (S)-enantiomer is 1%, the % ee of (R)-isomer is 99%–1% or 98%.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethane-sulfonyloxy, aryloxy (e.g., 2,4-dinitrophenoxy), methoxy, N,O-dimethylhydroxylamino, and the like.

"Pharmaceutically acceptable excipient" refers to an excipient that is useful in preparing a pharmaceutical composition that is generally safe, non-toxic and neither biologically nor otherwise undesirable, and includes excipient that is acceptable for veterinary use as well as human pharmaceutical use.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentane-propionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1carboxylic acid, glucoheptonic acid, 3-phenylpropionic acid, trimethylacetic acid, tertiary butylacetic acid, lauryl sulfuric acid, gluconic acid, glutamic acid, hydroxy-naphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to a pharmacologically substantially inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, *Design of Prodrugs*, pp. 7-9, 21-24, Elsevier, Amsterdam 1985 and Silverman, *The Organic Chemistry of Drug Design and Drug Action*, pp. 352-401, Academic Press, San Diego, Calif, 1992). Prodrugs commonly known in the art include acid derivatives that are well known to one skilled in the art, such as, but not limited to, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability. For example, a compound of the invention having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of the invention. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of a compound of the invention through the carbonyl carbon prodrug sidechain.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino or amine protecting groups include, formyl, acyl groups (such as acetyl, trifluoroacetyl, and benzoyl), benzyl, alkoxycarbonyl (such as benzyloxycarbonyl (CBZ), and tert-butoxycarbonyl (Boc)), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), sulfonyl, and the like.

"Corresponding protecting group" means an appropriate protecting group corresponding to the heteroatom (i.e., N, O, P or S) to which it is attached.

"A therapeutically effective amount" means the amount of a compound that, when administered to a mammal for treating a disease, is sufficient to effect such treatment for the disease. In general, the therapeutically effective amount will vary depending on the compound, the disease and its severity and the age, weight, etc., of the mammal to be treated.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

When describing a chemical reaction, the terms "treating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as any narrow definitions, if any.

One particular aspect of the invention provides a compound of the formula

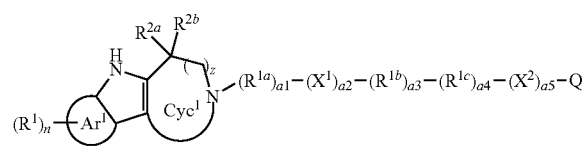

I where n is an integer from 0-4; each of z, a1, a2, a3, a4, and a5 is independently 0 or 1, provided at least one of a1-a5 is 1; $Ar^1$ is phenyl or a nitrogen atom containing 6-membered heteroaryl; $Cyc^1$ is 5, 6, or 7-membered nitrogen atom containing heterocyclyl optionally containing one to three additional substituents in addition to $R^{2a}$ and $R^{2b}$; $X^1$ is —C(=O)—, —C(=O)$NR^6$—, or —SO$_2$—NH—; each of $R^{1a}$ and $R^{1c}$ is independently $C_1$-$C_6$ alkylene; $R^{1b}$ is optionally substituted $C_1$-$C_6$ alkylene; $X^2$ is O or $NR^6$; each $R^1$ is independently halogen, optionally substituted $C_1$-$C_6$ alkyl, optionally substituted $C_1$-$C_6$ haloalkyl, optionally substituted cycloalkyl, optionally substituted heterocyclyl, —$OR^a$, or —$NR^bR^c$, where $R^a$ hydrogen, $C_1$-$C_6$ alkyl, $C_1$-$C_6$ haloalkyl, or a hydroxyl protecting group, and wherein each of $R^b$ and $R^c$ is independently hydrogen, $C_1$-$C_6$ alkyl, $C_1$-$C_6$ haloalkyl, optionally substituted cycloalkyl, optionally substituted heterocyclyl, or a nitrogen protecting group; each of $R^{2a}$ and $R^{2b}$ is independently hydrogen, halogen, optionally substituted $C_1$-$C_6$ alkyl, optionally substituted $C_1$-$C_6$ haloalkyl, optionally substituted cycloalkyl, optionally substituted heterocyclyl, —$OR^a$, or —$NR^bR^c$, where $R^a$ hydrogen, $C_1$-$C_6$ alkyl, $C_1$-$C_6$ haloalkyl, or a hydroxyl protecting group, and wherein each of $R^b$ and $R^c$ is independently hydrogen, $C_1$-$C_6$ alkyl, $C_1$-$C_6$ haloalkyl, optionally substituted cycloalkyl, optionally substituted heterocyclyl, or a nitrogen protecting group, or $R^{2a}$ and $R^{2b}$ together with the carbon atom to which they are attached to form a cycloalkyl group, such as cyclopropyl, cyclobutyl, cyclopentyl, cyclohexyl, cycloheptyl, or cyclooctyl, each of which is optionally substituted; and Q is an optionally substituted aryl, optionally substituted heteroaryl, or optionally substituted $C_3$-$C_8$ cycloalkyl.

Some of the compounds of Formula I are resistance-modifying agent ("RMA"). Without being bound by any theory, it is believed that RMAs target non-essential, resistance-conferring genes and restore antibiotic sensitivity of a bacteria. A notable advantage of RMAs is that they are capable of extending the market lifespan of known antibiotics that have already been optimized for large-scale production with well-studied toxicity profiles. In one particular aspect of the invention, some compounds of formula I selectively re-sensitizes methicillin-resistant S. aureus to β-lactam antibiotics, such as a penicillin, a cephalosporin, a penem, a monobactam, Amoxicillin/clavulanic acid, Imipenem/cilastatin, Ampicillin/flucloxacillin, Piperacillin/tazobactam, Piperacillin/sulbactam, Amoxicillin/sulbactam, Ampicillin/sulbactam (Sultamicillin), Amoxicillin/pivsulbactam, Ceftolozane/tazobactam, Cefoperazone/sulbactam, Cefoperazone/tazobactam, Ceftriaxone/tazobactam, Meropenem/vaborbactam, and Ceftazidime/avibactam, or a combination thereof.

In some embodiments, compounds of Formula I are capable of re-sensitizing the susceptibility of methicillin-resistant S. aureus to (i) a β-lactam antibiotic and/or (ii) a combination of a β-lactam antibiotic and a β-lactamase inhibitor.

Still in other embodiments, compounds of Formula I have antibiotic activity without a need for an additional antibiotic compound, such as a β-lactam antibiotic compound. Therefore, some compounds of the invention can be used alone or in combination with a β-lactam antibiotics and/or a β-lactamase inhibitor to treat bacterial infections. Yet in other embodiments, some compounds of the invention are effective antibiotics in and of themselves for both methicillin-sensitive S. aureus and methicillin-resistant S. aureus, E. faecium, E. coli, K. 11ydroxyl11, A. baumannii, Enterococcus, S. enterica, among others.

In some embodiments, compound of Formula I is selected from the group consisting of compounds of the following formulas

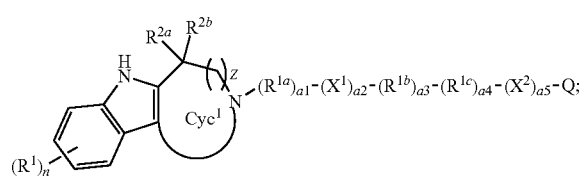

IA

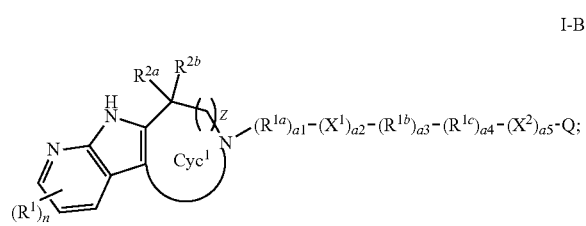

I-B

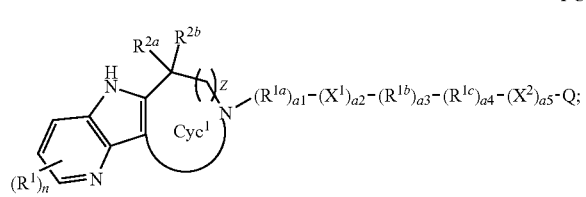

I-C

-continued

I-D

I-E
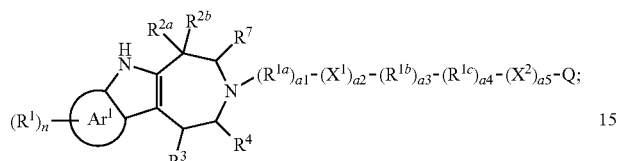

I-F
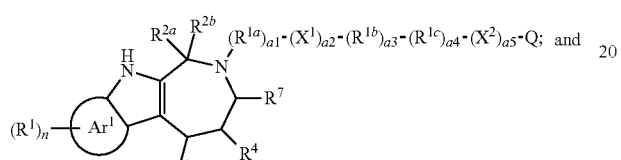

I-G
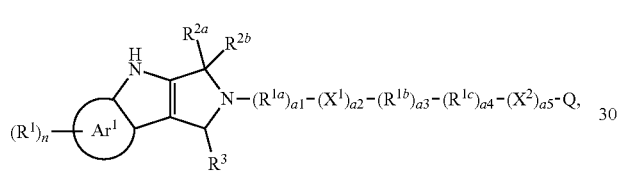

where n, a1, a2, a3, a4, a5, $Ar^1$, $Cyc^1$, $R^1$, $R^{2a}$, $R^{2b}$, $R^{1a}$, $X^{1b}$, $R^{1c}$, $R^{1c}$, $X^2$, $R^5$ and Q are those defined herein; and each of $R^3$, $R^4$, and $R^7$ is independently hydrogen, halogen, optionally substituted $C_1$-$C_6$ alkyl, optionally substituted $C_1$-$C_6$ haloalkyl, optionally substituted cycloalkyl, optionally substituted heterocyclyl, —$OR^a$, or —$NR^bR^c$, where $R^a$ hydrogen, $C_1$-$C_6$ alkyl, $C_1$-$C_6$ haloalkyl, or a hydroxyl protecting group, and wherein each of $R^b$ and $R^c$ is independently hydrogen, $C_1$-$C_6$ alkyl, $C_1$-$C_6$ haloalkyl, optionally substituted cycloalkyl, optionally substituted heterocyclyl. In some embodiments, compounds of the invention are of formula I-A. Still in other embodiments, compounds of the invention are of formula I-B. In yet other embodiments, compounds of the invention are of formula I-C. Yet in other embodiments, compounds of the invention are of formula I-D. In further embodiments, compounds of the invention are of formula I-E. Still in yet other embodiments, compounds of the invention are of formula I-F. Yet in other embodiments, compounds of the invention are of formula I-G.

Still in other embodiments, compound of Formula I is selected from the group consisting of compounds of the following formulas I-H
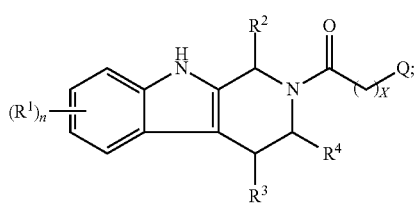

I-J
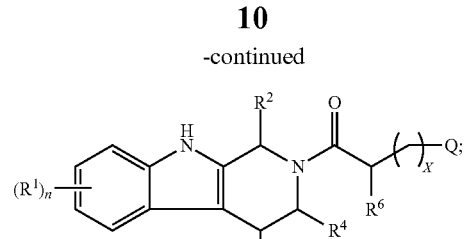

I-K
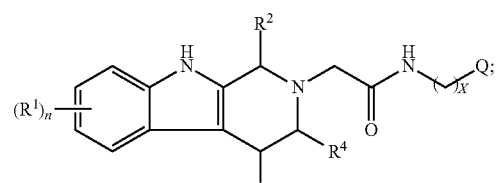

I-L
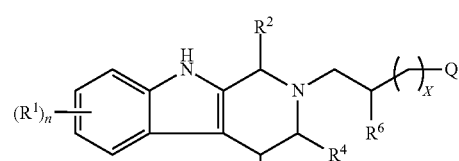

I-M
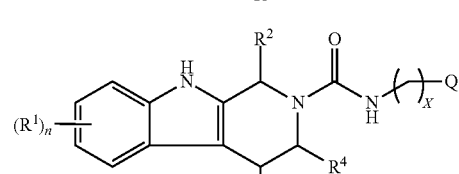

I-N
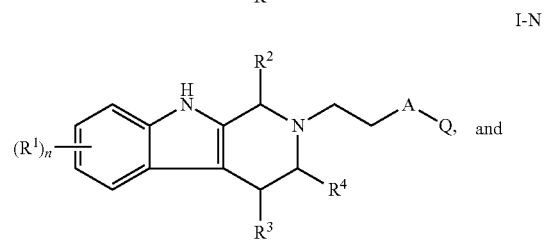

I-O
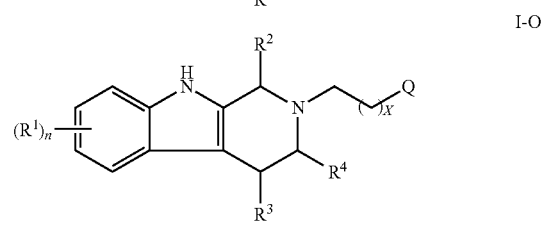

where x is an integer from 0 to 3; $R^6$ is $C_1$-$C_6$ alkyl, optionally substituted cycloalkyl, heterocyclyl, —$OR^a$, and —$NR^bR^c$; n, $R^1$, $R^2$, $R^3$, $R^4$, $R^a$, $R^b$, $R^c$ and Q are those defined herein; and A is O or NH. In one particular embodiment, compounds of the invention are of formula I-H. Yet in another embodiment, compounds of the invention are of formula I-J. Still in another embodiment, compounds of the invention are of formula I-K. Yet still in another embodiment, compounds of the invention are of formula I-L. Still yet in another embodiment, compounds of the invention are of formula I-M. In further embodiment, compounds of the invention are of formula I-N. Yet in some embodiments, compounds of the invention are of formula I-O.

Yet in other embodiments, Q is optionally substituted phenyl, optionally substituted heteroaryl, or optionally substituted cyclopropyl. In some embodiments, Q is selected from the group consisting of: (a) phenyl optionally having one, two or three substituents, wherein each of the substituent is independently selected from the group consisting of: chloro, trifluoromethoxy, trifluoromethyl, methyl, ethyl, nitro, —NH—C(=O)—(CH$_2$)$_2$—CO$_2$H, —NH—C(=O)—CH$_3$, —NH—C(=O)—CH$_2$—CN, bromomethyl, —PO$_4$(R$^x$)$_2$, —OCH$_2$PO$_4$(R$^x$)$_2$ and —CH$_2$PO$_4$(R$^x$)$_2$, wherein each R$^x$ is independently hydrogen or a metal ion; and (b) heteroaryl selected from the group consisting of isoxazolyl; thiophenyl; thiazolyl; furanyl; and 1H-pyrazolyl, pyridyl, pyrimidyl, isothiazolyl, etc., each of which is optionally substituted with one or two substituents, wherein each of the substituent is independently selected from the group consisting of halide, amino, hydroxyl, C$_1$-C$_6$ alkyl, alkoxyl, —CONR$^b$R$^c$, —NHCOR$^d$, —NHR$^d$, and optionally substituted phenyl, and wherein each of R$^b$, R$^c$ and R$^d$ is independently hydrogen, C$_1$-C$_6$ alkyl, C$_1$-C$_6$ haloalkyl, optionally substituted cycloalkyl, optionally substituted heterocyclyl. Still in other embodiments, Q is piperazine, pyrrolidine, imidazolidine, diazepane, (each of which is optionally substituted, for example with optionally substituted phenyl, optionally substituted heteroaryl such as pyridine), etc. Exemplary substituents for phenyl and heteroaryl such as pyridinyl are those disclosed herein.

In some embodiments, n is 0, 1 or 2. Still in other embodiments, n is 1 or 2.

Still in other embodiments, each R$^1$ is independently halogen, 14ydroxyl, C$_1$-C$_6$ alkyl, or C$_1$-C$_6$ alkoxy, —CONR$^b$R$^c$, —NHCOR$^d$, —NHR$^d$, and wherein each of R$^b$, R$^c$ and R$^d$ is independently hydrogen, C$_1$-C$_6$ alkyl, C$_1$-C$_6$ haloalkyl, optionally substituted cycloalkyl, optionally substituted heterocyclyl. In some instances, each R$^1$ is independently chloro, fluoro, methoxy, or hydroxyl.

In other embodiments, R$^{2a}$ is:
hydrogen,
methyl,
(1,3-dioxoisoindolin-2-yl)methyl,
aminomethyl or a salt thereof,
((3-(trifluoromethyl)benzoyl)oxy)-methyl,
((4-(trifluoromethyl)-benzoyl)oxy)-methyl,
—(CH$_2$)$_a$—NH—C(=NH)—NH$_2$ or a salt thereof, where a is 1 or 2,
2-hydroxyethyl,
3-hydroxyethyl,
1-hydroxyethyl,
(2-hydroxyethyloxy)methyl,
(1-pyridinium)-methyl,
2-(1-pyridinium)ethyl,
2-aminoethyl,
—C(=O)NR$^{a1}$R$^{a2}$ (where each of R$^{a1}$ and R$^{a2}$ is independently hydrogen or C$_{1-6}$ alkyl, such as methyl, ethyl, propyl, t-butyl, etc.),
—C(=O)NHCH$_2$CH$_2$X$^a$ (where X$^a$ is —OH, —SH, or —NH$_2$),
—CH$_2$NHC(=O)—CH$_2$NR$^{a1}$R$^{a2}$ where each of R$^{a1}$ and R$^{a2}$ is independently hydrogen or C$_{1-6}$ alkyl, such as methyl, ethyl, propyl, t-butyl, etc.) or a salt thereof,
—CH$_2$NHCH$_2$CH$_2$X$^a$ (where X$^a$ is —OH$^1$, —SR$^1$, or —NR$^{a1}$R$^{a2}$, where each of R$^{a1}$ and R$^{a2}$ is independently hydrogen or C$_{1-6}$ alkyl, such as methyl, ethyl, propyl, t-butyl, etc.) or a salt thereof,
—CH$_2$NHCH$_2$CH$_2$X$^a$ (where X$^a$ is —OH, —SH, or —NH$_2$) or a salt thereof, or
—R$^{x1}$—X$^a$, where R$^{x1}$ is C$_{1-6}$ alkylene, such as methylene, ethylene, etc., X$^a$ is —OR$^{a1}$, —S$^{a1}$, or —NR$^{a1}$R$^{a2}$ (where each of R$^{a1}$ and R$^{a2}$ is independently hydrogen, C$_{1-6}$ alkyl, (such as methyl, ethyl, propyl, t-butyl, etc.), or heterocycloalkyl (such as aziridinyl, azetidinyl, etc.)). Specific examples of —R$^{x1}$—X$^a$ include, but are not limited to, (dimethylamino)methyl, hydroxymethyl (HOCH$_2$—), (azetidinyl)methyl, etc.

Yet in some other embodiments, R$^{2b}$ is H and R$^{2a}$ is ethyl, isopropyl, trifluoromethyl, cyclopropyl, or fluoromethyl; or R$^{2a}$ and R$^{2b}$ are methyl; or R$^{2a}$ and R$^{2b}$ together with the carbon atom to which they are attached to form cyclopropyl.

Still yet in other embodiments, R$^3$ is hydrogen, aminomethyl (H$_2$NCH$_2$—) or a salt thereof, methylcarboxylate (—CO$_2$Me), carboxylate (—CO$_2$H), hydroxymethyl, —CH$_2$—NH—C(=NH)—NH$_2$ or a salt thereof, or aminomethyl or a salt thereof.

In other embodiments, a1, a2 and a4 are 0; and a3 is 1. In some instances, R$^{1b}$ is —CH$_2$CH(OH)—; or a hetaryl of the formula Yet in other embodiments, the moiety of the formula:

—(R$^{1a}$)$_{a1}$(X$^1$)$_{a2}$—(R$^{1b}$)$_{a3}$—(R$^{1c}$)$_{a4}$—(X$^2$)$_{a5}$— comprises: (R)- or (S)-isomers of —CH$_2$CH(OH)—; —C(=O)NH—; —C(=O)—NH—CH$_2$—; —CH$_2$C(=O)NH—; —C(=O)—; methylene; (R)- or (S)-isomers of —C(=O)CH(NH$_2$)— or a salt thereof; —C(=O)CH[NH(C(=O)CH$_3$)]; (R)- or (S)-isomers of —C(=O)CH(NH$_2$)CH$_2$— or a salt thereof; —C(=O)CH(N(C(=O)CH$_3$)$_2$)CH$_2$—; —(=O)C(=O)—; (R)- or (S)-isomers of —C(=O)CH(NHC(=O)CH$_3$)CH$_2$—; (R)- or (S)-isomers of —C(=O)CH(NHC(=O)CH$_3$)—; —C(=O)CH$_2$; (R)- or (S)-isomers of —C(=O)CH(NH$_2$)CH$_2$— or a salt thereof; (R)- or (S)-isomers of —C(=O)CH(NHC(=O)CH$_3$)CH$_2$—; (R)- or (S)-isomers of —C(=O)CH(OH)—; —C(=O)C(=NOH)—; —S(O)$_2$—NHC(=O)—; —C(=O)C(=NOCH$_2$CH$_2$N(CH$_3$)$_2$)— or a salt thereof; (R)- or (S)-isomers of —C(=O)CH(NH$_2$)— or a salt thereof; —S(O)$_2$NHC(=O)CH$_2$—; —CH$_2$C(=O)NH—; —CH$_2$C(=O)NHS(O)$_2$—; (R)- or (S)-isomers of —C(=O)CH(CH$_2$CH$_2$OH)—; (R)- or (S)-isomers of —C(=O)NHCH(CH$_2$OH)—; —CH$_2$C(=O)NHCH$_2$—; —C(=O)NH—; —C(=O)NHCH$_2$—; —S(O)$_2$NH—; —S(O)$_2$NHCH$_2$—; (R)- or (S)-isomers of —CH(CH$_2$OH)—; (R)- or (S)-isomers of —CH$_2$CH(OH)CH$_2$—; (R)- or (S)-isomers of —CH$_2$CH(OH)C(=O)NH—; (R)- or (S)-isomers of —CH(CH$_2$OH)C(=O)NH—; (R)- or (S)-isomers of —CH(CH$_2$OH)CH$_2$NH—; (R)- or (S)-isomers of —CH(CH$_2$OPO$_3$H$_2$)C(=O)NH— or a salt thereof; (R)- or (S)-isomers of —CH(CH$_2$OPO$_3$H$_2$)CH$_2$NH— or a salt thereof; —CH$_2$C(=O)NHS(O)$_2$—; (R)- or (S)-isomers of —CH(CH(OH)CH$_3$))C(=O)NH—; —CH$_2$CH$_2$NH—; —CH(CH$_2$NH$_2$)C(=O)NH— or a salt thereof; (R)- or (S)-isomers of —CH(CH$_2$CH$_2$OH)C(=O)NH—; —CH$_2$CH$_2$O—; —CH$_2$CH$_2$C(=O)NH—; (R)- or (S)-isomers of —CH$_2$CH(OH)C(=O)NH—; (R)- or (S)-isomers of —CH$_2$CH(NH$_2$)— or a salt thereof; —CH$_2$CH(OH)CH(OH)—; —CH$_2$C(=O)NH—; —CH$_2$CH$_2$CH(OH)—; or (S)-isomers of —CH$_2$CH$_2$CH(NH$_2$)— or a salt thereof; (R)- or (S)-isomers of —C(=O)CH(NH$_2$)CH$_2$— or a salt thereof;

—C(=O)CH(NHC(=O)CH₃)CH₂— or a salt thereof; —C(=O)CH(NHCH₂CH₂OH)— or a salt thereof; —C(=O)CH(NHCH₂CH₃)— or a salt thereof; —C(=O) CH(NHCH₂CH₂CH₃)— or a salt thereof; —C(=O)CH (NHCH₂CH₂NH₂)— or a salt thereof; —C(=O)CH (NHCH₃)— or a salt thereof; —C(=NH)NH— or a salt thereof; —C(=O)CH₂CH₂—; —C(=NH)NHCH₂— or a salt thereof; —C(=O)CH₂NH—; —C(=O)CH₂CH (NH₂)— or a salt thereof; or (S)-isomers of —C(=O)CH (OH)— or a salt thereof; (R)- or (S)-isomers of —C(=O) CH(CH₂OH)— or a salt thereof; (R)- or (S)-isomers of —C(=O)C[(OH)(CH₂OH)]— or a salt thereof; (R)- or (S)-isomers of —C(=O)CH(CH(OH)(CH₃))— or a salt thereof; (R)- or (S)-isomers of —C(=O)CH (CH₂CH₂OH)— or a salt thereof; —C(=O)NHCH (CH₂NH₂)— or a salt thereof; —C(=O)C (=NOCH₂CH₂N⁺(CH₃)₃)—; —C(=O)C (=NOCH₂CO₂H)—; —C(=O)C(=NOC(CH₃)(CH₃) CO₂H)—; an isomer or a mixture of —C(=O)CH(OH)CH (OH); C(=NH)NHCH₂— or a salt thereof; an isomer or a mixture of —C(=O)CH(NH₂)— or a salt thereof; —C(=O)NHCH₂—; an isomer or a mixture of —C(=O) CH(CH₂NH₂)— or a salt thereof; an isomer or a mixture of —C(=O)CH(OH)—; —CH₂CH(OPO₃H₂)— or a salt thereof; or —CH₂CH(O(CH₂OPO₃H₂))— or a salt thereof. Unless the context clearly require otherwise, the terms "(R)- or (S)-isomer" and "an isomer or a mixture of" are used interchangeably to indicate that the compound can be one particular isomer or an enantiomeric excess of a particular isomer or a racemic mixture of isomers. In fact, unless explicitly stated to the contrary all compounds having an optical rotation are deemed to include a pure isomer, enantiomeric excess of one or more isomer or a racemic mixture of such a compound.

Yet still in other embodiments, $R^4$ is hydrogen, methyl, hydroxymethyl (i.e., HOCH₂—), (1,3-dioxoisoindolin-2-yl) methyl, aminomethyl or a salt thereof, ((3-(trifluoromethyl) benzoyl)-oxy)methyl, ((4-(trifluoromethyl)benzoyl)oxy)- methyl, —(CH₂)ₐNHC(=NH)NH₂ or a salt thereof, where a is 1 or 2, 2-hydroxyethyl, 3-hydroxyethyl, 1-hydroxyethyl, (2-hydroxyethyloxy)methyl, (1-pyridinium)methyl, 2-(1- pyridinium)ethyl, 2-aminoethyl, 2-hydroxyethyl, —C(=O) NHCH₃, —C(=O)NHCH₂CH₂OH, —CH₂NHC(=O) CH₂NH₂ or a salt thereof, —CH₂NHCH₂CH₂OH or a salt thereof, —CH₂NHCH₂CH₂NH₂ or a salt thereof, or (dimethylamino)methyl.

Some of the specific representative compounds of the invention include those shown in the Examples section as well as the following specific compounds in Table A

TABLE A

Representative compounds of the invention (includes compounds shown below as well as compounds disclosed in the Examples section that fall within the general structure of Formula I)

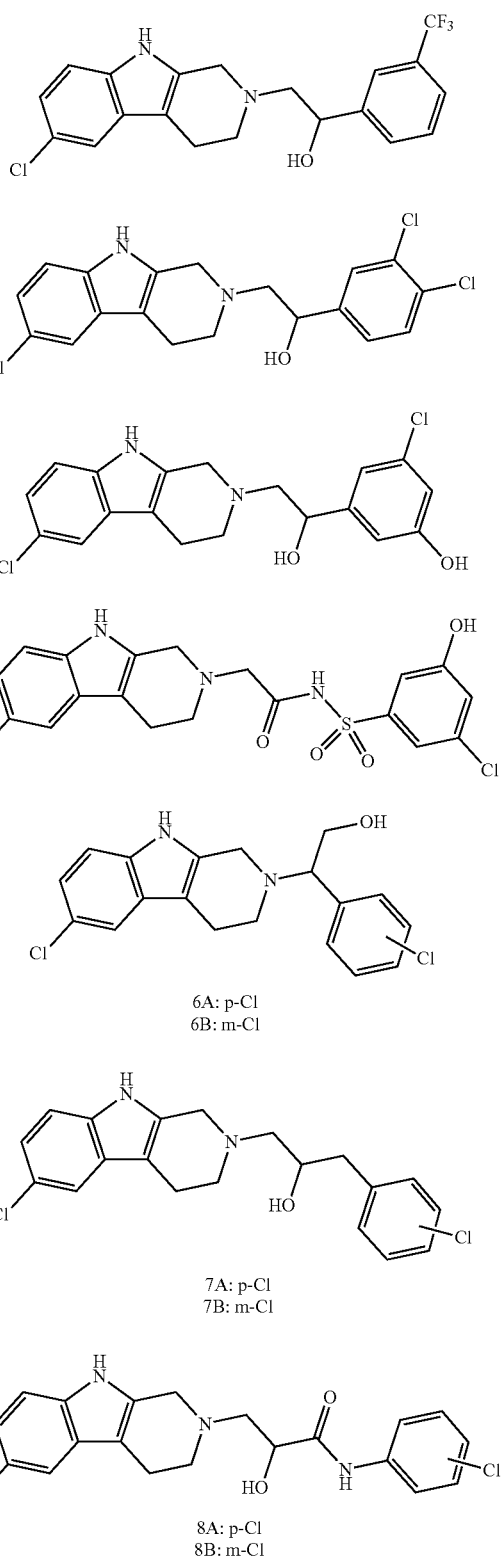

6A: p-Cl
6B: m-Cl

7A: p-Cl
7B: m-Cl

8A: p-Cl
8B: m-Cl

TABLE A-continued

Representative compounds of the invention (includes compounds shown below as well as compounds disclosed in the Examples section that fall within the general structure of Formula I)

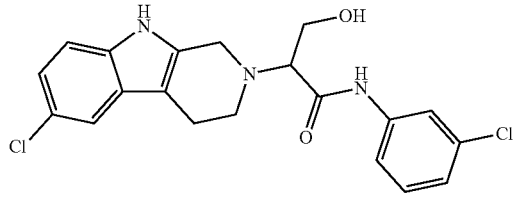

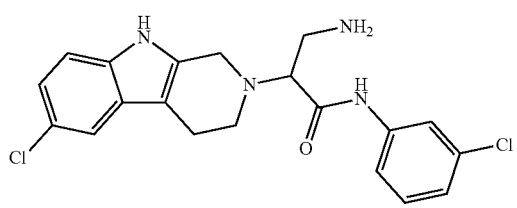 [SMILES: O=C(Nc1cccc(Cl)c1)C(CO)N1CCc2c([nH]c3ccc(Cl)cc23)C1]

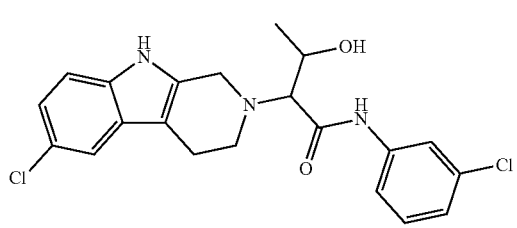 [SMILES: CC(O)C(C(=O)Nc1cccc(Cl)c1)N1CCc2c([nH]c3ccc(Cl)cc23)C1]

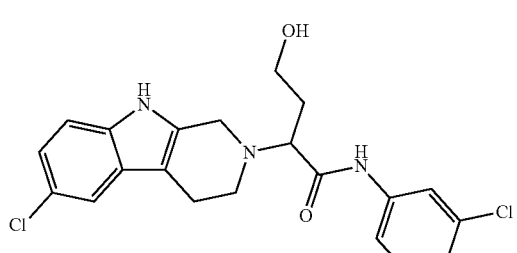

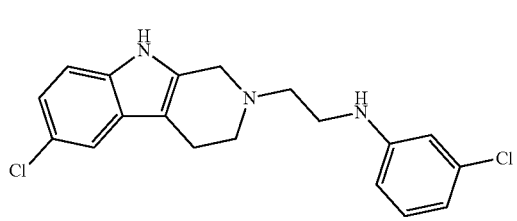 [SMILES: Clc1cccc(NCCN2CCc3c([nH]c4ccc(Cl)cc34)C2)c1]

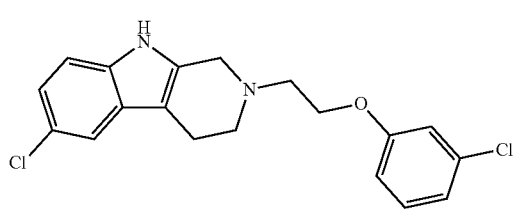 [SMILES: Clc1cccc(OCCN2CCc3c([nH]c4ccc(Cl)cc34)C2)c1]

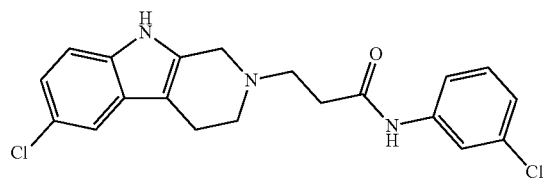 [SMILES: O=C(CCN1CCc2c([nH]c3ccc(Cl)cc23)C1)Nc1cccc(Cl)c1]

TABLE A-continued

Representative compounds of the invention (includes compounds shown below as well as compounds disclosed in the Examples section that fall within the general structure of Formula I)

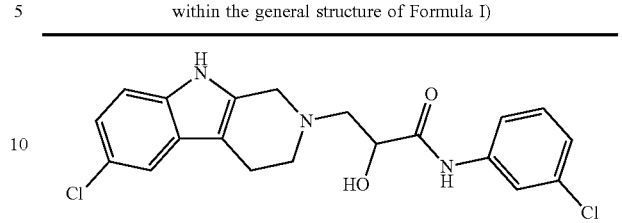

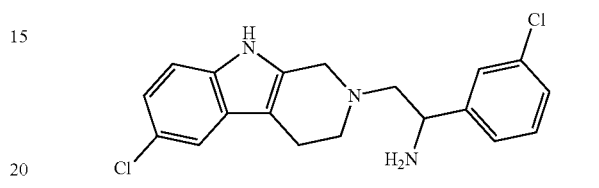


9A: p-Cl
9B: m-Cl

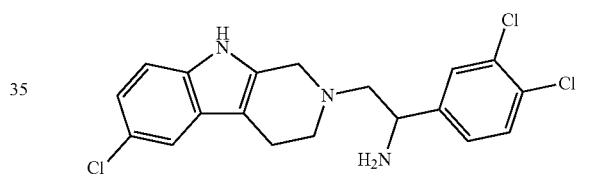


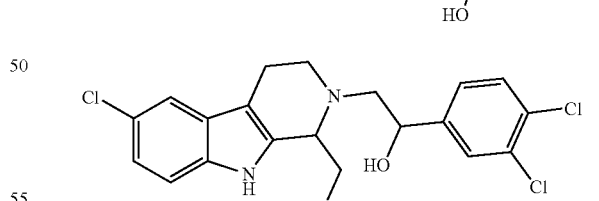

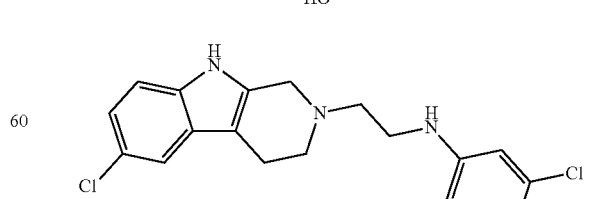

TABLE A-continued
Representative compounds of the invention (includes compounds shown below as well as compounds disclosed in the Examples section that fall within the general structure of Formula I)
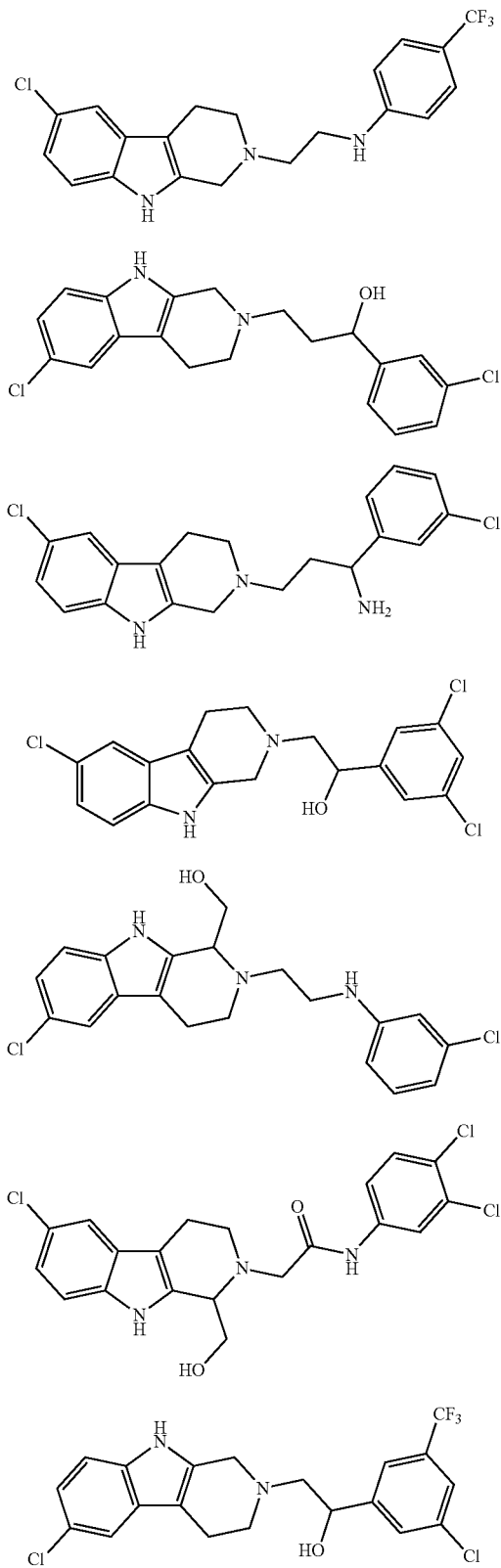
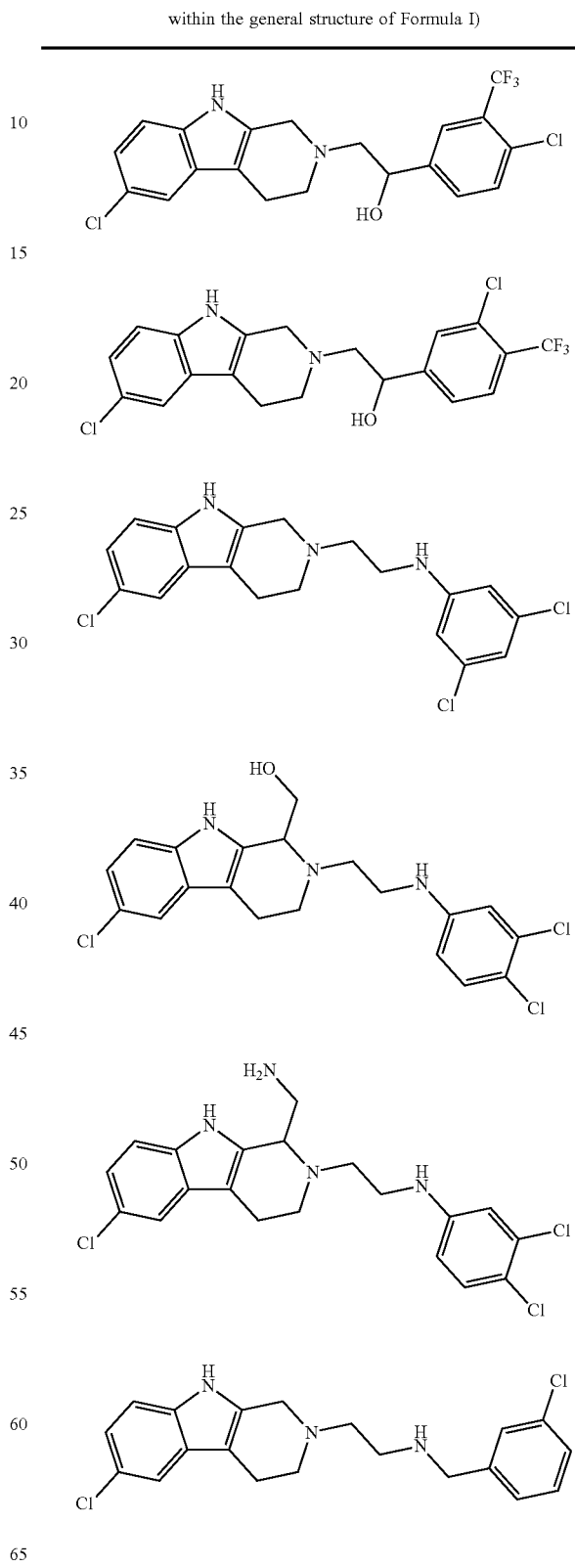

TABLE A-continued
Representative compounds of the invention (includes compounds shown below as well as compounds disclosed in the Examples section that fall within the general structure of Formula I)
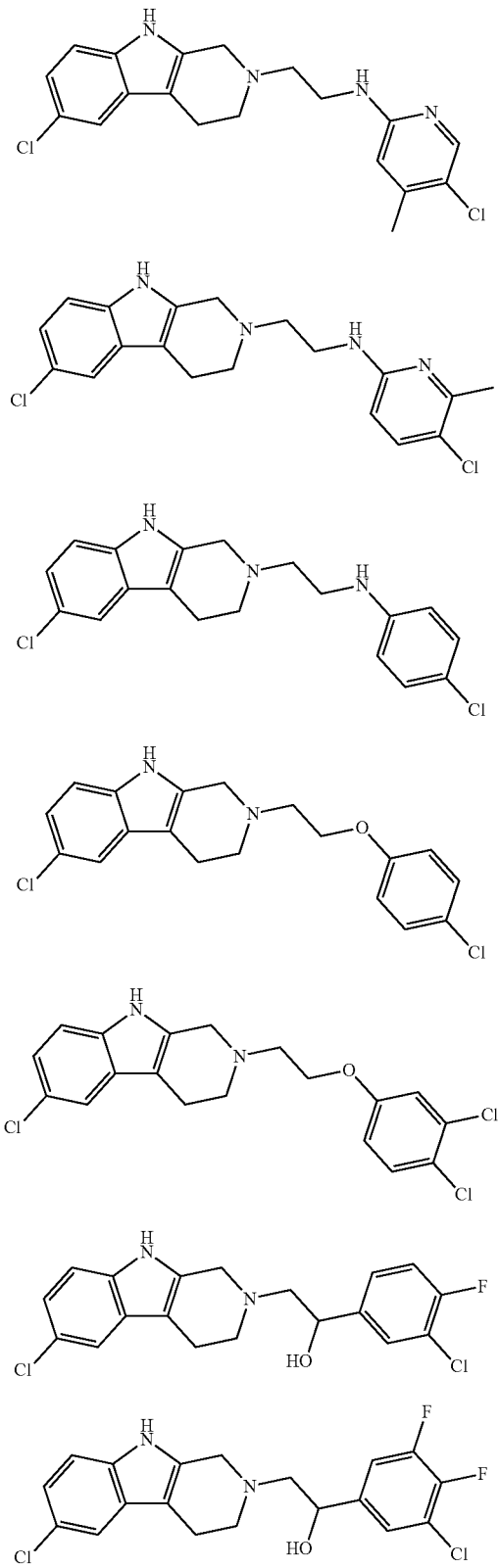

TABLE A-continued

Representative compounds of the invention (includes compounds shown below as well as compounds disclosed in the Examples section that fall within the general structure of Formula I)

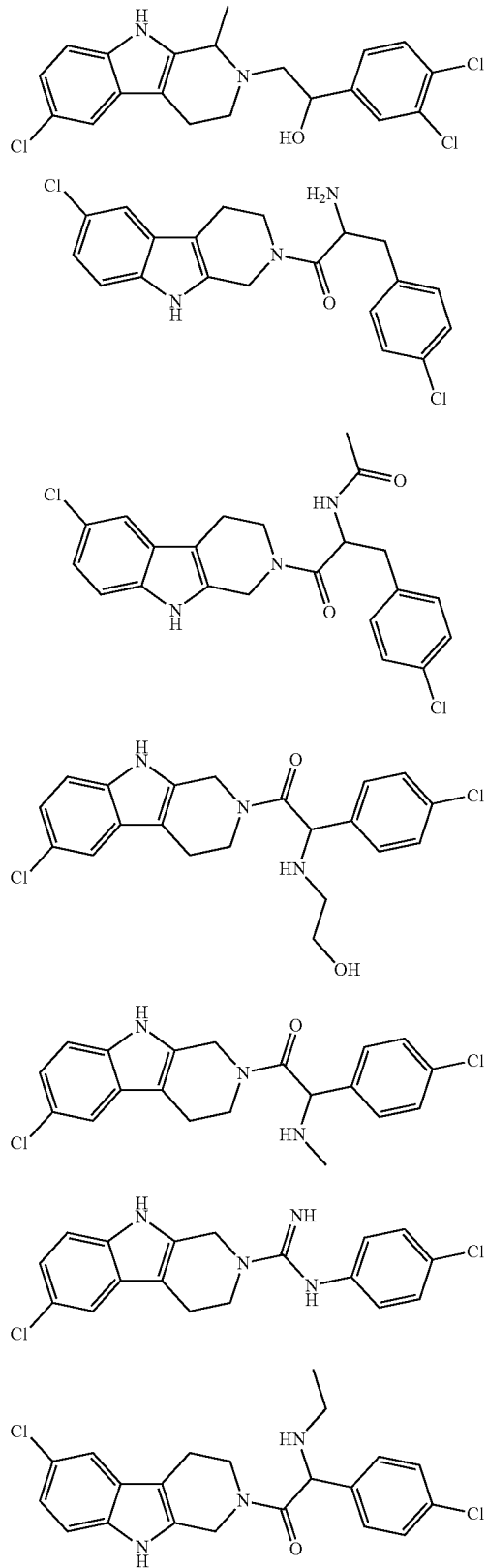

TABLE A-continued

Representative compounds of the invention (includes compounds shown below as well as compounds disclosed in the Examples section that fall within the general structure of Formula I)

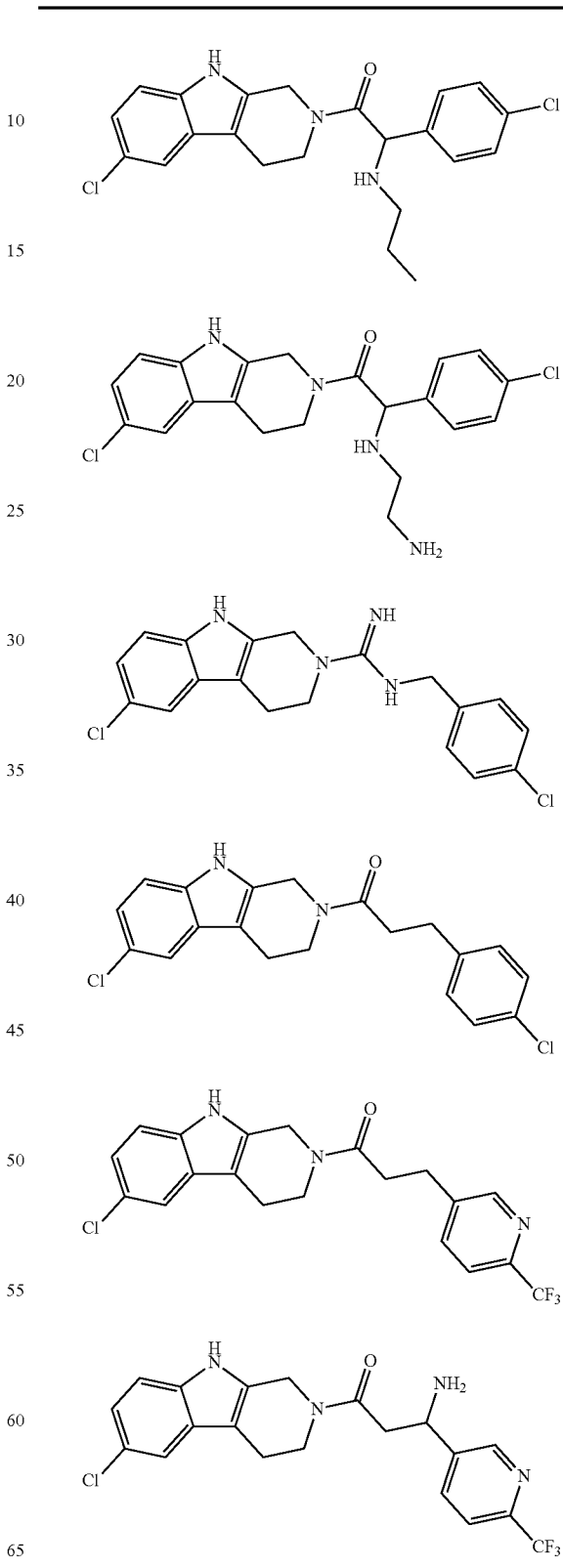

TABLE A-continued
Representative compounds of the invention (includes compounds shown below as well as compounds disclosed in the Examples section that fall within the general structure of Formula I)
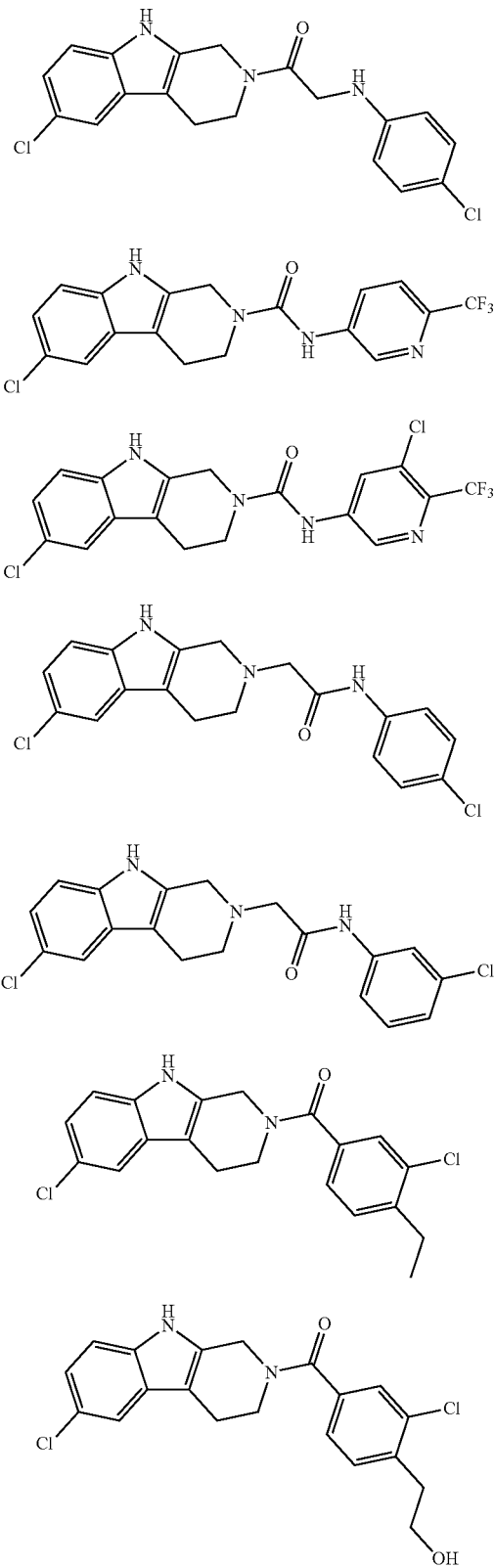
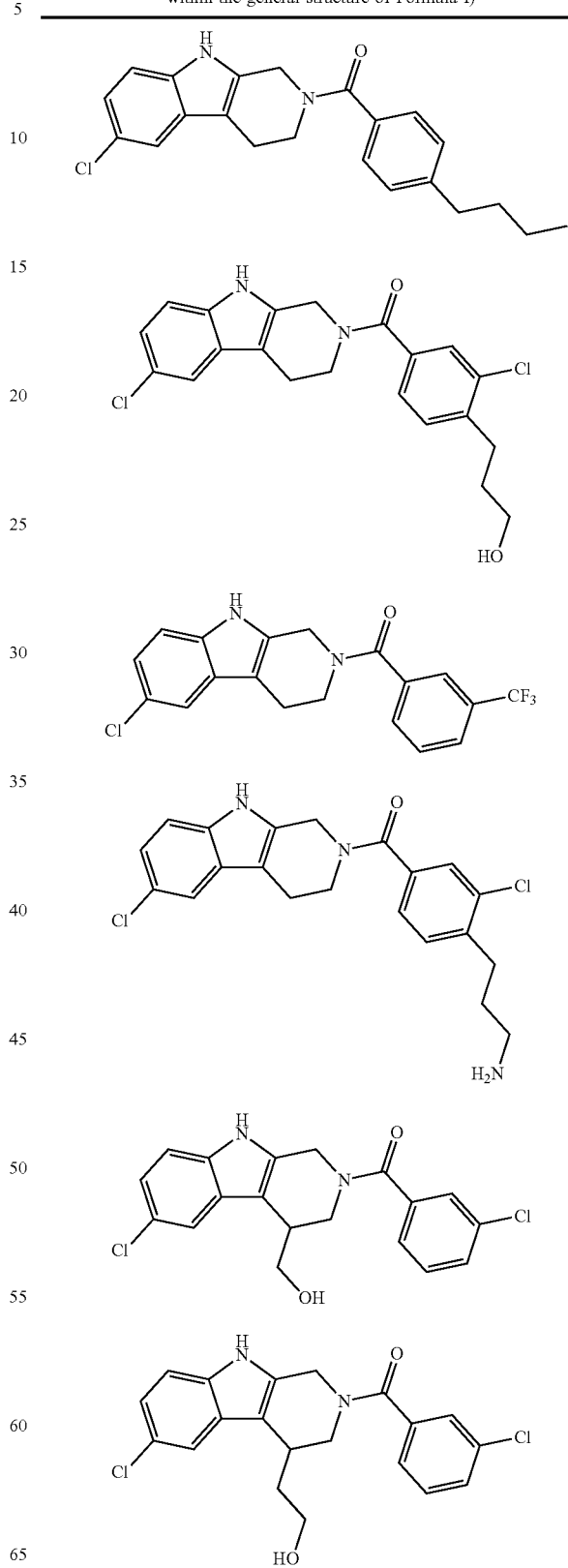

TABLE A-continued
Representative compounds of the invention (includes compounds shown below as well as compounds disclosed in the Examples section that fall within the general structure of Formula I)
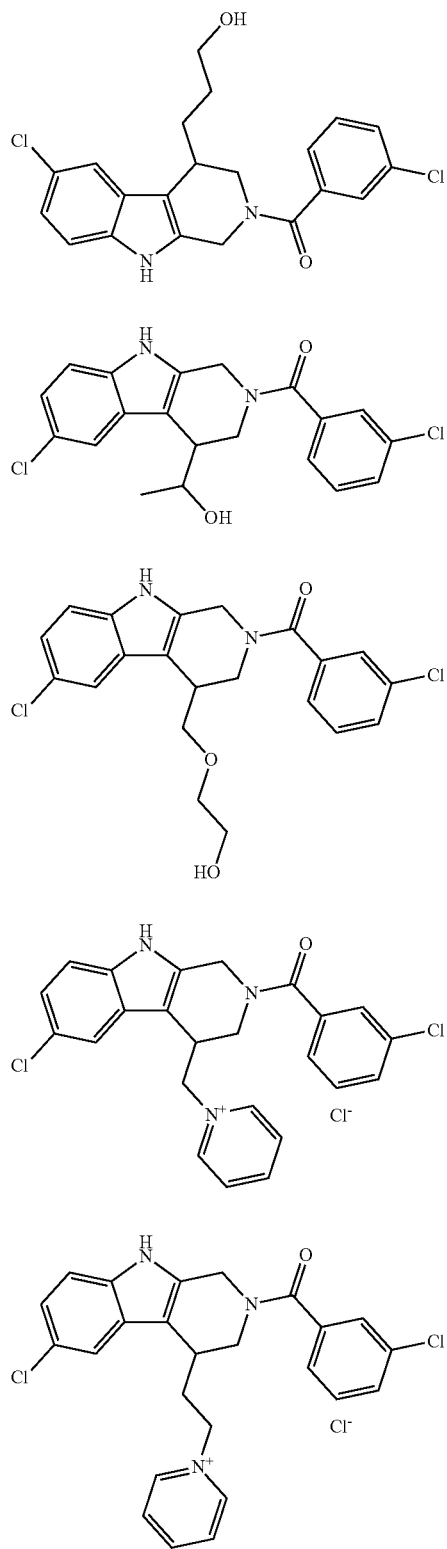
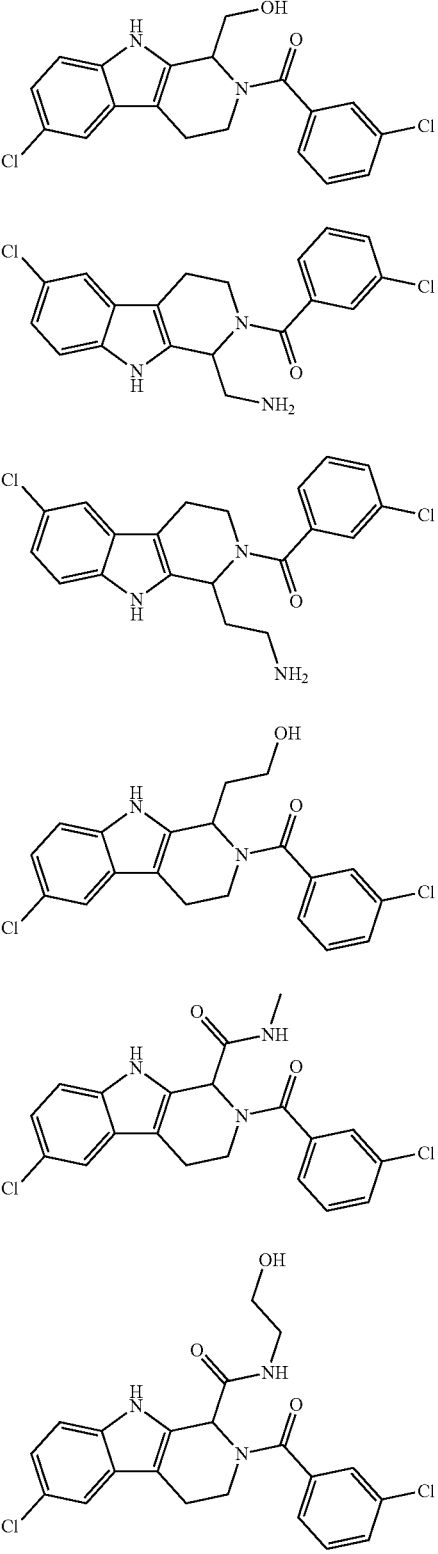

TABLE A-continued
Representative compounds of the invention (includes compounds shown below as well as compounds disclosed in the Examples section that fall within the general structure of Formula I)
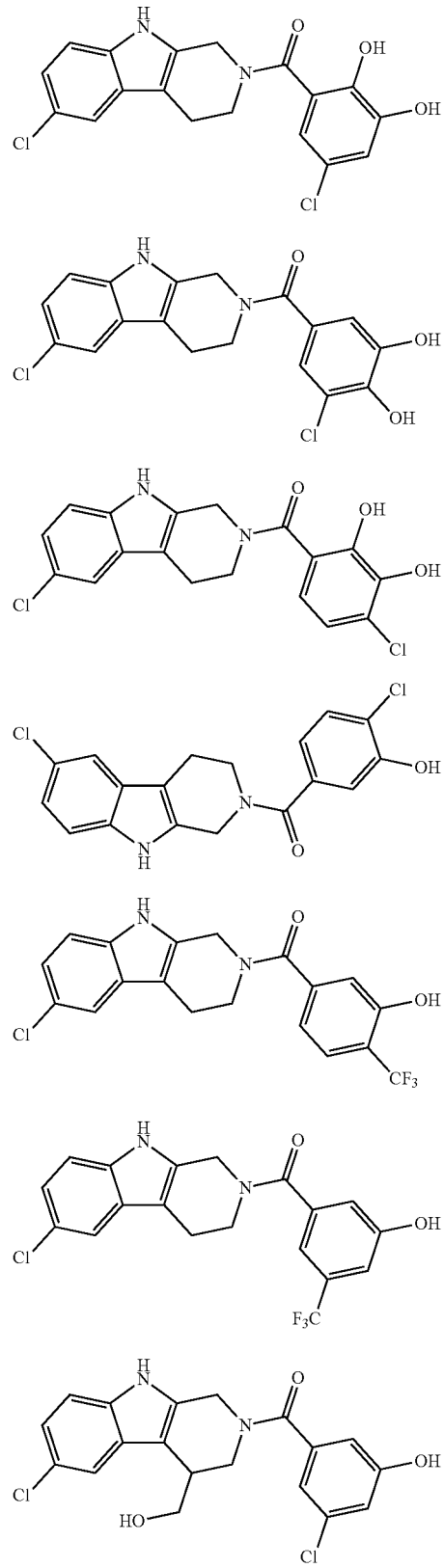
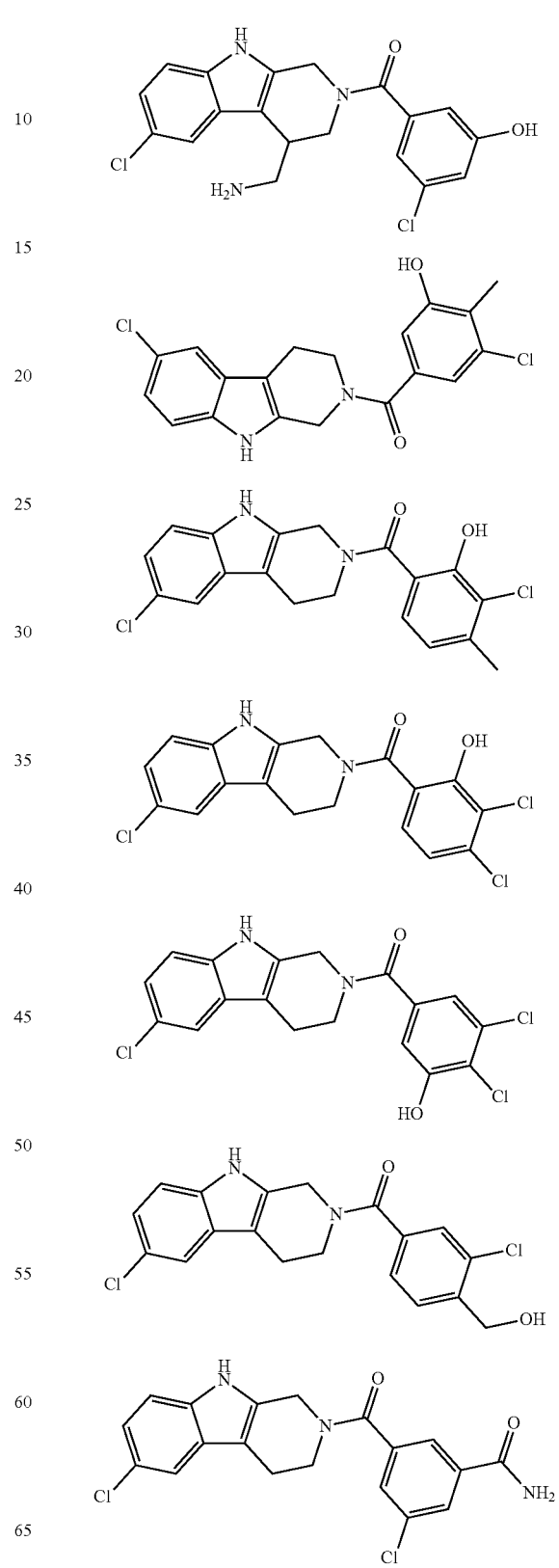

TABLE A-continued

Representative compounds of the invention (includes compounds shown below as well as compounds disclosed in the Examples section that fall within the general structure of Formula I)

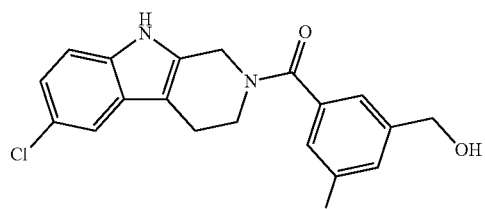

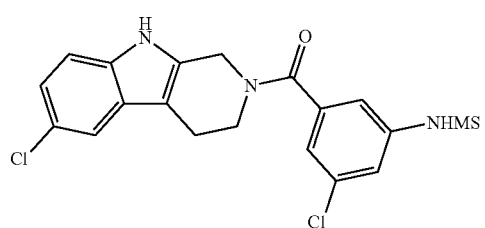

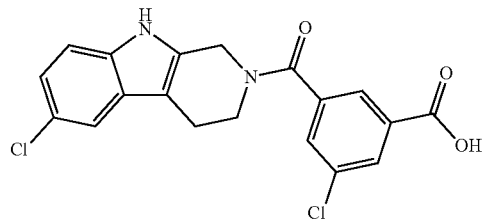 [SMILES: O=C(O)c1cc(Cl)cc(C(=O)N2CCc3c([nH]c4ccc(Cl)cc34)C2)c1]

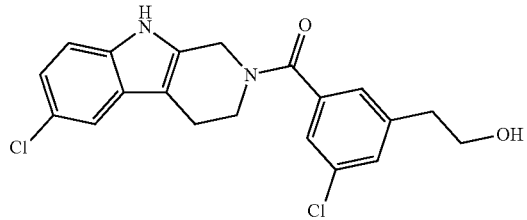 [SMILES: O=C(c1cc(Cl)cc(CCO)c1)N1CCc2c([nH]c3ccc(Cl)cc23)C1]

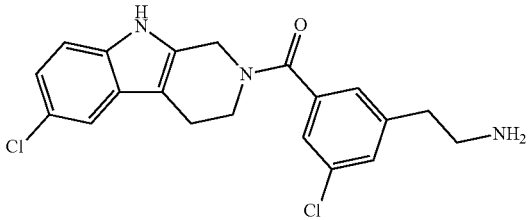 [SMILES: NCCc1cc(Cl)cc(C(=O)N2CCc3c([nH]c4ccc(Cl)cc34)C2)c1]

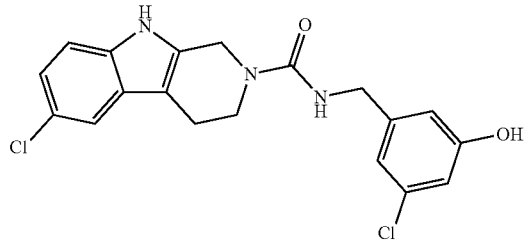 [SMILES: O=C(NCc1cc(O)cc(Cl)c1)N1CCc2c([nH]c3ccc(Cl)cc23)C1]

TABLE A-continued

Representative compounds of the invention (includes compounds shown below as well as compounds disclosed in the Examples section that fall within the general structure of Formula I)

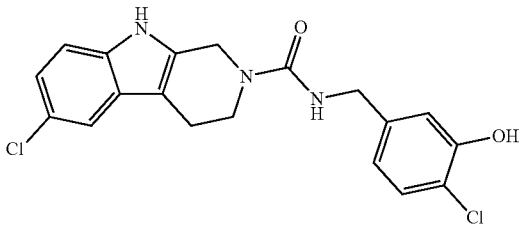 [SMILES: O=C(NCc1ccc(Cl)c(O)c1)N1CCc2c([nH]c3ccc(Cl)cc23)C1]

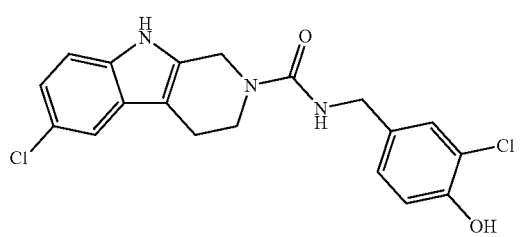 [SMILES: O=C(NCc1ccc(O)c(Cl)c1)N1CCc2c([nH]c3ccc(Cl)cc23)C1]

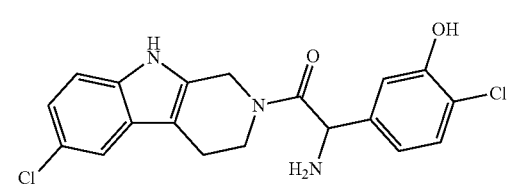 [SMILES: NC(C(=O)N1CCc2c([nH]c3ccc(Cl)cc23)C1)c1ccc(Cl)c(O)c1]

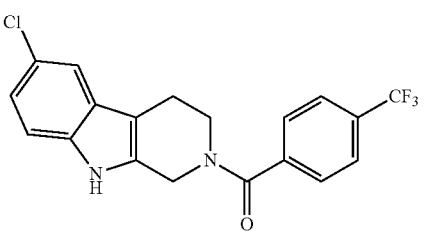 [SMILES: O=C(c1ccc(C(F)(F)F)cc1)N1CCc2c([nH]c3ccc(Cl)cc23)C1]

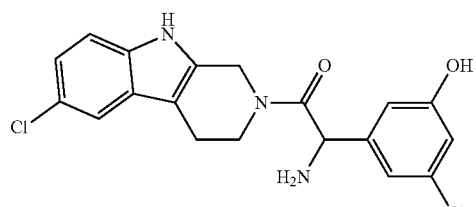

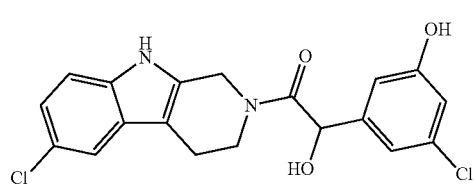 [SMILES: O=C(C(O)c1cc(O)cc(Cl)c1)N1CCc2c([nH]c3ccc(Cl)cc23)C1]

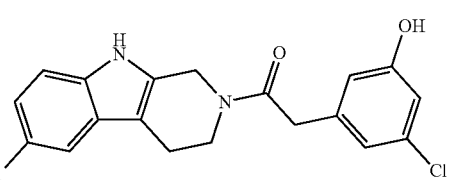

TABLE A-continued
Representative compounds of the invention (includes compounds shown below as well as compounds disclosed in the Examples section that fall within the general structure of Formula I)
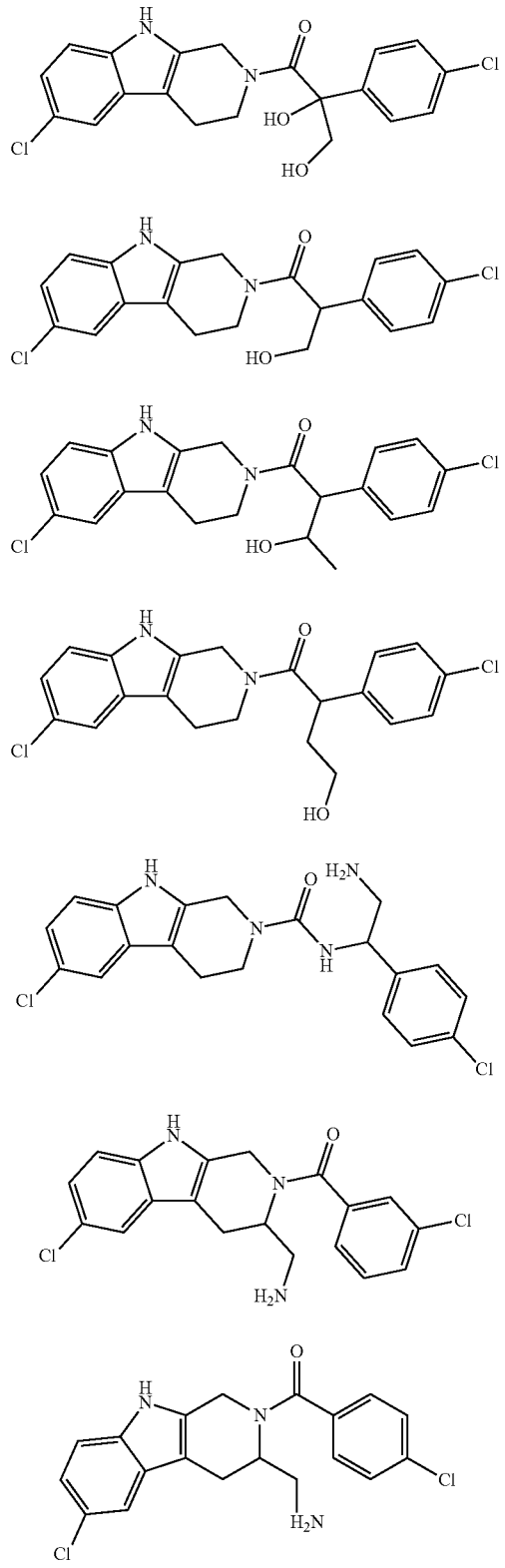
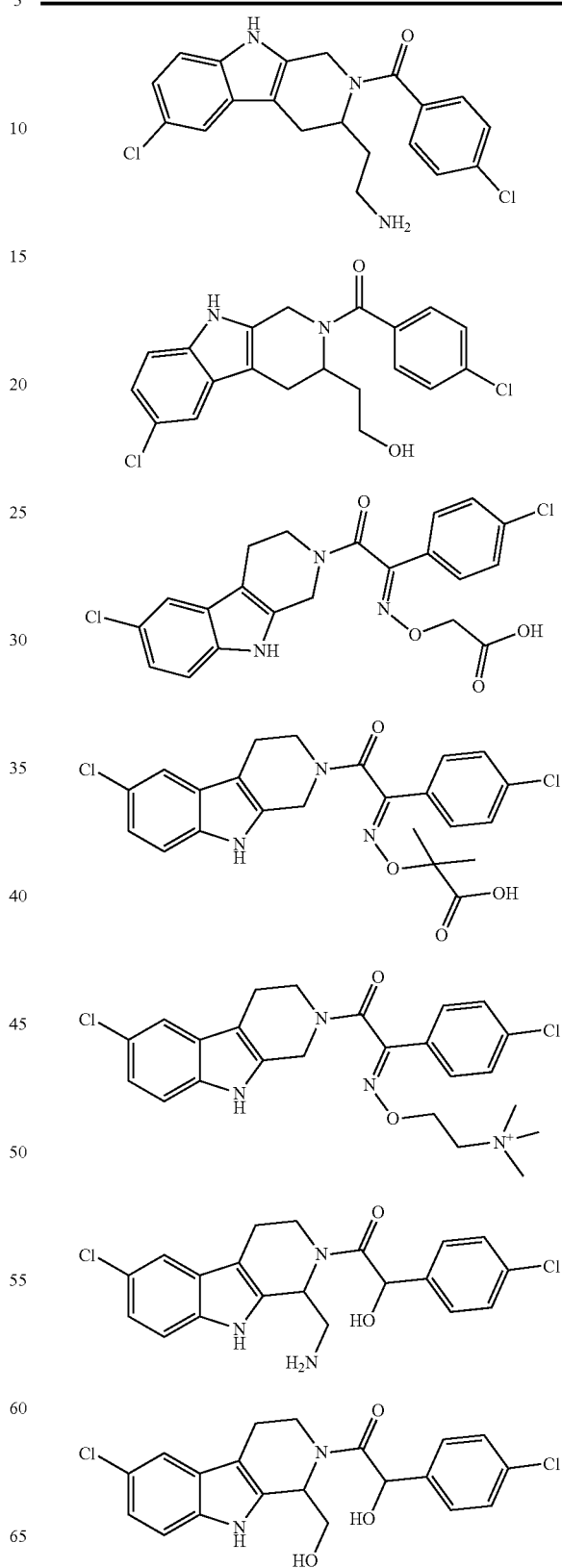

TABLE A-continued
Representative compounds of the invention (includes compounds shown below as well as compounds disclosed in the Examples section that fall within the general structure of Formula I)
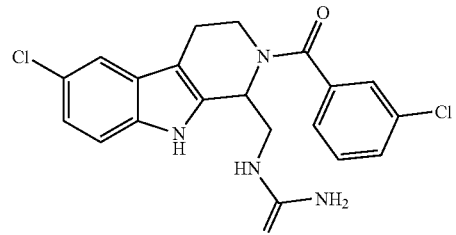
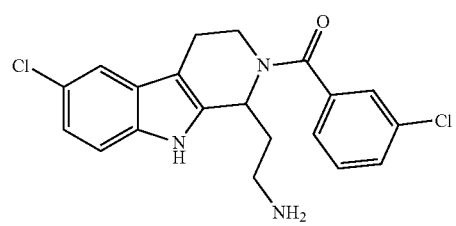 [SMILES: NCCC1c2[nH]c3ccc(Cl)cc3c2CCN1C(=O)c1cccc(Cl)c1]
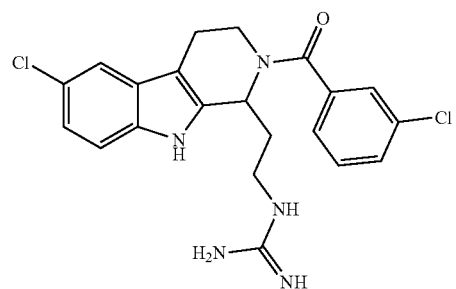 [SMILES: N=C(N)NCCC1c2[nH]c3ccc(Cl)cc3c2CCN1C(=O)c1cccc(Cl)c1]
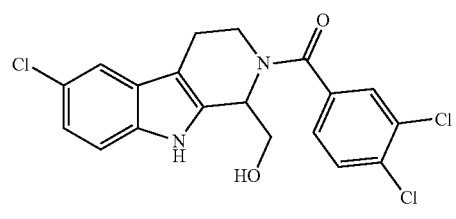 [SMILES: O=C(c1ccc(Cl)c(Cl)c1)N1CCc2c([nH]c3ccc(Cl)cc23)C1CO]
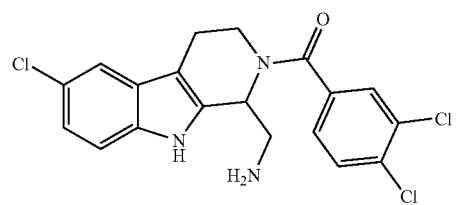 [SMILES: NCC1c2[nH]c3ccc(Cl)cc3c2CCN1C(=O)c1ccc(Cl)c(Cl)c1]
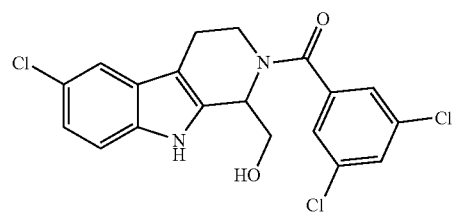 [SMILES: O=C(c1cc(Cl)cc(Cl)c1)N1CCc2c([nH]c3ccc(Cl)cc23)C1CO]
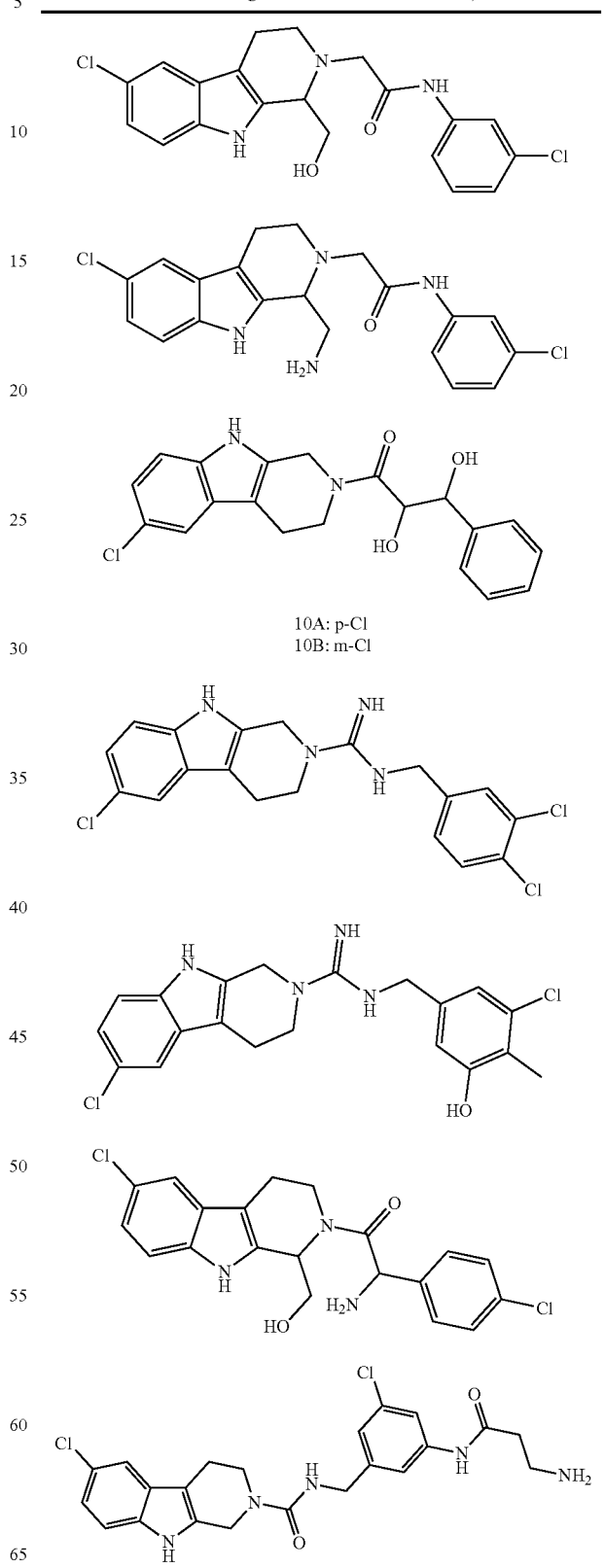
10A: p-Cl
10B: m-Cl TABLE A-continued
Representative compounds of the invention (includes compounds shown below as well as compounds disclosed in the Examples section that fall within the general structure of Formula I)
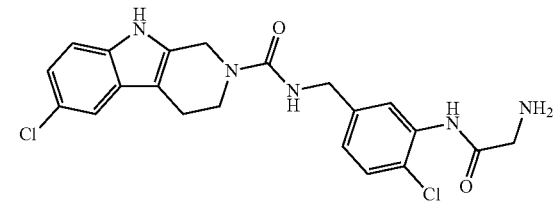 [SMILES: NCC(=O)Nc1cc(CNC(=O)N2CCc3c([nH]c4ccc(Cl)cc34)C2)ccc1Cl]
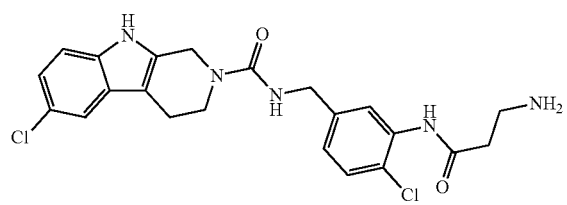 [SMILES: NCCC(=O)Nc1cc(CNC(=O)N2CCc3c([nH]c4ccc(Cl)cc34)C2)ccc1Cl]
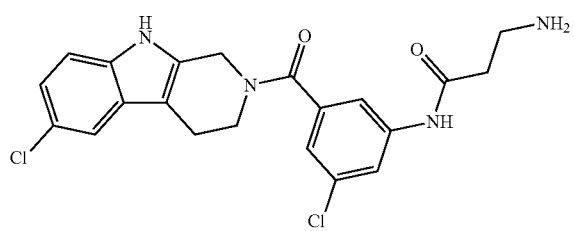 [SMILES: NCCC(=O)Nc1cc(Cl)cc(C(=O)N2CCc3c([nH]c4ccc(Cl)cc34)C2)c1]
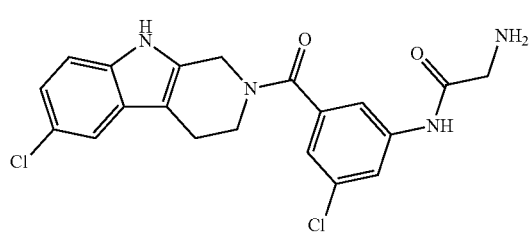 [SMILES: NCC(=O)Nc1cc(Cl)cc(C(=O)N2CCc3c([nH]c4ccc(Cl)cc34)C2)c1]
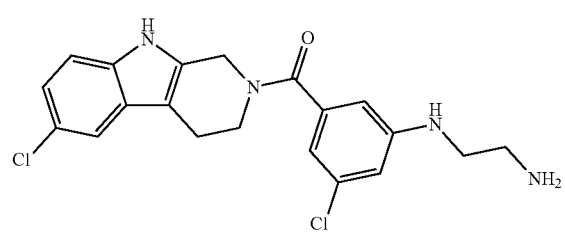 [SMILES: NCCNc1cc(Cl)cc(C(=O)N2CCc3c([nH]c4ccc(Cl)cc34)C2)c1]
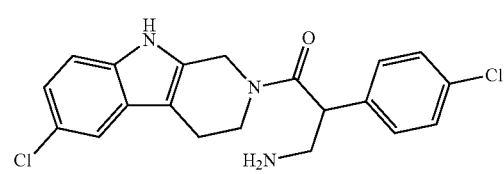 [SMILES: NCC(C(=O)N1CCc2c([nH]c3ccc(Cl)cc23)C1)c1ccc(Cl)cc1]
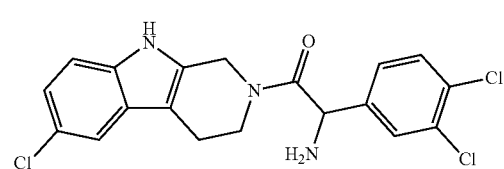
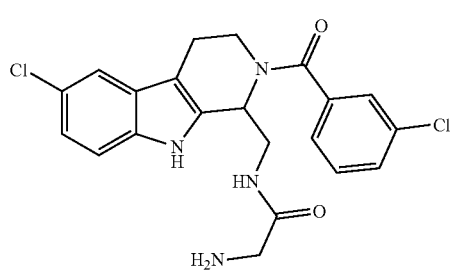 [SMILES: NCC(=O)NCC1c2[nH]c3ccc(Cl)cc3c2CCN1C(=O)c1cccc(Cl)c1]
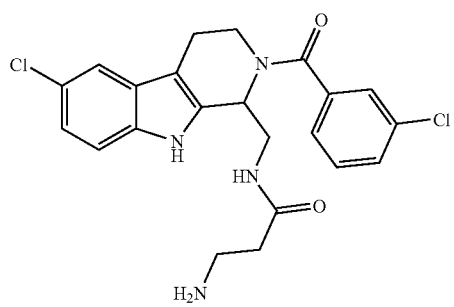 [SMILES: NCCC(=O)NCC1c2[nH]c3ccc(Cl)cc3c2CCN1C(=O)c1cccc(Cl)c1]
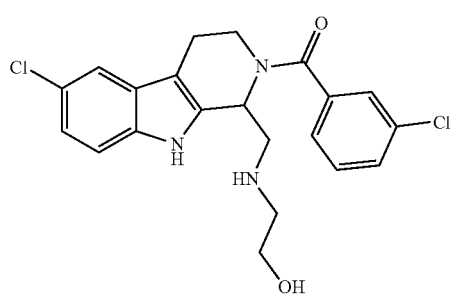 [SMILES: O=C(c1cccc(Cl)c1)N1CCc2c([nH]c3ccc(Cl)cc23)C1CNCCO]
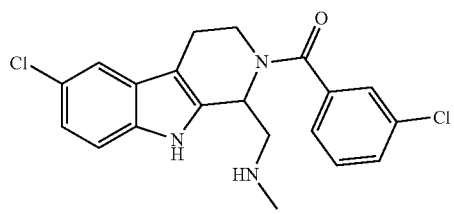 [SMILES: CNCC1c2[nH]c3ccc(Cl)cc3c2CCN1C(=O)c1cccc(Cl)c1]

TABLE A-continued

Representative compounds of the invention (includes compounds shown below as well as compounds disclosed in the Examples section that fall within the general structure of Formula I)

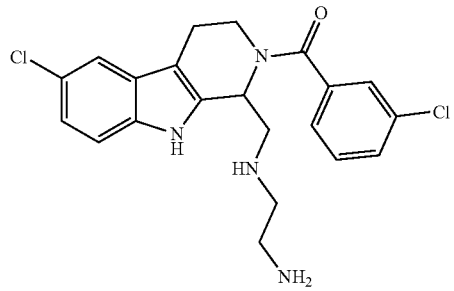 [SMILES: NCCNCC1c2[nH]c3ccc(Cl)cc3c2CCN1C(=O)c1cccc(Cl)c1]

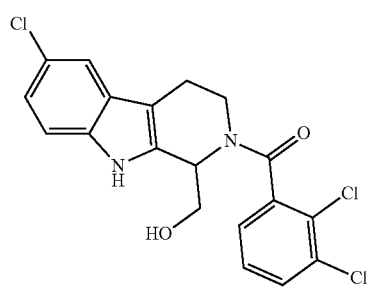 [SMILES: O=C(c1cccc(Cl)c1Cl)N1CCc2c([nH]c3ccc(Cl)cc23)C1CO]

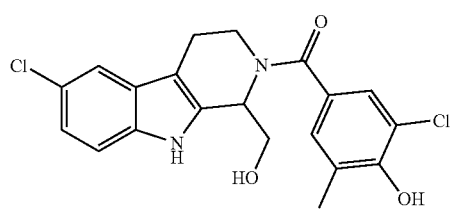 [SMILES: Cc1cc(C(=O)N2CCc3c([nH]c4ccc(Cl)cc34)C2CO)cc(Cl)c1O]

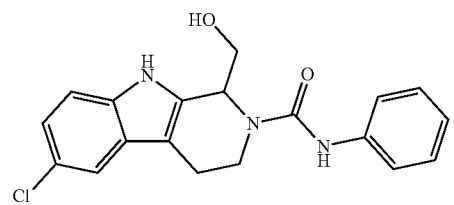

m-Cl and p-Cl

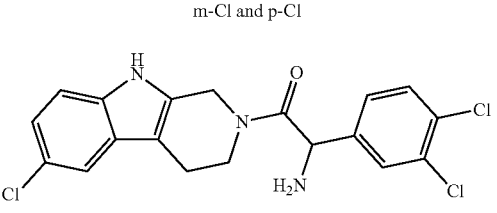

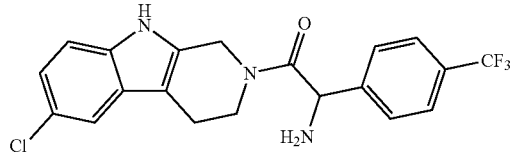

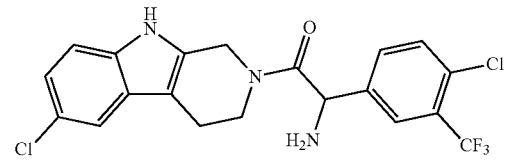 [SMILES: NC(C(=O)N1CCc2c([nH]c3ccc(Cl)cc23)C1)c1ccc(Cl)c(Cl)c1]

TABLE A-continued

Representative compounds of the invention (includes compounds shown below as well as compounds disclosed in the Examples section that fall within the general structure of Formula I)

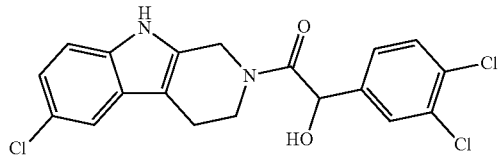 [SMILES: O=C(C(O)c1ccc(Cl)c(Cl)c1)N1CCc2c([nH]c3ccc(Cl)cc23)C1]

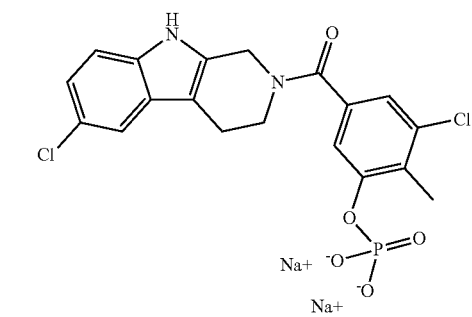

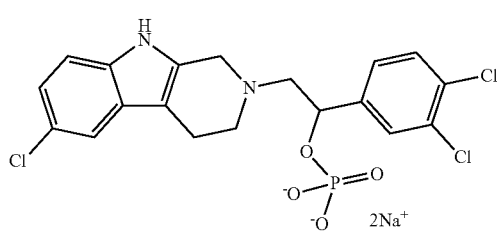

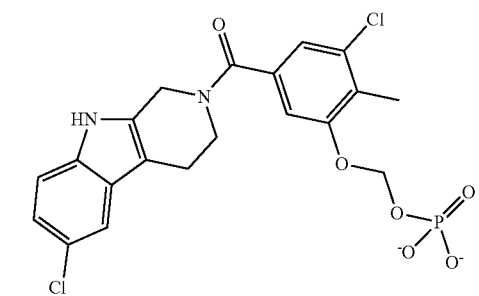

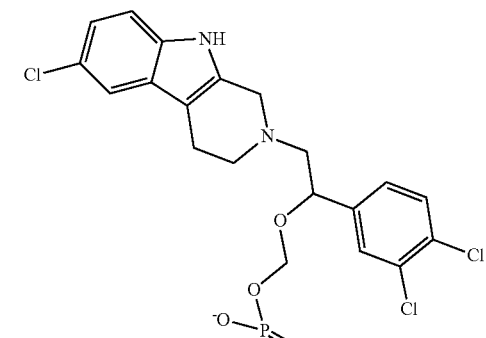

TABLE A-continued

Representative compounds of the invention (includes compounds shown below as well as compounds disclosed in the Examples section that fall within the general structure of Formula I)

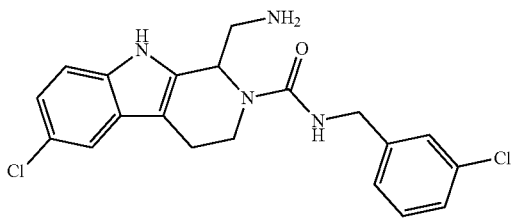 [SMILES: NCC1c2[nH]c3ccc(Cl)cc3c2CCN1C(=O)NCc1cccc(Cl)c1]

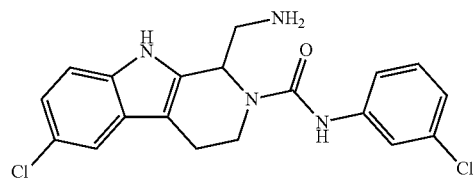 [SMILES: NCC1c2[nH]c3ccc(Cl)cc3c2CCN1C(=O)Nc1cccc(Cl)c1]

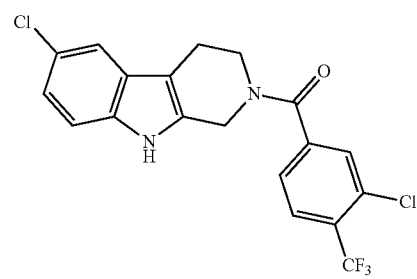 [SMILES: O=C(c1ccc(C(F)(F)F)c(Cl)c1)N1CCc2c([nH]c3ccc(Cl)cc23)C1]

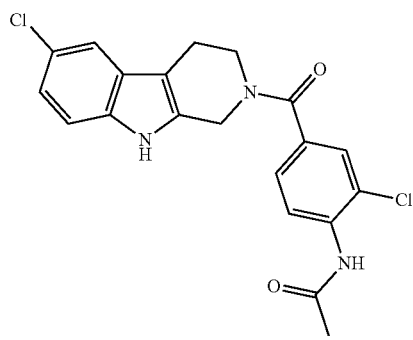 [SMILES: CC(=O)Nc1ccc(C(=O)N2CCc3c([nH]c4ccc(Cl)cc34)C2)cc1Cl]

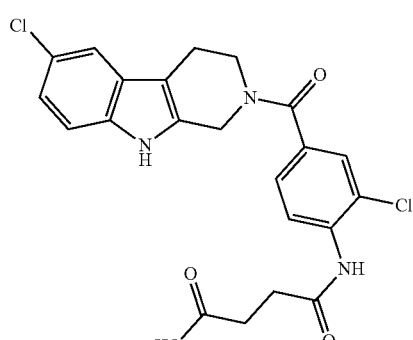

TABLE A-continued

Representative compounds of the invention (includes compounds shown below as well as compounds disclosed in the Examples section that fall within the general structure of Formula I)

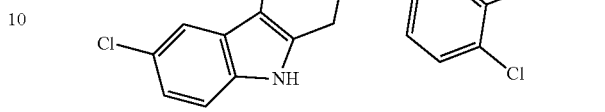

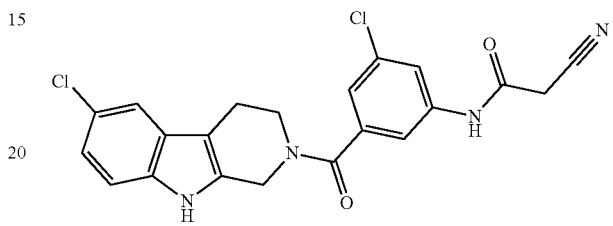

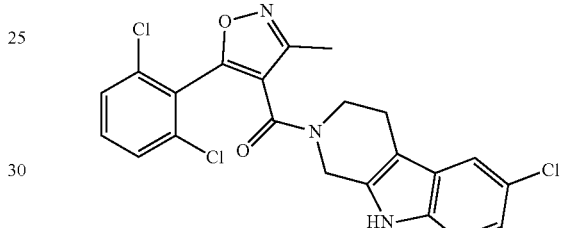

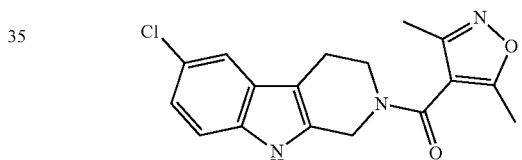

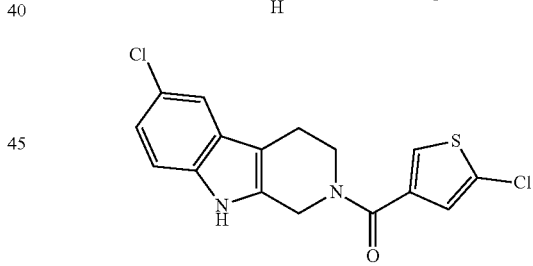

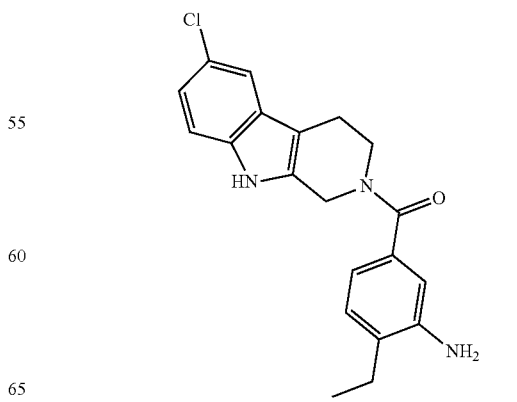

TABLE A-continued
Representative compounds of the invention (includes compounds shown below as well as compounds disclosed in the Examples section that fall within the general structure of Formula I)
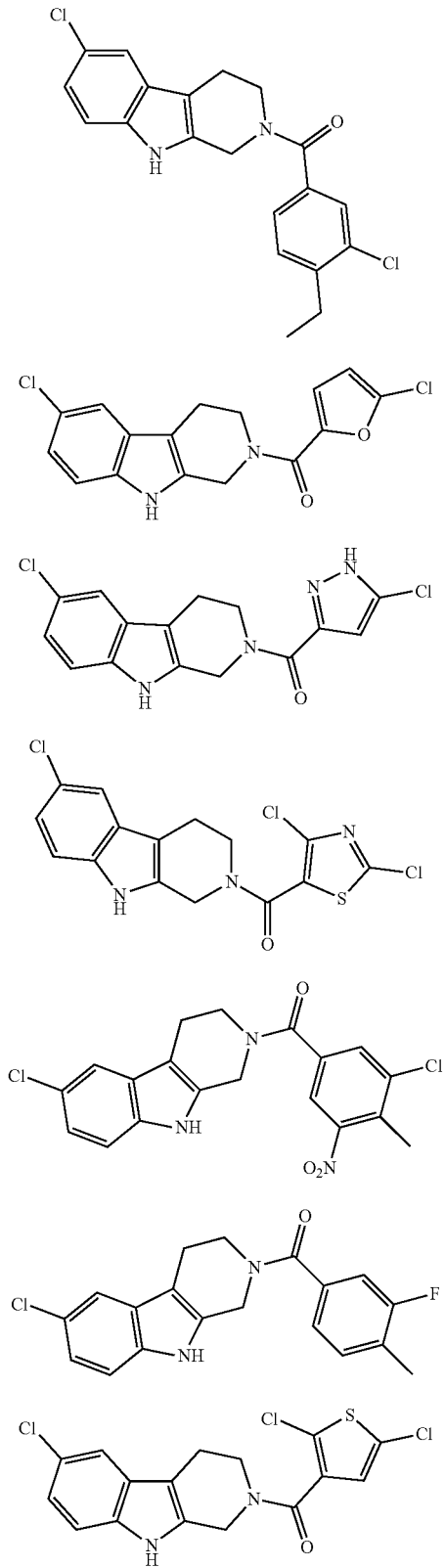
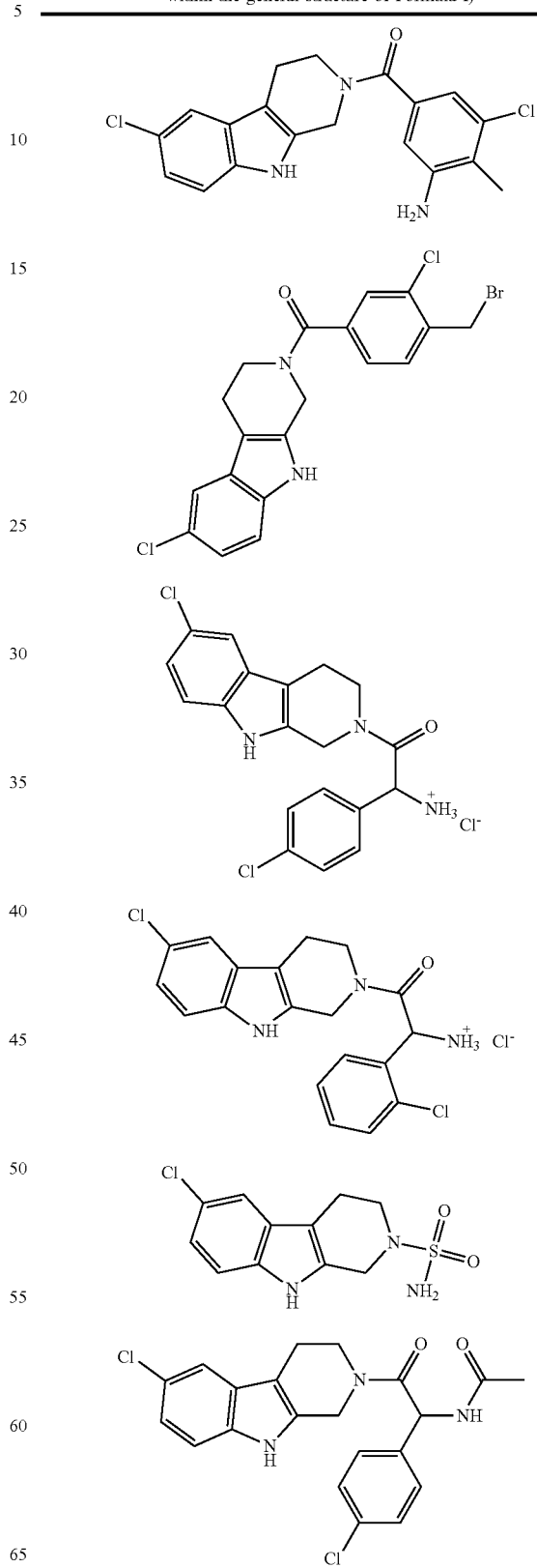

TABLE A-continued
Representative compounds of the invention (includes compounds shown below as well as compounds disclosed in the Examples section that fall within the general structure of Formula I)
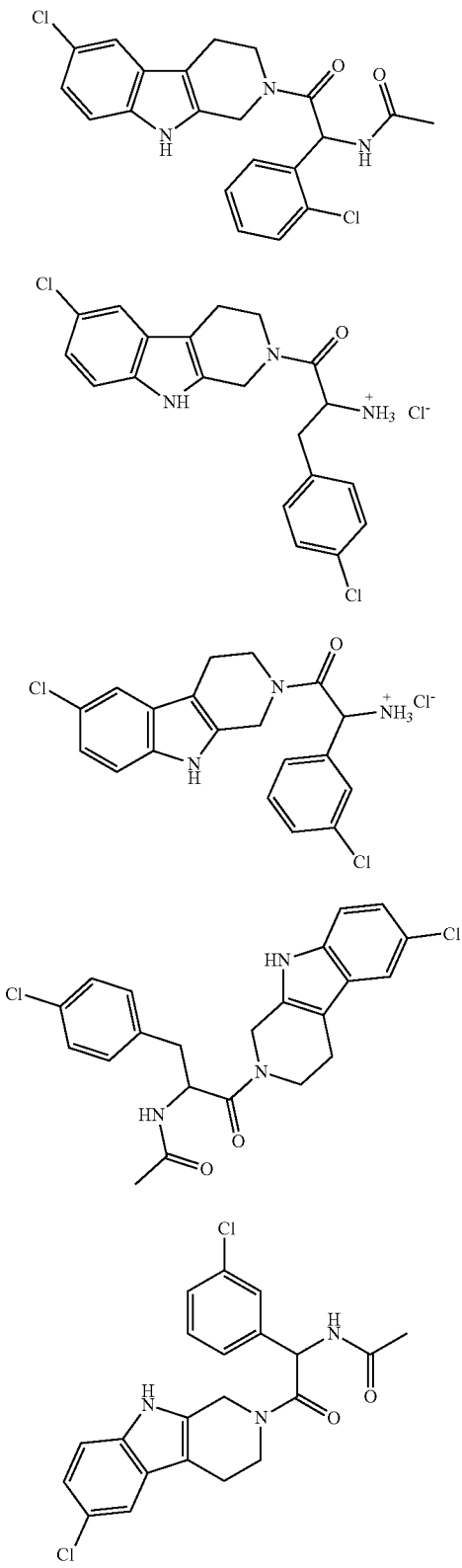
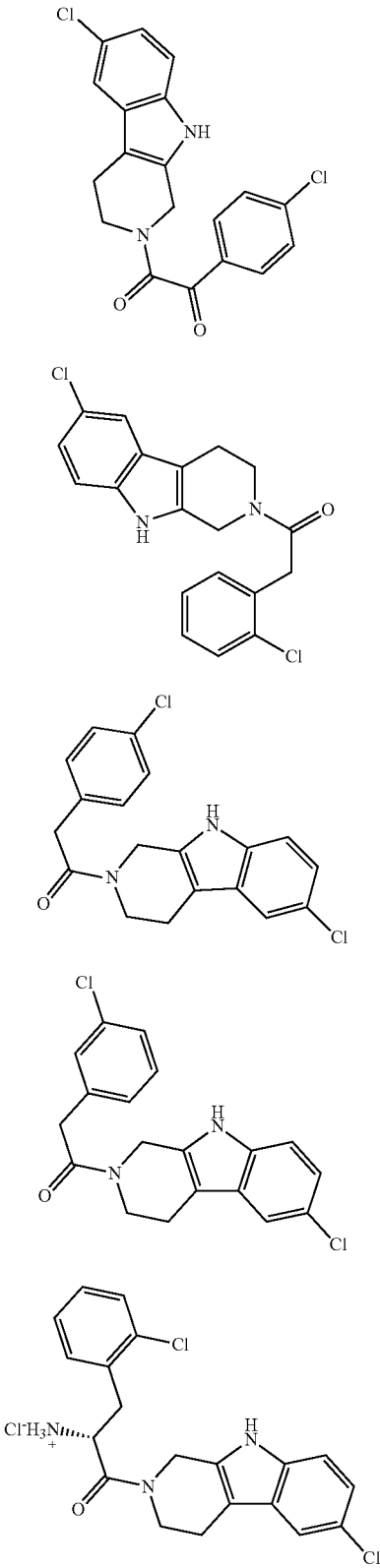

TABLE A-continued

Representative compounds of the invention (includes compounds shown below as well as compounds disclosed in the Examples section that fall within the general structure of Formula I)

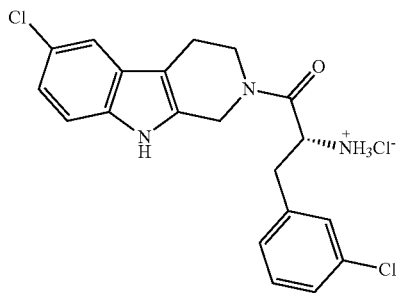

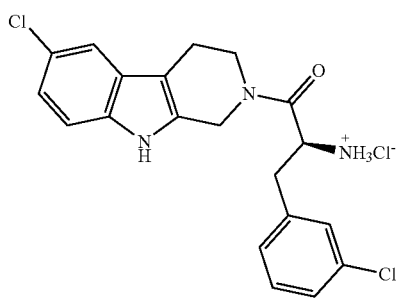

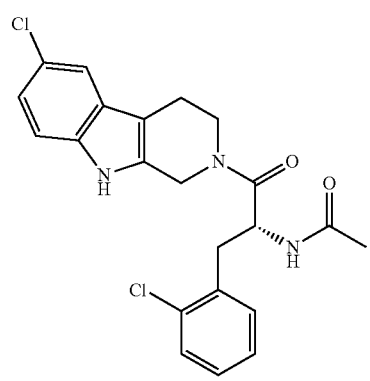 [SMILES: CC(=O)N[C@H](Cc1ccccc1Cl)C(=O)N1CCc2c([nH]c3ccc(Cl)cc23)C1]

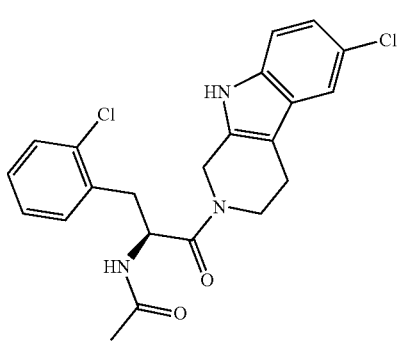 [SMILES: CC(=O)N[C@@H](Cc1ccccc1Cl)C(=O)N1CCc2c([nH]c3ccc(Cl)cc23)C1]

TABLE A-continued

Representative compounds of the invention (includes compounds shown below as well as compounds disclosed in the Examples section that fall within the general structure of Formula I)

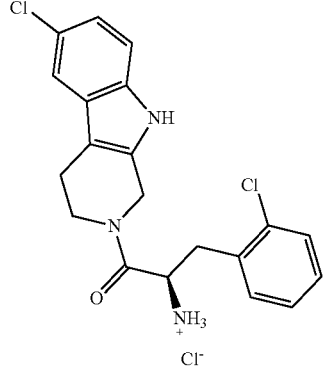 [SMILES: N[C@H](Cc1ccccc1Cl)C(=O)N1CCc2c([nH]c3ccc(Cl)cc23)C1 ; [Cl-]]

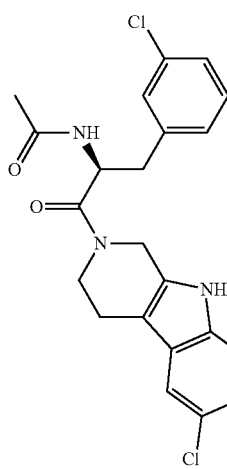

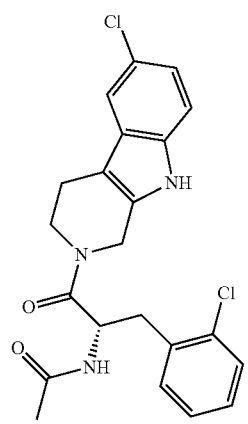 [SMILES: CC(=O)N[C@@H](Cc1ccccc1Cl)C(=O)N1CCc2c([nH]c3ccc(Cl)cc23)C1]

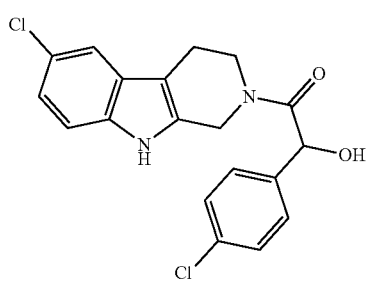 [SMILES: O=C(C(O)c1ccc(Cl)cc1)N1CCc2c([nH]c3ccc(Cl)cc23)C1]

TABLE A-continued

Representative compounds of the invention (includes compounds shown below as well as compounds disclosed in the Examples section that fall within the general structure of Formula I)

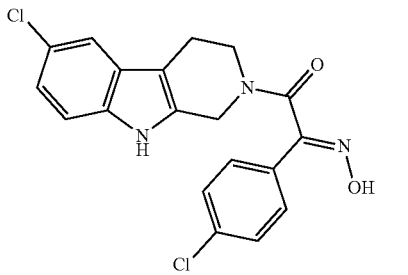 [SMILES: O=C(/C(=N/O)c1ccc(Cl)cc1)N1CCc2c([nH]c3ccc(Cl)cc23)C1]

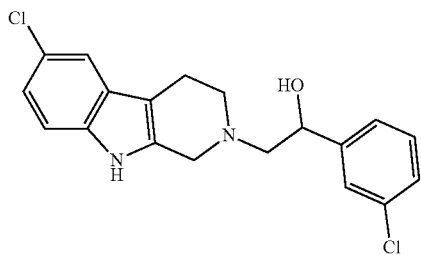 [SMILES: OC(CN1CCc2c([nH]c3ccc(Cl)cc23)C1)c1cccc(Cl)c1]

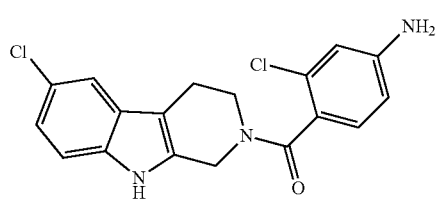 [SMILES: Nc1ccc(C(=O)N2CCc3c([nH]c4ccc(Cl)cc34)C2)c(Cl)c1]

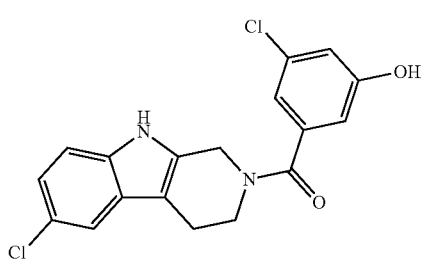 [SMILES: O=C(c1cc(O)cc(Cl)c1)N1CCc2c([nH]c3ccc(Cl)cc23)C1]

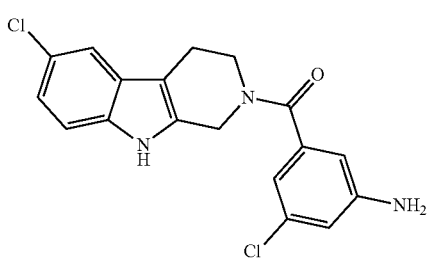 [SMILES: Nc1cc(Cl)cc(C(=O)N2CCc3c([nH]c4ccc(Cl)cc34)C2)c1]

TABLE A-continued

Representative compounds of the invention (includes compounds shown below as well as compounds disclosed in the Examples section that fall within the general structure of Formula I)

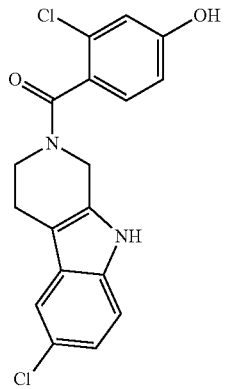 [SMILES: O=C(c1ccc(O)cc1Cl)N1CCc2c([nH]c3ccc(Cl)cc23)C1]

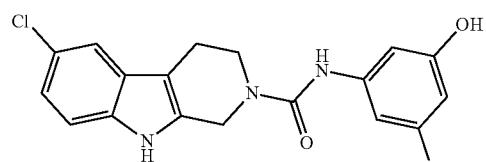

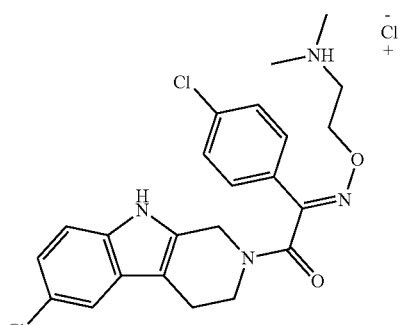

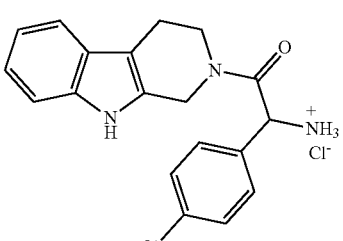

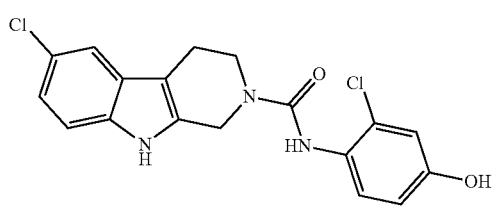 [SMILES: O=C(Nc1ccc(O)cc1Cl)N1CCc2c([nH]c3ccc(Cl)cc23)C1]

TABLE A-continued

Representative compounds of the invention (includes compounds shown below as well as compounds disclosed in the Examples section that fall within the general structure of Formula I)

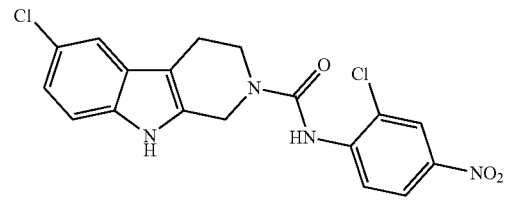 [SMILES: O=C(Nc1ccc([N+](=O)[O-])cc1Cl)N1CCc2c([nH]c3ccc(Cl)cc23)C1]

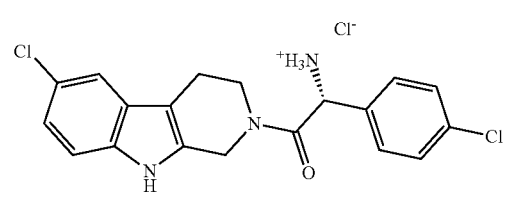 [SMILES: [Cl-] ; [NH3+][C@@H](C(=O)N1CCc2c([nH]c3ccc(Cl)cc23)C1)c1ccc(Cl)cc1]

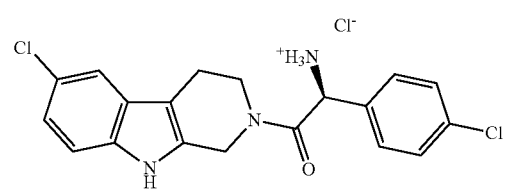 [SMILES: [Cl-] ; [NH3+][C@H](C(=O)N1CCc2c([nH]c3ccc(Cl)cc23)C1)c1ccc(Cl)cc1]

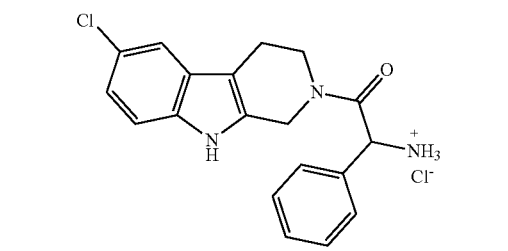 [SMILES: NC(C(=O)N1CCc2c([nH]c3ccc(Cl)cc23)C1)c1ccccc1 ; [Cl-]]

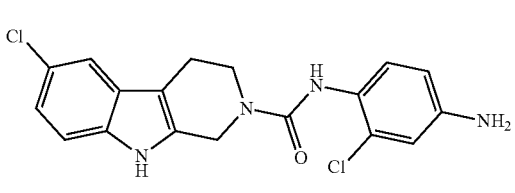 [SMILES: Nc1ccc(NC(=O)N2CCc3c([nH]c4ccc(Cl)cc34)C2)c(Cl)c1]

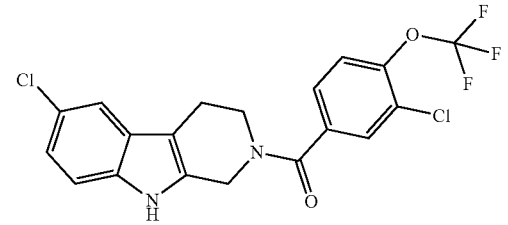 [SMILES: O=C(c1ccc(OC(F)(F)F)c(Cl)c1)N1CCc2c([nH]c3ccc(Cl)cc23)C1]

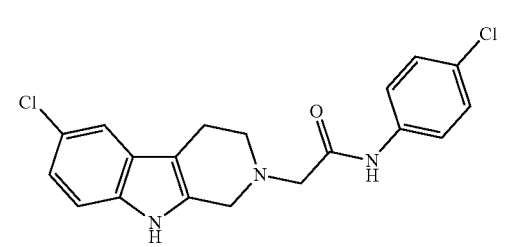 [SMILES: O=C(CN1CCc2c([nH]c3ccc(Cl)cc23)C1)Nc1ccc(Cl)cc1]

TABLE A-continued

Representative compounds of the invention (includes compounds shown below as well as compounds disclosed in the Examples section that fall within the general structure of Formula I)

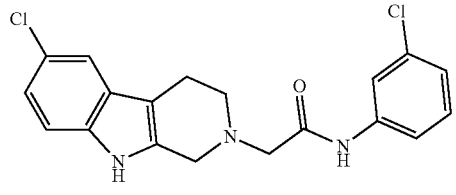 [SMILES: O=C(CN1CCc2c([nH]c3ccc(Cl)cc23)C1)Nc1cccc(Cl)c1]

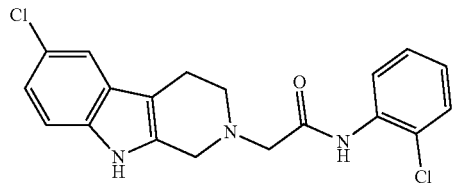 [SMILES: O=C(CN1CCc2c([nH]c3ccc(Cl)cc23)C1)Nc1ccccc1Cl]

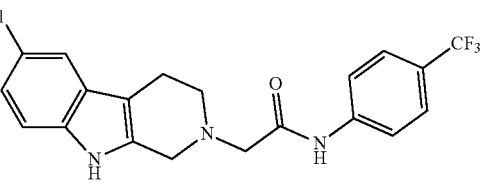

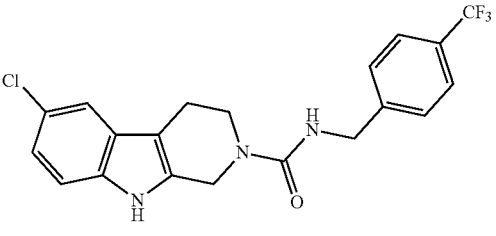 [SMILES: O=C(NCc1ccc(C(F)(F)F)cc1)N1CCc2c([nH]c3ccc(Cl)cc23)C1]

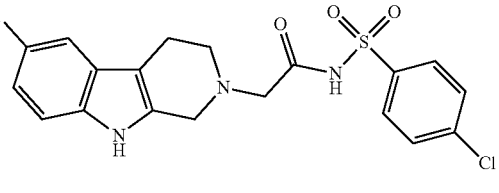

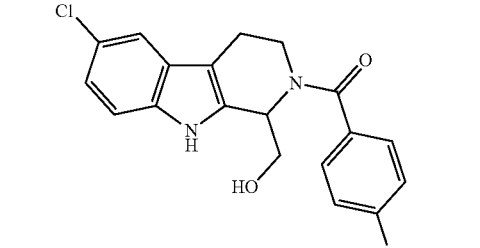 [SMILES: O=C(c1cccc(C(F)(F)F)c1)N1CCc2c([nH]c3ccc(Cl)cc23)C1CO]

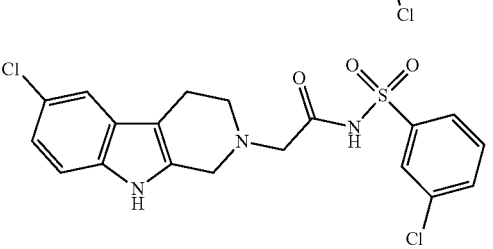

TABLE A-continued
Representative compounds of the invention (includes compounds shown below as well as compounds disclosed in the Examples section that fall within the general structure of Formula I)
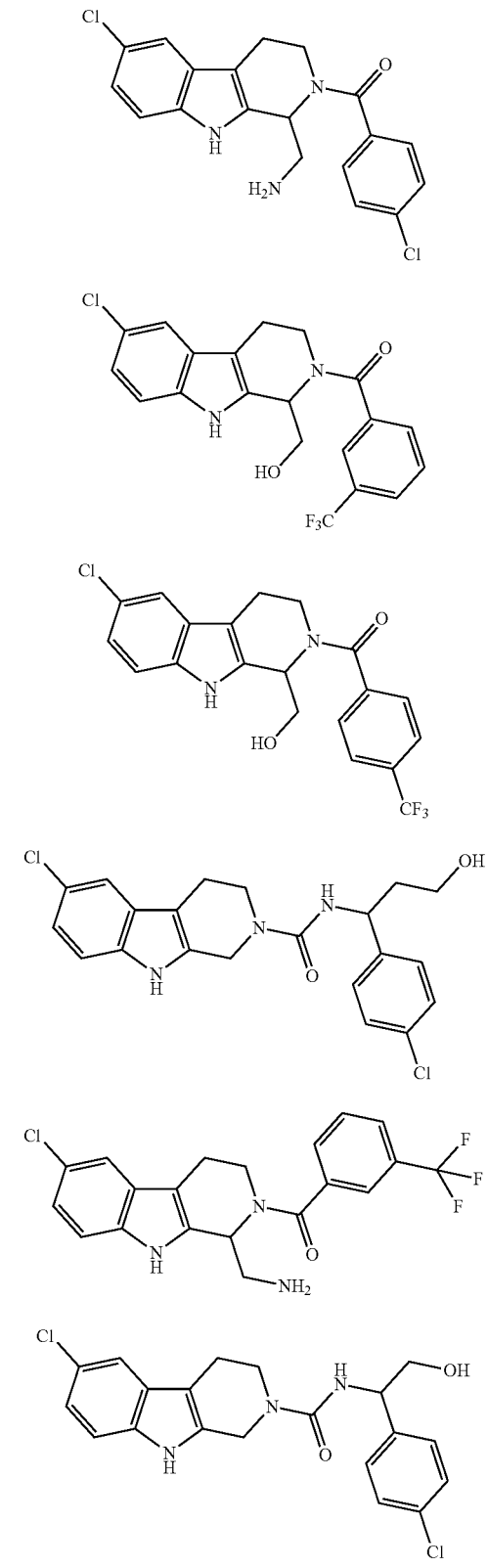
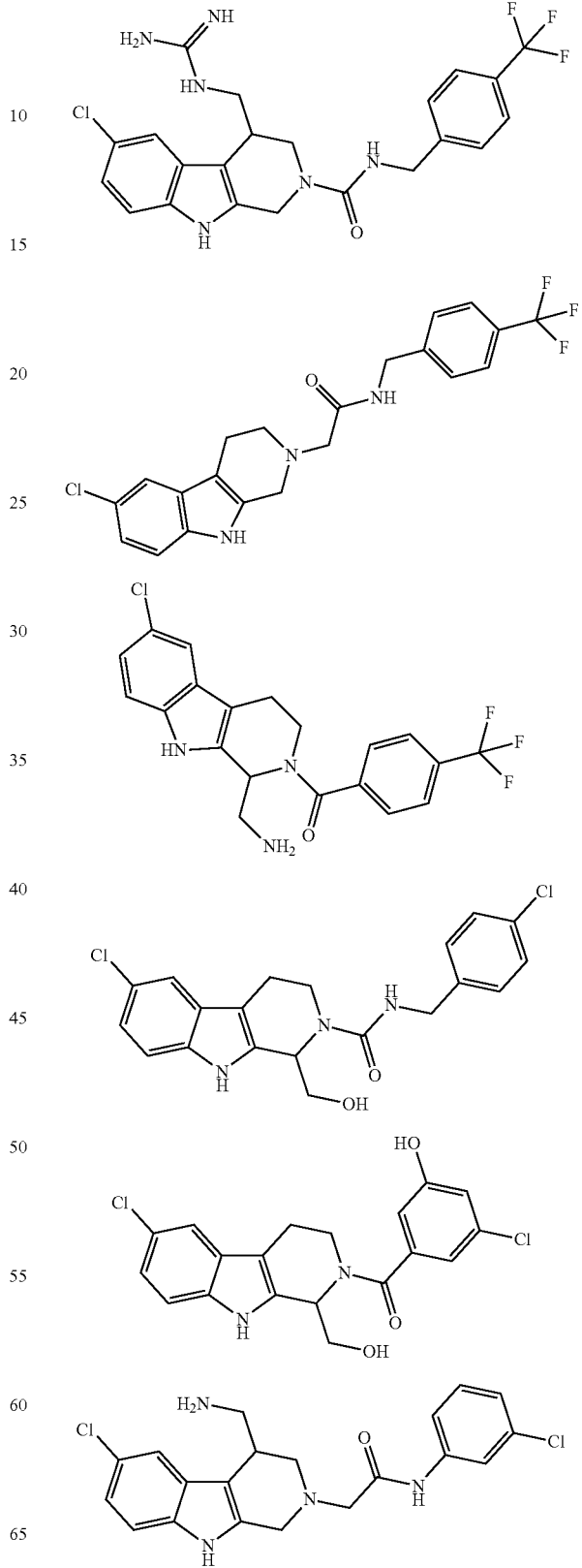

TABLE A-continued
Representative compounds of the invention (includes compounds shown below as well as compounds disclosed in the Examples section that fall within the general structure of Formula I)
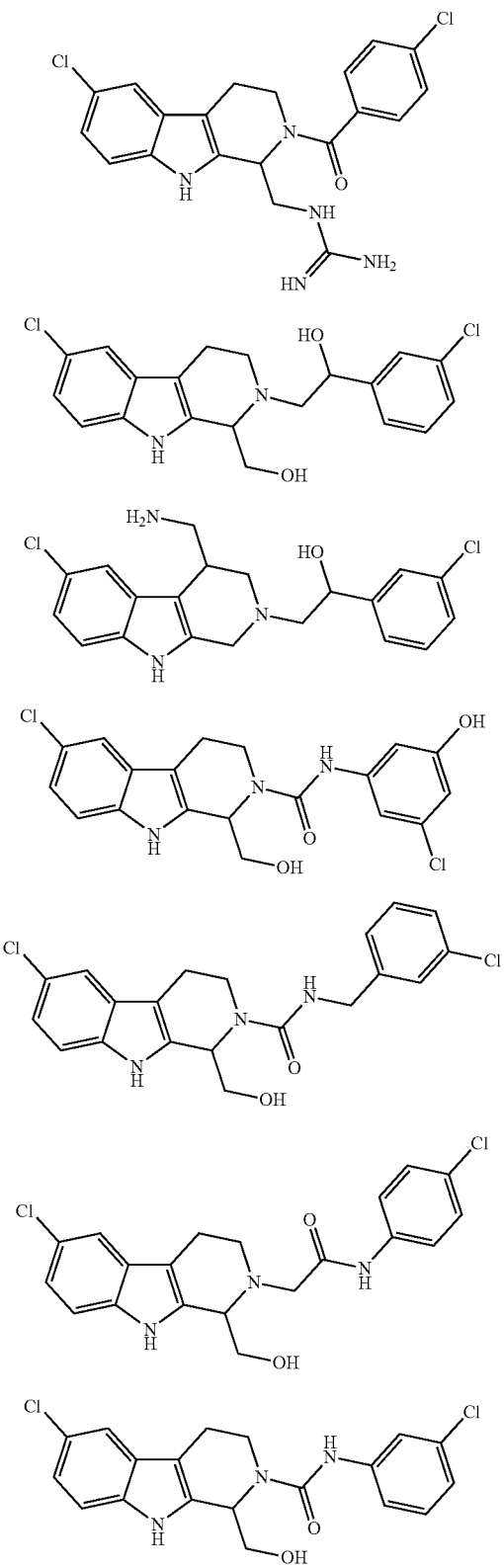
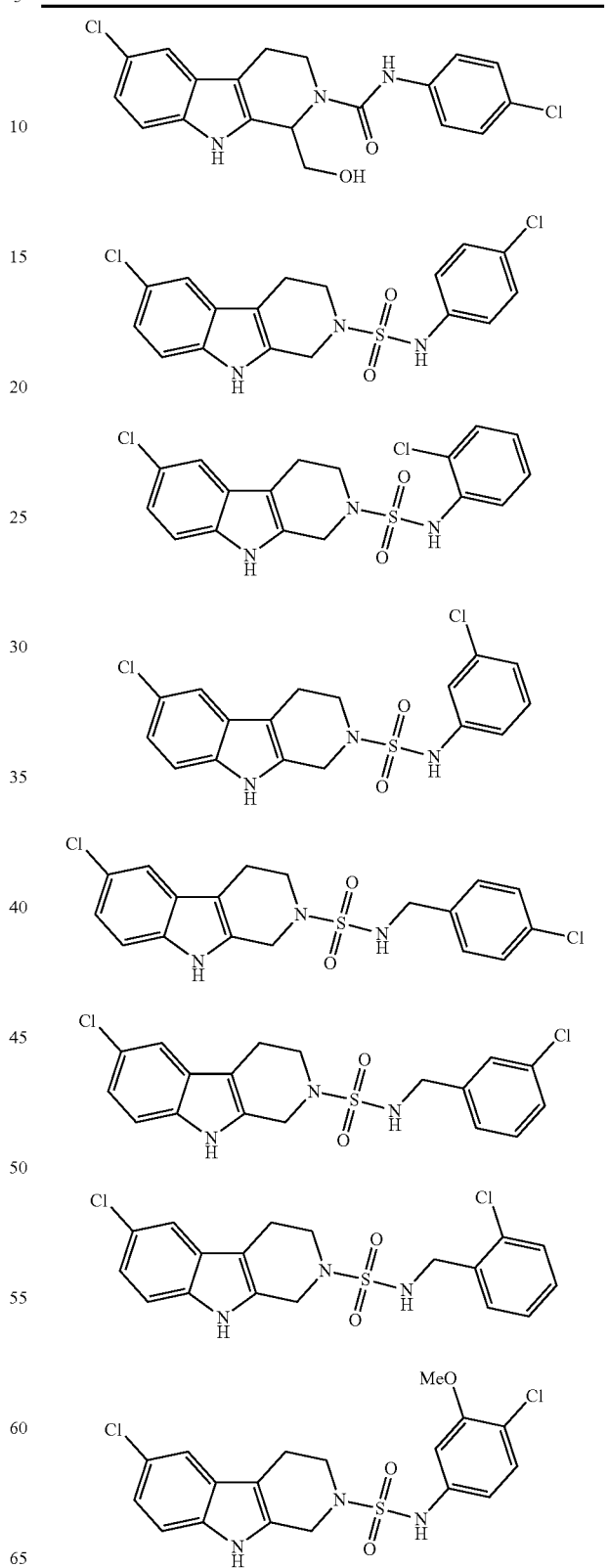

TABLE A-continued
Representative compounds of the invention (includes compounds shown below as well as compounds disclosed in the Examples section that fall within the general structure of Formula I)
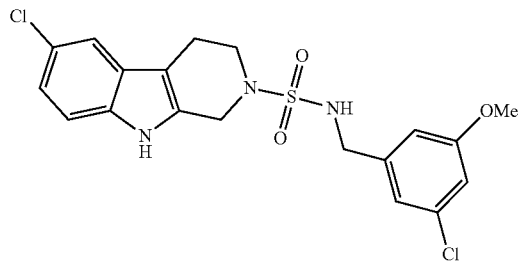 [SMILES: COc1cc(Cl)cc(CNS(=O)(=O)N2CCc3c([nH]c4ccc(Cl)cc34)C2)c1]
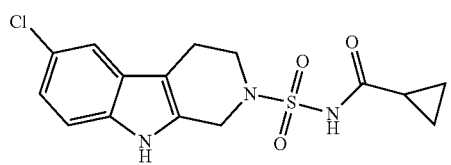 [SMILES: O=C(NS(=O)(=O)N1CCc2c([nH]c3ccc(Cl)cc23)C1)C1CC1]
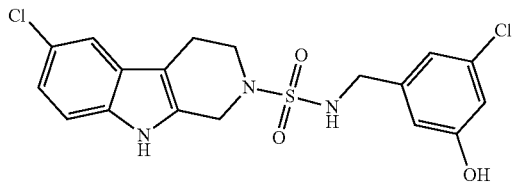 [SMILES: O=S(=O)(NCc1cc(O)cc(Cl)c1)N1CCc2c([nH]c3ccc(Cl)cc23)C1]
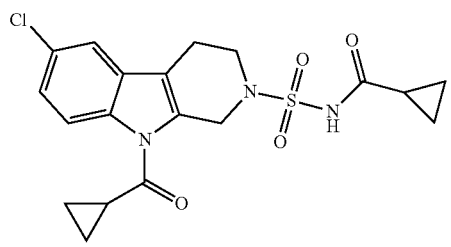 [SMILES: O=C(NS(=O)(=O)N1CCc2c(n(C(=O)C3CC3)c3ccc(Cl)cc23)C1)C1CC1]
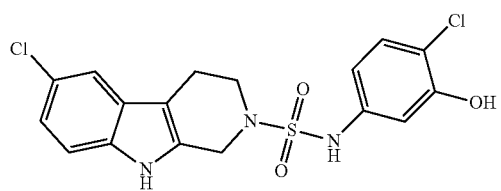 [SMILES: O=S(=O)(Nc1ccc(Cl)c(O)c1)N1CCc2c([nH]c3ccc(Cl)cc23)C1]
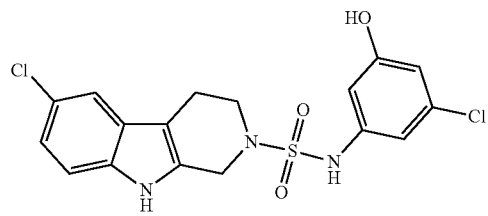 [SMILES: O=S(=O)(Nc1cc(O)cc(Cl)c1)N1CCc2c([nH]c3ccc(Cl)cc23)C1]
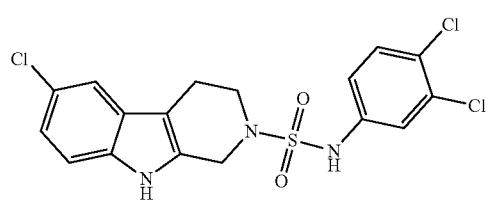 [SMILES: O=S(=O)(Nc1ccc(Cl)c(Cl)c1)N1CCc2c([nH]c3ccc(Cl)cc23)C1]
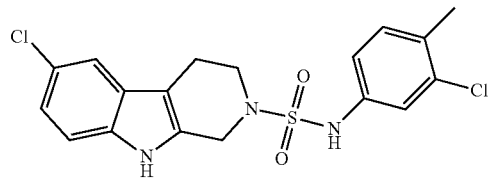 [SMILES: Cc1ccc(NS(=O)(=O)N2CCc3c([nH]c4ccc(Cl)cc34)C2)cc1Cl]
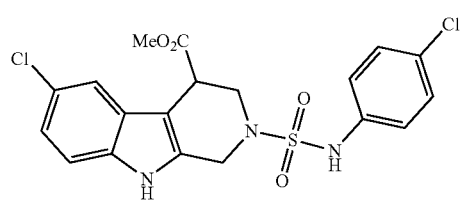 [SMILES: COC(=O)C1CN(S(=O)(=O)Nc2ccc(Cl)cc2)Cc2[nH]c3ccc(Cl)cc3c21]
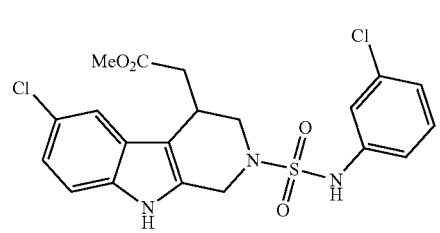 [SMILES: COC(=O)CC1CN(S(=O)(=O)Nc2cccc(Cl)c2)Cc2[nH]c3ccc(Cl)cc3c21]
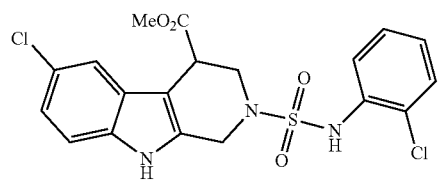 [SMILES: COC(=O)C1CN(S(=O)(=O)Nc2ccccc2Cl)Cc2[nH]c3ccc(Cl)cc3c21]
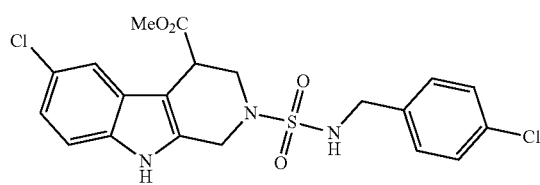 [SMILES: COC(=O)C1CN(S(=O)(=O)NCc2ccc(Cl)cc2)Cc2[nH]c3ccc(Cl)cc3c21]
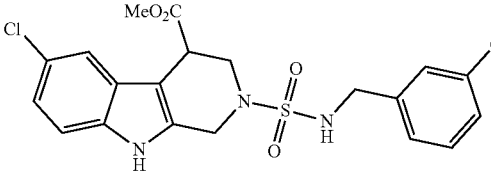
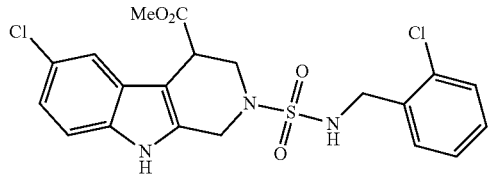 [SMILES: COC(=O)C1CN(S(=O)(=O)NCc2ccccc2Cl)Cc2[nH]c3ccc(Cl)cc3c21]

TABLE A-continued
Representative compounds of the invention (includes compounds shown below as well as compounds disclosed in the Examples section that fall within the general structure of Formula I)
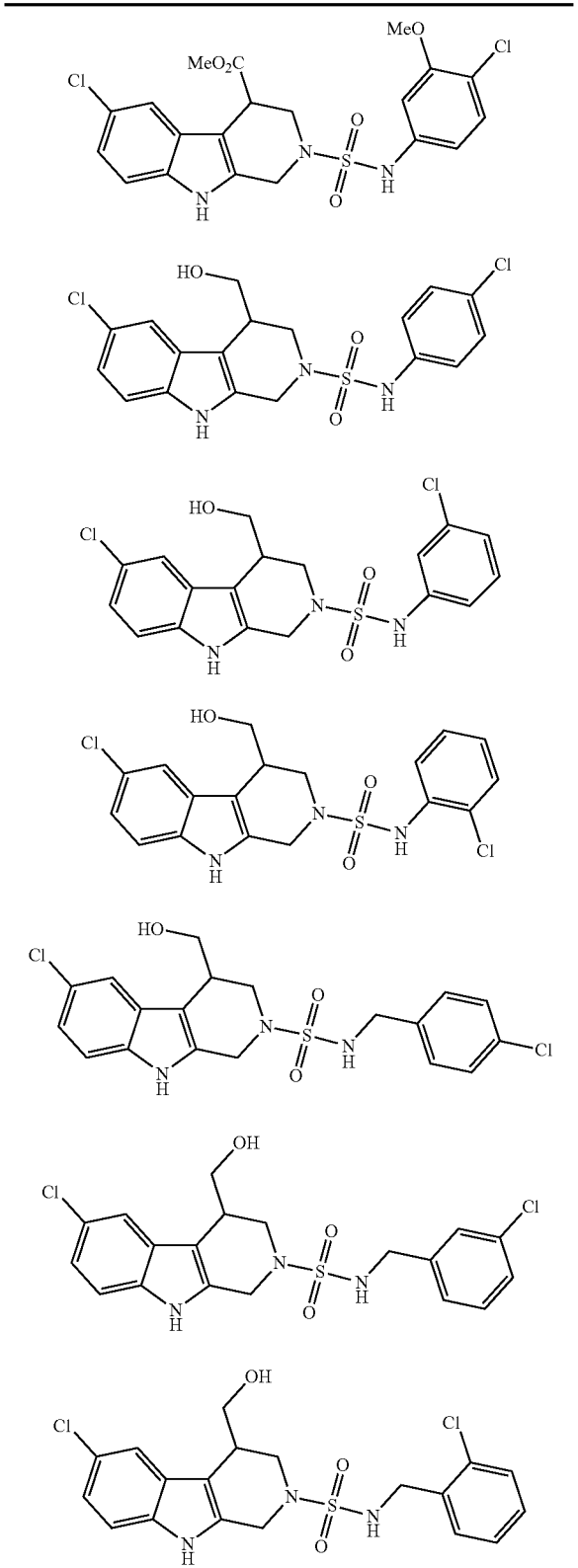
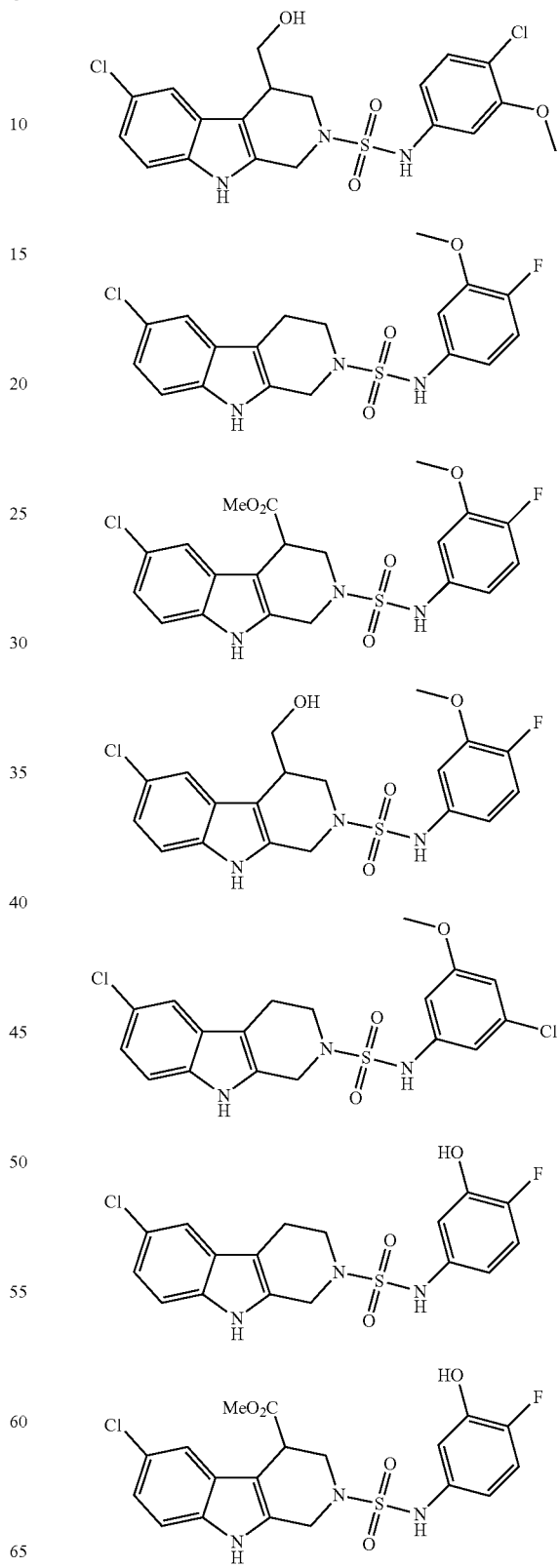

TABLE A-continued

Representative compounds of the invention (includes compounds shown below as well as compounds disclosed in the Examples section that fall within the general structure of Formula I)

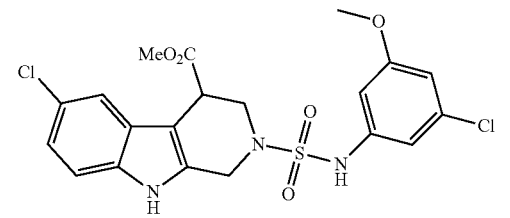 [SMILES: COC(=O)C1CN(S(=O)(=O)Nc2cc(Cl)cc(OC)c2)Cc2[nH]c3ccc(Cl)cc3c21]

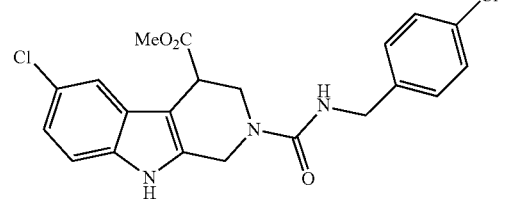

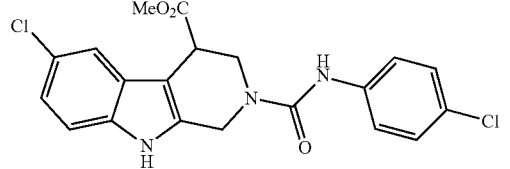 [SMILES: COC(=O)C1CN(C(=O)Nc2ccc(Cl)cc2)Cc2[nH]c3ccc(Cl)cc3c21]

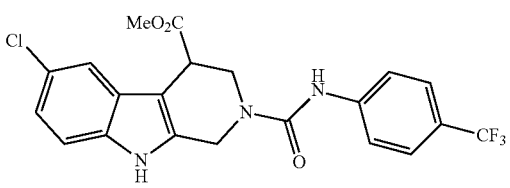 [SMILES: COC(=O)C1CN(C(=O)Nc2ccc(C(F)(F)F)cc2)Cc2[nH]c3ccc(Cl)cc3c21]

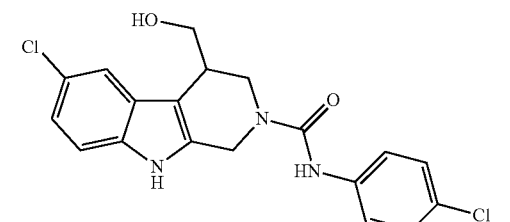

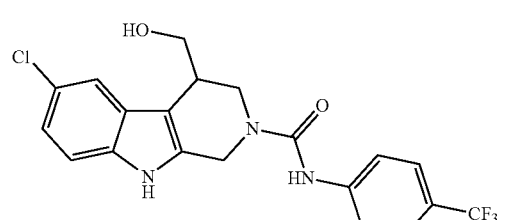

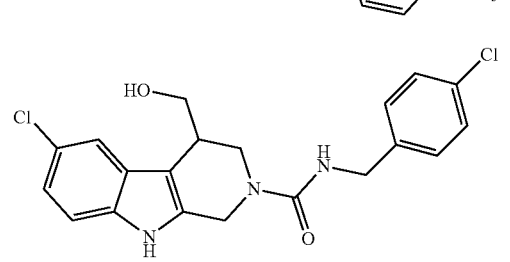

TABLE A-continued

Representative compounds of the invention (includes compounds shown below as well as compounds disclosed in the Examples section that fall within the general structure of Formula I)

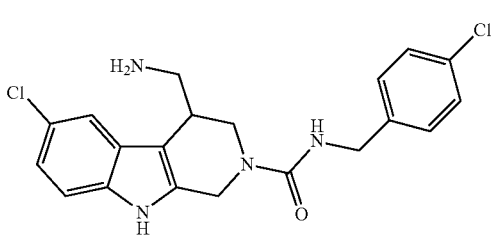 [SMILES: NCC1CN(C(=O)NCc2ccc(Cl)cc2)Cc2[nH]c3ccc(Cl)cc3c21]

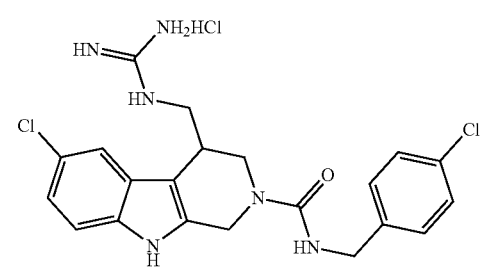

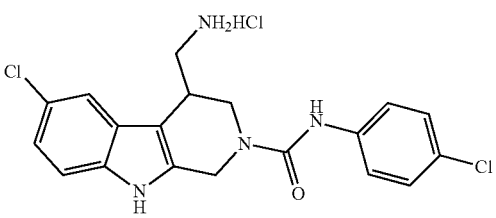

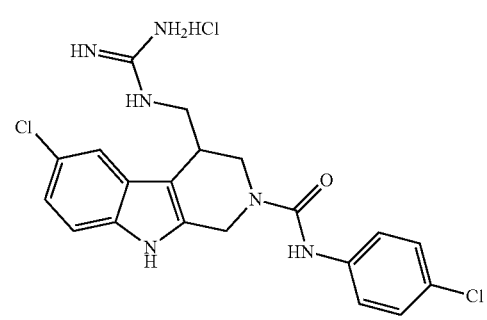

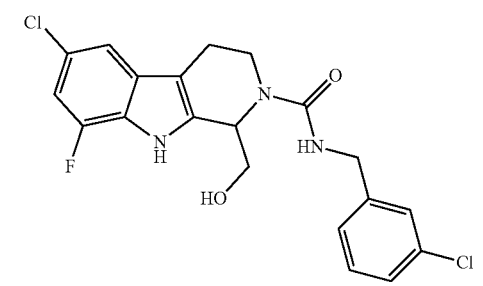 [SMILES: O=C(NCc1cccc(Cl)c1)N1CCc2c([nH]c3c(F)cc(Cl)cc23)C1CO]

TABLE A-continued

Representative compounds of the invention (includes compounds shown below as well as compounds disclosed in the Examples section that fall within the general structure of Formula I)

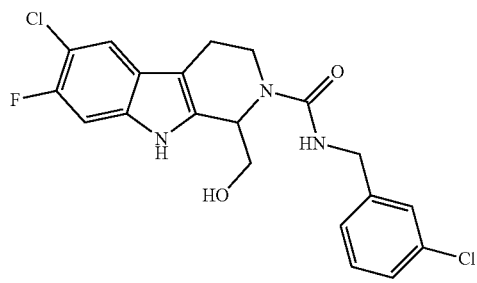 [SMILES: O=C(NCc1cccc(Cl)c1)N1CCc2c([nH]c3cc(F)c(Cl)cc23)C1CO]

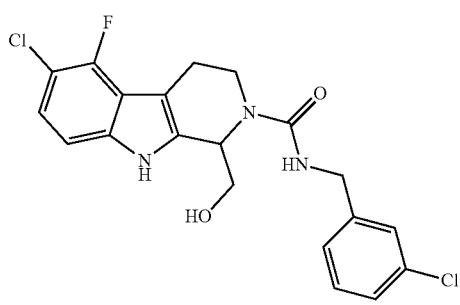 [SMILES: O=C(NCc1cccc(Cl)c1)N1CCc2c([nH]c3ccc(Cl)c(F)c23)C1CO]

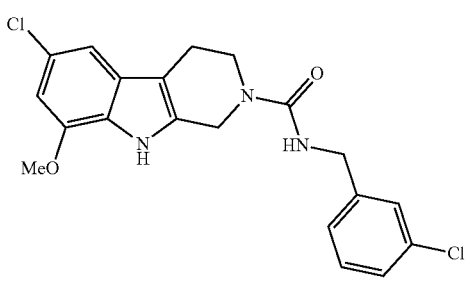 [SMILES: COc1cc(Cl)cc2c3c([nH]c12)CN(C(=O)NCc1cccc(Cl)c1)CC3]

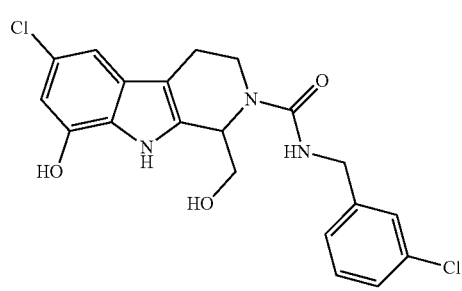 [SMILES: O=C(NCc1cccc(Cl)c1)N1CCc2c([nH]c3c(O)cc(Cl)cc23)C1CO]

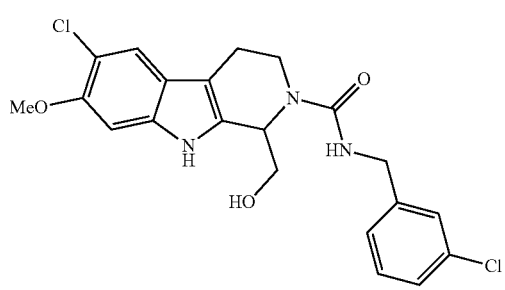 [SMILES: COc1cc2[nH]c3c(c2cc1Cl)CCN(C(=O)NCc1cccc(Cl)c1)C3CO]

TABLE A-continued

Representative compounds of the invention (includes compounds shown below as well as compounds disclosed in the Examples section that fall within the general structure of Formula I)

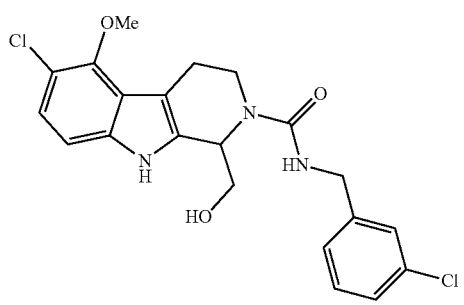 [SMILES: COc1c(Cl)ccc2[nH]c3c(c12)CCN(C(=O)NCc1cccc(Cl)c1)C3CO]

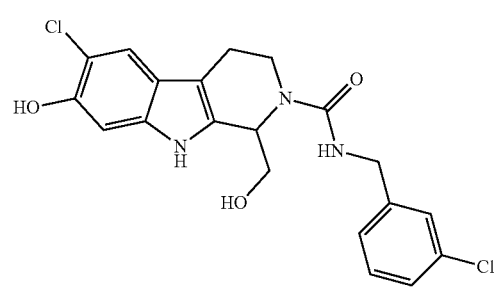 [SMILES: O=C(NCc1cccc(Cl)c1)N1CCc2c([nH]c3cc(O)c(Cl)cc23)C1CO]

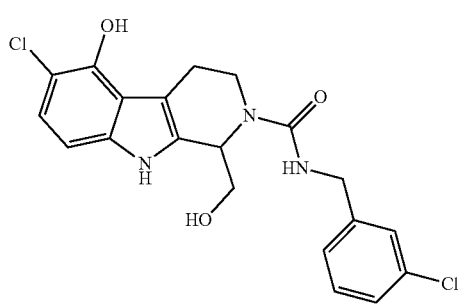 [SMILES: O=C(NCc1cccc(Cl)c1)N1CCc2c([nH]c3ccc(Cl)c(O)c23)C1CO]

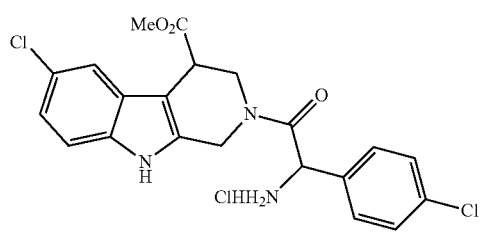

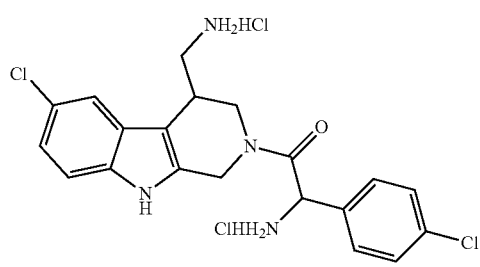

TABLE A-continued

Representative compounds of the invention (includes compounds shown below as well as compounds disclosed in the Examples section that fall within the general structure of Formula I)

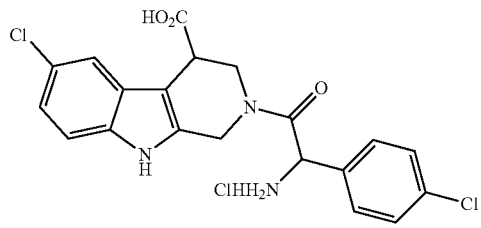

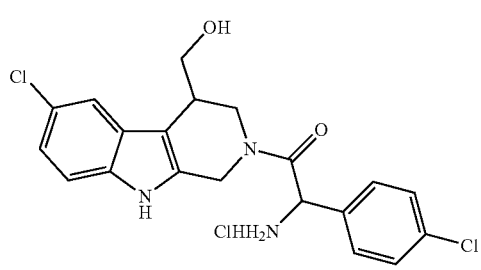

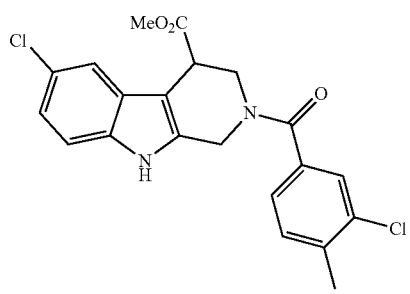 [SMILES: COC(=O)C1CN(C(=O)c2ccc(C)c(Cl)c2)Cc2[nH]c3ccc(Cl)cc3c21]

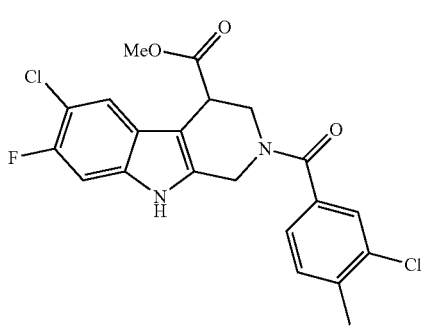 [SMILES: COC(=O)C1CN(C(=O)c2ccc(C)c(Cl)c2)Cc2[nH]c3cc(F)c(Cl)cc3c21]

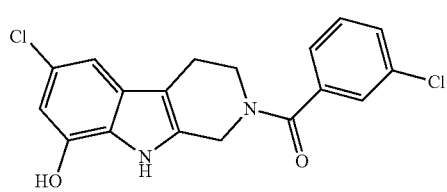 [SMILES: O=C(c1cccc(Cl)c1)N1CCc2c([nH]c3c(O)cc(Cl)cc23)C1]

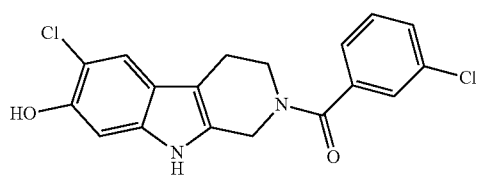 [SMILES: O=C(c1cccc(Cl)c1)N1CCc2c([nH]c3cc(O)c(Cl)cc23)C1]

TABLE A-continued

Representative compounds of the invention (includes compounds shown below as well as compounds disclosed in the Examples section that fall within the general structure of Formula I)

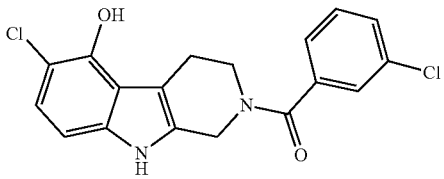 [SMILES: O=C(c1cccc(Cl)c1)N1CCc2c([nH]c3ccc(Cl)c(O)c23)C1]

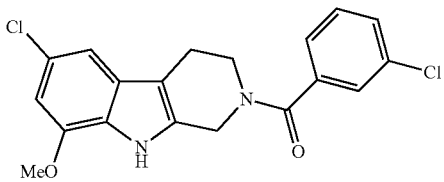 [SMILES: COc1cc(Cl)cc2c3c([nH]c12)CN(C(=O)c1cccc(Cl)c1)CC3]

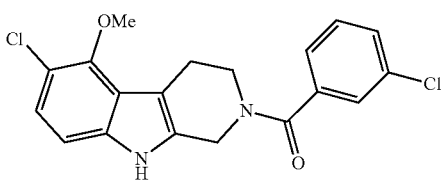 [SMILES: COc1c(Cl)ccc2[nH]c3c(c12)CCN(C(=O)c1cccc(Cl)c1)C3]

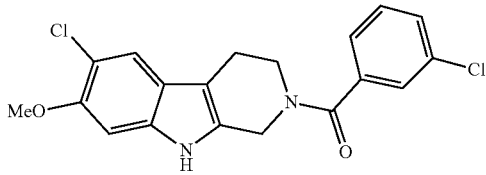 [SMILES: COc1cc2[nH]c3c(c2cc1Cl)CCN(C(=O)c1cccc(Cl)c1)C3]

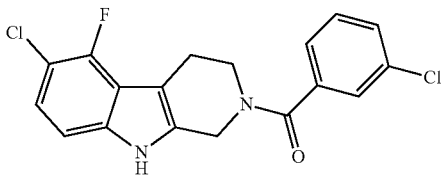 [SMILES: O=C(c1cccc(Cl)c1)N1CCc2c([nH]c3ccc(Cl)c(F)c23)C1]

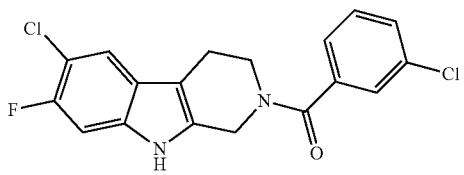 [SMILES: O=C(c1cccc(Cl)c1)N1CCc2c([nH]c3cc(F)c(Cl)cc23)C1]

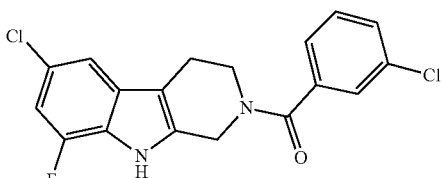

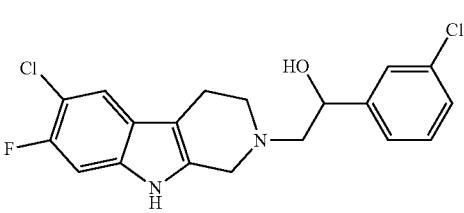 [SMILES: OC(CN1CCc2c([nH]c3cc(F)c(Cl)cc23)C1)c1cccc(Cl)c1]

TABLE A-continued
Representative compounds of the invention (includes compounds shown below as well as compounds disclosed in the Examples section that fall within the general structure of Formula I)
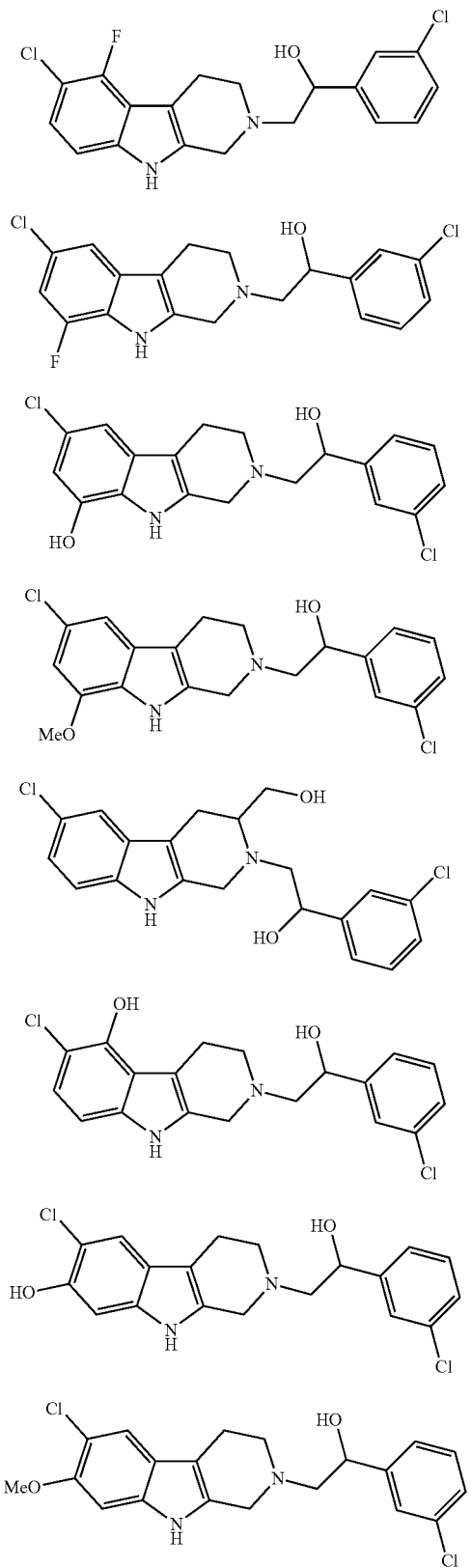
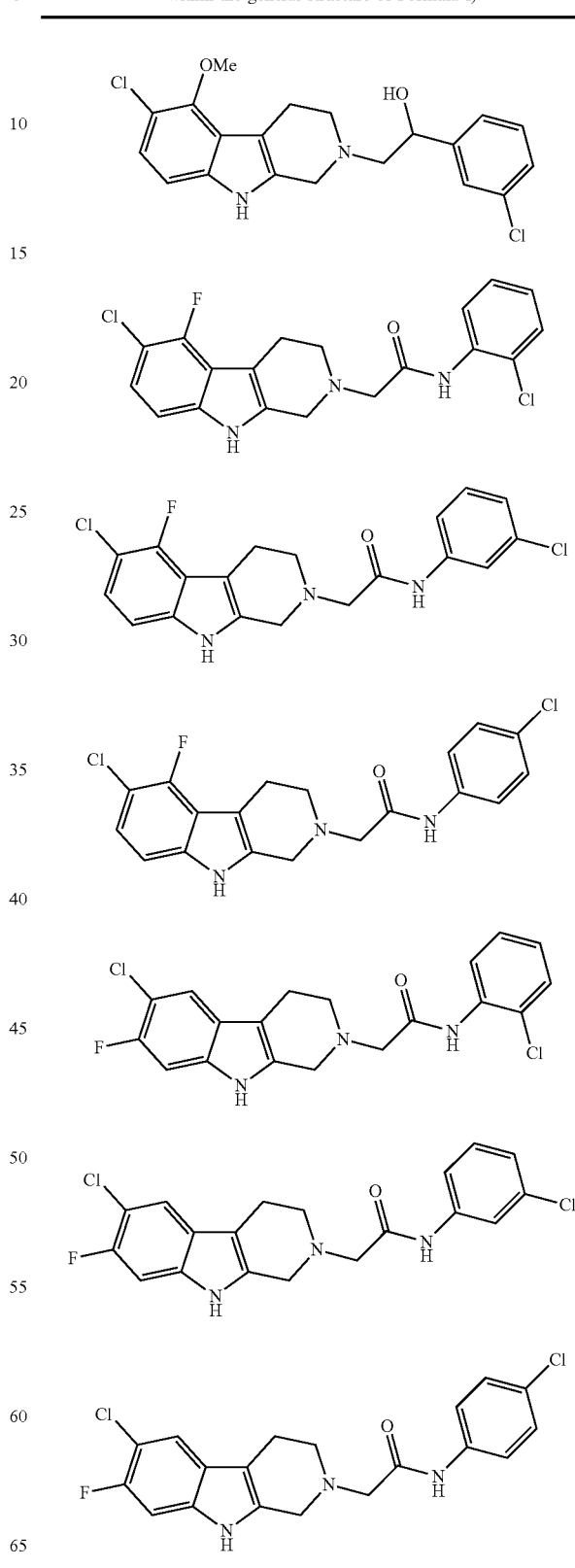

TABLE A-continued
Representative compounds of the invention (includes compounds shown below as well as compounds disclosed in the Examples section that fall within the general structure of Formula I)
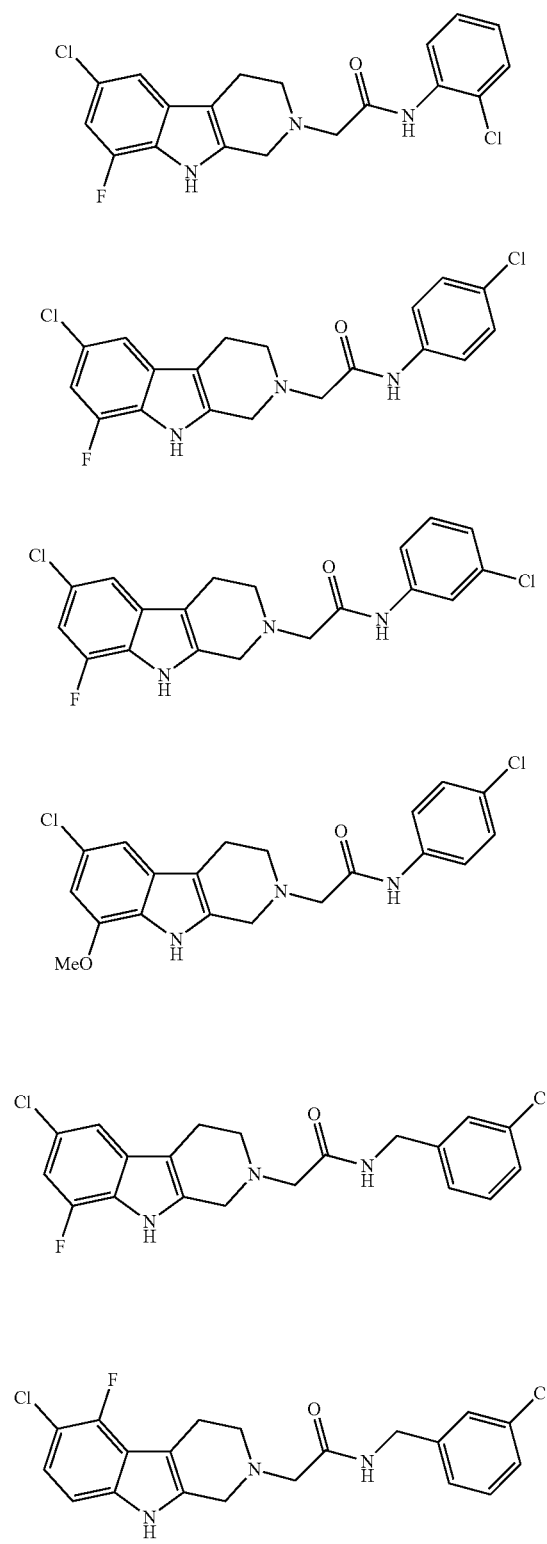
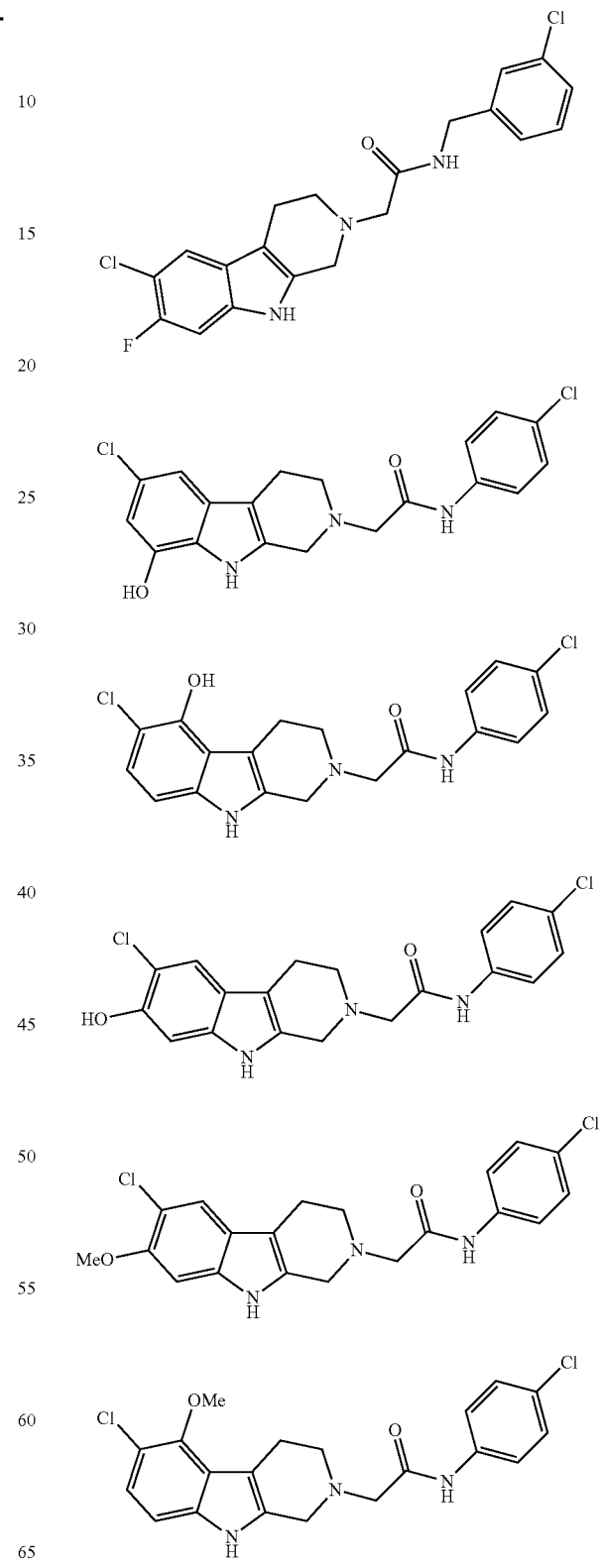

TABLE A-continued
Representative compounds of the invention (includes compounds shown below as well as compounds disclosed in the Examples section that fall within the general structure of Formula I)
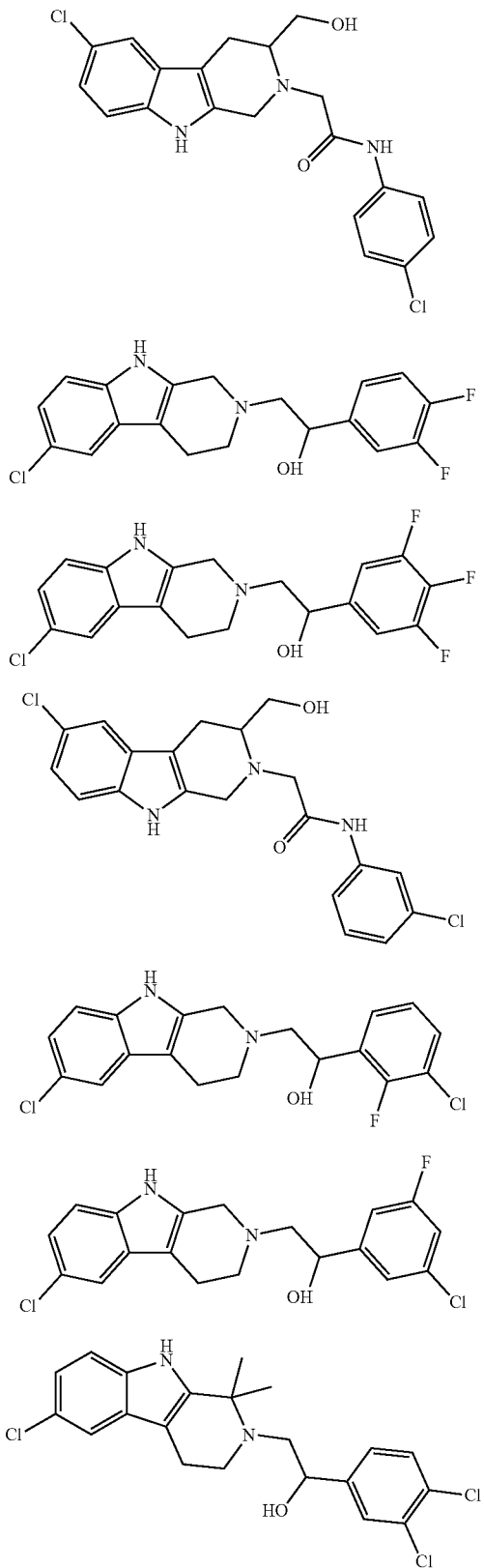
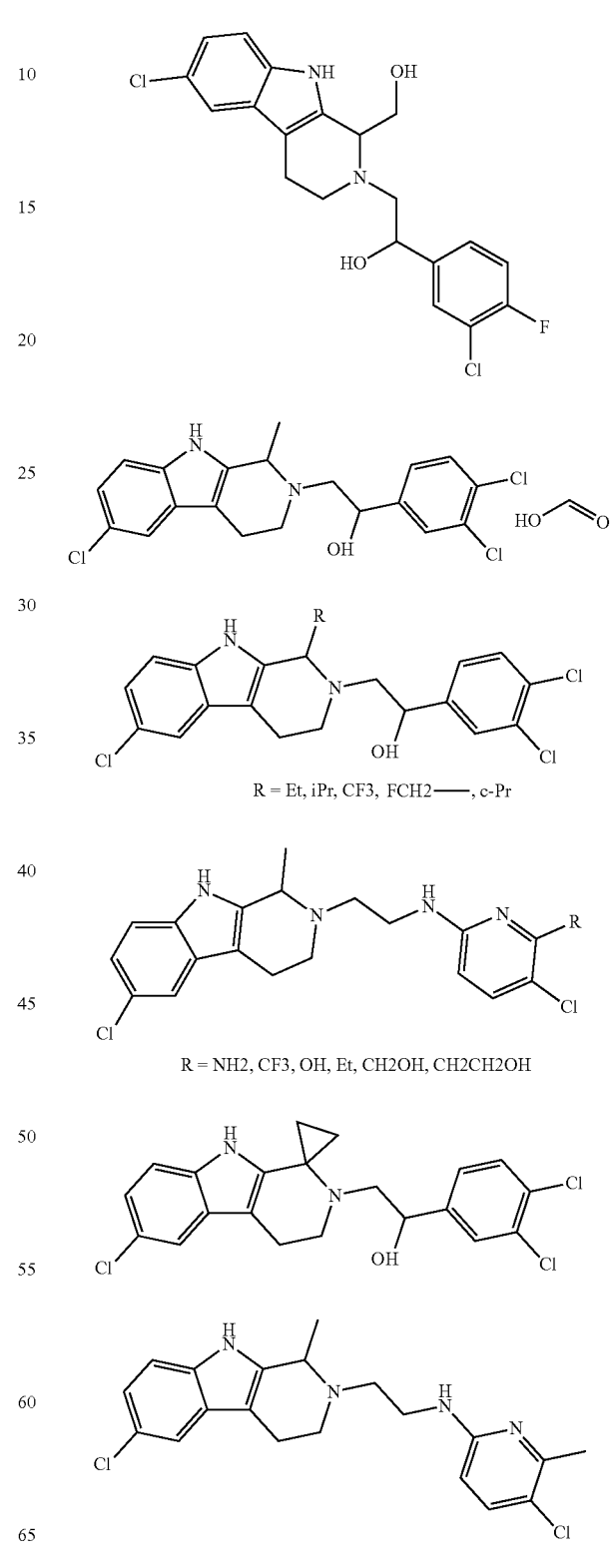
R = Et, iPr, CF3, FCH2——, c-Pr
R = NH2, CF3, OH, Et, CH2OH, CH2CH2OH TABLE A-continued Representative compounds of the invention (includes compounds shown below as well as compounds disclosed in the Examples section that fall within the general structure of Formula I)

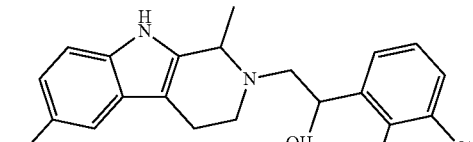

R = F, Cl, Me, CF3, Et

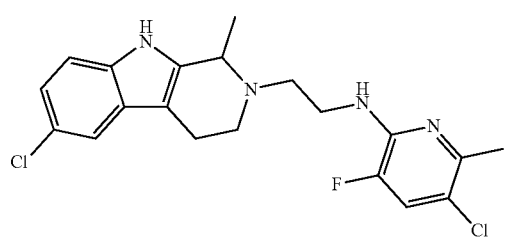 [SMILES: Cc1nc(NCCN2CCc3c([nH]c4ccc(Cl)cc34)C2C)c(F)cc1Cl]

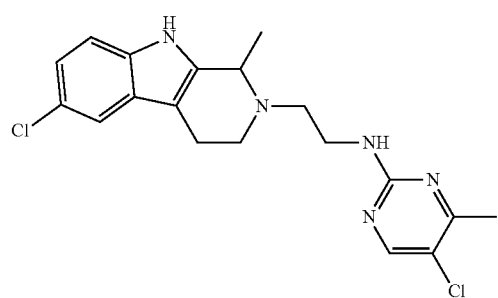 [SMILES: Cc1nc(NCCN2CCc3c([nH]c4ccc(Cl)cc34)C2C)ncc1Cl]

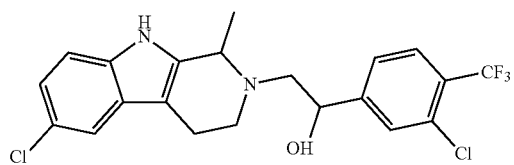 [SMILES: CC1c2[nH]c3ccc(Cl)cc3c2CCN1CC(O)c1ccc(C(F)(F)F)c(Cl)c1]

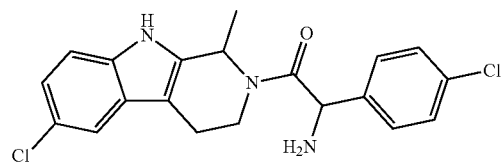 [SMILES: CC1c2[nH]c3ccc(Cl)cc3c2CCN1C(=O)C(N)c1ccc(Cl)cc1]

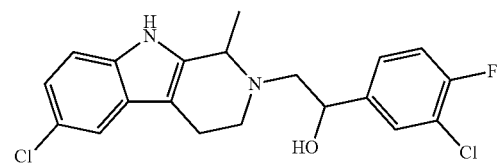 [SMILES: CC1c2[nH]c3ccc(Cl)cc3c2CCN1CC(O)c1ccc(F)c(Cl)c1]

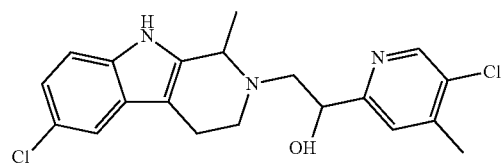 [SMILES: Cc1cc(C(O)CN2CCc3c([nH]c4ccc(Cl)cc34)C2C)ncc1Cl]

TABLE A-continued

Representative compounds of the invention (includes compounds shown below as well as compounds disclosed in the Examples section that fall within the general structure of Formula I)

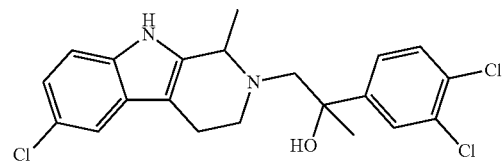 [SMILES: CC1c2[nH]c3ccc(Cl)cc3c2CCN1CC(C)(O)c1ccc(Cl)c(Cl)c1]

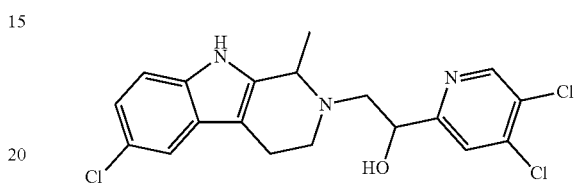

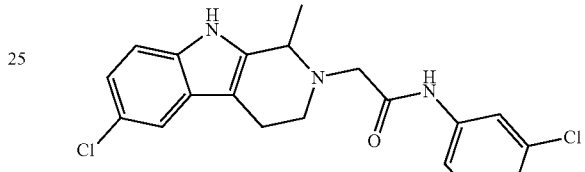

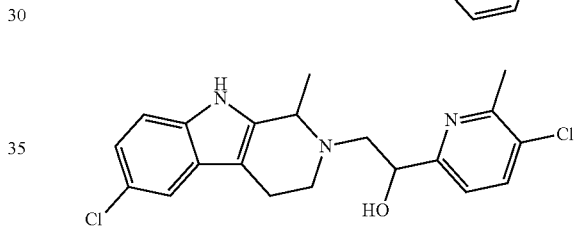

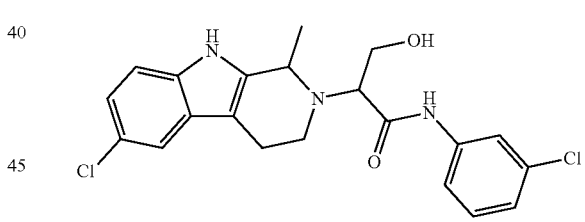

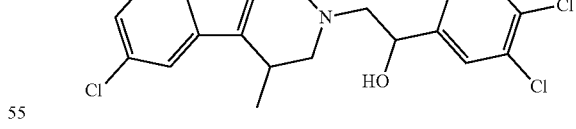

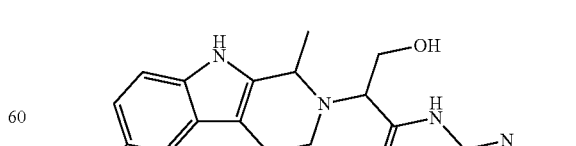

TABLE A-continued

Representative compounds of the invention (includes compounds shown below as well as compounds disclosed in the Examples section that fall within the general structure of Formula I)

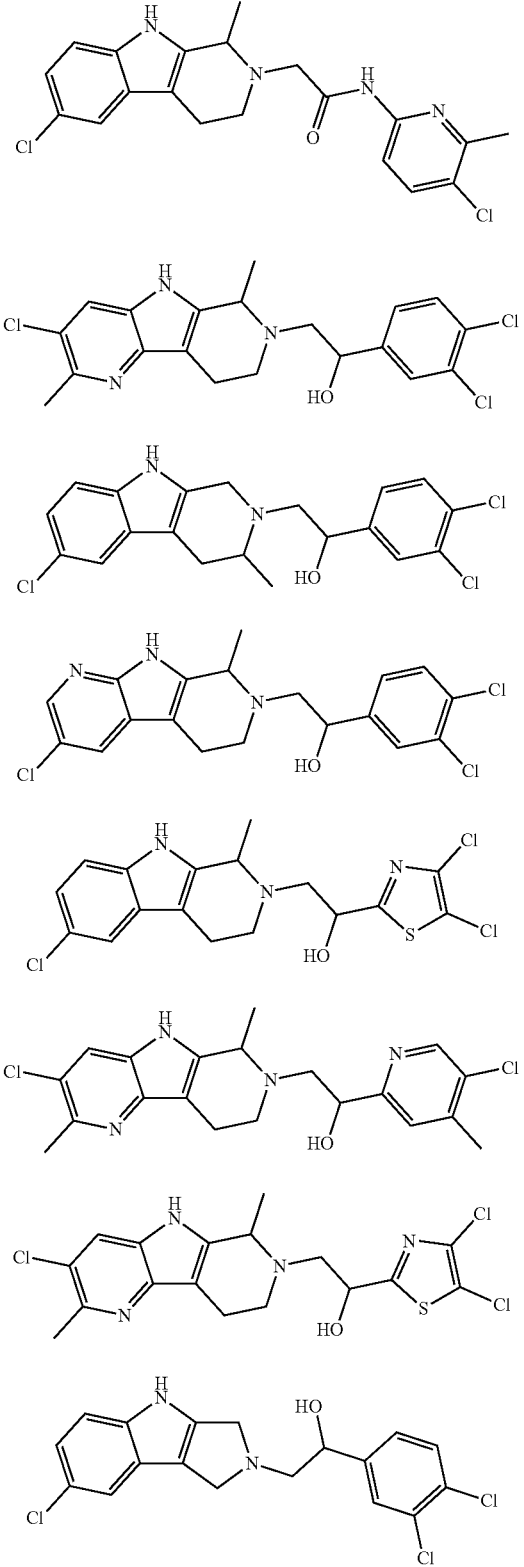

TABLE A-continued

Representative compounds of the invention (includes compounds shown below as well as compounds disclosed in the Examples section that fall within the general structure of Formula I)

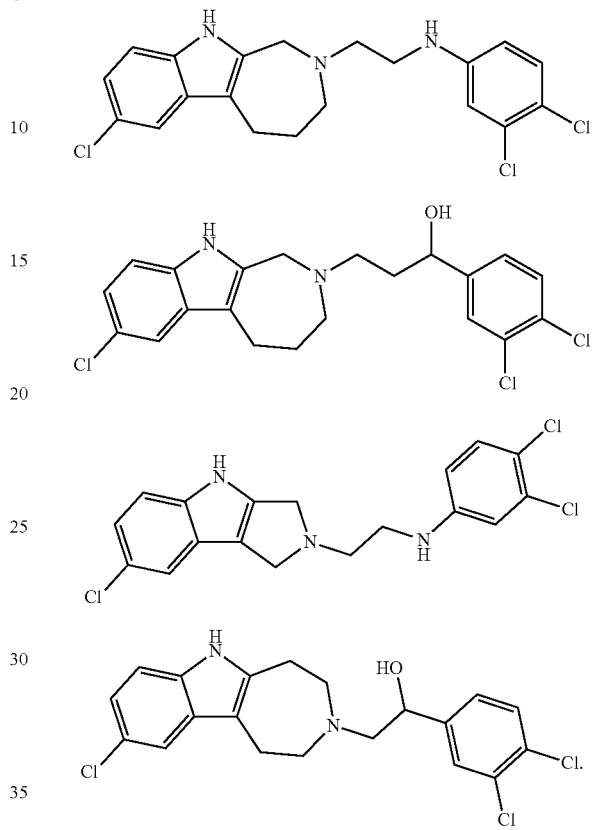

Another aspect of the invention provides an antibiotic composition comprising any one of the compounds disclosed herein. In some embodiments, the antibiotic composition further comprises a β-lactam antibiotic. Exemplary β-lactam antibiotics include, but are not limited to, a penicillin, a cephalosporin, a penem, a monobactam, Amoxicillin/clavulanic acid, Imipenem/cilastatin, Ampicillin/flucloxacillin, Piperacillin/tazobactam, Piperacillin/sulbactam, Amoxicillin/sulbactam, Ampicillin/sulbactam (Sultamicillin), Amoxicillin/pivsulbactam, Ceftolozane/tazobactam, Cefoperazone/sulbactam, Cefoperazone/tazobactam, Ceftriaxone/tazobactam, Meropenem/vaborbactam, and Ceftazidime/avibactam, or a combination thereof. In general, all known β-lactam antibiotics are included within the scope of the present invention. A list of β-lactam antibiotics can be found, for example, in $72^{nd}$ edition of the Physician's Desk Reference (see, also, the website pdr.net) as well as the Merck Index (see, also the online version at rsc.org/merck-index), all of which are incorporated herein by reference in their entirety.

One particular group of β-lactam antibiotic, namely, cephalosporin includes, but are not limited to, Cefathiamidine, Cefamandole, Cefacetrile (cephacetrile), Cefadroxil (cefadroxyl; Duricef), Cefadroxil/Trimethoprim, Cefalexin (cephalexin; Keflex), Cefalexin/Trimethoprim, Cefaloglycin (cephaloglycin), Cefalonium (cephalonium), Cefaloridine (cephaloradine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole, Cefaclor (Ceclor, Distaclor, Keflor, Raniclor), Cefonicid (Monocid), Cefprozil (cefproxil; Cefzil), Cefuroxime (Zefu, Zinnat, Zinacef, Ceftin, Biofuroksym,[19] Xorimax), Cefuzonam, Cefmetazole, Cefotetan, Loracarbef (Lorabid), Cefbuperazone, Cefmetazole (Zefazone), Cefminox, Cefotetan (Cefotan), Cefoxitin (Mefoxin), Cefotiam (Pansporin), Cefcapene, Cefdaloxime, Cefdinir (Sefdin, Zinir, Omnicef, Kefnir), Cefditoren, Cefetamet, Cefixime (Fixx, Zifi, Suprax), Cefmenoxime, Cefodizime, Cefotaxime (Claforan), Cefovecin (Convenia), Cefpimizole, Cefpodoxime (Vantin, PECEF, Simplicef), Cefteram, Ceftamere (Enshort), Ceftibuten (Cedax), Ceftiofur (Naxcel, Excenel), Ceftiolene, Ceftizoxime (Cefizox), Ceftriaxone (Rocephin), Cefoperazone (Cefobid), Ceftazidime (Meezat, Fortum, Fortaz), Latamoxef (moxalactam), Cefclidine, Cefepime (Maxipime), Cefluprenam, Cefoselis, Cefozopran, Cefpirome (Cefrom), Cefquinome, Flomoxef, Ceftobiprole, Ceftaroline, and Ceftolozane.

Exemplary penicillins that are useful in compositions of the invention include, but are not limited to, Piperacillin, Amoxicillin, Mezlocillin, Azlocillin, Ampicillin (Pivampicillin, Hetacillin, Bacampicillin, Metampicillin, Talampicillin), Epicillin, Mezlocillin, Mecillinam (Pivmecillinam), Sulbenicillin, Cloxacillin (Dicloxacillin, Flucloxacillin), Sultamicillin, Lenampicillin, Penicillin G, Furbenicillin, Oxacillin, Methicillin, Nafcillin, Benzathine benzylpenicillin, Procaine benzylpenicillin, Azidocillin, Clometocillin, Penamecillin, Nafcillin, Epicillin, Ticarcillin, Carbenicillin (Carindacillin), Temocillin, and Penicillin V (Phenoxymethylpenicillin).

Exemplary Penems that are useful in the present invention include, but are not limited to, Meropenem, Imipenem, Biapenem, Faropenem, Ritipenem, Panipenem, and Ertapenem.

Exemplary Monobactams that are useful in the invention include, but are not limited to, Aztreonam, Tigemonam, Carumonam, and Nocardicin A.

In some embodiments, the antibiotic composition can further include a β-lactamase inhibitor or other resistance-modifying agent or a combination thereof. Exemplary β-lactamase inhibitors include, but are not limited to, clavulanic acid, sulbactam, tazobactam, avibactam, relebactam (MK-7655), tebipenem, 6-methylidene penem2 and boron-based transition state inhibitors (BATSIs), and the like. Other β-lactamase inhibitors are well known to one skilled in the art.

Another aspect of the invention provides a method for treating bacterial infection in a subject. Such a method generally includes administering to the subject in need of such a treatment a therapeutically effective amount of any one of the compounds disclosed herein or any one of the antibiotic compositions disclosed herein. In one particular embodiment, the method is used to treat MRSA infection in a subject.

Combination of various embodiments can be combined with other embodiments. In this manner, a wide variety of compounds are encompassed within the scope of the invention. Some of the exemplary compounds of the invention where various embodiments are combined are shown in APPENDIX A. Accordingly, one particular embodiment of the invention includes compounds shown in APPENDIX A. It should also be appreciated that the scope of the invention also includes more generic structure of particular groups of variables represented in compounds in APPENDIX A. For example, where methyl group is present as a substituent (e.g., in a heteroaryl), a generic term "alkyl" can be used to include such a compound, and where a chloro is present, a generic term "halide" can be used. Accordingly, a wide number of generic substituents are included within the scope of the invention.

The compounds of the invention can be administered to a patient or a subject to achieve a desired physiological effect. Generally, the patient is an animal, typically a mammal, and often a human. The compound can be administered in a variety of forms adapted to the chosen route of administration, i.e., orally or parenterally. Parenteral administration in this respect includes administration by the following routes: intravenous; intramuscular; subcutaneous; intraocular; intrasynovial; transepithelially including transdermal, ophthalmic, sublingual and buccal; topically including ophthalmic, dermal, ocular, rectal and nasal inhalation via insufflation and aerosol; intraperitoneal; and rectal systemic.

The active compound can be orally administered, for example, with an inert diluent or with an assimilable edible carrier, or it can be enclosed in hard- or soft-shell gelatin capsules, or it can be compressed into tablets, or it can be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparation can contain at least 0.1% of active compound. The percentage of the compositions and preparation can, of course, be varied and can conveniently be between about 1 to about 10% of the weight of the unit. The amount of active compound in such therapeutically useful compositions is such that a suitable dosage will be obtained. Typical compositions or preparations according to the invention are prepared such that an oral dosage unit form contains from about 1 to about 1000 mg of active compound.

The tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound can be incorporated into sustained-release preparations and formulation. In addition to the common dosage forms set out above, the compounds of the invention may also be administered by controlled release means and/or delivery devices capable of releasing the active ingredient (prenylation inhibitor) at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. Examples of controlled release pharmaceutical compositions and delivery devices that may be adapted for the administration of the active ingredients of the present invention are described in U.S. Pat. Nos. 3,847,770; 3,916,899;

3,536,809; 3,598,123; 3,630,200; 4,008,719; 4,687,610; 4,769,027; 5,674,533; 5,059,595; 5,591,767; 5,120,548; 5,073,543; 5,639,476; 5,354,566; and 5,733,566, the disclosures of which are hereby incorporated by reference.

Pharmaceutical compositions for use in the methods of the present invention may be prepared by any of the methods of pharmacy, but all methods include the step of bringing the active ingredient into association with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent.

The active compound can also be administered parenterally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It can be stable under the conditions of manufacture and storage and must be preserved against the contaminating action of microorganisms such as bacterial and fungi. The carrier can be a solvent of dispersion medium containing, for example, water, ethanol, polyol (e.g., glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, e.g., sugars or sodium chloride. Prolonged absorption of the injectable compositions of agents delaying absorption, e.g., aluminum monostearate and gelatin.

Sterile injectable solutions are prepared by incorporating the active compound in the required amount in the appropriate solvent with various other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The compounds of the invention can be administered to a mammal alone or in combination with pharmaceutically acceptable carriers, as noted above, the proportion of which is determined by the solubility and chemical nature of the compound, chosen route of administration and standard pharmaceutical practice.

The physician can readily determine the dosage of the present therapeutic agents which will be most suitable for prophylaxis or treatment and it will vary with the form of administration and the particular compound chosen, and also, it will vary with the particular patient under treatment. The physician will generally wish to initiate treatment with small dosages by small increments until the optimum effect under the circumstances is reached. The therapeutic dosage can generally be from about 0.1 to about 1000 mg/day, and preferably from about 10 to about 500 mg/day, or from about 0.1 to about 250 mg/Kg of body weight per day and preferably from about 0.1 to about 500 mg/Kg of body weight per day and can be administered in several different dosage units. Higher dosages, on the order of about 2× to about 10×, may be required for oral administration.

While one skilled in the art having read the present disclosure can readily synthesize the compounds of Formula I, a general synthetic method for producing various substituents are shown in the synthetic scheme below. It should be appreciated some of the reactions shown in the synthetic scheme below can be combined to produce other combination of substituents of compounds of Formula I. For example, synthesis 1 can be combined with any one of synthesis 6-12 to produce different compounds of Formula I. In a similar manner synthesis 2 can be combined with any one of synthesis 6-12 to produce other compounds of Formula I. It should be appreciated that in some instances, one or more protection groups may need to be employed in order to prevent undesired substitution(s). Such methods will be readily apparent to one skilled in the art having read the present disclosure.

General Synthetic Scheme for Various Substituents of Compounds of Formula I

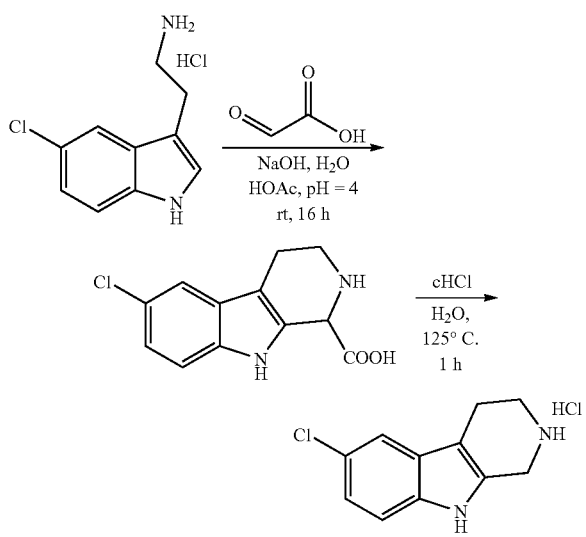

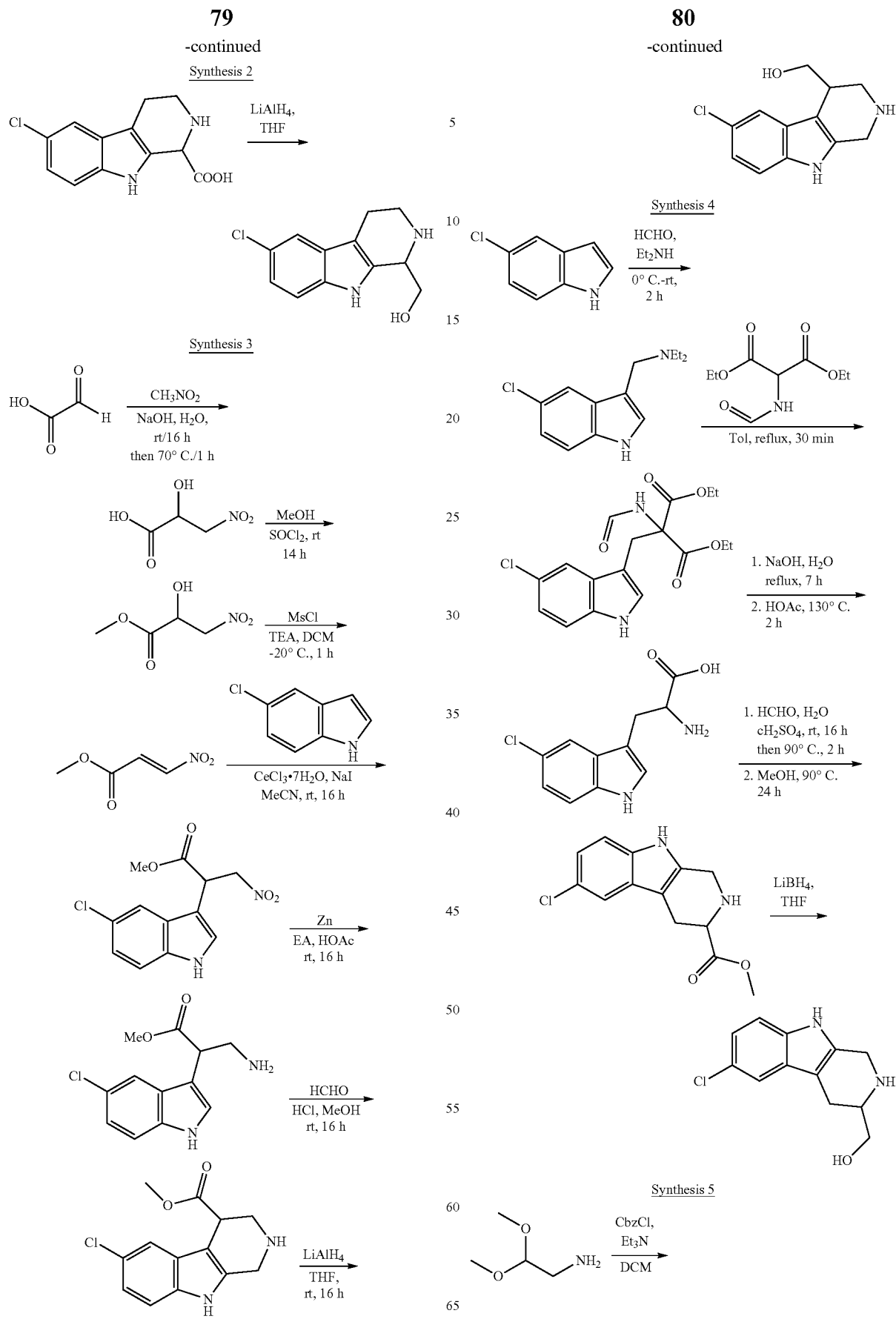

-continued
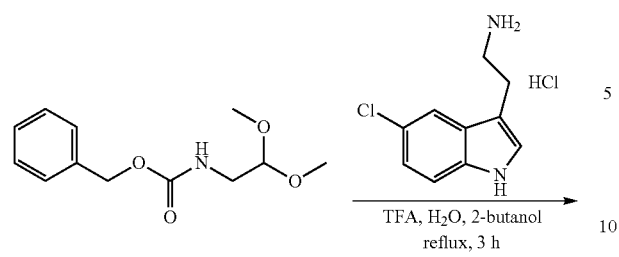
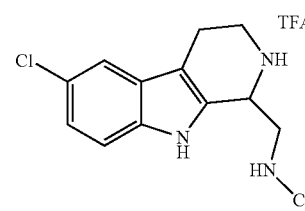
Synthesis 6
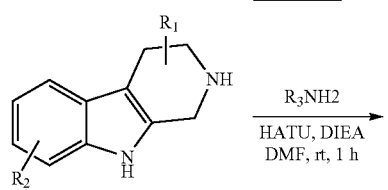
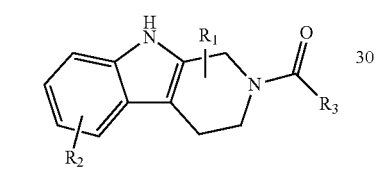
Synthesis 7
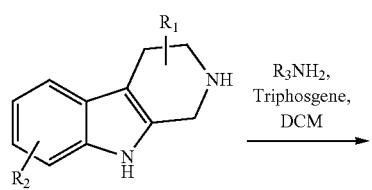
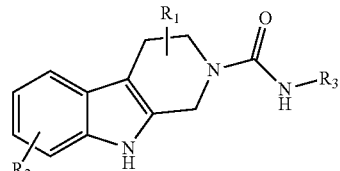
Synthesis 8
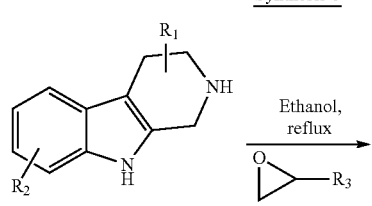
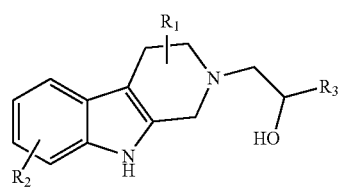
-continued
Synthesis 9
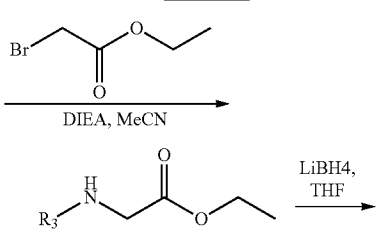
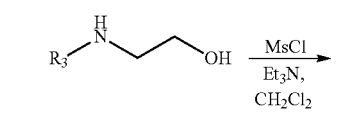
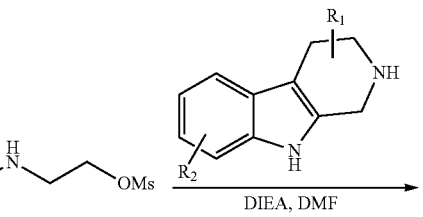
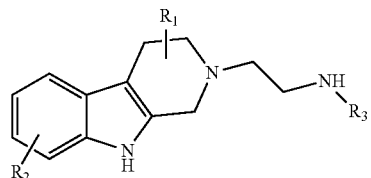
Synthesis 10
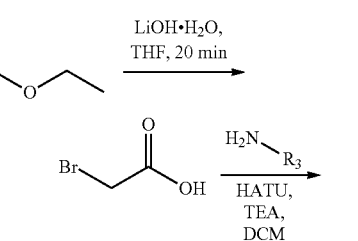
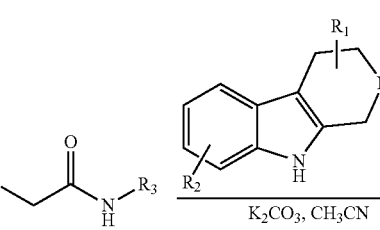
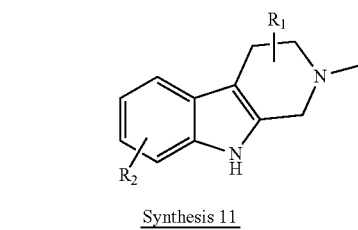
Synthesis 11
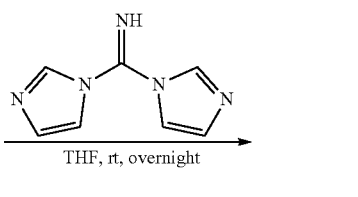
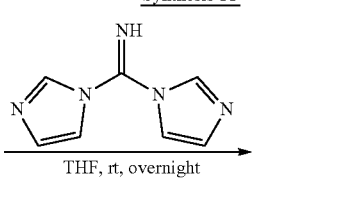

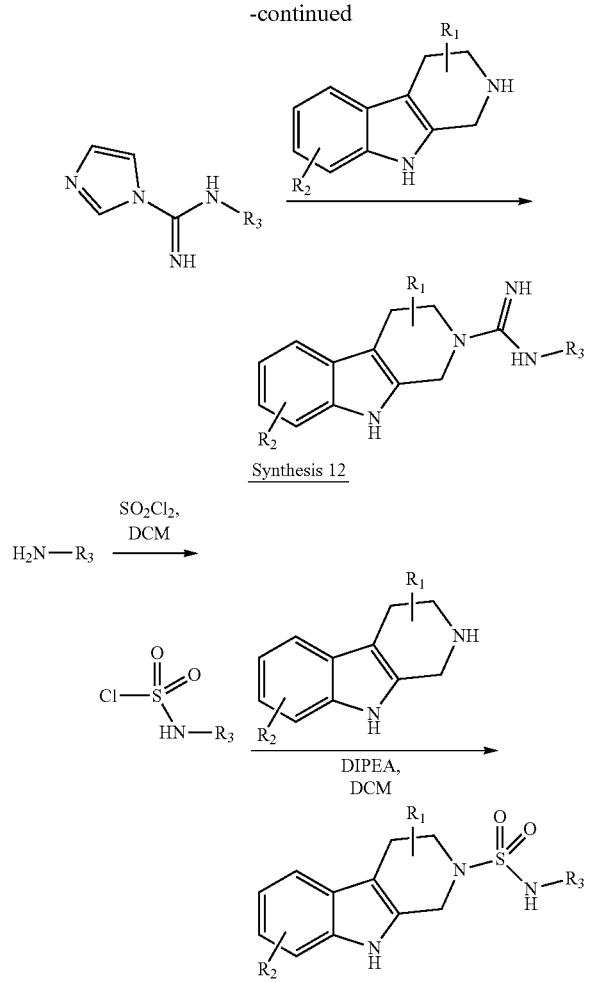

Synthesis 12

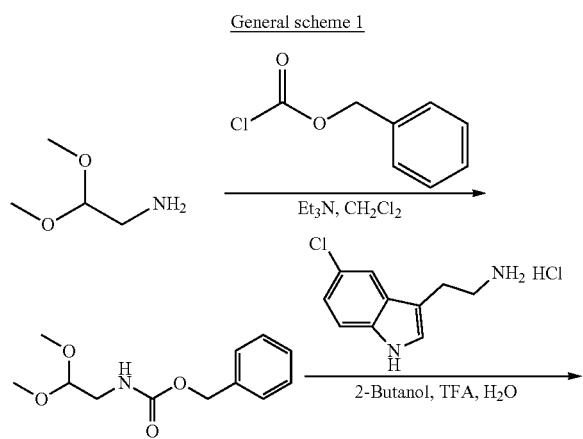

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

General scheme 1

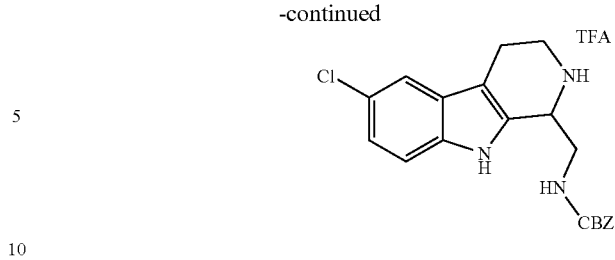

Benzyl (2, 2-dimethoxyethyl)carbamate: To a mixture of 2,2-dimethoxyethan-1-amine (8 g, 76.2 mmol) and Et₃N (23.1 g, 228.6 mmol) in DCM (80 mL) was added dropwise benzyl chloroformate (14.3 g, 83.8 mmol) at 0° C. The mixture was stirred at room temperature for 4 hrs. TLC showed the reaction was completed. The reaction was quenched with water (100 mL), extracted with DCM (3×100 mL). The combined organic layer was dried over anhydrous sodium sulfate and concentrated in vacuo to give a crude product. The crude product was purified by chromatography on silica gel (petroleum ether:EtOAc=4:1 to 2:1) to afford benzyl (2,2-dimethoxyethyl)carbamate (11 g, yield: 60.4%) as a colorless oil.

Benzyl((6-chloro-2-(3-chlorobenzoyl)-2,3,4,9-tetrahydro-1H-pyrido[3,4-b]indol-1-yl)methyl)carbamate trifluoroacetic acid: To a mixture of benzyl (2,2-dimethoxyethyl)-carbamate (1.71 g, 7.15 mmol) in 2-butanol (30 mL) was added 2-(5-chloro-1H-indol-3-yl)ethan-1-amine (1.53 g, 7.86 mmol), TFA (0.74 g) and H₂O (1 mL) The mixture was stirred at 100° C. for 16 hrs. Then the reaction was cooled to room temperature. The precipitates were collected via filtration to afford benzyl((6-chloro-2-(3-chlorobenzoyl)-2,3,4,9-tetrahydro-1H-pyrido[3,4-b]indol-1-yl) methyl)carbamate trifluoroacetic acid (3.5 g, yield: 98.9%) as a white solid. LCMS: [M+H]⁺=370.1.

General scheme 2

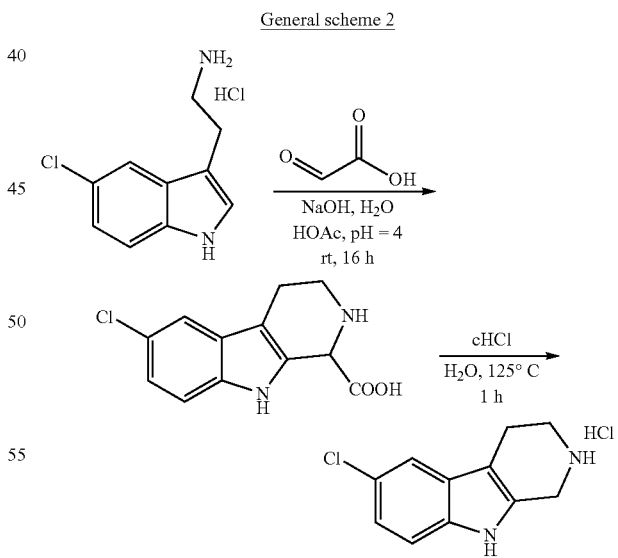

6-Chloro-2,3,4,9-tetrahydro-1H-pyrido[3,4-b]indole-1-carboxylic acid: 2-(5-Chloro-1H-indol-3-yl)ethanamine hydrochloride (23.1 g, 0.1 mol) was dissolved in water (300 ml) while heating. Glyoxylic acid (wt % 50% in water solution, 13.35 ml, 0.12 mol, 1.2 equiv.) was added into the reaction mixture, followed by the dropwise addition of NaOH solution (4.68 g, 0.117 mol, 1.17 equiv., in 100 ml water). The pH of the reaction solution was adjusted to 4.0 with acetic acid (around 11 ml) and the mixture was allowed to stir at room temperature until LCMS showed all starting material disappeared (around 16 h). Then the solution was chilled and vacuum filtered, giving an impure solid. The solid was dried under vacuum and suspended in MeOH at 0° C., then quickly filtered by suction to afford 6-chloro-2,3,4,9-tetrahydro-1H-pyrido[3,4-b]indole-1-carboxylic acid (20 g, yield 80%).

6-Chloro-2,3,4,9-tetrahydro-1H-pyrido[3,4-b]indole hydrochloride: 6-Chloro-2,3,4,9-tetrahydro-1H-pyrido[3,4-b]indole-1-carboxylic acid (10 g, 40 mmol) was dissolved in 10 ml conc. hydrochloric acid and 75 ml H$_2$O, and heated to 125° C. for 30 min. Then another 1 ml conc. HCl was added into the reaction mixture every 30 min until all the starting material disappeared as checked with LCMS. During the heating, bubbles formation and green solid precipitates were observed. After the solution was cooled to room temperature, then cooled to 0° C. for another 30 min, the solid precipitates were collected, and washed with H$_2$O (3×30 ml). The solid was then dried over oil pump in a dry box to afford 6-chloro-2,3,4,9-tetrahydro-1H-pyrido[3,4-b]indole hydrochloride (8.0 g, yield 82%). $^1$H NMR (500 MHz, DMSO-d$_6$) δ 11.35 (s, 1H), 9.61 (s, 2H), 7.53 (d, J=2.0 Hz, 1H), 7.39 (d, J=8.5 Hz, 1H), 7.10 (dd, J=8.6, 2.1 Hz, 1H), 4.33 (s, 2H), 3.40 (t, J=6.0 Hz, 2H), 2.92 (t, J=6.0 Hz, 2H).

General scheme 3

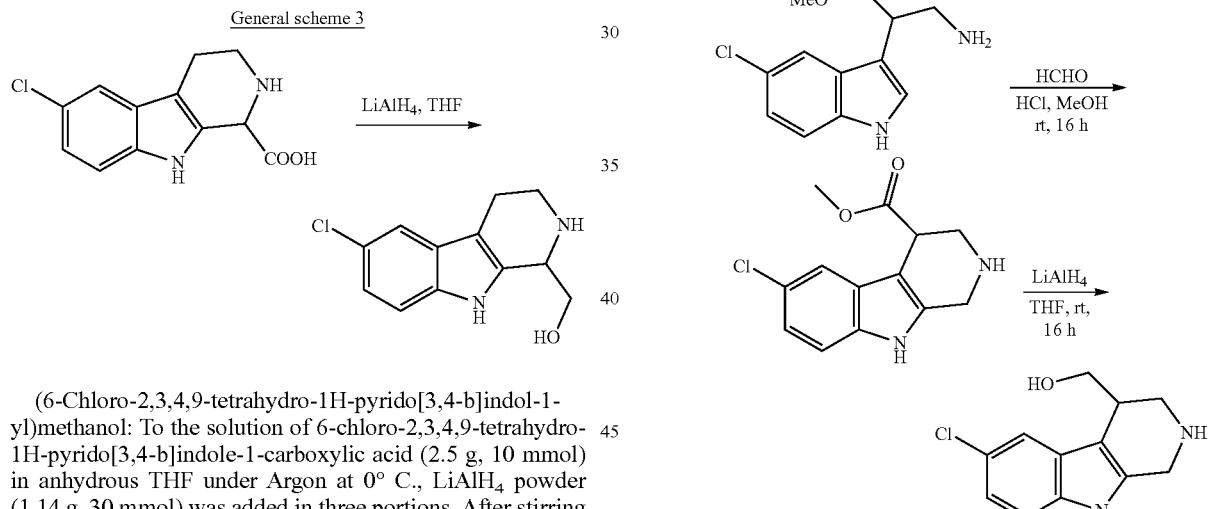

(6-Chloro-2,3,4,9-tetrahydro-1H-pyrido[3,4-b]indol-1-yl)methanol: To the solution of 6-chloro-2,3,4,9-tetrahydro-1H-pyrido[3,4-b]indole-1-carboxylic acid (2.5 g, 10 mmol) in anhydrous THF under Argon at 0° C., LiAlH$_4$ powder (1.14 g, 30 mmol) was added in three portions. After stirring at room temperature for 30 min, the reaction mixture was heated to reflux for 16 h, then was cooled to room temperature and quenched with water and sodium hydroxide solution. The resulting suspension was filtered and washed with diethyl ether (3×20 ml) The filtrates were concentrated and purified by silica gel chromatography (DCM/MeOH=10:1 to 5:1) to afford (6-chloro-2,3,4,9-tetrahydro-1H-pyrido[3,4-b]indol-1-yl)methanol (1.89 g, yield 80%). LC-MS: [M+H]$^+$: 237.1.

General scheme 4

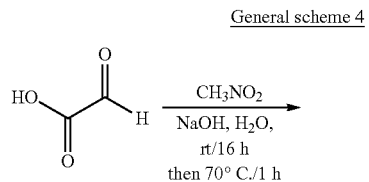

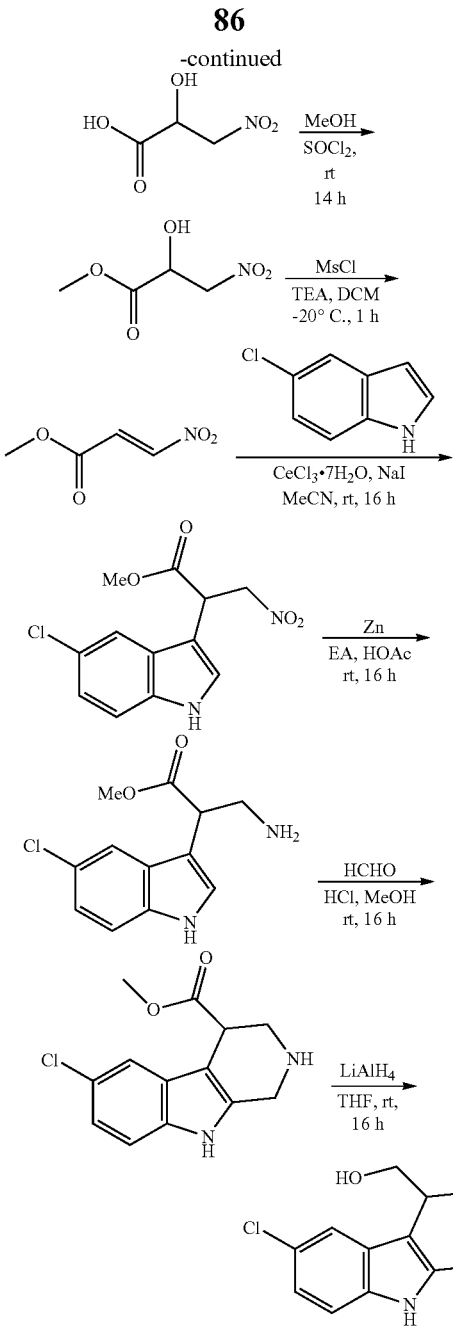

2-Hydroxy-3-nitropropanoic acid: In a round-bottom flask, cold 3 N sodium hydroxide (105 ml) and nitromethane (32 ml, 595 mmol) were successively added to glyoxylic acid monohydrate 1 (27.6 g, 300 mmol). The reaction mixture was stirred for 14 hours at room temperature, then heated for 1 hour at 70° C. After cooling the resulting solution with ice-water bath, cold 6 N H$_2$SO$_4$ (100 ml) was added to the reaction mixture at 0° C. The mixture was extracted with ethylacetate (1×100 ml, then 9×50 ml). The combined organic phase was dried over MgSO$_4$, and concentrated under reduced pressure at 40° C. to give a brown oil. Addition of dichloromethane to the crude residue gave a brown solid. The precipitates were filtered and dried in air to give 2-hydroxy-3-nitropropanoic acid (35 g, 86%). $^1$H NMR (300 MHz, DMSO-d$_6$) δ 4.86 (dd, J=13.3, 3.9 Hz, 1H), 4.72 (dd, J=13.3, 7.0 Hz, 1H), 4.59 (dd, J=7.0, 3.9 Hz, 1H), 4.01-3.61 (m, 1H).

Methyl 2-hydroxy-3-nitropropanoate: To the solution of 2-hydroxy-3-nitropropanoic acid (2.7 g, 20 mmol) in 20 ml anhydrous methanol was added SOCl$_2$(2.9 ml, 40 mmol) at 0° C. slowly, and then stirred at room temperature for 14 hrs. The reaction mixture was concentrated under reduced pressure and dried over oil-pump to afford methyl 2-hydroxy-3-nitropropanoate. The crude product was purified by silica gel flash column chromatography (hexane/ethyl acetate 3:1 to 1:1) to afford the methyl 2-hydroxy-3-nitropropanoate (2.86 g, yield 95%). $^1$H NMR (300 MHz, CDCl$_3$) δ 4.81-4.76 (m, 2H), 4.68 (q, J=4.4 Hz, 1H), 3.90 (s, 3H), 3.44 (dd, J=4.5, 1.2 Hz, 1H).

(E)-Methyl 3-nitroacrylate (Tetrahedron, 60(2), 397-403; 2004): Methyl 2-hydroxy-3-nitropropanoate (1.49 g, 10 mmol) was dissolved in anhydrous dichloromethane (10 ml) and cooled to −20° C. Triethylamine (4.2 ml, 30 mmol) and methanesulfonyl chloride (2.32 ml, 15 mmol) were added subsequently. The reaction mixture was stirred for 1 h at −20° C., then diluted with DCM and quenched with NaHCO$_3$ solution, extracted with DCM (3×10 ml). The combined organic phase was washed with brine and dried over Na$_2$SO$_4$, concentrated and purified via silica gel chromatography (hexane/EA 10:1 to 5:1) to provide (E)-methyl 3-nitroacrylate as a light yellow oil (1.10 g, yield 85%). $^1$H NMR (500 MHz, CDCl$_3$) δ 7.70 (d, J=13.5 Hz, 0H), 7.11 (d, J=13.5 Hz, 0H), 3.89 (s, H).

Methyl 2-(5-chloro-1H-indol-3-yl)-3-nitropropanoate (Journal of Organic Chemistry, 70(5), 1941-1944; 2005): Silica gel (5.0 g) was added to a mixture of CeCl$_3$7H$_2$O (11.2 g, 3 mmol) and NaI (0.134 g, 3 mmol) in acetonitrile (100 ml) and the reaction mixture was stirred for 12 hrs at room temperature. The solvent was removed by rotary evaporation. To the mixture of 5-chloride indole (303 mg, 2 mmol) and silica gel mixture (prepared above, 1.15 g) was added (E)-methyl 3-nitroacrylate (262 mg, 2 mmol), and the mixture was stirred for 2 hrs. The reaction mixture was filtered through a pad of celite and washed with ethylacetate (3×10 ml). The combined organic phase was concentrated and purified via silica gel chromatography (hexane/EA 8:1 to 5:1) to provide methyl 2-(5-chloro-1H-indol-3-yl)-3-nitropropanoate (424 mg, yield 75%). $^1$H NMR (500 MHz, CDCl$_3$) δ 8.37 (s, 1H), 7.65-7.60 (m, 1H), 7.32 (dd, J=8.7, 1.0 Hz, 1H), 7.21 (dt, J=8.7, 1.5 Hz, 1H), 7.19-7.15 (m, 1H), 5.20 (ddd, J=14.2, 9.3, 1.1 Hz, 1H), 4.75-4.63 (m, 2H), 3.77 (d, J=1.2 Hz, 3H).

Methyl 3-amino-2-(5-chloro-1H-indol-3-yl)propanoate: To the solution of methyl 2-(5-chloro-1H-indol-3-yl)-3-nitropropanoate (60 mg, 0.212 mmol) and Zinc (278 mg, 4.245 mmol) was added acetic acid (1.2 ml, 21.2 mmol) and the reaction mixture was stirred at room temperature for 16 hrs. LC-MS showed all the starting material disappeared. The reaction mixture was filtered off celite and washed with ethylacetate (3×3 ml). The filtrates was concentrated under reduced pressure, basified with 1N NaOH solution, and extracted with ethyl acetate (3×5 ml). The combined organic phase was washed with brine and dried over Na$_2$SO$_4$, concentrated and purified via silica gel chromatography (DCM/MeOH 20:1 to 3:1) to provide methyl 3-amino-2-(5-chloro-1H-indol-3-yl)propanoate (46 mg, yield 85%). $^1$H NMR (500 MHz, Methanol-d$_4$) δ 7.61 (d, J=2.1 Hz, 1H), 7.33 (d, J=8.6 Hz, 1H), 7.25 (s, 1H), 7.09 (dd, J=8.6, 2.0 Hz, 1H), 4.01 (dd, J=8.3, 6.4 Hz, 1H), 3.69 (s, 3H), 3.32 (q, J=1.6 Hz, 1H), 3.07 (dd, J=12.9, 6.4 Hz, 1H).

Methyl 6-chloro-2,3,4,9-tetrahydro-1H-pyrido[3,4-b]indole-4-carboxylate: Formalin (35% solution, 0.194 ml, 2.612 mmol) was added into the solution of methyl 3-amino-2-(5-chloro-1H-indol-3-yl) propanoate (550 mg, 2.176 mmol) and conc. HCl (0.181 ml, 2.176 mmol) in methanol (5 ml), and the mixture was stirred at room temperature for 16 hrs. The precipitate formed during the reaction was collected and washed with methanol twice, and dried over vacuum to give Methyl 6-chloro-2,3,4,9-tetrahydro-1H-pyrido[3,4-b]indole-4-carboxylate as its hydrochloride salt (374 mg, yield 65%). $^1$H NMR (500 MHz, Methanol-d$_4$) δ 11.11 (s, 1H), 7.67 (d, J=2.0 Hz, 1H), 7.36 (d, J=8.7 Hz, 1H), 7.16 (dd, J=8.7, 2.1 Hz, 1H), 4.55-4.41 (m, 2H), 4.29 (t, J=3.8 Hz, 1H), 4.03 (dd, J=12.9, 2.6 Hz, 1H), 3.80 (s, 3H), 3.57 (dd, J=12.9, 4.9 Hz, 1H).

(6-Chloro-2,3,4,9-tetrahydro-1H-pyrido[3,4-b]indol-4-yl)methanol: LiAlH$_4$ powder (182 mg, 4.8 mmol) was added in three portions to the solution of methyl 6-chloro-2,3,4,9-tetrahydro-1H-pyrido[3,4-b]indole-4-carboxylate (240 mg, 0.8 mmol) in anhydrous THF (6 ml) under Argon at 0° C. After stirring at room temperature for 30 min, the reaction mixture was heated to reflux for 16 hrs. The mixture was then cooled to room temperature, and quenched with water and sodium hydroxide solution. The suspension then underwent filtration and the filtrates were washed with diethyl ether (3×10 ml). The combined organic solution was concentrated and purified by silica gel flash chromatography (DCM/MeOH=10:1 to 5:1) to afford (6-chloro-2,3,4,9-tetrahydro-1H-pyrido[3,4-b]indol-4-yl)methanol (161 mg, yield 85%). $^1$H NMR (500 MHz, Chloroform-d) δ 8.37 (s, 1H), 7.47 (d, J=2.0 Hz, 1H), 7.13 (d, J=8.6 Hz, 1H), 7.06 (dd, J=8.6, 2.0 Hz, 1H), 4.07 (dd, J=10.5, 3.2 Hz, 1H), 4.01 (d, J=4.5 Hz, 1H), 3.91 (d, J=15.4 Hz, 1H), 3.81 (d, J=15.4 Hz, 1H), 3.40 (dd, J=12.4, 2.2 Hz, 1H), 3.12 (dd, J=12.4, 4.3 Hz, 1H), 3.00 (d, J=3.5 Hz, 1H).

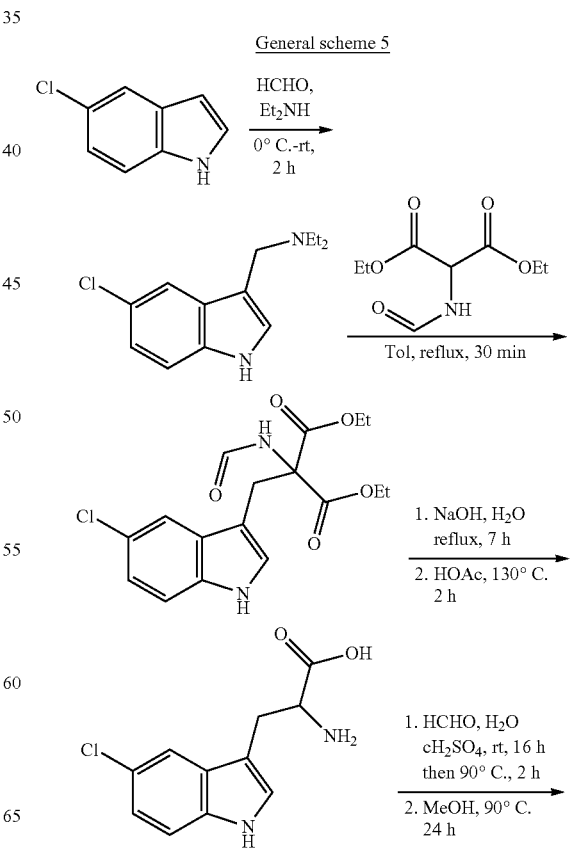

General scheme 5

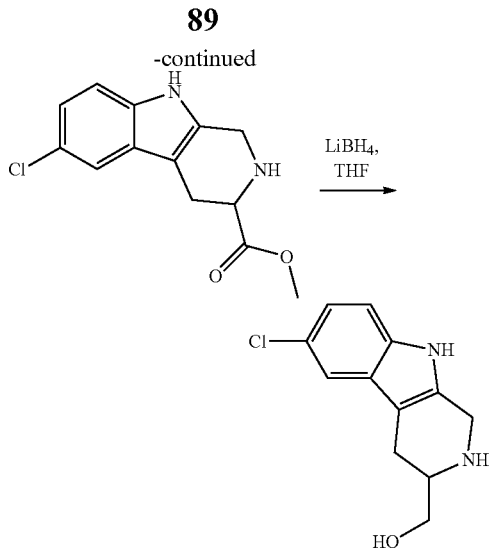

N-((5-chloro-1H-indol-3-yl)methyl)-N-ethylethanamine: To a mixture of 30% formaldehyde (6.0 mL) and dimethylamine (5.8 g, 79.2 mmol, 1.2 eq) in 60% acetic acid (18 mL) was added 5-chloro-1H-indole (10.0 g, 66.0 mmol, 1.0 eq). The mixture was stirred at room temperature for 4 hrs. The mixture was poured into 15% aq. NaOH solution (500 mL) at 0° C. The resulting mixture was extracted with CH$_2$Cl$_2$ (3×100 mL). The organic phase was dried over anhydrous sodium sulfate and concentrated in vacuo to give a crude product which was purified by silica gel column chromatography (CH$_2$Cl$_2$/CH$_3$OH=10:1~5:1) to give N-((5-chloro-1H-indol-3-yl)methyl)-N-ethylethanamine (3.3 g, yield: 21%) as a white solid.

N-((5-chloro-1H-indol-3-yl)methyl)-N-ethylethanamine: To a mixture of N-((5-chloro-1H-indol-3-yl)methyl)-N-ethylethanamine (3.30 g, 13.94 mmol, 1.0 eq) and diethyl 2-formamidomalonate (5.67 g, 27.88 mmol, 2.0 eq) in toluene (50 mL) was added NaOH (195 mg, 4.88 mmol, 0.35 eq). The mixture was stirred at 125° C. for 24 hrs. The reaction suspension was concentrated in vacuo to give a crude product which was purified by silica gel column chromatography (petroleum ether:EtOAc=5:1~0:1) to give N-((5-chloro-1H-indol-3-yl)methyl)-N-ethylethanamine (3.5 g, yield: 68%) as a yellowish white solid.

2-Amino-3-(5-chloro-1H-indol-3-yl)propanoic acid: To a mixture of N-((5-chloro-1H-indol-3-yl)methyl)-N-ethylethanamine (700 mg, 1.9 mmol, 1.0 eq) in H$_2$O (10 mL) was added NaOH (304 mg, 7.6 mmol, 4.0 eq). The mixture was stirred at 100° C. for 7 hrs. Acetic acid (1.5 mL) was added and the mixture was stirred at 130° C. for 5 hrs. After cooling the solution to room temperature, the precipitates were collected by filtration to give a crude product 2-amino-3-(5-chloro-1H-indol-3-yl)propanoic acid or 5-chlorotryptophan (550 mg, crude) as a white solid.

6-Chloro-2,3,4,9-tetrahydro-1H-pyrido[3,4-b]indole-3-carboxylic acid (Chemical & Pharmaceutical Bulletin, 35(8), 3284-91; 1987): 5-chlorotrytophan (239 mg, 1.0 mmol), 35% formalin (0.1 ml, 1.17 mmol) and 0.1 M H$_2$SO$_4$ (1.56 ml) in 0.55 ml H$_2$O and 0.78 ml EtOH was stirred for 18 hrs at room temperature. The resulting precipitates were collected and washed with water (3×1 ml), dried over high vacuum to afford 6-chloro-2,3,4,9-tetrahydro-1H-pyrido[3,4-b]indole-3-carboxylic acid (200 mg, yield: 80%). The crude product was taken to the next step without further purification. LC-MS: [M+H]$^+$: 251.0.

(6-Chloro-2,3,4,9-tetrahydro-1H-pyrido[3,4-b]indol-3-yl)methanol: LiAlH$_4$ powder (182 mg, 4.788 mmol) was added in three portions to the solution of 6-chloro-2,3,4,9-tetrahydro-1H-pyrido[3,4-b]indole-3-carboxylic acid (200 mg, 0.798 mmol) in anhydrous THF (5 ml) under Argon at 0° C. After stirring at room temperature for 30 min, the reaction mixture was heated to reflux for 16 hrs, then cooled to room temperature and quenched with water and sodium hydroxide solution. The suspension was filtered and washed with diethyl ether (3×10 ml). The filtrates was dried over sodium sulfate, concentrated and purified via silica gel flash chromatography (DCM/MeOH=10:1 to 3:1) to afford (6-chloro-2,3,4,9-tetrahydro-1H-pyrido[3,4-b]indol-3-yl)methanol (150 mg, yield 80%). $^1$H NMR (500 MHz, Methanol-d$_4$) δ 7.42 (d, J=2.0 Hz, 1H), 7.30 (d, J=8.6 Hz, 1H), 7.07 (dd, J=8.6, 2.1 Hz, 1H), 4.37-4.22 (m, 2H), 3.93 (dd, J=11.7, 4.1 Hz, 1H), 3.75 (dd, J=11.7, 7.0 Hz, 1H), 3.50-3.42 (m, 1H), 2.92 (ddd, J=15.7, 4.8, 1.1 Hz, 1H), 2.82-2.72 (m, 1H).

General scheme 6

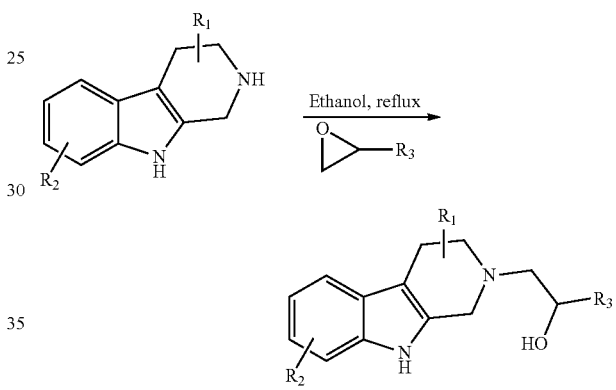

To the solution of the amine (1.0 equiv.) and N, N-diisopropylethylamine (3.0 equiv.) in anhydrous ethanol was added the epoxide (1.2 equiv.) in ethanol. The reaction mixture was heated at reflux for 12 hrs, then concentrated and purified by silica gel flash chromatography to afford the desired product (yields, 30-60%).

2-(6-Chloro-8-methoxy-1,3,4,9-tetrahydro-2H-pyrido[3,4-b]indol-2-yl)-1-(3-chlorophenyl)ethan-1-ol (Journal of Medicinal Chemistry, 51(6), 1925-1944; 2008)

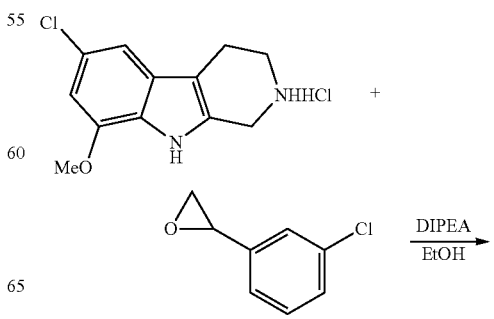

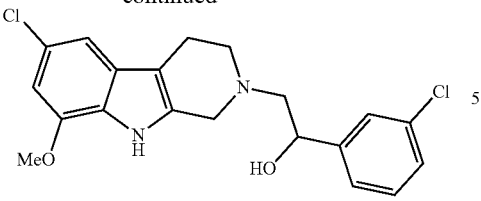

To the solution of 6-chloro-8-methoxy-2,3,4,9-tetrahydro-1H-pyrido[3,4-b]indole hydrochloride (41 mg, 0.15 mmol) and DIPEA (0.078 ml, 0.45 mmol) in anhydrous ethanol (2 ml) was added 2-(3-chlorophenyl)oxirane (28 mg, 0.18 mmol). Then the reaction mixture was heated to reflux overnight. The mixture was concentrated and purified by silica gel column chromatography to afford 2-(6-chloro-8-methoxy-1,3,4,9-tetrahydro-2H-pyrido[3,4-b]indol-2-yl)-1-(3-chlorophenyl)ethan-1-ol (17 mg, 60%). $^1$H NMR (500 MHz, Chloroform-d) δ 8.08 (s, 1H), 7.44 (d, J=2.1 Hz, 1H), 7.28 (d, J=3.5 Hz, 3H), 7.10 (d, J=1.6 Hz, 1H), 6.62 (s, 1H), 4.83 (dd, J=10.5, 3.3 Hz, 1H), 3.94 (s, 3H), 3.94-3.87 (m, 1H), 3.75 (d, J=14.6 Hz, 1H), 3.18-3.04 (m, 1H), 2.90 (ddd, J=11.8, 6.8, 4.9 Hz, 1H), 2.85 (dd, J=12.6, 3.4 Hz, 1H), 2.82-2.77 (m, 2H), 2.64 (dd, J=12.7, 10.5 Hz, 1H).

2-(6-Chloro-1-methyl-1,3,4,9-tetrahydro-2H-pyrido[3,4-b]indol-2-yl)-1-(3,4-dichlorophenyl)ethan-1-ol formate

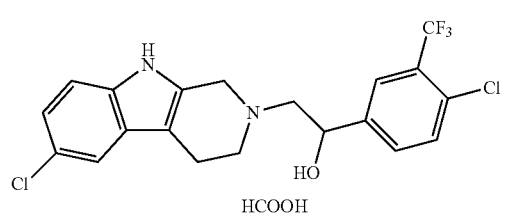 [SMILES: OC(CN1CCc2c([nH]c3ccc(Cl)cc23)C1)c1ccc(Cl)c(C(F)(F)F)c1 ; "HCOOH"]

$^1$H NMR (400 MHz, DMSO-d$_6$) δ 10.89 (d, J=10.0 Hz, 1H), 8.16 (s, 1H), 7.62 (t, J=2.2 Hz, 1H), 7.56 (dd, J=8.3, 3.4 Hz, 1H), 7.43-7.32 (m, 2H), 7.26 (dd, J=8.5, 3.5 Hz, 1H), 6.99 (dt, J=8.6, 1.6 Hz, 1H), 4.74 (t, J=6.3 Hz, 1H), 3.81 (dq, J=12.9, 6.7 Hz, 1H), 3.17-2.90 (m, 2H), 2.72 (dddt, J=38.0, 18.9, 13.0, 6.3 Hz, 4H), 2.46 (s, 1H), 1.26 (dd, J=53.0, 6.6 Hz, 3H). LCMS: [M+H]$^+$=409.1

2-(6-Chloro-1,3,4,9-tetrahydro-2H-pyrido[3,4-b]indol-2-yl)-1-(4-chloro-3-(trifluoromethyl)phenyl)ethan-1-ol formate

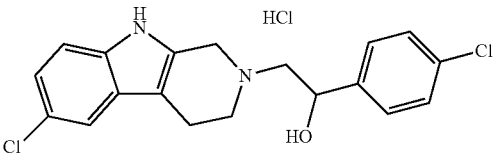 [SMILES: Cl ; OC(CN1CCc2c([nH]c3ccc(Cl)cc23)C1)c1ccc(Cl)cc1]

$^1$H NMR (400 MHz, DMSO-d$_6$) δ 10.92 (s, 1H), 8.15 (s, 1H), 7.87 (d, J=1.9 Hz, 1H), 7.76-7.64 (m, 2H), 7.38 (d, J=2.1 Hz, 1H), 7.27 (d, J=8.5 Hz, 1H), 6.99 (dd, J=8.5, 2.1 Hz, 1H), 5.51 (s, 1H), 4.93 (t, J=6.3 Hz, 1H), 3.80-3.63 (m, 2H), 2.95-2.66 (m, 4H), 2.64 (d, J=5.7 Hz, 2H). LCMS: [M+H]$^+$=429.1, 431.1.

2-(6-Chloro-1,3,4,9-tetrahydro-2H-pyrido[3,4-b]indol-2-yl)-1-(3-chloro-5-(trifluoromethyl)phenyl)ethan-1-ol formate

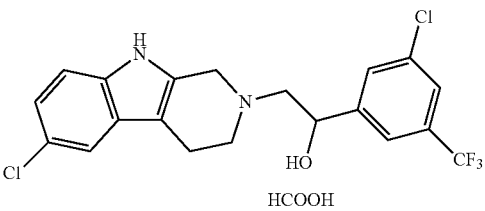 [SMILES: OC(CN1CCc2c([nH]c3ccc(Cl)cc23)C1)c1cc(Cl)cc(C(F)(F)F)c1 ; "HCOOH"]

$^1$H NMR (400 MHz, DMSO-d$_6$): δ 10.92 (s, 1H), 8.16 (s, 1H), 7.82-7.69 (m, 3H), 7.38 (d, J=1.7 Hz, 1H), 7.27 (d, J=8.5 Hz, 1H), 6.99 (m, J=8.5 Hz, 1H), 5.57 (s, 1H), 4.95 (t, J=6.1 Hz, 1H), 3.86-3.65 (m, 2H), 2.89 (m, J=5.6 Hz, 1H), 2.84-2.71 (m, 3H), 2.63 (t, J=4.8 Hz, 2H). LCMS: [M+H]$^+$=429.1, 431.1.

3-(6-Chloro-1,3,4,9-tetrahydro-2H-pyrido[3,4-b]indol-2-yl)-1-(3-chlorophenyl)propan-1-ol

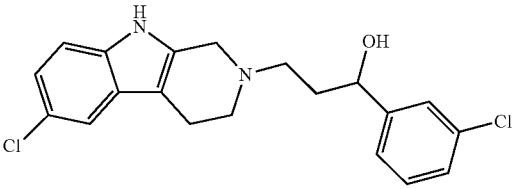 [SMILES: OC(CCN1CCc2c([nH]c3ccc(Cl)cc23)C1)c1cccc(Cl)c1]

$^1$H NMR (400 MHz, DMSO-d$_6$): δ 10.91 (s, 1H), 7.39 (d, J=8.3 Hz, 2H), 7.35 (d, J=7.6 Hz, 1H), 7.33-7.25 (m, 3H), 7.00 (m, 1H), 5.58 (s, 1H), 4.69 (t, J=6.1 Hz, 1H), 3.61 (s, 2H), 2.76 (s, 2H), 2.71-2.58 (m, 4H), 1.97-1.70 (m, 2H). LCMS: [M+H]$^+$=375.0, 377.0

2-(6-Chloro-3,4-dihydro-1H-pyrido[3,4-b]indol-2(9H)-yl)-1-(4-chlorophenyl)ethanol hydrochloride

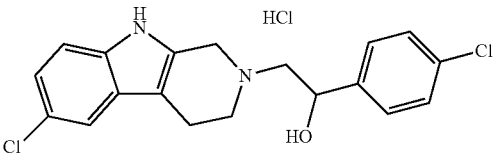 [SMILES: Cl ; OC(CN1CCc2c([nH]c3ccc(Cl)cc23)C1)c1ccc(Cl)cc1]

$^1$H NMR (400 MHz, DMSO-d$_6$): δ 11.36 (d, J=8.4 Hz, 1H), 10.65~10.58 (m, 1H), 7.56~7.52 (m, 2H), 7.45~7.38 (m, 4H), 7.13 (d, J=8.8 Hz, 1H), 6.51~6.43 (m, 1H), 5.32~5.25 (m, 1H), 4.77~4.54 (m, 2H), 3.92~3.63 (m, 1H), 3.55~3.41 (m, 2H), 3.13~2.96 (m, 2H). LCMS: [M+H]$^+$=361.0.

2-(6-Chloro-3,4-dihydro-1H-pyrido[3,4-b]indol-2 (9H)-yl)-1-(4-(trifluoromethyl)phenyl)ethanol

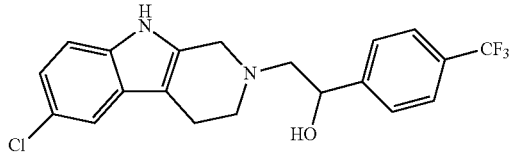 [SMILES: OC(CN1CCc2c([nH]c3ccc(Cl)cc23)C1)c1ccc(C(F)(F)F)cc1]

¹H NMR (400 MHz, DMSO-d₆): δ 10.92 (s, 1H), 7.69~7.61 (m, 4H), 7.38 (d, J=1.6 Hz, 1H), 7.28 (d, J=8.4 Hz, 1H), 7.00 (dd, J=8.4, 2.0 Hz, 1H), 5.4 (d, J=2.8 Hz, 1H), 4.92 (s, 1H), 3.78~3.70 (m, 2H), 2.89~2.63 (m, 6H). LCMS: [M+H]⁺=395.1.

2-(6-Chloro-3,4-dihydro-1H-pyrido[3,4-b]indol-2 (9H)-yl)-1-(3-(trifluoromethyl)phenyl)ethanol

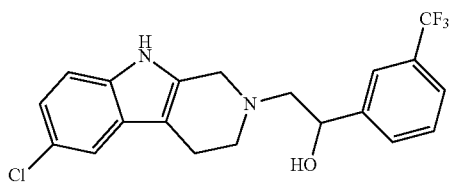 [SMILES: OC(CN1CCc2c([nH]c3ccc(Cl)cc23)C1)c1cccc(C(F)(F)F)c1]

¹H NMR (400 MHz, DMSO-d₆): δ 10.92 (s, 1H), 7.75 (s, 1H), 7.71 (d, J=7.2 Hz, 1H), 7.59~7.56 (m, 2H), 7.38 (d, J=2.0 Hz, 1H), 7.28 (d, J=8.4 Hz, 1H), 7.00 (dd, J=8.4, 2.0 Hz, 1H), 5.41 (s, 1H), 4.93 (t, J=5.2 Hz, 1H), 3.78~3.70 (m, 2H), 2.89~2.64 (m, 6H). LCMS: [M+H]⁺=395.0.

2-(6-Chloro-3,4-dihydro-1H-pyrido[3,4-b]indol-2 (9H)-yl)-1-(3,4-dichlorophenyl)ethanol formate

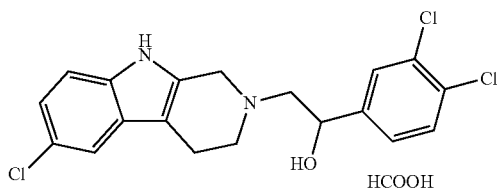 [SMILES: OC(CN1CCc2c([nH]c3ccc(Cl)cc23)C1)c1ccc(Cl)c(Cl)c1 ; "HCOOH"]

¹H NMR (400 MHz, DMSO-d₆): δ 10.92 (s, 1H), 8.18 (s, 1H), 7.64 (d, J=1.6 Hz, 1H), 7.59 (d, J=8.4 Hz, 1H), 7.40~7.37 (m, 2H), 7.28 (d, J=8.4 Hz, 1H), 7.00 (dd, J=8.4, 2.0 Hz, 2H), 4.84 (t, J=5.6 Hz, 2H), 3.76~3.68 (m, 2H), 2.91~2.62 (m, 6H). LCMS: [M+H]⁺=395.0.

3-Chloro-5-(2-(6-chloro-3,4-dihydro-1H-pyrido[3,4-b]indol-2(9H)-yl)-1-hydroxyethyl)phenol

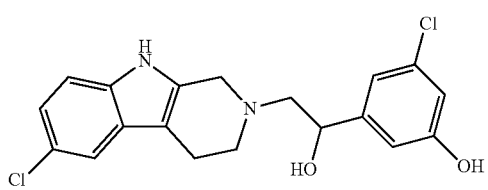 [SMILES: Oc1cc(Cl)cc(C(O)CN2CCc3c([nH]c4ccc(Cl)cc34)C2)c1]

¹H NMR (400 MHz, DMSO-d₆): δ 10.92 (s, 1H), 9.84 (s, 1H), 7.38 (d, J=1.6 Hz, 1H), 7.28 (d, J=8.8 Hz, 1H), 6.99 (dd, J=1.6, 8.4 Hz, 1H), 6.85 (s, 1H), 6.76 (s, 1H), 6.66~6.65 (m, 1H), 5.24 (s, 1H), 4.73 (s, 1H), 2.73 (s, 2H), 2.88~2.81 (m, 2H), 2.73~2.63 (m, 4H). LCMS: [M+H]⁺=377.2.

2-(6-Chloro-3,4-dihydro-1H-pyrido[3,4-b]indol-2 (9H)-yl)-1-(3-chlorophenyl)-ethanamine formate

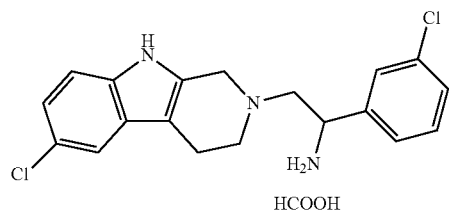 [SMILES: NC(CN1CCc2c([nH]c3ccc(Cl)cc23)C1)c1cccc(Cl)c1 ; "HCOOH"]

¹H NMR (400 MHz, CD₃OD): δ 7.46~7.42 (m, 3H), 7.34~7.31 (m, 2H), 7.21 (d, J=8.4 Hz, 1H), 6.99 (dd, J=8.4, 2.0 Hz, 1H), 4.14~4.1 (m, 1H), 3.82~3.72 (m, 2H), 3.62 (d, J=14.0 Hz 1H), 3.22 (dd, J=13.6, 5.2 Hz, 1H), 3.08~3.05 (m, 1H), 2.79~2.78 (m, 2H), 2.64~2.61 (m, 1H). LCMS: [M+H]⁺=360.2.

2-(6-Chloro-3,4-dihydro-1H-pyrido[3,4-b]indol-2 (9H)-yl)-1-(3-chloro-4-fluorophenyl)ethanol formate

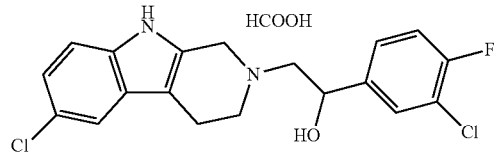 [SMILES: OC(CN1CCc2c([nH]c3ccc(Cl)cc23)C1)c1ccc(F)c(Cl)c1 ; "HCOOH"]

¹H NMR (400 MHz, DMSO-d₆): δ 10.92 (s, 1H), 8.39 (s, H), 7.59 (dd, J=7.2, 1.6 Hz, 1H), 7.42~7.33 (m, 3H), 7.28 (d, J=8.4 Hz, 1H), 7.00 (dd, J=8.8, 2.4 Hz, 1H), 4.84~4.81 (m, 1H), 3.76~3.58 (m, 2H), 2.89~2.62 (m, 6H). LCMS: [M+H]⁺=379.2.

2-(6-Chloro-3,4-dihydro-1H-pyrido[3,4-b]indol-2 (9H)-yl)-1-(2,3-dichlorophenyl)ethanol

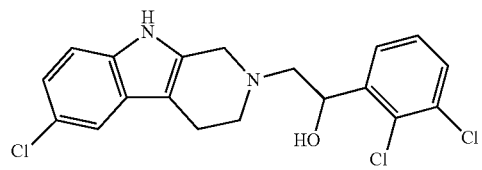 [SMILES: OC(CN1CCc2c([nH]c3ccc(Cl)cc23)C1)c1cccc(Cl)c1Cl]

¹H NMR (400 MHz, DMSO-d₆): δ 10.92 (s, 1H), 7.62~7.60 (m, 1H), 7.55~7.53 (m, 1H), 7.41~7.37 (m, 2H), 7.28 (d, J=8.4 Hz, 1H), 7.00~6.97 (m, 1H), 5.57 (s, 1H), 5.22~5.21 (m, 1H), 3.78~3.77 (m, 2H), 2.90 (t, 2H), 2.71~2.65 (m, 4H). LCMS: [M+H]⁺=395.0.

2-(6-Chloro-3,4-dihydro-1H-pyrido[3,4-b]indol-2(9H)-yl)-1-(4-(trifluoromethyl)phenyl)ethanol

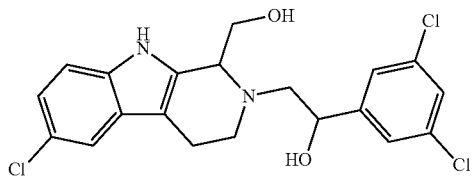 [SMILES: OCC1c2[nH]c3ccc(Cl)cc3c2CCN1CC(O)c1cc(Cl)cc(Cl)c1]

¹H NMR (400 MHz, DMSO-d₆): δ 10.87 (s, 1H), 7.47~7.45 (m, 3H), 7.41 (s, 1H), 7.30 (d, J=8.8 Hz, 1H), 7.0 (d, J=8.4 Hz, 1H), 5.49 (s, 1H), 4.80 (d, J=4.0 Hz, 2H), 3.79~3.77 (m, 1H), 3.68 (s, 2H), 3.07~3.04 (m, 1H), 2.91~2.87 (m, 1H), 2.83~2.73 (m, 2H), 2.69~2.64 (m, 1H), 2.45~2.42 (m, 1H). LCMS: [M+H]⁺=427.2

2-(6-Chloro-1-(hydroxymethyl)-3,4-dihydro-1H-pyrido[3,4-b]indol-2(9H)-yl)-1-(3-chloro-4-methylphenyl)ethanol formate

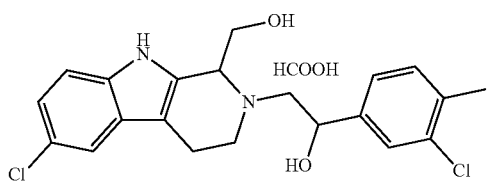 [SMILES: Cc1ccc(C(O)CN2CCc3c([nH]c4ccc(Cl)cc34)C2CO)cc1Cl ; "HCOOH"]

¹H NMR (400 MHz, DMSO-d₆): δ 10.88~10.84 (m, 1H), 8.23 (s, 1H), 7.42~7.39 (m, 2H), 7.31~7.20 (m, 3H), 7.02~6.99 (m, 1H), 5.25 (brs, 1H), 4.75~4.68 (m, 2H), 3.86~3.77 (m, 1H), 3.68~3.59 (m, 2H), 3.20~3.05 (m, 2H), 2.92~2.86 (m, 1H), 2.80~2.72 (m, 1H), 2.68~2.58 (m, 1H), 2.46~2.41 (m, 1H), 2.95~2.89 (m, 3H). LCMS: [M+H]⁺=405.0.

2-(6-Chloro-1-(morpholinomethyl)-1,3,4,9-tetrahydro-2H-pyrido[3,4-b]indol-2-yl)-1-(3,4-dichlorophenyl)ethan-1-ol dihydrochloride

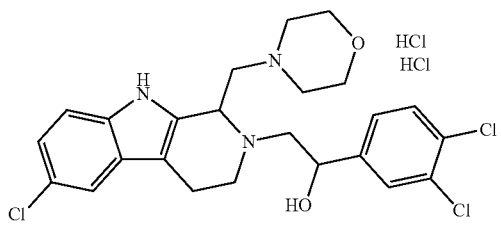 [SMILES: OC(CN1CCc2c([nH]c3ccc(Cl)cc23)C1CN1CCOCC1)c1ccc(Cl)c(Cl)c1 ; Cl ; Cl]

¹H NMR (400 MHz, Methanol-d₄): δ 7.69-7.64 (m, 1H), 7.53-7.49 (m, 2H), 7.42-7.36 (m, 2H), 7.18-7.15 (m, 1H), 5.30 (br, 1H), 4.40-2.80 (m, 18H). LCMS: [M+H]⁺=494.5

2-(6-Chloro-1-((4-methylpiperazin-1-yl)methyl)-1,3,4,9-tetrahydro-2H-pyrido[3,4-b]indol-2-yl)-1-(3,4-dichlorophenyl)ethan-1-ol trihydrochloride

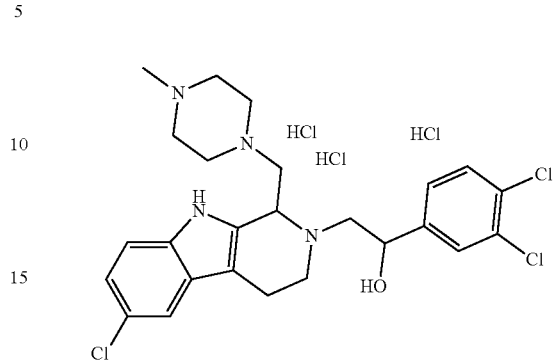

¹H NMR (400 MHz, Methanol-d₄) δ 7.70 (s, 1H), 7.53-7.50 (m, 2H), 7.45-7.34 (m, 2H), 7.17-7.13 (m, 1H), 5.57-5.45 (m, 1H), 5.32-5.23 (m, 1H), 3.95-3.72 (m, 2H), 3.59-3.39 (m, 7H), 3.30-3.10 (m, 5H), 2.95 (d, J=6.4 Hz, 3H), 2.91-2.58 (m, 2H). LCMS: [M+H]⁺=509.2.

2-(6-chloro-4-methyl-1,3,4,9-tetrahydro-2H-pyrido[3,4-b]indol-2-yl)-1-(2,3-dichlorophenyl)ethan-1-ol hydrochloride

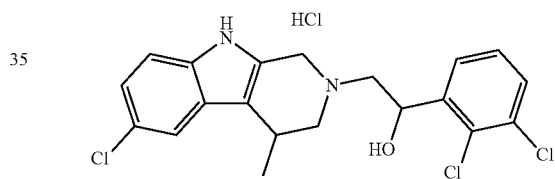

¹H NMR (400 MHz, Methanol-d₄) δ 10.91-10.85 (m, 0.49H), 7.75-7.72 (m, 1H), 7.63-7.56 (m, 2H), 7.44-7.33 (m, 2H), 7.13 (d, J=8.4 Hz, 1H), 5.73-5.21 (m, 1H), 4.85-4.51 (m, 2H), 4.10-3.90 (m, 1H), 3.86-3.54 (m, 2H), 3.48-3.40 (m, 1H), 3.29-3.11 (m, 1H), 1.58-1.47 (m, 3H). LCMS: [M+H]⁺=409.2.

General scheme 7

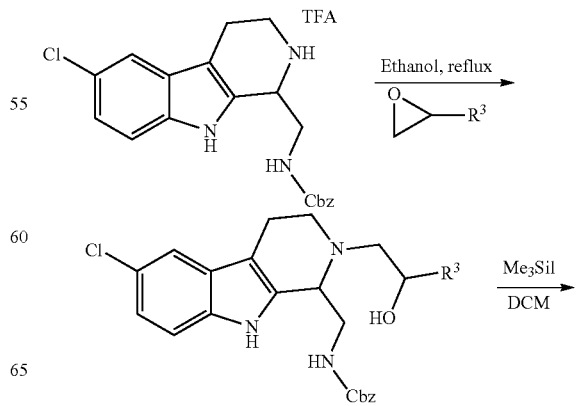

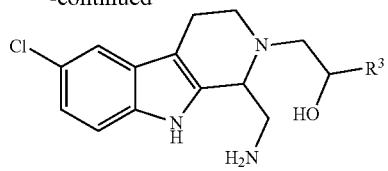

Representative synthesis of compound 2-(1-(aminomethyl)-6-chloro-1,3,4,9-tetrahydro-2H-pyrido[3,4-b]indol-2-yl)-1-(3,4-dichlorophenyl)ethan-1-ol To a mixture of DMSO (40 mL) was added 95% NaH (704 mg, 27.88 mmol). The mixture was stirred for 15 min at RT. To this was added trimethylsulfoxonium iodide (6.04 g, 27.43 mmol) in portions at RT. The mixture was stirred for 3 h at 40° C. Then 3,4-dichlorobenzaldehyde (4 g, 22.86 mmol) was added dropwise. The mixture was stirred for 3 hrs at RT, then was quench with aq. NH₄Cl and extracted with EtOAc (3*40 mL). The organic layer was dried with Na₂SO₄ and filtered. The filtrate was concentrated to afford 2-(3,4-dichlorophenyl)oxirane (1.3 g, yield: 30.1%)

To a mixture of 2-(3,4-dichlorophenyl)oxirane (89.08 mg, 0.471 mmol) in EtOH (10 mL) was added benzyl ((6-chloro-2-(2,2,2-trifluoroacetyl)-2,3,4,9-tetrahydro-1H-2l4-pyrido [3,4-b]indol-1-yl)methyl)carbamate (200 mg, 0.428 mmol) and Et₃N (130.05 mg, 1.29 mmol). The mixture was stirred at 80° C. for 16 hrs. The mixture was then concentrated, and the residue was purified by silica gel column chromatography (PE:EtOAc=3:1) to afford benzyl((6-chloro-2-(2-(3,4-dichlorophenyl)-2-hydroxyethyl)-2,3,4,9-tetrahydro-1H-pyrido[3,4-b]indol-1-yl)methyl)carbamate (110 mg, yield: 45.9%) as a colorless oil. This material was taken to the next step directly. LCMS: [M+H]⁺=559.8

To a mixture of benzyl((6-chloro-2-(2-(3,4-dichlorophenyl)-2-hydroxyethyl)-2,3,4,9-tetrahydro-1H-pyrido[3,4-b]indol-1-yl)methyl)carbamate (110 mg, 0.197 mmol) in DCM (10 mL) was added TMSI (0.22 mL, 1.35 mmol). The mixture was stirred at 0° C. to RT for 4 hrs. LCMS showed the reaction was completed. The mixture was added dropwise to the ice-water, then extracted with DCM (3*10 mL). The combined organic layer was concentrated to afford crude product which was further purified by prep-HPLC (mobile phase: 0.1% HCOOH/CH₃CN/H₂O) to give 2-(1-(aminomethyl)-6-chloro-1,3,4,9-tetrahydro-2H-pyrido[3,4-b]indol-2-yl)-1-(3,4-dichlorophenyl)ethan-1-ol(17 mg, yield: 20.3%) as a white solid. ¹H NMR (400 MHz, DMSO-d₆) δ 11.07 (s, 1H), 8.35 (s, 1H), 7.60 (ddd, J=18.8, 12.7, 5.0 Hz, 2H), 7.47-7.25 (m, 3H), 7.08-6.98 (m, 1H), 4.84 (d, J=9.2 Hz, 1H), 3.90 (s, 2H), 3.18-2.55 (m, 10H), 2.40 (s, 1H). LCMS: [M+1]⁺=424.0, 426.0.

General scheme 8

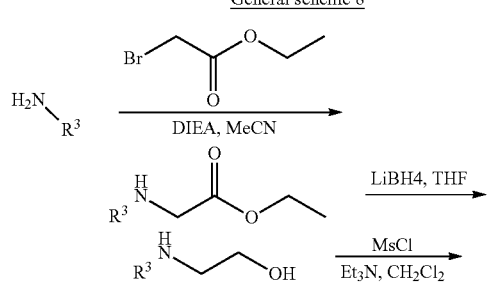

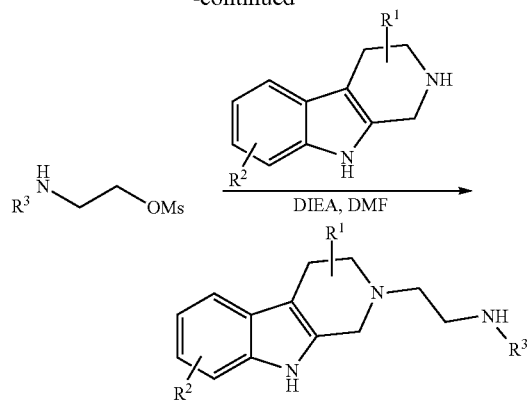

Representative synthesis of 3,5-dichloro-N-(2-(6-chloro-3,4-dihydro-1H-pyrido[3,4-b]indol-2(9H)-yl)ethyl)aniline

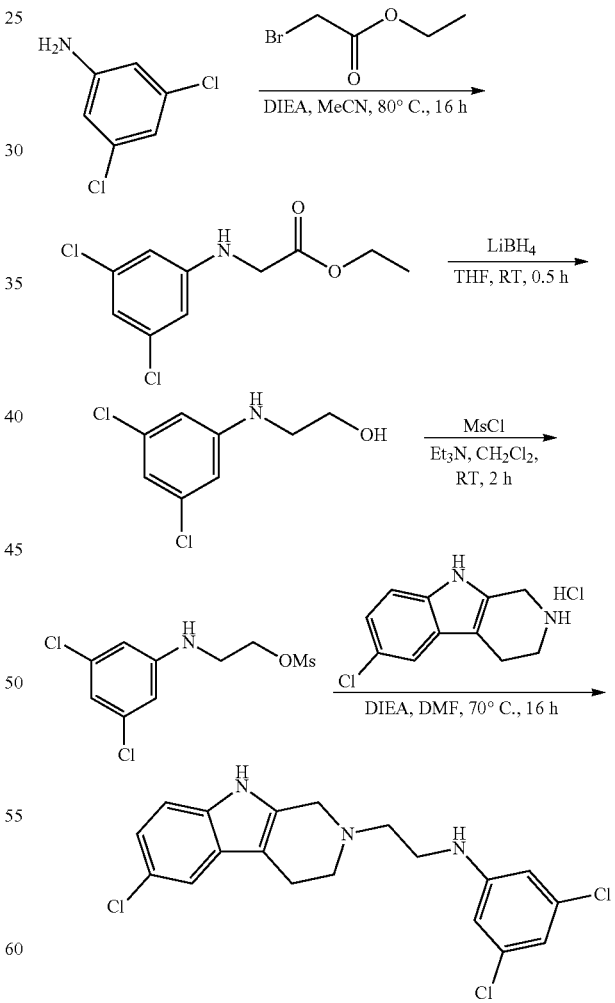

Ethyl 2-((3,5-dichlorophenyl)amino)acetate: A mixture of 3,5-dichloroaniline (500 mg, 3.51 mmol), ethyl 2-bromoacetate (585.6 mg, 3.51 mmol) and DIEA (1.36 g, 10.52 mmol) in MeCN (5 mL) was heated to 80° C. and stirred for 16 h.

The reaction solution was concentrated to give ethyl (3,5-dichlorophenyl)glycinate (800 mg, yield: 100%) as a yellow solid. LCMS: [M+H]$^+$=248.1

2-((3,5-Dichlorophenyl)amino)ethanol: To a solution of ethyl (3,5-dichlorophenyl)glycinate (800 mg, 3.23 mmol) in THF(10 mL) was drop-wise added LiBH$_4$ (2M in THF, 2.4 mL, 4.84 mmol). The reaction was stirred at RT for 2 h. The reaction was quenched with sat. NH$_4$Cl and extracted with EtOAc. The resulting solution was concentrated in vacuo to give a crude product which was purified by silica gel chromatography eluting with Petroleum ether:EtOAc=5:1 to give product 2-((3,5-dichlorophenyl)amino)ethan-1-ol (424 mg, yield: 67%) as a yellow oil. LCMS: [M+H]$^+$=206.1.

2-((3,5-Dichlorophenyl)amino)ethyl methanesulfonate: To a solution of 2-((3,5-dichlorophenyl)amino)ethan-1-ol (424 mg, 206 mmol) and Et$_3$N (624.8 mg, 6.17 mmol) in CH$_2$Cl$_2$ (10 mL) was drop-wise added MSCl (282.9 mg, 2.47 mmol). The reaction was stirred at RT for 2 h, then was quenched with water and extracted with CH$_2$Cl$_2$. The organic layer was dried over anhydrous Na$_2$SO$_4$, concentrated in vacuo to give 2-((3,5-dichlorophenyl) amino) ethyl methanesulfonate (640 mg, yield: 100%) as a brown oil. LCMS: [M+H]$^+$=283.9

3,5-Dichloro-N-(2-(6-chloro-3,4-dihydro-1H-pyrido[3,4-b]indol-2(9H)-yl)ethyl)aniline: A mixture of 2-((3,5-dichlorophenyl) amino) ethyl methanesulfonate (116.8 mg, 0.41 mmol), 6-chloro-2,3,4,9-tetrahydro-1H-pyrido[3,4-b]indole hydrochloride (100 mg, 0.41 mmol) and DIEA (159.2 mg, 1.23 mmol) in DMF (2 mL) was heated to 70° C. and stirred for 16 h. The reaction solution was concentrated, and the residue was purified by prep-HPLC (mobile phase: 0.1% NH$_4$HCO$_3$/CH$_3$CN/H$_2$O) to give 3,5-dichloro-N-(2-(6-chloro-1,3,4,9-tetrahydro-2H-pyrido[3,4-b]indol-2-yl)ethyl) aniline (25 mg, yield: 15%) as a yellow solid. $^1$H NMR (400 MHz, DMSO-d$_6$): δ 10.93 (s, 1H), 7.39 (d, J=2.0 Hz, 1H), 7.29 (d, J=8.4 Hz, 1H), 7.01 (dd, J=8.4, 2.0 Hz, 1H), 6.62 (d, J=2.0 Hz, 2H), 6.58 (t, J=2.0 Hz, 1H), 6.21 (t, J=5.2 Hz, 1H), 3.67 (s, 2H), 3.26~3.21 (m, 2H), 2.82 (t, J=6.0 Hz, 2H), 2.74 (t, J=8.4 Hz, 2H), 2.69-2.67 (m, 2H). LCMS: [M+H]$^+$=394.2

3-Chloro-N-(2-(6-chloro-3,4-dihydro-1H-pyrido[3,4-b]indol-2(9H)-yl)ethyl)aniline formate

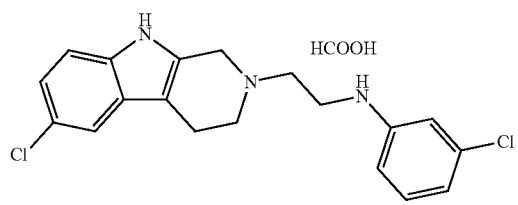 [SMILES: Clc1cccc(NCCN2CCc3c([nH]c4ccc(Cl)cc34)C2)c1 ; "HCOOH"]

$^1$H NMR (400 MHz, DMSO-d$_6$): δ 10.93 (s, 1H), 8.17 (s, 1H), 7.39 (d, J=2.0, Hz, 1H), 7.29 (d, J=8.8 Hz, 1H), 7.06 (t, J=8.0 Hz, 1H), 7.01 (dd, J=8.4, 2.0 Hz, 1H), 6.62 (t, J=2.0 Hz, 1H), 6.57~6.51 (m, 2H), 5.84 (s, 1H), 3.68 (s, 2H), 3.23 (d, J=4.4 Hz, 2H), 2.84~2.67 (m, 6H). LCMS: [M+H]$^+$=360.0.

4-Chloro-N-(2-(6-chloro-3,4-dihydro-1H-pyrido[3,4-b]indol-2 (9H)-yl)ethyl)aniline formate

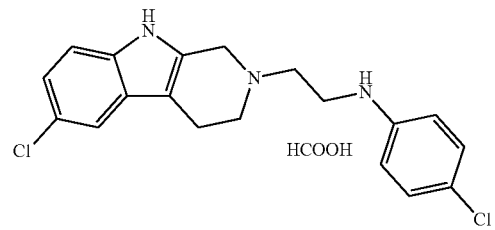 [SMILES: Clc1ccc(NCCN2CCc3c([nH]c4ccc(Cl)cc34)C2)cc1 ; "HCOOH"]

$^1$H NMR (400 MHz, DMSO-d$_6$): δ 10.94 (s, 1H), 8.22 (s, 1H), 7.39 (d, J=2.0 Hz, 1H), 7.28 (d, J=8.4 Hz, 1H), 7.08 (d, J=11.6 Hz, 2H), 6.99 (dd, J=2.0, 8.8 Hz, 1H), 6.61 (d, J=8.8 Hz, 2H), 5.69 (br, 1H), 3.68 (s, 2H), 3.22~3.19 (m, 2H), 2.84-2.81 (m, 2H), 2.77-2.74 (m, 2H), 2.69~2.68 (m, 2H). LCMS: [M+H]$^+$=360.2.

(6-Chloro-2-(2-((3-chlorophenyl)amino)ethyl)-2,3,4,9-tetrahydro-1H-pyrido[3,4-b]indol-1-yl)methanol

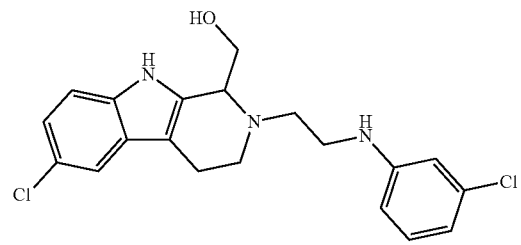 [SMILES: OCC1c2[nH]c3ccc(Cl)cc3c2CCN1CCNc1cccc(Cl)c1]

$^1$H NMR (400 MHz, DMSO-d$_6$): δ 10.85 (s, 1H), 7.41 (s, 1H), 7.40~7.24 (m, 1H), 7.01~6.79 (m, 2H), 6.61~6.58 (m, 3H), 5.83 (s, 1H), 4.76 (s, 1H), 3.71~3.62 (m, 3H), 3.17~3.10 (m, 3H), 2.90~2.71 (m, 4H), 2.47 (s, 1H). LCMS: [M+H]$^+$=390.3.

(6-Chloro-2-(2-((3,4-dichlorophenyl)amino)ethyl)-2,3,4,9-tetrahydro-1H-pyrido[3,4-b]indol-1-yl)methanol

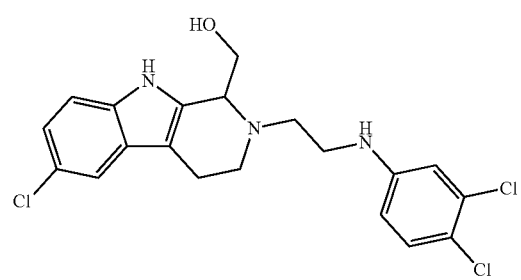 [SMILES: OCC1c2[nH]c3ccc(Cl)cc3c2CCN1CCNc1ccc(Cl)c(Cl)c1]

$^1$H NMR (400 MHz, DMSO-d$_6$): δ 10.85 (s, 1H), 7.41 (s, 1H), 7.40~7.24 (m, 2H), 7.01~6.99 (m, 1H), 6.80~6.79 (d, J=2.4 Hz, 1H), 6.61~6.58 (m, 1H), 6.05 (t, 1H), 4.76 (s, 1H), 3.71~3.62 (m, 3H), 3.17~3.10 (m, 3H), 2.90~2.71 (m, 4H), 2.44 (s, 1H). LCMS: [M+H]$^+$=426.3.

101

N-(2-(1-(Aminomethyl)-6-chloro-3,4-dihydro-1H-pyrido[3,4-b]indol-2(9H)-yl)ethyl)-3,4-dichloroaniline

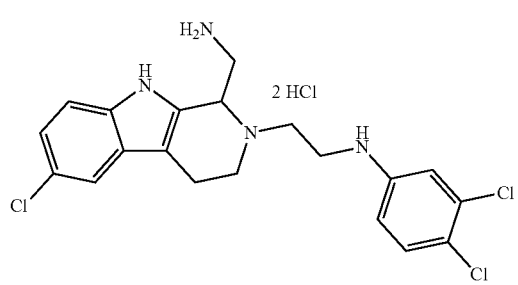 [SMILES: NCC1c2[nH]c3ccc(Cl)cc3c2CCN1CCNc1ccc(Cl)c(Cl)c1]

$^1$H NMR (400 MHz, DMSO-d$_6$): δ 11.31 (s, 1H), 8.20 (s, 2H), 7.46 (s, 1H), 7.34~7.32 (d, J=8.8 Hz, 1H), 7.26~7.24 (d, J=8.4 Hz, 1H), 7.07~7.04 (m, 1H), 6.88~6.87 (d, J=2.4 Hz, 1H), 6.69~6.66 (m, 1H), 6.52~6.22 (m, 1H), 4.04~4.02 (m, 2H), 3.20~3.16 (m, 3H), 3.09~3.03 (m, 2H), 2.96~2.93 (m, 1H), 2.86~2.71 (m, 3H), 2.54~2.52 (m, 2H). LCMS: [M+H]$^+$=423.0.

General scheme 9

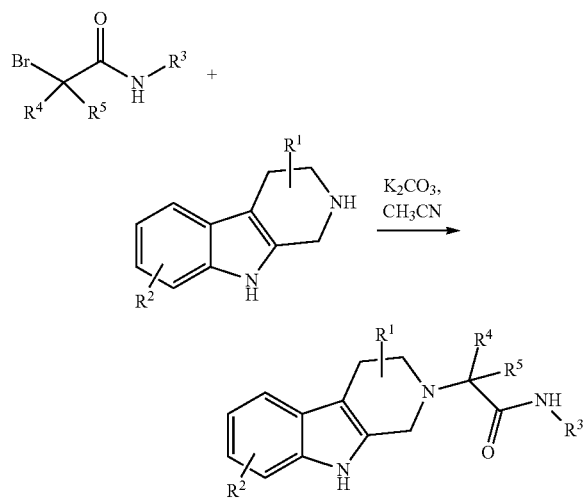

Representative synthesis of 2-(6-chloro-1-(hydroxymethyl)-1,3,4,9-tetrahydro-2H-pyrido[3,4-b]indol-2-yl)-N-(3-chlorophenyl)acetamide

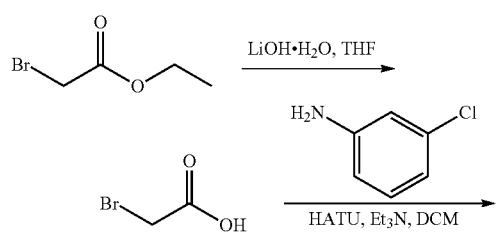

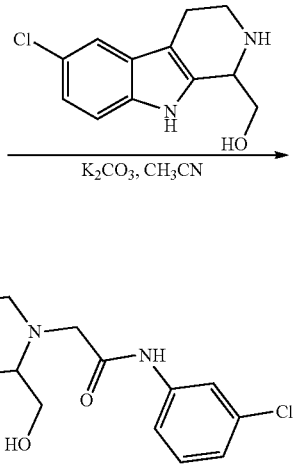

2-Bromoacetic acid: To a solution of 2-amino-2-(4-chlorophenyl)acetic acid (1 g, 5.90 mmol, 1.0 eq) in THF (10 mL) was added LiOH·H$_2$O (494 mg, 11.8 mmol, 2.0 eq), The reaction was stirred at 25° C. for 20 min. The reaction mixture was diluted with H$_2$O (5 mL) and acidified to pH=3-4 with 1 N HCl, extracted with ethyl acetate (20 mL×3). The organic solution was dried over Na$_2$SO$_4$ and concentrated to give 2-bromoacetic acid (1 g, 32.9% yield) as a colorless oil. [M–H]$^-$=137.0, 139.0.

2-Bromo-N-(3-chlorophenyl)acetamide: To a solution of 2-bromoacetic acid (1 g, 7.20 mmol, 1.0 eq), 3-chloroaniline (1.1 g, 7.90 mmol, 1.1 eq) and HATU (4 g, 10.80 mmol, 1.5 eq) in DCM (20 mL) was added Et$_3$N (1.45 g, 14.40 mmol, 2.0 eq) under argon. The reaction mixture was stirred at 25° C. for 3 hrs, was then quenched with H$_2$O (20 mL), extracted with EtOAc (20 mL×3). The organic solution was dried over Na$_2$SO$_4$ and concentrated. The residue was purified by silica gel chromatography (DCM:MeOH=20:1) to give 2-bromo-N-(3-chlorophenyl)acetamide (340 mg, 68.5% yield) as a colorless oil. LCMS: [M–H]$^-$=246.0, 248.0

2-(6-Chloro-1-(hydroxymethyl)-1,3,4,9-tetrahydro-2H-pyrido[3,4-b]indol-2-yl)-N-(3-chlorophenyl)acetamide: To a solution of 2-bromo-N-(3-chlorophenyl)acetamide (48 mg, 0.19 mmol, 1.0 eq) in DMF (2 mL) was added (6-chloro-2,3,4,9-tetrahydro-1H-pyrido[3,4-b]indol-1-yl)methanol (60 mg, 0.25 mmol, 1.3 eq) and K$_2$CO$_3$ (186 mg, 1.35 mmol, 7.0 eq). The reaction was stirred at 25° C. for 3 hrs, was then quenched with H$_2$O (20 mL), extracted with ethyl acetate (20 mL×3). The organic solution was dried over Na$_2$SO$_4$ and concentrated, and the residue was purified by prep-HPLC to give 2-(6-chloro-1-(hydroxymethyl)-1,3,4,9-tetrahydro-2H-pyrido[3,4-b]indol-2-yl)-N-(3-chlorophenyl) acetamide (9.29 mg, 11.88%) as a white solid.

$^1$H NMR (400 MHz, CDCl$_3$): δ 9.71 (s, 1H), 8.15 (s, 1H), 7.72 (s, 1H), 7.54-7.45 (m, 2H), 7.24-7.20 (m, 2H), 7.11 (m, J=8.3 Hz, 2H), 4.03-3.94 (m, 1H), 3.93-3.79 (m, 2H), 3.42 (q, J=17.2 Hz, 2H), 3.26 (d, J=8.9 Hz, 1H), 3.07 (d, J=13.2 Hz, 1H), 2.85 (d, J=5.4 Hz, 1H), 2.68 (d, J=15.8 Hz, 1H). LCMS: [M+H]$^+$=404.0, 406.0.

103

2-(6-Chloro-1,3,4,9-tetrahydro-2H-pyrido[3,4-b]indol-2-yl)-N-(3-chlorophenyl)-2-methylpropanamide

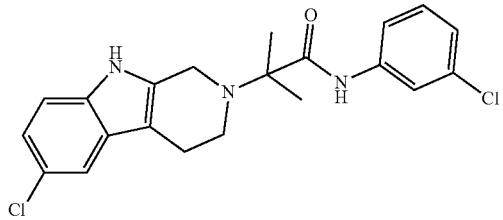 [SMILES: CC(C)(C(=O)Nc1cccc(Cl)c1)N1CCc2c([nH]c3ccc(Cl)cc23)C1]

¹H NMR (400 MHz, DMSO-d₆) δ 10.98 (s, 1H), 9.96 (s, 1H), 7.88 (t, J=2.0 Hz, 1H), 7.62-7.58 (m, 1H), 7.41 (d, J=2.0 Hz, 1H), 7.33-7.27 (m, 2H), 7.11-7.07 (m, 1H), 7.24-7.18 (m, 2H), 7.03-6.98 (dd, J=2,8.4 Hz, 1H), 3.81 (s, 2H), 2.72-2.63 (m, 4H), 1.32 (s, 6H). LCMS: [M+H]⁺=402.1, 404.1.

2-(6-Chloro-1,3,4,9-tetrahydro-2H-pyrido[3,4-b]indol-2-yl)-N1-(3-chlorophenyl)-N3-methylmalonamide

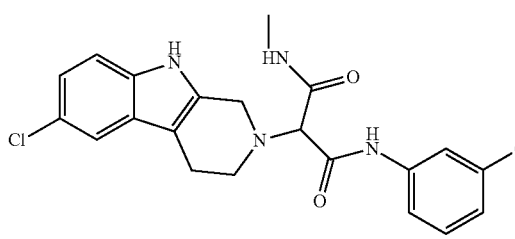

¹H NMR (400 MHz, CD₃OD) δ 7.82 (t, J=2.1 Hz, 1H), 7.49 (dd, J=8.0, 2.0 Hz, 2H), 7.35 (d, J=8.1 Hz, 1H), 7.33-7.28 (m, 1H), 7.19 (ddd, J=8.1, 2.1, 1.0 Hz, 1H), 7.10 (dd, J=8.6, 2.1 Hz, 1H), 4.72 (s, 1H), 4.50 (s, 2H), 3.62 (s, 2H), 3.08 (s, 2H), 2.87 (s, 3H). LCMS: [M+H]⁺=431.0, 433.0.

2-(6-Chloro-1-(hydroxymethyl)-1,3,4,9-tetrahydro-2H-pyrido[3,4-b]indol-2-yl)-N-(3-chlorophenyl)acetamide

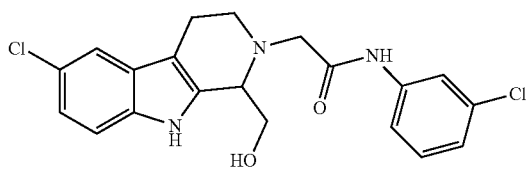 [SMILES: O=C(CN1CCc2c([nH]c3ccc(Cl)cc23)C1CO)Nc1cccc(Cl)c1]

¹H NMR (400 MHz, CDCl₃): δ 9.71 (s, 1H), 8.15 (s, 1H), 7.72 (s, 1H), 7.54-7.45 (m, 2H), 7.24-7.20 (m, 2H), 7.11 (m, J=8.3 Hz, 2H), 4.03-3.94 (m, 1H), 3.42 (q, J=17.2 Hz, 2H), 3.26 (d, J=8.9 Hz, 1H), 3.07 (d, J=13.2 Hz, 1H), 2.85 (d, J=5.4 Hz, 1H), 2.68 (d, J=15.8 Hz, 1H). LCMS: [M+H]⁺=404.0, 406.0.

104

2-(1-(Aminomethyl)-6-chloro-1,3,4,9-tetrahydro-2H-pyrido[3,4-b]indol-2-yl)-N-(3-chlorophenyl)acetamide diformate

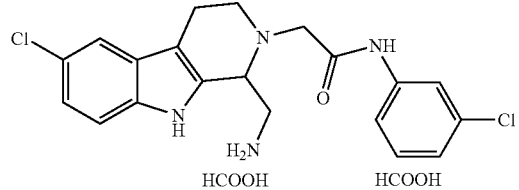 [SMILES: NCC1c2[nH]c3ccc(Cl)cc3c2CCN1CC(=O)Nc1cccc(Cl)c1 ; "HCOOH" ; "HCOOH"]

¹H NMR (400 MHz, CD₃OD): δ 8.52 (s, 1H), 7.84 (t, J=1.9 Hz, 1H), 7.45 (d, J=1.9 Hz, 1H), 7.41 (d, J=8.1 Hz, 1H), 7.32-7.25 (m, 2H), 7.14-7.05 (m, 2H), 4.01 (d, J=10.1 Hz, 1H), 3.71-3.58 (m, 2H), 3.40-3.33 (m, 1H), 3.27-3.17 (m, 2H), 3.13 (m, J=2.9 Hz, 1H), 2.92 (m, J=5.8 Hz, 1H), 2.64 (d, J=14.3 Hz, 1H). LCMS: [M+H]⁺=403.1, 405.1.

2-(1-(Aminomethyl)-6-chloro-1,3,4,9-tetrahydro-2H-pyrido[3,4-b]indol-2-yl)-N-(3-chlorophenyl)acetamide

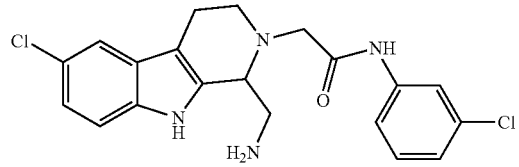 [SMILES: NCC1c2[nH]c3ccc(Cl)cc3c2CCN1CC(=O)Nc1cccc(Cl)c1]

¹H NMR (400 MHz, CD₃OD): δ 8.52 (s, 1H), 7.84 (t, J=1.9 Hz, 1H), 7.45 (d, J=1.9 Hz, 1H), 7.41 (d, J=8.1 Hz, 1H), 7.32-7.25 (m, 2H), 7.14-7.05 (m, 2H), 4.01 (d, J=10.1 Hz, 1H), 3.71-3.58 (m, 2H), 3.40-3.33 (m, 1H), 3.27-3.17 (m, 2H), 3.13 (m, J=2.9 Hz, 1H), 2.92 (m, J=5.8 Hz, 1H), 2.64 (d, J=14.3 Hz, 1H). LCMS: [M+H]⁺=403.1, 405.1.

2-(7-Chloro-3,4-dihydro-1H-pyrido[3,4-b]indol-2(9H)-yl)-N-(4-chlorophenyl)acetamide formate

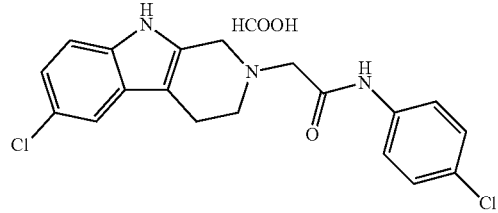 [SMILES: O=C(CN1CCc2c([nH]c3ccc(Cl)cc23)C1)Nc1ccc(Cl)cc1 ; "HCOOH"]

¹H NMR (400 MHz, DMSO-d₆) δ 10.95 (s, 1H), 9.98 (s, 1H), 7.70 (d, J=8.8 Hz, 2H), 7.41 (s, 1H), 7.37-7.34 (m, 2H), 7.30-7.28 (m, 1H), 7.01-6.99 (m, 1H), 3.79 (s, 2H), 3.40 (s, 2H), 2.91-2.81 (m, 2H), 2.74-2.73 (m, 2H). LCMS: [M+H]⁺=374.2

2-(7-Chloro-3,4-dihydro-1H-pyrido[3,4-b]indol-2(9H)-yl)-N-(4-chlorophenyl)acetamide formate

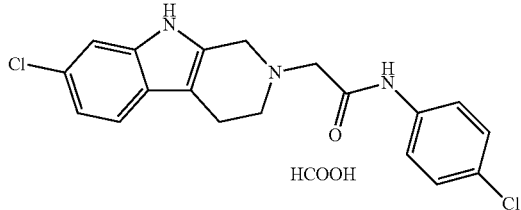 [SMILES: O=C(CN1CCc2c([nH]c3cc(Cl)ccc23)C1)Nc1ccc(Cl)cc1 ; "HCOOH"]

$^1$H NMR (400 MHz, DMSO-d$_6$) δ 10.95 (s, 1H), 10.03 (s, 1H), 8.26 (s, 1H), 7.88 (s, 1H), 7.56 (d, J=8.0 Hz, 1H), 7.41 (s, 1H), 7.35-7.28 (m, 3H), 7.11 (d, J=8.0 Hz, 1H), 7.02-6.99 (m, 1H), 3.79 (s, 2H), 3.41 (s, 2H), 2.91-2.89 (m, 2H), 2.74-2.73 (m, 2H). LCMS: [M+H]$^+$=374.2

2-(6-Chloro-1-(hydroxymethyl)-3,4-dihydro-1H-pyrido[3,4-b]indol-2(9H)-yl)-N-(4-chloro-2-hydroxyphenyl)acetamide formate

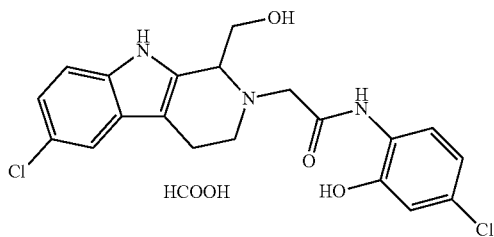 [SMILES: O=C(CN1CCc2c([nH]c3ccc(Cl)cc23)C1CO)Nc1ccc(Cl)cc1O ; "HCOOH"]

$^1$H NMR (400 MHz, DMSO-d$_6$): δ 10.95 (s, 1H), 10.50 (s, 1H), 8.03 (s, 1H), 7.59-7.65 (m, 1H), 7.45 (d, J=2.0 Hz, 1H), 7.29 (d, J=8.8 Hz, 1H), 7.02 (dd, J=10.8 Hz, 1H), 5.63 (s, 1H), 3.68~3.75 (m, 3H), 3.51 (d, J=17.2 Hz, 1H), 3.17~3.30 (m, 3H), 3.03~3.04 (m, 1H), 2.67~2.76 (m, 1H). LCMS: [M+H]$^+$=436.0.

2-(6-Chloro-1,3,4,9-tetrahydro-2H-pyrido[3,4-b]indol-2-yl)-N-(5-chloro-6-methylpyridin-2-yl)acetamide

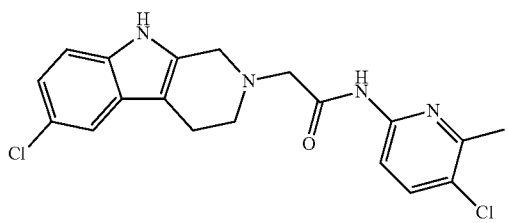 [SMILES: Cc1nc(NC(=O)CN2CCc3c([nH]c4ccc(Cl)cc34)C2)ccc1Cl]

$^1$H NMR (400 MHz, DMSO-d$_6$): δ 10.99 (s, 1H), 10.15 (s, 1H), 8.0 (d, J=8.8 Hz, 1H), 7.86 (d, J=8.4 Hz, 1H), 7.43 (s, 1H), 7.31 (d, J=8.8 Hz, 1H), 7.02 (dd, J=2.0 Hz, 8.4 Hz, 1H), 3.83 (s, 2H), 3.46 (s, 2H), 2.93 (t, J=5.2 Hz, 2H), 2.72 (brs, 2H), 2.45 (s, 3H). LCMS: [M+H]$^+$=389.2.

2-(6-Chloro-1-methyl-1,3,4,9-tetrahydro-2H-pyrido[3,4-b]indol-2-yl)-N-(5-chloro-6-(hydroxymethyl)pyridin-2-yl)acetamide

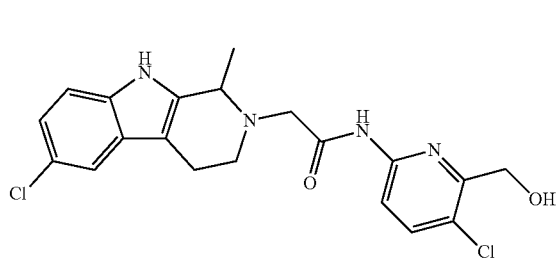 [SMILES: CC1c2[nH]c3ccc(Cl)cc3c2CCN1CC(=O)Nc1ccc(Cl)c(CO)n1]

$^1$H NMR (400 MHz, DMSO-d$_6$): δ 11.02 (brs, 1H), 10.11 (brs, 1H), 8.09 (d, J=8.8 Hz, 1H), 7.91 (d, J=8.4 Hz, 1H), 7.44 (d, J=1.6 Hz, 1H), 7.30 (d, J=8.4 Hz, 1H), 7.03 (dd, J=2.0 Hz, 8.8 Hz, 1H), 5.22 (t, 1H), 4.54 (d, J=6.0 Hz, 2H), 3.99-3.96 (m, 1H), 3.50-3.40 (m, 2H), 3.15-3.12 (m, 1H), 2.93-2.89 (m, 1H), 2.72-2.68 (m, 2H), 1.43 (d, J=6.8 Hz, 3H). LCMS: [M+H]$^+$=419.1.

2-(6-Chloro-1-(2-hydroxyethyl)-1,3,4,9-tetrahydro-2H-pyrido[3,4-b]indol-2-yl)-N-(5-chloro-6-methylpyridin-2-yl)acetamide

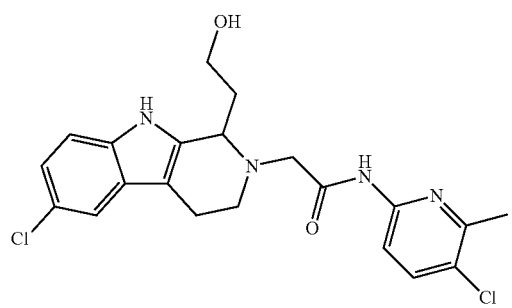 [SMILES: Cc1nc(NC(=O)CN2CCc3c([nH]c4ccc(Cl)cc34)C2CCO)ccc1Cl]

$^1$H NMR (400 MHz, DMSO-d$_6$): δ 10.92 (brs, 1H), 10.24 (brs, 1H), 7.98 (d, J=8.8 Hz, 1H), 7.86 (d, J=8.8 Hz, 1H), 7.43 (d, J=1.6 Hz, 1H), 7.30 (d, J=8.8 Hz, 1H), 7.03 (dd, J=2.0 Hz, 8.4 Hz, 1H), 4.75 (t, J=5.2 Hz, 1H), 3.89 (t, J=6.0 Hz, 1H), 3.70-3.58 (m, 4H), 3.19-3.11 (m, 1H), 2.97-2.92 (m, 1H), 2.70-2.72 (m, 1H), 2.55~2.54 (m, 1H), 2.47 (s, 3H), 1.98-1.94 (m, 2H). LCMS: [M+H]$^+$=433.2.

2-(6-Chloro-1,3,4,9-tetrahydro-2H-pyrido[3,4-b]indol-2-yl)-N-(5-chloro-6-(trifluoromethyl)pyridin-2-yl)acetamide formate

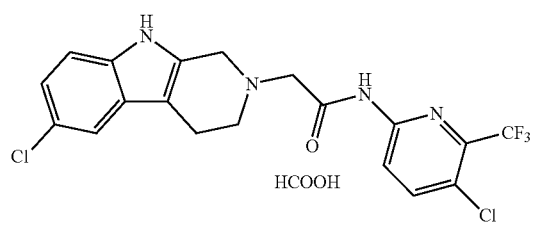 [SMILES: O=C(CN1CCc2c([nH]c3ccc(Cl)cc23)C1)Nc1ccc(Cl)c(C(F)(F)F)n1 ; "HCOOH"]

$^1$H NMR (400 MHz, DMSO-d6): δ 11.01 (brs, 1H), 10.66 (brs, 1H), 8.40 (d, J=9.2 Hz, 1H), 3.96 (br, 1H), 8.24 (d, J=9.2 Hz, 1H), 7.42 (s, 1H), 7.29 (d, J=8.4 Hz, 1H), 7.01 (dd, J=1.2, 8.4 Hz, 1H), 3.83 (s, 2H), 3.52 (s, 2H), 2.95-2.92 (m, 2H), 2.71 (br, 2H). $^{19}$F NMR (376.5 MHz, DMSO-d6): δ −64.69 LCMS: [M+H]$^+$=443.1.

2-(6-Chloro-1-methyl-1,3,4,9-tetrahydro-2H-pyrido[3,4-b]indol-2-yl)-N-(1-methyl-1H-imidazol-4-yl)acetamide formate

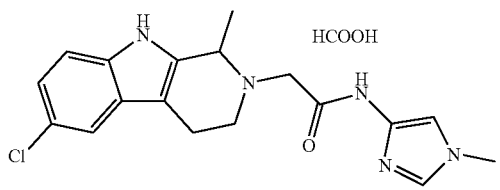 [SMILES: CC1c2[nH]c3ccc(Cl)cc3c2CCN1CC(=O)Nc1cn(C)cn1 ; "HCOOH"]

$^1$H NMR (400 MHz, DMSO-d6): δ 11.02 (brs, 1H), 9.73 (brs, 1H), 8.32 (br, 1H), 7.42-7.38 (m, 2H), 7.29 (d, J=8.8 Hz, 1H), 7.23 (s, 1H), 7.03 (dd, J=2.4 Hz, 8.8 Hz, 1H), 3.94~3.90 (m, 1H), 3.62 (s, 3H), 3.37 (d, J=2.4 Hz, 1H), 3.12-3.06 (m, 1H), 2.90-2.84 (m, 1H), 2.71-2.60 (m, 2H), 1.40 (d, J=5.6 Hz, 3H). LCMS: [M+H]$^+$=358.2.

2-(6-Chloro-1-methyl-1,3,4,9-tetrahydro-2H-pyrido[3,4-b]indol-2-yl)-N-(5-chloro-6-(2-hydroxyethyl)pyridin-2-yl)acetamide

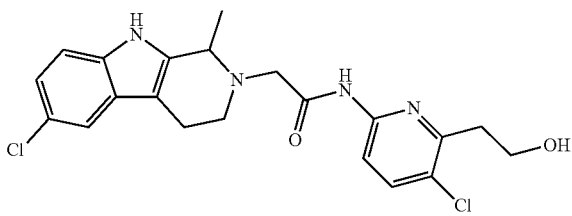 [SMILES: CC1c2[nH]c3ccc(Cl)cc3c2CCN1CC(=O)Nc1ccc(Cl)c(CCO)n1]

$^1$H NMR (400 MHz, DMSO-d$_6$): δ 11.02 (brs, 1H), 10.07 (brs, 1H), 7.99 (d, J=8.4 Hz, 1H), 7.87 (d, J=8.8 Hz, 1H), 7.44 (d, J=1.6 Hz, 1H), 7.30 (d, J=8.4 Hz, 1H), 7.03 (dd, J=8.8 Hz, 2.0 Hz, 1H), 4.70 (t, J=5.6 Hz, 1H), 3.99-3.95 (m, 1H), 3.75-3.69 (m, 2H), 3.51-3.39 (m, 2H), 3.15-3.11 (m, 1H), 2.97-2.90 (m, 3H), 2.71-2.64 (m, 2H), 1.42 (d, J=6.8 Hz, 3H). LCMS: [M+H]$^+$=433.1

2-(6-Chloro-1-(hydroxymethyl)-1,3,4,9-tetrahydro-2H-pyrido[3,4-b]indol-2-yl)-N-(5-chloro-2-methylpyridin-3-yl)acetamide

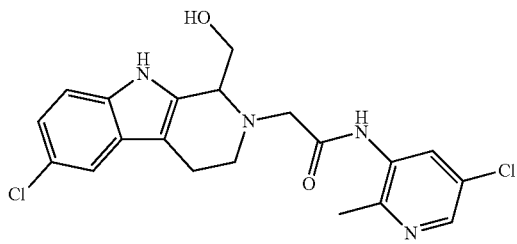 [SMILES: Cc1ncc(Cl)cc1NC(=O)CN1CCc2c([nH]c3ccc(Cl)cc23)C1CO]

$^1$H NMR (400 MHz, DMSO-d$_6$): δ 11.01 (brs, 1H), 10.14 (brs, 1H), 8.32-8.29 (m, 2H), 7.46 (d, J=1.6 Hz, 1H), 7.31 (d, J=8.4 Hz, 1H), 7.04 (dd, J=8.4 Hz, 2.0 Hz, 1H), 5.32-5.29 (m, 1H), 3.81-3.70 (m, 3H), 3.55-3.51 (m, 1H), 3.39-3.37 (m, 1H), 3.29-3.19 (m, 1H), 3.05-3.02 (m, 1H), 2.82-2.78 (m, 1H), 2.77-2.58 (m, 1H), 2.48-2.45 (m, 3H). LCMS: (M+H)$^+$=419.1

2-(6-chloro-1-(hydroxymethyl)-1,3,4,9-tetrahydro-2H-pyrido[3,4-b]indol-2-yl)-N-(3,5-dichloro-6-methylpyridin-2-yl)acetamide

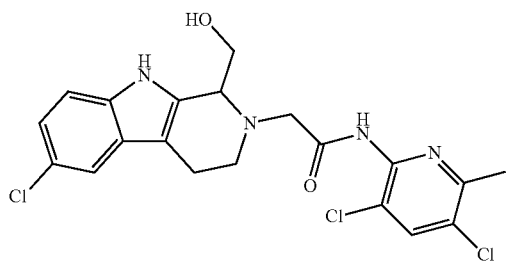 [SMILES: Cc1nc(NC(=O)CN2CCc3c([nH]c4ccc(Cl)cc34)C2CO)c(Cl)cc1Cl]

$^1$H NMR (400 MHz, DMSO-d$_6$): δ 10.99 (brs, 1H), 10.43 (brs, 1H), 8.23 (s, 1H), 7.45 (d, J=2.0 Hz, 1H), 7.32 (d, J=8.8 Hz, 1H), 7.05 (dd, J=8.4 Hz, 2.0 Hz, 1H), 5.18 (t, J=5.2 Hz, 1H), 3.84~3.81 (m, 1H), 3.73~3.70 (m, 2H), 3.51~3.39 (m, 2H), 3.22~3.18 (m, 1H), 3.02~2.99 (m, 1H), 2.83~2.76 (m, 1H), 2.57~2.51 (m, 1H), 2.51 (s, 3H). LCMS: [M+H]$^+$=455.1

2-(6-Chloro-1-(tetrahydrofuran-2-yl)-1,3,4,9-tetrahydro-2H-pyrido[3,4-b]indol-2-yl)-N-(5-chloro-6-methylpyridin-2-yl)acetamide

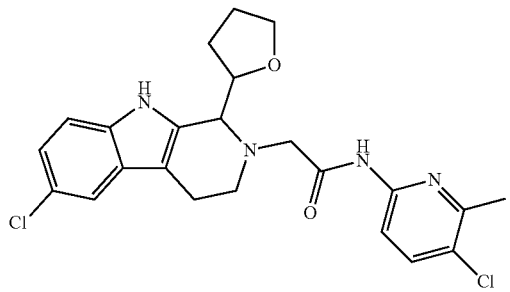 [SMILES: Cc1nc(NC(=O)CN2CCc3c([nH]c4ccc(Cl)cc34)C2C2CCCO2)ccc1Cl]

$^1$H NMR (400 MHz, MeOD): δ 8.01 (d, J=8.0 Hz, 1H), 7.74 (t, J=8.8 Hz, 1H), 7.51 (s, 1H), 7.34 (d, J=8.8 Hz, 1H), 7.12 (dd, J=8.8 Hz, 1.6 Hz, 1H), 4.48 (br, 2H), 4.00 (br, 2H), 3.80-3.31 (m, 4H), 3.16-2.93 (m, 2H), 2.49 (s, 3H), 2.41-2.07 (m, 2H), 1.94-1.87 (m, 2H). LCMS: [M+H]$^+$=459.2.

2-(6-Chloro-1-(hydroxymethyl)-1,3,4,9-tetrahydro-2H-pyrido[3,4-b]indol-2-yl)-N-(5-chloro-6-cyclopropylpyridin-2-yl)acetamide formate

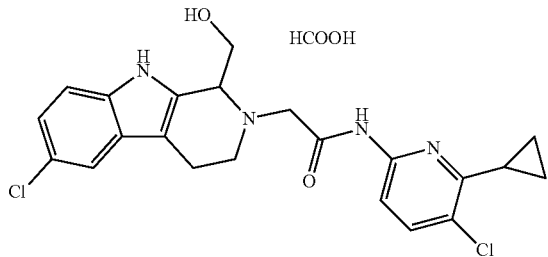 [SMILES: O=C(CN1CCc2c([nH]c3ccc(Cl)cc23)C1CO)Nc1ccc(Cl)c(C2CC2)n1 ; "HCOOH"]

$^1$H NMR (400 MHz, DMSO-d$_6$) δ 10.94 (s, 1H), 10.45 (s, 1H), 7.92 (d, J=8.0 Hz, 1H), 7.81 (d, J=8.0 Hz, 1H), 7.45 (d, J=4.0 Hz, 1H), 7.31 (d, J=8.0 Hz, 1H), 7.03 (dd, J=8.0, 2.0 Hz, 1H), 5.27 (br, 1H), 3.75-3.65 (m, 3H), 3.54 (d, J=20.0 Hz, 1H), 3.26-3.16 (m, 2H), 3.04-3.00 (m, 1H), 2.79-2.72 (m, 1H), 2.55-2.54 (m, 1H), 2.42-2.37 (m, 1H), 1.08-1.04 (m, 1H), 1.04-0.96 (m, 3H). LCMS: [M+H]$^+$=445.1.

2-(6-Chloro-1-(hydroxymethyl)-1,3,4,9-tetrahydro-2H-pyrido[3,4-b]indol-2-yl)-N-(5-chloro-6-propylpyridin-2-yl)acetamide

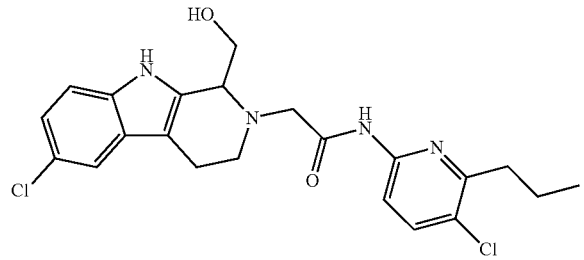 [SMILES: CCCc1nc(NC(=O)CN2CCc3c([nH]c4ccc(Cl)cc34)C2CO)ccc1Cl]

$^1$H NMR (400 MHz, DMSO-d$_6$) δ 10.94 (s, 1H), 10.49 (s, 1H), 8.01 (d, J=8.0 Hz, 1H), 7.85 (d, J=8.0 Hz, 1H), 7.45 (d, J=2.0 Hz, 1H), 7.31 (d, J=8.0 Hz, 1H), 7.03 (dd, J=8.0 Hz, 2.0 Hz, 1H), 5.20 (t, J=4.0 Hz, 1H), 3.76-3.67 (m, 3H), 3.55 (d, J=16.0 Hz, 1H), 3.36-3.32 (m, 1H), 3.22-3.16 (m, 1H), 3.02-2.98 (m, 1H), 2.78-2.74 (m, 3H), 2.56-2.51 (m, 1H), 1.72-1.66 (m, 2H), 0.94 (t, J=8.0 Hz, 3H). LCMS: [M+H]$^+$=447.0

2-(6-Chloro-1-(hydroxymethyl)-1,3,4,9-tetrahydro-2H-pyrido[3,4-b]indol-2-yl)-N-(6-chloro-5-methylpyridazin-3-yl)acetamide formate

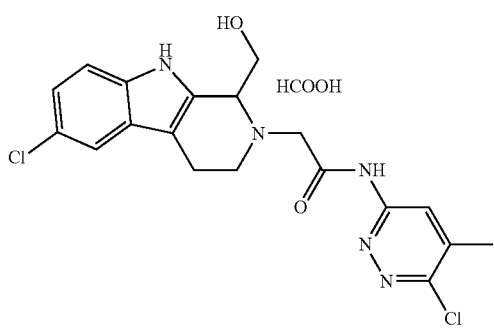 [SMILES: Cc1cc(NC(=O)CN2CCc3c([nH]c4ccc(Cl)cc34)C2CO)nnc1Cl ; "HCOOH"]

$^1$H NMR (400 MHz, DMSO-d$_6$) δ 11.10 (brs, 1H), 10.99 (brs, 1H), 8.41 (s, 1H), 7.45 (d, J=1.2 Hz, 1H), 7.31 (d, J=8.4 Hz, 1H), 7.03 (dd, J=8.4 Hz, 2.0 Hz, 1H), 3.80-3.56 (m, 5H), 3.04-3.01 (m, 2H), 2.78-2.74 (m, 2H), 2.40 (s, 3H). LCMS: [M+H]$^+$=420.1.

2-(6-chloro-1-(hydroxymethyl)-1,3,4,9-tetrahydro-2H-pyrido[3,4-b]indol-2-yl)-N-(6-methoxy-5-(trifluoromethyl)pyridin-2-yl)acetamide

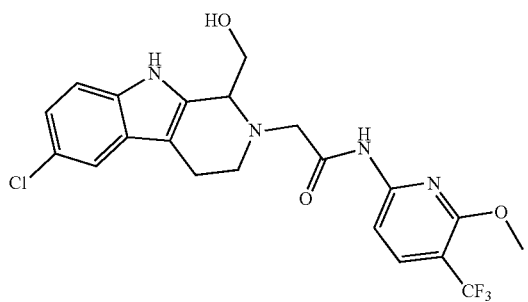 [SMILES: COc1nc(NC(=O)CN2CCc3c([nH]c4ccc(Cl)cc34)C2CO)ccc1C(F)(F)F]

$^1$H NMR (400 MHz, DMSO-d$_6$) δ 10.97 (s, 1H), 10.83 (s, 1H), 8.08 (d, J=8.4 Hz, 1H), 7.86 (d, J=8.4 Hz, 1H), 7.46 (d, J=2.0 Hz, 1H), 7.31 (d, J=8.8 Hz, 1H), 7.04 (dd, J=8.4 Hz, 2.0 Hz, 1H), 5.44-5.42 (m, 1H), 3.96 (s, 3H), 3.80-3.66 (m, 3H), 3.61 (d, J=17.6 Hz, 1H), 3.33-3.29 (m, 1H), 3.25-3.18 (m, 1H), 3.08-3.03 (m, 1H), 2.78-2.74 (m, 1H), 2.56-2.49 (m, 1H). LCMS: [M+H]$^+$=469.1.

General scheme 10

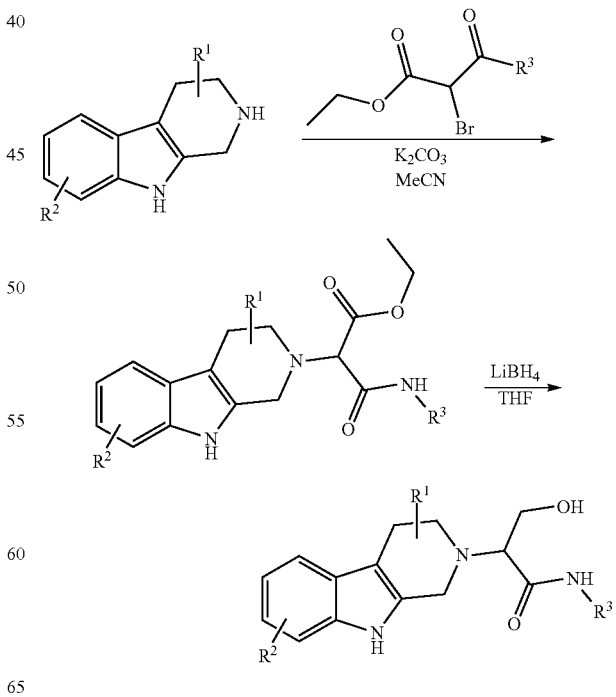

Representative of synthesis of 2-(6-chloro-1,3,4,9-tetrahydro-2H-pyrido[3,4-b]indol-2-yl)-N-(3-chlorophenyl)-3-hydroxypropanamide

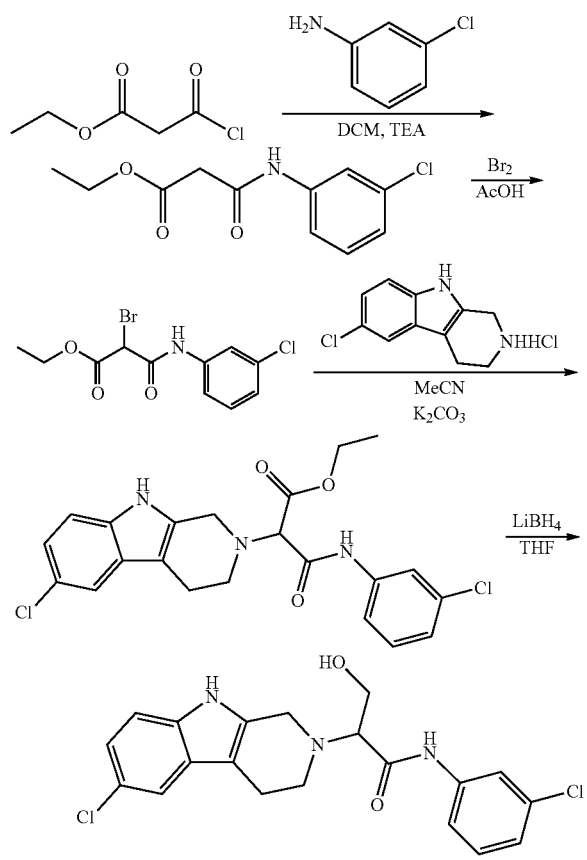

Ethyl 3-((3-chlorophenyl)amino)-3-oxopropanoate: Ethyl 3-chloro-3-oxopropanoate (2 g, 13.3 mmol, 1.0 eq) and 3-chloroaniline (1.7 g, 13.3 mmol, 1.0 eq) were dissolved in DCM (10 mL), then triethylamine (2.1 g, 19.95 mmol, 1.5 eq) was added, and the mixture was stirred at room temperature for 12 hrs. The mixture was concentrated in vacuo to give a crude product which was further purified by silica gel chromatography to afford ethyl 3-((3-chlorophenyl)amino)-3-oxopropanoate (2.57 g, yield 80%)

Ethyl 2-bromo-3-((3-chlorophenyl)amino)-3-oxopropanoate: To a mixture of ethyl 3-((3-chlorophenyl)amino)-3-oxopropanoate (1.1 g, 4.55 mmol, 1.0 eq) in acetic acid (AcOH, 5 mL) was added dibromine (727.4 mg, 4.55 mmol, 1.0 eq). After stirring at room temperature for 1 h, the reaction mixture was poured into water (20 mL), extracted with ethylacetate (3×60 mL). The organic phase was dried over anhydrous sodium sulfate and concentrated in vacuo. The residue was further purified by silica gel column chromatography (eluent: PE/EA=5:1) to give ethyl 2-bromo-3-((3-chlorophenyl)amino)-3-oxopropanoate (1.2 g, yield 82.3%).

Ethyl 2-(6-chloro-1,3,4,9-tetrahydro-2H-pyrido[3,4-b]indol-2-yl)-3-((3-chlorophenyl)amino)-3-oxopropanoate: To a mixture of ethyl 2-bromo-3-((3-chlorophenyl)amino)-3-oxopropanoate (344 mg, 1.07 mmol, 1.0 eq) in MeCN (5 mL) was added 6-chloro-2,3,4,9-tetrahydro-1H-pyrido[3,4-b]indole hydrochloride (260.9 mg, 1.07 mmol, 1.0 eq), and potassium carbonate (444.3 mg, 3.22 mmol, 3.0 eq). The mixture was stirred at 50° C. for 2 hrs, and was then cooled to the room temperature and filtered. The filtrate was concentrated in vacuo. The residue was purified by silica gel column chromatography (eluent: PE/EA=5:1) to give ethyl 2-(6-chloro-1,3,4,9-tetrahydro-2H-pyrido[3,4-b]indol-2-yl)-3-((3-chlorophenyl)amino)-3-oxopropanoate (532 mg, yield 100%).

2-(6-Chloro-1,3,4,9-tetrahydro-2H-pyrido[3,4-b]indol-2-yl)-N-(3-chlorophenyl)-3-hydroxypropanamide: To a 0° C. solution of ethyl 2-(6-chloro-1,3,4,9-tetrahydro-2H-pyrido[3,4-b]indol-2-yl)-3-((3-chlorophenyl)amino)-3-oxopropanoate (328 mg, 0.73 mmol, 1.0 eq) in THF (5 mL) was added LiBH$_4$ (32.01 mg, 1.46 mmol, 2.0 eq) slowly. The mixture was stirred at room temperature for 0.5 h. Then reaction mixture was poured into ice water (20 mL), extracted with ethylacetate (3×60 mL). The organic phase was dried over anhydrous sodium sulfate and concentrated in vacuo. The residue was purified by prep-HPLC (mobile phase: 0.07% HCOOH/CH$_3$CN/H$_2$O) to give 2-(6-chloro-1,3,4,9-tetrahydro-2H-pyrido[3,4-b]indol-2-yl)-N-(3-chlorophenyl)-3-hydroxypropanamide (27.78 mg, yield 8.4%) as a white solid. $^1$H NMR: (400 MHz, DMSO-d$_6$) δ 10.92 (s, 1H), 10.12 (s, 1H), 7.90 (t, J=2.1 Hz, 1H), 7.52 (dt, J=8.3, 1.4 Hz, 1H), 7.40-7.23 (m, 3H), 7.11 (ddd, J=7.9, 2.0, 1.0 Hz, 1H), 6.99 (dd, J=8.6, 2.1 Hz, 1H), 4.88 (t, J=5.2 Hz, 1H), 4.01 (d, J=15.0 Hz, 1H), 3.93 (dt, J=11.8, 6.2 Hz, 1H), 3.87-3.75 (m, 2H), 3.49 (t, J=6.1 Hz, 1H), 2.95 (dp, J=22.9, 5.8 Hz, 2H), 2.67 (t, J=5.6 Hz, 2H). LCMS: [M+H]$^+$=404.

General scheme 11

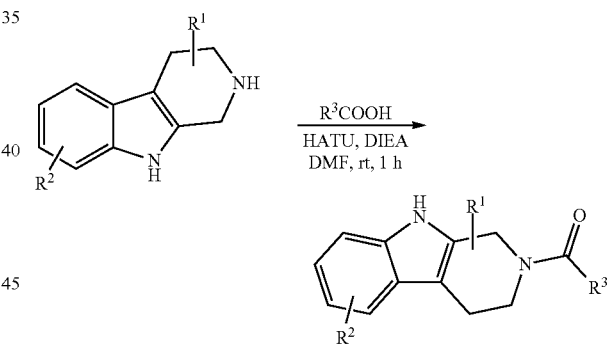

Representative of synthesis of ((6-chloro-1-(hydroxymethyl)-1,3,4,9-tetrahydro-2H-pyrido[3,4-b]indol-2-yl)(3,4-dichlorophenyl)methanone

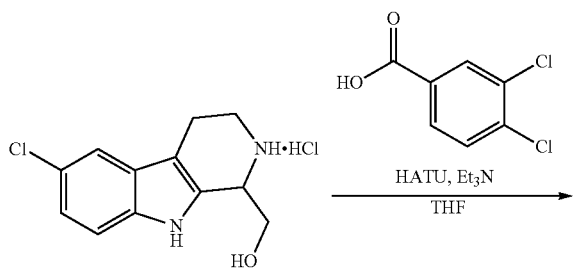

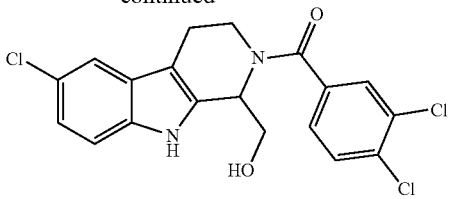

((6-Chloro-1-(hydroxymethyl)-1,3,4,9-tetrahydro-2H-pyrido[3,4-b]indol-2-yl)(3,4-dichlorophenyl)methanone: To a mixture of 6-chloro-2,3,4,9-tetrahydro-1H-pyrido[3,4-b]indol-1-yl)methanol hydrochloride (45 mg, 190.11 umol) in THF (10 mL) was added 3,4-dichlorobenzoic acid (36.31 mg, 190.11 umol), HATU (144.49 mg, 380.23 umol) and Et$_3$N (38.48 mg, 380.23 umol). The mixture was stirred at RT for 16 hrs. Water was added and the mixture was extracted with EtOAc (3×20 mL). The organic layer was dried by Na$_2$SO$_4$, and filtered. The filtrate was concentrated in vacuo to give a crude product which was purified by prep-HPLC (mobile phase: 0.1% NH$_4$OH/CH$_3$CN/H$_2$O) to afford ((6-chloro-1-(hydroxymethyl)-1,3,4,9-tetrahydro-2H-pyrido[3,4-b]indol-2-yl)(3,4-dichlorophenyl)methanone. $^1$H NMR (400 MHz, DMSO-d$_6$) δ 11.21-10.81 (m, 1H), 7.87-7.63 (m, 2H), 7.46 (d, J=6.8 Hz, 2H), 7.33 (dd, J=30.7, 8.5 Hz, 1H), 7.06 (d, J=8.6 Hz, 1H), 5.63 (s, 1H), 5.46 (s, 0H), 5.22 (s, 1H), 4.83-4.60 (m, 1H), 3.89 (s, 1H), 3.65 (dt, J=21.8, 13.9 Hz, 2H), 2.78 (s, 1H), 2.66 (d, J=4.1 Hz, 1H). LCMS: [M+H]$^+$=409.0, 411.0.

(6-Chloro-1-(hydroxymethyl)-1,3,4,9-tetrahydro-2H-pyrido[3,4-b]indol-2-yl)(3,5-dichlorophenyl)methanone

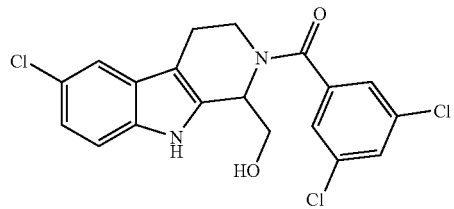 [SMILES: O=C(c1cc(Cl)cc(Cl)c1)N1CCc2c([nH]c3ccc(Cl)cc23)C1CO]

$^1$H NMR (400 MHz, DMSO-d$_6$) δ 11.01 (d, J=107.7 Hz, 1H), 7.73 (d, J=18.0 Hz, 1H), 7.56 (d, J=9.7 Hz, 2H), 7.46 (d, J=11.8 Hz, 1H), 7.36 (d, J=8.6 Hz, 1H), 7.29 (d, J=8.5 Hz, 0H), 7.05 (d, J=8.4 Hz, 1H), 5.62 (s, 0.59H), 5.49 (s, 0.33H), 5.22 (s, 0.57H), 4.74 (d, J=22.7 Hz, 0.7H), 3.88 (s, 1H), 3.66 (ddd, J=30.0, 22.9, 11.6 Hz, 2H), 2.88-2.59 (m, 2H). LCMS: [M+H]$^+$=409.0, 411.0.

(1-(Aminomethyl)-6-chloro-1,3,4,9-tetrahydro-2H-pyrido[3,4-b]indol-2-yl)(3,4-dichlorophenyl)methanone

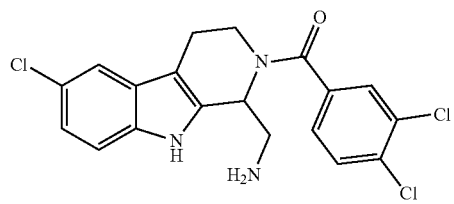 [SMILES: NCC1c2[nH]c3ccc(Cl)cc3c2CCN1C(=O)c1ccc(Cl)c(Cl)c1]

$^1$H NMR (400 MHz, DMSO-d$_6$) δ 11.08 (s, 1H), 8.73 (t, J=5.5 Hz, 1H), 8.15 (d, J=2.0 Hz, 1H), 7.86 (d, J=2.0 Hz, 1H), 7.77 (d, J=8.4 Hz, 1H), 7.41 (d, J=2.0 Hz, 1H), 7.29 (s, 1H), 7.02 (dd, J=8.5, 2.1 Hz, 1H), 4.18 (d, J=6.1 Hz, 1H), 3.93-3.80 (m, 1H), 3.43-3.33 (m, 1H), 3.17-3.07 (m, 1H), 2.94-2.80 (m, 1H), 2.59 (s, 2H). LCMS: [M+H]$^+$=408.0

(1-(Aminomethyl)-6-chloro-1,3,4,9-tetrahydro-2H-pyrido[3,4-b]indol-2-yl)(3-chlorophenyl)methanone formate

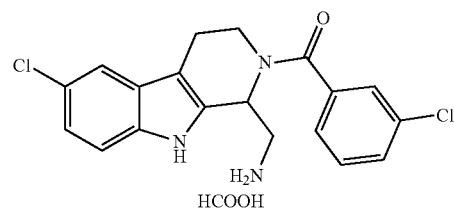 [SMILES: NCC1c2[nH]c3ccc(Cl)cc3c2CCN1C(=O)c1cccc(Cl)c1 ; "HCOOH"]

$^1$H NMR (400 MHz, DMSO-d$_6$) δ 11.10 (s, 1H), 8.67 (s, 1H), 8.21 (s, 1H), 7.95 (s, 1H), 7.85 (d, J=7.7 Hz, 1H), 7.60 (s, 1H), 7.53 (d, J=7.7 Hz, 1H), 7.42 (s, 1H), 7.31 (d, J=8.6 Hz, 1H), 7.02 (dd, J=8.5, 2.0 Hz, 1H), 4.21 (d, J=6.6 Hz, 1H), 3.89 (d, J=14.1 Hz, 1H), 3.17-3.12 (m, 2H), 2.95-2.81 (m, 1H), 2.60 (s, 2H). LCMS: [M+H]$^+$=374.0, 376.0.

(1-(2-Aminoethyl)-6-chloro-1,3,4,9-tetrahydro-2H-pyrido[3,4-b]indol-2-yl)(3-chlorophenyl)methanone

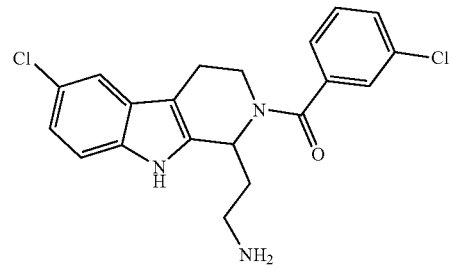 [SMILES: NCCC1c2[nH]c3ccc(Cl)cc3c2CCN1C(=O)c1cccc(Cl)c1]

$^1$H NMR (400 MHz, DMSO-d$_6$) δ 10.95 (s, 1H), 8.86 (t, J=5.3 Hz, 1H), 7.87 (t, J=1.9 Hz, 1H), 7.80 (dt, J=7.7, 1.4 Hz, 1H), 7.59 (ddd, J=8.0, 2.2, 1.1 Hz, 1H), 7.50 (t, J=7.9 Hz, 1H), 7.37 (d, J=2.0 Hz, 1H), 7.27 (d, J=8.5 Hz, 1H), 6.98 (dd, J=8.5, 2.1 Hz, 1H), 4.03 (d, J=8.5 Hz, 1H), 3.46 (q, J=6.5 Hz, 2H), 3.18-3.08 (m, 1H), 2.88 (dt, J=12.7, 6.1 Hz, 1H), 2.59 2.54 (m, 2H), 2.15 (dt, J=10.3, 3.3 Hz, 1H), 1.82 (dq, J=13.2, 6.5 Hz, 1H). LCMS: [M+H]$^+$=388.1, 390.1.

1-((6-Chloro-2-(3-chlorobenzoyl)-2,3,4,9-tetra-
hydro-1H-pyrido[3,4-b]indol-1-yl)methyl)guanidine
hydrochloride

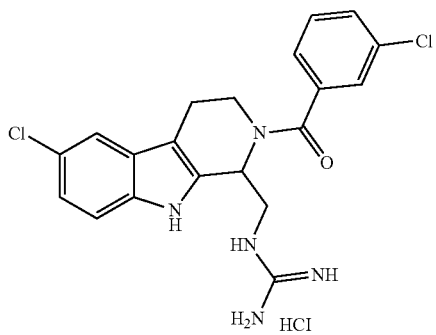

¹H NMR (400 MHz, DMSO-d₆) δ 11.43 (s, 1H), 7.85 (t, J=6.4 Hz, 1H), 7.63 (s, 1H), 7.60 7.50 (m, 3H), 7.50-7.39 (m, 4H), 7.32-7.15 (m, 1H), 7.10 (dd, J=8.6, 2.1 Hz, 2H), 5.94 (d, J=8.2 Hz, 1H), 3.93-3.83 (m, 1H), 3.73-3.49 (m, 4H), 2.67 (d, J=6.2 Hz, 2H). LCMS: [M+H]⁺=416.1, 418.1.

1-(2-(6-Chloro-2-(3-chlorobenzoyl)-2,3,4,9-tetra-
hydro-1H-pyrido[3,4-b]indol-1-yl)ethyl)guanidine
hydrochloride

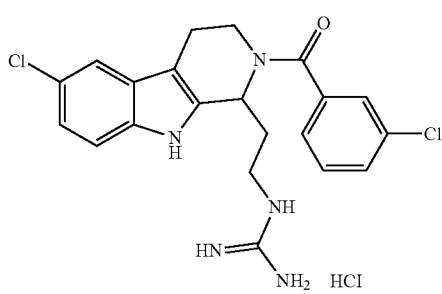

¹H NMR (400 MHz, DMSO-d₆) δ 11.37 (s, 1H), 7.62-7.44 (m, 7H), 7.37 (d, J=8.6 Hz, 2H), 7.22 (s, 1H), 7.08 (dd, J=8.5, 2.1 Hz, 1H), 5.77 (d, J=9.8 Hz, 1H), 5.32 (t, J=4.9 Hz, 1H), 3.69 (d, J=13.4 Hz, 1H), 2.67 (d, J=4.6 Hz, 2H), 2.14 (d, J=46.3 Hz, 2H), 1.99 (p, J=7.0, 6.5 Hz, 2H). LCMS: [M+H]⁺=430.1, 432.1.

(6-Chloro-1-(((2-hydroxyethyl)amino)methyl)-1,3,4,
9-tetrahydro-2H-pyrido[3,4-b]indol-2-yl)(3-chloro-
phenyl)methanone

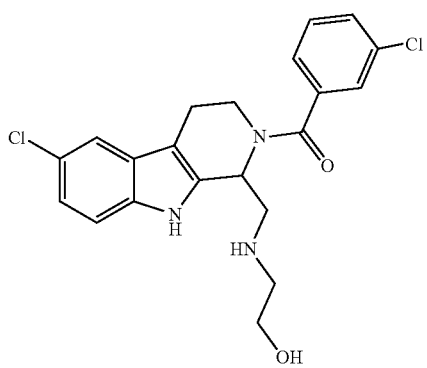 [SMILES: O=C(c1cccc(Cl)c1)N1CCc2c([nH]c3ccc(Cl)cc23)C1CNCCO]

¹H NMR (400 MHz, CD₃OD) δ 8.48 (s, 1H), 7.64 (d, J=2.2 Hz, 1H), 7.59-7.47 (m, 4H), 7.46 (dd, J=4.9, 2.0 Hz, 1H), 7.33 (d, J=8.6 Hz, 1H), 7.10 (dt, J=8.7, 2.9 Hz, 1H), 6.05 (dd, J=9.6, 3.7 Hz, 1H), 3.92 (dd, J=14.3, 5.2 Hz, 1H), 3.85 (t, J=5.3 Hz, 2H), 3.65-3.51 (m, 3H), 3.28 (t, J=5.2 Hz, 1H), 3.15 (dt, J=12.6, 5.2 Hz, 1H), 2.94-2.83 (m, 1H), 2.74 (dd, J=15.6, 3.9 Hz, 1H). LCMS: [M+H]⁺=418.1, 420.1.

(6-Chloro-1-((methylamino)methyl)-1,3,4,9-tetra-
hydro-2H-pyrido[3,4-b]indol-2-yl)(3-chlorophenyl)
methanone formate

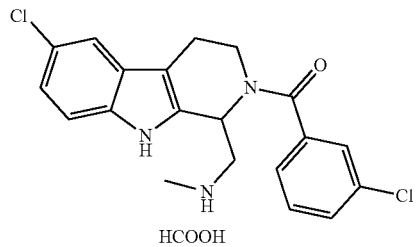 [SMILES: CNCC1c2[nH]c3ccc(Cl)cc3c2CCN1C(=O)c1cccc(Cl)c1 ; "HCOOH"]

¹H NMR (400 MHz, CD₃OD) δ 7.37 (d, J=2.0 Hz, 1H), 7.24 (d, J=8.4 Hz, 1H), 7.08 (d, J=8.0 Hz, 1H), 7.02 (dd, J=8.6, 2.0 Hz, 1H), 6.91 (d, J=7.8 Hz, 1H), 5.01 (d, J=117.8 Hz, 2H), 3.79 (s, 2H), 2.81 (s, 2H), 2.40 (s, 3H). LCMS: [M+H]⁺=388.1, 390.1.

2-Amino-1-(6-chloro-1,3,4,9-tetrahydro-2H-pyrido
[3,4-b]indol-2-yl)-2-(3,4-dichlorophenyl)ethan-1-one
hydrochloride

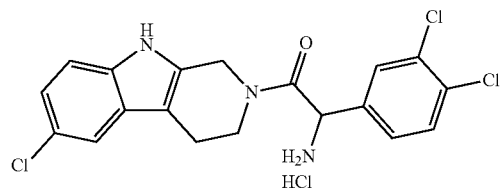 [SMILES: NC(C(=O)N1CCc2c([nH]c3ccc(Cl)cc23)C1)c1ccc(Cl)c(Cl)c1 ; Cl]

¹H NMR (400 MHz, DMSO-d₆) δ 11.12 (d, J=52.6 Hz, 1H), 8.77 (s, 2H), 7.93 (d, J=2.1 Hz, 1H), 7.82-7.71 (m, 1H), 7.54 (d, J=8.4, 2.1 Hz, 1H), 7.47-7.40 (m, 1H), 7.31 (dd, J=14.9, 8.6 Hz, 1H), 7.03 (dd, J=8.6, 2.1 Hz, 1H), 5.84 (d, J=30.9 Hz, 1H), 4.93-4.74 (m, 2H), 4.30-4.15 (m, 1H), 3.81-3.47 (m, 2H), 2.77-2.62 (m, 1H), 2.36-2.09 (m, 1H). LCMS: [M+H]⁺=408.0, 410.0.

2-Amino-1-(6-chloro-1,3,4,9-tetrahydro-2H-pyrido
[3,4-b]indol-2-yl)-2-(4-chloro-3-hydroxyphenyl)
ethan-1-one formate

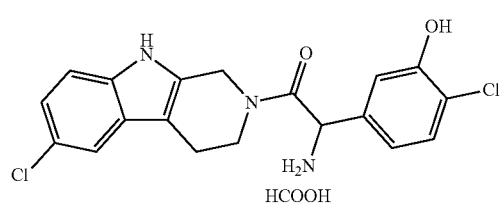 [SMILES: NC(C(=O)N1CCc2c([nH]c3ccc(Cl)cc23)C1)c1ccc(Cl)c(O)c1 ; "HCOOH"]

117

¹H NMR (400 MHz, DMSO-d₆) δ 11.03 (d, J=30.1 Hz, 1H), 8.19 (s, 1H), 7.46-7.36 (m, 1H), 7.36-7.24 (m, 2H), 7.07-6.93 (m, 2H), 6.90-6.75 (m, 1H), 5.06-4.61 (m, 3H), 3.72 (q, J=6.8, 6.3 Hz, 2H), 2.64 (d, J=16.6 Hz, 1H). LCMS: [M+H]⁺=390.0, 392.0.

2-Amino-1-(6-chloro-1,3,4,9-tetrahydro-2H-pyrido[3,4-b]indol-2-yl)-2-(4-chloro-3-(trifluoromethyl)phenyl)ethan-1-one hydrochloride

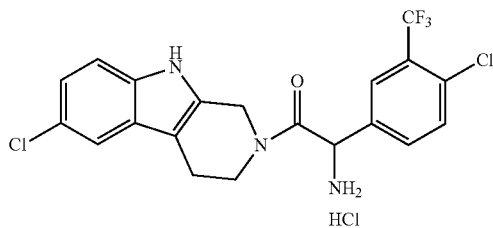 [SMILES: NC(C(=O)N1CCc2c([nH]c3ccc(Cl)cc23)C1)c1ccc(Cl)c(C(F)(F)F)c1 ; Cl]

¹H NMR (400 MHz, DMSO-d₆) δ 11.07 (d, J=76.6 Hz, 1H), 8.78 (t, J=7.1 Hz, 2H), 8.09 (dd, J=84.7, 2.1 Hz, 1H), 7.93-7.72 (m, 2H), 7.41 (d, J=2.1 Hz, 1H), 7.30 (dd, J=23.4, 8.6 Hz, 1H), 7.03 (ddd, J=8.6, 4.1, 2.1 Hz, 1H), 5.95 (dd, J=30.1, 5.4 Hz, 1H), 4.91-4.67 (m, 2H), 4.32-4.11 (m, 1H), 3.88-3.55 (m, 2H), 2.70 (dd, J=13.5, 7.7 Hz, 1H), 2.21-2.02 (m, 1H). LCMS: [M+H]⁺=442.0, 444.0.

3-Amino-N-((6-chloro-2-(3-chlorobenzoyl)-2,3,4,9-tetrahydro-1H-pyrido[3,4-b]indol-1-yl)methyl)propanamide

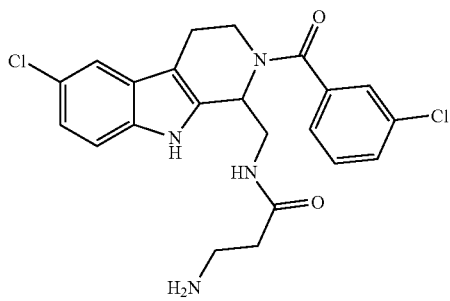 [SMILES: NCCC(=O)NCC1c2[nH]c3ccc(Cl)cc3c2CCN1C(=O)c1cccc(Cl)c1]

¹H NMR (400 MHz, CD₃OD): δ 7.62-7.46 (m, 3H), 7.42 (d, J=7.4 Hz, 2H), 7.31 (d, J=8.6 Hz, 1H), 7.08 (m, J=8.6 Hz, 1H), 6.07 (d, J=6.8 Hz, 1H), 3.99-3.79 (m, 2H), 3.71-3.62 (m, 1H), 3.61-3.52 (m, 1H), 3.21 (m, J=6.6 Hz, 2H), 2.79-2.70 (m, 2H), 2.60 (m, J=11.8, 6.0 Hz, 2H). LCMS: [M+H]⁺=445.1, 447.1.

118

(6-Chloro-1-((dimethylamino)methyl)-1,3,4,9-tetrahydro-2H-pyrido[3,4-b]indol-2-yl)(3-chlorophenyl)methanone formate

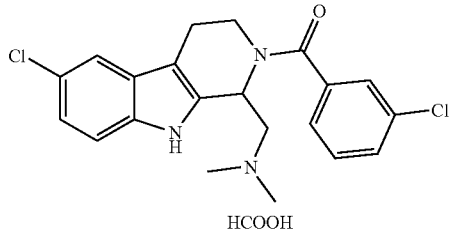 [SMILES: CN(C)CC1c2[nH]c3ccc(Cl)cc3c2CCN1C(=O)c1cccc(Cl)c1 ; "HCOOH"]

¹H NMR (400 MHz, CD₃OD): δ 7.59 (s, 1H), 7.56-7.37 (m, 4H), 7.31 (d, J=8.2 Hz, 1H), 7.06 (d, J=8.2 Hz, 1H), 5.99 (s, 1H), 3.86 (m, J=4.7 Hz, 1H), 3.67-3.54 (m, 1H), 3.16-3.01 (m, 1H), 2.76 (m, J=16.5, 14.5 Hz, 3H), 2.54 (s, 6H). LCMS: [M+H]⁺=402.0, 404.0.

(6-Chloro-1-((methylamino)methyl)-1,3,4,9-tetrahydro-2H-pyrido[3,4-b]indol-2-yl)(3-chlorophenyl)methanone formate

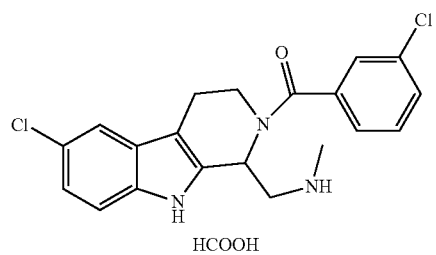 [SMILES: CNCC1c2[nH]c3ccc(Cl)cc3c2CCN1C(=O)c1cccc(Cl)c1 ; "HCOOH"]

¹H NMR (400 MHz, CD₃OD) δ 7.37 (d, J=2.0 Hz, 1H), 7.24 (d, J=8.4 Hz, 1H), 7.08 (d, J=8.0 Hz, 1H), 7.02 (dd, J=8.6, 2.0 Hz, 1H), 6.91 (d, J=7.8 Hz, 1H), 5.01 (d, J=117.8 Hz, 2H), 3.79 (s, 2H), 2.81 (s, 2H), 2.40 (s, 3H). LCMS: [M+H]⁺=388.1, 390.1.

2-Amino-N-((6-chloro-2-(3-chlorobenzoyl)-2,3,4,9-tetrahydro-1H-pyrido[3,4-b]indol-1-yl)methyl)acetamide formate

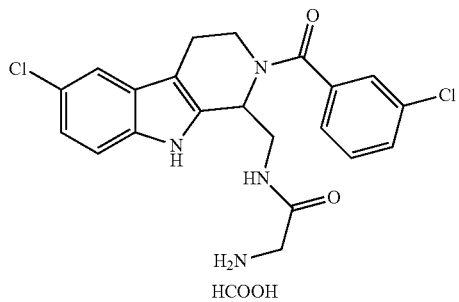 [SMILES: NCC(=O)NCC1c2[nH]c3ccc(Cl)cc3c2CCN1C(=O)c1cccc(Cl)c1 ; "HCOOH"]

¹H NMR (400 MHz, DMSO-d₆) δ 11.26 (d, J=126.3 Hz, 1H), 8.65 (s, 1H), 8.02 (d, J=100.2 Hz, 3H), 7.61-7.26 (m, 6H), 7.09 (dd, J=8.8, 2.0 Hz, 1H), 5.85-5.28 (m, 1H), 4.82-3.84 (m, 1H), 3.68 (d, J=13.6 Hz, 1H), 3.62-3.42 (m, 4H), 2.67 (d, J=4.0 Hz, 2H). LC-MS: [M+H]⁺=431.1, 433.1.

(6-Chloro-1,3,4,9-tetrahydro-2H-pyrido[3,4-b]indol-2-yl)(4-chloro-2,3-dihydroxyphenyl)methanone

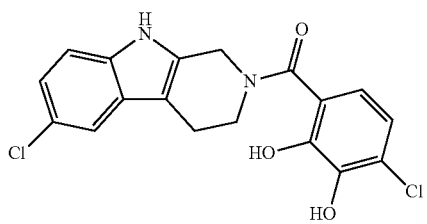 [SMILES: O=C(c1ccc(Cl)c(O)c1O)N1CCc2c([nH]c3ccc(Cl)cc23)C1]

¹H NMR (400 MHz, CD₃OD) δ 7.37 (d, J=1.6 Hz, 1H), 7.24 (d, J=8.4 Hz, 1H), 7.02 (dd, J=8.4, 2.0 Hz, 1H), 6.90 (d, J=8.4 Hz, 1H), 6.73 (d, J=8.4 Hz, 1H), 4.58 (s, 2H), 3.77 (s, 2H), 2.81 (s, 2H). LCMS: [M+H]⁺=377.0, 379.0.

(6-Chloro-1,3,4,9-tetrahydro-2H-pyrido[3,4-b]indol-2-yl)(3-chloro-2-hydroxy-4-methylphenyl)methanone

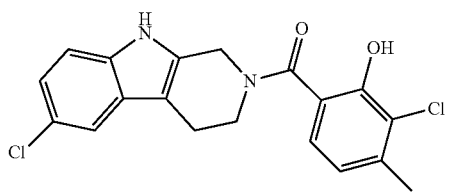 [SMILES: Cc1ccc(C(=O)N2CCc3c([nH]c4ccc(Cl)cc34)C2)c(O)c1Cl]

¹H NMR (400 MHz, CD₃OD) δ 7.37 (d, J=2.0 Hz, 1H), 7.24 (d, J=8.4 Hz, 1H), 7.08 (d, J=8.0 Hz, 1H), 7.02 (dd, J=8.6, 2.0 Hz, 1H), 6.91 (d, J=7.8 Hz, 1H), 5.01 (d, J=117.8 Hz, 2H), 3.79 (s, 2H), 2.81 (s, 2H), 2.40 (s, 3H). LC-MS: [M+H]⁺=375.0, 377.0.

(3-((2-Aminoethyl)amino)-5-chlorophenyl)(6-chloro-1,3,4,9-tetrahydro-2H-pyrido[3,4-b]indol-2-yl)methanone formate

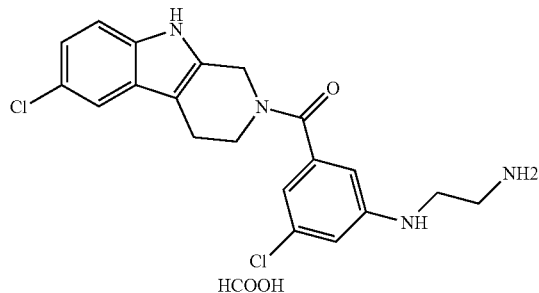 [SMILES: NCCNc1cc(Cl)cc(C(=O)N2CCc3c([nH]c4ccc(Cl)cc34)C2)c1 ; "HCOOH"]

¹H NMR (400 MHz, CD₃OD) δ 8.54 (s, 1H), 7.38 (s, 1H), 7.28-7.19 (m, 1H), 7.05 (m, 1H), 6.80 (br, 1H), 6.72 (br, 1H), 6.63 (m, 1H), 4.86 (br, 2H), 4.65-4.07 (m, 1H), 3.74 (s, 1H), 3.36 (m, 2H), 3.09 (m, 2H), 2.85 (m, 2H). LC-MS: [M+H]⁺=403.1, 405.1.

3-Amino-1-(6-chloro-1,3,4,9-tetrahydro-2H-pyrido[3,4-b]indol-2-yl)-2-(4-chlorophenyl)propan-1-one formate

¹H NMR (400 MHz, DMSO-d₆) δ 11.12 (m, 1H), 8.32 (m, 1H), 7.43-7.26 (m, 6H), 7.02 (m, 1H), 4.80-4.62 (m, 2H), 4.36 (br, 2H), 3.96-3.70 (m, 4H), 3.17 (br, 2H), 2.81-2.62 (m, 3H), 2.13 (m, 1H). LCMS: [M+H]⁺=388.0, 390.0.

1-(6-Chloro-1,3,4,9-tetrahydro-2H-pyrido[3,4-b]indol-2-yl)-2-(3,4-dichlorophenyl)-2-hydroxyethan-1-one

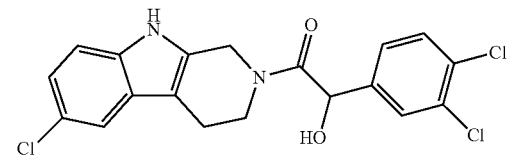 [SMILES: O=C(C(O)c1ccc(Cl)c(Cl)c1)N1CCc2c([nH]c3ccc(Cl)cc23)C1]

¹H NMR (400 MHz, CD₃OD) δ 7.66 (d, J=2.0 Hz, 1H), 7.54 (d, J=8.3 Hz, 1H), 7.44-7.16 (m, 3H), 7.01 (dd, J=8.6, 1.9 Hz, 1H), 5.57 (d, J=29.7 Hz, 1H), 4.79-4.45 (m, 2H), 4.09-3.71 (m, 2H), 2.83-2.33 (m, 2H). LCMS: [M+H]⁺=409.0, 411.0.

2-Amino-1-(6-chloro-3,4-dihydro-1H-pyrido[3,4-b]indol-2(9H)-yl)-3-(4-chlorophenyl)propan-1-one hydrochloride

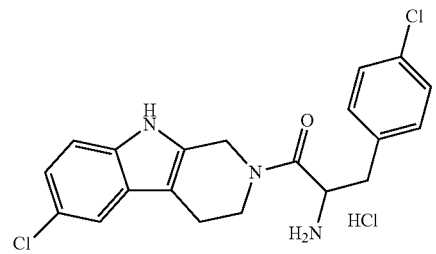 [SMILES: NC(Cc1ccc(Cl)cc1)C(=O)N1CCc2c([nH]c3ccc(Cl)cc23)C1 ; Cl]

¹H NMR (400 MHz, DMSO-d₆): δ 11.20~11.03 (m, 1H), 8.36 (br, 3H), 7.43~7.22 (m, 6H), 7.06 (dd, J=8.8, 2.0 Hz, 1H), 4.88~4.71 (m, 2H), 4.55~4.25 (m, 1H), 3.92~3.42 (m, 2H), 3.13~2.97 (m, 2H), 2.73~2.21 (m, 2H). LCMS: [M+H]⁺=388.2

121

1-(6-Chloro-3,4-dihydro-1H-pyrido[3,4-b]indol-2 (9H)-yl)-3-(4-chlorophenyl)-2-((2-hydroxyethyl) amino)propan-1-one

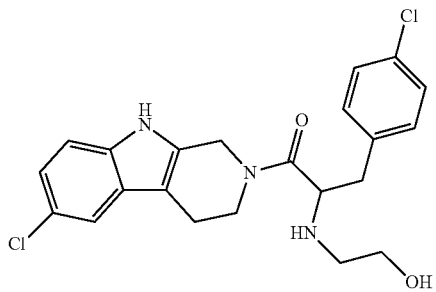 [SMILES: O=C(C(Cc1ccc(Cl)cc1)NCCO)N1CCc2c([nH]c3ccc(Cl)cc23)C1]

$^1$H NMR (400 MHz, DMSO-d$_6$): δ 11.06~10.92 (m, 1H), 7.40-7.39 (m, 1H), 7.32~7.29 (m, 1H), 7.27~7.24 (m, 3H), 7.19~7.13 (m, 1H), 7.03~7.01 (m, 1H), 4.80~4.75 (t, 1H), 4.57~4.41 (m, 2H), 4.01~3.79 (m, 1H), 3.78~3.52 (m, 2H), 3.39~3.34 (m, 2H), 2.79~2.54 (m, 4H), 2.43~2.38 (m, 2H), 2.08 (br, 1H). LCMS: [M+H]$^+$=432.1.

1-(6-Chloro-3,4-dihydro-1H-pyrido[3,4-b]indol-2 (9H)-yl)-3-(4-chlorophenyl)-2-(ethylamino)propan-1-one formate

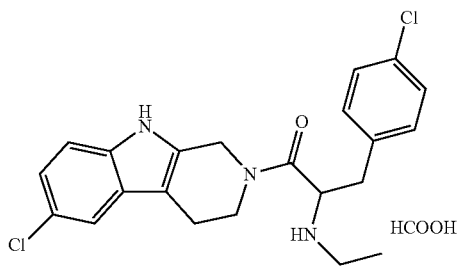 [SMILES: CCNC(Cc1ccc(Cl)cc1)C(=O)N1CCc2c([nH]c3ccc(Cl)cc23)C1 ; "HCOOH"]

$^1$H NMR (400 MHz, CDCl$_3$) δ 8.38 (s, 1H), 8.10 (d, J=20.0 Hz, 1H), 7.395 (d, J=2.0 Hz, 1H), 7.24-7.12 (m, 5H), 6.96 (d, J=4.0 Hz, 1H), 4.97 (d, J=8.0 Hz, 1H), 4.57-4.43 (m, 2H), 4.13-4.03 (m, 1H), 3.91-3.54 (m, 2H), 3.25-3.11 (m, 2H), 2.96-2.87 (m, 2H), 2.73-2.61 (m, 2H), 2.33-2.11 (m, 1H), 1.45-1.09 (m, 3H). LCMS: [M+H]$^+$=416.1.

2-((2-Aminoethyl)amino)-1-(6-chloro-3,4-dihydro-1H-pyrido[3,4-b]indol-2(9H)-yl)-3-(4-chlorophenyl) propan-1-one formate

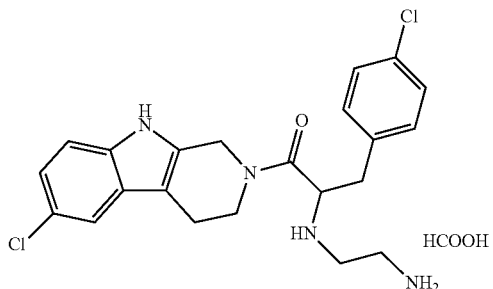

122

$^1$H NMR (400 MHz, DMSO-d$_6$): δ 11.21 (s, 1H), 8.41 (br, 1H), 7.42~7.39 (m, 1H), 7.33~7.14 (m, 5H), 7.04~7.01 (m, 1H), 4.80~4.74 (m, 1H), 4.57~4.40 (m, 1H), 4.03~3.89 (m, 1H), 3.79~3.48 (m, 2H), 2.82~2.55 (m, 7H), 2.45~2.40 (m, 1H). LCMS: [M+H]$^+$=431.1.

1-(6-Chloro-3,4-dihydro-1H-pyrido[3,4-b]indol-2 (9H)-yl)-3-(4-chlorophenyl)propan-1-one

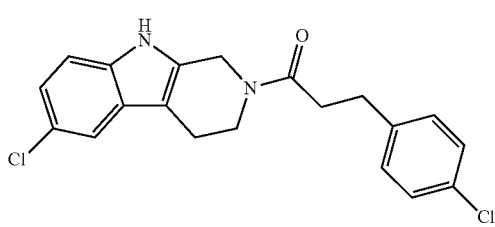 [SMILES: O=C(CCc1ccc(Cl)cc1)N1CCc2c([nH]c3ccc(Cl)cc23)C1]

$^1$H NMR (400 MHz, DMSO-d$_6$): δ 8.28~7.74 (m, 1H), 7.45~7.41 (m, 1H), 7.26~7.09 (m, 6H), 4.81~4.54 (m, 1H), 3.97~3.72 (m, 2H), 3.04~2.97 (m, 2H), 2.78~2.66 (m, 4H). LCMS: [M+H]$^+$=373.1.

1-(6-Chloro-3,4-dihydro-1H-pyrido[3,4-b]indol-2 (9H)-yl)-3-(6-(trifluoromethyl) pyridin-3-yl)propan-1-one

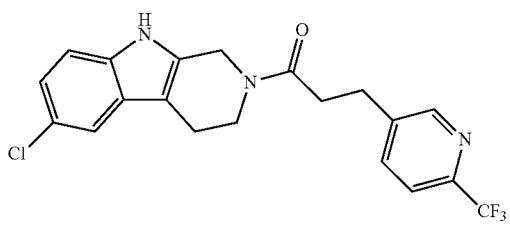 [SMILES: O=C(CCc1ccc(C(F)(F)F)nc1)N1CCc2c([nH]c3ccc(Cl)cc23)C1]

$^1$H NMR (400 MHz, DMSO-d$_6$): δ 8.64~8.61 (m, 1H), 8.09~7.84 (br, 1H), 7.79~7.75 (m, 2H), 7.61~7.53 (m, 1H), 7.45~7.41 (m, 1H), 7.24~7.21 (m, 1H), 7.13~7.10 (m, 1H), 4.80~4.59 (m, 2H), 3.97~3.75 (m, 2H), 3.16~3.11 (m, 2H), 2.85~2.73 (m, 4H). LCMS: [M+H]$^+$=408.1.

1-(6-Chloro-3,4-dihydro-1H-pyrido[3,4-b]indol-2 (9H)-yl)-3-(6-(trifluoromethyl) pyridine-3-yl)propan-1-one

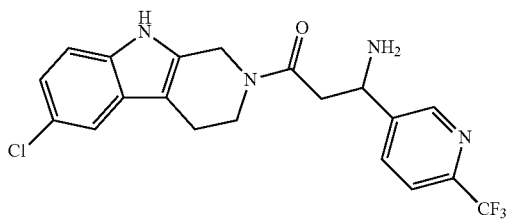 [SMILES: NC(CC(=O)N1CCc2c([nH]c3ccc(Cl)cc23)C1)c1ccc(C(F)(F)F)nc1]

$^1$H NMR (400 MHz, DMSO-d$_6$): δ 11.11~11.04 (m, 1H), 8.83-8.81 (m, 1H), 8.26 (br, 1H), 8.16~8.11 (m, 1H), 7.89~7.82 (m, 1H), 7.43 (s, 1H), 7.35~7.31 (m, 1H), 7.04~7.02 (m, 1H), 4.68 (s, 2H), 4.52 (s, 1H), 3.83~3.74 (m, 3H), 2.99~2.94 (m, 2H), 2.76~2.63 (m, 2H). LCMS: [M+H]⁺=423.2.

1-(6-Chloro-3,4-dihydro-1H-pyrido[3,4-b]indol-2 (9H)-yl)-2-((4-chlorophenyl) amino)ethanone formate

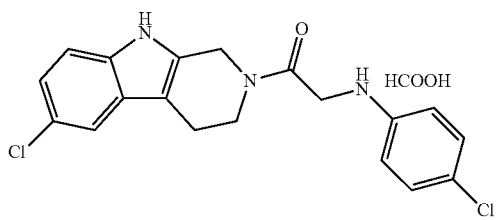 [SMILES: O=C(CNc1ccc(Cl)cc1)N1CCc2c([nH]c3ccc(Cl)cc23)C1 ; "HCOOH"]

¹H NMR (400 MHz, DMSO-d₆) δ 11.08 (s, 1H), 7.46 (s, 1H), 7.35-7.33 (m, 1H), 7.10-7.02 (m, 3H), 6.70-6.65 (m, 2H), 5.91-5.87 (m, 1H), 4.76-4.71 (m, 2H), 4.07-4.02 (m, 2H), 3.84-3.80 (m, 2H), 2.79-2.67 (m, 2H). LCMS: [M+H]⁺=374.2.

(6-Chloro-3,4-dihydro-1H-pyrido[3,4-b]indol-2(9H)-yl) (3-chloro-4-(2-hydroxyethyl)phenyl)methanone

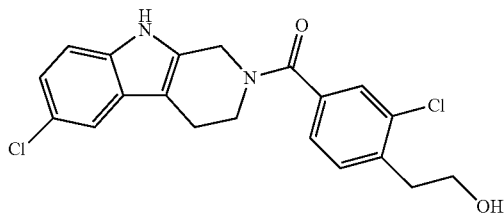 [SMILES: O=C(c1ccc(CCO)c(Cl)c1)N1CCc2c([nH]c3ccc(Cl)cc23)C1]

¹H NMR (400 MHz, DMSO-d₆): δ 11.18~10.87 (m, 1H), 7.51~7.46 (m, 1H), 7.38~7.30 (m, 2H), 7.05 (d, J=7.2 Hz, 1H), 4.82~4.63 (m, 3H), 3.96~3.65 (m, 4H), 2.93~2.90 (m, 2H), 2.75 (s, 2H). LCMS: [M+H]⁺=389.2.

(4-Butylphenyl)(6-chloro-3,4-dihydro-1H-pyrido[3,4-b]indol-2(9H)-yl)methanone

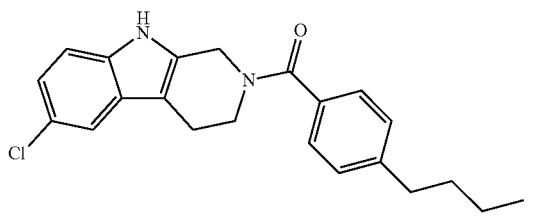 [SMILES: CCCCc1ccc(C(=O)N2CCc3c([nH]c4ccc(Cl)cc34)C2)cc1]

¹H NMR (400 MHz, DMSO-d₆) δ 11.16-10.86 (m, 1H), 7.45 (s, 1H), 7.38-7.28 (m, 5H), 7.04 (d, J=8.0 Hz, 1H), 4.80-4.59 (m, 2H), 3.96-3.62 (m, 2H), 2.75 (br s, 1H), 2.64 (t, J=7.6 Hz, 2H), 1.62-1.54 (m, 2H), 1.37-1.28 (m, 2H), 0.91 (t, J=7.2 Hz, 3H). LCMS: [M+H]⁺=367.2.

(6-Chloro-3,4-dihydro-1H-pyrido[3,4-b]indol-2(9H)-yl)(3-chloro-4-(3-hydroxypropyl)phenyl)methanone

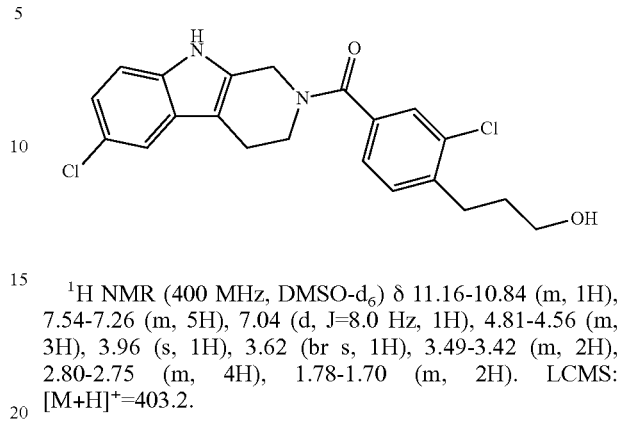

¹H NMR (400 MHz, DMSO-d₆) δ 11.16-10.84 (m, 1H), 7.54-7.26 (m, 5H), 7.04 (d, J=8.0 Hz, 1H), 4.81-4.56 (m, 3H), 3.96 (s, 1H), 3.62 (br s, 1H), 3.49-3.42 (m, 2H), 2.80-2.75 (m, 4H), 1.78-1.70 (m, 2H). LCMS: [M+H]⁺=403.2.

(6-Chloro-3,4-dihydro-1H-pyrido[3,4-b]indol-2(9H)-yl)(3-(trifluoromethyl) phenyl)methanone

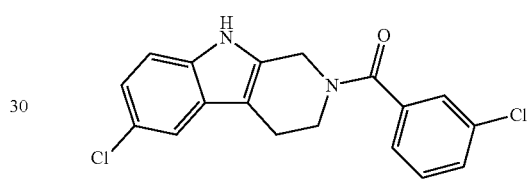

¹H NMR (400 MHz, DMSO-d₆) δ 11.17-10.83 (m, 1H), 7.89-7.72 (m, 4H), 7.46 (s, 1H), 7.37-7.26 (m, 1H), 7.06-7.01 (m, 1H), 4.85-4.59 (m, 2H), 3.99-3.56 (m, 2H), 2.79-2.66 (m, 2H). LCMS: [M+H]⁺=379.2.

(4-(3-Aminopropyl)-3-chlorophenyl)(6-chloro-3,4-dihydro-1H-pyrido[3,4-b]indol-2(9H)-yl)methanone

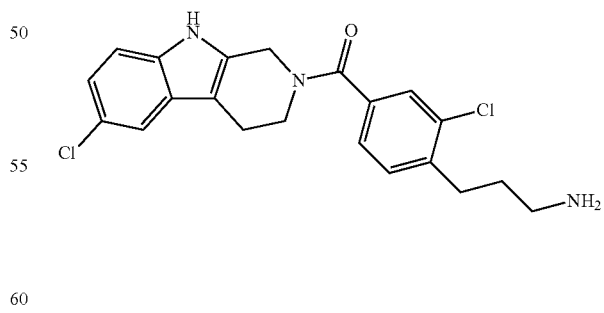

¹H NMR (400 MHz, DMSO-d₆): δ 11.26 (br, 1H), 7.47~7.43 (m, 3H), 7.34~7.32 (m, 2H), 6.99 (s, 1H), 4.80~4.59 (m, 2H), 3.95~3.47 (m, 3H), 2.95~2.56 (m, 6H), 1.69~1.62 (m, 2H). LCMS: [M+H]⁺=402.1.

125

(6-Chloro-4-(hydroxymethyl)-3,4-dihydro-1H-pyrido[3,4-b]indol-2(9H)-yl)(3-chlorophenyl)methanone

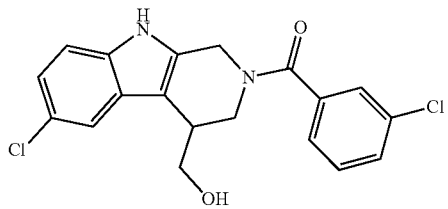 [SMILES: O=C(c1cccc(Cl)c1)N1Cc2[nH]c3ccc(Cl)cc3c2C(CO)C1]

$^1$H NMR (400 MHz, DMSO-d$_6$): δ 11.23~10.89 (m, 1H), 7.56~7.27 (m, 6H), 7.28~6.87 (m, 1H), 6.64~6.59 (m, 0.5H), 5.07~5.02 (m, 0.5H), 4.74~4.43 (m, 2.5H), 3.81~3.71 (m, 1.5H), 3.56 (dd, J=13.2, 4.4 Hz, 1H), 3.17~3.02 (m, 1H). LCMS: [M+H]$^+$=375.1.

(6-Chloro-1-(hydroxymethyl)-3,4-dihydro-1H-pyrido[3,4-b]indol-2 (9H)-yl)(3-chlorophenyl) methanone

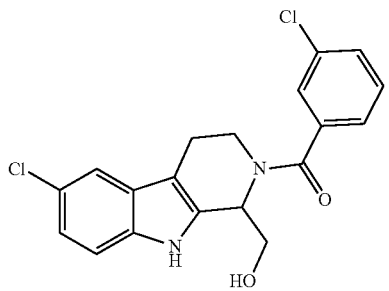 [SMILES: O=C(c1cccc(Cl)c1)N1CCc2c([nH]c3ccc(Cl)cc23)C1CO]

$^1$H NMR (400 MHz, DMSO-d$_6$): δ 11.14~10.89 (m, 1H), 7.56~7.27 (m, 6H), 7.05 (d, J=8.4 Hz, 1H), 5.63~4.74 (m, 2H), 3.89~3.87 (m, 1H), 3.80~3.57 (m, 2H), 2.80~2.73 (m, 1H), 2.65 (d, J=4.4 Hz, 1H). LCMS: [M+H]$^+$=375.1.

(6-Chloro-1-(hydroxymethyl)-3,4-dihydro-1H-pyrido[3,4-b]indol-2(9H)-yl) (3-chlorophenyl) methanone

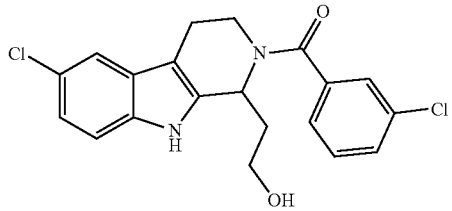 [SMILES: O=C(c1cccc(Cl)c1)N1CCc2c([nH]c3ccc(Cl)cc23)C1CCO]

$^1$H NMR (400 MHz, DMSO-d$_6$): δ 11.17~10.86 (m, 1H), 7.58~7.25 (m, 6H), 7.07 (dd, J=8.4, 2.0 Hz, 1H), 5.80 (dd, J=9.2, 4.0 Hz, 0.8H), 4.86~4.56 (m, 1.2H), 3.69~3.44 (m, 4H), 2.83~2.65 (m, 2H), 2.20~1.96 (m, 2H). LCMS: [M+H]$^+$=389.3.

126

6-Chloro-2-(3-chlorobenzoyl)-N-methyl-2,3,4,9-tetrahydro-1H-pyrido[3,4-b]indole-1-carboxamide

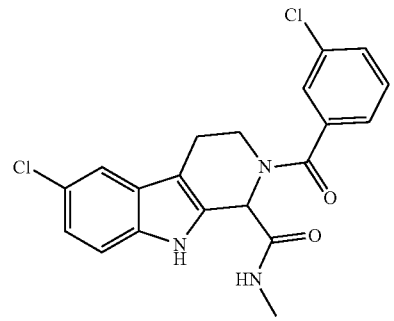 [SMILES: CNC(=O)C1c2[nH]c3ccc(Cl)cc3c2CCN1C(=O)c1cccc(Cl)c1]

$^1$H NMR (400 MHz, DMSO-d$_6$): δ 11.04~10.74 (m, 1H), 8.18 (s, 1H), 7.62~7.34 (m, 6H), 7.09~7.07 (m, 1H), 5.94 (s, 0.8H), 5.12~4.82 (m, 0.3H), 3.83~3.59 (m, 1.8H), 2.78~2.69 (m, 5.3H). LCMS: [M+H]$^+$=402.1.

6-Chloro-2-(3-chlorobenzoyl)-N-(2-hydroxyethyl)-2,3,4,9-tetrahydro-1H-pyrido[3,4-b]indole-1-carboxamide

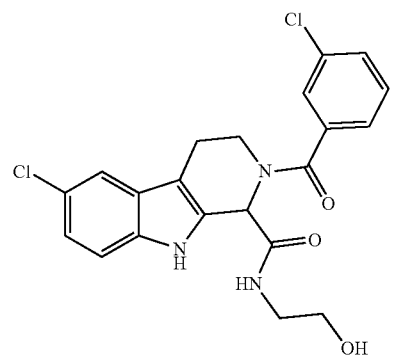 [SMILES: O=C(NCCO)C1c2[nH]c3ccc(Cl)cc3c2CCN1C(=O)c1cccc(Cl)c1]

$^1$H NMR (400 MHz, DMSO-d$_6$) δ 7.59-7.45 (m, 5H), 7.40-7.30 (m, 1H), 7.08 (d, J=7.6 Hz, 1H), 6.06 (s, 1H), 4.00-3.95 (m, 1H), 3.81-3.75 (m, 1H), 3.69-3.62 (m, 2H), 3.48-3.35 (m, 3H), 2.91-2.76 (m, 2H). LCMS: [M+H]$^+$=432.2.

(5-Chloro-2,3-dihydroxyphenyl)(6-chloro-3,4-dihydro-1H-pyrido[3,4-b]indol-2(9H)-yl)methanone

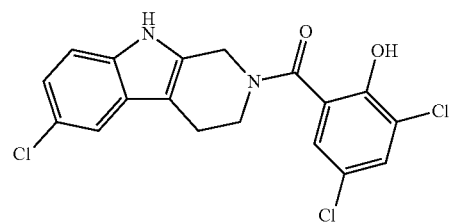 [SMILES: O=C(c1cc(Cl)cc(Cl)c1O)N1CCc2c([nH]c3ccc(Cl)cc23)C1]

$^1$H NMR (400 MHz, DMSO-d$_6$): δ 11.13~10.86 (m, 1H), 7.43~7.28 (m, 2H), 7.04 (d, J=8.4 Hz, 1H), 6.85 (s, 1H), 6.63

(s, 1H), 4.81~4.46 (m, 2H), 3.94~3.52 (m, 2H), 2.73~2.68 (m, 2H). LCMS: [M+H]⁺=377.0.

(6-Chloro-3,4-dihydro-1H-pyrido[3,4-b]indol-2(9H)-yl)(3-chloro-4,5-dihydroxyphenyl)methanone

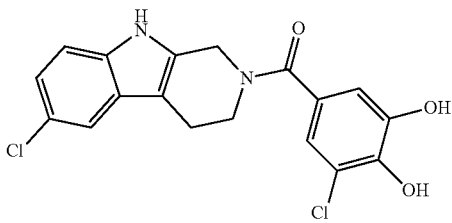 [SMILES: O=C(c1cc(O)c(O)c(Cl)c1)N1CCc2c([nH]c3ccc(Cl)cc23)C1]

¹H NMR (400 MHz, DMSO-d₆): δ 11.11 (br, 1H), 10.11 (s, 1H), 9.62 (s, 1H), 7.45 (d, J=2 Hz, 1H), 7.34 (d, J=8 Hz, 1H), 7.05~7.02 (m, 1H), 6.91~6.84 (m, 2H), 4.71 (s, 2H), 3.72 (br, 2H), 2.74 (s, 2H). LCMS: [M+H]⁺=377.0.

(6-Chloro-3,4-dihydro-1H-pyrido[3,4-b]indol-2(9H)-yl)(4-chloro-3-hydroxyphenyl)methanone

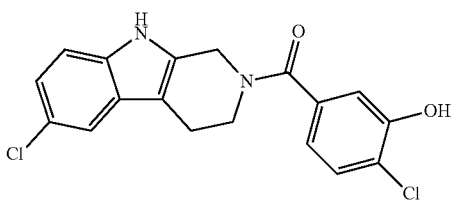 [SMILES: O=C(c1ccc(Cl)c(O)c1)N1CCc2c([nH]c3ccc(Cl)cc23)C1]

¹H NMR (400 MHz, DMSO-d₆): δ 11.16~10.84 (m, 1H), 10.59 (br, 1H), 7.46~7.27 (m, 3H), 7.05~6.87 (m, 3H), 4.79~4.62 (m, 2H), 4.04~3.62 (m, 2H), 2.74~2.68 (m, 2H). LCMS: [M+H]⁺=361.0.

(6-Chloro-3,4-dihydro-1H-pyrido[3,4-b]indol-2(9H)-yl)(3-hydroxy-4-(trifluoromethyl)phenyl)methanone

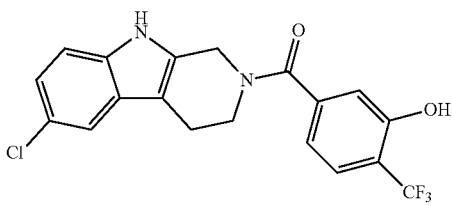 [SMILES: O=C(c1ccc(C(F)(F)F)c(O)c1)N1CCc2c([nH]c3ccc(Cl)cc23)C1]

¹H NMR (400 MHz, DMSO-d₆): δ 11.18~10.84 (m, 2H), 7.61 (d, J=7.6 Hz, 1H), 7.46 (s, 1H), 7.37~7.30 (m, 1H), 7.06~6.98 (m, 3H), 4.82~4.55 (m, 2H), 3.97~3.60 (m, 2H), 2.78~2.73 (m, 2H). LCMS: [M+H]⁺=395.1.

(6-Chloro-3,4-dihydro-1H-pyrido[3,4-b]indol-2(9H)-yl)(3-hydroxy-5-(trifluoromethyl)phenyl)methanone

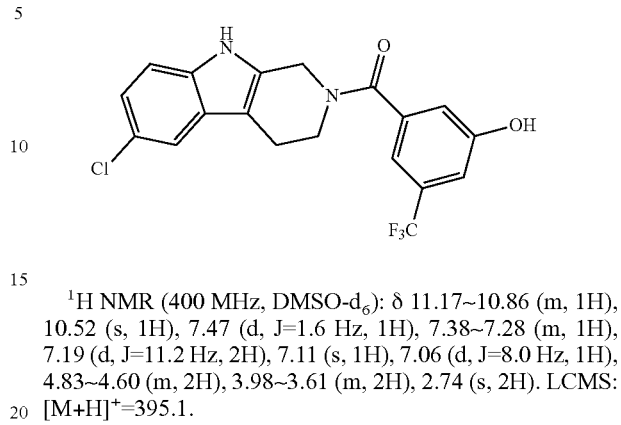

¹H NMR (400 MHz, DMSO-d₆): δ 11.17~10.86 (m, 1H), 10.52 (s, 1H), 7.47 (d, J=1.6 Hz, 1H), 7.38~7.28 (m, 1H), 7.19 (d, J=11.2 Hz, 2H), 7.11 (s, 1H), 7.06 (d, J=8.0 Hz, 1H), 4.83~4.60 (m, 2H), 3.98~3.61 (m, 2H), 2.74 (s, 2H). LCMS: [M+H]⁺=395.1.

(6-Chloro-4-(hydroxymethyl)-3,4-dihydro-1H-pyrido[3,4-b]indol-2(9H)-yl)(3-chloro-5-hydroxyphenyl)methanone

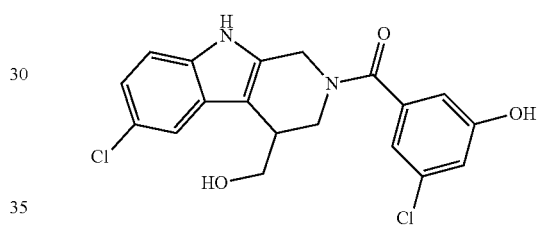

¹H NMR (400 MHz, DMSO-d₆): δ 11.21~10.90 (m, 1H), 10.06 (br, 1H), 7.55~7.51 (m, 1H), 7.35~7.27 (m, 1H), 3.90 (d, J=1.6 Hz, 2H), 7.04 (d, J=8.0 Hz, 1H), 6.74 (s, 1H), 5.01~4.40 (m, 3.5H), 3.80~3.42 (m, 2.5H), 3.12~3.02 (m, 1H). LCMS: [M−H]⁻=389.1.

(6-Chloro-3,4-dihydro-1H-pyrido[3,4-b]indol-2(9H)-yl)(3-chloro-5-hydroxy-4-methylphenyl)methanone

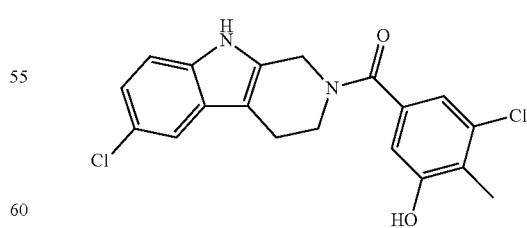

¹H NMR (400 MHz, DMSO-d₆): δ 11.16~10.83 (m, 1H), 10.20 (s, 1H), 7.46 (d, J=2.0 Hz, 1H), 7.35~7.28 (m, 1H), 7.05 (d, J=8.0 Hz, 1H), 6.86~6.78 (m, 1H), 4.78~4.58 (m, 2H), 3.93~3.59 (m, 2H), 2.74~2.71 (m, 2H), 2.21 (s, 3H). LCMS: [M+H]⁺=375.1.

129

(6-Chloro-3,4-dihydro-1H-pyrido[3,4-b]indol-2(9H)-yl)(3,4-dichloro-5-hydroxyphenyl)methanone

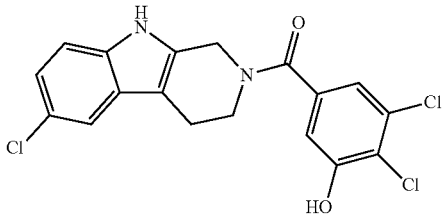 [SMILES: O=C(c1cc(O)c(Cl)c(Cl)c1)N1CCc2c([nH]c3ccc(Cl)cc23)C1]

$^1$H NMR (400 MHz, DMSO-d$_6$): δ 11.16~10.82 (m, 1H), 7.46 (s, 1H), 7.45~7.30 (m, 1H), 7.13 (s, 1H), 7.05~6.98 (m, 2H), 4.79~4.60 (m, 2H), 3.94~3.62 (m, 2H), 2.74 (s, 2H). LCMS: [M+H]$^+$=395.0.

(6-Chloro-3,4-dihydro-1H-pyrido[3,4-b]indol-2(9H)-yl)(3-chloro-4-(hydroxymethyl)phenyl)methanone

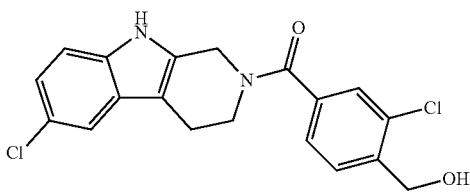 [SMILES: O=C(c1ccc(CO)c(Cl)c1)N1CCc2c([nH]c3ccc(Cl)cc23)C1]

$^1$H NMR (400 MHz, DMSO-d$_6$): δ 11.17~10.84 (m, 1H), 7.65 (d, J=7.6 Hz, 1H), 7.50~7.45 (m, 3H), 7.36~7.29 (m, 1H), 7.05 (d, J=8.0 Hz, 1H), 5.52~4.82 (m, 2H), 4.61 (s, 2H), 3.96~3.62 (m, 2H), 2.75 (s, 2H). LCMS: [M+H]$^+$=375.2.

N-(3-Chloro-5-(6-chloro-2,3,4,9-tetrahydro-1H-pyrido[3,4-b]indole-2-carbonyl)phenyl)methane-sulfonamide

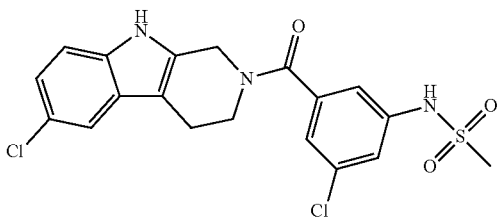 [SMILES: CS(=O)(=O)Nc1cc(Cl)cc(C(=O)N2CCc3c([nH]c4ccc(Cl)cc34)C2)c1]

$^1$H NMR (400 MHz, DMSO-d$_6$): δ 11.17~10.87 (m, 1H), 7.46 (d, J=1.6 Hz, 1H), 7.37~7.33 (m, 2H), 7.23~7.20 (m, 2H), 7.05 (d, J=7.6 Hz, 1H), 4.81~4.60 (m, 2H), 3.96~3.62 (m, 2H), 3.10 (s, 3H), 2.51 (s, 2H). LCMS: [M+H]$^+$=438.0.

130

(6-Chloro-3,4-dihydro-1H-pyrido[3,4-b]indol-2(9H)-yl)(3-chloro-5-(2-hydroxyethyl)phenyl)methanone

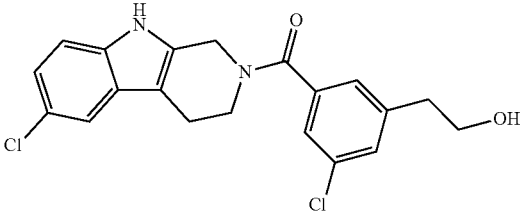 [SMILES: O=C(c1cc(Cl)cc(CCO)c1)N1CCc2c([nH]c3ccc(Cl)cc23)C1]

$^1$H NMR (400 MHz, DMSO-d$_6$): δ 11.16~10.86 (m, 1H), 7.46~7.44 (m, 2H), 7.34~7.26 (m, 3H), 7.06 (d, J=8.4 Hz, 1H), 4.82~4.60 (m, 3H), 3.96~3.62 (m, 4H), 2.78~2.73 (m, 4H). LCMS: [M+H]$^+$=389.1.

(6-Chloro-3,4-dihydro-1H-pyrido[3,4-b]indol-2(9H)-yl)(4-(trifluoromethyl) phenyl)methanone

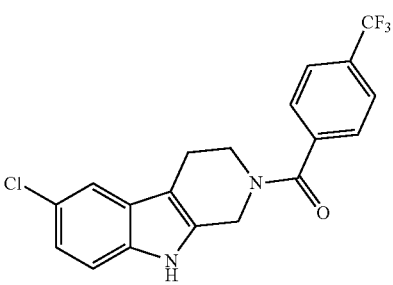 [SMILES: O=C(c1ccc(C(F)(F)F)cc1)N1CCc2c([nH]c3ccc(Cl)cc23)C1]

$^1$H NMR (400 MHz, DMSO-d$_6$): δ 11.20~10.83 (m, 1H), 7.87 (d, J=8.0, Hz, 2H), 7.71 (d, J=7.6 Hz, 2H), 7.46 (s, 1H), 7.38~7.27 (m, 1H), 7.07~7.02 (m, 1H), 4.86·4.55 (m, 2H), 4.01~3.59 (m, 2H), 2.80~2.74 (m, 2H). LCMS: [M+H]$^+$=379.1.

(6-Chloro-3,4-dihydro-1H-pyrido[3,4-b]indol-2(9H)-yl)(3-chloro-5-hydroxyphenyl) methanone

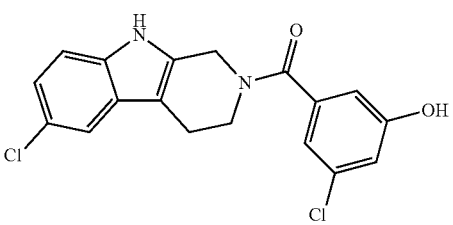 [SMILES: O=C(c1cc(O)cc(Cl)c1)N1CCc2c([nH]c3ccc(Cl)cc23)C1]

$^1$H NMR (400 MHz, DMSO-d$_6$): δ 11.16~10.86 (m, 1H), 10.21 (br, 1H), 7.46 (d, J=2.0 Hz, 1H), 7.36~7.30 (m, 1H), 7.06 (d, J=7.6 Hz, 1H), 6.90~6.76 (m, 3H), 4.79~4.55 (m, 2H), 3.94~3.60 (m, 2H), 3.32~2.72 (m, 2H). LCMS: [M+H]$^+$=361.1.

131

2-Amino-1-(6-chloro-3,4-dihydro-1H-pyrido[3,4-b]indol-2(9H)-yl)-2-(3-chloro-5-hydroxyphenyl)ethanone

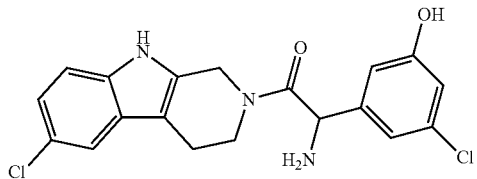 [SMILES: NC(C(=O)N1CCc2c([nH]c3ccc(Cl)cc23)C1)c1cc(O)cc(Cl)c1]

$^1$H NMR (400 MHz, DMSO-d$_6$): δ 11.08~11.02 (m, 1H), 9.92 (br, 1H), 7.42~7.40 (m, 1H), 7.32~7.29 (m, 1H), 7.03 (dd, J=8.4, 2.0 Hz, 1H), 6.90~6.82 (m, 1H), 6.73~6.64 (m, 2H), 4.92~4.39 (m, 3H), 4.04~3.65 (m, 2H), 2.69~2.62 (m, 1H), 2.33~2.26 (m, 1H), 2.19 (br, 2H). LCMS: [M+H]$^+$=390.0

1-(6-Chloro-3,4-dihydro-1H-pyrido[3,4-b]indol-2(9H)-yl)-2-(4-chlorophenyl)-3-hydroxypropan-1-one

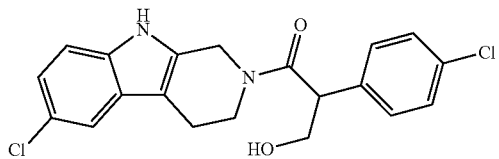 [SMILES: O=C(C(CO)c1ccc(Cl)cc1)N1CCc2c([nH]c3ccc(Cl)cc23)C1]

$^1$H NMR (400 MHz, DMSO-d$_6$): δ 11.08~10.96 (m, 1H), 7.41~7.27 (m, 6H), 7.02 (dd, J=8.8, 2.4 Hz, 1H), 4.84~4.72 (m, 2H), 4.46~3.78 (m, 4H), 3.52 (dd, J=10.0, 5.6 Hz, 1H), 2.67~2.62 (m, 1.2H), 2.29~2.24 (m, 0.8H). LCMS: [M+H]$^+$=389.3.

1-(6-Chloro-3,4-dihydro-1H-pyrido[3,4-b]indol-2(9H)-yl)-2-(4-chlorophenyl)-3-hydroxybutan-1-one

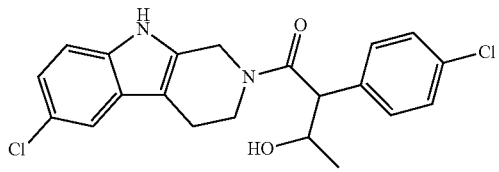 [SMILES: CC(O)C(C(=O)N1CCc2c([nH]c3ccc(Cl)cc23)C1)c1ccc(Cl)cc1]

$^1$H NMR (400 MHz, DMSO-d$_6$): δ 11.08~10.96 (m, 1H), 7.43~7.28 (m, 6H), 7.02~6.99 (m, 1H), 4.92~4.42 (m, 3H), 4.17~4.09 (m, 1H), 4.01~3.99 (m, 1H), 3.85~3.80 (m, 2H), 2.68~2.62 (m, 1H), 2.28~2.24 (m, 1H), 1.11~1.07 (m, 3H). LCMS: [M+H]$^+$=403.2.

132

1-(6-Chloro-3,4-dihydro-1H-pyrido[3,4-b]indol-2(9H)-yl)-2-(4-chlorophenyl)-4-hydroxybutan-1-one

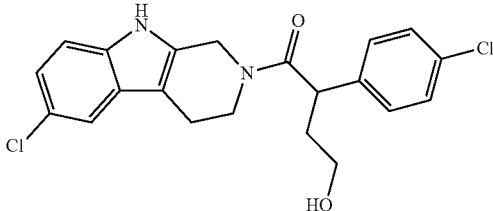 [SMILES: O=C(C(CCO)c1ccc(Cl)cc1)N1CCc2c([nH]c3ccc(Cl)cc23)C1]

$^1$H NMR (400 MHz, DMSO-d$_6$): δ 11.07~10.95 (m, 1H), 7.40~7.28 (m, 6H), 7.02 (dd, J=8.8, 2.0 Hz, 1H), 4.89~4.42 (m, 3H), 4.33~3.21 (m, 1H), 3.93~3.68 (m, 2H), 3.32~3.29 (m, 2H), 2.68~2.62 (m, 1H), 2.27~2.07 (m, 2H), 1.76~1.69 (m, 1H). LCMS: [M+H]$^+$=403.3.

1-(1-(Aminomethyl)-6-chloro-3,4-dihydro-1H-pyrido[3,4-b]indol-2(9H)-yl)-2-(4-chlorophenyl)-2-hydroxyethanone hydrochloride

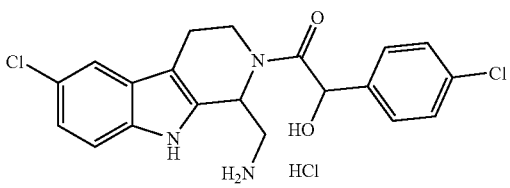 [SMILES: NCC1c2[nH]c3ccc(Cl)cc3c2CCN1C(=O)C(O)c1ccc(Cl)cc1 ; Cl]

$^1$H NMR (400 MHz, DMSO-d$_6$): δ 11.40~11.05 (m, 1H), 8.58~8.14 (m, 3H), 7.55~7.05 (m, 7H), 8.56~8.47 (m, 1H), 5.85~5.57 (m, 2H), 4.77~4.11 (m, 1H), 3.44~3.38 (m, 1H), 3.29~3.16 (m, 1H), 2.68~2.59 (m, 1H), 2.47~2.33 (m, 1H). LCMS: [M+H]$^+$=404.0.

1-(6-Chloro-1-(hydroxymethyl)-3,4-dihydro-1H-pyrido[3,4-b]indol-2(9H)-yl)-2-(4-chlorophenyl)-2-hydroxyethanone

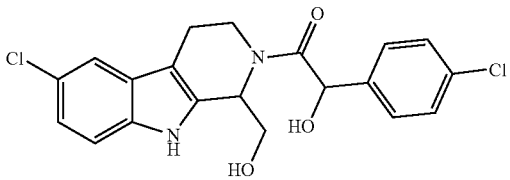 [SMILES: O=C(C(O)c1ccc(Cl)cc1)N1CCc2c([nH]c3ccc(Cl)cc23)C1CO]

$^1$H NMR (400 MHz, DMSO-d$_6$): δ 11.09~10.91 (m, 1H), 7.44~7.24 (m, 6H), 7.06~7.00 (m, 1H), 6.17~6.40 (m, 3H), 5.11~4.12 (m, 1H), 4.21~4.11 (m, 1H), 3.82~3.66 (m, 2H), 3.44~3.05 (m, 1H), 2.66~2.19 (m, 2H). LCMS: [M−H]$^+$=405.0.

133

1-(6-Chloro-3,4-dihydro-1H-pyrido[3,4-b]indol-2(9H)-yl)-3-(4-chlorophenyl)-2,3-dihydroxypropan-1-one

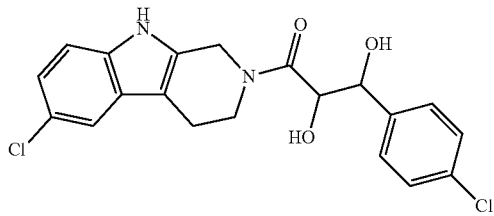 [SMILES: O=C(C(O)C(O)c1ccc(Cl)cc1)N1CCc2c([nH]c3ccc(Cl)cc23)C1]

$^1$H NMR (400 MHz, DMSO-d$_6$): δ 11.0~611.01 (m, 1H), 7.43~7.08 (m, 6H), 7.05 (dd, J=8.4, 1.6 Hz, 1H), 5.59 (br, 1H), 5.15~5.12 (m, 1H), 4.92~4.52 (m, 4H), 3.90~3.66 (m, 2H), 2.76~2.61 (m, 2H). LCMS: [M+H]$^+$=405.0.

1-(6-Chloro-3,4-dihydro-1H-pyrido[3,4-b]indol-2(9H)-yl)-3-(3-chlorophenyl)-2,3-dihydroxypropan-1-one

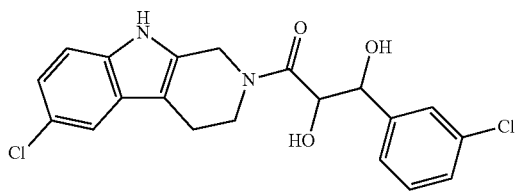 [SMILES: O=C(C(O)C(O)c1cccc(Cl)c1)N1CCc2c([nH]c3ccc(Cl)cc23)C1]

$^1$H NMR (400 MHz, DMSO-d$_6$): δ 11.05~11.00 (m, 1H), 7.42~7.23 (m, 6H), 7.04 (dd, J=8.4, 1.6 Hz, 1H), 5.54~5.52 (m, 1H), 5.17~5.11 (m, 1H), 4.89~4.48 (m, 4H), 3.87~3.63 (m, 2H), 2.74~2.60 (m, 2H). LCMS: [M+H]$^+$=405.0.

2-Amino-N-(3-chloro-5-(6-chloro-2,3,4,9-tetrahydro-1H-pyrido[3,4-b]indole-2-carbonyl)phenyl) acetamide formate

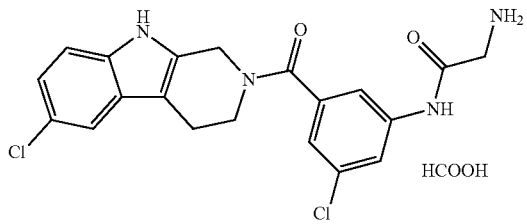 [SMILES: NCC(=O)Nc1cc(Cl)cc(C(=O)N2CCc3c([nH]c4ccc(Cl)cc34)C2)c1 ; "HCOOH"]

$^1$H NMR (400 MHz, DMSO-d$_6$): δ 11.22~10.90 (m, 1H), 8.32 (br, 1H), 7.91 (s, 1H), 7.70~7.62 (m, 1H), 7.46 (d, J=8.4 Hz, 1H), 7.36 (d, J=8.4 Hz, 1H), 7.21 (s, 1H), 7.05 (d, J=7.6 Hz, 1H), 4.82~4.60 (m, 2H), 3.62 (s, 2H), 3.44 (s, 2H), 2.76 (s, 2H). LCMS: [M+H]$^+$=417.2.

134

3-Amino-N-(3-chloro-5-(6-chloro-2,3,4,9-tetrahydro-1H-pyrido[3,4-b]indole-2-carbonyl)phenyl) propanamide formate

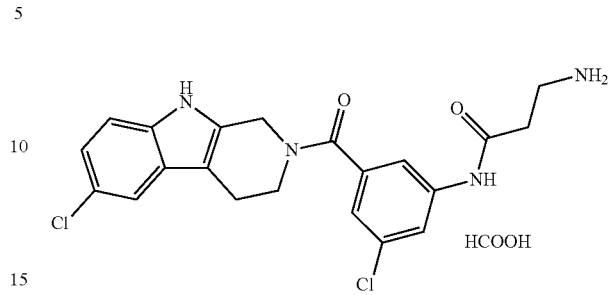

$^1$H NMR (400 MHz, DMSO-d$_6$): δ 11.25~10.96 (m, 1H), 8.41 (s, 1H), 7.88 (s, 1H), 7.62-7.58 (m, 1H), 7.46 (d, J=2.0 Hz, 1H), 7.37~7.30 (m, 1H), 7.20 (s, 1H), 7.05 (d, J=8.4 Hz, 1H), 4.82~4.59 (m, 2H), 3.95~3.62 (m, 2H), 2.98 (s, 2H), 2.76 (s, 2H), 2.62 (s, 2H). LCMS: [M+H]$^+$=431.2.

(6-Chloro-1-(hydroxymethyl)-3,4-dihydro-1H-pyrido[3,4-b]indol-2(9H)-yl)(2,3-dichlorophenyl) methanone formate

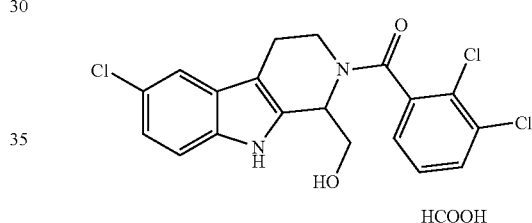

$^1$H NMR (400 MHz, DMSO-d$_6$): δ 11.23~10.92 (m, 1H), 8.50 (s, 0.2H), 7.87~7.66 (m, 1H), 7.54~7.29 (m, 4H), 7.11~7.04 (m, 1H), 5.69~4.84 (m, 2H), 4.60~3.85 (m, 2H), 3.73~3.41 (m, 2H), 2.81~2.59 (m, 2H). LCMS: [M+H]$^+$=409.2.

(6-Chloro-1-(hydroxymethyl)-3,4-dihydro-1H-pyrido[3,4-b]indol-2(9H)-yl) (3-chloro-4-hydroxy-5-methylphenyl)methanone

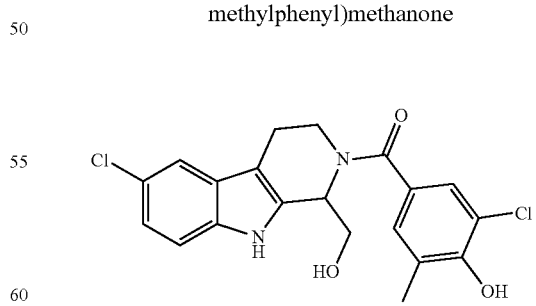

$^1$H NMR (400 MHz, DMSO-d$_6$): δ 11.11 (br, 1H), 8.44 (s, 0.59H), 7.44 (d, J=2.0 Hz, 1H), 7.34~7.29 (m, 1H), 7.19 (s, 1H), 7.06 (dd, J=8.4, 2.0 Hz, 3H), 5.69~5.0 (m, 1H), 3.84 (s, 2H), 3.35 (s, 2H), 2.68 (s, 2H), 2.22 (s, 3H). LCMS: [M+H]$^+$=405.3.

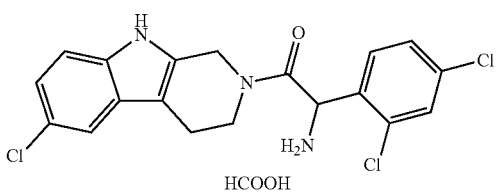 [SMILES: NC(C(=O)N1CCc2c([nH]c3ccc(Cl)cc23)C1)c1ccc(Cl)cc1Cl ; "HCOOH"]

2-Amino-1-(6-chloro-1,3,4,9-tetrahydro-2H-pyrido[3,4-b]indol-2-yl)-2-(2,4-dichlorophenyl)ethan-1-one formate $^1$H NMR (400 MHz, Methanol-$d_4$): δ 7.68-7.57 (m, 1H), 7.38-7.14 (m, 4H), 7.03-6.98 (m, 1H), 5.55-5.49 (m, 1H), 5.00-4.95 (m, 1H), 4.73-4.63 (m, 1H), 4.24-3.60 (m, 2H), 2.78-2.00 (m, 2H). LCMS: [M+H]$^+$=410.0

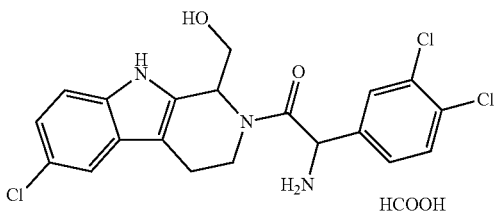 [SMILES: NC(C(=O)N1CCc2c([nH]c3ccc(Cl)cc23)C1CO)c1ccc(Cl)c(Cl)c1 ; "HCOOH"]

2-Amino-1-(6-chloro-1-(hydroxymethyl)-1,3,4,9-tetrahydro-2H-pyrido[3,4-b]indol-2-yl)-2-(3,4-dichlorophenyl)ethan-1-one formate $^1$H NMR (400 MHz, Methanol-$d_4$): δ 8.09-8.07 (m, 1H), 7.94-7.10 (m, 6H), 5.90-5.67 (m, 2H), 4.05-3.31 (m, 4H), 3.01-1.54 (m, 2H). LCMS: [M+H]$^+$=439.9

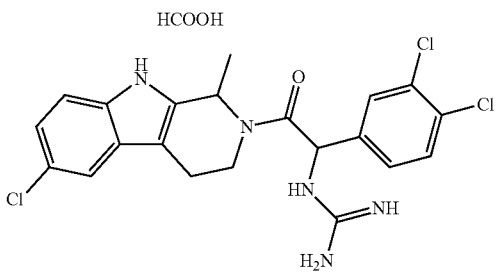 [SMILES: "HCOOH" ; CC1c2[nH]c3ccc(Cl)cc3c2CCN1C(=O)C(NC(=N)N)c1ccc(Cl)c(Cl)c1]

1-(2-(6-Chloro-1-methyl-1,3,4,9-tetrahydro-2H-pyrido[3,4-b]indol-2-yl)-1-(3,4-dichlorophenyl)-2-oxoethyl)guanidine formate $^1$H NMR (400 MHz, Methanol-$d_4$): δ 8.51 (brs, 1H), 7.69-6.99 (m, 6H), 6.07-5.62 (m, 2H), 4.10-4.04 (m, 1H), 3.56-3.50 (m, 1H), 3.31-2.15 (m, 2H), 1.75-1.38 (m, 3H). LCMS: [M+H]$^+$=466.0

General scheme 12

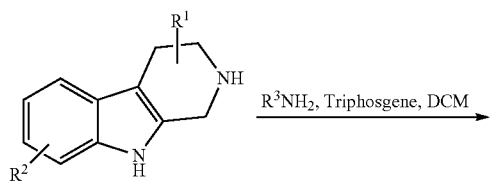

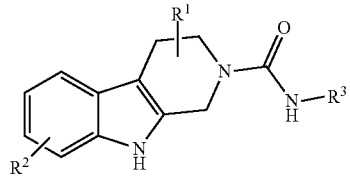

-continued

Representative of synthesis of (N-(3-(3-aminopropanamido)-5-chlorobenzyl)-6-chloro-1,3,4,9-tetrahydro-2H-pyrido[3,4-b]indole-2-carboxamide: To a solution of 3-amino-5-chlorobenzonitrile (1.0 g, 6.55 mmol, 1.0 eq), 3-((tert-butoxycarbonyl) amino) propanoic acid (1.24 g, 6.55 mmol, 1.0 eq) and HATU (2.98 g, 7.86 mmol, 1.2 eq) in DMF (15 mL) was added DIEA (2.5 g, 19.65 mmol, 3.0 eq) at 25° C. Then the reaction mixture was stirred at 25° C. for 1 hr. TLC showed 3-amino-5-chlorobenzonitrile was consumed completely and one new spot formed. The reaction mixture was diluted with water (100 mL) and extracted with ethyl acetate (100 mL×3). The combined organic phase was concentrated in vacuo. The residue was purified by silica gel column chromatography (eluent: PE/EA=5/1 to 3/1) to give tert-butyl (3-((3-chloro-5-cyanophenyl) amino)-3-oxopropyl) carbamate (1.5 g, yield: 70.8%) as a yellow solid. $^1$H NMR (400 MHz, DMSO-$d_6$) δ 10.42 (s, 1H), 7.98 (d, J=1.6 Hz, 1H), 7.92 (s, 1H), 7.71-7.67 (m, 1H), 6.90 (t, J=5.2 Hz, 1H), 3.32 (s, 2H), 3.22 (dd, J=12.8, 6.8 Hz, 2H), 1.37 (s, 9H).

To a solution of tert-butyl (3-((3-chloro-5-cyanophenyl) amino)-3-oxopropyl) carbamate (500 mg, 1.54 mmol, 1.0 eq) in methanol (10.0 mL) was added Raney-Ni (180 mg, 3.08 mmol, 2.0 eq) and NH$_3$H$_2$O (0.1 mL). The reaction was stirred at 25° C. for 4 hrs under H$_2$. LCMS showed the complete consumption of the starting material, and the desired product mass was detected. The reaction mixture was filtered and concentrated in vacuo to give tert-butyl (3-((3-(aminomethyl)-5-chlorophenyl) amino)-3-oxopropyl) carbamate (460 mg, yield: 90.9%) as a yellow oil. LCMS: [M+H]$^+$=328.1

To a solution of tert-butyl (3-((3-(aminomethyl)-5-chlorophenyl) amino)-3-oxopropyl) carbamate (240 mg, 0.73 mmol, 1.0 eq) in dichloromethane (5.0 mL) was added triethylamine (221 mg, 2.2 mmol, 3.0 eq) and bis (trichloromethyl) carbonate (65.0 mg, 0.22 mmol, 0.3 eq) at 0° C. After 30 mins, 6-chloro-2,3,4,9-tetrahydro-1H-pyrido[3,4-b]indole hydrochloride (178 mg, 0.73 mmol, 1.0 eq) was added into the reaction mixture. Then reaction mixture was stirred at 25° C. for 3 hrs. LCMS showed the complete consumption of the starting material and the desired product mass was detected. The reaction was quenched with water (20 mL) and extracted with ethyl acetate (30 mL×3). The combined organic phase was concentrated in vacuo. Then the residue was purified by prep-HPLC (mobile phase: 0.1% HCOOH/CH$_3$CN/H$_2$O) to give tert-butyl (3-((3-chloro-5-((6-chloro-2,3,4,9-tetrahydro-1H-pyrido[3,4-b]indole-2-carboxamido) methyl) phenyl) amino)-3-oxopropyl) carbamate (130 mg, yield: 31.7%) as a white solid. LCMS: [M+H−100]$^+$=460.1

To a solution of tert-butyl (3-((3-chloro-5-((6-chloro-2,3,4,9-tetrahydro-1H-pyrido[3,4-b]indole-2-carboxamido) methyl)phenyl)amino)-3-oxopropyl)carbamate (60 mg, 0.10 mmol, 1.0 eq) in dichloromethane (5.0 mL) was added HCl/dioxane (1.0 mL, 4.0 M). The reaction mixture was stirred at 25° C. for 1 hr. The reaction mixture was concentrated in vacuo. The resulting residue was purified by prep-HPLC (mobile phase: 0.1% HCOOH/CH₃CN/H₂O) to give N-(3-(3-aminopropanamido)-5-chlorobenzyl)-6-chloro-1,3,4,9-tetrahydro-2H-pyrido[3,4-b]indole-2-carboxamide (13.30 mg, yield: 27.0%) as a pale yellow solid. ¹H NMR (400 MHz, DMSO-d6) δ 11.18 (s, 1H), 10.53 (s, 1H), 8.41 (s, 2H), 7.72 (s, 1H), 7.46-7.25 (m, 4H), 7.01 (d, J=13.6 Hz, 2H), 4.59 (s, 2H), 4.22 (d, J=4.8 Hz, 2H), 3.70 (s, 2H), 3.01 (s, 2H), 2.74-2.61 (m, 4H). LCMS: [M+H]⁺=460.1.

N-(3-(3-Aminopropanamido)-4-chlorobenzyl)-6-chloro-1,3,4,9-tetrahydro-2H-pyrido[3,4-b]indole-2-carboxamide formate

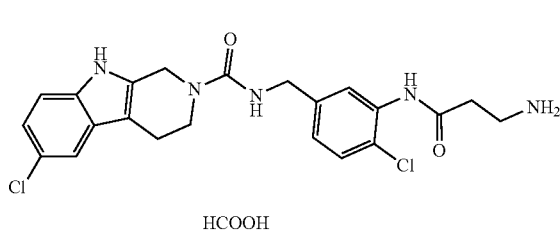 [SMILES: NCCC(=O)Nc1cc(CNC(=O)N2CCc3c([nH]c4ccc(Cl)cc34)C2)ccc1Cl ; "HCOOH"]

HCOOH

¹H NMR (400 MHz, DMSO-d₆) δ 11.09 (s, 1H), 8.32 (s, 1H), 7.69 (s, 1H), 7.45-7.34 (m, 3H), 7.31 (d, J=8.5 Hz, 1H), 7.08 (d, J=8.3 Hz, 1H), 7.02 (dd, J=8.5, 2.1 Hz, 1H), 4.57 (s, 2H), 4.23 (d, J=5.5 Hz, 2H), 3.69 (t, J=5.5 Hz, 2H), 2.99 (t, J=6.6 Hz, 2H), 2.72-2.57 (m, 4H). LCMS: [M+H]⁺=460.1, 462.1.

N-(3-(2-Aminoacetamido)-4-chlorobenzyl)-6-chloro-1,3,4,9-tetrahydro-2H-pyrido[3,4-b]indole-2-carboxamide formate

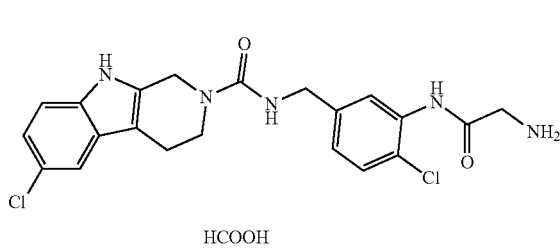 [SMILES: NCC(=O)Nc1cc(CNC(=O)N2CCc3c([nH]c4ccc(Cl)cc34)C2)ccc1Cl ; "HCOOH"]

HCOOH

¹H NMR (400 MHz, DMSO-d₆) δ 11.07 (s, 1H), 8.13 (d, J=27.5 Hz, 2H), 7.46-7.35 (m, 3H), 7.30 (d, J=8.6 Hz, 1H), 7.08-7.02 (m, 1H), 7.01 (d, J=2.1 Hz, 0H)), 4.57 (s, 2H), 4.24 (d, J=5.6 Hz, 2H), 3.69 (t, J=5.6 Hz, 2H), 3.43 (s, 2H), 2.68 (t, J=5.4 Hz, 2H). LCMS: [M+H]⁺=446.1, 448.1.

1-(Aminomethyl)-6-chloro-N-(3-chlorophenyl)-1,3,4,9-tetrahydro-2H-pyrido[3,4-b]indole-2-carboxamide formate

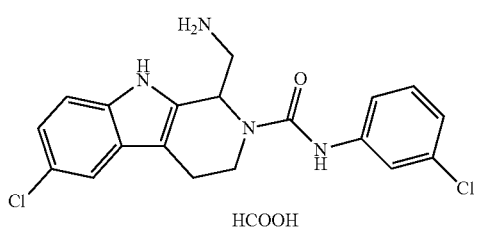 [SMILES: NCC1c2[nH]c3ccc(Cl)cc3c2CCN1C(=O)Nc1cccc(Cl)c1 ; "HCOOH"]

HCOOH

¹H NMR (400 MHz, DMSO-d₆) δ 8.19 (s, 1H), 7.65 (s, 1H), 7.49 (d, J=2.0 Hz, 1H), 7.34 (s, 2H), 7.27 (t, J=8.0 Hz, 1H), 7.10-6.96 (m, 2H), 5.37 (s, 1H), 4.36 (d, J=11.5 Hz, 1H), 3.20 (s, 2H), 3.15-3.05 (m, 1H), 2.69 (d, J=17.5 Hz, 2H). LCMS: [M+H]⁺=389.0, 391.0.

N-(3-(3-Aminopropanamido)-5-chlorobenzyl)-6-chloro-1,3,4,9-tetrahydro-2H-pyrido[3,4-b]indole-2-carboxamide formate

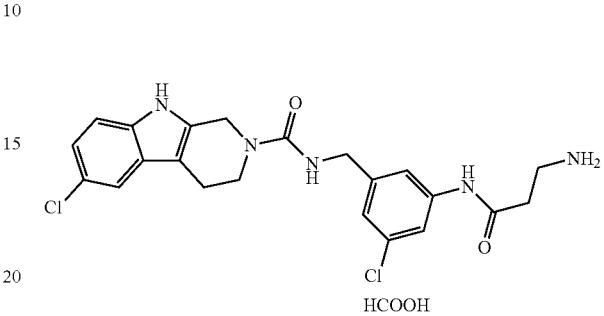

HCOOH

¹H NMR (400 MHz, DMSO-d₆) δ 11.18 (s, 1H), 10.53 (s, 1H), 8.41 (s, 2H), 7.72 (s, 1H), 7.46-7.25 (m, 4H), 7.01 (d, J=13.6 Hz, 2H), 4.59 (s, 2H), 4.22 (d, J=4.8 Hz, 2H), 3.70 (s, 2H), 3.01 (s, 2H), 2.74-2.61 (m, 4H). LCMS: [M+H]⁺=460.1, 462.1.

1-(Aminomethyl)-6-chloro-N-(3-chlorobenzyl)-1,3,4,9-tetrahydro-2H-pyrido[3,4-b]indole-2-carboxamide formate

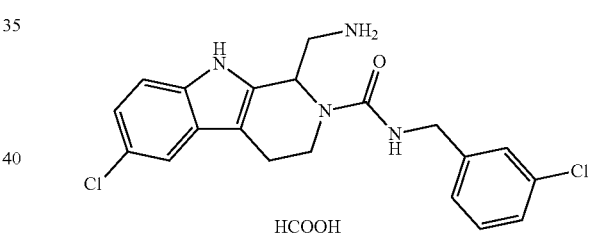

HCOOH

¹H NMR (400 MHz, DMSO-d₆) δ 11.28 (s, 1H), 8.38 (s, 1H), 7.58 (s, 1H), 7.47 (s, 1H), 7.38-7.24 (m, 5H), 7.06 (d, J=7.2 Hz, 1H), 5.40 (s, 1H), 4.30 (s, 2H), 4.19 (d, J=12.8 Hz, 1H), 3.93 (s, 1H), 3.17 (dd, J=38.4, 22.4 Hz, 4H), 2.75-2.54 (m, 4H). LCMS: [M+H]⁺=403.1, 405.1

6-Chloro-N-(2-chlorophenyl)-1-(hydroxymethyl)-3,4-dihydro-1H-pyrido[3,4-b]indole-2(9H)-carboxamide

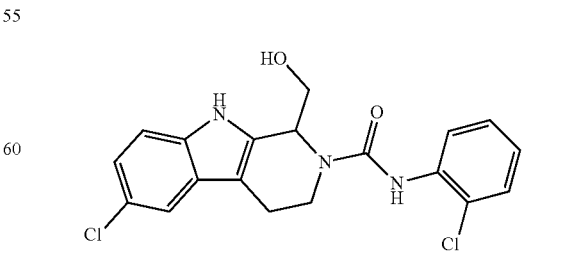

¹H NMR (400 MHz, DMSO-d₆): δ 11.15 (s, 1H), 8.71 (s, 1H), 7.74 (d, J=8.4 Hz, 1H), 7.48-7.00 (m, 7H), 5.98 (brs, 1H), 5.25 (dd, J=8.8, 3.2 Hz, 1H), 4.43 (d, J=13.2 Hz, 1H), 4.00-3.79 (m, 2H), 3.30-3.15 (m, 2H), 2.73-2.71 (m, 2H). LCMS: [M−H]⁻=388.1.

General scheme 13

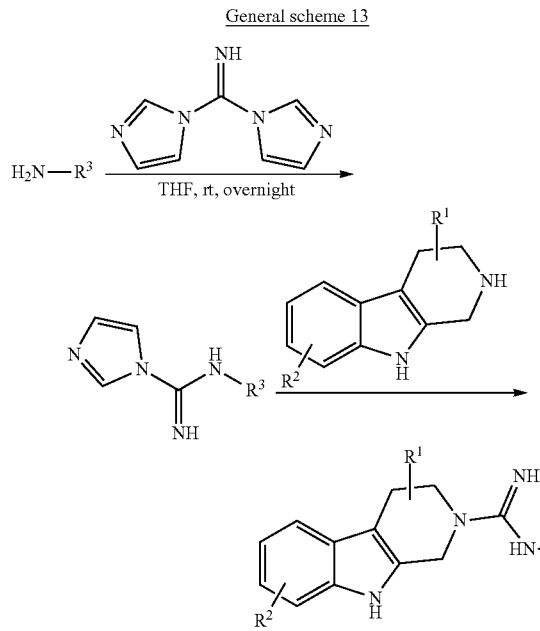

Representative synthesis of 6-chloro-N-(4-chlorophenyl)-3,4-dihydro-1H-pyrido[3,4-b]indole-2(9H)-carboximidamide hydrochloride

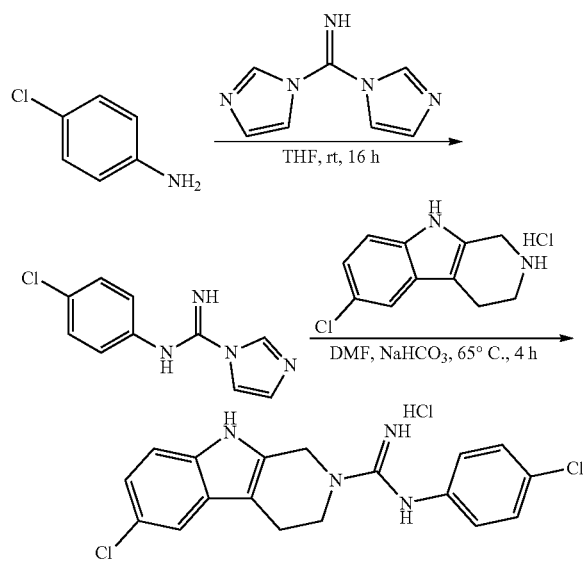

N-(4-Chlorophenyl)-1H-imidazole-1-carboximidamide: To a solution of 4-chloroaniline (500 mg, 3.92 mmol) in THF (8 mL) was added di(1H-imidazol-1-yl)methanimine (757 mg, 4.7 mmol) at RT and stirred for 16 h. The reaction suspension was concentrated and purified by silica gel chromatography eluting with EtOAc to give N-(4-chlorophenyl)-1H-imidazole-1-carboximidamide (300 mg, yield: 35%) as a white solid.

6-Chloro-N-(4-chlorophenyl)-3,4-dihydro-1H-pyrido[3,4-b]indole-2(9H)-carboximidamide hydrochloride: To a solution of N-(4-chlorophenyl)-1H-imidazole-1-carboximidamide (100 mg, 0.45 mmol) in DMF (4 mL) was added 6-chloro-2,3,4,9-tetrahydro-1H-pyrido[3,4-b]indole hydrochloride (94 mg, 0.45 mmol), and NaHCO₃ (190 mg, 2.26 mmol). The reaction mixture was stirred at 65° C. under Ar for 4 hrs, and was then poured into water, extracted with EtOAc, washed with brine, dried over Na₂SO₄, evaporated. The residue was purified by prep-HPLC (mobile phase 0.1% TFA/CH₃CN/H₂O) to give 6-chloro-N-(4-chlorophenyl)-3,4-dihydro-1H-pyrido[3,4-b]indole-2(9H)-carboximidamide (HCl salt, 28.15 mg, yield: 17%) as a white solid. ¹H NMR (400 MHz, DMSO-d₆): δ 11.36 (d, J=5.2 Hz, 1H), 10.22~10.17 (m, 1H), 8.21 (s, 2H), 7.52~7.48 (m, 3H), 7.36~7.31 (m, 3H), 7.07 (dd, J=2.0, 8.8 Hz, 1H), 4.79 (s, 2H), 3.90~3.87 (m, 2H), 2.89 (s, 2H). LCMS: [M+H]⁺=359.1.

6-Chloro-N-(4-chlorobenzyl)-3,4-dihydro-1H-pyrido[3,4-b]indole-2(9H)-carboximidamide hydrochloride

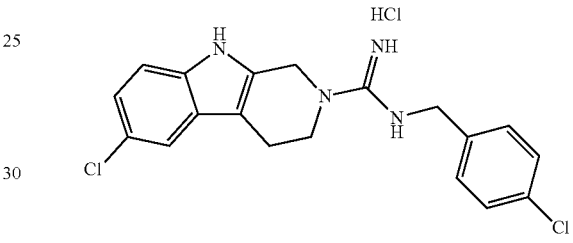

¹H NMR (400 MHz, DMSO-d₆): δ 11.37 (s, 1H), 8.72 (s, 1H), 8.03 (s, 2H), 7.50 (d, J=2.4 Hz, 1H), 7.45~7.40 (m, 4H), 7.35 (d, J=8.4 Hz, 1H), 7.07 (dd, J=1.6, 10.0 Hz, 2H), 4.73 (s, 2H), 4.53 (d, J=5.2 Hz, 2H), 3.85~3.82 (m, 2H), 2.83 (s, 2H). LCMS: [M+H]⁺=373.2.

6-Chloro-N-(3,4-dichlorobenzyl)-3,4-dihydro-1H-pyrido[3,4-b]indole-2(9H)-carboximidamide hydrochloride

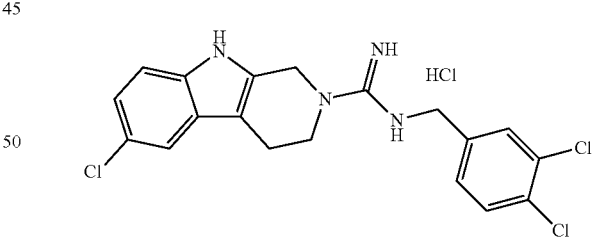

¹H NMR (400 MHz, DMSO-d₆): δ 11.29 (s, 1H), 8.55 (s, 1H), 7.96 (s, 2H), 7.66 (d, J=8.4 Hz, 2H), 7.51 (s, 1H), 7.38~7.33 (m, 2H), 7.08~7.05 (m, 1H), 4.70 (s, 2H), 4.51~4.49 (d, J=5.2 Hz, 2H), 3.82 (t, 2H), 2.82 (s, 2H). LCMS: [M+H]⁺=407.0.

General scheme 14

1. ClSO₃H, DCM;
2. PCl₅, toluene

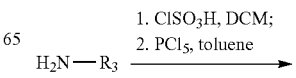

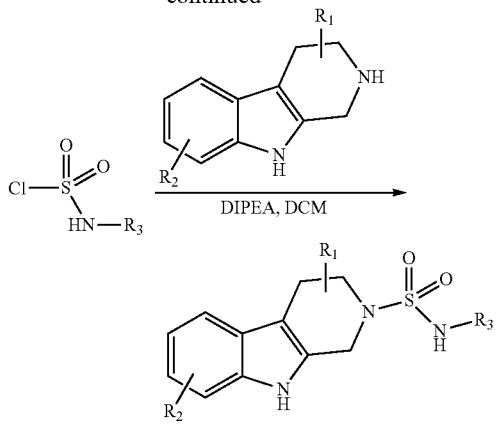

To the solution of aryl amine in anhydrous DCM at 0° C., was added chlorosulfonic acid slowly. The reaction mixture was stirred at 0° C. for 30 min and then warmed up to room temperature for 1 h. The precipitates were collected by filtration and dried under high vacuum. This solid was suspended in toluene and phosphorus pentachloride was added. The mixture was stirred at 100° C. for 2 hrs, then cooled down to room temperature and filtered. The solid residue was washed with toluene three times. The filtrate was evaporated and dried under high vacuum. The crude sulfamonyl chloride was used in the next step without purification. To the tryptoline (1.0 equiv.) and DIPEA (3.0 equiv.) mixture in DCM was added sulfamonyl chloride (prepared above, 1.2 equiv.). The reaction mixture was stirred at room temperature for 12 hrs, concentrate and purified by silica gel flash chromatography to afford the desired product (yield 15%-70%).

Representative synthesis of 6-chloro-N-(4-chlorobenzyl)-1,3,4,9-tetrahydro-2H-pyrido[3,4-b]indole-2-sulfonamide (PCT Int. Appl., 2002050041, 27 Jun. 2002)

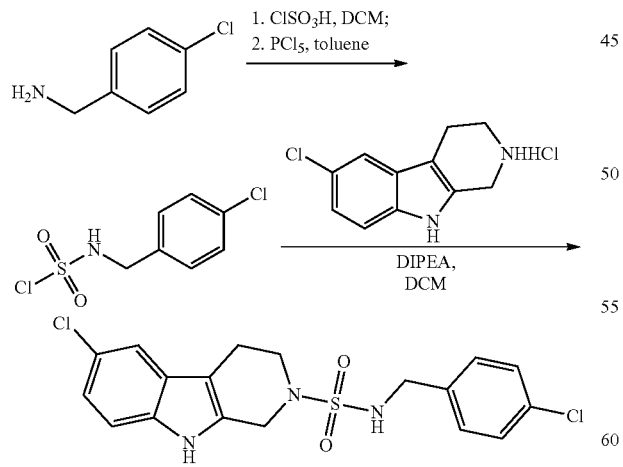

To the solution of (4-chlorophenyl)methanamine (1.374 g, 12 mmol) in anhydrous DCM (10 ml) at 0° C., was added chlorosulfonic acid (0.266 ml, 4 mmol) slowly. The reaction mixture was stirred at 0° C. for 30 min and then warmed up to room temperature for 1 h. The precipitates were collected by filtration and dried under high vacuum. This solid was suspended in toluene (6 ml) and phosphorus pentachloride (833 mg, 4 mmol) was added. The mixture was stirred at 100° C. for 2 hrs, then cooled to room temperature and filtered. The solid residue was washed with toluene (3×5 ml). The filtrate was evaporated and dried under high vacuum. The crude sulfamonyl chloride (0.864 g, 3.6 mmol, 90%) was used in the next step without purification. To the tryptoline (48.6 mg, 0.2 mmol.) and DIPEA (0.104 ml, 0.6 mmol.) mixture in DCM (2 ml) was added sulfamonyl chloride (prepared above, 58 mg, 0.24 mmol). The reaction mixture was stirred at room temperature for 12 hrs, concentrate and purified by silica gel flash chromatography to afford 6-chloro-N-(4-chlorobenzyl)-1,3,4,9-tetrahydro-2H-pyrido[3,4-b]indole-2-sulfonamide (5.4 mg, yield 13%). $^1$H NMR (500 MHz, Chloroform-d) δ 7.90 (s, 1H), 7.44 (d, J=1.9 Hz, 1H), 7.26 (d, J=2.3 Hz, 1H), 7.24 (d, J=2.5 Hz, 2H), 7.20 (s, 1H), 7.19 (d, J=6.3 Hz, 1H), 7.14 (dd, J=8.6, 2.1 Hz, 1H), 4.43 (s, 2H), 4.17 (s, 2H), 3.62 (t, J=5.8 Hz, 2H), 2.82 (td, J=5.8, 4.9, 2.8 Hz, 2H).

General scheme 15

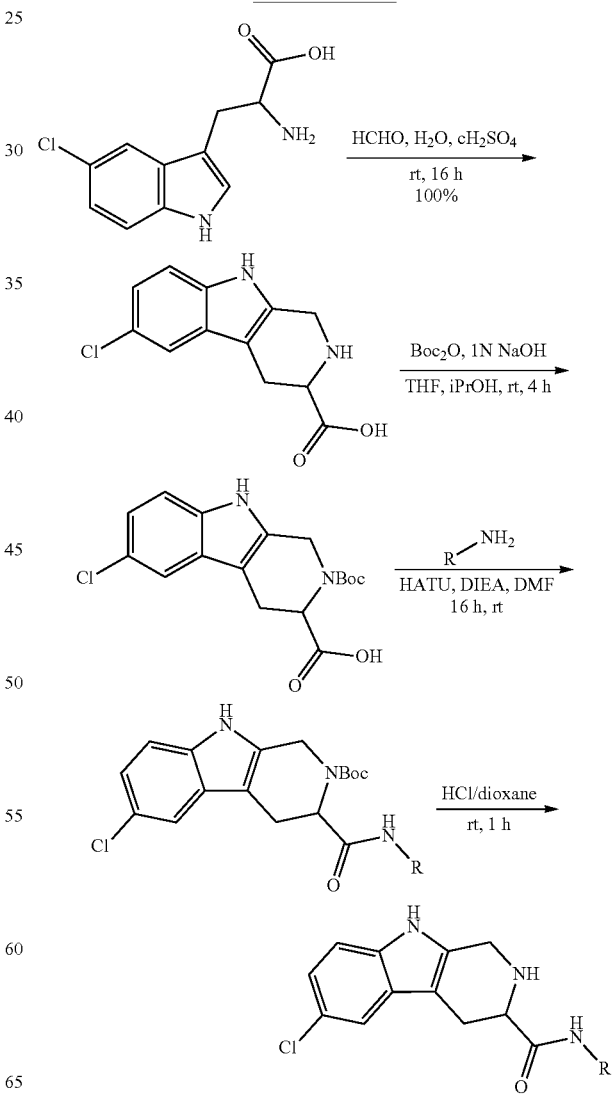

Representative of synthesis of compound 6-chloro-N-(4-chlorophenyl)-2,3,4,9-tetrahydro-1H-pyrido[3,4-b]indole-3-carboxamide (Target-A4-1)

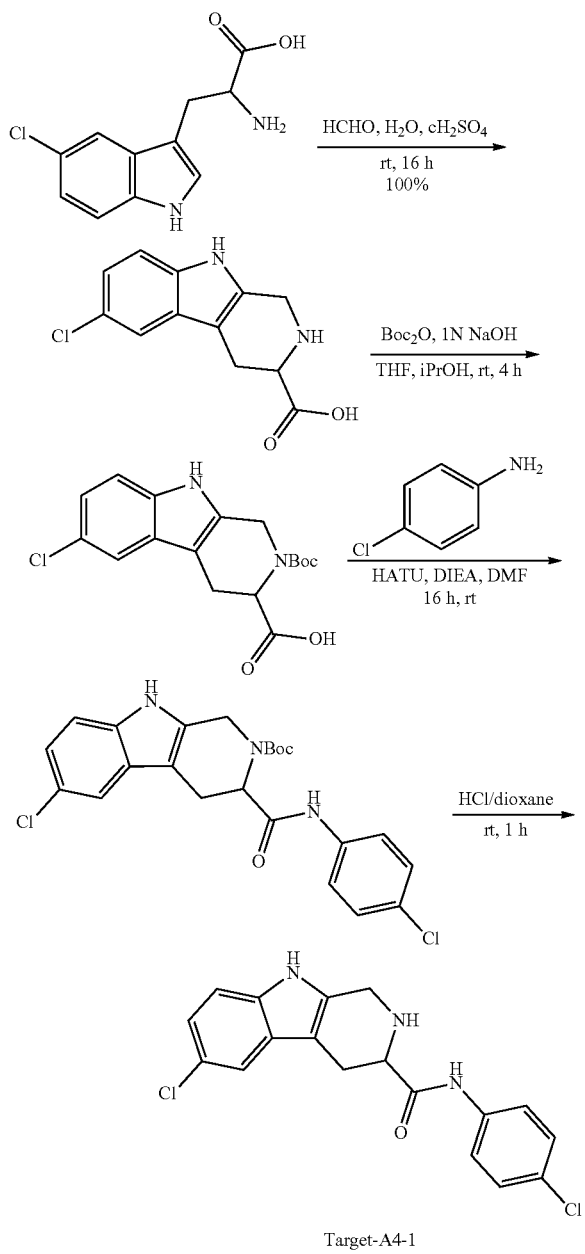

Target-A4-1

6-Chloro-2,3,4,9-tetrahydro-1H-pyrido[3,4-b]indole-3-carboxylic acid: To a mixture of 2-amino-3-(5-chloro-1H-indol-3-yl)propanoic acid (979 mg, 4.1 mmol, 1.0 eq), $H_2SO_4$ (410 mg, 4.18 mmol, 1.02 eq) in $H_2O$ (16 mL) was added 30% formaldehyde (1.6 mL). The mixture was stirred at room temperature for 16 hrs. The reaction was monitored by LC-MS. The pH was adjusted to 6-7 with $NH_3 \cdot H_2O$, then the solids were collected and washed with $H_2O$ to give 6-chloro-2,3,4,9-tetrahydro-1H-pyrido[3,4-b]indole-3-carboxylic acid: (1.08 g, yield: 100%) as an off-white solid. LCMS: $[M+H]^+=250.1$.

2-(tert-Butoxycarbonyl)-6-chloro-2,3,4,9-tetrahydro-1H-pyrido[3,4-b]indole-3-carboxylic acid: A mixture of 6-chloro-2,3,4,9-tetrahydro-1H-pyrido[3,4-b]indole-3-carboxylic acid (1.08 g, 4.32 mmol, 1.0 eq), $Boc_2O$ (1.4 g, 6.48 mmol, 1.5 eq), aq. 1N NaOH (10 mL) in THF/i-PrOH (80 mL/80 mL) was stirred at room temperature for 4 hrs. The reaction was monitored by LC-MS. The solution was concentrated under reduced pressure and adjusted pH to 7 with aq. 1N HCl, extracted with EtOAc (3×50 mL). The combined organic layers were combined and washed with water (2×50 mL) then brine (2×50 mL), then dried over anhydrous $Na_2SO_4$ and concentrated. The residue was washed with petroleum ether:EtOAc (100:1) to give 2-(tert-butoxycarbonyl)-6-chloro-2,3,4,9-tetrahydro-1H-pyrido[3,4-b]indole-3-carboxylic acid (2.05 g, 100%) as an off-white solid. LCMS: $[M+H]^+=360.1$.

tert-Butyl 6-chloro-3-((4-chlorophenyl)carbamoyl)-3,4-dihydro-1H-pyrido[3,4-b]indole-2(9H)-carboxylate: A mixture of 2-(tert-butoxycarbonyl)-6-chloro-2,3,4,9-tetrahydro-1H-pyrido[3,4-b]indole-3-carboxylic acid (350 mg, 1 mmol, 1.0 eq), 4-chloroaniline (153 mg, 1.2 mmol, 1.2 eq), HATU (570 mg, 1.5 mmol, 1.5 eq) and DIEA (387 mg, 3 mmol, 3.0 eq) in DMF (3 mL) was stirred at room temperature for 16 hrs. The reaction was monitored by LC-MS and quenched with $H_2O$, extracted with EtOAc (3×20 mL). The combined organic layers were washed with water (2×20 mL) and brine (2×20 mL), dried over anhydrous $Na_2SO_4$ and concentrated. The residue was purified by column chromatography (petroleum ether:EtOAc=3:1) to give tert-butyl 6-chloro-3-((4-chlorophenyl)carbamoyl)-3,4-dihydro-1H-pyrido[3,4-b]indole-2(9H)-carboxylate (22 mg, yield: 5%) as a light-yellow solid.

6-Chloro-N-(4-chlorophenyl)-2,3,4,9-tetrahydro-1H-pyrido[3,4-b]indole-3-carboxamide: A solution of tert-butyl 6-chloro-3-((4-chlorophenyl)carbamoyl)-3,4-dihydro-1H-pyrido[3,4-b]indole-2(9H)-carboxylate (22 mg, 0.048 mmol, 1.0 eq) in 4 N HCl/dioxane (4 mL) was stirred at room temperature for 1 h. The reaction was monitored by LC-MS. The solution was concentrated and purified by prep-HPLC (mobile phase: 0.1% $NH_4OHMeCN/H_2O$) to give 6-chloro-N-(4-chlorophenyl)-2,3,4,9-tetrahydro-1H-pyrido[3,4-b]indole-3-carboxamide (4.37 mg, yield: 25%) as a white solid. $^1$H NMR (400 MHz, DMSO-$d_6$): δ7.66-7.62 (m, 2H), 7.39 (d, J=2.0 Hz, 1H), 7.35-7.32 (m, 2H), 7.24 (d, J=8.4 Hz, 1H), 7.02-7.00 (m, 1H), 4.15-4.05 (m, 2H), 3.76-3.72 (m, 1H), 3.11-3.06 (m, 1H), 2.90-2.83 (m, 1H). LCMS: $[M+H]^+=360.1$.

6-Chloro-N-(3-chlorophenyl)-2,3,4,9-tetrahydro-1H-pyrido[3,4-b]indole-3-carboxamide

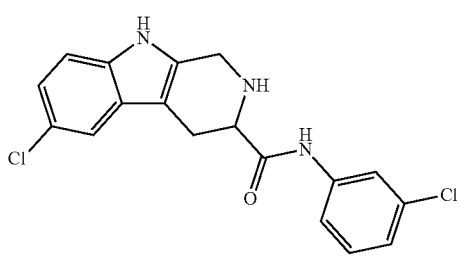 [SMILES: O=C(Nc1cccc(Cl)c1)C1Cc2c([nH]c3ccc(Cl)cc23)CN1]

$^1$H NMR (400 MHz, DMSO-$d_6$): δ 10.95 (br, 1H), 10.13 (br, 1H), 7.92 (t, J=2.0 Hz, 1H), 7.60-7.58 (m, 1H), 7.44 (d, J=1.6 Hz, 1H), 7.35 (t, J=8.0 Hz, 1H), 7.29 (d, J=8.4 Hz, 1H), 7.13-7.11 (m, 1H), 7.02-6.99 (m, 1H), 4.00 (s, 2H), 3.70-3.64 (m, 1H), 2.97-2.92 (m, 1H), 2.85 (br, 1H), 2.78-2.72 (m, 1H). LCMS: [M+H]⁺=360.1.

6-Chloro-N-(4-chlorobenzyl)-2,3,4,9-tetrahydro-1H-pyrido[3,4-b]indole-3-carboxamide

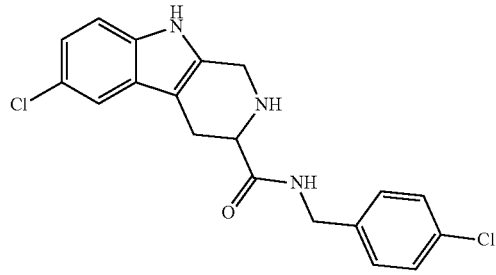 [SMILES: O=C(NCc1ccc(Cl)cc1)C1Cc2c([nH]c3ccc(Cl)cc23)CN1]

¹H NMR (400 MHz, DMSO-d₆): 10.91 (br, 1H), 8.48 (t, J=6.0 Hz, 1H), 7.41-7.27 (m, 6H), 7.01-6.98 (m, 1H), 4.31 (d, J=6.0 Hz, 2H), 3.95-3.92 (m, 2H), 3.53-3.49 (m, 1H), 2.90-2.85 (m, 1H), 2.70-2.64 (m, 2H). LCMS: [M+H]⁺=374.1.

6-Chloro-N-(3-chlorobenzyl)-2,3,4,9-tetrahydro-1H-pyrido[3,4-b]indole-3-carboxamide

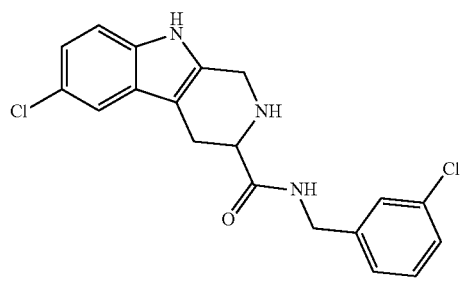 [SMILES: O=C(NCc1cccc(Cl)c1)C1Cc2c([nH]c3ccc(Cl)cc23)CN1]

¹H NMR (400 MHz, DMSO-d₆): δ 10.92 (br, 1H), 8.52 (br, 1H), 7.41-7.23 (m, 6H), 7.00 (d, J=8.8 Hz, 1H), 4.33 (d, J=6.0 Hz, 2H), 3.95 (s, 2H), 3.53 (br, 1H), 2.90-2.88 (m, 1H), 2.71-2.65 (m, 2H). LCMS: [M+H]⁺=374.1.

General scheme 16

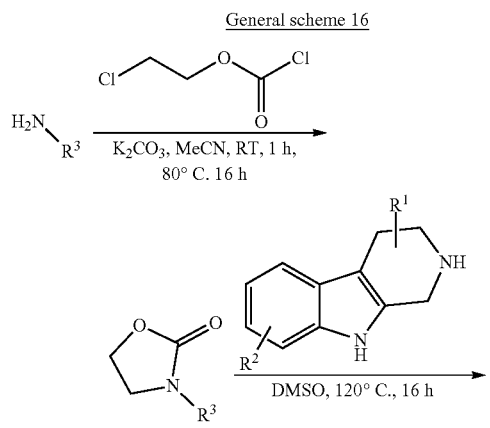

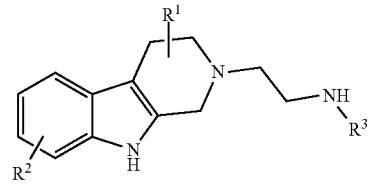

Representative synthesis of compound 3,4-dichloro-N-(2-(6-chloro-3,4-dihydro-1H-pyrido[3,4-b]indol-2(9H)-yl)ethyl)aniline

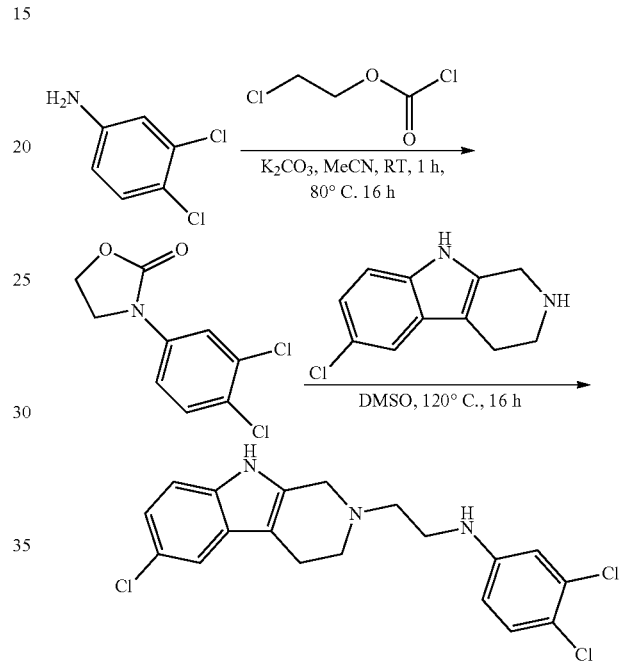

3-(3,4-Dichlorophenyl)oxazolidin-2-one: To the suspension of 3,4-dichloroaniline (800 mg, 4.94 mmol) and K₂CO₃ (1.7 g, 12.35 mmol) in MeCN (10 mL) was added 2-chloroethyl carbonochloridate (883 mg, 6.18 mmol). The reaction mixture was stirred at RT for 1 hr, then 80° C. for 16 hrs. The reaction mixture was poured onto H₂O and the resulting precipitates were collected, and washed with H₂O and dried in vacuo to give 3-(3,4-dichlorophenyl)oxazolidin-2-one (600 mg, yield: 52%) as a white solid. ¹H NMR (400 MHz, DMSO-d₆): δ 7.87 (d, J=2.4 Hz, 1H), 7.63 (d, J=8.8 Hz, 1H), 7.55-7.53 (m, 1H), 4.43 (t, J=16 Hz, 2H), 4.04 (t, J=15.6 Hz, 2H).

3,4-Dichloro-N-(2-(6-chloro-3,4-dihydro-1H-pyrido[3,4-b]indol-2(9H)-yl)ethyl)aniline: A mixture of 3-(3,4-dichlorophenyl)oxazolidin-2-one (50 mg, 0.22 mmol) and 6-chloro-2,3,4,9-tetrahydro-1H-pyrido[3,4-b]indole in DMSO (1 mL) was stirred at 120° C. for 16 hrs. The reaction mixture was purified by prep-HPLC (mobile phase: 0.1% NH₄HCO₃/CH₃CN/H₂O) to gave 3,4-dichloro-N-(2-(6-chloro-3,4-dihydro-1H-pyrido[3,4-b]indol-2(9H)-yl)ethyl)aniline (18.8 mg, yield: 22%) as a yellow solid. ¹H NMR (400 MHz, DMSO-d₆): δ 10.91 (d, J=5.2 Hz, 1H), 7.37 (d, J=5.6 Hz, 1H), 7.29~7.21 (m, 2H), 6.98 (s, 1H), 6.78 (d, J=4.4 Hz, 1H), 6.59 (s, 1H), 5.99 (s, 1H), 3.65 (d, J=5.2 Hz, 2H), 3.21 (s, 2H), 2.80~2.66 (m, 6H). LCMS: [M+H]⁺=394.0.

N-(2-(6-chloro-3,4-dihydro-1H-pyrido[3,4-b]indol-2(9H)-yl)ethyl)-4-(trifluoromethyl)aniline

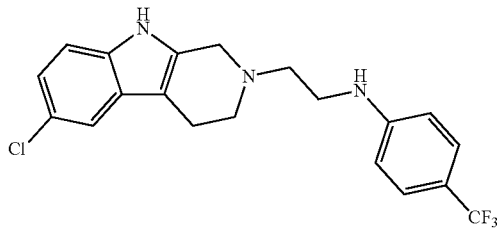 [SMILES: FC(F)(F)c1ccc(NCCN2CCc3c([nH]c4ccc(Cl)cc34)C2)cc1]

¹H NMR (400 MHz, DMSO-d₆): δ 10.92 (s, 1H), 7.26~7.38 (m, 4H), 6.98~7.00 (m, 1H), 6.70 (d, J=8.4 Hz, 2H), 6.27 (s, 1H), 3.68 (s, 2H), 3.26 (s, 2H), 2.68~2.84 (m, 6H). LCMS: [M+H]⁺=394.0

General scheme 17

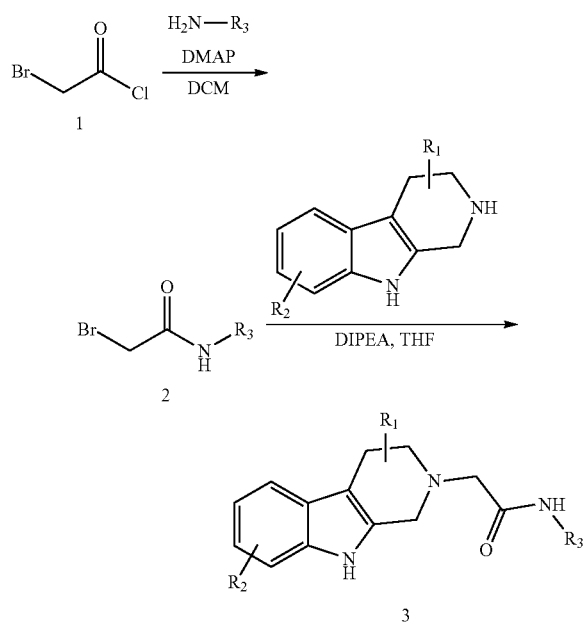

To the solution of 2-bromoacetyl chloride (1.0 equiv.) and DMAP (0.1 equiv.) in anhydrous DCM at 0° C., was added aryl amine (1.0 equiv.) slowly and stirred at 0° C. for 3 hrs. The mixture was then diluted with DCM and washed with water, brine and dried over sodium sulfate, and concentrated under reduced pressure to afford 2-bromoacetamide as a white solid which was taken directly to the next step without further purification (yield 80%). To the solution of tryptoline (1.0 equiv.) and DIPEA (3.0 equiv.) in anhydrous THF, was added 2-bromoacetamide (1.2 equiv.) and heated to reflux for 2 hrs. After cooling down to room temperature, the reaction mixture was diluted with ethyl acetate and washed with water, brine and dried over sodium sulfate, and concentrated. The residue was purified by silica gel flash chromatography to afford the desire product (yield 35%-80%).

2-Bromo-N-(4-chlorophenyl)acetamide (Bioorganic & Medicinal Chemistry Letters, 22(5), 1985-1988; 2012)

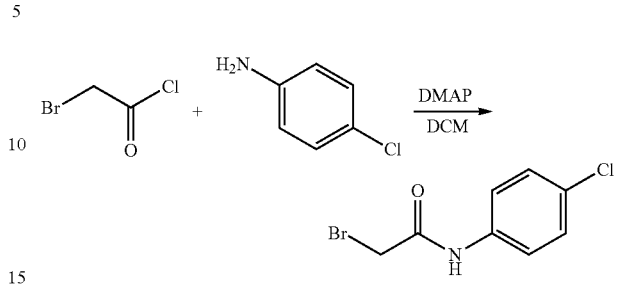

To the solution of 4-chloroaniline (256 mg, 2 mmol) and 4-Dimethylaminopyridine (25 mg, 0.2 mmol) in anhydrous DCM (5 ml) at 0° C. was added 2-bromoacetyl chloride (0.166 ml, 2 mmol) slowly. The reaction mixture was stirred for 3 hrs at 0° C., then diluted with DCM and washed with water and brine, dried over sodium sulfate, and concentrated to afford 2-bromo-N-(4-chlorophenyl)acetamide as a white solid, which was taken directly to the next step without further purification (400 mg, 1.6 mmol, 80%). ¹H NMR (500 MHz, Chloroform-d) δ 8.15 (s, 1H), 7.54-7.45 (m, 2H), 7.41-7.30 (m, 2H), 4.04 (s, 2H).

2-(6-Chloro-8-fluoro-1,3,4,9-tetrahydro-2H-pyrido[3,4-b]indol-2-yl)-N-(4-chlorophenyl)acetamide (PCT Int. Appl., 2008025694, 6 Mar. 2008)

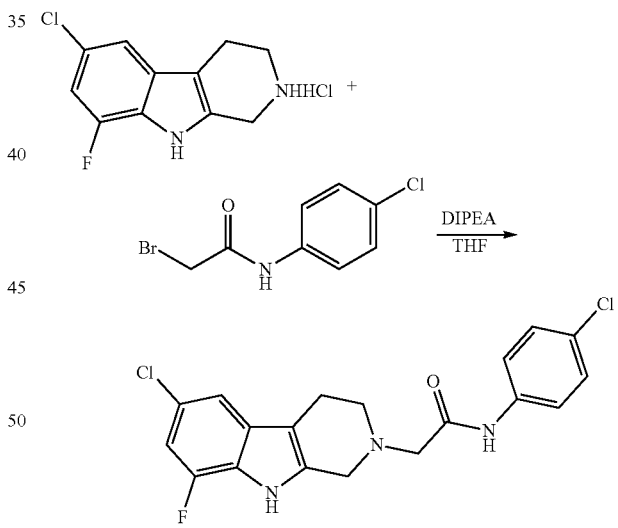

To the solution of 6-chloro-8-fluoro-2,3,4,9-tetrahydro-1H-pyrido[3,4-b]indole hydrochloride (39 mg, 0.15 mmol) and DIPEA (0.08 ml, 0.45 mmol) in anhydrous THF (2 ml), was added 2-bromo-N-(4-chlorophenyl)acetamide(45 mg, 0.18 mmol) and heated to reflux for 2 hrs. After cooling down to room temperature, the reaction mixture was diluted with ethyl acetate and washed with water, brine and dried over sodium sulfate, and concentrated. The residue was purified by silica gel flash chromatography to afford 2-(6-chloro-8-fluoro-1,3,4,9-tetrahydro-2H-pyrido[3,4-b]indol-2-yl)-N-(4-chlorophenyl)acetamide (20 mg, 0.0525 mmol, 35%). ¹H NMR (500 MHz, Chloroform-d) δ 7.58-7.48 (m, 2H), 7.32-7.17 (m, 3H), 6.98-6.83 (m, 1H), 3.85 (t, J=2.4 Hz, 1H), 3.40 (d, J=1.1 Hz, 4H), 3.02 (t, J=5.7 Hz, 2H), 2.88-2.75 (m, 1H).

General scheme 18

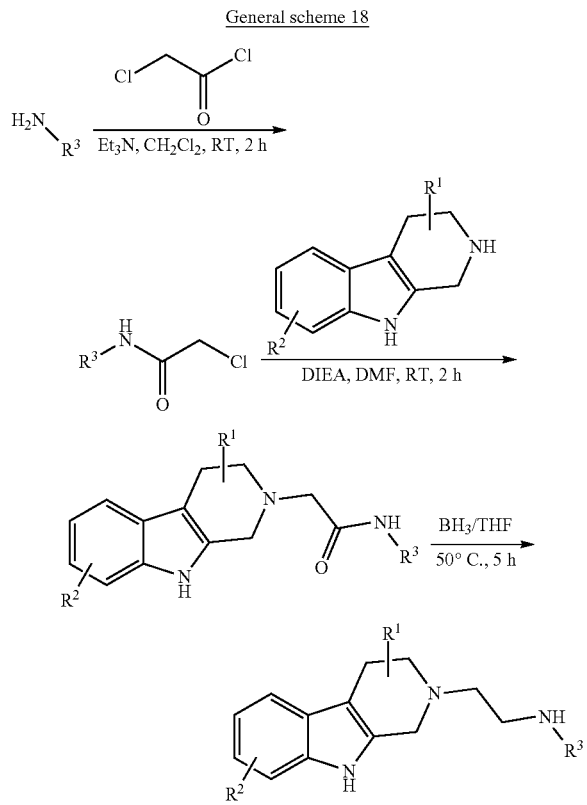

Representative synthesis of 5-chloro-N-(2-(6-chloro-3,4-dihydro-1H-pyrido[3,4-b]indol-2(9H)-yl)ethyl)-6-methylpyridin-2-amine

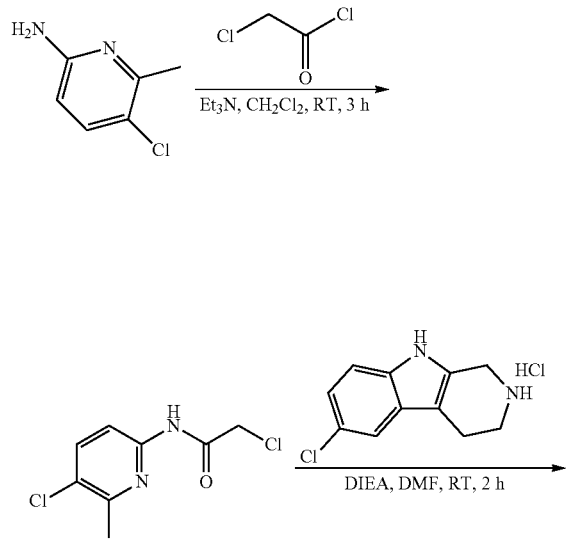

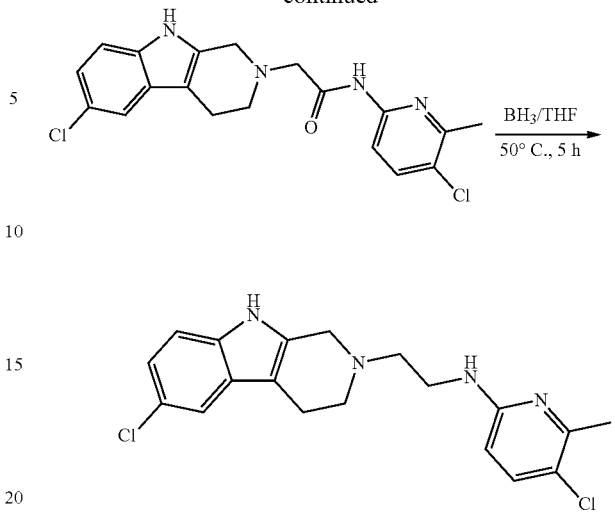

2-Chloro-N-(5-chloro-6-methylpyridin-2-yl)acetamide: To a 0° C. solution of 5-chloro-6-methylpyridin-2-amine (500 mg, 3.51 mmol) and Et$_3$N (1.2 g, 11.57 mmol) in CH$_2$Cl$_2$ (10 mL) under N$_2$, was added 2-chloroacetyl chloride (436 mg, 3.86 mmol) drop-wise. The reaction was stirred at RT for 3 hrs. The reaction solution was then washed with brine (2×10 mL), dried over anhydrous Na$_2$SO$_4$ and concentrated. The residue was purified by silica gel chromatography eluting with petroleum ether:EtOAc=5:1 to give 2-chloro-N-(5-chloro-6-methylpyridin-2-yl)acetamide (500 mg, yield: 65%) as a white solid. LCMS: [M+H]$^+$=219.0.

2-(6-Chloro-3,4-dihydro-1H-pyrido[3,4-b]indol-2(9H)-yl)-N-(5-chloro-6-methylpyridin-2-yl)acetamide: A mixture of 6-chloro-2,3,4,9-tetrahydro-1H-pyrido[3,4-b]indole hydrochloride (150 mg, 0.62 mmol), 2-chloro-N-(5-chloro-6-methylpyridin-2-yl)acetamide (149 mg, 0.68 mmol), DIEA (399 mg, 3.08 mmol) and NaI (115 mg, 0.62 mmol) in DMF (3 mL) was stirred at 50° C. for 16 hrs. The reaction solution was then poured into water and the resulting precipitates were collected to give 2-(6-chloro-3,4-dihydro-1H-pyrido[3,4-b]indol-2(9H)-yl)-N-(5-chloro-6-methylpyridin-2-yl)acetamide (210 mg, yield: 87%) as a white solid. LCMS: [M+H]$^+$=3 89.0.

5-chloro-N-(2-(6-chloro-3,4-dihydro-1H-pyrido[3,4-b]indol-2(9H)-yl)ethyl)-6-methylpyridin-2-amine: To a solution of 2-(6-chloro-3,4-dihydro-1H-pyrido[3,4-b]indol-2(9H)-yl)-N-(5-chloro-6-methylpyridin-2-yl)acetamide (170 mg, 0.44 mmol) in anhydrous THF (10 mL) was added BH$_3$/THF (1 M, 1.75 mL, 1.75 mmol) drop-wise. The reaction was stirred at 50° C. for 16 hrs, and quenched with sat. NH$_4$Cl. EtOAc (20 mL) was added and the resulting mixture was washed with brine (2×20 mL), dried over anhydrous Na$_2$SO$_4$ and concentrated. The residue was purified by prep-HPLC (Mobile phase: 0.1% NH$_4$HCO$_3$/H$_2$O/MeCN) to give 2-(6-chloro-3,4-dihydro-1H-pyrido[3,4-b]indol-2(9H)-yl)-N-(5-chloro-6-methylpyridin-2-yl)acetamide (35.04 mg, yield: 21%) as a white solid. $^1$H NMR (400 MHz, DMSO-d$_6$): δ 10.93 (s, 1H), 7.39 (d, J=1.6 Hz, 1H), 7.35 (d, J=8.4 Hz, 1H), 7.29 (d, J=8.8 Hz, 1H), 7.00 (dd, J=8.4, 2.0 Hz, 1H), 6.54 (t, J=5.6 Hz, 1H), 6.38 (d, J=8.8 Hz, 1H), 3.67 (s, 2H), 3.45~3.40 (m, 2H), 2.81 (t, J=5.6 Hz, 2H), 2.72 (t, J=6.4 Hz, 2H), 2.67 (t, J=5.2 Hz, 2H), 2.33 (s, 3H). LCMS: [M+H]$^+$=375.1.

5-chloro-N2-(2-(6-chloro-1-methyl-1,3,4,9-tetra-hydro-2H-pyrido[3,4-b]indol-2-yl)ethyl)pyridine-2,6-diamine hydrochloride

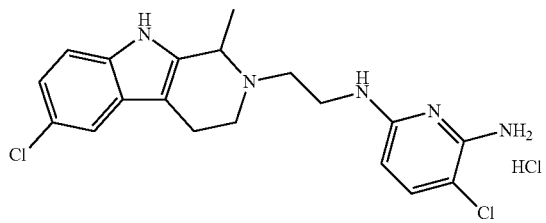 [SMILES: CC1c2[nH]c3ccc(Cl)cc3c2CCN1CCNc1ccc(Cl)c(N)n1 ; Cl]

$^1$H NMR (400 MHz, DMSO-d$_6$): δ 11.54 (brs, 1H), 11.17 (brs, 1H), 7.57-7.37 (m, 4H), 7.14-7.11 (m, 1H), 6.00-5.98 (m, 1H), 4.91-4.89 (m, 1H), 3.93-3.02 (m, 8H), 1.72 (d, J=5.6 Hz, 3H). LCMS: [M+H]$^+$=390.2

(6-chloro-2-(2-((5-chloro-6-ethoxypyridin-2-yl)amino)ethyl)-2,3,4,9-tetrahydro-1H-pyrido[3,4-b]indol-1-yl)methanol

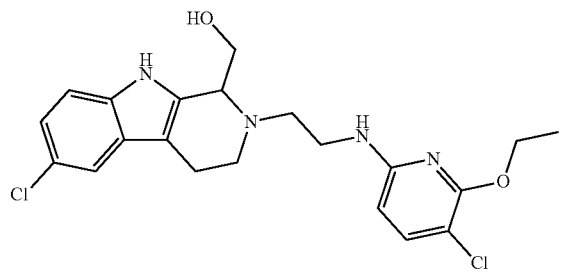 [SMILES: CCOc1nc(NCCN2CCc3c([nH]c4ccc(Cl)cc34)C2CO)ccc1Cl]

$^1$H NMR (400 MHz, DMSO-d$_6$): δ 10.84 (brs, 1H), 7.41-7.29 (m, 3H), 7.00 (dd, J=8.4 Hz, 2.0 Hz, 1H), 6.68 (d, J=4.8 Hz, 1H), 6.05 (d, J=8.8 Hz, 1H), 4.75-4.72 (m, 1H), 4.33-4.24 (m, 2H), 3.74-3.60 (m, 2H), 3.35-3.13 (m, 2H), 3.14-2.43 (m, 6H), 1.28 (d, J=7.2 Hz, 3H). LCMS: [M+H]$^+$=435.2

(6-chloro-2-(2-((5-chloro-6-methoxypyridin-2-yl)amino)ethyl)-2,3,4,9-tetrahydro-1H-pyrido[3,4-b]indol-1-yl)methanol

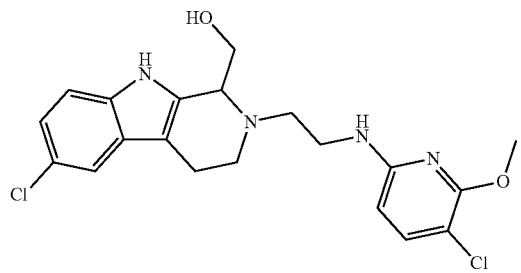 [SMILES: COc1nc(NCCN2CCc3c([nH]c4ccc(Cl)cc34)C2CO)ccc1Cl]

$^1$H NMR (400 MHz, DMSO-d$_6$): δ 10.84 (brs, 1H), 7.41-7.29 (m, 3H), 7.00 (dd, J=8.8 Hz, 2.0 Hz, 1H), 6.71-6.68 (m, 1H), 6.06 (d, J=8.4 Hz, 1H), 4.75-4.72 (m, 1H), 3.82 (s, 3H), 3.75-3.50 (m, 3H), 3.43-3.38 (m, 2H), 3.17-3.11 (m, 1H), 2.91-2.70 (m, 4H), 2.50-2,40 (s, 1H). LCMS: [M+H]$^+$=421.2

(6-chloro-2-(2-((5-chloro-6-(methylamino)pyridin-2-yl)amino)ethyl)-2,3,4,9-tetrahydro-1H-pyrido[3,4-b]indol-1-yl)methanol hydrochloride

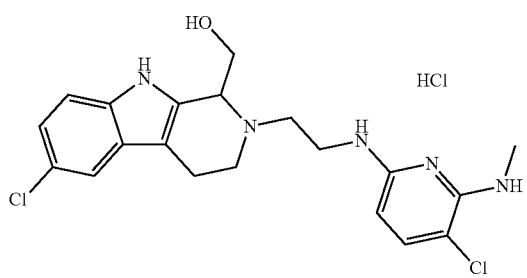 [SMILES: CNc1nc(NCCN2CCc3c([nH]c4ccc(Cl)cc34)C2CO)ccc1Cl ; Cl]

$^1$H NMR (400 MHz, DMSO-d$_6$): δ 10.84 (brs, 1H), 7.40 (d, J=1.6 Hz, 1H), 7.30 (d, J=8.4 Hz, 1H), 7.11 (d, J=8.4 Hz, 1H), 7.00 (dd, J=8.8 Hz, 2.0 Hz, 1H), 6.24 (t, J=5.6 Hz, 1H), 5.95-5.93 (m, 1H), 5.65 (d, J=8.4 Hz, 1H), 4.75-4.72 (m, 1H), 3.75-3.57 (m, 3H), 3.17-3.10 (m, 1H), 2.91-2.86 (m, 1H), 2.79-2.67 (m, 6H), 2.50-2.43 (m, 1H). LCMS: [M+H]$^+$=420.2

(3-chloro-6-((2-(6-chloro-1-methyl-1,3,4,9-tetra-hydro-2H-pyrido[3,4-b]indol-2-yl)ethyl)amino)pyridin-2-yl)methanol

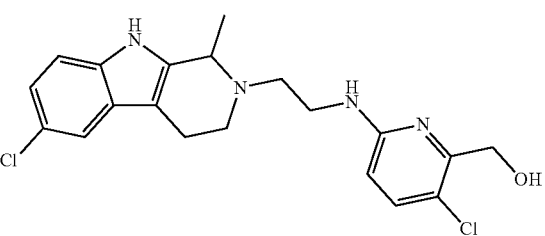 [SMILES: CC1c2[nH]c3ccc(Cl)cc3c2CCN1CCNc1ccc(Cl)c(CO)n1]

$^1$H NMR (400 MHz, DMSO-d$_6$): δ 10.94 (brs, 1H), 7.39 (d, J=8.4 Hz, H), 7.39 (s, 1H), 7.27 (d, J=8.8 Hz, 1H), 6.99 (d, J=8.4 Hz, 1H), 6.66 (br, 1H), 6.46 (d, J=8.8 Hz, 1H), 4.86-4.84 (m, 1H), 4.44 (d, J=4.8 Hz, 2H), 3.85-3.82 (m, 1H), 3.48-3.44 (m, 2H), 3.10-3.07 (m, 2H), 2.83-2.76 (m, 2H), 2.70-2.66 (m, 2H), 1.35 (d, J=6.4 Hz, 3H). LCMS: [M+H]$^+$=405.2

153

2-(6-chloro-2-(2-((5-chloro-6-methylpyridin-2-yl)amino)ethyl)-2,3,4,9-tetrahydro-1H-pyrido[3,4-b]indol-1-yl)ethan-1-ol

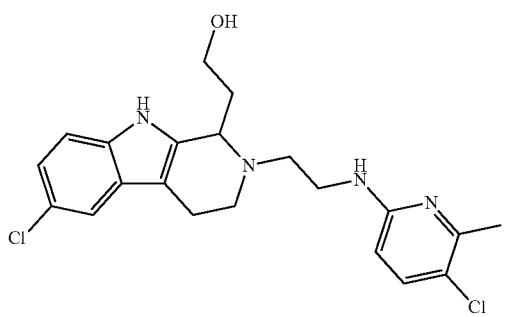 [SMILES: Cc1nc(NCCN2CCc3c([nH]c4ccc(Cl)cc34)C2CCO)ccc1Cl]

$^1$H NMR (400 MHz, DMSO-d$_6$): δ 10.92 (brs, 1H), 7.39 (s, 1H), 7.33 (d, J=8.8 Hz, 1H), 7.28 (d, J=8.4 Hz, 1H), 7.00 (dd, J=1.6 Hz, 8.4 Hz, 1H), 6.54-6.50 (m, 1H), 6.33 (d, J=8.8 Hz, 1H), 4.76 (br, 1H), 3.89-3.86 (m, 1H), 3.67-3.53 (m, 4H), 3.13-3.08 (m, 1H), 2.92-2.88 (m, 1H), 2.77-2.63 (m, 4H), 2.32 (s, 3H), 1.92-1.85 (m, 2H). LCMS: [M+H]$^+$=419.2

5-chloro-N-(2-(6-chloro-1,3,4,9-tetrahydro-2H-pyrido[3,4-b]indol-2-yl)ethyl)-6-(trifluoromethyl)pyridin-2-amine formate

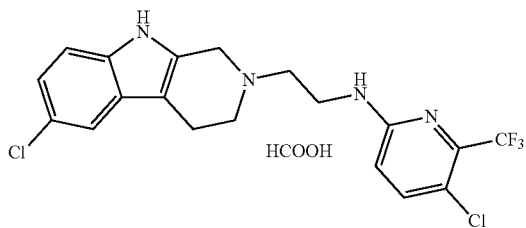 [SMILES: FC(F)(F)c1nc(NCCN2CCc3c([nH]c4ccc(Cl)cc34)C2)ccc1Cl ; "HCOOH"]

$^1$H NMR (400 MHz, DMSO-d6): δ 10.96 (brs, 1H), 8.25 (s, 1H), 7.64 (d, J=8.8 Hz, 1H), 7.38 (d, J=1.6 Hz, 1H), 7.29 (d, J=8.4 Hz, 1H), 7.01 (dd, J=2.0 Hz, 8.4 Hz, 1H), 6.82 (d, J=9.2 Hz, 1H), 3.67 (brs, 2H), 3.50-3.45 (m, 2H), 2.84-2.80 (m, 2H), 2.76-2.72 (m, 2H), 2.68-2.66 (m, 2H).
$^{19}$F NMR (376.5 MHz, DMSO-d6): δ −64.71 LCMS: [M+H]$^+$=429.1

(6-chloro-2-(2-((3,5-dichloropyridin-2-yl)amino)ethyl)-2,3,4,9-tetrahydro-1H-pyrido[3,4-b]indol-1-yl)methanol formate

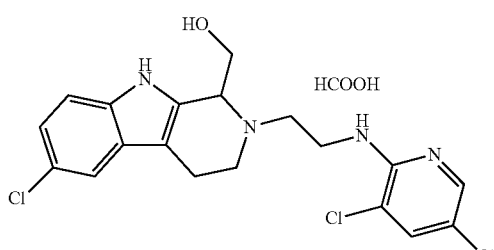

154

$^1$H NMR (400 MHz, DMSO-d6): δ 10.84 (brs, 1H), 8.21 (brs, 1H), 8.03 (d, J=2.0 Hz, 1H), 7.80 (d, J=2.4 Hz, 1H), 7.40 (d, J=2.0 Hz, 1H), 7.32 (d, J=8.4 Hz, 1H), 7.00 (dd, J=2.0 Hz, 8.4 Hz, 1H), 6.68-6.66 (m, 1H), 3.78-3.60 (m, 3H), 3.56~3.44 (m, 2H), 3.18~3.12 (m, 1H), 2.90~2.86 (m, 1H), 2.81~2.67 (m, 3H), 2.47~2.43 (m, 1H). LCMS: [M+H]$^+$=427.0

(6-chloro-2-(2-((5-chloro-2-methylpyridin-3-yl)amino)ethyl)-2,3,4,9-tetrahydro-1H-pyrido[3,4-b]indol-1-yl)methanol

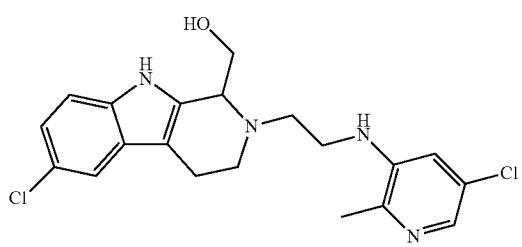 [SMILES: Cc1ncc(Cl)cc1NCCN1CCc2c([nH]c3ccc(Cl)cc23)C1CO]

$^1$H NMR (400 MHz, DMSO-d$_6$): δ 11.87 (brs, 1H), 7.66 (d, J=2.0 Hz, 1H), 7.42 (d, J=1.6 Hz, 1H), 7.31 (d, J=8.8 Hz, 1H), 7.00 (dd, J=8.8 Hz, 2.0 Hz, 1H), 6.94 (d, J=1.6 Hz, 1H), 5.47 (t, J=4.8 Hz, 1H), 4.86-4.83 (m, 1H), 3.77-3.65 (m, 3H), 3.23-3.13 (m, 3H), 3.92-2.85 (m, 3H), 2.76-2.72 (m, 1H), 2.50-2.45 (m, 1H), 2.28 (s, 3H). LCMS: (M+H)$^+$=405.1

(6-chloro-2-(2-((3,5-dichloro-6-methylpyridin-2-yl)amino)ethyl)-2,3,4,9-tetrahydro-1H-pyrido[3,4-b]indol-1-yl)methanol formate

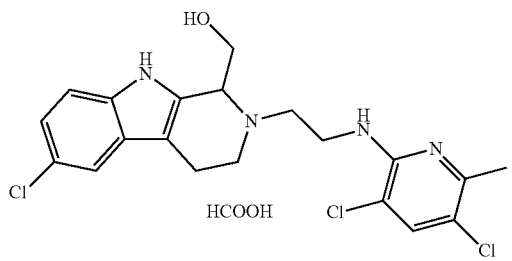 [SMILES: Cc1nc(NCCN2CCc3c([nH]c4ccc(Cl)cc34)C2CO)c(Cl)cc1Cl ; "HCOOH"]

$^1$H NMR (400 MHz, DMSO-d$_6$): δ 10.83 (brs, 1H), 8.15 (s, 1H), 7.68 (s, 1H), 7.40 (d, J=1.6 Hz, 1H), 7.32 (d, J=8.4 Hz, 1H), 7.01 (dd, J=8.8 Hz, 2.0 Hz, 1H), 6.56 (t, J=5.2 Hz, 1H), 3.81~3.77 (m, 1H), 3.74~3.70 (m, 1H), 3.67~3.61 (m, 1H), 3.56~3.46 (m, 2H), 3.18~3.09 (m, 1H), 2.91~2.88 (m, 1H), 2.80~2.70 (m, 3H), 2.50~2.44 (m, 1H), 2.36 (s, 3H). LCMS: [M+H]$^+$=441.3

(6-Chloro-2-(2-((3,5-dichloro-6-(trifluoromethyl)pyridin-2-yl)amino)ethyl)-2,3,4,9-tetrahydro-1H-pyrido[3,4-b]indol-1-yl)methanol hydrochloride $^1$H NMR (400 MHz, DMSO-d$_6$): δ 11.50 (s, 1H), 10.85-10.51 (m, 1H), 8.15 (s, 1H), 7.62-7.55 (m, 2H), 7.39 (d, J=8.4 Hz, 1H), 7.12 (d, J=8.8 Hz, 1H), 5.81-5.67 (m, 1H), 4.87-4.81 (m, 1H), 4.27-3.53 (m, 8H), 3.02 (br, 2H). LCMS: [M+H]$^+$=495.1

(6-Chloro-2-(2-((6-ethyl-5-(trifluoromethyl)pyridin-2-yl)amino)ethyl)-2,3,4,9-tetrahydro-1H-pyrido[3,4-b]indol-1-yl)methanol

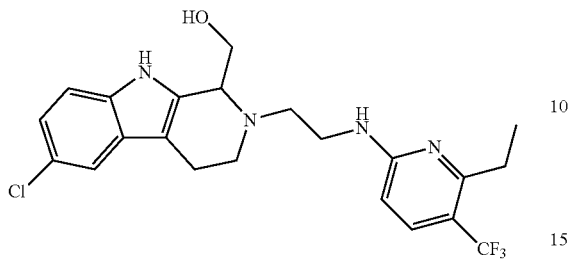

$^1$H NMR (400 MHz, DMSO-d$_6$): δ 10.86 (s, 1H), 8.26 (s, 1H), 7.54 (d, J=8.8 Hz, 1H), 7.40 (d, J=1.6 Hz, 1H), 7.30 (d, J=8.8 Hz, 1H), 7.14 (s, 1H), 7.00 (dd, J=8.4 Hz, 2.0 Hz, 1H), 6.40 (d, J=8.8 Hz, 1H), 3.74-3.63 (m, 3H), 3.47 (d, J=4.8 Hz, 2H), 3.15-3.11 (m, 1H), 2.92-2.89 (m, 1H), 2.81-2.64 (m, 5H), 2.45-2.33 (m, 2H), 1.18 (t, J=7.2 Hz, 3H). LCMS: [M+H]$^+$=453.2

5-Chloro-N-(2-(6-chloro-4-methyl-1,3,4,9-tetrahydro-2H-pyrido[3,4-b]indol-2-yl)ethyl)-6-ethylpyridin-2-amine formate

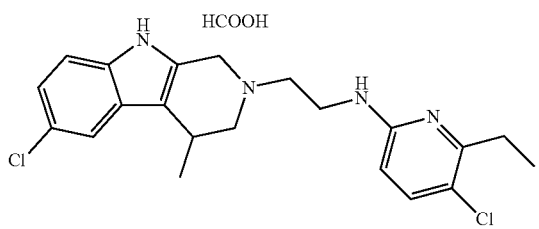 [SMILES: "HCOOH" ; CCc1nc(NCCN2Cc3[nH]c4ccc(Cl)cc4c3C(C)C2)ccc1Cl]

$^1$H NMR (400 MHz, MeOD) δ 8.61-8.39 (m, 1H), 7.49 (d, J=2.0 Hz, 1H), 7.34 (d, J=8.8 Hz, 1H), 7.26 (d, J=8.4 Hz, 1H), 7.03 (dd, J=8.4 Hz, 2.0 Hz, 1H), 6.37 (d, J=8.8 Hz, 1H), 4.10-3.90 (m, 2H), 3.62 (t, J=6.0 Hz, 2H), 3.31-3.29 (m, 2H), 3.08-3.04 (m, 2H), 2.70-2.65 (m, 3H), 1.39 (d, J=6.4 Hz, 3H), 1.14 (t, J=7.6 Hz, 3H). LCMS: [M+H]$^+$=403.2

5-Chloro-N-(2-(6-chloro-1-((dimethylamino)methyl)-4-methyl-1,3,4,9-tetrahydro-2H-pyrido[3,4-b]indol-2-yl)ethyl)-6-(trifluoromethyl)pyridin-2-amine

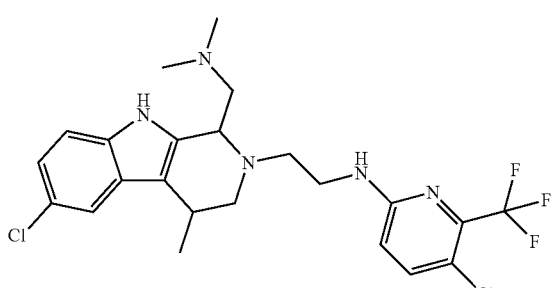

$^1$H NMR (400 MHz, MeOD) δ 7.54-7.44 (m, 2H), 7.27-7.23 (m, 1H), 7.00-6.95 (m, 1H), 6.67 (d, J=8.8 Hz, 1H), 3.90-3.80 (m, 1H), 3.56-3.45 (m, 2H), 3.20-2.99 (m, 2H), 2.93-2.68 (m, 4H), 2.51 (br, 1H), 2.45-2.35 (m, 6H), 1.32 (d, J=6.8 Hz, 3H). LCMS: [M+H]$^+$=500.1

(6-Chloro-2-(2-((4-chloro-3-(trifluoromethyl)phenyl)amino)ethyl)-2,3,4,9-tetrahydro-1H-pyrido[3,4-b]indol-1-yl)methanol formate

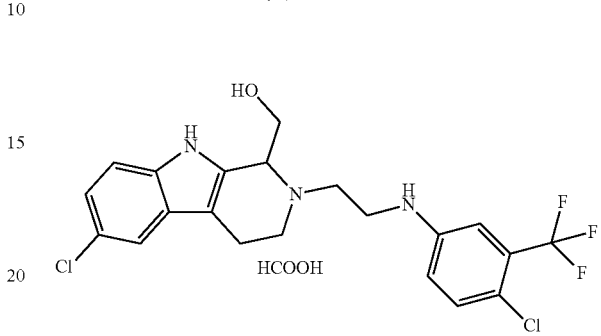

$^1$H NMR (400 MHz, MeOD) δ 8.24 (brs, 1H), 7.41 (d, J=2.0 Hz, 1H), 7.30-7.25 (m, 2H), 7.06-7.01 (m, 2H), 6.83 (dd, J=9.2 Hz, 2.8 Hz, 1H), 4.13 (brs, 1H), 3.91-3.88 (m, 2H), 3.53-3.43 (m, 1H), 3.39 (t, J=6.0 Hz, 2H), 3.23-3.18 (m, 1H), 3.14-3.07 (m, 2H), 2.99-2.88 (m, 1H), 2.72-2.68 (m, 1H). LCMS: [M+H]$^+$=458.1.

5-Chloro-N-(2-(6-chloro-1-(tetrahydrofuran-2-yl)-1,3,4,9-tetrahydro-2H-pyrido[3,4-b]indol-2-yl)ethyl)-6-methylpyridin-2-amine formate

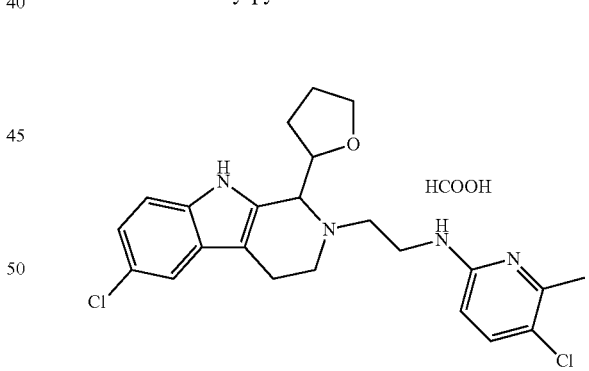

$^1$H NMR (400 MHz, MeOD): δ 8.28 (brs, 1H), 7.40 (dd, J=16.0 Hz, 5.2 Hz, 2H), 7.30 (d, J=8.4 Hz, 1H), 7.04 (dd, J=8.4 Hz, 2.0 Hz, 1H), 6.40 (d, J=8.8 Hz, 1H), 4.28-4.22 (m, 1H), 4.02-3.98 (m, 1H), 3.91-3.78 (m, 2H) 3.67-3.58 (m, 1H), 3.53-3.49 (m, 2H), 3.33-3.30 (m, 1H), 3.12-2.93 (m, 3H), 2.74-2.65 (m, 1H), 2.36 (s, 3H), 2.23-2.17 (m, 1H), 2.04-1.90 (m, 1H), 1.89-1.85 (m, 2H). LCMS: [M+H]$^+$=445.2

(6-Chloro-2-(2-((5-chloro-6-(trifluoromethyl)pyridin-2-yl)amino)ethyl)-4-methyl-2,3,4,9-tetrahydro-1H-pyrido[3,4-b]indol-1-yl)methanol formate

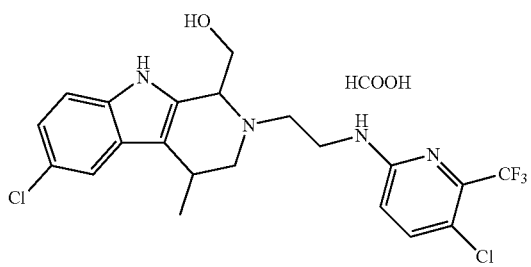 [SMILES: CC1CN(CCNc2ccc(Cl)c(C(F)(F)F)n2)C(CO)c2[nH]c3ccc(Cl)cc3c21 ; "HCOOH"]

¹H NMR (400 MHz, MeOD): δ 8.25 (brs, 1H), 7.57-7.52 (m, 2H), 7.29 (dd, J=12.0 Hz, 8.0 Hz, 1H), 7.08-7.03 (m, 1H), 6.74-6.69 (m, 1H), 4.32-4.14 (m, 1H), 4.05-3.84 (m, 2H), 3.75-3.60 (m, 3H), 3.38-3.34 (m, 1H), 3.30-2.76 (m, 3H), 1.43-1.35 (m, 3H). LCMS: [M+H]⁺=475.0

(6-Chloro-2-(2-((5-chloro-6-ethylpyridin-2-yl)amino)ethyl)-4-methyl-2,3,4,9-tetrahydro-1H-pyrido[3,4-b]indol-1-yl)methanol formate

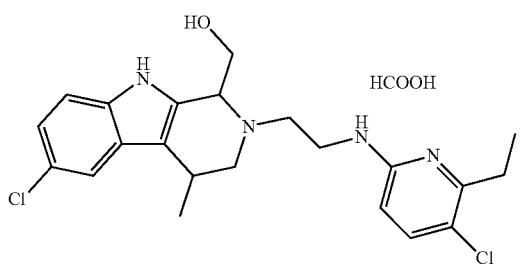 [SMILES: CCc1nc(NCCN2CC(C)c3c([nH]c4ccc(Cl)cc34)C2CO)ccc1Cl ; "HCOOH"]

¹H NMR (400 MHz, MeOD): δ 8.35 (brs, 1H), 7.54 (s, 1H), 7.38-7.27 (m, 2H), 7.09-7.05 (m, 1H), 6.42-6.36 (m, 1H), 4.32-4.27 (m, 1H), 4.09-3.92 (m, 2H), 3.79-3.70-3.35 (m, 3H), 3.30-3.10 (m, 1H), 2.90 (br, 1H), 2.71-2.64 (m, 2H), 1.43-1.36 (m, 3H), 1.14 (t, J=7.6 Hz, 3H). LCMS: [M+H]⁺=433.1

6-((2-(6-Chloro-1-methyl-1,3,4,9-tetrahydro-2H-pyrido[3,4-b]indol-2-yl)ethyl)amino)-N,N,2-trimethylnicotinamide formate

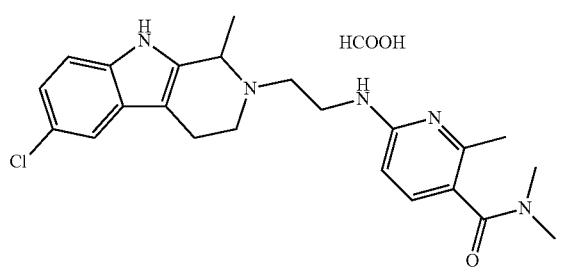 [SMILES: Cc1nc(NCCN2CCc3c([nH]c4ccc(Cl)cc34)C2C)ccc1C(=O)N(C)C ; "HCOOH"]

¹H NMR (400 MHz, MeOD): δ 8.40 (brs, 1H), 7.46 (d, J=2.0 Hz, 1H), 7.31 (dd, J=8.8 Hz, 1.2 Hz, 2H), 7.11 (dd, J=8.8 Hz, 2.0 Hz, 1H), 6.51 (d, J=8.4 Hz, 1H), 4.74-4.71 (m, 1H), 3.82-3.74 (m, 3H), 3.62-3.42 (m, 2H), 3.41-3.32 (m, 1H), 3.05-3.29 (m, 5H), 2.87 (s, 3H), 2.06 (s, 3H), 1.71 (d, J=6.8 Hz, 3H). LCMS: [M+H]⁺=426.3

N-(2-(6-Chloro-1-methyl-1,3,4,9-tetrahydro-2H-pyrido[3,4-b]indol-2-yl)ethyl)-6-methyl-5-(morpholinomethyl)pyridin-2-amine diformate

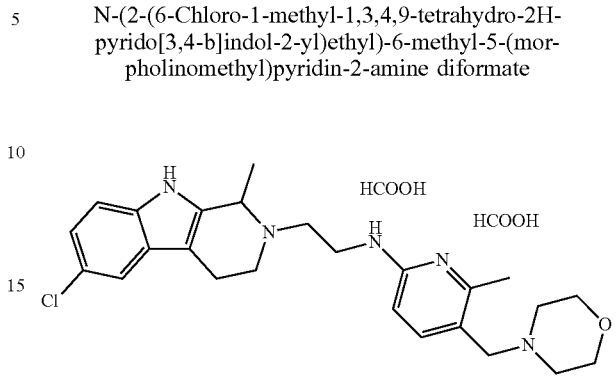

¹H NMR (400 MHz, MeOD): δ 8.34 (brs, 2H), 7.47-7.42 (m, 2H), 7.33 (d, J=8.4 Hz, 1H), 7.13 (dd, J=8.4 Hz, 2.0 Hz, 1H), 6.53 (d, J=8.8 Hz, 1H), 4.72-4.70 (m, 1H), 3.83-3.79 (m, 1H), 3.73-3.71 (m, 2H), 3.65-3.61 (m, 4H), 3.62-3.46 (m, 2H), 3.37 (br, 3H), 3.07-3.03 (m, 2H), 2.45-2.42 (m, 4H), 2.10 (s, 3H), 1.72 (d, J=6.8 Hz, 3H). LCMS: [M+H]⁺=454.2

(6-Chloro-2-(2-((5-chloro-6-(trifluoromethyl)pyridin-2-yl)(methyl)amino)ethyl)-2,3,4,9-tetrahydro-1H-pyrido[3,4-b]indol-1-yl)methanol

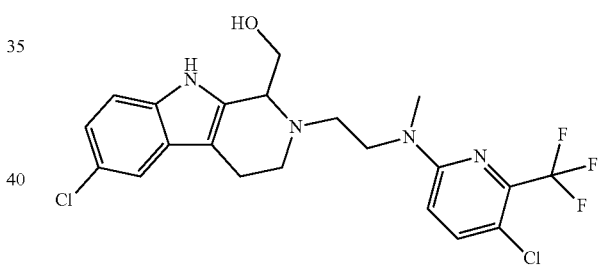

¹H NMR (400 MHz, MeOD): δ 7.60 (d, J=8.0 Hz, 1H), 7.35 (d, J=2.0 Hz, 1H), 7.24 (d, J=12.0 Hz, 1H), 6.99 (dd, J=8.0 Hz, 2.0 Hz, 1H), 6.80 (d, J=8.0 Hz, 1H), 3.87-3.73 (m, 5H), 3.30-3.24 (m, 1H), 3.10 (s, 3H), 3.02-2.97 (m, 1H), 2.92-2.90 (m, 2H), 2.88-2.78 (m, 1H), 2.58-2.53 (m, 1H). LCMS: [M+H]⁺=473.1

(6-((2-(6-Chloro-1-methyl-1,3,4,9-tetrahydro-2H-pyrido[3,4-b]indol-2-yl)ethyl)amino)-2-methylpyridin-3-yl)methanol

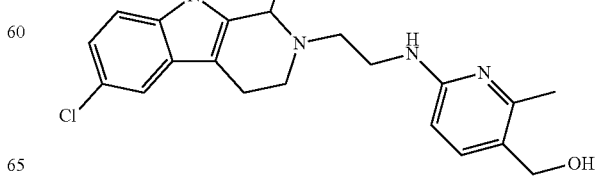

¹H NMR (400 MHz, MeOD) δ 7.40 (d, J=8.4 Hz, 1H), 7.35 (d, J=2.0 Hz, 1H), 7.22 (d, J=8.4 Hz, 1H), 7.00 (dd, J=8.8 Hz, 2.0 Hz, 1H), 6.36 (d, J=8.4 Hz, 1H), 4.48 (s, 2H), 3.96 (br, 1H), 3.57-3.38 (m, 2H), 3.02-2.60 (m, 6H), 2.37 (s, 3H), 1.48 (d, J=6.8 Hz, 3H). LCMS: [M+H]⁺=373.2

2-(6-Chloro-1,3,4,9-tetrahydro-2H-pyrido[3,4-b]indol-2-yl)-3-((5-chloro-6-ethylpyridin-2-yl)amino)propan-1-ol formate

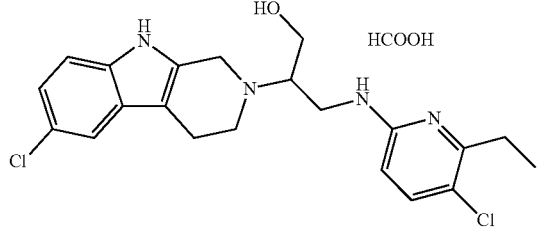 [SMILES: CCc1nc(NCC(CO)N2CCc3c([nH]c4ccc(Cl)cc34)C2)ccc1Cl ; "HCOOH"]

¹H NMR (400 MHz, DMSO) δ 10.89 (s, 1H), 8.39 (brs, 1H), 7.37-7.31 (m, 2H), 7.26 (d, J=8.8 Hz, 1H), 6.98 (dd, J=8.4 Hz, 2.0 Hz, 1H), 6.43 (br, 1H), 6.37 (d, J=8.8 Hz, 1H), 4.57 (br, 1H), 4.00-3.90 (m, 2H), 3.68-3.59 (m, 2H), 3.59-3.56 (m, 2H), 3.01-2.95 (m, 4H), 2.70-2.60 (m, 3H), 1.17 (t, J=7.6 Hz, 3H). LCMS: [M+H]⁺=419.1

(6-Chloro-2-(2-((5-chloro-6-cyclopropylpyridin-2-yl)amino)ethyl)-2,3,4,9-tetrahydro-1H-pyrido[3,4-b]indol-1-yl)methanol formate

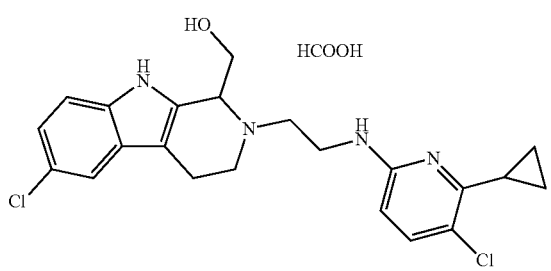 [SMILES: OCC1c2[nH]c3ccc(Cl)cc3c2CCN1CCNc1ccc(Cl)c(C2CC2)n1 ; "HCOOH"]

¹H NMR (400 MHz, DMSO-d₆) δ 10.82 (s, 1H), 8.16 (s, 1H), 7.40 (d, J=2.0 Hz, 1H), 7.30 (dd, J=8.8 Hz, 1.6 Hz, 2H), 7.00 (dd, J=8.4 Hz, 2.0 Hz, 1H), 6.57-6.54 (m, 1H), 6.27 (d, J=8.8 Hz, 1H), 3.72-3.59 (m, 3H), 3.37-3.28 (m, 2H), 3.17-3.09 (m, 1H), 2.89-2.84 (m, 1H), 2.77-2.67 (m, 3H), 2.48-2.44 (m, 1H), 2.30-2.24 (m 1H), 0.95-0.89 (m, 4H). LCMS: [M+H]⁺=431.2

(6-Chloro-2-(2-((5-chloro-6-propylpyridin-2-yl)amino)ethyl)-2,3,4,9-tetrahydro-1-pyrido[3,4-b]indol-1-yl)methanol formate

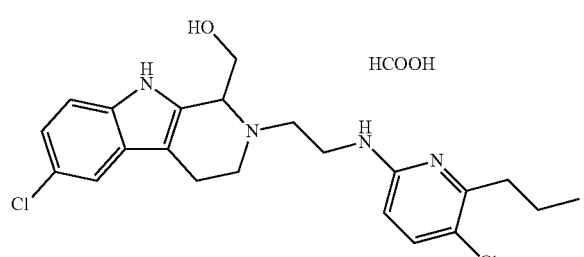

¹H NMR (400 MHz, DMSO-d₆) δ 10.82 (s, 1H), 8.14 (s, 1H), 7.40 (d, J=4.0 Hz, 1H), 7.32 (dd, J=12.0 Hz, 8.0 Hz, 2H), 7.00 (dd, J=8.0 Hz, 2.0 Hz, 1H), 6.57 (t, J=6.0 Hz, 1H), 6.35 (d, J=8.0 Hz, 1H), 3.74-3.60 (m, 3H), 3.40-3.36 (m, 3H), 3.17-3.11 (m, 1H), 2.91-2.88 (m, 1H), 2.79-2.74 (m, 2H), 2.64-2.60 (m, 2H), 2.48-2.44 (m, 1H), 1.66-1.60 (m, 2H), 0.90 (t, J=8.0 Hz, 3H). LCMS: [M+H]⁺=433.2

(6-Chloro-2-(2-((6-chloro-5-methylpyridazin-3-yl)amino)ethyl)-2,3,4,9-tetrahydro-1H-pyrido[3,4-b]indol-1-yl)methanol formate

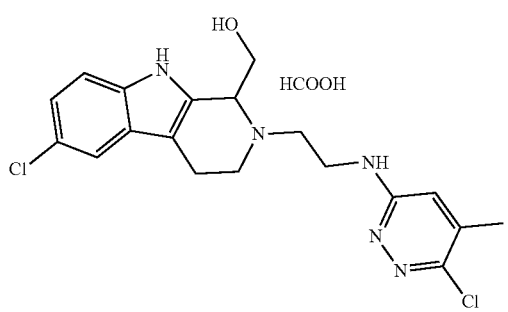 [SMILES: Cc1cc(NCCN2CCc3c([nH]c4ccc(Cl)cc34)C2CO)nnc1Cl ; "HCOOH"]

¹H NMR (400 MHz, DMSO-d₆) δ 10.83 (s, 1H), 8.25 (br, 1H), 7.40 (s, 1H), 7.30 (d, J=8.8 Hz, 1H), 7.00 (d, J=8.4 Hz, 1H), 6.90-6.84 (m, 2H), 3.76-3.60 (m, 3H), 3.48-3.42 (m, 2H), 3.18-3.11 (m, 2H), 2.98-2.67 (m, 4H), 2.19 (s, 3H). LCMS: [M+H]⁺=406.1

(6-Chloro-2-(2-((6-methoxy-5-(trifluoromethyl)pyridin-2-yl)amino)ethyl)-2,3,4,9-tetrahydro-1H-pyrido[3,4-b]indol-1-yl)methanol formate

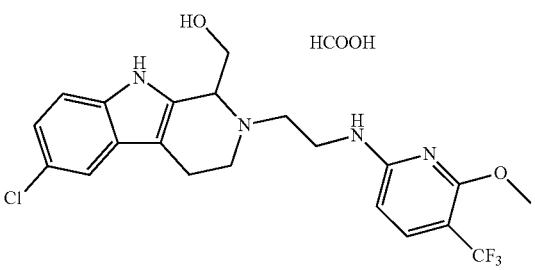 [SMILES: COc1nc(NCCN2CCc3c([nH]c4ccc(Cl)cc34)C2CO)ccc1C(F)(F)F ; "HCOOH"]

¹H NMR (400 MHz, DMSO-d₆) δ 10.84 (s, 1H), 8.16 (s, 1H), 7.51 (d, J=12.0 Hz, 1H), 7.40 (d, J=2.0 Hz, 1H), 7.31 (d, J=8.0 Hz, 1H), 7.00 (dd, J=8.0, 4.0 Hz, 1H), 6.11 (d, J=8.0 Hz, 1H), 4.75 (br, 1H), 3.86 (s, 3H), 3.77-3.60 (m, 3H), 3.51-3.43 (m, 2H), 3.18-3.11 (m, 1H), 2.93-2.88 (m, 3H), 2.48-2.44 (m, 1H). LCMS: [M+H]⁺=455.1

161

(6-Chloro-2-(2-((5-ethyl-6-(trifluoromethyl)pyridin-2-yl)amino)ethyl)-2,3,4,9-tetrahydro-1H-pyrido[3,4-b]indol-1-yl)methanol

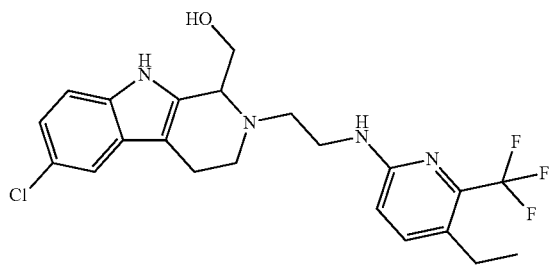 [SMILES: CCc1ccc(NCCN2CCc3c([nH]c4ccc(Cl)cc34)C2CO)nc1C(F)(F)F]

$^1$H NMR (400 MHz, DMSO-d$_6$) δ 10.82 (s, 1H), 7.47 (d, J=8.8 Hz, 1H), 7.40 (s, 1H), 7.30 (d, J=8.4 Hz, 1H), 7.00 (dd, J=8.4 Hz, 1.6 Hz, 1H), 6.78-6.71 (m, 2H), 4.72-4.69 (m, 1H), 3.72-3.61 (m, 3H), 3.40-3.33 (m, 2H), 3.18-3.11 (m, 1H), 2.92-2.88 (m, 1H), 2.81-2.71 (m, 3H), 2.57-2.52 (m, 2H), 2.45-2.43 (m, 1H), 1.11 (t, J=7.2 Hz, 3H). LCMS: [M+H]$^+$=453.1

(6-((2-(6-Chloro-1-(hydroxymethyl)-1,3,4,9-tetrahydro-2H-pyrido[3,4-b]indol-2-yl)ethyl)amino)-2-(trifluoromethyl)pyridin-3-yl)dimethylphosphine oxide

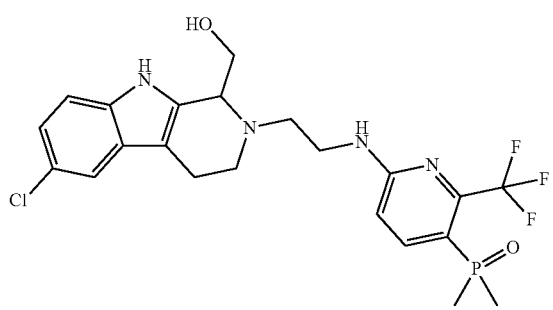 [SMILES: CP(C)(=O)c1ccc(NCCN2CCc3c([nH]c4ccc(Cl)cc34)C2CO)nc1C(F)(F)F]

$^1$H NMR (400 MHz, MeOD): δ 8.04 (brs, 1H), 7.40 (s, 1H), 7.27 (d, J=8.8 Hz, 1H), 7.05 (d, J=8.4 Hz, 1H), 6.80 (brs, 1H), 4.43-3.44 (m, 6H), 3.20-2.70 (m, 5H), 1.83 (s, 3H), 1.79 (s, 3H). LCMS: [M+H]$^+$=501.2

2-(6-Chloro-4-ethyl-1,3,4,9-tetrahydro-2H-pyrido[3,4-b]indol-2-yl)-N-((5-chloro-6-ethylpyridin-2-yl)methyl)ethan-1-amine

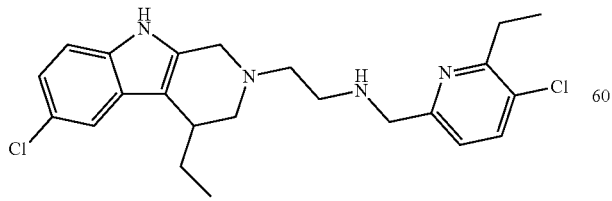

$^1$H NMR (400 MHz, MeOD) δ 7.73 (d, J=8.0 Hz, 1H), 7.40 (d, J=2.0 Hz, 1H), 7.22 (dd, J=8.4 Hz, 2.8 Hz, 2H), 6.99 (dd, J=8.4 Hz, 2.0 Hz, 1H), 3.95 (s, 2H), 3.67-3.54 (m, 2H), 2.94-2.80 (m, 8H), 2.70-2.66 (m, 1H), 2.04-1.91 (m, 1H), 1.70-1.66 (m, 1H), 1.15 (t, J=7.6 Hz, 3H), 0.98 (t, J=7.6 Hz, 3H). LCMS: [M+H]$^+$=431.2

162

N-(2-(1-(((azetidin-3-ylmethyl)amino)methyl)-6-chloro-1,3,4,9-tetrahydro-2H-pyrido[3,4-b]indol-2-yl)ethyl)-5-chloro-6-(trifluoromethyl)pyridin-2-amine triformate

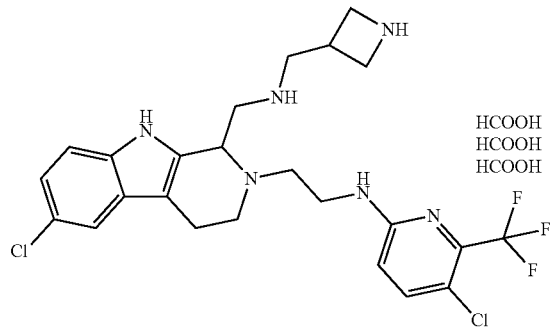 [SMILES: FC(F)(F)c1nc(NCCN2CCc3c([nH]c4ccc(Cl)cc34)C2CNCC2CNC2)ccc1Cl]

$^1$H NMR (400 MHz, MeOD) δ 8.41 (brs, 2H), 7.54 (d, J=8.8 Hz, 1H), 7.38 (s, 1H), 7.25 (d, J=8.8 Hz, 1H), 7.03 (dd, J=8.8 Hz, 1.6 Hz, 1H), 6.70 (d, J=9.2 Hz, 1H), 4.13-4.05 (m, 3H), 3.87-3.82 (m, 2H), 3.55 (t, J=6.0 Hz, 2H), 3.13-2.87 (m, 10H), 2.58-2.53 (m, 1H). LCMS: [M+H]$^+$=527.1

5-Chloro-N-(2-(6-chloro-1-(pyrrolidin-2-yl)-1,3,4,9-tetrahydro-2H-pyrido[3,4-b]indol-2-yl)ethyl)-6-methylpyridin-2-amine

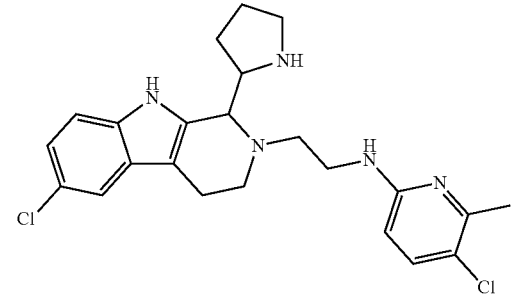 [SMILES: Cc1nc(NCCN2CCc3c([nH]c4ccc(Cl)cc34)C2C2CCCN2)ccc1Cl]

$^1$H NMR (400 MHz, DMSO-d$^6$) δ 10.24 (brs, 1H), 7.32-7.22 (m, 3H), 6.98 (d, J=8.0 Hz, 1H), 6.76-6.73 (m, 1H), 6.26 (d, J=8.8 Hz, 1H), 4.03-4.00 (m, 1H), 3.51-3.36 (m, 3H), 3.29-3.15 (m, 2H), 2.99-2.70 (m, 4H), 2.43-2.05 (m, 5H), 1.80-1.60 (m, 2H), 1.55-1.40 (m, 2H). LCMS: [M+H]$^+$=444.2

5-Chloro-N-(2-(6-chloro-1-(1-methylpyrrolidin-2-yl)-1,3,4,9-tetrahydro-2H-pyrido[3,4-b]indol-2-yl)ethyl)-6-methylpyridin-2-amine

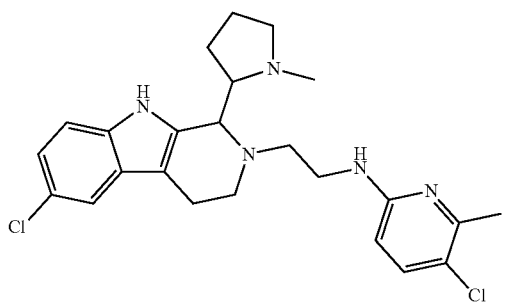 [SMILES: Cc1nc(NCCN2CCc3c([nH]c4ccc(Cl)cc34)C2C2CCCN2C)ccc1Cl]

¹H NMR (400 MHz, DMSO) δ 10.41 (brs, 1H), 8.27 (brs, 1H), 7.42-7.32 (m, 3H), 6.97 (dd, J=8.4 Hz, 2.0 Hz, 1H), 6.57 (s, 1H), 6.33 (d, J=8.8 Hz, 1H), 3.82 (brs, 1H), 3.53-3.20 (m, 3H), 3.19-3.05 (m, 1H), 2.94-2.86 (m, 1H), 2.73-2.60 (m, 5H), 2.39 (s, 3H), 2.34 (s, 3H), 2.18-1.97 (m, 1H), 1.69-1.67 (m, 1H), 1.50-1.48 (m, 1H), 1.29-1.17 (m, 2H). LCMS: [M+H]⁺=458.2

(6-Chloro-2-(2-((5-chloro-6-(trifluoromethyl)pyridin-2-yl)(cyclopropyl)amino)ethyl)-2,3,4,9-tetrahydro-1H-pyrido[3,4-b]indol-1-yl)methanol

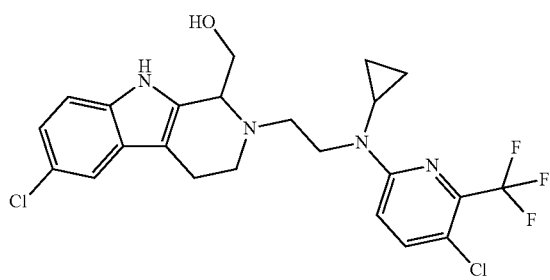 [SMILES: OCC1c2[nH]c3ccc(Cl)cc3c2CCN1CCN(c1ccc(Cl)c(C(F)(F)F)n1)C1CC1]

¹H NMR (400 MHz, DMSO): δ 10.75 (brs, 1H), 7.82 (brs, 1H), 7.37-7.32 (m, 2H), 7.21 (brs, 1H), 7.00 (brs, 1H), 4.60 (brs, 1H), 3.90-3.46 (m, 5H), 3.20-3.10 (m, 1H), 2.90-2.60 (m, 5H), 2.44 (br, 1H), 0.94 (brs, 2H), 0.67 (brs, 2H). LCMS: [M+H]⁺=499.2

2-(6-Chloro-2-(2-((5-chloro-6-(trifluoromethyl)pyridin-2-yl)amino)ethyl)-2,3,4,9-tetrahydro-1H-pyrido[3,4-b]indol-1-yl)propane-1,3-diol

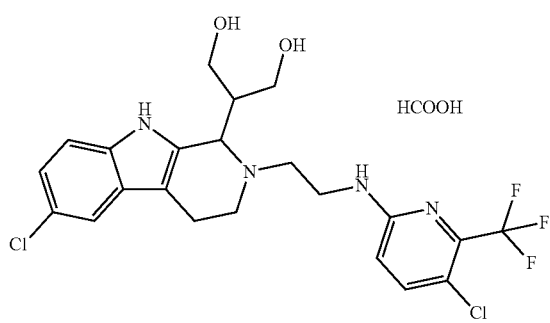 [SMILES: OCC(CO)C1c2[nH]c3ccc(Cl)cc3c2CCN1CCNc1ccc(Cl)c(C(F)(F)F)n1 ; "HCOOH"]

¹H NMR (400 MHz, CD₃OD) δ 8.47 (br, 1H), 7.52 (d, J=8.8 Hz, 1H), 7.42 (d, J=1.2 Hz, 1H), 7.29 (d, J=8.8 Hz, 1H), 7.06 (dd, J=8.4 Hz, 1.6 Hz, 1H), 6.69 (d, J=8.8 Hz, 1H), 4.25 (d, J=8.8 Hz, 1H), 3.92-3.80 (m, 2H), 3.74-3.52 (m, 5H), 3.50-3.41 (m, 1H), 3.13-2.87 (m, 3H), 2.70-2.66 (m, 1H), 2.21 (br, 1H). LCMS: [M+H]⁺: 503.2

N-(2-(1-(2-aminoethyl)-6-chloro-1,3,4,9-tetrahydro-2H-pyrido[3,4-b]indol-2-yl)ethyl)-5-chloro-6-(trifluoromethyl)pyridin-2-amine diformate

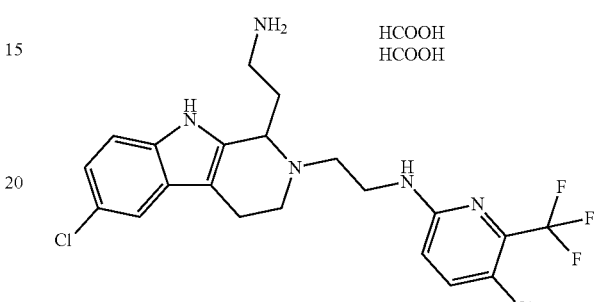

¹H NMR (400 MHz, DMSO-d₆): δ 11.14 (brs, 1H), 8.38 (brs, 2H), 7.63 (d, J=8.8 Hz, 1H), 7.40 (d, J=2.0 Hz, 2H), 7.29 (d, J=8.4 Hz, 1H), 7.02 (dd, J=8.4 Hz, 2.0 Hz, 1H), 6.81 (d, J=9.2 Hz, 1H), 3.86~3.83 (m, 1H), 3.48~3.41 (m, 2H), 3.11~3.09 (m, 1H), 2.90~2.71 (m, 6H), 2.47~2.43 (m, 3H), 2.05~1.99 (m, 2H). ¹⁹F NMR (376 MHz, CDCl₃): δ −64.68. LCMS: [M+H]⁺=472.2

(6-Chloro-2-(2-((6-methyl-5-(trifluoromethyl)pyridin-2-yl)amino)ethyl)-2,3,4,9-tetrahydro-1H-pyrido[3,4-b]indol-1-yl)methanol

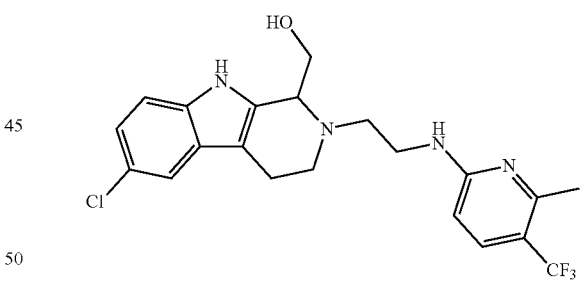

¹H NMR (400 MHz, DMSO-d₆): δ 10.85 (s, 1H), 7.54 (d, J=8.8 Hz, 1H), 7.40 (d, J=1.6 Hz, 1H), 7.30 (d, J=8.4 Hz, 1H), 7.13 (brs, 1H), 7.00 (dd, J=8.4 Hz, 2.0 Hz, 1H), 6.40 (d, J=8.8 Hz, 1H), 4.75~4.73 (m, 1H), 3.77~3.62 (m, 3H), 3.48~3.45 (m, 2H), 3.15~3.12 (m, 1H), 2.92~2.89 (m, 1H), 2.78~2.73 (m, 3H), 2.45~2.44 (m, 1H), 2.40 (s, 3H). ¹⁹F NMR (376 MHz, CDCl₃): δ −57.60. LCMS: [M+H]⁺=439.2

Representative synthesis of 5-chloro-N-(2-(6-chloro-1,1-dimethyl-1,3,4,9-tetrahydro-2H-pyrido[3,4-b]indol-2-yl)ethyl)-6-methylpyridin-2-amine: A mixture of 2-(5-chloro-1H-indol-3-yl)ethan-1-amine (1.386 g, 6 mmol), acetone (0.384 ml, 5.2 mmol) and Ti(O-iPr)₄ was heated to 80° C. for 3 h under Argon. To the mixture was added a mixture of CF₃COOH and (CF₃CO)₂O at 0° C., then the mixture was heated at 70° C. for 3 h. The reaction mixture was diluted with MeOH (100 mL) and passed through a short silica gel column to remove TiO$_2$. The eluent was concentrated in vacuo to around 50 mL volume and the residue was extracted with CHCl$_3$. After concentrated under reduced pressure, the residue was purified by silica gel flash chromatography to afford the title compound (366 mg, 30%). $^1$H NMR (500 MHz, Chloroform-d) δ 7.86 (s, 1H), 7.43 (d, J=2.0 Hz, 1H), 7.21 (d, J=8.5 Hz, 1H), 7.08 (dd, J=8.5, 2.0 Hz, 1H), 3.20 (t, J=5.7 Hz, 2H), 2.66 (t, J=5.7 Hz, 2H), 1.47 (s, 6H). LCMS: [M+H]$^+$=235.1.

To the mixture of 6-chloro-1,1-dimethyl-2,3,4,9-tetrahydro-1H-pyrido[3,4-b]indole (75 mg, 0.3 mmol), 2-bromo-N-(5-chloro-6-methylpyridin-2-yl)acetamide (79 mg, 0.36 mmol) and KI (50 mg, 0.3 mmol) in anhydrous CH$_3$CN was added DIPEA (0.156 mL, 0.9 mmol). The mixture was heated to reflux overnight. The reaction was quenched with water, extracted with ethyl acetate, washed with brine and dried over Na$_2$SO$_4$. The organic phase was concentrated under reduced pressure and the residue was purified by silica gel flash chromatography (hexane/EA=5:1 to 3:1) to afford the title compound (61 mg, 48%). $^1$H NMR (500 MHz, Chloroform-d) δ 9.82 (s, 1H), 8.10 (d, J=8.7 Hz, 1H), 7.96 (s, 1H), 7.63 (d, J=8.7 Hz, 1H), 7.47 (d, J=2.0 Hz, 1H), 7.25 (d, J=8.6 Hz, 1H), 7.14 (dd, J=8.6, 2.1 Hz, 1H), 3.39 (s, 2H), 3.02 (t, J=5.7 Hz, 2H), 2.84 (t, J=5.7 Hz, 2H), 2.50 (s, 3H), 1.50 (s, 6H). LCMS: [M+H]$^+$=417.0.

To the mixture of 2-(6-chloro-1,1-dimethyl-1,3,4,9-tetrahydro-2H-pyrido[3,4-b]indol-2-yl)-N-(5-chloro-6-methylpyridin-2-yl)acetamide (10 mg, 0.024 mmol) in 1 mL anhydrous THF was added 10 uL 10 M BH$_3$ in THF solution. The reaction mixture was heated to reflux overnight. The reaction was quenched with MeOH, concentrated under reduced pressure and purified by silica gel flash chromatography (DCM/MeOH=20:1) to afford the title compound (6.4 mg, 66%). $^1$H NMR (500 MHz, Chloroform-d) δ 7.91 (s, 1H), 7.41 (d, J=2.0 Hz, 1H), 7.32 (d, J=8.7 Hz, 1H), 7.21 (d, J=8.5 Hz, 1H), 7.08 (dd, J=8.6, 2.0 Hz, 1H), 6.21 (d, J=8.7 Hz, 1H), 5.14 (d, J=17.8 Hz, 1H), 3.37 (t, J=6.0 Hz, 2H), 2.92 (t, J=5.7 Hz, 2H), 2.78 (t, J=5.9 Hz, 2H), 2.67 (t, J=5.7 Hz, 2H), 2.42 (s, 3H), 1.39 (s, 6H). LCMs: [M+H]$^+$=403.1.

General scheme 19

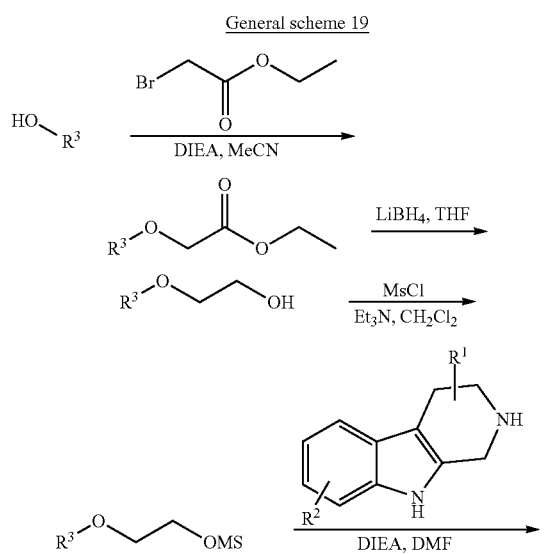

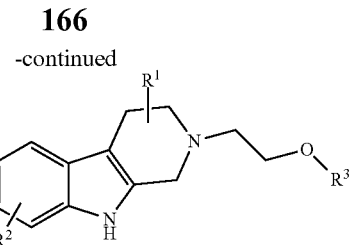

Representative synthesis of 6-chloro-2-(2-(4-chlorophenoxy)ethyl)-2,3,4,9-tetrahydro-1H-pyrido[3,4-b]indole

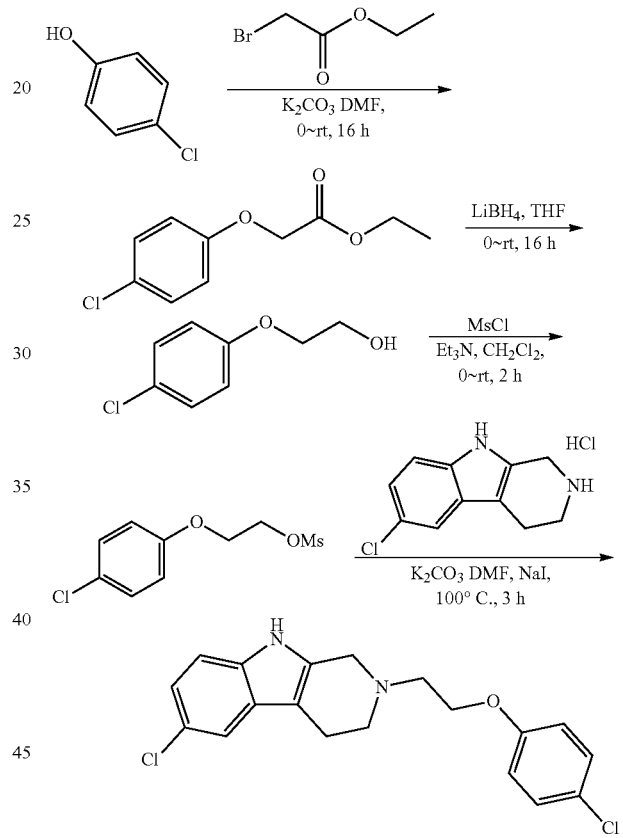

Ethyl 2-(4-chlorophenoxy)acetate: To a suspension of 4-dichlorophenol (1.0 g, 7.81 mmol) and K$_2$CO$_3$ (2.2 g, 15.62 mmol) in DMF (10 mL) was added ethyl 2-bromoacetate (1.9 g, 11.72 mmol) at 0° C. The reaction was stirred at RT for 16 hrs, then was poured into H$_2$O (15 mL) and the resulting mixture was extracted with EtOAc (3×10 mL). The combined organic layers were dried over Na$_2$SO$_4$ and concentrated to give ethyl 2-(4-chlorophenoxy)acetate (1.2 g, yield: 71.8%) as a yellow oil. $^1$H NMR (400 MHz, DMSO-d$_6$): δ 7.35~7.31 (m, 2H), 7.00~6.94 (m, 2H), 4.93 (s, 2H), 4.20~4.12 (m, 2H), 1.23~1.18 (m, 3H).

2-(4-Chlorophenoxy)ethanol: To a solution of ethyl 2-(4-chlorophenoxy)acetate (1.86 g, 8.7 mmol) in anhydrous THF (10 mL) was added LiBH$_4$ (2M in THF, 8.7 mL, 17.4 mmol) drop-wise at 0° C. The reaction was stirred at RT for 2 hrs, then was quenched with sat. NH$_4$Cl and the resulting mixture was extracted with EtOAc (3×10 mL). The combined organic layers were dried over Na₂SO₄ and concentrated to give product 2-(4-chlorophenoxy)ethanol (1.28 g, yield: 85.6%) as a yellow oil. ¹H NMR (400 MHz, DMSO-d₆): δ 7.33 (dd, J=6.8, 2.0 Hz, 2H), 6.97 (dd, J=6.4, 2.0 Hz, 2H), 4.87 (t, J=5.6 Hz, 1H), 3.97 (t, J=4.4 Hz, 2H), 3.72~3.68 (m, 2H).

2-(4-Chlorophenoxy)ethyl methanesulfonate: To a solution of 2-(4-chlorophenoxy)ethanol (500 mg, 2.906 mmol) and Et₃N (882 g, 8.718 mmol) in CH₂Cl₂ (10 mL) was added MsCl (663 mg, 5.813 mmol) drop-wise at 0° C. The reaction was stirred at RT for 2 hrs, then was quenched with H₂O (10 mL) and extracted with CH₂Cl₂ (3×10 mL). The combined organic layers were dried over Na₂SO₄ and concentrated to give product 2-(4-chlorophenoxy)ethyl methanesulfonate (324 mg, yield: 61.8%) as a yellow oil. ¹H NMR (400 MHz, DMSO-d₆): δ 7.36 (dd, J=6.8, 2.0 Hz, 2H), 7.03 (dd, J=5.6, 3.6 Hz, 2H), 4.53 (dd, J=4.4, 2.8 Hz, 2H), 4.26 (dd, J=4.4, 2.4 Hz, 2H), 3.23 (s, 3H).

6-Chloro-2-(2-(4-chlorophenoxy)ethyl)-2,3,4,9-tetrahydro-1H-pyrido[3,4-b]indole: To a solution of 6-chloro-2,3,4,9-tetrahydro-1H-pyrido[3,4-b]indole hydrochloride (100 mg, 0.413 mmol), NaI (124 mg, 0.826 mmol) and K₂CO₃ (685 mg, 4.956 mmol) in DMF (10 mL) was added 2-(3,4-dichlorophenoxy)ethyl methanesulfonate (234 mg, 0.826 mmol). The mixture was stirred at 100° C. for 3 hrs, then was queched with H₂O (10 mL) and extracted with EtOAc (3×10 mL). The combined organic layers were dried over Na₂SO₄ and concentrated. The residue was purified via prep-HPLC (mobile phase: 0.1% NH₃/H₂O/CH₃CN/H₂O) to give 6-chloro-2-(2-(4-chlorophenoxy)ethyl)-2,3,4,9-tetrahydro-1H-pyrido[3,4-b]indole (35.38 mg, yield: 11.9%) as a yellow oil. ¹H NMR (400 MHz, DMSO-d₆): δ 10.95 (s, 1H), 7.39~7.27 (m, 4H), 7.02~6.98 (m, 2H), 4.17 (t, J=5.6 Hz, 2H), 3.73 (s, 2H), 2.97~2.85 (m, 4H), 2.67 (t, J=5.2 Hz, 2H). LCMS: [M+H]⁺=361.1

6-Chloro-2-(2-(3-chlorophenoxy)ethyl)-2,3,4,9-tetrahydro-1H-pyrido[3,4-b]indole formate

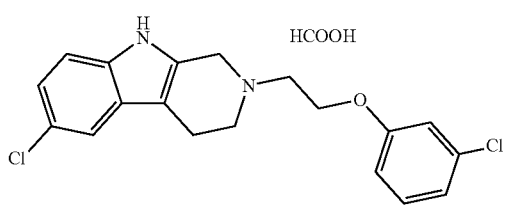 [SMILES: Clc1cccc(OCCN2CCc3c([nH]c4ccc(Cl)cc34)C2)c1 ; "HCOOH"]

¹H NMR (400 MHz, DMSO-d₆): δ 10.94 (s, 1H), 8.19 (s, 1H), 7.39 (d, J=2.0 Hz, 1H), 7.33~7.27 (m, 2H), 7.07 (t, J=2.0 Hz, 1H), 7.01~6.94 (m, 2H), 4.21 (t, J=5.6 Hz, 2H), 3.74 (s, 2H), 2.96 (t, J=5.6 Hz, 2H), 2.87 (t, J=5.6 Hz, 2H), 2.67 (t, J=5.6 Hz, 2H). LCMS: [M+H]⁺=361.0.

6-Chloro-2-(2-(3,4-dichlorophenoxy)ethyl)-2,3,4,9-tetrahydro-1H-pyrido[3,4-b]indole

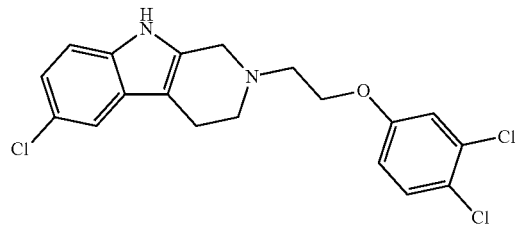 [SMILES: Clc1ccc2[nH]c3c(c2c1)CCN(CCOc1ccc(Cl)c(Cl)c1)C3]

¹H NMR (400 MHz, DMSO-d₆): δ 10.94 (s, 1H), 7.53~7.27 (m, 4H), 7.01~6.99 (m, 2H), 4.22 (s, 2H), 3.73 (s, 2H), 2.95~2.85 (m, 4H), 2.67 (s, 2H). LCMS: [M+H]⁺=395.0.

General scheme 20

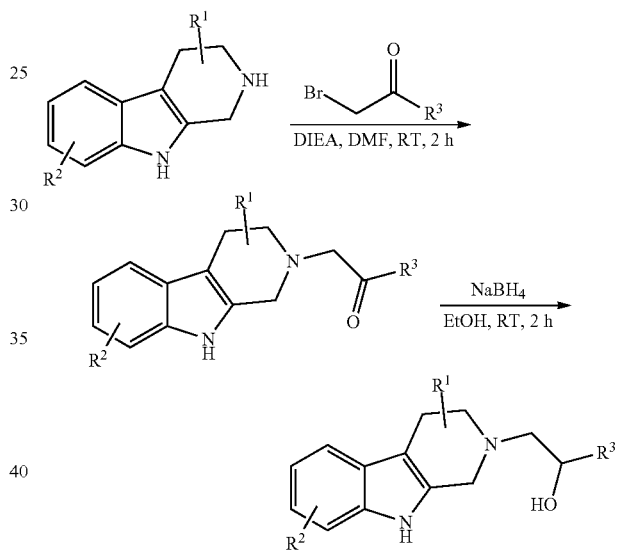

Representative synthesis of 2-(6-chloro-3,4-dihydro-1H-pyrido[3,4-b]indol-2(9H)-yl)-1-(3,5-dichlorophenyl)ethanone formate

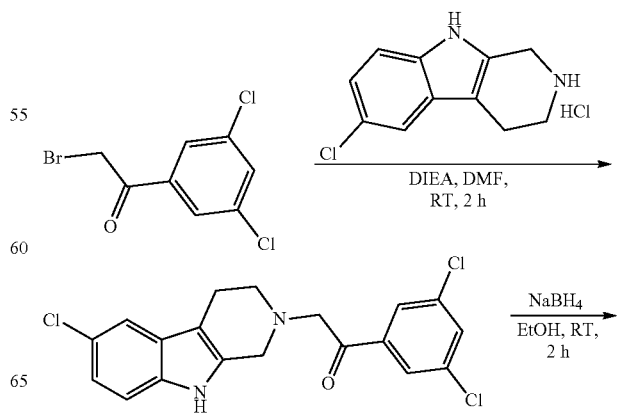

-continued

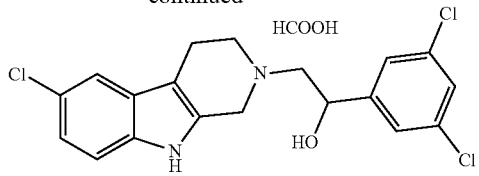

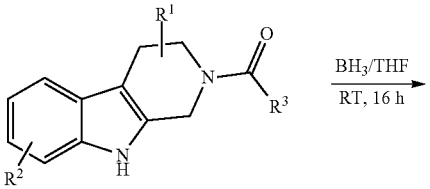

General Scheme 21

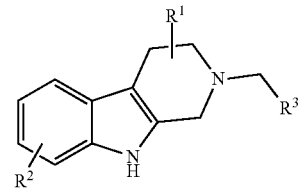

Representative synthesis of 3-(6-chloro-3,4-di-hydro-1H-pyrido[3,4-b]indol-2(9H)-yl)-1-(4-chloro-phenyl)propane-1,2-diol

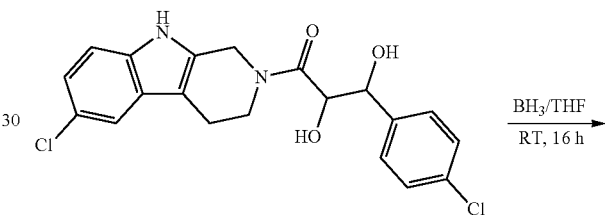

2-(6-chloro-3,4-dihydro-1H-pyrido[3,4-b]indol-2(9H)-yl)-1-(3,5-dichlorophenyl) ethanone: To a solution of 2-bromo-1-(3,5-dichlorophenyl)ethan-1-one (500 mg, 1.9 mmol) and 6-chloro-2,3,4,9-tetrahydro-1H-pyrido[3,4-b]indole hydrochloride (310 mg, 1.9 mmol) in DMF (10 ml) was added DIEA (0.7 mL). The resulting mixture was stirred at rt for 2 hrs, was then poured into water and extracted with EtOAc (3×20 mL). The organic layer was washed with saturated aqueous NaCl, dried over $Na_2SO_4$, and concentrated. The residue was purified by silica gel chromatography eluting with $CH_2Cl_2$:MeOH=200:1 to give 2-(6-chloro-1,3,4,9-tetrahydro-2H-pyrido[3,4-b]indol-2-yl)-1-(3,5-dichlorophenyl)ethan-1-one (128 mg, yield: 26%) as a brown oil. LCMS: $[M+H]^+$=393.0, 395.0

2-(6-Chloro-3,4-dihydro-1H-pyrido[3,4-b]indol-2(9H)-yl)-1-(3,5-dichlorophenyl) ethanone: To a solution of 2-(6-chloro-1,3,4,9-tetrahydro-2H-pyrido[3,4-b]indol-2-yl)-1-(3,5-dichlorophenyl)ethan-1-one (120 mg, 0.31 mmol) in EtOH (10 mL) was added $NaBH_4$ (23 mg, 0.61 mmol). The reaction solution was stirred for 2 hrs at RT. The solvent was evaporated, and the residue was purified by prep-HPLC (mobile phase: 0.1% $HCOOH/CH_3CN/H_2O$) to give 2-(6-chloro-1,3,4,9-tetrahydro-2H-pyrido[3,4-b]indol-2-yl)-1-(3,5-dichlorophenyl)ethan-1-ol (33.56 mg, yield: 28%) as a white solid. $^1H$ NMR (400 MHz, DMSO-$d_6$): δ 10.94 (s, 1H), 8.32 (s, 1H), 7.46~7.44 (m, 3H), 7.38 (d, J=2.0 Hz, 1H), 7.28 (d, J=8.8 Hz, 1H), 7.00 (dd, J=8.4, 2.0 Hz, 1H), 4.86 (t, J=5.6 Hz 1H), 3.77~3.68 (m, 2H), 2.89~2.67 (m, 5H), 2.65~2.62 (m, 2H). LCMS: $[M+H]^+$=395.2

2-(6-Chloro-1-(hydroxymethyl)-3,4-dihydro-1H-pyrido[3,4-b]indol-2(9H)-yl)-1-(3,4-dichlorophenyl) ethanol formate

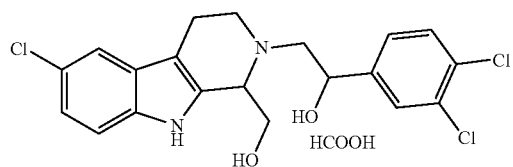 [SMILES: OCC1c2[nH]c3ccc(Cl)cc3c2CCN1CC(O)c1ccc(Cl)c(Cl)c1 ; "HCOOH"]

$^1H$ NMR (400 MHz, DMSO-$d_6$): δ 10.87 (s, 1H), 8.24 (s, 1H), 7.66-7.63 (m, 1H), 7.58~7.54 (m, 1H), 7.43~7.36 (m, 2H), 7.31~7.28 (m, 1H), 7.02 (dd, J=4.8, 2.0 Hz, 1H), 4.79~4.73 (m, 1H), 3.85~3.77 (m, 2H), 3.68 (d, J=6.4 Hz, 1H), 3.63~3.55 (m, 2 Hz), 3.18~3.05 (m, 1H), 2.90~2.85 (m, 1H), 2.82~2.75 (m, 1H), 2.73~2.62 (m, 2H), 2.46~2.41 (m, 1H). LCMS: $[M+H]^+$=427.0

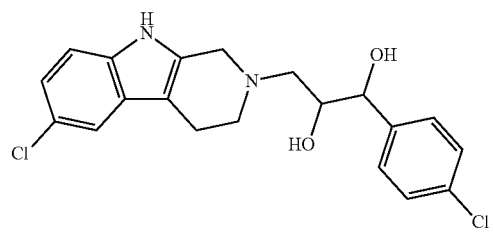

To a solution of 1-(6-chloro-3,4-dihydro-1H-pyrido[3,4-b]indol-2(9H)-yl)-3-(4-chlorophenyl)-2,3-dihydroxypropan-1-one (150 mg. 0.37 mmol) in anhydrous THF (5 mL) was added $BH_3/THF$ (1M, 1.11 mL, 1.11 mmol) drop-wise. The reaction was stirred at RT for 16 hrs, and was quenched with sat. $NH_4Cl$. EtOAc (20 mL) was added and the resulting mixture was washed with brine (2×20 mL), dried over anhydrous $Na_2SO_4$ and concentrated. The residue was purified by (Mobile phase: 0.1% $NH_4HCO_3/H_2O$/MeCN) to give 3-(6-chloro-3,4-dihydro-1H-pyrido[3,4-b]indol-2(9H)-yl)-1-(4-chlorophenyl)propane-1,2-diol (29.92 mg, yield: 21%) as a white solid. $^1H$ NMR (400 MHz, DMSO-$d_6$): δ 10.89 (s, 1H), 7.38~7.26 (m, 6H), 7.00 (d, J=7.2 Hz, 1H), 5.42 (s, 1H), 4.61 (s, 2H), 3.81-3.62 (m, 3H), 2.77~2.59 (m, 5H), 2.41~2.36 (m, 1H). LCMS: $[M+H]^+$=391.3.

3-(6-Chloro-3,4-dihydro-1H-pyrido[3,4-b]indol-2 (9H)-yl)-1-(3-chlorophenyl) propane-1, 2-diol

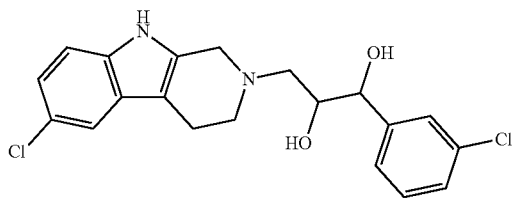 [SMILES: OC(CN1CCc2c([nH]c3ccc(Cl)cc23)C1)C(O)c1cccc(Cl)c1]

$^1$H NMR (400 MHz, DMSO-d$_6$): δ 10.89 (s, 1H), 7.42-7.26 (m, 6H), 7.00 (d, J=8.0 Hz, 1H), 5.46~5.42 (m, 1H), 4.63 (d, J=3.2 Hz, 2H), 3.82~3.63 (m, 3H), 2.79~2.50 (m, 5H), 2.44~2.39 (m, 1H). LCMS: [M+H]$^+$=391.3.

General scheme 22

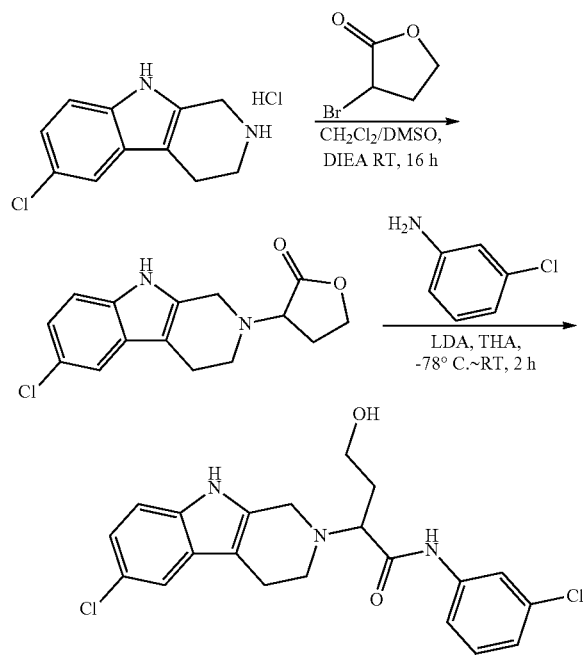

Representative synthesis of 3-(6-chloro-3,4-dihydro-1H-pyrido[3,4-b]indol-2(9H)-yl)dihydrofuran-2(3H)-one: To the solution of 6-chloro-2,3,4,9-tetrahydro-1H-pyrido[3,4-b]indole hydrochloride (400 mg, 1.66 mmol) in CH$_2$Cl$_2$ (10 mL) and DMSO (2 mL) was added 3-bromodihydrofuran-2(3H)-one (274 mg, 1.66 mmol) and DIEA (1 g, 8.3 mmol). The reaction mixture was stirred at RT for 16 hrs, was then filtered to give 3-(6-chloro-1,3,4,9-tetrahydro-2H-pyrido[3,4-b]indol-2-yl)dihydrofuran-2(3H)-one (320 mg, yield: 66%). LCMS: [M+H]$^+$=391.0.

3-(6-Chloro-3,4-dihydro-1H-pyrido[3,4-b]indol-2(9H)-yl)dihydrofuran-2(3H)-one: To the solution of 3-chloroaniline (88 mg, 0.7 mmol) in anhydrous THF (5 mL) was added 2 M LDA (0.9 mL, 1.8 mmol) at −78° C. The reaction was stirred at −78° C. for 30 min, then warmed up to room temperature. 3-(6-Chloro-1,3,4,9-tetrahydro-2H-pyrido[3,4-b]indol-2-yl)dihydrofuran-2(3H)-one (200 mg, 0.7 mmol) in THF (2 mL) was added to the reaction, and stirred at room temperature for 2 hrs. The reaction was then treated with saturated ammonium chloride (10 mL) and extracted with ethyl acetate (3×10 mL). The combined organics were drive over Na$_2$SO$_4$ and concentrated. The residue was purified via prep-HPLC (mobile phase: 0.1% NH$_3$/CH$_3$CN/H$_2$O) to give 2-(6-chloro-1,3,4,9-tetrahydro-2H-pyrido[3,4-b]indol-2-yl)-N-(3-chlorophenyl)-4-hydroxybutanamide (20.34 mg, yield: 7%). $^1$H NMR (400 MHz, DMSO-d$_6$): δ 10.92 (s, 1H), 10.20 (s, 1H), 7.88 (s, 1H), 7.51~7.49 (m, 1H), 7.37~7.26 (m, 3H), 7.11~7.09 (m, 1H), 7.00~6.79 (m, 1H), 4.59 (t, 1H), 3.90 (m, 2H), 3.66~3.41 (m, 3H), 2.93~2.65 (m, 4H), 1.98~1.87 (m, 2H). LCMS: [M+H]$^+$=418.1.

General scheme 23

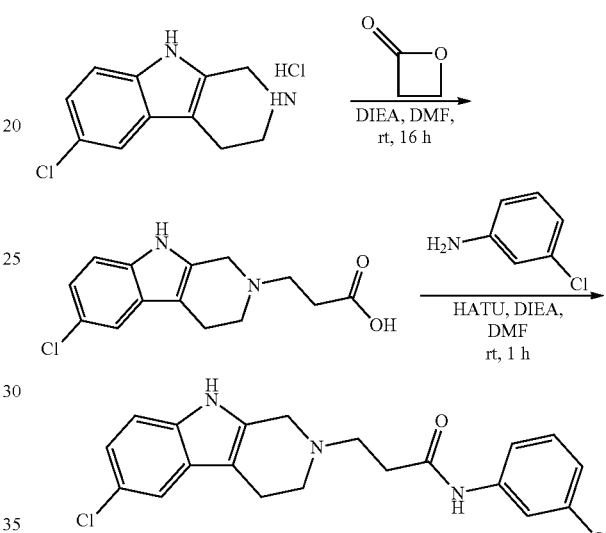

3-(6-chloro-3,4-dihydro-1H-pyrido[3,4-b]indol-2(9H)-yl)propanoic acid: To a solution of 6-chloro-2,3,4,9-tetrahydro-1H-pyrido[3,4-b]indole hydrochloride (300 mg, 1.23 mmol) in DMF (5 mL) was added oxetan-2-one (89 mg, 1.23 mmol), DIEA (476 mg, 3.69 mmol). The reaction was stirred at RT for 16 hrs, was then poured into water. The resulting mixture was adjusted to pH≈6 with 3M aq. HCl, extracted with EtOAc, washed with brine, dried over Na$_2$SO$_4$ and evaporated to give 3-(6-chloro-3,4-dihydro-1H-pyrido[3,4-b]indol-2(9H)-yl)propanoic acid (100 mg, yield: 29%).

3-(6-Chloro-3,4-dihydro-1H-pyrido[3,4-b]indol-2(9H)-yl)propanoic acid: To a solution of 3-(6-chloro-3,4-dihydro-1H-pyrido[3,4-b]indol-2(9H)-yl)propanoic acid (80 mg, 0.287 mmol) in DMF (4 mL) was added 3-chloroaniline (73 mg, 0.574 mmol), HATU (218 mg, 0.574 mmol) and DIEA (111 mg, 0.861 mmol). The reaction was stirred at room temperature for 1 h, and was then poured into water, extracted with EtOAc, washed with brine, dried over Na$_2$SO$_4$, and concentrated. The residue was purified via prep-HPLC (0.1% HCOOH/CH$_3$CN/H$_2$O) to give 3-(6-chloro-3,4-dihydro-1H-pyrido[3,4-b]indol-2(9H)-yl)-N-(3-chlorophenyl)propanamide (100 mg, yield: 90%) as a white solid. $^1$H NMR (400 MHz, DMSO-d$_6$): δ 10.97 (s, 1H), 10.29~10.27 (m, 1H), 8.16 (d, J=6.0 Hz, 0.6H), 7.83 (s, 1H), 7.43~7.38 (m, 2H), 7.31~7.27 (m, 2H), 7.08 (dd, J=1.2, 8.0 Hz, 1H), 6.99 (dd, J=2.0, 8.8 Hz, 1H), 3.68 (s, 2H), 2.94~2.90 (m, 2H), 2.84~2.82 (m, 2H), 2.68~2.67 (m, 2H), 2.63~2.59 (m, 2H). LCMS: [M+H]$^+$=388.2.

General scheme 24

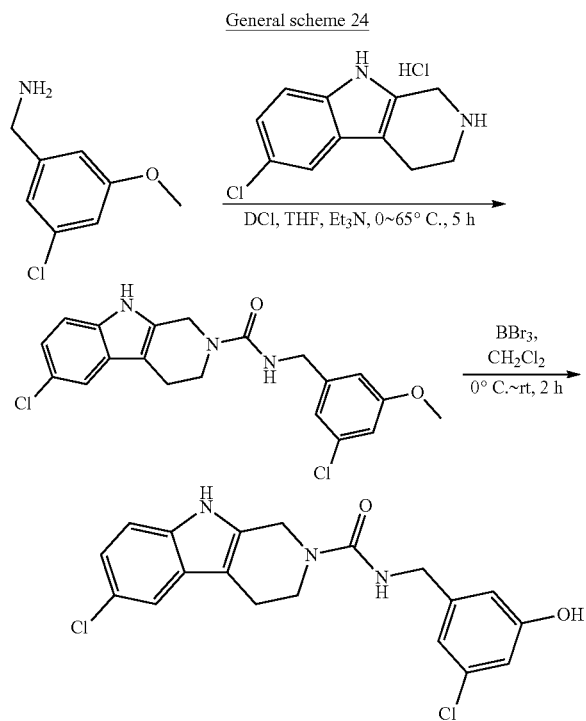

6-Chloro-N-(3-chloro-5-methoxybenzyl)-3,4-dihydro-1H-pyrido[3,4-b]indole-2(9H)-carboxamide: To a solution of (3-chloro-5-methoxyphenyl)methanamine (255 mg, 1.491 mmol) and Et$_3$N (905 mg, 8.946 mmol) in THF (8 mL) was added CDI (265 mg, 1.640 mmol) at 0° C. The mixture was stirred at 0° C. for 1 h. Then 6-chloro-2,3,4,9-tetrahydro-1H-pyrido[3,4-b]indole hydrochloride (361 mg, 1.491 mmol) was added and the mixture was stirred at 0° C. for 1 h and 65° C. for 2 hrs. The reaction mixture was then filtered, and the filtrate was concentrated. The residue was purified via prep-HPLC (Mobile phase: 0.1% NH$_4$HCO$_3$/CH$_3$CN/H$_2$O) to give 6-chloro-N-(3-chloro-5-methoxybenzyl)-3,4-dihydro-1H-pyrido[3,4-b]indole-2(9H)-carboxamide (330 mg, yield: 55%) as a colorless oil. $^1$H NMR (400 MHz, DMSO-d$_6$): δ 11.07 (s, 1H), 7.44~7.30 (m, 3H), 7.03 (dd, J=8.4, 2.0 Hz, 1H), 6.88~6.79 (m, 3H), 4.59 (s, 2H), 4.23 (d, J=5.6 Hz, 2H), 3.72..3.68 (m, 5H), 2.68 (s, 2H). LCMS: [M+H]$^+$=404.2.

6-Chloro-N-(3-chloro-5-hydroxybenzyl)-3,4-dihydro-1H-pyrido[3,4-b]indole-2(9H)-carboxamide: To a solution of 6-chloro-N-(3-chloro-5-methoxybenzyl)-3,4-dihydro-1H-pyrido[3,4-b]indole-2(9H)-carboxamide (100 mg, 0.249 mmol) in anhydrous CH$_2$Cl$_2$ (5 mL) was added BBr$_3$ (2.5 mL) drop-wise at 0° C. The reaction was stirred at room temperature for 2 hrs, then was quenched with sat. NaHCO$_3$. The resulting solution was adjusted to pH 8-9 by sat. NaHCO$_3$ and extracted with EtOAc (3×10 mL). The combined organic layers were dried over Na$_2$SO$_4$ and concentrated. The residue was purified via prep-HPLC (Mobile phase: 0.1% NH$_3$·H$_2$O/CH$_3$CN/H$_2$O) to give 6-chloro-N-(3-chloro-5-hydroxybenzyl)-3,4-dihydro-1H-pyrido[3,4-b]indole-2(9H)-carboxamide (19.95 mg, yield: 10.3%) as a white solid. $^1$H NMR (400 MHz, DMSO-d$_6$): δ 11.08 (s, 1H), 7.44 (d, J=1.6 Hz, 1H), 7.32~7.30 (m, 2H), 7.04 (dd, J=8.8, 2.0 Hz, 1H), 6.72 (s, 1H), 6.63 (s, 2H), 4.58 (s, 2H), 4.18 (d, J=5.6 Hz, 2H), 3.69 (d, J=5.6 Hz, 2H), 2.68 (s, 2H). LCMS: [M+H]$^+$=390.1.

General scheme 25

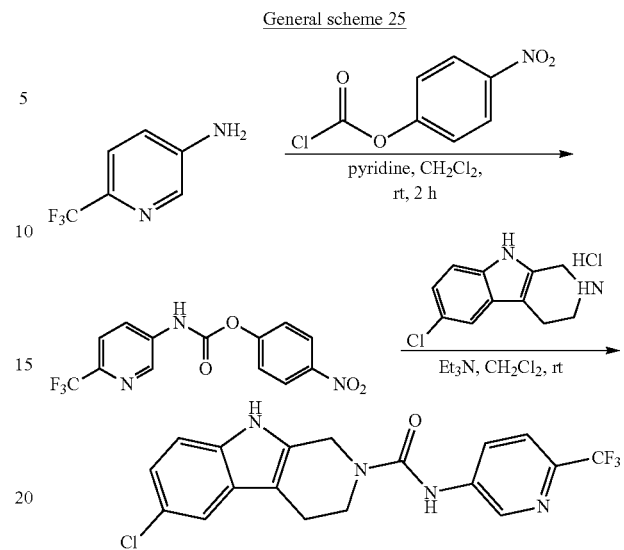

4-Nitrophenyl (6-(trifluoromethyl)pyridin-3-yl)carbamate: To a solution of 6-(trifluoromethyl)pyridin-3-amine (500 mg, 3.08 mmol) in CH$_2$Cl$_2$ (20 mL) was added 4-nitrophenyl carbonochloridate (620 mg, 3.08 mmol), pyridine (244 mg, 3.08 mmol) at RT and stirred for 2 hrs. The mixture was then poured into water, extracted with CH$_2$Cl$_2$, washed with brine, dried over Na$_2$SO$_4$, and concentrated. The residue was purified by silica gel chromatography eluting with petroleum ether:EtOAc=4:1 to give 4-nitrophenyl (6-(trifluoromethyl)pyridin-3-yl)carbamate (350 mg, yield: 35%).

6-Chloro-N-(6-(trifluoromethyl)pyridin-3-yl)-3,4-dihydro-1H-pyrido[3,4-b]indole-2(9H)-carboxamide: To a solution of 6-chloro-2,3,4,9-tetrahydro-1H-pyrido[3,4-b]indole hydrochloride (100 mg, 0.306 mmol) in CH$_2$Cl$_2$ (2 mL) was added 4-nitrophenyl (6-(trifluoromethyl)pyridin-3-yl) carbamate (63 mg, 0.306 mmol), Et$_3$N (218 mg, 0.574 mmol) at room temperature, and stirred for 2 hrs. The reaction was concentrated, and the residue was purified via prep-HPLC (mobile phase 0.1% NH$_4$HCO$_3$/CH$_3$CN/H$_2$O) to give 6-chloro-N-(6-(trifluoromethyl)pyridin-3-yl)-3,4-dihydro-1H-pyrido[3,4-b]indole-2(9H)-carboxamide (35.18 mg, yield: 29%) as a white solid. $^1$H NMR (400 MHz, DMSO-d$_6$): δ 11.14 (s, 1H), 9.35 (s, 1H), 8.84 (d, J=2.4 Hz, 1H), 8.18 (dd, J=2.4, 8.8 Hz, 1H), 7.79 (d, J=8.4 Hz, 1H), 7.48 (d, J=2.0 Hz, 1H), 7.34 (d, J=8.8 Hz, 1H), 7.05 (dd, J=2.0, 8.4 Hz, 1H), 4.73 (s, 2H), 3.87-3.85 (m, 2H), 2.80-2.77 (m, 2H). LCMS: [M+H]$^+$=395.1.

General Scheme 26

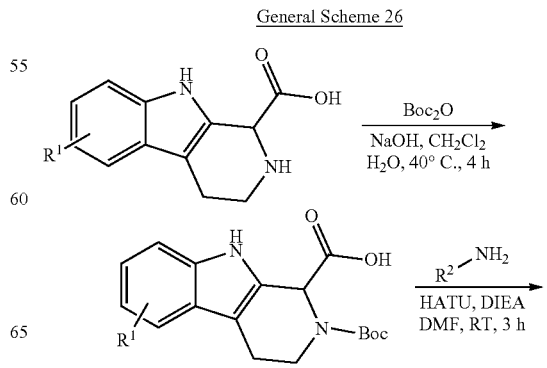

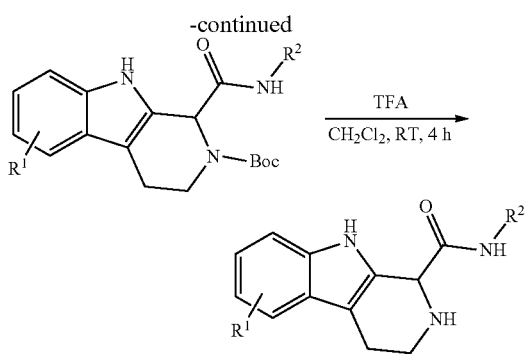

Representative synthesis of 6-chloro-N-(4-chlorophenyl)-2,3,4,9-tetrahydro-1H-pyrido[3,4-b]indole-1-carboxamide

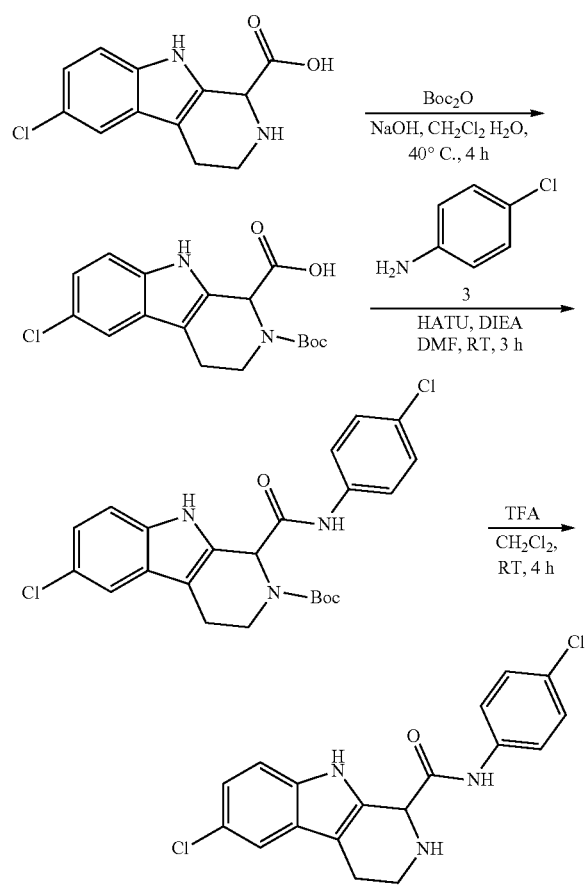

2-(tert-butoxycarbonyl)-6-chloro-2,3,4,9-tetrahydro-1H-pyrido[3,4-b]indole-1-carboxylic acid: To a mixture of 6-chloro-2,3,4,9-tetrahydro-1H-pyrido[3,4-b]indole-1-carboxylic acid (2.0 g, 8.0 mmol) and NaOH (960 mg, 24.0 mmol) in H₂O (40 mL) and CH₂Cl₂ (10 mL) was added Boc₂O (2.6 g, 12.0 mmol). The mixture was stirred at 40° C. for 4 hrs. The reaction was then cooled to 10° C., and was adjusted to pH~6. The precipitates were collected by filtration and dried in vacuo to give 2-(tert-butoxycarbonyl)-6-chloro-2,3,4,9-tetrahydro-1H-pyrido[3,4-b]indole-1-carboxylic acid (2.1 g, yield: 75%) as a white solid. ¹H NMR (400 MHz, DMSO-d₆): δ 13.41 (br, 1H), 11.16 (m, 1H), 7.47 (s, 1H), 7.39 (d, J=8.8 Hz, 1H), 7.09 (dd, J=8.4, 1.6 Hz, 1H), 5.56~5.47 (m, 1H), 4.34~4.22 (m, 1H), 3.30~3.12 (m, 2H), 2.78~2.60 (m, 2H), 1.45~1.42 (m 9H).

tert-Butyl 6-chloro-1-((4-chlorophenyl)carbamoyl)-3,4-dihydro-1H-pyrido[3,4-b]indole-2(9H)-carboxylate: To a mixture of 2-(tert-butoxycarbonyl)-6-chloro-2,3,4,9-tetrahydro-1H-pyrido[3,4-b]indole-1-carboxylic acid (200 mg, 0.57 mmol, 1.0 eq), 3 (109 mg, 0.86 mmol, 1.5 eq) and HATU (433 mg, 1.14 mmol, 2.0 eq) in DMF (10 mL) was added DIEA (221 mg, 1.71 mmol, 3.0 eq) at 0° C. The mixture was stirred at room temperature for 3 hrs, and was then poured into water (30 mL), extracted with EtOAc (3×60 mL). The combined organic phases were dried over anhydrous sodium sulfate and concentrated in vacuo. The residue was purified by silica gel column chromatography eluting with petroleum ether:EtOAc=2:1 to give tert-butyl 6-chloro-1-((4-chlorophenyl)carbamoyl)-3,4-dihydro-1H-pyrido[3,4-b]indole-2(9H)-carboxylate (140 mg, yield: 53%) as a white solid. ¹H NMR (400 MHz, DMSO-d₆): δ 11.17~11.02 (m, 1H), 10.71~10.62 (m, 1H), 7.72~7.68 (m, 2H), 7.50 (br, 1H), 7.41 (d, J=8.0 Hz, 1H), 7.09 (dd, J=8.4, 2.0 Hz, 1H), 5.76~5.63 (m, 1H), 4.26~4.22 (m, 1H), 3.63~3.51 (m, 1H), 2.85~2.76 (m, 1H), 2.71~2.62 (m, 1H), 1.45~1.36 (m, 9H).

6-Chloro-N-(4-chlorophenyl-2,3,4,9-tetrahydro-1H-pyrido[3,4-b]indole-1-carboxamide: To a mixture of tert-butyl 6-chloro-1-((4-chlorophenyl)carbamoyl)-3,4-dihydro-1H-pyrido[3,4-b]indole-2(9H)-carboxylate (120 mg, 0.26 mmol) in CH₂Cl₂ (9 mL) was added TFA (3 mL). The mixture was stirred at room temperature for 3 hrs. The solvent was evaporated in vacuo. The residue was purified via prep-HPLC (mobile phase: 0.1% NH₃·H₂O/CH₃CN/H₂O) to give 6-chloro-N-(4-chlorophenyl)-2,3,4,9-tetrahydro-1H-pyrido[3,4-b]indole-1-carboxamide (65 mg, yield: 69%) as a white solid. ¹H NMR (400 MHz, DMSO-d₆): δ 10.94 (s, 1H), 10.25 (s, 1H), 7.75 (d, J=8.8 Hz, 2H), 7.43-7.34 (m, 4H), 7.02 (dd, J=8.4 Hz, 2.0 Hz, 1H), 4.70 (d, J=6.0 Hz, 1H), 3.22-3.19 (m, 1H), 3.08-3.04 (m, 2H), 2.66-2.63 (m, 2H). LCMS: [M+H]⁺=360.1.

6-Chloro-N-(3-chlorophenyl)-2,3,4,9-tetrahydro-1H-pyrido[3,4-b]indole-1-carboxamide hydrochloride

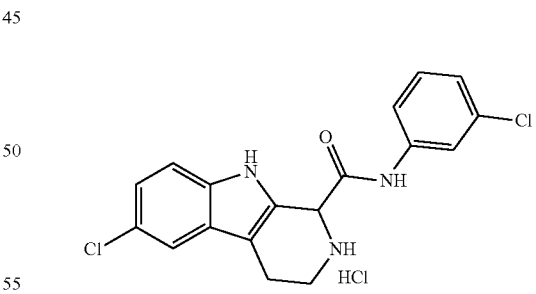

¹H NMR (400 MHz, DMSO-d₆): δ 11.75 (s, 1H), 11.60 (s, 1H), 10.31 (br, 1H), 9.60 (br, 1H), 7.90~7.88 (m, 1H), 7.71 (d, J=8.4 Hz, 1H), 7.60 (d, J=1.6 Hz, 1H), 7.46~7.41 (m, 2H), 7.25~7.14 (m, 2H), 5.64 (s, 1H), 3.81~3.75 (m, 1H), 3.60~3.54 (m, 1H), 3.08~3.02 (m, 1H), 2.97~2.90 (m, 1H). LCMS: [M+H]⁺=360.1.

General scheme 27

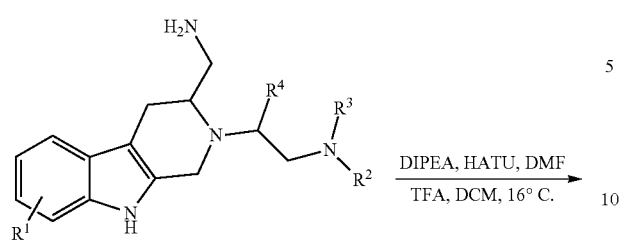

tert-Butyl (2-((((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)amino)-2-oxoethyl)carbamate

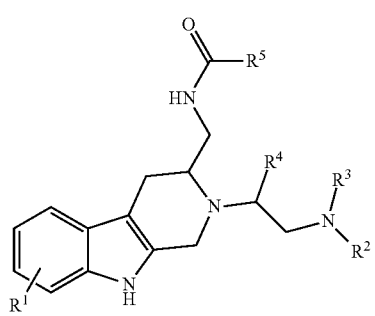

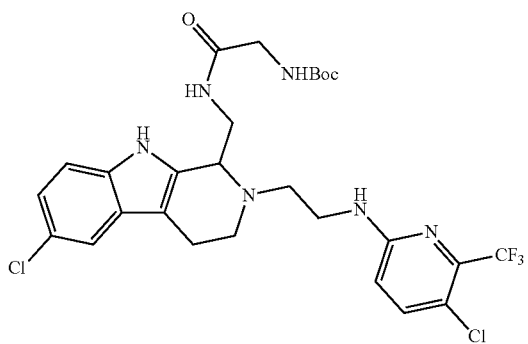 [SMILES: CC(C)(C)OC(=O)NCC(=O)NCC1c2[nH]c3ccc(Cl)cc3c2CCN1CCNc1ccc(Cl)c(C(F)(F)F)n1]

To a solution of N-(2-(1-(aminomethyl)-6-chloro-1,3,4,9-tetrahydro-2H-pyrido[3,4-b]indol-2-yl)ethyl)-5-chloro-6-(trifluoromethyl)pyridin-2-amine (200 mg, 0.44 mmol) in DMF (5 mL) was added DIPEA (171 mg, 1.32 mmol), (tert-butoxycarbonyl)glycine (100 mg, 0.57 mmol) and HATU (251 mg, 0.66 mmol). The resulting mixture was stirred at 16° C. for 2 h. The mixture was diluted with ethyl acetate (50 mL) and washed with water (50 mL). The organic layer was dried over sodium sulfate and filtered, and the filtrate was concentrated to give crude tert-butyl (2-((((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)amino)-2-oxoethyl)carbamate (300 mg, crude) as a light yellow oil. LCMS: [M+H]⁺615.0

2-amino-N-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)acetamide

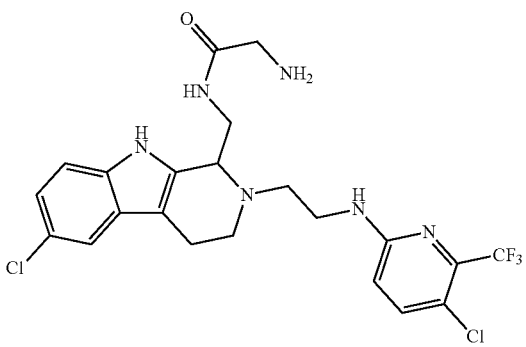 [SMILES: NCC(=O)NCC1c2[nH]c3ccc(Cl)cc3c2CCN1CCNc1ccc(Cl)c(C(F)(F)F)n1]

To a solution of tert-butyl (2-((((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)amino)-2-oxoethyl)carbamate (230 mg, 0.37 mmol) in DCM (80 mL) was added TFA (1 mL). The mixture was stirred at 16° C. for 2 h. The mixture was concentrated under reduced pressure and the residue was purified by prep-HPLC to give 2-(1-(aminomethyl)-6-chloro-1,3,4,9-tetrahydro-2H-pyrido[3,4-b]indol-2-yl)-N-(5-chloro-6-(trifluoromethyl)pyridin-2-yl)acetamide (30.52 mg) as a white solid. $^1$H NMR (400 MHz, DMSO-$d_6$) δ 11.03 (s, 1H), 7.93-7.89 (m, 1H), 7.64 (d, J=12.0 Hz, 1H), 7.42 (d, J=4.0 Hz, 1H), 7.30 (d, J=8.0 Hz, 1H), 7.18-7.15 (m, 1H), 7.02 (dd, J=8.0 Hz, 2.0 Hz, 1H), 6.80 (d, J=8.0 Hz, 1H), 3.81 (dd, J=8.0 Hz, 4.0 Hz, 1H), 3.74-3.68 (m, 1H), 3.42-3.38 (m, 2H), 3.28-3.22 (m, 1H), 3.18-3.13 (m, 1H), 3.07 (s, 2H), 2.92 (dd, J=8.0 Hz, 4.0 Hz, 1H), 2.81-2.71 (m, 3H), 2.47-2.45 (m, 1H), 1.89 (brs, 2H). LCMS: [M+H]⁺=515.1

(2S)-2,6-diamino-N-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)hexanamide

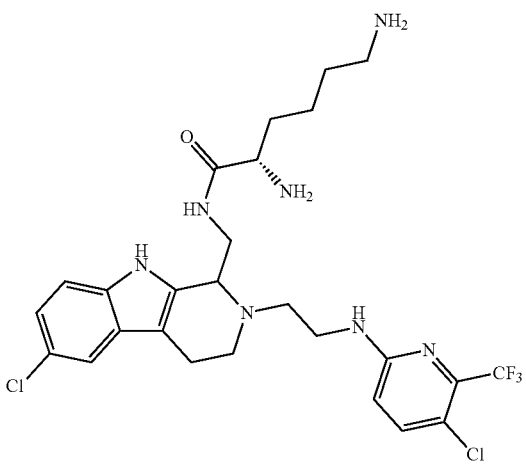 [SMILES: NCCCC[C@H](N)C(=O)NCC1c2[nH]c3ccc(Cl)cc3c2CCN1CCNc1ccc(Cl)c(C(F)(F)F)n1]

$^1$H NMR (400 MHz, MeOD) δ 7.53 (d, J=8.8 Hz, 1H), 7.38 (d, J=1.6 Hz, 1H), 7.24 (dd, J=8.8 Hz, 2.8 Hz, 1H), 7.02

(d, J=8.8 Hz, 1H), 6.71 (d, J=9.2 Hz, 1H), 3.88-3.86 (m, 1H), 3.69-3.66 (m, 1H), 3.56-3.47 (m, 3H), 3.24-3.15 (m, 1H), 2.97-2.91 (m, 2H), 2.87-2.81 (m, 2H), 2.61-2.53 (m, 3H), 1.50-1.12 (m, 7H). LCMS: [M+H]$^+$=586.3

(2S)-2,4-diamino-N-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)butanamide

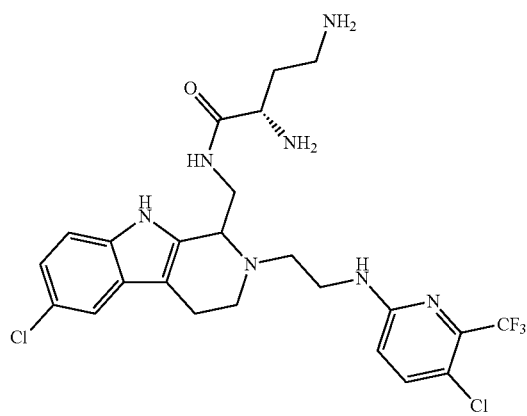 [SMILES: NCC[C@H](N)C(=O)NCC1c2[nH]c3ccc(Cl)cc3c2CCN1CCNc1ccc(Cl)c(C(F)(F)F)n1]

$^1$H NMR (400 MHz, DMSO-d$_6$): δ 11.11-11.08 (m, 1H), 8.33 (s, 2H), 8.10-8.09 (m, 1H), 7.63 (d, J=8.8 Hz, 1H), 7.41 (s, 1H), 7.30 (dd, J=8.8 Hz, 2.0 Hz, 1H), 7.32-7.26 (m, 1H), 7.02 (d, J=8.8 Hz, 1H), 6.80 (d, J=8.8 Hz, 1H), 3.82-3.78 (m, 1H), 3.67-3.55 (m, 2H), 3.42-3.38 (m, 2H), 3.30-3.23 (m, 3H), 3.19-3.13 (m, 2H), 2.93-2.72 (m, 5H), 2.49-2.46 (m, 1H), 1.87-1.83 (m, 1H), 1.55-1.53 (m, 1H). LCMS: [M+H]$^+$=558.3

N-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)acetamide

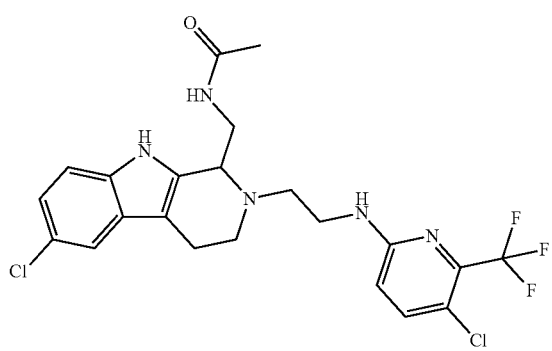 [SMILES: CC(=O)NCC1c2[nH]c3ccc(Cl)cc3c2CCN1CCNc1ccc(Cl)c(C(F)(F)F)n1]

$^1$H NMR (400 MHz, MeOD) δ 7.53 (d, J=8.8 Hz, 1H), 7.37 (s, 1H), 7.25 (d, J=8.4 Hz, 1H), 7.01 (d, J=8.4 Hz, 1H), 6.70 (d, J=8.8 Hz, 1H), 3.87-3.84 (m, 1H), 3.73-3.67 (m, 1H), 3.48-3.42 (m, 3H), 3.30-2.85 (m, 5H), 2.56-2.52 (m, 1H), 1.87 (s, 3H). LCMS: [M+H]$^+$=500.2

(2S)-2-amino-N-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)-3-hydroxypropanamide hydrochloride

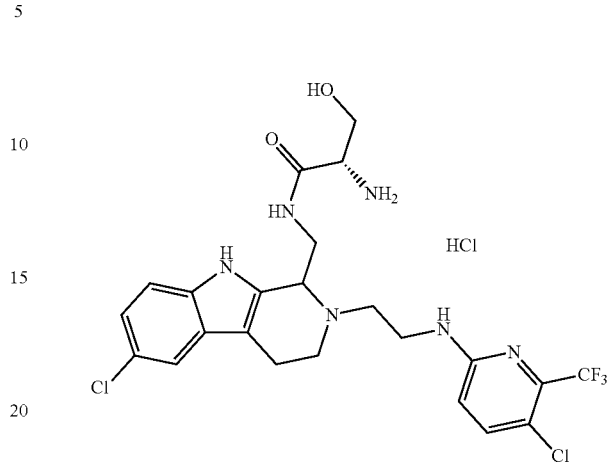

$^1$H NMR (400 MHz, DMSO-d$_6$): δ 11.63-11.47 (m, 1H), 11.15~10.74 (m, 1H), 9.08~8.94 (d, J=58 Hz, 1H), 8.28 (s, 3H), 7.73~7.68 (m, 2H), 7.57 (s, 1H), 7.42~7.40 (m, 1H), 7.15~7.13 (m, 1H), 6.88~6.83 (m, 1H), 5.60 (br, 1H), 4.95~4.84 (m, 1H), 4.16~3.49 (m, 10H), 3.22~3.05 (m, 3H). $^{19}$F NMR (376 MHz, CDCl$_3$): δ −64.57. LCMS: [M+H]$^+$=545.3

(2S)-2-amino-N-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)-5-guanidinopentanamide formate

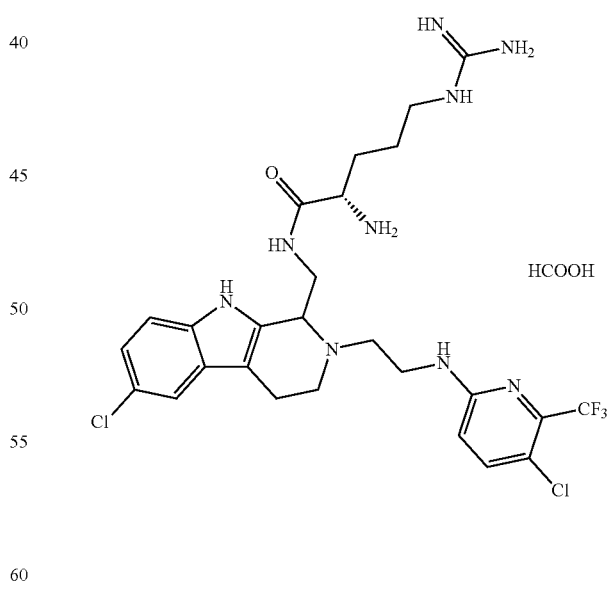

$^1$H NMR (400 MHz, MeOD-d$_6$): δ 7.53 (d, J=6.8 Hz, 1H), 7.46~7.24 (m, 2H), 7.14~7.00 (m, 1H), 6.77~6.72 (m, 1H), 5.67~5.64 (m, 1H), 4.08~3.37 (m, 7H), 3.18~2.56 (m, 7H), 1.62~1.29 (m, 4H). LCMS: [M+H]$^+$=644.2

181

2-amino-N-((6-chloro-2-(2-((5,6-dichloropyridin-2-yl)(methyl)amino)ethyl)-2,3,4,9-tetrahydro-1H-pyrido[3,4-b]indol-1-yl)methyl)acetamide dihydrochloride

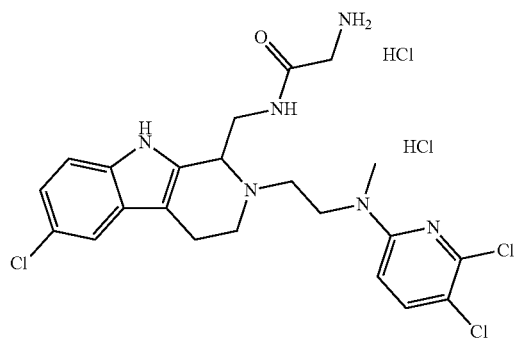 [SMILES: CN(CCN1CCc2c([nH]c3ccc(Cl)cc23)C1CNC(=O)CN)c1ccc(Cl)c(Cl)n1 ; Cl ; Cl]

$^1$H NMR (400 MHz, DMSO-d$_6$): δ 11.63~11.59 (m, 1H), 11.32~10.95 (m, 1H), 8.96~8.80 (m, 1H), 8.20~8.13 (m, 3H), 7.75 (d, J=8.8 Hz, 1H), 7.58 (s, 1H), 7.43 (d, J=8.8 Hz, 1H), 7.15 (d, J=8.0 Hz, 1H), 6.76 (d, J=8.8 Hz, 1H), 4.95 (br, 1H), 4.20-4.09 (m, 2H), 3.99~3.83 (m, 3H), 3.67~3.61 (m, 4H), 3.43~3.33 (m, 1H), 3.24~3.21 (m, 1H), 3.06 (br, 4H). LCMS: [M+H]$^+$=497.1

182

General scheme 28

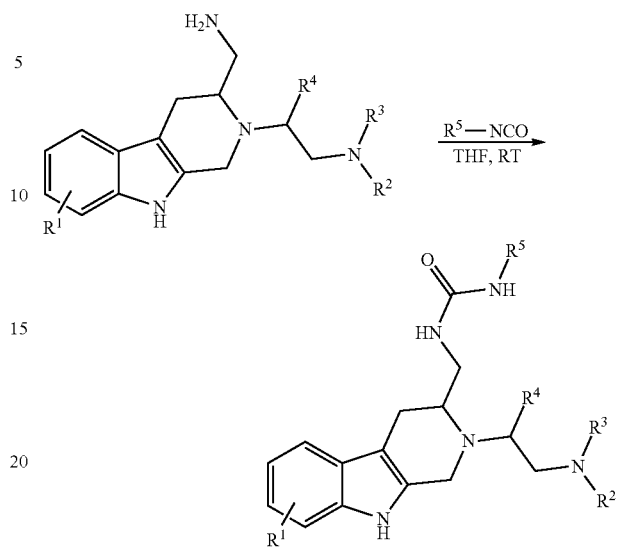

Representative of synthesis of compound 1-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)-3-(2-(dimethylamino)ethyl)urea

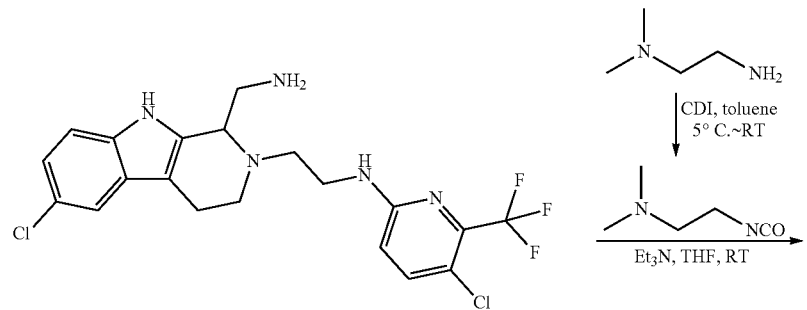

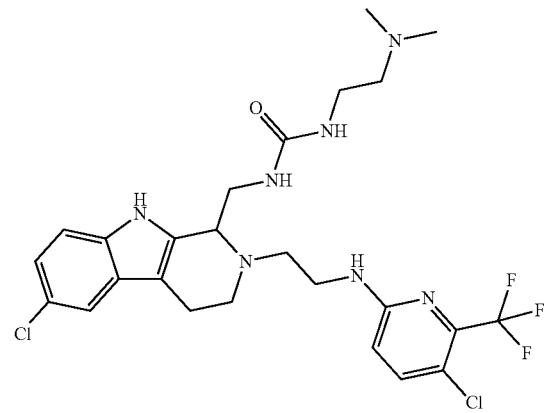

183

2-isocyanato-N,N-dimethylethan-1-amine

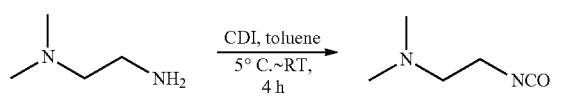

To a solution of CDI (1.84 g, 11.34 mmol) in toluene (5 mL) was added the solution of N¹,N¹-dimethylethane-1,2-diamine (1 g, 11.34 mmol) in toluene (2 mL) at 5~10° C. The reaction solution was stirred at 5~10° C. for 3 h, then stirring at 20~25° C. for another 3 h to yield a clear colorless solution. The resulting solution was used next step directly.

1-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)-3-(2-(dimethylamino)ethyl)urea

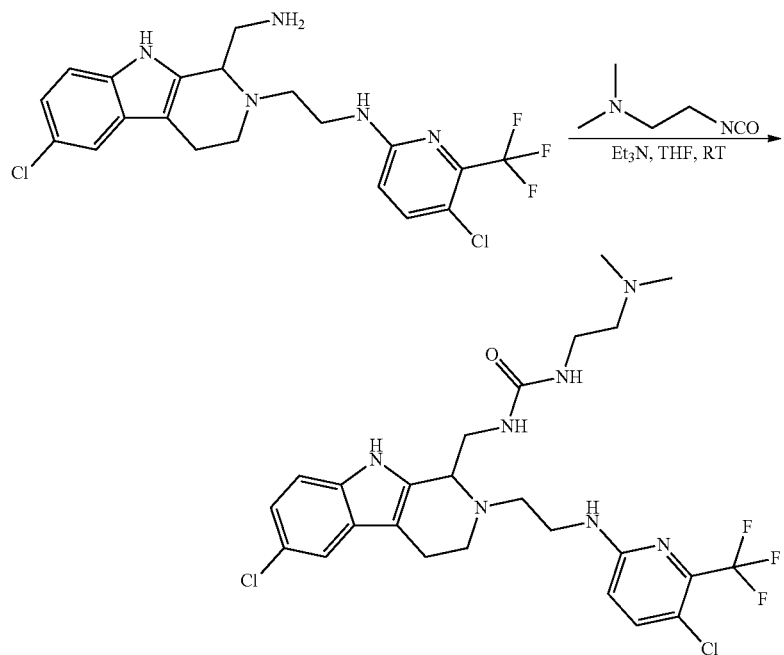

To a solution of N-(2-(1-(aminomethyl)-6-chloro-1,3,4,9-tetrahydro-2H-pyrido[3,4-b]indol-2-yl)ethyl)-5-chloro-6-(trifluoromethyl)pyridin-2-amine (250 mg, 0.23 mmol) and Et$_3$N (234.1 mg, 1.16 mmol) in THF (5 mL) was added the solution of 2-isocyanato-N,N-dimethylethan-1-amine (53 mg, 0.23 mmol) in toluene prepared above (0.14 mL). The resulting mixture was stirred at RT for 16 h. The solvent was evaporated and the residue was purified by prep-HPLC (mobile phase: 0.1% HCOOH/CH$_3$CN/H$_2$O) to give 1-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)-3-(2-(dimethylamino)ethyl)urea (53.31 mg, yield: 20%) as a white solid. $^1$H NMR (400 MHz, DMSO-d$_6$): δ 11.01 (s, 1H), 8.16 (s, 1H), 7.65 (d, J=9.2 Hz, 1H), 7.41 (d, J=2.0 Hz, 1H), 7.30 (d, J=8.4 Hz, 1H), 7.19 (t, J=5.2 Hz, 1H), 7.03 (dd, J=8.8 Hz, 2.0 Hz, 1H), 6.83 (d, J=8.8 Hz, 1H), 6.12 (t, J=5.2 Hz, 1H), 6.02 (dd, J=6.4 Hz, 4.0 Hz, 1H), 3.75~3.72 (m, 1H), 3.63~3.58 (m, 1H), 3.46~3.35 (m, 4H), 3.24~3.09 (m, 4H), 2.87~2.83 (m, 1H), 2.76~2.71 (m, 2H), 2.43~2.39 (m, 2H), 2.27 (s, 6H). $^{19}$F NMR (376 MHz, CDCl$_3$): δ −64.66. LCMS: [M+H]$^+$=572.3

184

1-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)urea

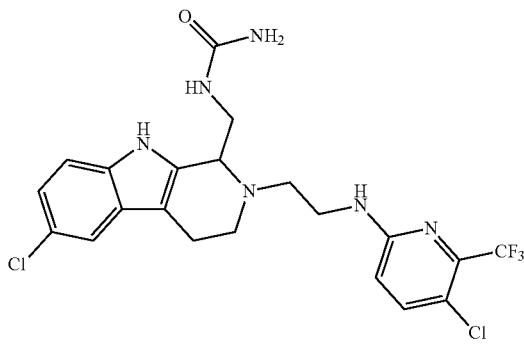 [SMILES: NC(=O)NCC1c2[nH]c3ccc(Cl)cc3c2CCN1CCNc1ccc(Cl)c(C(F)(F)F)n1]

$^1$H NMR (400 MHz, DMSO-d$_6$) δ 11.02 (brs, 1H), 7.62 (d, J=8.0 Hz, 1H), 7.40 (d, J=4.0 Hz, 1H), 7.29 (d, J=8.0 Hz, 1H), 7.18 (t, J=4.0 Hz, 1H), 7.01 (dd, J=8.0 Hz, 2.0 Hz, 1H), 6.82 (d, J=12.0 Hz, 1H), 5.92 (brs, 1H), 5.55 (brs, 2H), 3.72-3.71 (m, 1H), 3.63-3.61 (m, 1H), 3.43-3.39 (m, 3H), 3.16-3.12 (m, 2H), 2.86-2.83 (m, 1H), 2.76-2.73 (m, 3H). LCMS: [M+H]$^+$: 501.2

General scheme 29

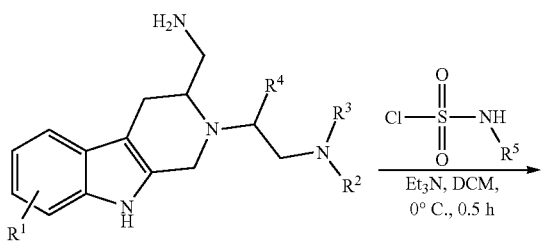

-continued

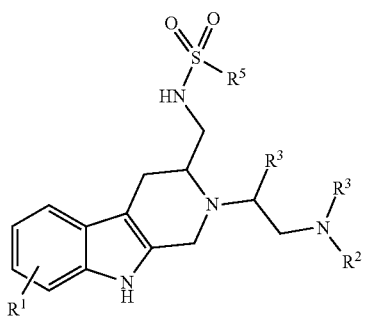

Representative of synthesis of compound N-(2-(1-(aminosulfonaminomethyl)-6-chloro-3,4-dihydro-1H-pyrido[3,4-b]indol-2(9H)-yl)ethyl)-5-chloro-6-(trifluoromethyl)pyridin-2-amine

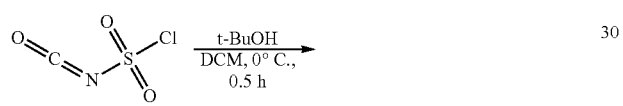

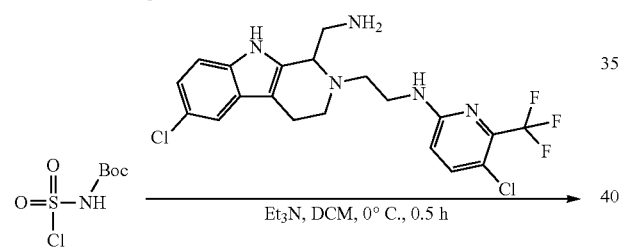

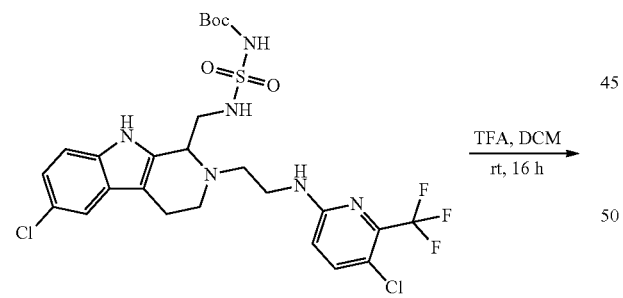

tert-butyl (chlorosulfonyl)carbamate

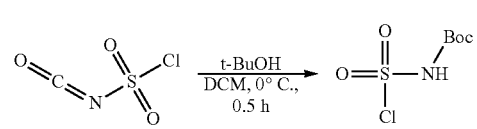 [SMILES: "t-BuOH" ; O=C=NS(=O)(=O)Cl ; "DCM, 0° C.,0.5 h" ; CC(C)(C)OC(=O)NS(=O)(=O)Cl]

To a solution of sulfurisocyanatidic chloride (160 mg, 1.09 mmol) in DCM (10 mL) was added drop-wise a solution of t-BuOH (80 mg, 1.09 mmol) in DCM (5 mL) at 0° C. The mixture was stirred at 0° C. for 0.5 h. The resulting solution was used in the next step directly.

tert-butyl (N-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)sulfamoyl) carbamate

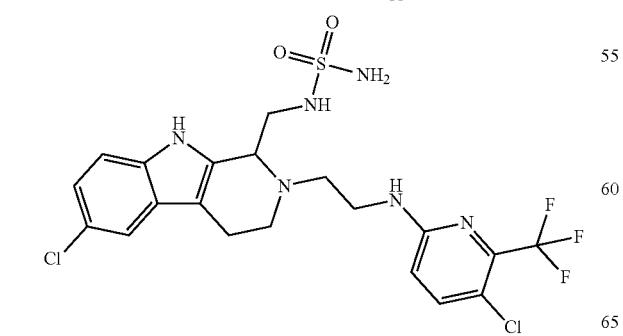

To a solution of N-(2-(1-(aminomethyl)-6-chloro-1,3,4,9-tetrahydro-2H-pyrido[3,4-b]indol-2-yl)ethyl)-5-chloro-6-(trifluoromethyl)pyridin-2-amine (500 mg, 1.09 mmol) and Et₃N (1.1 g, 10.9 mmol) in DCM (15 ml) was added drop-wise the solution of tert-butyl (chlorosulfonyl)carbamate (prepared in the previous step) at 0° C. After stirring at RT for 4 h, the mixture was poured into water and extracted with DCM. The organic solution was washed with brine, dried over Na₂SO₄ and evaporated. The residue was purified by silica gel column chromatography to give tert-butyl (N-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)sulfamoyl)carbamate (600 mg, yield: 86%) as a white solid. LCMS: [M+H]⁺=637.3

187

N-(2-(1-(aminosulfonaminomethyl)-6-chloro-3,4-dihydro-1H-pyrido[3,4-b]indol-2(9H)-yl)ethyl)-5-chloro-6-(0fluoromethyl)pyridin-2-amine

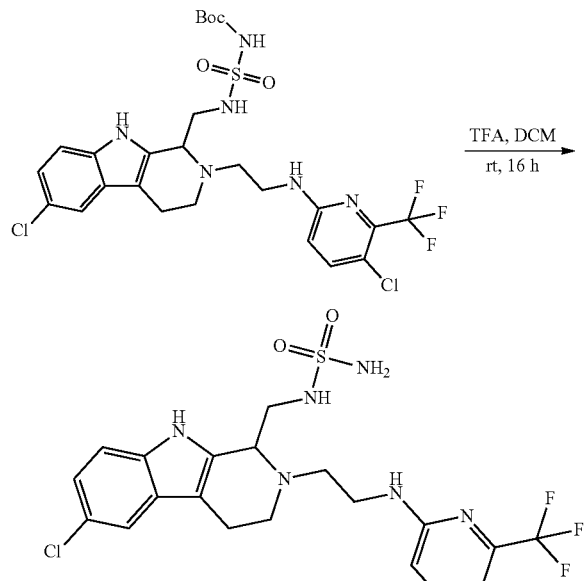

To a solution of tert-butyl (N-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)sulfamoyl) carbamate (400 mg, 0.627 mmol) in DCM (15 mL) was added TFA (1 mL) at rt. The mixture was stirred at rt for 16 h. The mixture was poured into water and extracted with DCM. The organic solution was washed with sat. NaHCO$_3$ and brine, then dried over Na$_2$SO$_4$ and evaporated. The residue was purified by Prep-HPLC to give N-(2-(1-(aminosulfonaminomethyl)-6-chloro-3,4-dihydro-1H-pyrido[3,4-b]indol-2(9H)-yl)ethyl)-5-chloro-6-(trifluoromethyl)pyridin-2-amine (46 mg, yield: 14%) as a white solid. $^1$H NMR (400 MHz, DMSO-d$_6$): δ 10.94 (s, 1H), 7.64 (d, J=8.8 Hz, 1H), 7.42 (d, J=1.6 Hz, 1H), 7.31 (d, J=8.4 Hz, 1H), 7.25 (t, J=5.2 Hz, 1H), 7.03 (dd, J=8.8 Hz, 2.0 Hz, 1H), 6.80 (d, J=9.2 Hz, 1H), 6.61 (s, 2H), 6.15~6.11 (m, 1H), 3.90~3.86 (m, 1H), 3.45~3.40 (m, 2H), 3.31~3.25 (m, 1H), 3.22~3.15 (m, 1H), 3.12~3.06 (m, 1H), 2.97~2.89 (m, 1H), 2.82~2.68 (m, 3H), 2.47~2.43 (m, 1H). $^{19}$F NMR (376 MHz, CDCl$_3$): δ −64.65. LCMS: [M+H]$^+$=537.1

General scheme 30

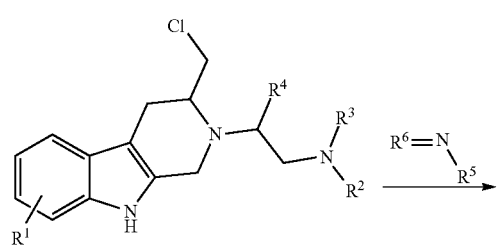

188

-continued

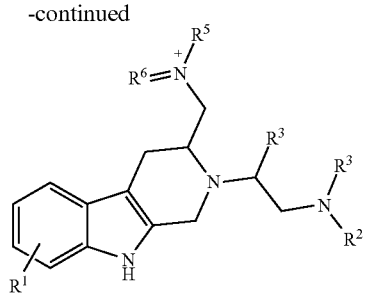

Representative synthesis of 3-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)-1-methyl-1H-imidazol-3-ium: (6-Chloro-2-(2-((5-chloro-6-(trifluoromethyl)pyridin-2-yl)amino)ethyl)-2,3,4,9-tetrahydro-1H-pyrido[3,4-b]indol-1-yl)methanol (300 mg, 0.65 mmol, 1.0 eq) was dissolved in THF (20 mL) and then SOCl$_2$ (155 g, 1.30 mmol, 2 eq) was added. The reaction was stirred at 20° C. for 16 h. The reaction mixture was concentrated to give crude 5-chloro-N-(2-(6-chloro-1-(chloromethyl)-1,3,4,9-tetrahydro-2H-pyrido[3,4-b]indol-2-yl)ethyl)-6-(trifluoromethyl)pyridin-2-amine (300 mg, 73.47% yield) as a brown solid, which was used without further purification. LCMS: [M+H]$^+$=477.1

3-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)-1-methyl-1H-imidazol-3-ium

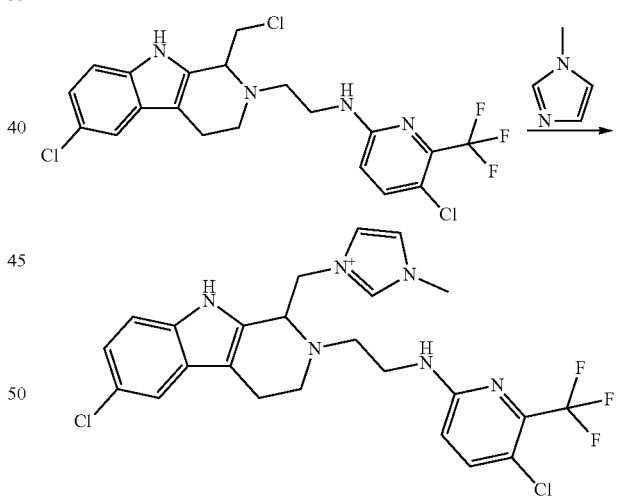

5-chloro-N-(2-(6-chloro-1-(chloromethyl)-1,3,4,9-tetrahydro-2H-pyrido[3,4-b]indol-2-yl)ethyl)-6-(trifluoromethyl)pyridin-2-amine (150 mg, 0.31 mmol, 1.0 eq) was dissolved in 1-methyl-1H-imidazole (10 mL) and the solution was stirred at 25° C. for 18 h. The reaction solution was purified by Pre-HPLC (HCOOH) directly to give 3-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)-1-methyl-1H-imidazol-3-ium (20.19 mg, yield; 12.26%) as a brown solid. $^1$H NMR (400 MHz, MeOD): δ 8.68 (brs, 0.5H), 8.55 (brs, 1H), 7.66 (brs, 1H), 7.56-7.52 (m, 2H), 7.45 (brs, 1H), 7.27 (d, J=8.4 Hz, 1H), 7.14 (d, J=8.4 Hz, 1H), 6.62 (d, J=8.8 Hz, 1H), 5.77 (brs, 1H), 3.79 (s, 3H), 3.54-3.39 (m, 3H), 3.28-3.23 (m, 2H), 3.11 (br, 2H), 2.90-2.83 (m, 3H). LCMS: [M+H]$^+$=523.2

1-((6-chloro-2-(2-((5-chloro-6-(trifluoromethyl)pyridin-2-yl)(methyl)amino)ethyl)-2,3,4,9-tetrahydro-1H-pyrido[3,4-b]indol-1-yl)methyl)-4-(dimethylamino)pyridin-1-ium

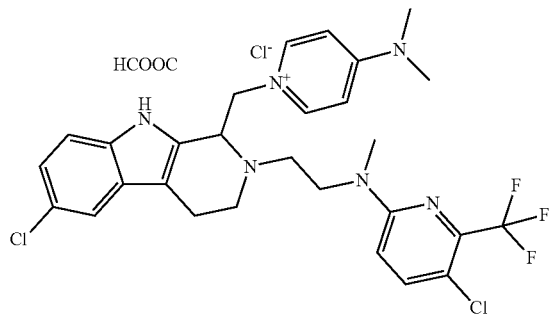 [SMILES: CN(C)c1cc[n+](CC2c3[nH]c4ccc(Cl)cc4c3CCN2CCN(C)c2ccc(Cl)c(C(F)(F)F)n2)cc1 ; "HCOOC" ; [Cl-]]

$^1$H NMR (400 MHz, MeOD): δ 8.50 (br, 1H), 8.07 (d, J=7.6 Hz, 2H), 7.63-7.55 (m, 2H), 7.27-7.23 (m, 1H), 7.15-7.12 (m, 1H), 6.84 (d, J=8.0 Hz, 2H), 6.73-6.70 (m, 1H), 5.65 (brs, 1H), 3.61-3.54 (m, 2H), 3.53-3.41 (m, 3H), 3.20 (s, 6H), 3.15-3.03 (m, 2H), 2.94 (s, 3H), 2.85-2.80 (m, 3H). LCMS: [M+H]$^+$=577.3

3-((6-chloro-2-(2-((5-chloro-6-(trifluoromethyl)pyridin-2-yl)(methyl)amino)ethyl)-2,3,4,9-tetrahydro-1H-pyrido[3,4-b]indol-1-yl)methyl)-1-methyl-1H-imidazol-3-ium

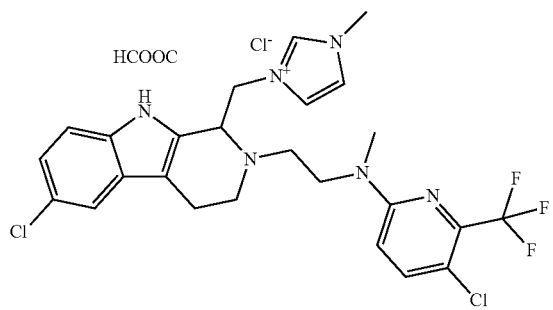 [SMILES: CN(CCN1CCc2c([nH]c3ccc(Cl)cc23)C1C[n+]1ccn(C)c1)c1ccc(Cl)c(C(F)(F)F)n1 ; "HCOOC" ; [Cl-]]

$^1$H NMR (400 MHz, MeOD): δ 8.62 (brs, 1H), 8.51 (brs, 1H), 7.65-7.62 (m, 2H), 7.54 (d, J=2.0 Hz, 1H), 7.50 (d, J=1.6 Hz, 1H), 7.27 (d, J=8.8 Hz, 1H), 7.14 (d, J=8.8 Hz, 2.0 Hz, 1H), 6.75 (d, J=9.2 Hz, 1H), 5.75 (d, J=2.0 Hz, 1H), 3.84 (s, 3H), 3.70-3.63 (m, 1H), 3.56-3.42 (m, 3H), 3.39-3.32 (m, 1H), 3.14-3.07 (m, 1H), 3.02-2.93 (m, 4H), 2.87-2.77 (m, 3H). LCMS: [M+H]$^+$=537.2

5-amino-2-((6-chloro-2-(2-((5-chloro-6-(trifluoromethyl)pyridin-2-yl)(methyl)amino)ethyl)-2,3,4,9-tetrahydro-1H-pyrido[3,4-b]indol-1-yl)methyl)-1-methyl-1H-pyrazol-2-ium chloride

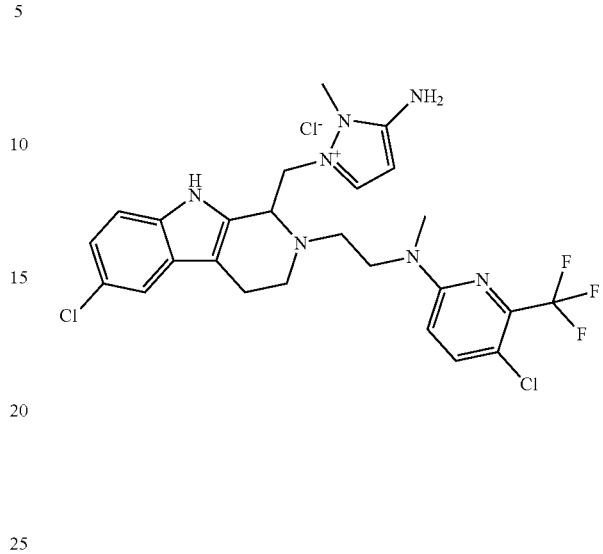

$^1$H NMR (400 MHz, MeOD): δ 7.60 (d, J=9.2 Hz, 1H), 7.38 (d, J=1.6 Hz, 1H), 7.22 (d, J=8.4 Hz, 1H), 7.16 (d, J=2.4 Hz, 1H), 6.98 (dd, J=8.4 Hz, 2.0 Hz, 1H), 6.79 (d, J=9.2 Hz, 1H), 5.50 (d, J=2.0 Hz, 1H), 4.56 (dd, J=7.2 Hz, 2.0 Hz, 1H), 3.84-3.73 (m, 2H), 3.60 (s, 3H), 3.27-3.20 (m, 1H), 3.17-3.06 (m, 5H), 3.00-2.87 (m, 5H). LCMS: [M+H]$^+$=552.2

3-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)-1-(2-hydroxyethyl)-1H-imidazol-3-ium chloride trihydrochloride

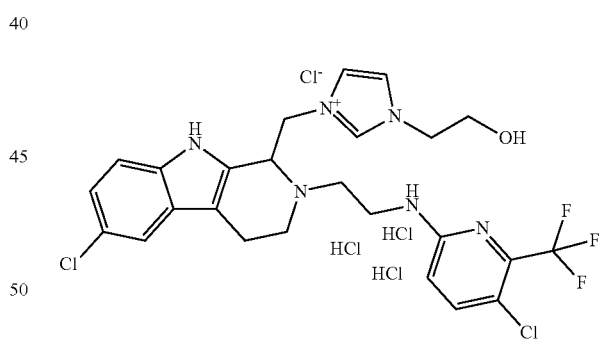

$^1$H NMR (400 MHz, DMSO-d$_6$): δ 14.76 (s, 0.5H), 11.85~11.72 (m, 1.5H), 9.49~8.94 (m, 1.5H), 7.95~7.84 (m, 2.5H), 7.75∫7.66 (m, 3H), 7.41 (d, J=8.4 Hz, 1H), 7.18 (d, J=8.0 Hz, 1H), 6.89 (d, J=8.8 Hz, 1H), 6.56 (br, 1H), 4.26~4.06 (m, 4.5H), 3.72 (br, 6H), 3.49~3.38 (m, 4.5H). $^{19}$F NMR (376 MHz, CDCl$_3$): δ −64.65. LCMS: [M+]$^+$=553.3

191

1-(2-aminoethyl)-3-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)-1H-imidazol-3-ium chloride dihydrochloride

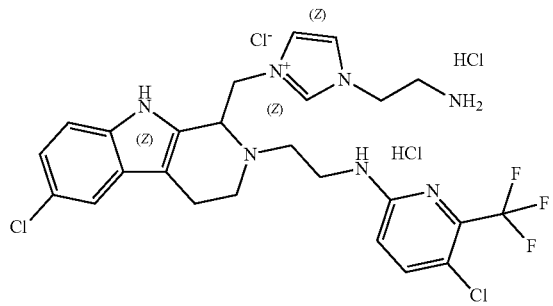 [SMILES: NCCn1cc[n+](CC2c3[nH]c4ccc(Cl)cc4c3CCN2CCNc2ccc(Cl)c(C(F)(F)F)n2)c1 ; [Cl-] ; Cl ; Cl]

¹H NMR (400 MHz, DMSO-d₆): δ 11.76~11.45 (m, 2H), 9.01 (br, 0.6H), 8.58~8.44 (m, 3H), 8.00~7.71 (m, 5H), 7.39 (br, 1H), 7.18 (br, 1H), 6.87 (d, J=8.8 Hz, 1H), 6.50 (br, 0.4H), 4.49 (br, 3H), 4.14 (br, 1H), 3.85~3.75 (m, 2H), 3.43~3.36 (m, 9H). ¹⁹F NMR (376 MHz, CDCl₃): δ −64.64. LCMS: [M+]⁺=552.2

3-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)-1-(2-(dimethylamino)ethyl)-1H-imidazol-3-ium chloride trihydrochloride

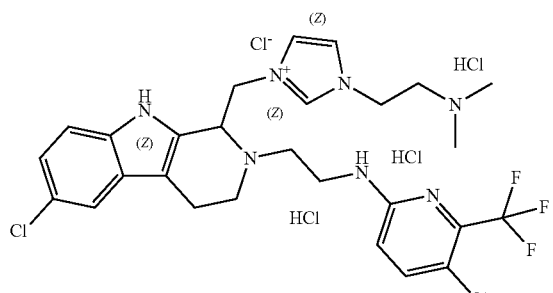

¹H NMR (400 MHz, DMSO-d₆): δ 11.80~11.61 (m, 2H), 11.00~10.60 (m, 1H), 9.68~9.20 (m, 1H), 8.01~7.72 (m, 5H), 7.40~7.38 (m, 1H), 7.20 (d, J=7.6 Hz, 1H), 6.89 (d, J=9.2 Hz, 1H), 6.58 (br, 1H), 4.69~4.48 (m, 3H), 4.15~4.12 (m, 1H), 3.84~3.75 (m, 6H), 3.51~3.39 (m, 5H), 2.82 (s, 6H). ¹⁹F NMR (376 MHz, CDCl₃): δ −64.64. LCMS: [M+]⁺=580.2

192

3-(2-(6-chloro-2-(2-((5-chloro-6-(trifluoromethyl)pyridin-2-yl)amino)ethyl)-2,3,4,9-tetrahydro-1H-pyrido[3,4-b]indol-1-yl)ethyl)-1-methyl-1H-imidazol-3-ium chloride dihydrochloride

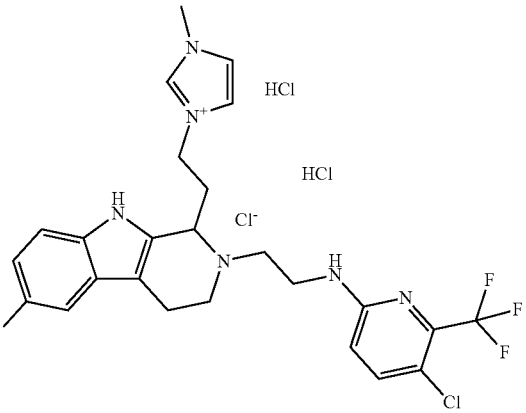

¹H NMR (400 MHz, DMSO-d₆): 11.72~11.69 (m, 1H), 11.22 (br, 0.5H), 10.81 (br, 0.5H), 9.52 (s, 0.5H), 9.26 (s, 0.5H), 7.92~7.66 (m, 5H), 7.37 (d, J=8.8 Hz, 1H), 7.17~7.12 (m, 1H), 6.84 (dd, J=8.4 Hz, 6.8 Hz, 1H), 6.62~6.57 (m, 0.5H), 6.18 (dd, J=11.2 Hz, 3.2 Hz, 0.5H), 3.89 (d, J=13.6 Hz, 3H), 3.68~3.13 (m, 11H), 2.89~2.79 (m, 1.5H), 2.54~2.50 (m, 0.5H). ¹⁹F NMR (376 MHz, CDCl₃): δ −64.68. LCMS: [M+]⁺=537.1

1-(Azetidin-3-yl)-3-((6-chloro-2-(2-((5-chloro-6-(trifluoromethyl)pyridin-2-yl)(methyl)amino)ethyl)-2,3,4,9-tetrahydro-1H-pyrido[3,4-b]indol-1-yl)methyl)-1H-imidazol-3-ium chloride hydrochloride

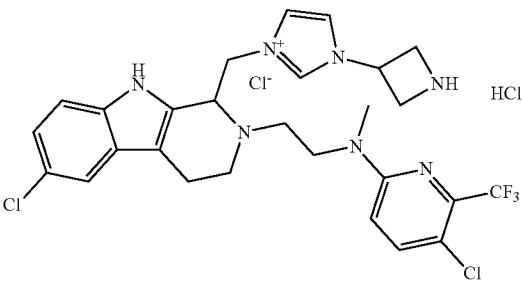 [SMILES: CN(CCN1CCc2c([nH]c3ccc(Cl)cc23)C1C[n+]1ccn(C2CNC2)c1)c1ccc(Cl)c(C(F)(F)F)n1 ; [Cl-] ; Cl]

¹H NMR (400 MHz, MeOD-d₄): δ 8.15-8.14 (m, 1H), 7.91 (s, 1H), 7.75-7.69 (m, 2H), 7.37 (d, J=8.4 Hz, 1H), 7.23 (dd, J=8.8 Hz, 1.6 Hz, 1H), 6.96 (d, J=9.2 Hz, 1H), 6.45-6.38 (m, 1H), 5.59 (t, J=7.2 Hz, 1H), 4.66-4.55 (m, 5H), 4.26-4.06 (m, 3H), 3.96-3.91 (m, 1H), 3.63-3.56 (m, 4H), 3.49-3.38 (m, 2H), 3.15 (s, 3H). LCMS: [M]⁺=578.0

1-(Azetidin-3-ylmethyl)-3-((6-chloro-2-(2-((5-chloro-6-(trifluoromethyl)pyridin-2-yl)(methyl)amino)ethyl)-2,3,4,9-tetrahydro-1H-pyrido[3,4-b]indol-1-yl)methyl)-1H-imidazol-3-ium chloride hydrochloride

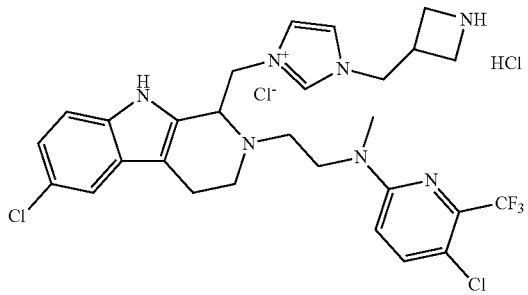 [SMILES: CN(CCN1CCc2c([nH]c3ccc(Cl)cc23)C1C[n+]1ccn(CC2CNC2)c1)c1ccc(Cl)c(C(F)(F)F)n1 ; [Cl-] ; Cl]

$^1$H NMR (400 MHz, MeOD-$d_4$): δ 8.91 (brs, 1H), 7.80~7.39 (m, 4H), 7.39~7.36 (d, J=8.8 Hz, 1H), 7.23~7.21 (d, J=7.6 Hz, 1H), 6.98~6.96 (d, J=8.8 Hz, 1H), 6.52 (brs, 1H), 4.32 (s, 3H), 4.28~3.89 (m, 9H), 3.61~3.34 (m, 6H), 3.19 (s, 3H). LCMS: [M]$^+$=592.1

3-((6-Chloro-2-(2-((5-chloro-6-(trifluoromethyl)pyridin-2-yl)(sulfo)amino)ethyl)-2,3,4,9-tetrahydro-1H-pyrido[3,4-b]indol-1-yl)methyl)-1-(2-hydroxyethyl)-1H-imidazol-3-ium chloride

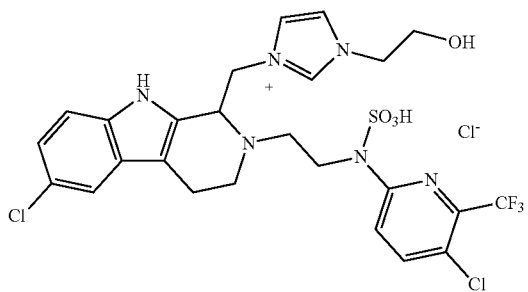

$^1$H NMR (400 MHz, MeOD-$d_4$): δ 8.84~8.77 (m, 1H), 7.86 (d, J=9.2 Hz, 1H), 7.76 (d, J=9.2 Hz, 1H), 7.60~7.51 (m, 3H), 7.28~7.25 (m, 1H), 7.14~7.11 (m, 1H), 5.82~5.76 (m, 1H), 4.28~4.20 (m, 2H), 4.0~3.94 (m, 2H), 3.82~3.78 (m, 2H), 3.58~3.35 (m, 3H), 3.10~2.82 (m, 5H). $^{19}$F NMR (400 MHz, MeOD-$d_4$): δ −67.14 LCMS: [M]$^+$=552.9

1-(Azetidin-3-ylmethyl)-3-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)-1H-imidazol-3-ium chloride

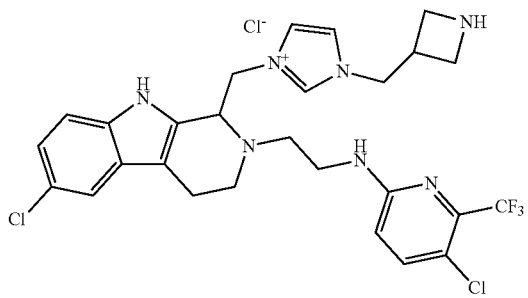 [SMILES: FC(F)(F)c1nc(NCCN2CCc3c([nH]c4ccc(Cl)cc34)C2C[n+]2ccn(CC3CNC3)c2)ccc1Cl ; [Cl-]]

$^1$H NMR (400 MHz, CD$_3$OD): δ 7.01 (d, J=8.4 Hz, 2H), 7.60-7.52 (m, 2H), 7.29-7.11 (m, 2H), 6.73 (d, J=8.8 Hz, 1H), 6.39 (brs, 1H), 4.96-4.89 (m, 1H), 4.43 (s, 2H), 4.19-4.08 (m, 3H), 4.0-3.95 (m, 2H), 3.85-3.80 (m, 3H), 3.64-3.43 (m, 5H), 3.38-3.31 (m, 2H). LCMS: [M]$^+$=578.1

General scheme 31

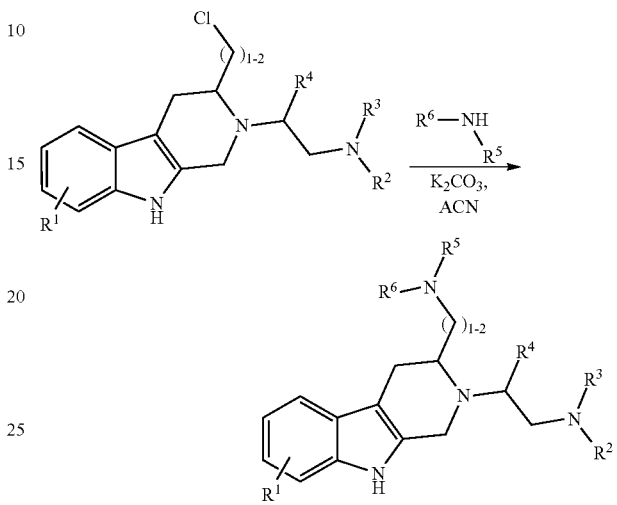

Representative synthesis of (1-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)pyrrolidin-2-yl)methanol

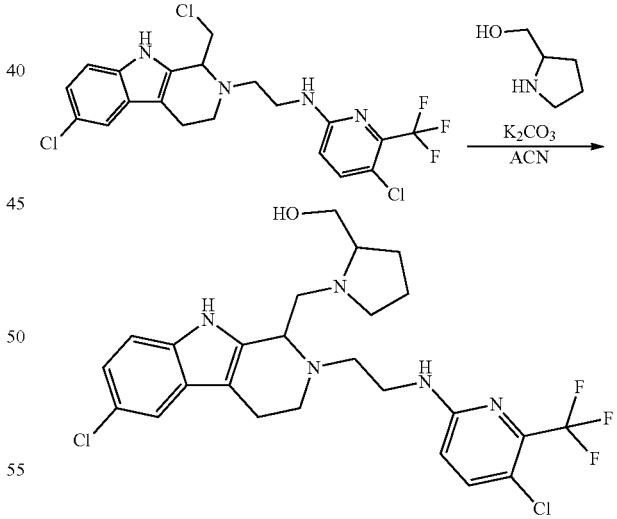

To the mixture of 5-chloro-N-(2-(6-chloro-1-(chloromethyl)-3,4-dihydro-1H-pyrido[3,4-b]indol-2(9H)-yl)ethyl)-6-(trifluoromethyl)pyridin-2-amine (100 mg, 0.209 mmol) and K$_2$CO$_3$ (57 mg, 0.418 mmol) in acetonitrile (10 mL) was added pyrrolidin-2-ylmethanol (422 mg, 4.18 mmol) at RT, and the mixture was stirred at RT overnight. The mixture was filtered and the filtrate was concentrated. The residue was purified by prep-HPLC to give two isomers. Diastereomer 1: 18.72 mg, 17% yield, white solid. $^1$H NMR (400

MHz, DMSO-d₆): δ 10.67 (s, 1H), 7.63 (d, J=8.8 Hz, 1H), 7.40 (d, J=1.6 Hz, 1H), 7.31 (d, J=8.8 Hz, 1H), 6.99 (br, 1H), 6.98 (dd, J=8.8 Hz, 2.4 Hz, 1H), 6.79 (d, J=8.8 Hz, 1H), 4.25-4.16 (m, 2H), 3.45-3.41 (m, 2H), 3.24-3.21 (m, 1H), 3.07-2.74 (m, 11H), 2.65-2.55 (m, 1H), 1.75-1.53 (m, 4H). LCMS: [M+H]⁺=542.1. Diastereomer 2: 11.3 mg, 11% yield, white solid. ¹H NMR (400 MHz, DMSO) δ 10.77 (s, 1H), 7.63 (d, J=8.8 Hz, 1H), 7.44 (d, J=1.6 Hz, 1H), 7.29 (d, J=8.4 Hz, 1H), 7.20-7.16 (m, 1H), 6.98 (dd, J=8.4 Hz, 2.0 Hz, 1H), 6.76 (d, J=9.2 Hz, 1H), 4.48-4.46 (m, 1H), 4.11 (brs, 1H), 3.47-3.36 (m, 2H), 3.27-3.03 (m, 6H), 2.90-2.66 (m, 5H), 2.59-2.54 (m, 1H), 2.44-2.24 (m, 1H), 1.61-1.46 (m, 4H). LCMS: [M+H]⁺: 542.1

5-chloro-N-(2-(6-chloro-1-((cyclopropylamino)methyl)-1,3,4,9-tetrahydro-2H-pyrido[3,4-b]indol-2-yl)ethyl)-6-(trifluoromethyl)pyridin-2-amine

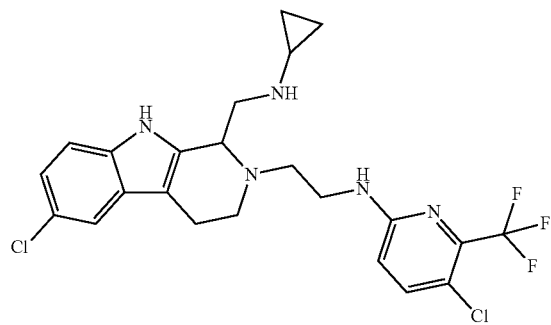 [SMILES: FC(F)(F)c1nc(NCCN2CCc3c([nH]c4ccc(Cl)cc34)C2CNC2CC2)ccc1Cl]

¹H NMR (400 MHz, MeOD): δ 7.50 (d, J=8.8 Hz, 1H), 7.37 (d, J=2.0 Hz, 1H), 7.22 (d, J=8.4 Hz, 1H), 6.98 (dd, J=8.4 Hz, 2.0 Hz, 1H), 6.70 (d, J=8.8 Hz, 1H), 3.84 (d, J=4.4 Hz, 1H), 3.60-3.48 (m, 2H), 3.28-3.21 (m, 2H), 2.90-2.82 (m, 5H), 2.57-2.50 (m, 1H), 1.85-1.82 (m, 1H), 0.43-0.27 (m, 4H). LCMS: [M+H]⁺: 498.1.

1-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)piperidin-4-ol formate

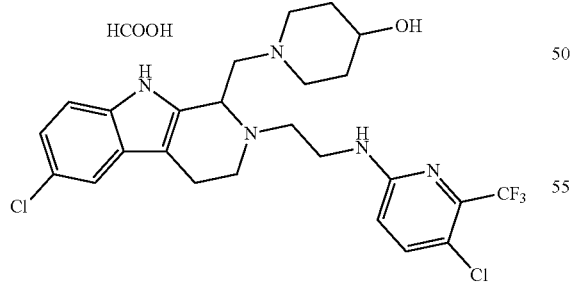

¹H NMR (400 MHz, MeOD): δ 8.45 (brs, 1H), 7.55 (d, J=8.8 Hz, 1H), 7.50 (d, J=2.0 Hz, 1H), 7.32 (d, J=8.8 Hz, 1H), 7.11 (dd, J=8.8 Hz, 2.0 Hz, 1H), 6.71 (d, J=8.8 Hz, 1H), 4.25 (d, J=4.4 Hz, 1H), 3.78 (br, 1H), 3.71-3.62 (m, 3H), 3.48-3.42 (m, 1H), 3.27-3.01 (m, 7H), 2.89-2.82 (m, 3H), 1.96-1.91 (m, 2H), 1.74-1.70 (m, 2H). LCMS: [M+H]⁺: 542.2.

N-(2-(1-((azetidin-3-ylamino)methyl)-6-chloro-1,3,4,9-tetrahydro-2H-pyrido[3,4-b]indol-2-yl)ethyl)-5-chloro-6-(trifluoromethyl)pyridin-2-amine triformate

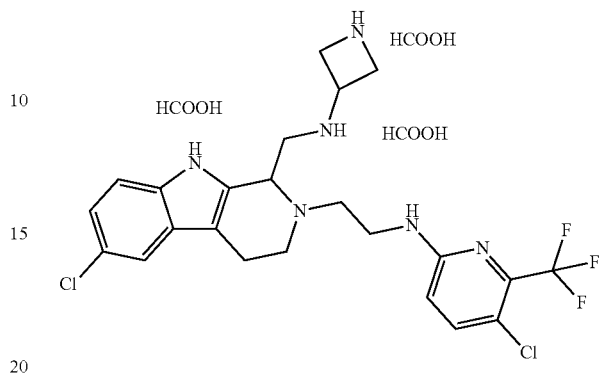

¹H NMR (400 MHz, MeOD): δ 8.51 (brs, 1H), 7.64 (d, J=8.8 Hz, 1H), 7.55-7.50 (m, 1H), 7.41-7.24 (m, 1H), 7.13-7.10 (m, 1H), 6.82 (d, J=8.8 Hz, 1H), 4.72 (brs, 2H), 4.44 (d, 13.2 Hz, 2H), 4.29 (d, 10.0 Hz, 2H), 4.10-3.91 (m, 3H), 3.89-3.53 (m, 4H), 3.40-3.34 (m, 2H), 2.99-2.82 (m, 3H). LCMS: [M+H]⁺: 513.2.

5-chloro-N-(2-(6-chloro-1-((3-methylpiperazin-1-yl)methyl)-1,3,4,9-tetrahydro-2H-pyrido[3,4-b]indol-2-yl)ethyl)-6-(trifluoromethyl)pyridin-2-amine

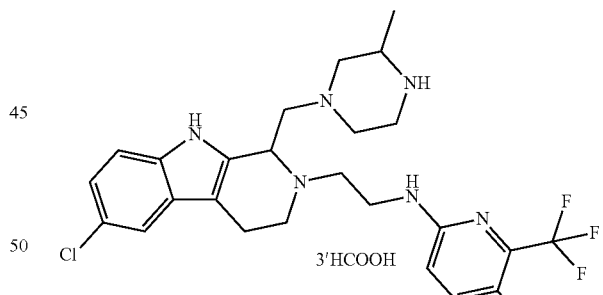

¹H NMR (400 MHz, MeOD): δ 8.45 (brs, 0.5H), 7.54 (d, J=8.4 Hz, 1H), 7.43 (s, 1H), 7.30 (d, J=8.4 Hz, 1H), 7.04 (d, J=8.4 Hz, 1H), 6.82 (d, J=7.6 Hz, 1H), 4.14 (brs, 1H), 3.90-3.39 (m, 8H), 3.30-2.90 (m, 7H), 2.69 (br, 1H), 2.48 (br, 1H), 1.30-1.17 (m, 3H). LCMS: [M+H]⁺: 541.1.

197

((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)proline

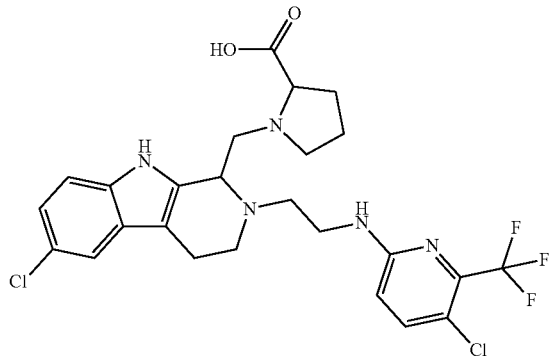 [SMILES: O=C(O)C1CCCN1CC1c2[nH]c3ccc(Cl)cc3c2CCN1CCNc1ccc(Cl)c(C(F)(F)F)n1]

$^1$H NMR (400 MHz, DMSO-$d_6$): δ 11.31 (s, 1H), 7.73 (d, J=9.2 Hz, 1H), 7.63 (br, 1H), 7.49-7.47 (m, 1H), 7.36 (d, J=8.8 Hz, 1H), 7.10 (dd, J=8.8 Hz, 2.0 Hz, 1H), 6.83 (d, J=8.8 Hz, 1H), 4.37-4.35 (m, 1H), 3.77-3.50 (m, 6H), 3.40-3.32 (m 2H), 3.29-3.17 (m, 2H), 3.05-3.00 (m, 2H), 2.83-2.81 (m, 1H), 2.67-2.50 (m, 1H), 2.17-2.14 (m, 1H), 1.95-1.90 (m, 1H), 1.76-1.64 (m, 2H). LCMS: [M+H]$^+$: 556.2.

2-(4-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)piperazin-1-yl)ethan-1-ol

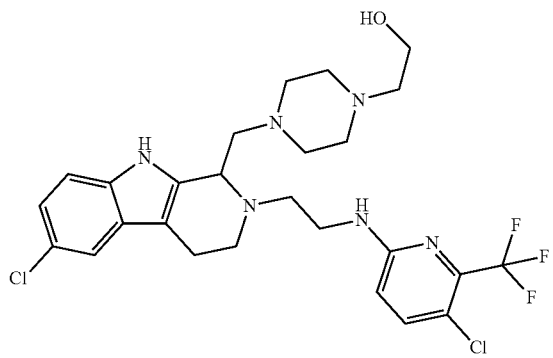 [SMILES: OCCN1CCN(CC2c3[nH]c4ccc(Cl)cc4c3CCN2CCNc2ccc(Cl)c(C(F)(F)F)n2)CC1]

$^1$H NMR (400 MHz, DMSO-$d_6$): δ 10.65 (brs, 1H), 7.63 (d, J=9.2 Hz, 1H), 7.42 (d, J=2.0 Hz 1H), 7.33 (d, J=8.4 Hz, 1H), 7.19 (d, J=4.8 Hz, 1H), 6.99 (dd, J=8.8 Hz, 2.0 Hz, 1H), 6.78 (d, J=9.2 Hz, 1H), 4.24 (br, 1H), 3.78-3.76 (m, 1H), 3.46-3.39 (m, 4H), 3.14-2.92 (m, 4H), 2.83-2.60 (m, 7H), 2.50-2.49 (m, 1H), 2.39-2.31 (m, 6H). LCMS: [M+H]$^+$: 571.3.

198

5-chloro-N-(2-(6-chloro-1-(((3,3,3-trifluoropropyl)amino)methyl)-1,3,4,9-tetrahydro-2H-pyrido[3,4-b]indol-2-yl)ethyl)-6-(trifluoromethyl)pyridin-2-amine

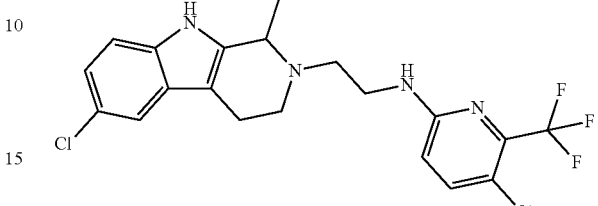

$^1$H NMR (400 MHz, CD$_3$OD) δ 7.53 (d, J=8.0 Hz, 1H), 7.41 (d, J=2.0 Hz, 1H), 7.25 (d, J=8.0 Hz, 1H), 7.02 (dd, J=8.0 Hz, 2.0 Hz, 1H), 6.70 (d, J=12.0 Hz, 1H), 3.80 (d, J=4.0 Hz, 1H), 3.56-3.54 (m, 2H), 3.30-3.24 (m, 2H), 2.91-2.86 (m, 5H), 2.74-2.70 (m, 1H), 2.60-2.53 (m, 2H), 2.33-2.22 (m, 2H). LCMS: [M+H]$^+$: 554.2.

2,2'-((((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)azanediyl)bis(ethan-1-ol)

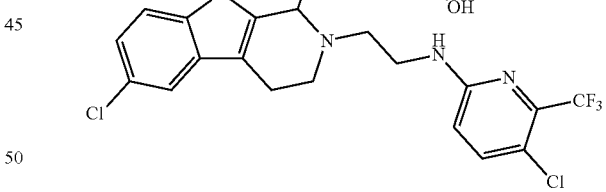

$^1$H NMR (400 MHz, CDCl$_3$) δ 10.07 (brs, 1H), 7.47 (d, J=8.8 Hz, 1H), 7.40 (d, J=1.2 Hz, 1H), 7.21 (d, J=8.4 Hz, 1H), 7.05 (dd, J=8.4 Hz, 1.6 Hz, 1H), 6.54 (d, J=8.8 Hz, 1H), 5.48 (brs, 1H), 4.28 (d, J=8.8 Hz, 1H), 3.81-3.75 (m, 2H), 3.66-3.63 (m, 2H), 3.52-3.50 (m, 2H), 3.28-3.24 (m, 1H), 3.17-3.13 (m, 1H), 3.00-2.75 (m, 10H). LCMS: [M+1]$^+$: 546.1.

199

1-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)pyrrolidin-3-ol

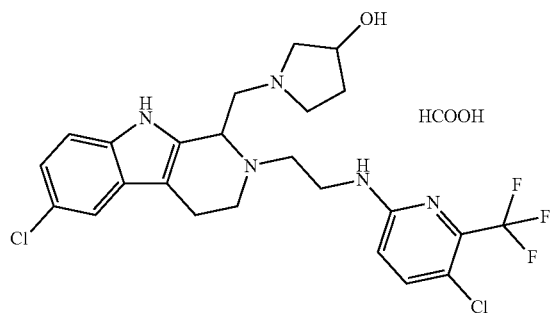 [SMILES: OC1CCN(CC2c3[nH]c4ccc(Cl)cc4c3CCN2CCNc2ccc(Cl)c(C(F)(F)F)n2)C1 ; "HCOOH"]

1H NMR (400 MHz, DMSO-$d_6$) δ 10.92 (d, J=4.0 Hz, 1H), 8.15 (s, 1H), 7.63 (d, J=8.8 Hz, 1H), 7.45 (s, 1H), 7.31-7.28 (m, 1H), 7.23 (d, J=2.8 Hz, 1H), 7.00 (dd, J=8.4 Hz, 1.6 Hz, 1H), 6.79 (dd, J=8.8 Hz, 4.8 Hz, 1H), 4.73 (br, 1H), 4.15 (br, 1H), 3.82 (br, 1H), 3.45-3.40 (m, 2H), 3.21-3.12 (m, 1H), 3.08-3.03 (m, 1H), 2.92-2.52 (m, 9H), 2.45-2.39 (m, 1H), 1.98-1.92 (m, 1H), 1.55-1.50 (m, 1H). LCMS: [M+H]$^+$: 528.2.

N-(2-(1-((3-aminopyrrolidin-1-yl)methyl)-6-chloro-1,3,4,9-tetrahydro-2H-pyrido[3,4-b]indol-2-yl)ethyl)-5-chloro-6-(trifluoromethyl)pyridin-2-amine triformate

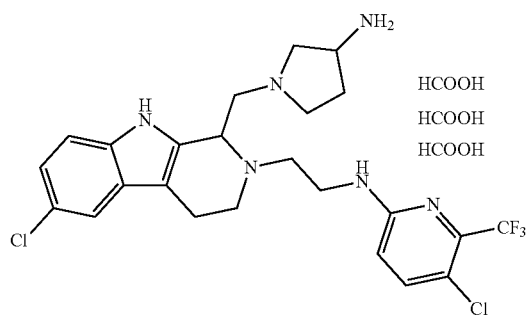 [SMILES: NC1CCN(CC2c3[nH]c4ccc(Cl)cc4c3CCN2CCNc2ccc(Cl)c(C(F)(F)F)n2)C1 ; "HCOOH" ; "HCOOH" ; "HCOOH"]

$^1$H NMR (400 MHz, DMSO-$d_6$) δ 11.41 (br, 1H), 8.05-7.75 (m, 2H), 7.74-7.70 (m, 1H), 7.65-7.45 (m, 2H), 7.39-7.33 (m, 1H), 7.10-7.06 (m, 1H), 6.84 (dd, J=8.4 Hz, 4.0 Hz, 1H), 4.06-3.93 (m 1H), 3.88-3.50 (m, 8H), 3.20-2.90 (m, 4H), 2.85-2.50 (m, 2H), 2.48-2.10 (m, 2H), 1.78-1.70 (m, 1H). LCMS: [M+1]$^+$: 527.1.

200

N-(2-(1-(azetidin-1-ylmethyl)-6-chloro-1,3,4,9-tetrahydro-2H-pyrido[3,4-b]indol-2-yl)ethyl)-5-chloro-6-(trifluoromethyl)pyridin-2-amine formate

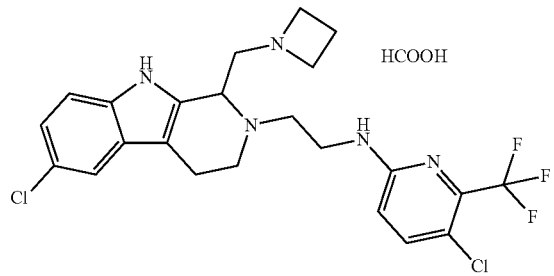 [SMILES: FC(F)(F)c1nc(NCCN2CCc3c([nH]c4ccc(Cl)cc34)C2CN2CCC2)ccc1Cl ; "HCOOH"]

$^1$H NMR (400 MHz, CD$_3$OD) δ 8.51 (brs, 1H), 7.55 (d, J=8.0 Hz, 1H), 7.52 (d, J=4.0 Hz, 1H), 7.34 (d, J=8.0 Hz, 1H), 7.15 (dd, J=8.0, 2.0 Hz, 1H), 6.71 (d, J=12.0 Hz, 1H), 4.43 (d, J=4.0 Hz, 1H), 4.18-4.12 (m, 2H), 3.97 (brs, 2H), 3.60-3.57 (m, 2H), 3.49-3.38 (m, 2H), 3.02-2.97 (m, 5H), 2.71-2.64 (m, 1H), 2.47-2.40 (m, 2H). LCMS: [M+1]$^+$: 498.2.

5-chloro-N-(2-(6-chloro-1-((4,4-difluoropiperidin-1-yl)methyl)-1,3,4,9-tetrahydro-2H-pyrido[3,4-b]indol-2-yl)ethyl)-6-(trifluoromethyl)pyridin-2-amine

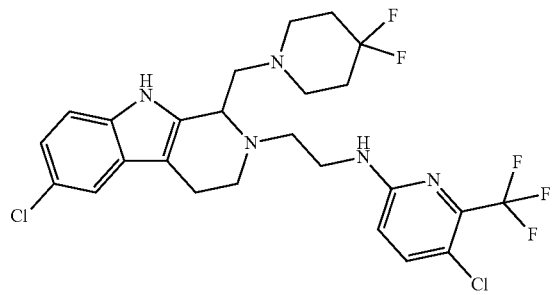 [SMILES: FC1(F)CCN(CC2c3[nH]c4ccc(Cl)cc4c3CCN2CCNc2ccc(Cl)c(C(F)(F)F)n2)CC1]

$^1$H NMR (400 MHz, CD$_3$OD) δ 7.50 (d, J=8.0 Hz, 1H), 7.38 (d, J=2.0 Hz, 1H), 7.27 (d, J=8.0 Hz, 1H), 7.00 (dd, J=8.0 Hz, 2.0 Hz, 1H), 6.67 (d, J=8.0 Hz, 1H), 4.03-4.01 (m, 1H), 3.56-3.55 (m, 3H), 3.16-3.09 (m, 3H), 2.93-2.88 (m, 5H), 2.79-2.73 (m, 4H), 2.03-1.98 (m, 4H). LCMS: [M+1]$^+$: 562.3.

201

5-chloro-N-(2-(6-chloro-1-((pyrrolidin-3-ylamino)
methyl)-1,3,4,9-tetrahydro-2H-pyrido[3,4-b]indol-2-
yl)ethyl)-6-(trifluoromethyl)pyridin-2-amine diformate

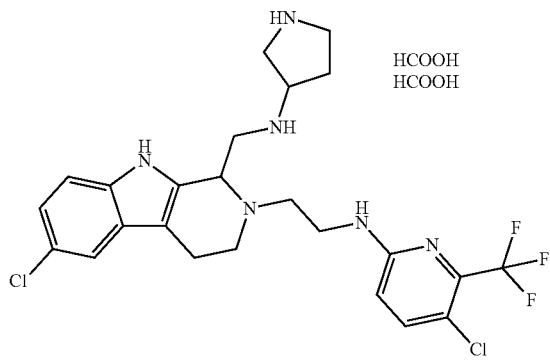 [SMILES: FC(F)(F)c1nc(NCCN2CCc3c([nH]c4ccc(Cl)cc34)C2CNC2CCNC2)ccc1Cl]

¹H NMR (400 MHz, CD₃OD) δ 8.34 (br, 2H), 7.55 (d, J=9.2 Hz, 1H), 7.41 (d, J=2.0 Hz, 1H), 7.26 (d, J=8.4 Hz, 1H), 7.02 (dd, J=8.4 Hz, 2.0 Hz, 1H), 6.72 (d, J=8.8 Hz, 1H), 3.93 (br, 1H), 3.66-3.60 (m, 2H), 3.48-3.40 (m, 3H), 3.31-3.30 (m, 1H), 3.30-3.20 (m, 1H), 3.13-3.12 (m, 1H), 3.09-2.82 (m, 8H), 2.10-2.05 (m, 1H), 3.05-1.95 (m, 1H). LCMS: [M+1]⁺: 527.2.

5-chloro-N-(2-(6-chloro-1-((pyrrolidin-3-ylamino)
methyl)-1,3,4,9-tetrahydro-2H-pyrido[3,4-b]indol-2-
yl)ethyl)-6-(trifluoromethyl)pyridin-2-amine diformate

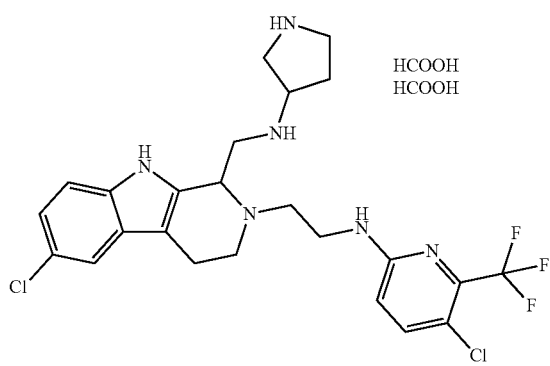 [SMILES: FC(F)(F)c1nc(NCCN2CCc3c([nH]c4ccc(Cl)cc34)C2CNC2CCNC2)ccc1Cl]

¹H NMR (400 MHz, CD₃OD) δ 8.34 (br, 2H), 7.55 (d, J=9.2 Hz, 1H), 7.41 (d, J=2.0 Hz, 1H), 7.24 (d, J=8.4 Hz, 1H), 7.02 (dd, J=8.4 Hz, 2.0 Hz, 1H), 6.72 (d, J=9.2 Hz, 1H), 3.93 (br, 1H), 3.63-3.58 (m, 2H), 3.50-3.33 (m, 3H), 3.27-2.76 (m, 9H), 1.98-1.73 (m, 2H). LCMS: [M+1]⁺: 527.2.

202

1-((6-chloro-2-(2-((5-chloro-6-(trifluoromethyl)pyri-
din-2-yl)amino)ethyl)-2,3,4,9-tetrahydro-1H-pyrido
[3,4-b]indol-1-yl)methyl)azetidin-3-ol

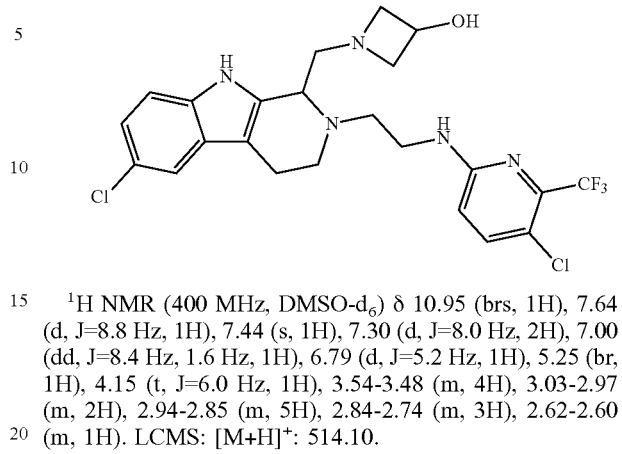

¹H NMR (400 MHz, DMSO-d₆) δ 10.95 (brs, 1H), 7.64 (d, J=8.8 Hz, 1H), 7.44 (s, 1H), 7.30 (d, J=8.0 Hz, 2H), 7.00 (dd, J=8.4 Hz, 1.6 Hz, 1H), 6.79 (d, J=5.2 Hz, 1H), 5.25 (br, 1H), 4.15 (t, J=6.0 Hz, 1H), 3.54-3.48 (m, 4H), 3.03-2.97 (m, 2H), 2.94-2.85 (m, 5H), 2.84-2.74 (m, 3H), 2.62-2.60 (m, 1H). LCMS: [M+H]⁺: 514.10.

N-(2-(1-((3-aminoazetidin-1-yl)methyl)-6-chloro-1,
3,4,9-tetrahydro-2H-pyrido[3,4-b]indol-2-yl)ethyl)-
5-chloro-6-(trifluoromethyl)pyridin-2-amine

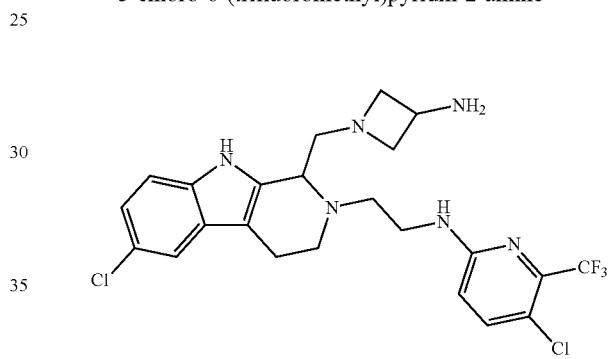

¹H NMR (400 MHz, DMSO-d₆) δ 10.90 (brs, 1H), 7.63 (d, J=8.8 Hz, 1H), 7.43 (s, 1H), 7.34-7.29 (m, 2H), 6.99 (d, J=8.4 Hz, 1H), 6.79 (d, J=8.8 Hz, 1H), 3.52-3.45 (m, 2H), 3.45-3.39 (m, 3H), 2.97-2.89 (m, 3H), 2.85-2.72 (m, 7H), 2.67-2.50 (m, 1H). ¹⁹F NMR (376.5 MHz, DMSO-d₆) δ −64.72 LCMS: [M+H]⁺: 513.20.

5-chloro-N-(2-(6-chloro-1-((oxetan-3-ylamino)
methyl)-1,3,4,9-tetrahydro-2H-pyrido[3,4-b]indol-2-
yl)ethyl)-6-(trifluoromethyl)pyridin-2-amine

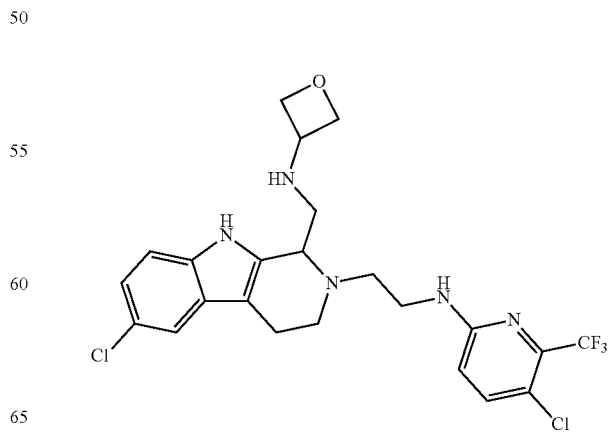

¹H NMR (400 MHz, DMSO-d₆) δ 10.91 (brs, 1H), 7.65 (d, J=8.0 Hz, 1H), 7.42 (d, J=2.0 Hz, 1H), 7.29-7.27 (m, 2H), 6.98 (dd, J=8.0 Hz, 2.0 Hz, 1H), 6.85 (d, J=8.0 Hz, 1H), 4.56-4.53 (m, 1H), 4.26 (t, J=6.0 Hz, 1H), 4.05-4.02 (m, 1H), 3.95-3.90 (m, 1H), 3.78-3.70 (m, 2H), 3.44-3.42 (m, 2H), 3.10-3.08 (m, 1H), 3.04-2.99 (m, 2H), 2.85-2.71 (m, 4H), 2.56-2.54 (m, 2H). LCMS: [M+H]⁺: 514.2.

5-chloro-N-(2-(6-chloro-1-(2-(dimethylamino)ethyl)-1,3,4,9-tetrahydro-2H-pyrido[3,4-b]indol-2-yl)ethyl)-6-(trifluoromethyl)pyridin-2-amine formate

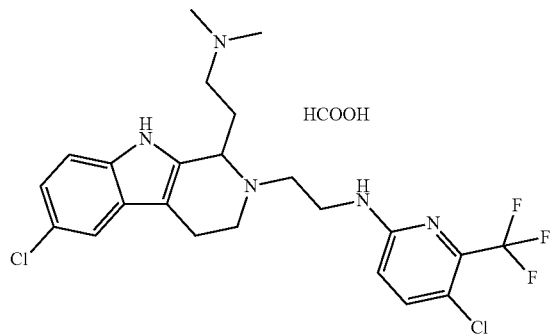 [SMILES: CN(C)CCC1c2[nH]c3ccc(Cl)cc3c2CCN1CCNc1ccc(Cl)c(C(F)(F)F)n1 ; "HCOOH"]

¹H NMR (400 MHz, DMSO-d₆): δ 10.95 (brs, 1H), 8.24 (s, 1H), 7.64 (d, J=9.2 Hz, 1H), 7.39 (d, J=2.0 Hz, 1H), 7.30~7.24 (m, 2H), 7.01 (dd, J=8.4 Hz, 2.0 Hz, 1H), 6.79 (d, J=9.2 Hz, 1H), 3.78~3.74 (m, 1H), 3.44~3.39 (m, 2H), 3.14~3.08 (m, 1H), 2.90~2.85 (m, 1H), 2.75~2.69 (m, 3H), 2.58~2.53 (m, 1H), 2.47~2.41 (m, 1H), 2.34~2.27 (m, 1H), 2.21 (s, 6H), 1.93~1.77 (m, 2H). ¹⁹F NMR (376 MHz, CDCl₃): δ -64.72. LCMS: [M+H]⁺: 500.2

5-chloro-N-(2-(6-chloro-1-(2-(methylamino)ethyl)-1,3,4,9-tetrahydro-2H-pyrido[3,4-b]indol-2-yl)ethyl)-6-(trifluoromethyl)pyridin-2-amine diformate

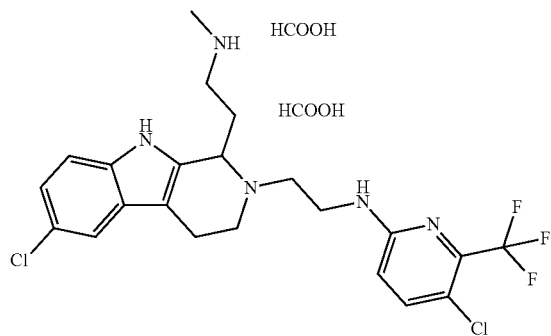 [SMILES: CNCCC1c2[nH]c3ccc(Cl)cc3c2CCN1CCNc1ccc(Cl)c(C(F)(F)F)n1 ; "HCOOH" ; "HCOOH"]

Diastereomer 1: ¹H NMR (400 MHz, DMSO-d₆): δ 11.79~11.69 (m, 1H), 11.53~11.43 (m, 1H), 9.22 (br, 2H), 7.83 (br, 1H), 7.73~7.68 (m, 1H), 7.56 (d, J=2.0 Hz, 1H), 7.44~7.39 (m, 1H), 7.15 (dd, J=8.4 Hz, 1.6 Hz, 1H), 6.88~6.83 (m, 1H), 5.14~5.03 (m, 1H), 3.89~3.66 (m, 4H), 3.40~3.21 (m, 4H), 3.04~3.00 (m, 2H), 2.77~2.70 (m, 1H), 2.59~2.57 (m, 3H), 2.44~2.33 (m, 1H). ¹⁹F NMR (376 MHz, CDCl₃): δ -64.57. LCMS: [M+H]⁺: 486.2.

Diastereomer 2: ¹H NMR (400 MHz, DMSO-d₆): δ 11.89~11.76 (m, 1H), 10.70~10.55 (m, 1H), 10.31~10.30 (m, 1H), 10.06~9.73 (m, 1H), 7.74~7.70 (m, 3H), 7.44 (d, J=8.8 Hz, 1H), 7.19~7.15 (m, 1H), 6.84 (d, J=8.8 Hz, 1H), 5.38 (br, 0.6H), 4.67 (br, 0.4H), 3.67~3.03 (m, 9.5H), 2.89~2.74 (m, 2H), 2.65~2.55 (m, 3H), 2.25~2.19 (m, 0.5H). ¹⁹F NMR (376 MHz, CDCl₃): δ -64.68. LCMS: [M+H]⁺: 486.1.

N1-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)-N2,N2-dimethyl-ethane-1,2-diamine diformate

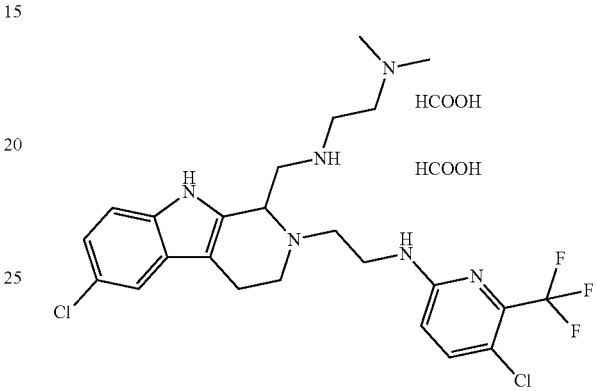

¹H NMR (400 MHz, DMSO-d₆): δ 11.13 (brs, 1H), 8.31 (brs, 2H), 7.64 (d, J=8.8 Hz, 1H), 7.42 (d, J=2.0 Hz, 1H), 7.29 (d, J=8.4 Hz, 1H), 7.24 (br, 1H), 6.97 (dd, J=8.4 Hz, 2.0 Hz, 1H), 6.79 (d, J=8.8 Hz, 1H), 3.79 (br, 1H), 3.68-3.65 (m, 1H), 3.44-3.41 (m, 2H), 3.11-3.03 (m, 2H), 2.86-2.80 (m, 4H), 2.72-2.61 (m, 3H), 2.51-2.40 (m, 2H), 2.38-2.17 (m, 1H), 2.09 (s, 6H). ¹⁹F NMR (376 MHz, CDCl₃): δ -64.71. LCMS: [M+H]⁺: 529.3.

N-(2-(1-(((azetidin-2-ylmethyl)amino)methyl)-6-chloro-3,4-dihydro-1H-pyrido[3,4-b]indol-2(9H)-yl)ethyl)-5-chloro-6-(trifluoromethyl)pyridin-2-amine

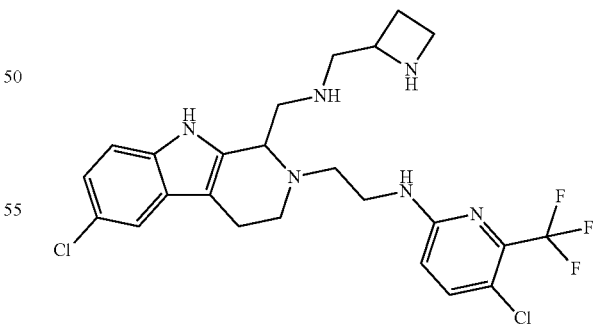

¹H NMR (400 MHz, MeOD-d₄): δ 7.60~7.53 (m, 2H), 7.40~7.38 (m, 1H), 7.20~7.17 (m, 1H), 6.84~6.81 (m, 1H), 5.42 (d, J=7.6 Hz, 1H), 5.02 5.00 (m, 1H), 4.13~3.79 (m, 9H), 3.71~3.62 (m, 3H), 3.22~3.17 (m, 2H), 2.73~2.61 (m, 2H). ¹⁹F NMR (400 MHz, MeOD-d₄): δ -67.23 LCMS: [M+1]⁺=527.1

205

5-Chloro-N-(2-(6-chloro-1-(((pyrrolidin-2-ylmethyl)amino)methyl)-3,4-dihydro-1H-pyrido[3,4-b]indol-2(9H)-yl)ethyl)-6-(trifluoromethyl)pyridin-2-amine

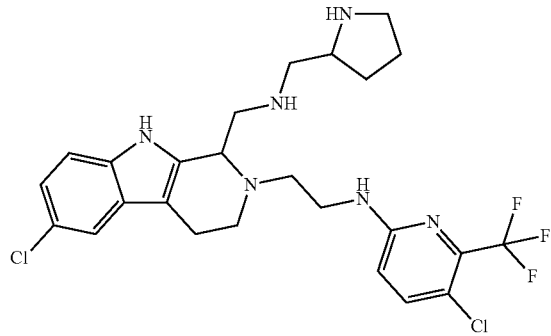 [SMILES: FC(F)(F)c1nc(NCCN2CCc3c([nH]c4ccc(Cl)cc34)C2CNCC2CCCN2)ccc1Cl]

$^1$H NMR (400 MHz, MeOD-d$_4$): δ 7.52 (dd, J=12.8 Hz, 8.8 Hz, 2H), 7.38 (d, J=8.8 Hz, 1H), 7.16 (dd, J=8.8 Hz, 2.0 Hz, 1H), 6.83 (d, J=8.8 Hz, 1H), 5.49 (d, J=7.6 Hz, 1H), 4.21-4.15 (m, 2H), 3.97-3.87 (m, 5H), 3.76-3.61 (m, 4H), 3.49-3.43 (m, 2H), 3.21-3.16 (m, 2H), 2.43-2.41 (m, 1H), 2.17-1.98 (m, 3H). LCMS: [M+1]$^+$=541.5

1-Carbamimidoyl-N-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)azetidine-3-carboxamide

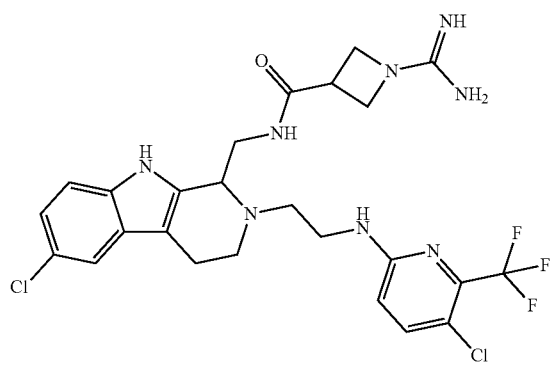 [SMILES: N=C(N)N1CC(C(=O)NCC2c3[nH]c4ccc(Cl)cc4c3CCN2CCNc2ccc(Cl)c(C(F)(F)F)n2)C1]

$^1$H NMR (400 MHz, MeOD-d$_4$): δ 7.60-7.50 (m, 2H), 7.35 (d, J=8.4 Hz, 1H), 7.14 (dd, J=8.4 Hz, 1.6 Hz, 1H), 6.82 (d, J=8.8 Hz, 1H), 4.96-4.89 (m, 1H), 4.20-3.72 (m, 10H), 3.59-3.55 (m, 1H), 3.45-3.42 (m, 1H), 3.30-3.31 (m, 1H), 3.17-3.00 (m, 2H). LCMS: [M+1]$^+$=583.2.

206

3-((((6-Chloro-2-(2-((5-chloro-6-(trifluoromethyl)pyridin-2-yl)amino)ethyl)-2,3,4,9-tetrahydro-1H-pyrido[3,4-b]indol-1-yl)methyl)amino)methyl)azetidine-1-carboximidamide

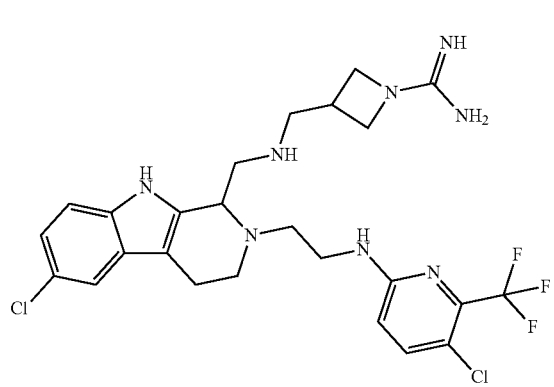 [SMILES: N=C(N)N1CC(CNCC2c3[nH]c4ccc(Cl)cc4c3CCN2CCNc2ccc(Cl)c(C(F)(F)F)n2)C1]

$^1$H NMR (400 MHz, MeOD-d$_4$): δ 7.58-7.52 (m, 2H), 7.38 (d, J=8.4 Hz, 1H), 7.17 (dd, J=8.8 Hz, 2.0 Hz, 1H), 6.80 (d, J=8.8 Hz, 1H), 5.22-5.21 (m, 1H), 4.36-4.31 (m, 2H), 4.12-4.07 (m, 2H), 3.97-3.69 (m, 6H), 3.59-3.47 (m, 4H), 3.34-3.30 (m, 1H), 3.22-3.13 (m, 1H), 3.07-3.02 (m, 1H). LCMS: [M+1]$^+$=569.2

N-(2-aminoethyl)-3-((((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)amino)methyl)azetidine-1-carboxamide

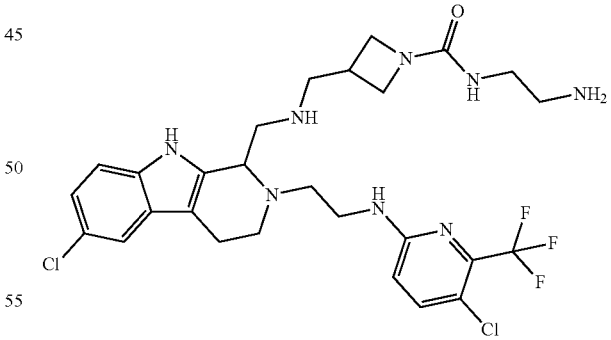

$^1$H NMR (400 MHz, MeOD-d$_4$): δ 7.56-7.54 (m, 1H), 7.46 (s, 1H), 7.34-7.31 (m, 1H), 7.11 (s, 1H), 6.82-6.73 (m, 1H), 4.20-4.07 (m, 1H), 3.85-3.80 (m, 1H), 3.73-3.69 (m, 4H), 3.66-3.61 (m, 3H), 3.56-3.38 (m, 4H), 3.31-3.02 (m, 7H), 2.94-2.69 (m, 1H), 2.68 (brs, 1H). LCMS: [M+1]$^+$=615.2

207

N-(2-(1-(((azetidin-3-ylmethyl)amino)methyl)-6-chloro-3,4-dihydro-1H-pyrido[3,4-b]indol-2(9H)-yl)ethyl)-5-chloro-6-(trifluoromethyl)pyridin-2-amine

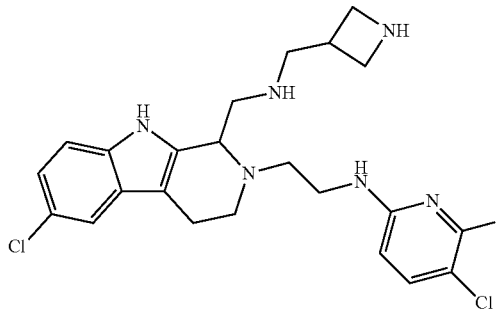

$^1$H NMR (400 MHz, MeOD-d$_4$): δ 7.62~7.60 (m, 2H), 7.43 (d, J=8.8 Hz, 1H), 7.23 (dd, J=8.8, 2.0 Hz, 1H), 6.84 (d, J=8.8 Hz, 1H), 5.05 (br, 1H), 4.32~4.27 (m, 1H), 4.20~3.93 (m, 8H), 3.71~3.55 (m, 4H), 3.48~3.31 (m, 3H), 3.30~3.20 (m, 1H). $^{19}$F NMR (400 MHz, MeOD-d$_4$): δ −67.25 LCMS: [M+1]$^+$=527.0

5-Chloro-N-(2-(6-chloro-1-((((S)-pyrrolidin-3-ylmethyl)amino)methyl)-3,4-dihydro-1H-pyrido[3,4-b]indol-2(9H)-yl)ethyl)-6-(trifluoromethyl)pyridin-2-amine

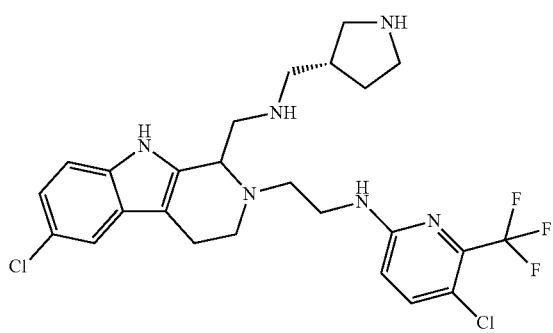 [SMILES: FC(F)(F)c1nc(NCCN2CCc3c([nH]c4ccc(Cl)cc34)C2CNC[C@H]2CCNC2)ccc1Cl]

$^1$H NMR (400 MHz, DMSO-d$_6$): δ 11.02 (d, J=14.8 Hz, 1H), 8.31 (s, 1.5H), 7.64 (d, J=8.0 Hz, 1H), 7.43 (d, J=1.6 Hz, 1H), 7.33-7.30 (m, 2H), 6.98 (dd, J=8.4 Hz, 2.0 Hz, 1H), 6.84 (d, J=8.8 Hz, 1H), 3.79 (s, 1H), 3.43 (d, J=4.8 Hz, 2H), 3.20-3.13 (m, 5H), 3.12-3.04 (m, 6H), 2.81-2.54 (m, 1.5H), 2.51-2.33 (m, 2.6H), 1.92-1.90 (m 1H), 1.52-1.49 (m, 1H). LCMS: [M−1]$^-$=539.2

208

3-(2-(((6-Chloro-2-(2-((5-chloro-6-(trifluoromethyl)pyridin-2-yl)amino)ethyl)-2,3,4,9-tetrahydro-1H-pyrido[3,4-b]indol-1-yl)methyl)amino)ethyl)-1-methyl-1H-imidazol-3-ium chloride hydrochloride

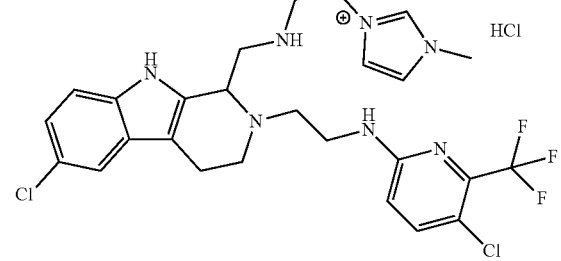

$^1$H NMR (400 MHz, MeOD-d$_4$): δ 8.56 (s, 1H), 7.53~7.49 (m, 2H), 7.40~7.38 (d, J=8 Hz, 2H), 7.26~7.24 (d, J=8 Hz, 2H), 7.04~7.02 (m, 1H), 6.71~6.68 (d, J=8.8 Hz, 1H), 4.22~4.21 (m, 2H), 3.94~3.86 (m, 1H), 3.62~3.47 (m, 5H), 3.12~2.57 (m, 10H). LCMS: [M]$^+$=566.1

Representative synthesis of di-tert-butyl ((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl) phosphate General Scheme 32

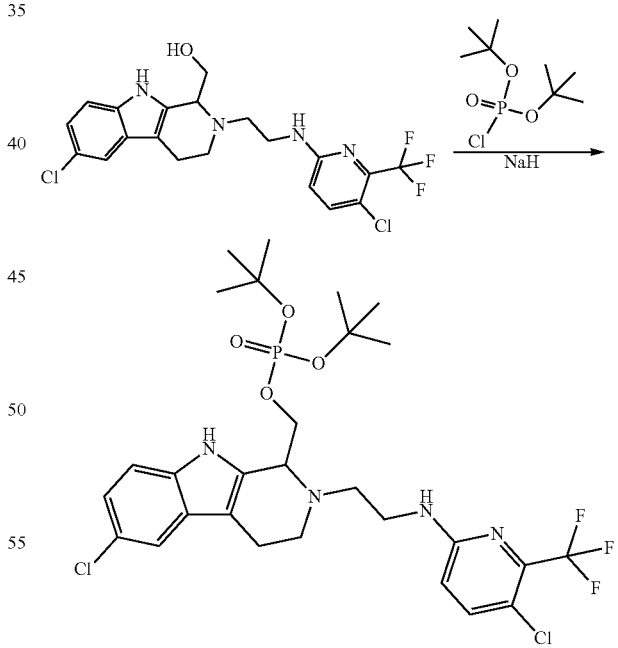

To the mixture of (6-chloro-2-(2-((5-chloro-6-(trifluoromethyl)pyridin-2-yl)amino)ethyl)-2,3,4,9-tetrahydro-1H-pyrido[3,4-b]indol-1-yl)methanol (1 g, 2.1 mmol) in THF (20 ml) was added NaH (210 mg, 5.25 mmol) at 0° C., then the mixture was stirred at r.t for 2 h. Di-tert-butyl phosphorochloridate (505 mg, 2.94 mmol) in THF (4 ml) was added drop-wise to the mixture at 0° C. Then the mixture was stirred at RT overnight. The reaction was quenched by water and the mixture was extracted with ethyl acetate. The organic solution was dried over Na₂SO₄, and concentrated. The residue was purified by silica gel chromatography (PE:EA=1:1) to give di-tert-butyl ((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl) phosphate (600 mg, 44% yield) as a yellow solid. The solid was used directly in the next step without further purification.

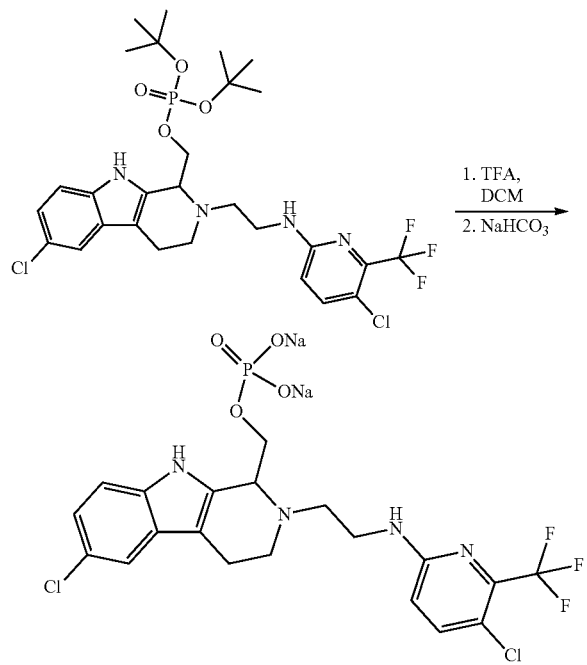

The solution of di-tert-butyl ((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl) phosphate (600 mg, 0.923 mmol) in TFA (1 mL) and DCM (20 mL) was stirred at 0° C. to RT overnight. The reaction solution was concentrated and the residue was purified by prep-HPLC to give (6-chloro-2-(2-((5-chloro-6-(trifluoromethyl)pyridin-2-yl)amino)ethyl)-2,3,4,9-tetrahydro-1H-pyrido[3,4-b]indol-1-yl)methyl dihydrogen phosphate (67.77 mg, 13% yield) as a yellow solid. ¹H NMR (400 MHz, DMSO) δ 12.16 (br, 1H), 7.86-7.83 (m, 1H), 7.55-7.53 (m, 1H), 7.37 (s, 1H), 7.25 (d, J=8.4 Hz, 1H), 7.00 (d, J=9.2 Hz, 1H), 6.96 (d, J=8.8 Hz, 2H), 4.04-3.83 (m, 4H), 3.20-3.05 (m, 3H), 2.84-2.67 (m, 4H). LCMS: [M+H]⁺: 539.1.

General Scheme 33

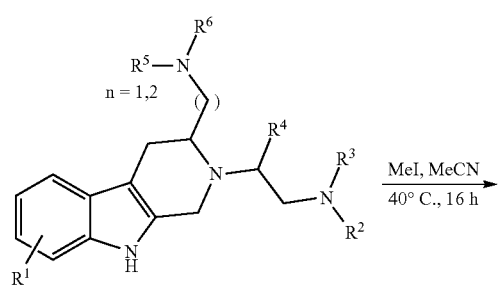

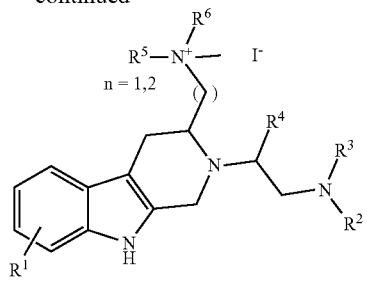

Representative of synthesis of compound 3-amino-1-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)-1-methylpyrrolidin-1-ium chloride hydrochloride: 5-Chloro-N-(2-(6-chloro-1-(chloromethyl)-1,3,4,9-tetrahydro-2H-pyrido[3,4-b]indol-2-yl)ethyl)-6-(trifluoromethyl)pyridin-2-amine (100 mg, 0.21 mmol) was added to the solution of tert-butyl pyrrolidin-3-ylcarbamate (240 mg, 1.26 mmol) in MeCN (1 mL) at 70° C. The reaction was then stirred at 70° C. overnight. The mixture was purified by prep-HPLC to give tert-butyl (1-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)pyrrolidin-3-yl)carbamate (60 mg, yield: 45.64%). LCMS: [M+H]⁺=627.3

3-((tert-butoxycarbonyl)amino)-1-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)-1-methylpyrrolidin-1-ium iodide

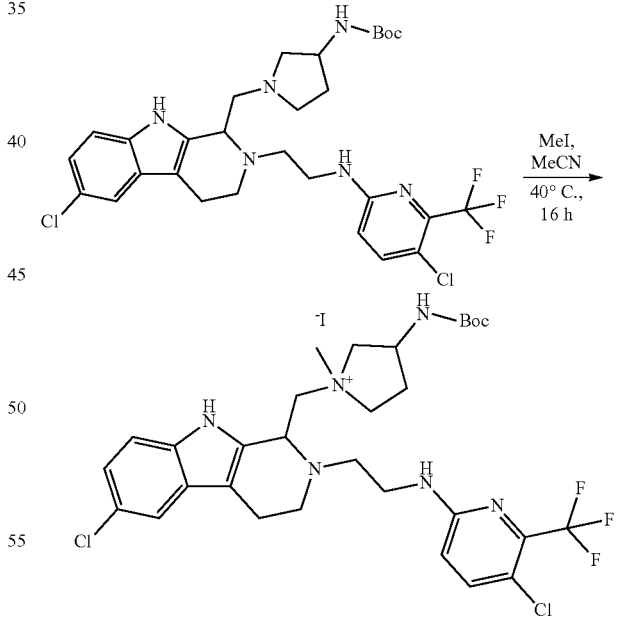

The solution of tert-butyl (1-((6-chloro-2-(2-((5-chloro-6-(trifluoromethyl) pyridin-2-yl)amino)ethyl)-2,3,4,9-tetrahydro-1H-pyrido[3,4-b]indol-1-yl)methyl)pyrrolidin-3-yl)carbamate (60 mg, 0.096 mmol) and MeI (2 mL) in acetone (0.5 mL) was stirred at 40° C. in a sealed tube overnight. The mixture was purified by prep-HPLC to give 3-((tert-butoxycarbonyl)amino)-1-((6-chloro-2-(2-((5-chloro-6-(trifluoromethyl)pyridine-2-yl)amino)ethyl)-2,3,4,9-tetrahydro-

211

1H-pyrido[3,4-b]indol-1-yl)methyl)-1-methylpyrrolidin-1-ium iodide (2 mg, 2.71%). LCMS: [M]⁺=641.2 amino-1-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)-1-methylpyrrolidin-1-ium chloride hydrochloride

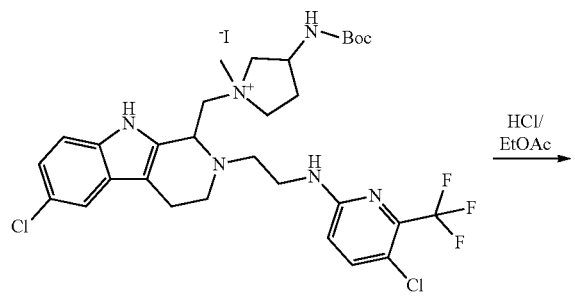

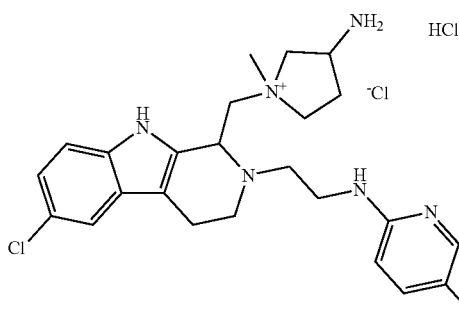

3-((tert-butoxycarbonyl)amino)-1-((6-chloro-2-(24(5-chloro-6-(trifluoromethyl)pyridin-2-yl)amino)ethyl)-2,3,4,9-tetrahydro-1H-pyrido[3,4-b]indol-1-yl)methyl)-1-methylpyrrolidin-1-ium iodide (2 mg, 0.003 mmol) was dissolved in HCl/ethyl acetate (10 mL) and stirred at RT overnight. The reaction mixture was concentrated and the residue was purified by prep-HPLC to give 3-amino-1-((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)-1-methylpyrrolidin-1-iumchloridehydrochloride (1.21 mg, yield: 42%) as a white solid. ¹H NMR (400 MHz, MeOD-d₆): δ 7.62 (d, J=8.8 Hz, 1H), 7.48 (s, 1H), 7.35 (d, J=8.4 Hz, 1H), 7.13-7.08 (m, 1H), 6.82 (dd, J=8.8 Hz, 1.2 Hz, 1H), 4.81 (m, 1H), 4.06-3.78 (m, 9H), 3.54 (s, 3H), 3.34-3.30 (m, 2H), 3.12-2.58 (m, 4H), 2.39 (br, 1H), 1.95-1.92 (m, 1H). LCMS: [M]⁺=541.2

212

1-((6-Chloro-2-(2-((5-chloro-6-(trifluoromethyl)pyridin-2-yl)amino)ethyl)-2,3,4,9-tetrahydro-1H-pyrido[3,4-b]indol-1-yl)methyl)-3-hydroxy-1-methylpyrrolidin-1-ium chloride hydrochloride

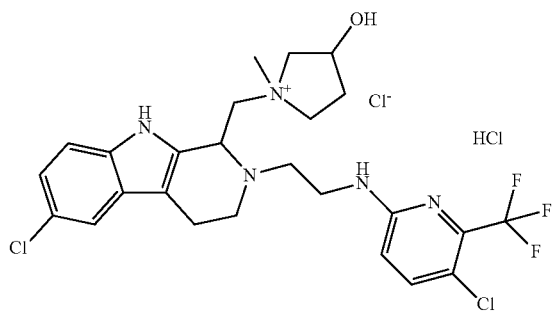 [SMILES: C[N+]1(CC2c3[nH]c4ccc(Cl)cc4c3CCN2CCNc2ccc(Cl)c(C(F)(F)F)n2)CCC(O)C1 ; [Cl-] ; Cl]

¹H NMR (400 MHz, MeOD-d₄): δ 11.13~11.11 (m, 1H), 7.75~7.72 (d, J=8.8 Hz, 2H), 7.54 (s, 1H), 7.37~7.35 (d, J=8.4 Hz, 1H), 7.08~7.05 (m, 1H), 6.90~6.88 (d, J=8.8 Hz, 1H), 4.93~4.87 (m, 1H), 4.67~4.65 (m, 1H), 4.23 (s, 1H), 3.99~3.64 (m, 8H), 3.44~3.43 (m, 4H), 3.22~3.17 (m, 2H), 2.93~2.90 (m, 1H), 2.70~2.38 (m, 2H), 2.32~1.71 (m, 2H). LCMS: [M]⁺=542.2

General scheme 34

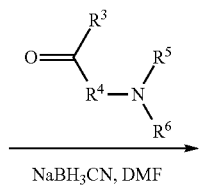

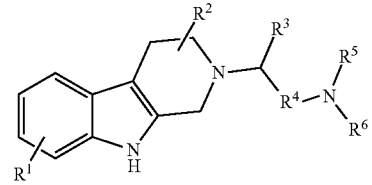

Representative of synthesis of compound (6-chloro-2-((1-(5,6-dichloropyridin-2-yl)pyrrolidin-2-yl)methyl)-2,3,4,9-tetrahydro-1H-pyrido[3,4-b]indol-1-yl)methanol: To a solution of 2-chloro-6-fluoropyridine (3.0 g, 22.81 mmol, 1.0 eq) and methyl prolinate hydrochloride (5.7 g, 34.21 mmol, 1.5 eq) in DMSO (40 mL) was added DIPEA (14.7 g, 114.03 mmol, 5.0 eq). The mixture was stirred at 120° C. for 16 h. Water (20 mL) was then added and the mixture was extracted with EtOAc (4×50 mL). The combined organic layers were washed with brine (5×50 mL), dried over Na₂SO₄ and concentrated. The residue was purified by column chromatography (SiO₂, Petroleum ether:EtOAc=10:1~5:1) to give methyl (6-chloropyridin-2-yl)prolinate (3.3 g, yield 60%) as a light yellow oil.

To a solution of methyl (6-chloropyridin-2-yl)prolinate (2.8 g, 11.61 mmol, 1.0 eq) in CH₃CN (20 mL) was added NCS (1.6 g, 12.19 mmol, 1.05 eq) in portions. The reaction was stirred at 50° C. for 5 h. The mixture was purified by column chromatography (SiO₂, Petroleum ether:EtOAc=10:

1) to give methyl (5,6-dichloropyridin-2-yl)prolinate (2.5 g, yield 78%) as a light yellow oil. ¹H NMR: (400 MHz, DMSO-d₆) δ 7.72 (d, J=8.8 Hz, 1H), 6.52 (d, J=8.8 Hz, 1H), 4.47-4.44 (m, 1H), 3.61 (s, 3H), 3.53-3.38 (m, 2H), 2.03-1.99 (m, 1H). LCMS: [M+H]⁺=275.0.

(1-(5,6-dichloropyridin-2-yl)pyrrolidin-2-yl)methanol

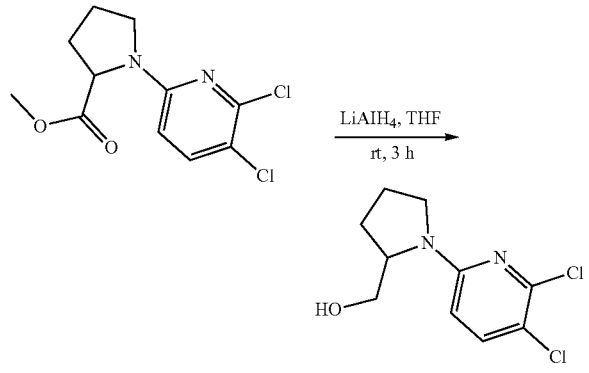

To a solution of methyl (5,6-dichloropyridin-2-yl)prolinate (1.9 g, 6.98 mmol, 1.0 eq) in THF (20 mL) was added LiAlH₄ (800 mg, 20.95 mmol, 3.0 eq) at 0° C. The reaction was stirred at rt for 3 h. The mixture was quenched with NaOH (aq. 15%, 800 uL) and H₂O (2.5 mL). The residue was purified by column chromatography (SiO₂, Petroleum ether:EtOAc=5:1) to give (1-(5,6-dichloropyridin-2-yl)pyrrolidin-2-yl)methanol (1.5 g, yield 88%) as a colorless oil. LCMS: [M+H]⁺=247.0.

1-(5,6-dichloropyridin-2-yl)pyrrolidine-2-carbaldehyde

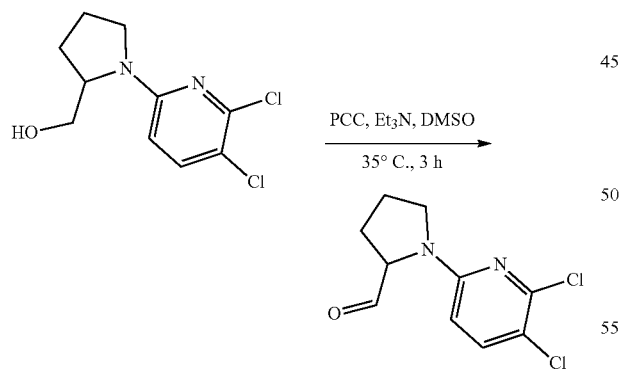

To a solution of (1-(5,6-dichloropyridin-2-yl)pyrrolidin-2-yl)methanol (700 mg, 2.833 mmol, 1.0 eq) in DMSO (10 mL) was added Et₃N (2.87 g, 28.33 mmol, 10.0 eq) and PCC (1.35 g, 8.498 mmol, 3.0 eq). The mixture was stirred at 35° C. for 3 h. The mixture was washed with H₂O (10 mL) and the aqueous layer was extracted with EtOAc (3×10 mL). The combined organic was washed with brine (4×30 mL), dried over Na₂SO₄ and concentrated. The residue was purified with column chromatography (SiO₂, PE:EtOAc=10:1) to give 1-(5,6-dichloropyridin-2-yl)pyrrolidine-2-carbaldehyde (161 mg, yield 23%) as a light brown oil. LCMS: [M+H]⁺=245.0.

(6-Chloro-2-((1-(5,6-dichloropyridin-2-yl)pyrrolidin-2-yl)methyl)-2,3,4,9-tetrahydro-1H-pyrido[3,4-b]indol-1-yl)methanol

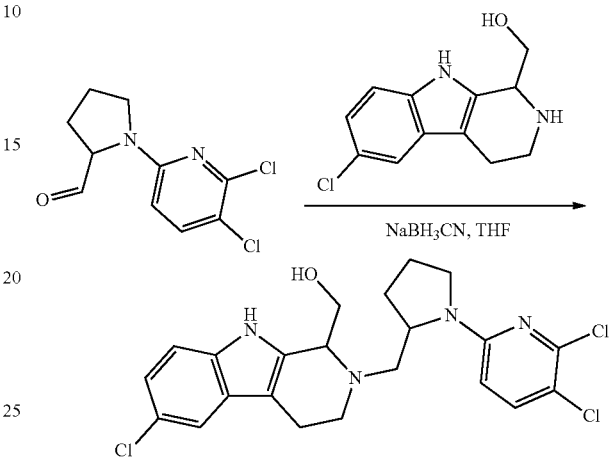

To a solution of 1-(5,6-dichloropyridin-2-yl)pyrrolidine-2-carbaldehyde (113 mg, 0.46 mmol, 1.0 eq) and (6-chloro-2,3,4,9-tetrahydro-1H-pyrido[3,4-b]indol-1-yl)methanol (120 mg, 0.51 mmol, 1.1 eq) in THF (5 mL) was added 3 drops of CH₃COOH. The mixture was stirred at 40° C. for 2 h. NaBH₃CN (157 mg, 1.38 mmol, 3.0 eq) was added at rt in portions. The mixture was stirred at 40° C. for 2 h. The reaction mixture was diluted with EtOAc (20 mL) and washed with brine (10 mL). The solution was dried over Na₂SO₄ and concentrated. The residue was purified by prep-HPLC to give (6-chloro-2-((1-(5,6-dichloropyridin-2-yl)pyrrolidin-2-yl)methyl)-2,3,4,9-tetrahydro-1H-pyrido[3,4-b]indol-1-yl)methanol (37.33 mg, yield: 17%) as a white solid. ¹H NMR (400 MHz, DMSO-d₆): δ 10.80 (s, 1H), 7.61 (d, J=8.8 Hz, 1H), 7.37 (d, J=2, 0 Hz, 1H), 7.32 (d, J=8.4 Hz, 1H), 6.99 (dd, J=8.8 Hz, 2.0 Hz, 1H), 6.42 (d, J=8.8 Hz, 1H), 4.64-4.61 (m, 1H), 4.13-4.03 (m, 2H), 3.72-3.62 (m, 2H), 3.44-3.39 (m, 1H), 3.20-3.12 (m, 2H), 2.95-2.91 (m, 1H), 2.75-2.63 (m, 2H), 2.47-2.34 (m, 2H), 2.08-1.91 (m, 4H). LCMS: [M+H]⁺=467.2

3-((6-Chloro-2-((1-(5-chloro-6-(trifluoromethyl)pyridin-2-yl)pyrrolidin-2-yl)methyl)-2,3,4,9-tetrahydro-1H-pyrido[3,4-b]indol-1-yl)methyl)-1-methyl-1H-imidazol-3-ium chloride hydrochloride

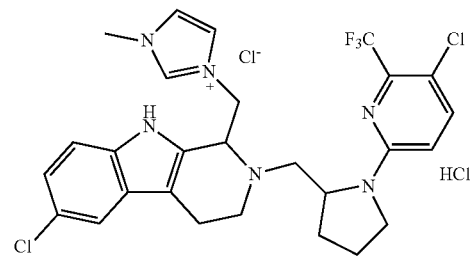

215

¹H NMR (400 MHz, MeOD-d₄) δ 8.92 (d, J=38.1 Hz, 1H), 7.97-7.44 (m, 5H), 7.30 (d, J=8.7 Hz, 1H), 7.18 (d, J=8.8 Hz, 1H), 6.78 (s, 1H), 4.51 (s, 1H), 3.95 (s, 6H), 3.51 (d, J=27.7 Hz, 4H), 2.08 (t, J=50.5 Hz, 5H), 1.29 (s, 2H). LCMS: [M+1]⁺=563.2

1-(Azetidin-3-yl)-N-((6-chloro-2-((1-(5-chloro-6-(trifluoromethyl)pyridin-2-yl)pyrrolidin-2-yl)methyl)-2,3,4,9-tetrahydro-1H-pyrido[3,4-b]indol-1-yl)methyl)methanamine

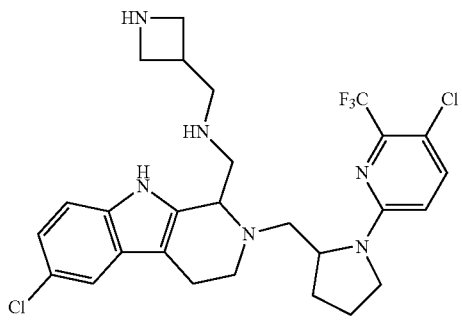 [SMILES: FC(F)(F)c1nc(N2CCCC2CN2CCc3c([nH]c4ccc(Cl)cc34)C2CNCC2CNC2)ccc1Cl]

¹H NMR (400 MHz, CD₃OD) δ 7.75 (d, J=9.0 Hz, 1H), 7.58 (s, 1H), 7.43 (d, J=8.7 Hz, 1H), 7.22 (d, J=8.7 Hz, 1H), 6.84 (d, J=9.1 Hz, 1H), 4.96 (s, 4H), 4.22-3.95 (m, 7H), 3.61 (m, 8H), 2.41-2.13 (m, 5H). LCMS: [M+1]⁺=567.2

3-((6-chloro-2-(((2S, 4R)-1-(5-chloro-6-(trifluoromethyl)pyridin-2-yl)-4-hydroxypyrrolidin-2-yl)methyl)-2,3,4,9-tetrahydro-1H-pyrido[3,4-b]indol-1-yl)methyl)-1-methyl-1H-imidazol-3-ium

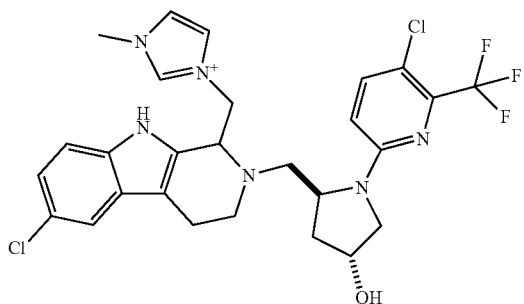

Diastereomer 1: ¹H NMR (400 MHz, DMSO-d₆): δ 9.03 (s, 1H), 7.63-7.52 (m, 3H), 7.40-7.41 (m, 1H), 7.32 (d, J=8.4 Hz, 1H), 7.09-7.06 (m, 1H), 6.59-6.54 (m, 1H), 4.60-4.27 (m, 4H), 3.99 (s, 3H), 3.65-3.47 (m, 3H), 3.16-3.08 (m, 3H), 3.01-2.79 (m, 1H), 2.52-2.33 (m, 2H), 2.10-2.05 (m, 1H), 1.70-1.63 (m, 1H). LCMS: [M]⁺=579.0

Diastereomer 2: ¹H NMR (400 MHz, DMSO-d₆): δ 8.95 (s, 1H), 7.64-7.59 (m, 3H), 7.59-7.40 (m, 2H), 7.39-7.27 (m, 1H), 7.08-7.05 (m, 1H), 6.64 (d, J=9.2 Hz, 1H), 4.55-4.40 (m, 3H), 4.03-3.94 (m, 4H), 3.57-3.35 (m, 6H), 3.13-3.02 (m, 1H), 2.50-2.46 (m, 1H), 2.19-2.18 (m, 1H), 1.91-1.89 (m, 1H), 1.69-1.66 (m, 1H). LCMS: [M]⁺=579.0

(3R, 5S)-5-((1-(((azetidin-3-ylmethyl)amino)methyl)-6-chloro-1,3,4,9-tetrahydro-2H-pyrido[3,4-b]indol-2-yl)methyl)-1-(5-chloro-6-(trifluoromethyl)pyridin-2-yl)pyrrolidin-3-ol

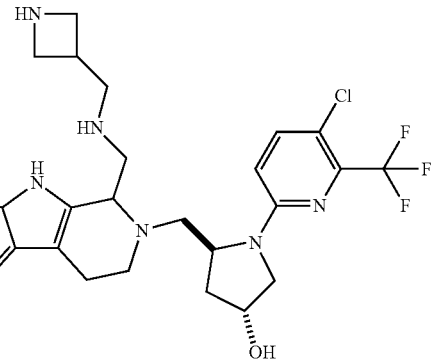

¹H NMR (400 MHz, DMSO-d₆): δ 7.75-7.72 (m, 1H), 7.55-7.50 (m, 1H), 7.40-7.38 (m, 1H), 7.18-7.16 (m, 1H), 6.85-6.83 (m, 1H), 4.70-4.62 (m, 3H), 4.23-3.94 (m, 6H), 3.79-3.72 (m, 6H), 3.20-3.11 (m, 3H), 2.39-2.37 (m, 2H). LCMS: [M+1]⁺=583.2

(6-Chloro-2-(1-(5-chloro-6-(trifluoromethyl)pyridin-2-yl)pyrrolidin-3-yl)-2,3,4,9-tetrahydro-1H-pyrido[3,4-b]indol-1-yl)methanol hydrochloride

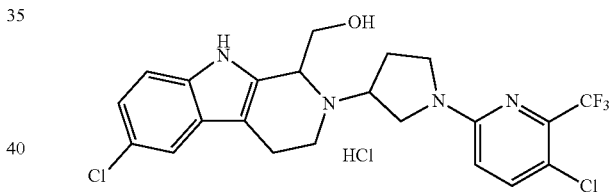

¹H NMR (400 MHz, DMSO-d₆): δ 11.38~11.35 (m, 1H), 10.95 (brs, 1H), 7.86 (d, J=8.8 Hz, 1H), 7.60 (s, 1H), 7.43 (d, J=8.8 Hz, 1H), 7.15 (d, J=8.0 Hz, 1H), 6.85 (d, J=9.2 Hz, 1H), 5.89 (brs, 1H), 4.75~4.70 (m, 1H), 4.19~4.05 (m, 4H), 3.82~3.71 (m, 4H), 3.03 (brs, 2H), 2.60~2.54 (m, 2H). ¹⁹F NMR (376 MHz, DMSO-d₆): δ −64.73 LCMS: [M+H]⁺=485.1

(6-Chloro-2-(1-(5-chloro-6-(trifluoromethyl)pyridin-2-yl)azetidin-3-yl)-2,3,4,9-tetrahydro-1H-pyrido[3,4-b]indol-1-yl)methanol hydrochloride

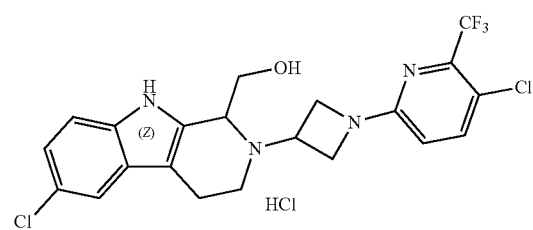 [SMILES: OCC1c2[nH]c3ccc(Cl)cc3c2CCN1C1CN(c2ccc(Cl)c(C(F)(F)F)n2)C1 ; Cl]

217

¹H NMR (400 MHz, DMSO-d₆): δ 12.15~11.21 (m, 2H), 7.92 (d, J=8.8 Hz, 1H), 7.60 (s, 1H), 7.41 (d, J=8.4 Hz, 1H), 7.15 (dd, J=8.8 Hz, 2.0 Hz, 1H), 6.84 (d, J=8.8 Hz, 1H), 5.89-5.69 (m, 1H), 4.86~4.29 (m, 6H), 4.06 (d, J=2.0 Hz, 2H), 3.79~3.42 (m, 3H), 3.05~2.89 (m, 2H). ¹⁹F NMR (376 MHz, DMSO-d₆): δ −64.73 LCMS: [M+H]⁺=471.1

(6-Chloro-2-((1-(5,6-dichloropyridin-2-yl)azetidin-2-yl)methyl)-2,3,4,9-tetrahydro-1H-pyrido[3,4-b]indol-1-yl)methanol hydrochloride

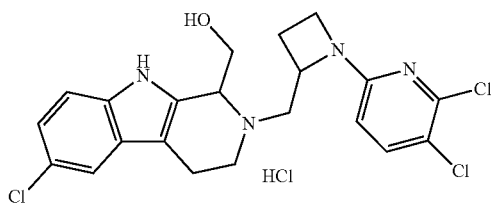 [SMILES: OCC1c2[nH]c3ccc(Cl)cc3c2CCN1CC1CCN1c1ccc(Cl)c(Cl)n1 ; Cl]

¹H NMR (400 MHz, DMSO-d₆): δ 11.52~11.50 (m, 1H), 10.43~9.85 (m, 1H), 7.86~7.83 (m, 1H), 7.59~7.56 (m, 1H), 7.41 (dd, J=8.8 Hz, 2.4 Hz, 1H), 7.15 (d, J=8.4 Hz, 1H), 6.62~6.53 (m, 1H), 5.87~5.75 (m, 1H), 4.93~4.77 (m, 2H), 4.19~3.66 (m, 8H), 3.12~3.07 (m, 2H), 2.54~2.50 (m, 1H), 2.37~2.31 (m, 1H). LCMS: [M+H]⁺=451.0

6-Chloro-2-((1-(5-chloro-6-(trifluoromethyl)pyridin-2-yl)piperazin-2-yl)methyl)-2,3,4,9-tetrahydro-1H-pyrido[3,4-b]indole hydrochloride

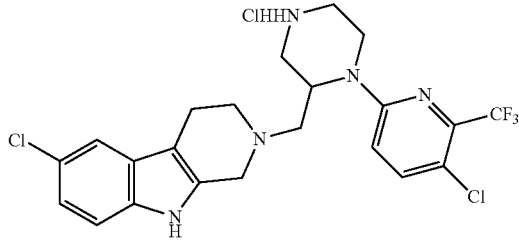

¹H NMR (500 MHz, DMSO-d₆) δ 11.36 (d, J=19.5 Hz, 1H), 10.64 (s, 1H), 10.33 (s, 1H), 8.00 (d, J=8.7 Hz, 1H), 7.55 (s, 1H), 7.40 (s, 1H), 7.34 (d, J=9.2 Hz, 1H), 7.11 (d, J=8.5 Hz, 1H), 5.45 (d, J=49.1 Hz, 1H), 4.89-4.63 (m, 1H), 4.52 (s, 1H), 4.21 (m, 2H), 4.01 (m, 2H), 3.88 (s, 1H), 3.67 (s, 1H), 3.57 (m, 1H), 3.29 (m, 2H), 3.09 (m, 3H), 2.91 (s, 1H). LCMS: [M+H]⁺=484.1

218

6-Chloro-2-((1-(5-chloro-6-(trifluoromethyl)pyridin-2-yl)-4-methylpiperazin-2-yl)methyl)-2,3,4,9-tetrahydro-1H-pyrido[3,4-b]indole

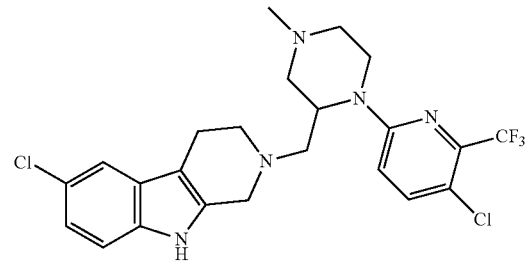 [SMILES: CN1CCN(c2ccc(Cl)c(C(F)(F)F)n2)C(CN2CCc3c([nH]c4ccc(Cl)cc34)C2)C1]

¹H NMR (500 MHz, Chloroform-d) δ 7.50 (d, J=9.0 Hz, 1H), 7.40 (d, J=2.0 Hz, 1H), 7.28 (dd, J=8.6, 2.1 Hz, 1H), 7.11 (dd, J=8.6, 2.1 Hz, 1H), 6.64 (d, J=9.1 Hz, 1H), 4.81 (s, 1H), 3.88 (d, J=15.1 Hz, 1H), 3.75 (d, J=15.2 Hz, 1H), 3.68 (d, J=12.7 Hz, 1H), 3.17 (qd, J=8.2, 3.3 Hz, 2H), 3.09 (dd, J=12.3, 9.5 Hz, 1H), 3.00 (dt, J=11.7, 5.8 Hz, 1H), 2.91-2.80 (m, 2H), 2.67 (d, J=5.7 Hz, 2H), 2.53 (dd, J=12.3, 4.6 Hz, 1H), 2.29 (s, 3H), 2.08 (ddd, J=23.8, 11.9, 3.8 Hz, 2H). LCMS: [M+H]⁺=498.1

6-Chloro-2-((1-(5-chloro-6-(trifluoromethyl)pyridin-2-yl)-4-ethylpiperazin-2-yl)methyl)-2,3,4,9-tetrahydro-1H-pyrido[3,4-b]indole

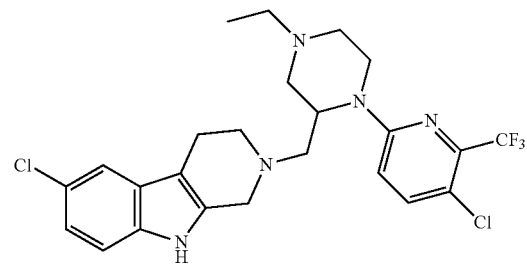 [SMILES: CCN1CCN(c2ccc(Cl)c(C(F)(F)F)n2)C(CN2CCc3c([nH]c4ccc(Cl)cc34)C2)C1]

¹H NMR (500 MHz, Chloroform-d) δ 7.69 (s, 1H), 7.48 (d, J=9.0 Hz, 1H), 7.40 (d, J=2.0 Hz, 1H), 7.20 (d, J=8.5 Hz, 1H), 7.06 (dd, J=8.5, 1.9 Hz, 1H), 6.64 (d, J=9.1 Hz, 1H), 4.74 (s, 1H), 3.94 (d, J=15.3 Hz, 1H), 3.78 (d, J=15.3 Hz, 1H), 3.66 (d, J=12.0 Hz, 1H), 3.31 (d, J=11.3 Hz, 1H), 3.17 (td, J=12.3, 3.6 Hz, 1H), 3.10 (dd, J=12.3, 9.5 Hz, 1H), 2.98 (ddt, J=20.7, 14.6, 7.7 Hz, 3H), 2.77-2.60 (m, 2H), 2.51 (dd, J=12.2, 7.2 Hz, 1H), 2.46 (dd, J=12.2, 4.0 Hz, 1H), 2.41-2.32 (m, 1H), 2.13 (td, J=11.8, 3.7 Hz, 1H), 2.10-2.01 (m, 1H), 1.12 (t, J=7.2 Hz, 3H). LCMS: [M+H]⁺=512.1

2-(3-((6-Chloro-1,3,4,9-tetrahydro-2H-pyrido[3,4-b]indol-2-yl)methyl)-4-(5-chloro-6-(trifluoromethyl)pyridin-2-yl)piperazin-1-yl)ethan-1-ol

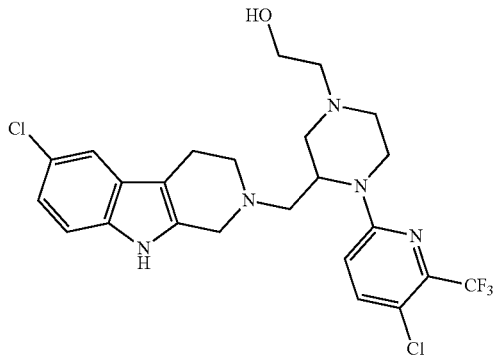 [SMILES: OCCN1CCN(c2ccc(Cl)c(C(F)(F)F)n2)C(CN2CCc3c([nH]c4ccc(Cl)cc34)C2)C1]

¹H NMR (500 MHz, Chloroform-d) δ 7.78 (s, 1H), 7.51 (d, J=9.1 Hz, 1H), 7.40 (d, J=2.0 Hz, 1H), 7.19 (d, J=8.5 Hz, 1H), 7.06 (dd, J=8.6, 2.1 Hz, 1H), 6.65 (d, J=9.1 Hz, 1H), 4.78 (d, J=9.6 Hz, 1H), 3.88 (d, J=15.1 Hz, 1H), 3.76 (d, J=15.2 Hz, 1H), 3.71 (ddd, J=11.3, 7.4, 3.9 Hz, 2H), 3.65 (ddd, J=11.2, 5.5, 4.4 Hz, 1H), 3.35 (dt, J=11.5, 2.0 Hz, 1H), 3.19 (td, J=12.3, 3.6 Hz, 1H), 3.12-2.98 (m, 2H), 2.98-2.85 (m, 2H), 2.69 (t, J=5.8 Hz, 2H), 2.65 (td, J=7.7, 3.7 Hz, 1H), 2.55 (ddd, J=12.6, 5.5, 4.0 Hz, 1H), 2.50-2.41 (m, 1H), 2.34 (td, J=11.7, 3.7 Hz, 1H), 2.23 (dd, J=11.4, 3.7 Hz, 1H). LCMS; [M+H]⁺=528.2.

2-((12-Chloranyl)amino)-1-(3-((6-chloro-1,3,4,9-tetrahydro-2H-pyrido[3,4-b]indol-2-yl)methyl)-4-(5-chloro-6-(trifluoromethyl)pyridin-2-yl)piperazin-1-yl)ethan-1-one

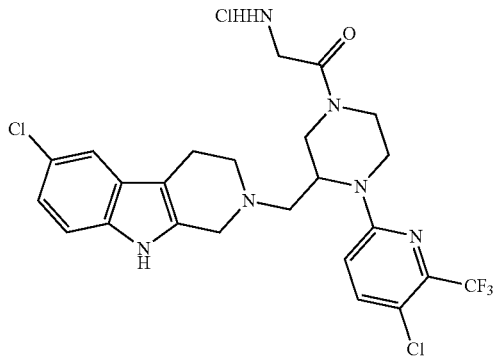

¹H NMR (500 MHz, Methanol-d₄) δ 7.83 (d, J=9.1 Hz, 1H), 7.46 (d, J=2.0 Hz, 1H), 7.31 (d, J=8.7 Hz, 1H), 7.22 (d, J=9.3 Hz, 2H), 7.10 (dd, J=8.7, 2.0 Hz, 1H), 5.56 (s, 1H), 4.70 (s, 2H), 4.50 (d, J=14.1 Hz, 1H), 4.29 (d, J=15.8 Hz, 1H), 4.08 (dd, J=29.4, 15.3 Hz, 2H), 3.95 (d, J=16.0 Hz, 1H), 3.87 (d, J=31.5, 10.4 Hz, 1H), 3.79-3.69 (m, 2H), 3.65 (q, J=5.3, 4.9 Hz, 2H), 3.61-3.51 (m, 2H), 3.45-3.36 (m, 1H), 3.25-3.18 (m, 1H), 3.14 (d, J=15.7 Hz, 1H). LCMS: [M+H]⁺=512.1.

N-(2-(3-((6-Chloro-1,3,4,9-tetrahydro-2H-pyrido[3,4-b]indol-2-yl)methyl)-4-(5-chloro-6-(trifluoromethyl)pyridin-2-yl)piperazin-1-yl)ethyl)-12-chloranamine

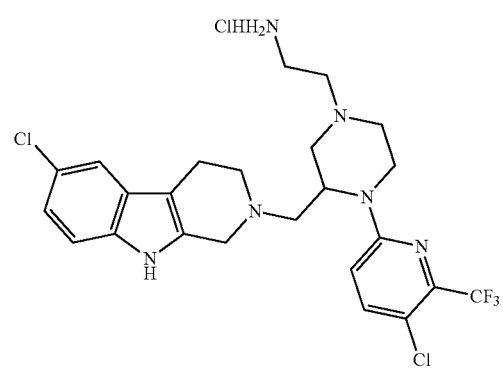

¹H NMR (500 MHz, DMSO-d₆) δ 11.39 (s, 1H), 8.12 (d, J=9.1 Hz, 1H), 7.56-7.51 (m, 1H), 7.39 (d, J=8.6 Hz, 1H), 7.11 (dd, J=8.7, 2.1 Hz, 1H), 6.94 (d, J=9.2 Hz, 1H), 4.60 (d, J=28.0 Hz, 2H), 4.37-4.19 (m, 2H), 3.94 (d, J=34.6 Hz, 1H), 3.84-3.53 (m, 10H), 3.44 (dd, J=8.7, 7.2 Hz, 2H), 3.01 (s, 3H).

Representative synthesis of 1-((6-chloro-2-((1-(5-chloro-6-(trifluoromethyl)pyridin-2yl)piperazin-2-yl)methyl)-2,3,4,9-tetrahydro-1H-pyrido[3,4-b]indol-1yl)methyl)guanidine

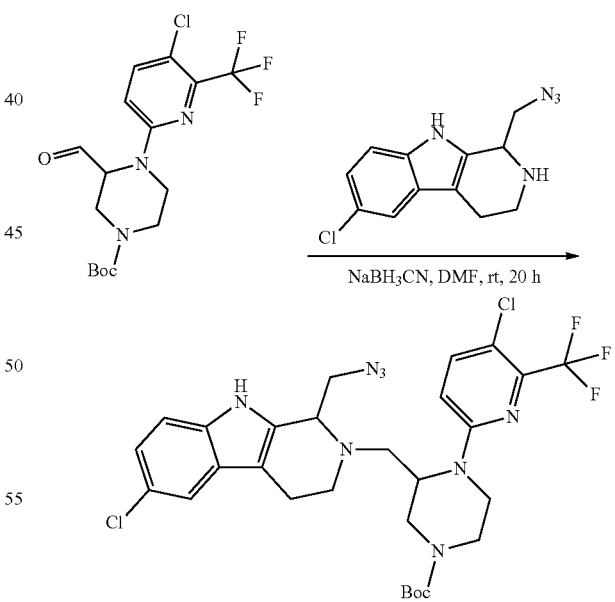

To a solution of tert-butyl4-(5-chloro-6-(trifluoromethyl)pyridin-2-yl)-3-formylpiperazine-1-carboxylate (1.0 g, 2.5 mmol, 1.0 eq) in DMF (10 mL) was added 1-(azidomethyl)-6-chloro-2,3,4,9-tetrahydro-1H-pyrido[3,4-b]indole (670.0 mg, 2.5 mmol, 1.0 eq). The reaction was stirred at 40° C. for 14 h. Then NaBH₃CN (488.0 mg, 7.5 mmol, 3.0 eq) was added, and the reaction was stirred at rt for 30 min. The mixture was concentrated and purified by silica gel column chromatography to afford tert-butyl3-((1-(azidomethyl)-6-chloro-1,3,4,9-tetrahydro-2H-pyrido[3,4-b]indol-2-yl)methyl)-4-(5-chloro-6-(trifluoromethyl)pyridin-2-yl)piperazine-1-carboxylate (1.1 g, yield: 68.0%) as a yellow solid. LCMS: [M+1]$^+$=639.2 organic layer was dried over $Na_2SO_4$ and concentrated. The residue was purified by silica gel column chromatography to afford tert-butyl3-((1-(aminomethyl)-6-chloro-1,3,4,9-tetrahydro-2H-pyrido-[3,4-b]indol-2-yl)methyl)-4-(5-chloro-6-(trifluoromethyl)pyridin-2-yl)piperazine-1-carboxylate(1.0 g, 70.0% yield) as a yellow solid. LCMS: [M+1]$^+$=613.3

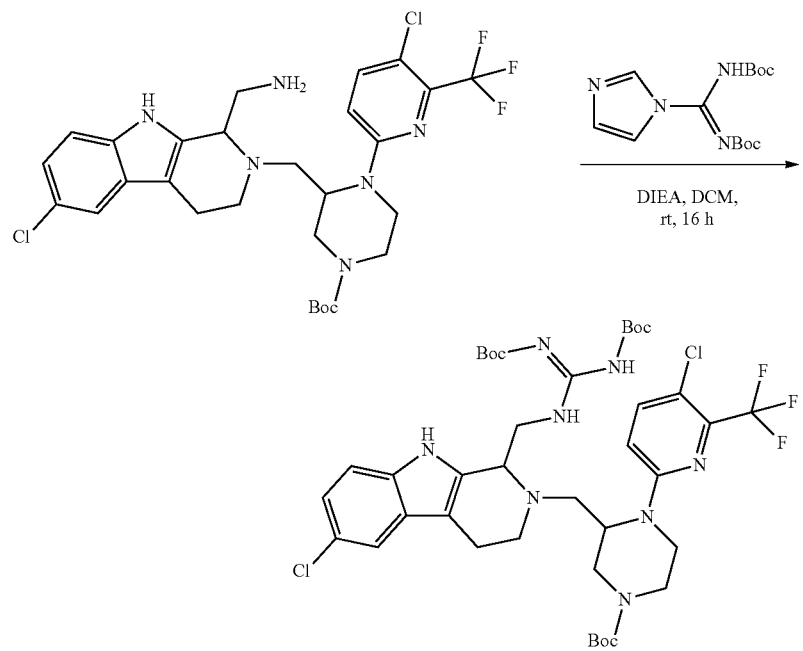

To a solution of tert-butyl3-((1-(aminomethyl)-6-chloro-1,3,4,9-tetrahydro-2H-pyrido[3,4-b]indol-2-yl)methyl)-4-(5-chloro-6-(trifluoromethyl)pyridin-2-yl)piperazine-1-carboxylate (500.0 mg, 0.8 mmol, 1.0 eq) in DCM (10 mL) was added DIEA (210.0 mg, 1.6 mmol, 2.0 eq) and tert-butyl (E)-(((tert-butoxycarbonyl)imino)(1H-imidazol-1-yl)methyl)carbamate (301.0 mg, 1.0 mmol, 1.2 eq). The mixture was stirred at rt for 16 h, and then concentrated to afford tert-butyl (E)-3-((1-((2,3-bis(tert-butoxycarbonyl)guanidino)methyl)-6-chloro-1,3,4,9-tetrahydro-2H-pyrido[3,4-b]indol-2-yl)methyl)-4-(5-chloro-6-(trifluoromethyl)pyridin-2-yl)piperazine-1-carboxylate (700.0 mg crude, yield: >99%) as a white solid. LCMS: [M+1]$^+$=855.2

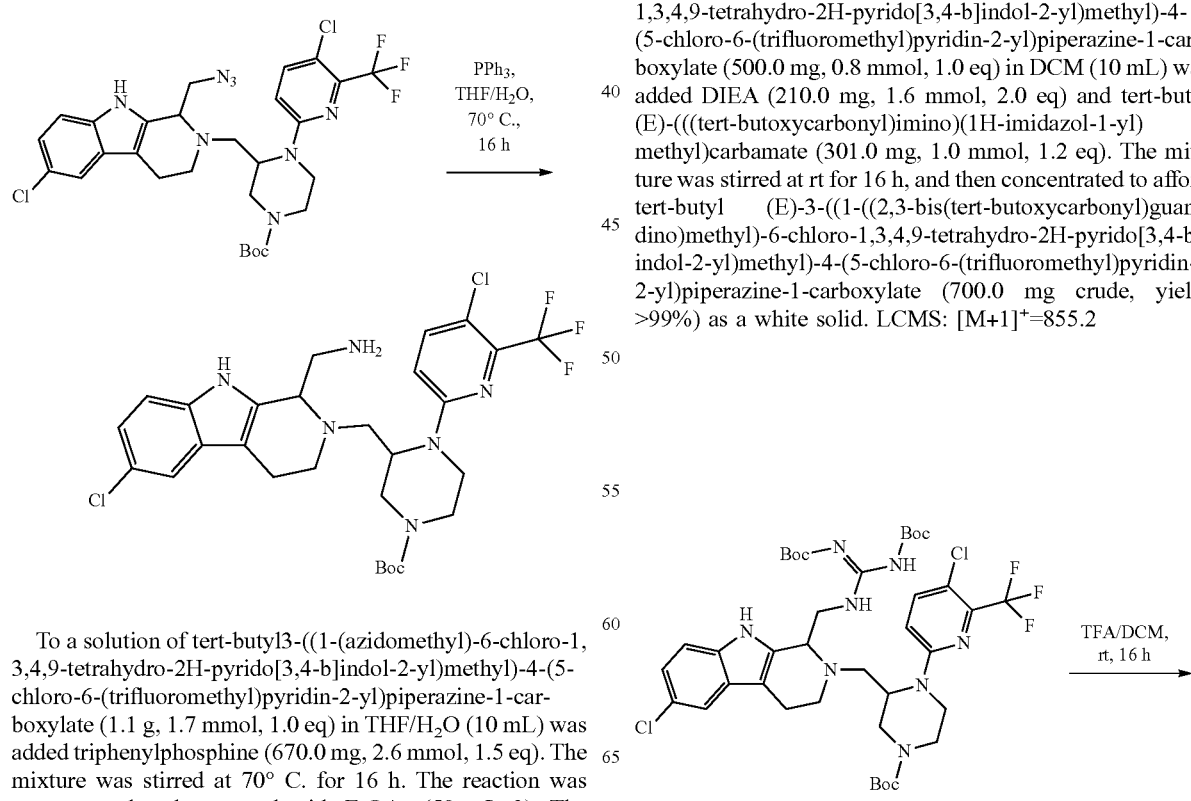

To a solution of tert-butyl3-((1-(azidomethyl)-6-chloro-1,3,4,9-tetrahydro-2H-pyrido[3,4-b]indol-2-yl)methyl)-4-(5-chloro-6-(trifluoromethyl)pyridin-2-yl)piperazine-1-carboxylate (1.1 g, 1.7 mmol, 1.0 eq) in THF/H$_2$O (10 mL) was added triphenylphosphine (670.0 mg, 2.6 mmol, 1.5 eq). The mixture was stirred at 70° C. for 16 h. The reaction was concentrated and extracted with EtOAc (50 mL×3). The

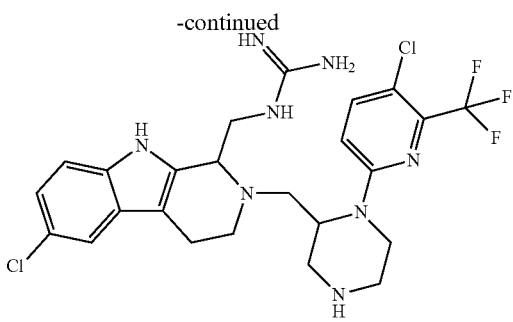

To a solution of tert-butyl (E)-3-((1-((2,3-bis(tert-butoxy-carbonyl)guanidino)-methyl)-6-chloro-1,3,4,9-tetrahydro-2H-pyrido[3,4-b]indol-2-yl)methyl)-4-(5-chloro-6-(trifluoromethyl)pyridin-2-yl)piperazine-1-carboxylate (1.6 g, 1.8 mmol, 1.0 eq) in DCM (15 mL) was added TFA (5 mL). The mixture was stirred at rt for 3 h, and then purified by prep-HPLC to afford two diastereomers: diastereomer 1 (450.0 mg, yield: 43%) and diastereomer 2 (400.0 mg, yield: 38.0%) as yellow solids. Each diastereomer could be further separated into their two enantiomers via chiral SFC separation.

Diastereomer 1: $^1$H NMR (400 MHz, CD$_3$OD) δ 7.71 (d, J=8.0 Hz, 1H), 7.37 (s, 1H), 7.26 (d, J=8.6 Hz, 1H), 7.08-7.02 (m, 2H), 4.28-4.12 (m, 2H), 3.87 (d, J=13.1 Hz, 1H), 3.62-3.47 (m, 3H), 3.40-3.30 (m, 4H), 3.23-3.15 (m, 2H), 3.03-3.09 (m, 1H), 2.73-2.89 (m, 2H), 2.53-2.50 (m, 1H). LCMS: [M+1]$^+$=555.2

Diastereomer 2: $^1$H NMR (400 MHz, CD$_3$OD) δ 7.75 (d, J=9.1 Hz, 1H), 7.33 (d, J=1.8 Hz, 1H), 7.23 (d, J=8.6 Hz, 1H), 7.09-6.99 (m, 2H), 5.20 (s, 1H), 4.21 (d, J=13.6 Hz, 1H), 4.05-3.95 (m, 1H), 3.82 (d, J=12.9 Hz, 1H), 3.63-3.50 (m, 4H), 3.31-3.10 (m, 4H), 2.96-2.86 (m, 3H), 2.52-2.48 (m, 1H). LCMS: [M+1]$^+$=555.2

3-((6-Chloro-2-((4-(5-chloro-6-(trifluoromethyl)pyridin-2-yl)piperazin-2-yl)methyl)-2,3,4,9-tetrahydro-1H-pyrido[3,4-b]indol-1-yl)methyl)-1-methyl-1H-imidazol-3-ium chloride hydrochloride

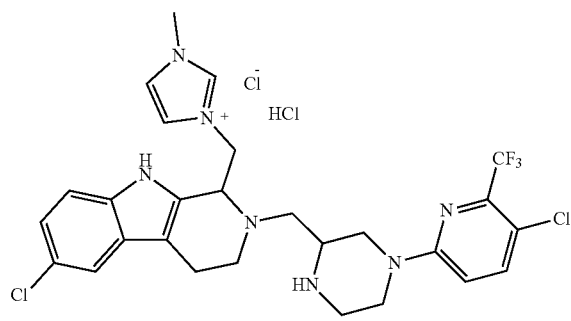

Diastereomer 1: $^1$H NMR (400 MHz, DMSO-d$_6$): δ 9.09-9.02 (m, 1H), 7.79 (d, J=8.8 Hz, 1H), 7.64-7.56 (m, 2H), 7.44 (s, 1H), 7.31 (d, J=8.4 Hz, 1H), 7.15-7.08 (m, 2H), 4.88-4.70 (m, 2H), 4.44-4.38 (m, 3H), 3.94 (s, 1H), 3.55-3.52 (m, 2H), 3.45-3.39 (m, 3H), 3.31-3.22 (m, 3H), 3.18-2.90 (m, 4H), 2.60-2.56 (m, 1H). LCMS: [M]$^+$=578.0

Diastereomer 2: $^1$H NMR (400 MHz, DMSO-d$_6$): δ 9.22-9.12 (m, 1H), 8.00 (s, 1H), 7.82-7.79 (m, 1H), 7.72-7.65 (m, 1H), 7.52 (s, 1H), 7.45 (d, J=1.6 Hz, 1H), 7.32 (d, J=8.4 Hz, 1H), 7.17-7.08 (m, 2H), 4.76-4.67 (m, 2H), 4.41-4.33 (m, 2H), 3.95 (s, 1H), 4.53-3.36 (m, 4H), 3.32-3.12 (m, 3H), 3.01 (s, 3H), 3.97-2.94 (m, 2H), 2.87 (s, 2H), 2.70-2.60 (m, 1H). LCMS: [M]$^+$=578.0

3-((6-Chloro-2-((4-(5-chloro-6-(trifluoromethyl)pyridin-2-yl)morpholin-3-yl)methyl)-2,3,4,9-tetrahydro-1H-pyrido[3,4-b]indol-1-yl)methyl)-1-methyl-1H-imidazol-3-ium chloride

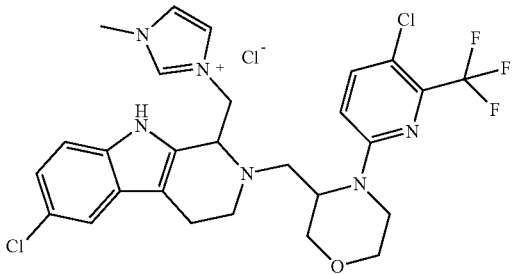

$^1$H NMR (400 MHz, CD$_3$OD): δ 8.90 (s, 1H), 7.59-7.52 (m, 2H), 7.51-7.34 (m, 2H), 7.22-7.18 (m, 1H), 7.01-6.97 (m, 1H), 6.88-6.84 (m, 1H), 4.81 (s, 3H), 4.59 (s, 2H), 3.91-3.86 (m, 4H), 3.76-3.57 (m, 4H), 3.36 (s, 3H), 2.88-2.60 (m, 3H). LCMS: [M]$^+$=579.0

1-(2-Amino-2-oxoethyl)-3-((6-chloro-2-((1-(5-chloro-6-(trifluoromethyl)pyridine-2-yl)piperazin-2-yl)methyl)-2,3,4,9-tetrahydro-1H-pyrido[3,4-b]indol-1-yl)methyl)-1H-imidazol-3-ium chloride

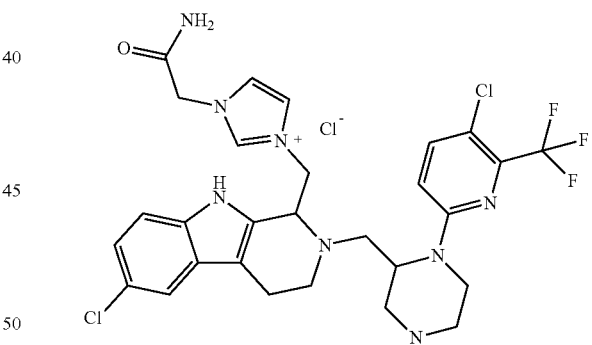

Diastereomer 1: $^1$H NMR (400 MHz, CD$_3$OD): δ 9.14 (s, 1H), 7.73 (d, J=8.8 Hz, 1H), 7.64-7.67 m, 2H), 7.44 (s, 1H), 7.31 (d, J=8.0 Hz, 1H), 7.07-7.10 (m, 2H), 5.20 (s, 2H), 4.79-4.55 (m, 4H), 4.18 (d, J=14.4 Hz, 1H), 3.42-3.48 (m, 5H), 3.09-3.25 (m, 4H), 3.00-2.90 (m, 1H), 2.02-2.67 (m, 1H). LCMS: [M]$^+$=621.9

Diastereomer 2: $^1$H NMR (400 MHz, DMSO-d$_6$): δ 11.30 (s, 1H), 9.48 (s, 2H), 9.21 (s, 1H), 7.90 (d, J=9.1 Hz, 1H), 7.83 (s, 1H), 7.73 (s, 1H), 7.37 (d, J=8.6 Hz, 1H), 7.15 (d, J=9.1 Hz, 2H), 7.07 (d, J=2.0 Hz, 1H), 7.05 (d, J=2.0 Hz, 1H), 5.19-5.08 (m, 2H), 4.73-4.64 (m, 2H), 4.56-4.44 (m, 2H), 4.08 (d, J=13.6 Hz, 1H), 3.27-3.07 (m, 3H), 3.00-2.92 (m, 2H), 2.85-2.77 (m, 2H), 2.76-2.71 (m, 2H), 2.67-2.39 (m, 2H). LCMS: [M]$^+$=621.9

225

1-(Azetidin-3-ylmethyl)-3-((6-chloro-2-((1-(5-chloro-6-(trifluoromethyl)pyridin-2-yl)piperazin-2-yl)methyl)-2,3,4,9-tetrahydro-1H-pyrido[3,4-b]indol-1-yl)methyl)-1H-imidazol-3-ium chloride hydrochloride

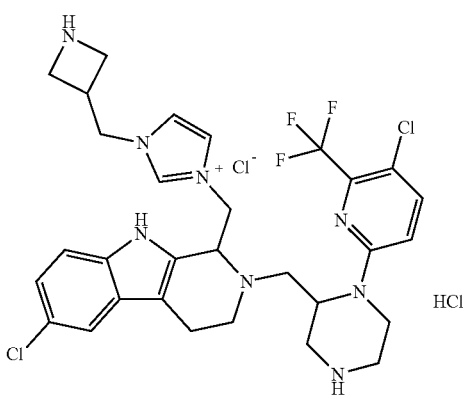

Diastereomer 1: $^1$H NMR (400 MHz, DMSO-d$_6$): δ 10.55 (s, 1H), 9.26 (s, 1H), 7.77-7.72 (m, 3H), 7.32-7.30 (m, 2H), 7.06-7.02 (m, 2H), 4.72-4.68 (m, 1H), 4.60-4.49 (m, 3H), 4.33-4.28 (m, 3H), 4.17-4.08 (m, 4H), 3.67-3.65 (m, 1H), 3.48-3.31 (m, 5H), 3.20-3.13 (m, 4H), 3.10-2.85 (m, 2H), 2.49-2.54 (m, 1H). LCMS: [M]$^+$=633.1

Diastereomer 2: $^1$H NMR (400 MHz, DMSO-d$_6$): δ 9.37 (s, 1H), 7.83 (d, J=8.8 Hz, 1H), 7.70-7.65 (m, 2H), 7.53 (d, J=1.6 Hz, 1H), 7.38 (d, J=8.8 Hz, 1H), 7.29 (d, J=9.2 Hz, 1H), 7.18-78.15 (m, 1H), 5.16-4.89 (m, 4H), 4.62 (d, J=7.2 Hz, 2H), 4.29-4.19 (m, 6H), 4.09-3.53 (m, 8H), 3.42-3.39 (m, 1H), 3.17-3.07 (m, 3H). LCMS: [M]$^+$=633.1

3-((6-Chloro-2-((1-(5-chloro-6-(trifluoromethyl)pyridin-2-yl)piperazin-2-yl)methyl)-2,3,4,9-tetrahydro-1H-pyrido[3,4-b]indol-1-yl)methyl)-1-methyl-1H-imidazol-3-ium chloride hydrochloride

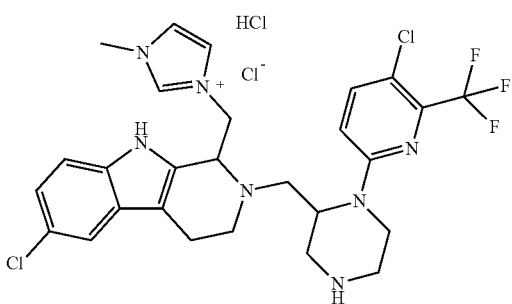

Diastereomer 1: $^1$H NMR (400 MHz, CD$_3$OD): δ 9.06 (s, 1H), 7.81-7.78 (d, J=12 Hz, 1H), 7.59-7.48 (m, 3H), 7.34-7.32 (d, J=8 Hz, 1H), 7.19-7.11 (m, 2H), 4.85-4.91 (m, 5H), 4.24-4.20 (d, J=16 Hz, 1H), 3.96 (s, 3H), 3.68-3.41 (m, 6H), 3.20-3.07 (m, 3H), 2.80 (s, 1H). LCMS: [M]$^+$=578.1

Diastereomer 2: $^1$H NMR (400 MHz, CD$_3$OD): δ 9.00 (s, 1H), 7.76-7.74 (d, J=8 Hz, 1H), 7.67 (s, 1H), 7.54 (s, 1H), 7.34-7.26 (m, 2H), 7.06-7.03 (m, 2H), 5.10-5.08 (m, 2H), 4.61-4.52 (m, 3H), 4.14-4.11 (d, J=12 Hz, 1H), 3.47-3.38 (m, 6H), 3.17-3.29 (m, 4H), 2.93-2.88 (m, 2H), 2.54-2.49 (m, 1H). LCMS: [M]$^+$=578.1

226

N-((6-chloro-2-((1-(5-chloro-6-(trifluoromethyl)pyridin-2-yl)piperazin-2-yl)methyl)-2,3,4,9-tetrahydro-1H-pyrido[3,4-b]indol-1-yl)methyl)azetidin-3-amine hydrochloride

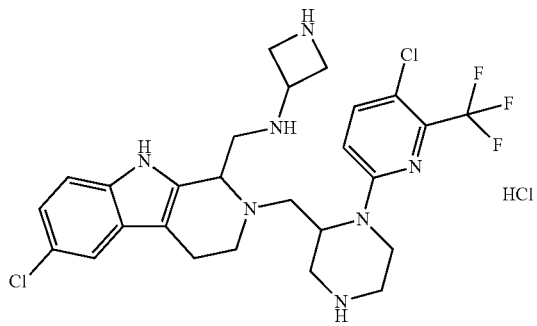 [SMILES: FC(F)(F)c1nc(N2CCNCC2CN2CCc3c([nH]c4ccc(Cl)cc34)C2CNC2CNC2)ccc1Cl ; Cl]

Diastereomer 1: $^1$H NMR (400 MHz, CD$_3$OD): δ 7.78 (d, J=9.2 Hz, 1H), 7.43 (d, J=2.0 Hz, 1H), 7.32-7.28 (m, 2H), 6.84 (dd, J=8.4, 2.0 Hz, 1H), 5.34 (brs, 1H), 4.56-4.53 (m, 1H), 4.46-4.45 (m, 1H), 4.40-4.32 (m, 4H), 4.04-4.0 (m, 1H), 3.57-3.36 (m, 9H), 3.25-3.21 (m, 2H), 3.07-3.00 (m, 1H), 2.78-2.74 (m, 1H). LCMS: [M+1]$^+$=568.1

Diastereomer 2: $^1$H NMR (400 MHz, CD$_3$OD): δ 7.77 (d, J=9.2 Hz, 1H), 7.35 (s, 1H), 7.26 (d, J=8.4, Hz, 1H), 7.09-7.04 (m, 2H), 5.29 (brs, 1H), 4.65-4.17 (m, 8H), 3.53-3.39 (m, 5H), 3.27-3.17 (m, 4H), 3.02-2.94 (m, 2H), 2.57-2.53 (m, 1H). LCMS: [M+1]$^+$=568.1

(6-Chloro-2-((1-(5-chloro-6-(trifluoromethyl)pyridin-2-yl)piperazin-2-yl)methyl)-2,3,4,9-tetrahydro-1H-pyrido[3,4-b]indol-1-yl)methanamine

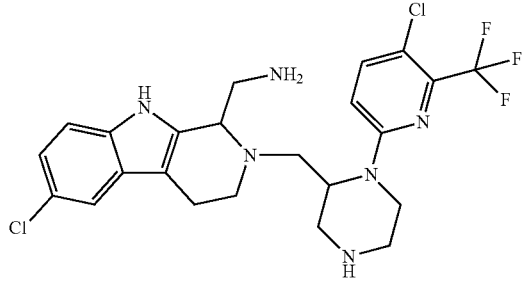 [SMILES: NCC1c2[nH]c3ccc(Cl)cc3c2CCN1CC1CNCCN1c1ccc(Cl)c(C(F)(F)F)n1]

Diastereomer 1: $^1$H NMR (400 MHz, CD$_3$OD): δ 7.76 (d, J=8.8 Hz 1H), 7.42 (s, 1H), 7.31 (d, J=8.8 Hz, 1H), 7.18 (d, J=8.4 Hz, 1H), 7.09 (d, J=8.4 Hz, 1H), 5.04-4.93 (m, 2H), 4.28-4.24 (m, 2H), 3.88-3.83 (m, 1H), 3.63-3.13 (m, 8H), 3.03-2.86 (m, 3H). LCMS: [M+1]$^+$=513.0

Diastereomer 2: $^1$H NMR (400 MHz, CD$_3$OD): δ 7.76 (d, J=9.2 Hz, 1H), 7.32 (s, 1H), 7.25 (d, J=8.8 Hz, 1H), 7.07-7.02 (m, 2H), 5.25 (d, J=9.2 Hz, 1H), 4.43-4.12 (m, 2H), 4.17-4.02 (m, 2H), 3.53 (d, J=12.8 Hz, 1H), 3.45-3.35 (m, 3H), 3.26-3.13 (m, 5H), 2.94-2.83 (m, 2H), 2.51 (d, J=15.2 Hz, 1H). LCMS: [M+1]$^+$=513.0

227

N-(2-aminoethyl)-6-chloro-2-(0-(5-chloro-6-(trifluoromethyl)pyridin-2-yl)piperazin-2-yl)methyl)-2,3,4,9-tetrahydro-1H-pyrido[3,4-b]indol-1-carbxamide dihydrochloride

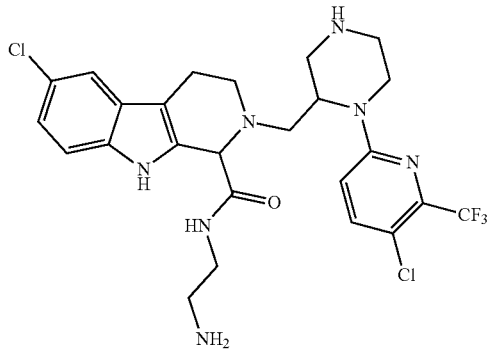 [SMILES: NCCNC(=O)C1c2[nH]c3ccc(Cl)cc3c2CCN1CC1CNCCN1c1ccc(Cl)c(C(F)(F)F)n1]

Diastereomer 1: ¹H NMR (300 MHz, Methanol-d₄) δ 7.82 (d, J=9.1 Hz, 1H), 7.45 (d, J=2.0 Hz, 1H), 7.37 (d, J=8.6 Hz, 1H), 7.21 (d, J=9.2 Hz, 1H), 7.11 (dd, J=8.7, 2.0 Hz, 1H), 5.33 (s, 1H), 4.27 (d, J=14.9 Hz, 1H), 3.84 (s, 1H), 3.77-3.59 (m, 2H), 3.58-3.34 (m, 5H), 3.26 (dd, J=14.0, 5.2 Hz, 2H), 3.17 (d, J=6.9 Hz, 2H), 3.07-2.61 (m, 4H). LCMS: [M+H⁺]=570.2

Diastereomer 2: ¹H NMR (300 MHz, Methanol-d₄) δ 7.87 (d, J=9.0 Hz, 1H), 7.48 (d, J=2.0 Hz, 1H), 7.44-7.34 (m, 1H), 7.24 (d, J=9.2 Hz, 1H), 7.15 (dd, J=8.7, 2.0 Hz, 1H), 5.53 (s, 1H), 4.27 (d, J=15.0 Hz, 1H), 3.90 (d, J=13.3 Hz, 1H), 3.81-3.56 (m, 4H), 3.56-3.37 (m, 3H), 3.32-3.12 (m, 6H), 3.05 (d, J=21.4 Hz, 2H). LCMS: [M+H⁺]=570.0

6-Chloro-2-((1-(5-chloro-6-(trifluoromethyl)pyridin-2-yl)piperazin-2-yl)methyl)-N-methyl-2,3,4,9-tetrahydro-1H-pyrido[3,4-b]indole-1-carboxamide hydrochloride

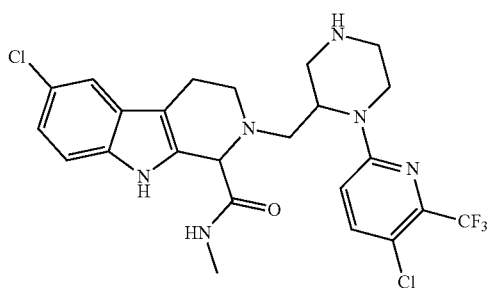 [SMILES: CNC(=O)C1c2[nH]c3ccc(Cl)cc3c2CCN1CC1CNCCN1c1ccc(Cl)c(C(F)(F)F)n1]

¹H NMR (300 MHz, Methanol-d₄) δ 7.87 (dd, J=9.1, 4.0 Hz, 1H), 7.46 (dd, J=7.0, 2.0 Hz, 1H), 7.40-7.32 (m, 1H), 7.23 (d, J=9.2 Hz, 1H), 7.12 (ddd, J=8.6, 4.8, 2.0 Hz, 1H), 5.43 (s, 1H), 4.30 (d, J=15.1 Hz, 1H), 3.83 (d, J=13.1 Hz, 1H), 3.74-3.35 (m, 5H), 3.32-3.11 (m, 4H), 2.97 (s, 2H), 2.87 (d, J=3.7 Hz, 3H). LCMS: [M+H⁺]=541.1

228

6-Chloro-2-((1-(5-chloro-6-(trifluoromethyl)pyridin-2-yl)piperazin-2-yl)methyl)-2,3,4,9-tetrahydro-1H-pyrido[3,4-b]indole-1-carboxamide hydrochloride (10)

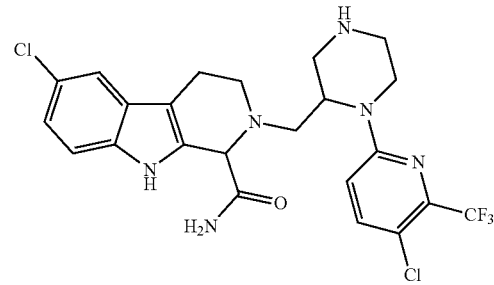 [SMILES: NC(=O)C1c2[nH]c3ccc(Cl)cc3c2CCN1CC1CNCCN1c1ccc(Cl)c(C(F)(F)F)n1]

¹H NMR (300 MHz, Methanol-d4) δ 7.78 (d, J=9.1 Hz, 1H), 7.39 (dd, J=2.1, 0.6 Hz, 1H), 7.31 (dd, J=8.6, 0.6 Hz, 1H), 7.11 (d, J=9.1 Hz, 1H), 7.05 (dd, J=8.6, 2.1 Hz, 1H), 5.12 (s, 1H), 4.50 (s, 1H), 4.30 (d, J=14.4 Hz, 1H), 3.83 (d, J=13.1 Hz, 1H), 3.55-3.36 (m, 4H), 3.29-3.15 (m, 2H), 3.05 (d, J=7.0 Hz, 1H), 2.98 (s, 1H), 2.82 (s, 1H), 2.55 (d, J=15.6 Hz, 1H). LCMS: [M+H⁺]=527.1

(1-(Aminomethyl)-6-chloro-1,3,4,9-tetrahydro-2H-pyrido[3,4-b]indol-2-yl)(1-(5-chloro-6-(trifluoromethyl)pyridin-2-yl)piperazin-2-yl)methanone dihydrochloride

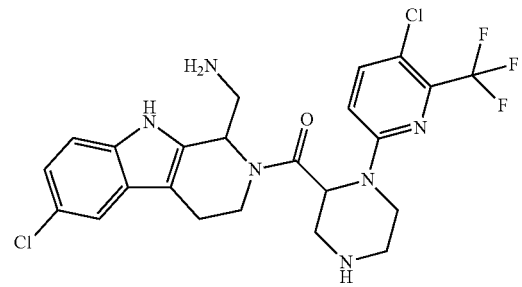 [SMILES: NCC1c2[nH]c3ccc(Cl)cc3c2CCN1C(=O)C1CNCCN1c1ccc(Cl)c(C(F)(F)F)n1]

¹H NMR (500 MHz, Methanol-d₄) δ 7.92 (d, J=9.0 Hz, 1H), 7.45 (d, J=2.0 Hz, 1H), 7.32 (dd, J=8.9, 3.6 Hz, 2H), 7.09 (dd, J=8.6, 2.0 Hz, 1H), 6.15 (d, J=4.2 Hz, 1H), 6.04-5.90 (m, 1H), 4.56-4.41 (m, 1H), 4.29 (d, J=15.3 Hz, 1H), 4.00-3.83 (m, 1H), 3.61 (d, J=13.3 Hz, 1H), 3.53 (td, J=12.7, 11.8, 3.7 Hz, 1H), 3.49-3.36 (m, 4H), 3.28-3.17 (m, 1H), 3.08-2.97 (m, 1H), 2.80 (dd, J=15.6, 3.7 Hz, 1H). LCMS; [M+H]⁺=527.1

229

1-((6-Chloro-2-(1-(5-chloro-6-(trifluoromethyl)pyridin-2-yl)piperazine-2-carbonyl)-2,3,4,9-tetrahydro-1H-pyrido[3,4-b]indol-1-yl)methyl)guanidine dihydrochloride

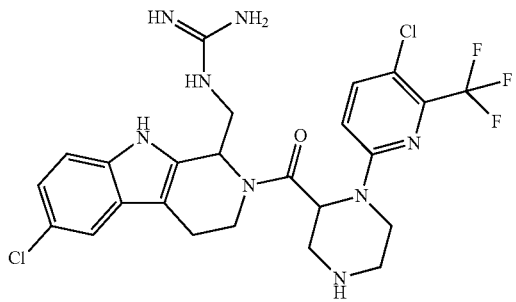 [SMILES: N=C(N)NCC1c2[nH]c3ccc(Cl)cc3c2CCN1C(=O)C1CNCCN1c1ccc(Cl)c(C(F)(F)F)n1]

$^1$H NMR (500 MHz, Methanol-$d_4$) δ 7.94 (d, J=9.0 Hz, 1H), 7.47 (d, J=2.0 Hz, 1H), 7.34 (dd, J=10.2, 8.8 Hz, 2H), 7.10 (dd, J=8.6, 2.0 Hz, 1H), 6.14 (d, J=4.4 Hz, 1H), 5.95 (dd, J=8.5, 4.4 Hz, 1H), 4.47 (dd, J=14.4, 5.0 Hz, 1H), 4.38-4.25 (m, 1H), 3.86 (ddd, J=15.4, 12.7, 3.2 Hz, 1H), 3.76 (dd, J=14.2, 4.6 Hz, 1H), 3.72-3.61 (m, 2H), 3.59-3.48 (m, 2H), 3.37 (dd, J=13.3, 4.6 Hz, 1H), 3.27 (td, J=12.7, 3.8 Hz, 1H), 3.06-2.94 (m, 1H), 2.88-2.80 (m, 1H). LCMS: [M+H]$^+$=569.2

(1-((Azetidin-3-ylamino)methyl)-6-chloro-1,3,4,9-tetrahydro-2H-pyrido[3,4-b]indol-2-yl)(1-(5-chloro-6-(trifluoromethyl)pyridin-2-yl)piperazin-2-yl)methanone trihydrochloride

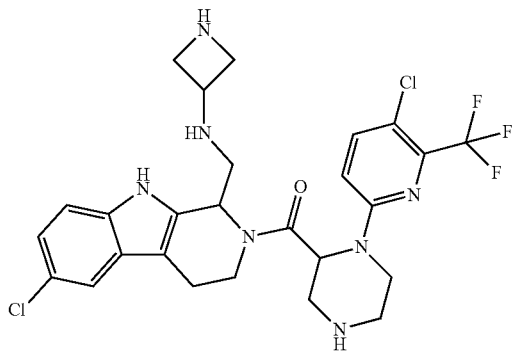 [SMILES: O=C(C1CNCCN1c1ccc(Cl)c(C(F)(F)F)n1)N1CCc2c([nH]c3ccc(Cl)cc23)C1CNC1CNC1]

230

$^1$H NMR (500 MHz, Methanol-$d_4$) δ 7.92 (d, J=9.0 Hz, 1H), 7.47 (d, J=2.0 Hz, 1H), 7.34 (dd, J=8.9, 5.1 Hz, 2H), 7.12 (dd, J=8.6, 2.0 Hz, 1H), 6.18 (d, J=4.3 Hz, 1H), 6.02 (s, 1H), 4.59-4.41 (m, 2H), 4.40-4.25 (m, 5H), 4.08 (t, J=14.1 Hz, 1H), 3.66 (d, J=13.2 Hz, 1H), 3.62-3.52 (m, 1H), 3.51-3.42 (m, 4H), 3.35 (td, J=3.2, 1.6 Hz, 2H), 2.82 (dd, J=15.6, 3.8 Hz, 1H). LCMS: [M+H]$^+$=582.1

General scheme 35

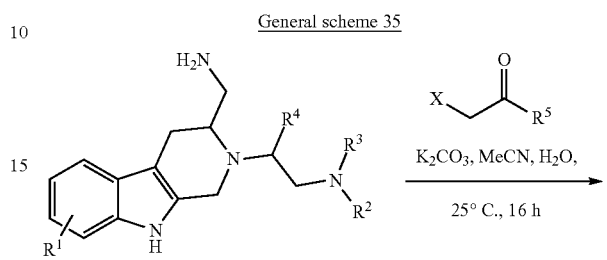

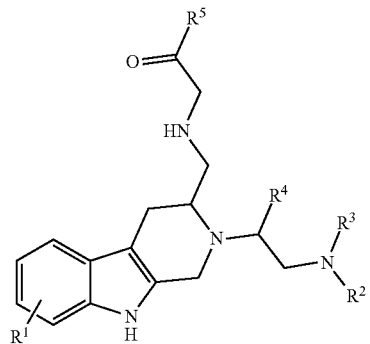

Representative of synthesis of compound 2-(((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)amino)acetamide triformate

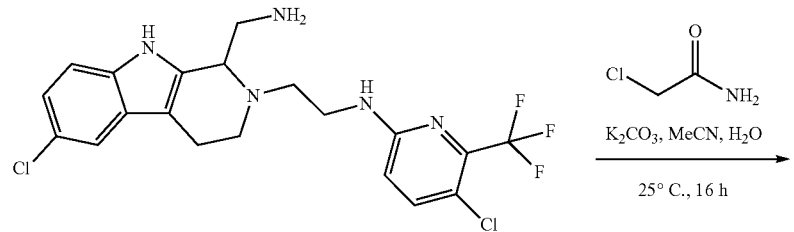

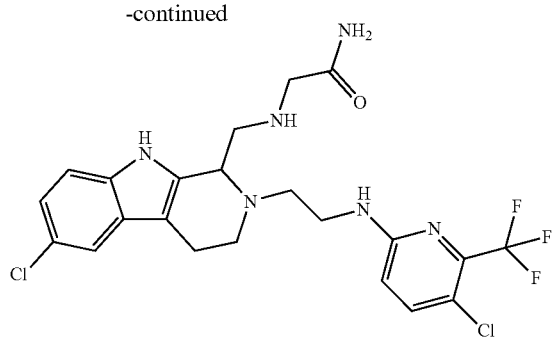

The mixture of N-(2-(1-(aminomethyl)-6-chloro-1,3,4,9-tetrahydro-2H-pyrido[3,4-b]indol-2-yl)ethyl)-5-chloro-6-(trifluoromethyl)pyridin-2-amine (300 mg, 0.66 mmol), 2-chloroacetamide (60 mg, 0.66 mmol), $K_2CO_3$ (230 mg, 1.65 mmol) and NaI (100 mg, 0.66 mmol) in MeCN (2 mL)/$H_2O$ (0.5 mL) was stirred at 30° C. for 3 days. The mixture was filtered and the filtrate was purified by prep-HPLC to give 2-(((6-chloro-2-(2-((5-chloro-6-(trifluoromethyl) pyridin-2-yl)amino)ethyl)-2,3,4,9-tetrahydro-1H-pyrido[3,4-b]indol-1-yl)methyl)amino)acetamide (17.00 mg, yield: 5%) as a white solid. $^1$H NMR (400 MHz, DMSO-$d_6$): δ 10.98 (s, 1H), 8.37 (brs, 3H), 7.62 (d, J=8.8 Hz, 1H), 7.39~7.27 (m, 4H), 7.08 (brs, 1H), 6.99 (dd, J=8.4 Hz, 2.0 Hz, 1H), 6.81 (d, J=8.8 Hz, 1H), 3.78~3.50 (m, 4H), 3.08 (s, 3H), 2.89~2.70 (m, 6H), 2.45~2.41 (m, 1H). LCMS: [M+H]$^+$=515.2

Representative synthesis of key intermediate 3-(5-chloro-6-(trifluoromethyl)pyridin-2-yl)-1,2,3-oxathiazolidine 2,2-dioxide: The mixture of 2-chloro-6-(trifluoromethyl)pyridine (1.82 g, 10 mmol) and 2-aminoethan-1-ol (3 ml, 50 mmol) was heated to 120° C. for 8 h. The mixture was cooled to rt and diluted with ethyl acetate (60 ml), washed with saturated ammonium chloride solution (30 ml) and brine (20 ml), then dried over $Na_2SO_4$ and concentrated to afford 2-((6-(trifluoromethyl)pyridin-2-yl)amino)ethan-1-ol as a light yellow oil (1.85 g, yield 90%) which was taken to the next step without further purification. $^1$H NMR (500 MHz, Chloroform-d) δ 7.55-7.41 (m, 1H), 6.89 (d, J=7.1 Hz, 1H), 6.57 (d, J=8.5 Hz, 1H), 5.52 (t, J=5.8 Hz, 1H), 4.37 (s, 1H), 3.82-3.73 (m, 2H), 3.49 (td, J=5.6, 4.2 Hz, 2H).

The mixture of 2-((6-(trifluoromethyl)pyridin-2-yl)amino)ethan-1-ol (2.06 g, 10 mmol) and NCS (1.40 g, 10.05 mmol) in 20 mL acetonitrile was heated to 65° C. overnight. The mixture was concentrated and the residue was triturated with hexane/ethyl acetate (v:v=3:1) to remove the solid. The filtrate was concentrated and purified by silica gel flash chromatography using hexane and ethyl acetate to afford 2-((5-chloro-6-(trifluoromethyl)pyridin-2-yl)amino)ethan-1-ol as a light yellow oil (2.0 g, 85%). $^1$H NMR (500 MHz, Chloroform-d) δ 7.43 (d, J=8.9 Hz, 1H), 6.53 (d, J=8.9 Hz, 1H), 5.47 (t, J=5.7 Hz, 1H), 3.89 (s, 1H), 3.83-3.69 (m, 2H), 3.51-3.32 (m, 2H).

To the solution of thionyl chloride (2.5 mmol, 181 ul) in anhydrous DCM (6 ml) at 0° C. was added a solution of 2-((5-chloro-6-(trifluoromethyl)pyridin-2-yl)amino)ethan-1-ol (481 mg, 2 mmol) in 4 ml anhydrous DCM dropwise. The reaction mixture was stirred for 10 min at 0° C., then pyridine (0.483 ml, 6 mmol) was added. After stirred at room temperature for 1 h, the reaction mixture was quenched with water, extracted with DCM three time. The combined organic phase was washed with brine and dried over $Na_2SO_4$, concentrated and purified by silica gel flash chromatography using hexane and ethyl acetate to afford 3-(5-chloro-6-(trifluoromethyl)pyridin-2-yl)-1,2,3-oxathiazolidine 2-oxide (415 mg, 72%). $^1$H NMR (500 MHz, Chloroform-d) δ 7.80 (d, J=8.7 Hz, 1H), 6.94 (d, J=8.7 Hz, 1H), 5.16 (ddd, J=10.5, 8.9, 6.4 Hz, 1H), 4.88 (ddd, J=9.1, 7.2, 2.3 Hz, 1H), 4.05 (ddd, J=8.9, 6.4, 2.3 Hz, 1H), 3.78 (ddd, J=10.5, 9.1, 7.2 Hz, 1H).

3-(5-Chloro-6-(trifluoromethyl)pyridin-2-yl)-1,2,3-oxathiazolidine 2,2-dioxide To the solution of 3-(5-chloro-6-(trifluoromethyl)pyridin-2-yl)-1,2,3-oxathiazolidine 2-oxide (52 mg, 0.18 mmol) in $CH_3CN$ (2 ml) and water (2 ml) at 0° C. was added ruthenium chloride (1.86 mg, 0.009 mmol) and sodium periodate (58 mg, 0.27 mmol). The reaction mixture was stirred at 0° C. for 30 min. Diluted with ethyl acetate (10 ml) and water (10 ml), extracted with ethyl acetate three time. The combined organic phase was washed with brine and dried over $Na_2SO_4$, and concentrated. The crude product was used in the next step without further purification. $^1$H NMR (500 MHz, Chloroform-d) δ 7.87 (d, J=8.8 Hz, 1H), 7.50 (d, J=8.8 Hz, 1H), 4.84 (t, J=6.5 Hz, 2H), 4.40 (t, J=6.5 Hz, 2H).

Representative synthesis of key intermediate 6-chloro-1-(chloromethyl)-2,3,4,9-tetrahydro-1H-pyrido[3,4-b]indole hydrochloride: To the mixture of 2-(5-chloro-1H-indol-3-yl)ethan-1-amine hydrochloride (925 mg, 4 mmol) and 2-chloroacetaldehyde 50 wt % solution (0.56 ml, 4.4 mmol) was added 4 N HCl (4 mmol) solution. The reaction mixture was heated to 100° C. for 12 h. After cooling down to room temperature and filtering off the brown solid, the filtrate was washed with water and diethyl ether, and dried over high vacuum pump to afford 6-chloro-1-(chloromethyl)-2,3,4,9-tetrahydro-1H-pyrido[3,4-b]indole hydrochloride as a brown solid (905 mg, yield 77%). $^1$H NMR (500 MHz, DMSO-$d_6$) δ 11.68 (s, 1H), 10.42 (s, 1H), 9.63 (s, 1H), 7.58 (d, J=2.0 Hz, 1H), 7.41 (d, J=8.6 Hz, 1H), 7.14 (dd, J=8.6, 2.1 Hz, 1H), 5.12 (dd, J=6.8, 3.0 Hz, 1H), 4.56-4.46 (m, 1H), 4.34 (ddd, J=12.3, 7.0, 1.5 Hz, 1H), 3.60 (dt, J=12.5, 4.9 Hz, 1H), 3.39-3.30 (m, 1H), 3.12-2.76 (m, 2H).

6-Chloro-1-(chloromethyl)-2,3,4,9-tetrahydro-1H-pyrido[3,4-b]indole 6-Chloro-1-(chloromethyl)-2,3,4,9-tetrahydro-1H-pyrido[3,4-b]indole hydrochloride was basified with 2 N NaOH solution, extracted with ethyl acetate three times, washed with brine, dried over sodium sulfate, and concentrated to afford a light brown solid, which was pure enough for further reactions. $^1$H NMR (500 MHz, Chloroform-d) δ 8.17 (s, 1H), 7.48 (d, J=2.0 Hz, 1H), 7.27 (d, J=8.0 Hz, 1H), 7.15 (dd, J=8.6, 2.0 Hz, 1H), 4.38 (td, J=6.3, 3.1 Hz, 1H), 3.83 (d, J=6.2 Hz, 2H), 3.30 (dt, J=12.7, 5.3 Hz, 1H), 3.13 (ddd, J=12.5, 6.9, 5.3 Hz, 1H), 2.84-2.67 (m, 2H).

Representative synthesis of key intermediate 1-(azidomethyl)-6-chloro-2,3,4,9-tetrahydro-1H-pyrido[3,4-b]indole 2-Azido-1,1-diethoxyethane

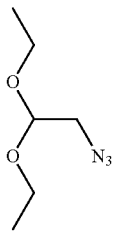

A mixture of NaN₃ (2.5 g, 0.038 mol, 1.5 eq), KI (0.5 g, 0.0030 mol, 0.1 eq) and 2-bromo-1,1-diethoxyethane (5.0 g, 0.026 mol, 1.0 eq) was stirred at 90° C. for 48 h. The reaction was then poured into H₂O (100 mL), extracted with EtOAc (50 mL×3). The combined organic was dried over anhydrous Na₂SO₄ and concentrated in vacuo to afford 2-azido-1,1-diethoxyethane (2.4 g, yield: 58.1%) as a colorless oil. ¹H NMR (400 MHz, CDCl₃): δ 4.60 (t, J=5.3 Hz, 1H), 3.77-3.55 (m, 4H), 3.25-3.24 (d, J=5.2 Hz, 2H), 1.24 (t, 6H).

1-(Azidomethyl)-6-chloro-2,3,4,9-tetrahydro-1H-pyrido[3,4-b]indole

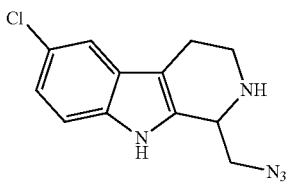 [SMILES: [N-]=[N+]=NCC1NCCc2c1[nH]c1ccc(Cl)cc21]

A mixture of 2-azido-1,1-diethoxyethane (1.9 g, 0.012 mol, 1.5 eq), 2-(5-chloro-1H-indol-3-yl)ethan-1-amine hydrochloride (1.8 g, 0.008 mol, 1.0 eq) and TFA (1.8 g, 0.016 mol, 2.0 eq) in butanol (40 mL)/H₂O (3 mL) was stirred at 100° C. in a sealed tube for 16 h. Then the mixture reaction was cooled down to RT, and purified by reverse phase HPLC to afford 1-(azidomethyl)-6-chloro-2,3,4,9-tetrahydro-1H-pyrido[3,4-b]indole (1.3 g). Further chiral SFC separation afforded two respective enantiomers: P1 (437.5 mg, yield: 14.1%) and P2 (446.7 mg, yield: 14.3%) as brown solids.

P1: ¹H NMR (400 MHz, DMSO-d₆): δ 10.96 (s, 1H), 7.42 (s, 1H), 7.31 (d, J=8.4 Hz, 1H), 7.02 (dd, J=8.4 Hz, 2.4 Hz, 1H), 4.17 (s, 1H), 3.66-3.54 (m, 2H), 3.12-3.07 (m, 1H), 2.94-2.90 (m, 1H), 2.59-2.55 (m, 3H). LCMS: [M+1]⁺=262.0

P2: ¹H NMR (400 MHz, DMSO-d₆): δ 10.96 (s, 1H), 7.42 (s, 1H), 7.31 (d, J=8.4 Hz, 1H), 7.04-7.02 (m, 1H), 4.17 (s, 1H), 3.66-3.53 (m, 2H), 3.12-3.07 (m, 1H), 2.93-2.90 (m, 1H), 2.59-2.55 (m, 3H). LCMS: [M+1]⁺=262.0

Representative synthesis of key intermediate 1-((1H-imidazol-1-yl)methyl)-6-chloro-2,3,4,9-tetrahydro-1H-pyrido[3,4-b]indole

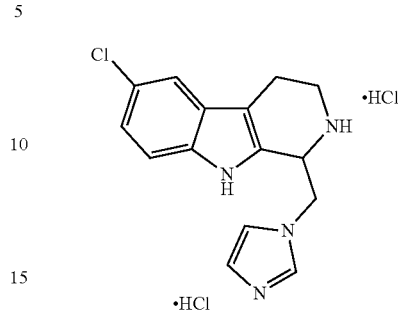

The solution of imidazole (0,68 g, 10 mmol) in DMF (4 mL) was added dropwise over a period of 10 min to a stirred, cooled NaH (mineral oil suspension of 60%) in DMF suspension (3 mL). When the vigorous evolution of hydrogen subsided, the mixture was stirred on a water bath at 50° C. for 20 min to complete salt formation. The mixture was again cooled in an ice-H₂O bath, and a solution of 2-bromo-1,1-diethoxyethane (1.5 mL, 10 mmol) in DMF (1 mL) was added dropwise over a period of 10 min. Then, stirring was continued at 135° C. for 75 min. The mixture was cooled and filtered to remove the NaBr. The DMF was removed on a rotary evaporator to give 1-(2,2-diethoxyethyl)-1H-imidazole (1.81 g, 98%), which was used in the next step without further purification. ¹H NMR (300 MHz, Methanol-d₄) δ 7.66 (t, J=1.2 Hz, 1H), 7.16 (t, J=1.3 Hz, 1H), 6.96 (t, J=1.2 Hz, 1H), 4.69 (t, J=5.2 Hz, 1H), 4.12 (d, J=5.2 Hz, 2H), 3.74 (dq, J=9.4, 7.0 Hz, 2H), 3.50 (dq, J=9.4, 7.0 Hz, 2H), 1.17 (t, J=7.0 Hz, 6H).

To the mixture of 1-(2,2-diethoxyethyl)-1H-imidazole (1.06 g, 5.7 mmol) and 5-chlorotryptamine hydrochloride (1.2 g, 5.2 mmol) was added 2 N HCl (3.9 mL, 7.8 mmol) and H₂O (1.3 mL). The mixture was stirred at reflux for 16 h. Then the mixture was cooled to 0° C. for 2 h, filtered to give the desired product 1-((1H-imidazol-1-yl)methyl)-6-chloro-2,3,4,9-tetrahydro-1H-pyrido[3,4-b]indole as a white solid (1.02 g, 55% yield). ¹H NMR (300 MHz, DMSO-d₆) δ 11.97 (s, 1H), 10.60 (m, 2H), 9.31 (s, 1H), 7.93 (s, 1H), 7.75 (s, 1H), 7.61 (s, 1H), 7.46 (d, J=8.6 Hz, 1H), 7.17 (d, J=8.8 Hz, 1H), 5.48-5.15 (m, 2H), 5.02 (dd, J=14.7, 9.5 Hz, 1H), 3.28 (t, J=11.7 Hz, 2H), 2.98 (q, J=6.4, 5.3 Hz, 2H).

Representative Synthesis key intermediate tert-butyl 4-(5-chloro-6-(trifluoromethyl)pyridin-2-yl)-2-formylpiperazine-1-carboxylate

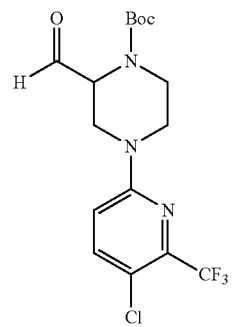

To a solution of tert-butyl 2-(hydroxymethyl)piperazine-1-carboxylate (6.0 g, 27.8 mmol, 1.2 eq) in NMP (10 mL) was added 3,6-dichloro-2-(trifluoromethyl)pyridine (5.0 g, 23.2 mmol, 1.0 eq) and DIPEA (8.9 g, 69.5 mmol, 3.0 eq). The mixture was stirred at 140° C. for 2 d. The mixture was purified directly by reverse phase HPLC to afford tert-butyl 4-(5-chloro-6-(trifluoromethyl)pyridin-2-yl)-2-(hydroxymethyl)piperazine-1-carboxylate (2.2 g, yield: 25.1%) as a light yellow solid. LCMS: [M+1]$^+$=395.9

To a solution of compound tert-butyl 4-(5-chloro-6-(trifluoromethyl)pyridin-2-yl)-2-(hydroxymethyl)piperazine-1-carboxylate (2.4 g, 6.1 mmol, 1.0 eq) in DCM (30 mL) was added Dess-Martin Periodinane (3.9 g, 9.1 mmol, 1.5 eq). The mixture was stirred at rt for 2 h. The mixture was purified directly by silica gel column chromatography (PE:EA=10:1) to afford tert-butyl 4-(5-chloro-6-(trifluoromethyl)pyridin-2-yl)-2-formylpiperazine-1-carboxylate (1.6 g, yield: 65.1%) as a white solid. LCMS: [M+1]$^+$=394.0

General Scheme 36

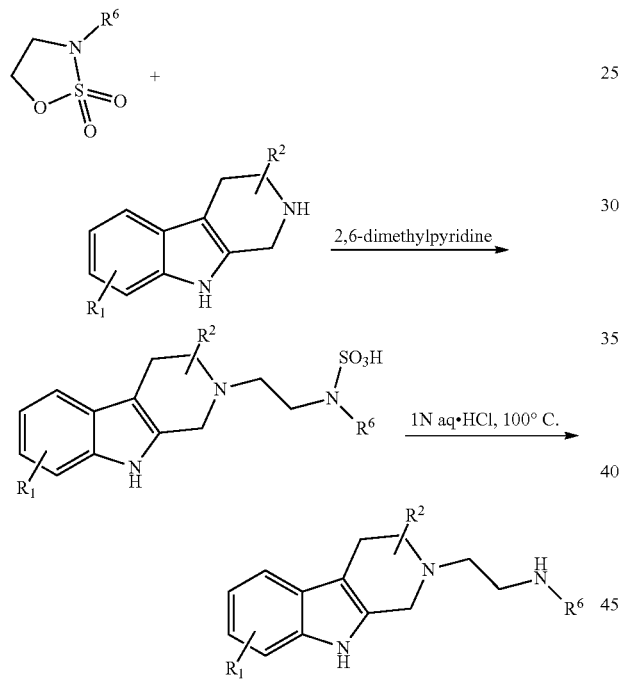

Representative synthesis of N-(2-(1-((azetidin-3ylamino)methyl)-6-chloro-1,3,4,9-tetrahydro-2Hpyrido[3,4-b]indol-2yl)ethyl)-5-chloro-6-(trifluoromethyl)pyridin-2-amine: To the solution of 6-chloro-1-(chloromethyl)-2,3,4,9-tetrahydro-1H-pyrido[3,4-b]indole (0.1 mmol) and 2,6-dimethylpyridine (0.12 mmol) in 0.5 mL acetonitrile was added the freshly prepared 3-(5-chloro-6-(trifluoromethyl)pyridin-2-yl)-1,2,3-oxathiazolidine 2,2-dioxide (0.15 mmol). The reaction mixture was stirred at room temperature for 1 h. Then the reaction mixture was added into the solution of tert-butyl 3-aminoazetidine-1-carboxylate (2 mmol) in acetonitrile (0.1 ml) at 80° C., and stirred for 1 h at 80° C. After LCMS showed the starting material disappeared, the solvent was removed under reduced pressure. The resulting residue was redissolved in 1 mL 1 N HCl solution and was heated to 100° C. for 30 min. After cooling down to room temperature, the mixture was basified with 2 N sodium hydroxide solution, extracted with ethyl acetate three times.

The combined organic phase was washed with brine and dried over sodium sulfate and concentrated. The residue was purified by prepared TCL plate (DCM/MeOH 9:1, Rf=0.6) to afford tert-butyl 3-(((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)amino)azetidine-1-carboxylate (14.2 mg, yield 23%).

To a solution of tert-butyl 3-(((6-chloro-2-(2-((5-chloro-6-(trifluoromethyl)pyridin-2-yl)amino)ethyl)-2,3,4,9-tetrahydro-1H-pyrido[3,4-b]indol-1-yl)methyl)amino)azetidine-1-carboxylate (14 mg) in 1 mL dioxane was added 4 N HCl in dioxane (34 uL, 5 eq). The resulting solution was stirred at RT for 3 h and concentrated. The residue was purified via reverse phase HPLC to afford N-(2-(1-((azetidin-3-ylamino)methyl)-6-chloro-1,3,4,9-tetrahydro-2H-pyrido[3,4-b]indol-2-yl)ethyl)-5-chloro-6-(trifluoromethyl)pyridin-2-amine (8.2 mg) as an off-white solid. $^1$H NMR (400 MHz, CD$_3$OD): δ 7.65-7.54 (m, 1H), 7.50-7.37 (m, 1H), 7.31-7.22 (m, 1H), 7.12-7.00 (m, 1H), 6.83-6.71 (m, 1H), 4.67-4.41 (m, 1H), 4.28-4.04 (m, 2H), 3.75-3.53 (m, 5H), 3.37-3.31 (m, 2H), 3.30-3.08 (m, 2H), 2.91-2.80 (m, 3H), 2.71-2.52 (m, 1H). LCMS: [M+1]$^+$=512.9

(2-(1-(((azetidin-3-ylmethyl)amino)methyl)-6-chloro-1,3,4,9-tetrahydro-2H-pyrido[3,4-b]indol-2-yl)ethyl)(5-chloro-6-(trifluoromethyl)pyridin-2-yl)sulfamic acid $^1$H NMR (400 MHz, CD$_3$OD): δ 7.61-7.59 (m, 2H), 7.45-7.41 (m, 1H), 7.23-7.19 (m, 1H), 6.84 (d, J=8.8 Hz, 1H), 5.16 (brs, 1H), 4.37-4.33 (m, 1H), 4.20-3.94 (m, 8H), 3.74-3.64 (m, 4H), 3.56-3.37 (m, 4H), 3.30-3.10 (m, 1H). LCMS: [M+1]$^+$=527.0

General Scheme 37

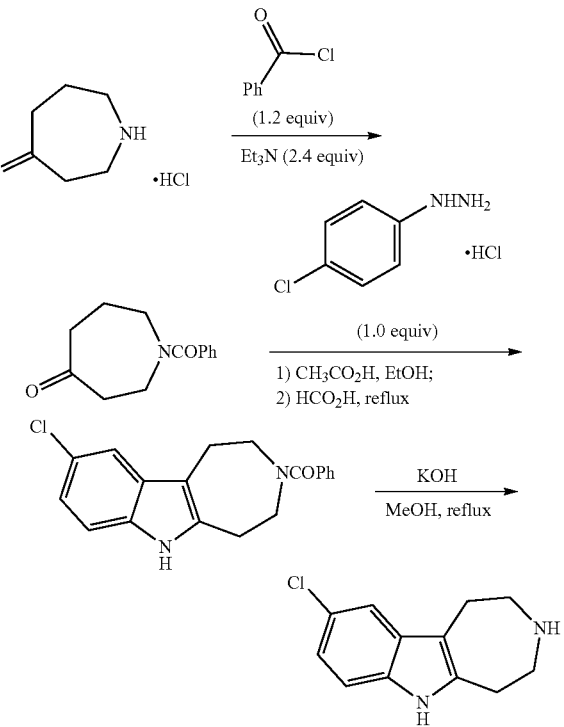

1-Benzoylazepan-4-one To a mixture of azepan-4-one hydrochloride (4.35 g, 29.1 mmol) and benzoyl chloride (4.1 mL, 35.6 mmol) was added Et$_3$N (9.9 mL, 71.2 mmol) After the mixture was stirred for 16 h, DCM (50 mL) was added.

The mixture was washed with water, dried over Na₂SO₄, and evaporated. The residue was purified by silica gel column chromatography to give 1-benzoylazepan-4-one (4.81 g, 76%).

(9-Chloro-1,2,4,5-tetrahydroazepino[4,5-b]indol-3(6H)-yl)(phenyl)methanone A stirred solution of 1-benzoylazepan-4-one (4.81 g, 22 mmol), 4-chlorophenylhydrazine hydrochloride (3.96 g, 22 mmol), and CH₃CO₂H (0.5 mL) in EtOH (50 mL) was refluxed for 30 min, then the solvent was removed under reduced pressure. HCO₂H (40 mL) was added and the mixture was heated to refluxing temperature for 30 min. The mixture was concentrated and washed with aq. NaOH solution (2N). The resulting solution was extracted with DCM three times and the combined organic layer was dried over Na₂SO₄, filtered, and evaporated in vacuo to give the crude product. The mixture was purified by silica gel flash chromatography on silica gel to give (9-chloro-1,2,4,5-tetrahydroazepino[4,5-b]indol-3(6H)-yl)(phenyl)methanone (1.05 g, 15%). ¹H NMR (300 MHz, CDCl₃) δ 8.50-8.10 (m, 1H), 7.48-7.35 (m, 14H), 7.17-7.01 (m, 2H), 3.99 (t, J=5.5 Hz, 2H), 3.65 (t, J=5.6 Hz, 2H), 3.15-2.75 (m, 4H).

9-Chloro-1,2,3,4,5,6-hexahydroazepino[4,5-b]indole A mixture of (9-chloro-1,2,4,5-tetrahydroazepino[4,5-b]indol-3(6H)-yl)(phenyl)methanone (0.2 g, 0.6 mmol), KOH (1.4 g, 25.0 mmol), and MeOH (10 mL) was heated to refluxing temperature. Upon the disappearance of starting material, the reaction was cooled to room temperature, diluted with water and extracted with DCM. The combined organic layers were washed with brine, dried over Na₂SO₄, and concentrated. The crude product could be used directly in the next step without further purification. ¹H NMR (300 MHz, CDCl₃) δ 7.77 (s, 1H), 7.43 (d, J=2.0 Hz, 1H), 7.24-7.15 (m, 1H), 7.07 (dd, J=8.5, 2.0 Hz, 1H), 3.17-3.02 (m, 5H), 2.98-2.93 (m, 2H), 2.90-2.85 (m, 2H).

2-(9-Chloro-1,2,4,5-tetrahydroazepino[4,5-b]indol-3(6H)-yl)-1-(3,4-dichlorophenyl)ethanol

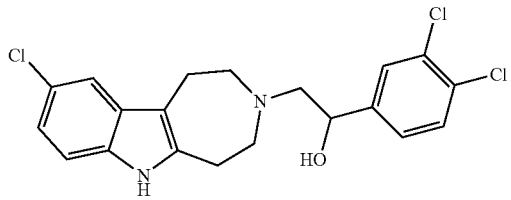 [SMILES: OC(CN1CCc2[nH]c3ccc(Cl)cc3c2CC1)c1ccc(Cl)c(Cl)c1]

¹H NMR (300 MHz, CDCl₃) δ 7.79 (s, 1H), 7.53 (d, J=1.8 Hz, 1H), 7.44-7.37 (m, 2H), 7.25-7.01 (m, 3H), 4.72 (dd, J=10.5, 3.3 Hz, 1H), 3.17-2.76 (m, 10H), 2.49 (dd, J=12.6, 10.5 Hz, 1H). LCMS [M+H⁺] 409.0

2-(9-Chloro-1,2,4,5-tetrahydroazepino[4,5-b]indol-3(6H)-yl)-N-(5-chloro-6-methylpyridin-2-yl)acetamide

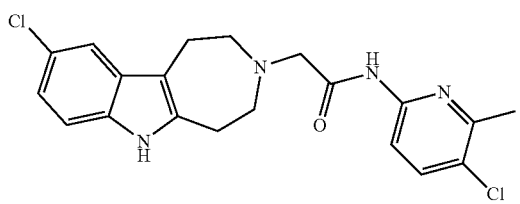 [SMILES: Cc1nc(NC(=O)CN2CCc3[nH]c4ccc(Cl)cc4c3CC2)ccc1Cl]

¹HNMR (300 MHz, CDCl₃) δ 9.67 (s, 1H), 8.09 (d, J=8.7 Hz, 1H), 7.88 (s, 1H), 7.64 (d, J=8.7 Hz, 1H), 7.40 (d, J=1.8 Hz, 1H), 7.22-7.13 (m, 1H), 7.11-7.03 (m, 1H), 3.45 (s, 2H), 3.14-2.96 (m, 6H), 2.95-2.83 (m, 2H), 2.52 (s, 3H). LCMS [M+H⁺] 403.1

5-Chloro-N-(2-(9-chloro-1,2,4,5-tetrahydroazepino[4,5-b]indol-3(6H)-yl)ethyl)-6-methylpyridin-2-amine

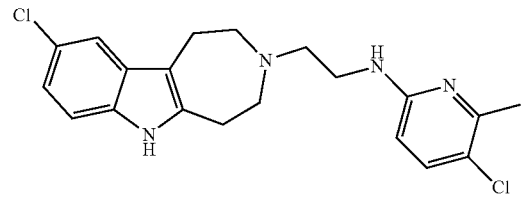 [SMILES: Cc1nc(NCCN2CCc3[nH]c4ccc(Cl)cc4c3CC2)ccc1Cl]

¹HNMR (300 MHz, CDCl₃) δ 7.74 (s, 1H), 7.40 (d, J=2.1 Hz, 1H), 7.34 (d, J=8.7 Hz, 1H), 7.19-7.13 (m, 1H), 7.09-7.03 (m, 1H), 6.22 (d, J=8.7 Hz, 1H), 5.13 (s, 1H), 3.40-3.34 (m, 2H), 3.10-2.84 (m, 10H), 2.45 (s, 3H). LCMS [M+H⁺] 389.1

General Scheme 38

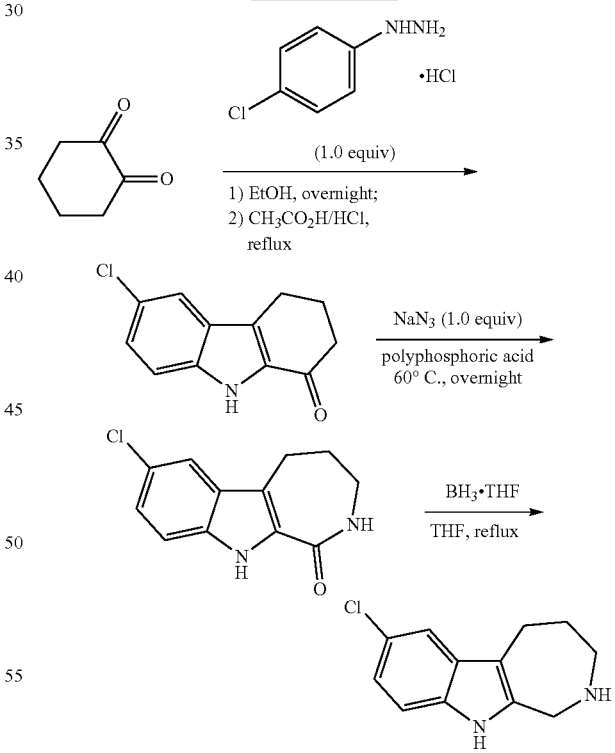

6-Chloro-2,3,4,9-tetrahydro-1H-carbazol-1-one 4-Chlorophenylhydrazine hydrochloride (5.37 g, 30 mmol) was added portionwise to a stirred solution of cyclohexane-1,2-dione (3.36 g, 30 mmol) in EtOH (30 mL) at room temperature. The reaction mixture turned bright orange within 5 min. The reaction was stirred for 16 h at room temperature, whereupon the heterogeneous reaction mixture was filtered and the solid was collected. The filtrate was concentrated and combined with solid. Then concentrated HCl (3 mL) and CH₃CO₂H (12 mL) was added and reaction mixture was heated at 120° C. for 20 min. The mixture was cooled slightly and ice was added. The resulting precipitate was collected by filtration to give the crude product. The crude product was purified by silica gel column chromatography, and then further purified via recrystallization (CH₂Cl₂/Hexane) to give the pure 6-chloro-2,3,4,9-tetrahydro-1H-carbazol-1-one (1.60 g, 7.3 mmol, 24% yield). ¹HNMR (300 MHz, CDCl₃) δ 9.12 (s, 1H), 7.67-7.58 (m, 1H), 7.39-7.34 (m, 1H), 7.33-7.28 (m, 1H), 2.97 (t, J=6.0 Hz, 2H), 2.76-2.60 (m, 2H), 2.37-2.19 (m, 2H). LCMS [M+H⁺] 220.1

7-Chloro-2,3,4,5-tetrahydroazepino[3,4-b]indol-1(10H)-one A stirred mixture of 6-chloro-2,3,4,9-tetrahydro-1H-carbazol-1-one (0.66 g, 3 mmol) in polyphosphoric acid (15 g) was warmed to 60° C. and treated with NaN₃ (0.25 g, 3.9 mmol) over 20 min. After heating at the same temperature overnight, the mixture was poured into ice-water. The product was extracted with CH₂Cl₂; the extract was washed with water, dried over MgSO₄ and concentrated. The crude product 7-chloro-2,3,4,5-tetrahydroazepino[3,4-b]indol-1(10H)-one could be used directly in the next step. ¹HNMR (300 MHz, CDCl₃) δ 9.15 (s, 1H), 7.33-7.24 (m, 1H), 7.20-7.13 (m, 1H), 7.10-7.03 (m, 1H), 6.10 (s, 1H), 3.60-3.45 (m, 2H), 2.33-2.12 (m, 2H). LCMS [M+H⁺] 235.1

7-Chloro-1,2,3,4,5,10-hexahydroazepino[3,4-b]indole A stirred mixture of 7-chloro-2,3,4,5-tetrahydroazepino[3,4-b]indol-1(10H)-one (47 mg, 0.2 mmol) and BH₃·THF (0.6 mL, 0.6 mmol) was heated to reflux for 24 h. After the reaction was completed, the solvent was removed under reduced pressure. Then MeOH was added and the mixture was concentrated again. The crude product was purified by silica gel column chromatography to give the pure 7-chloro-1,2,3,4,5,10-hexahydroazepino[3,4-b]indole (14.8 mg, 0.067 mmol, 34% yield). ¹H NMR (300 MHz, CDCl₃) δ 7.78 (s, 1H), 7.51-7.41 (m, 1H), 7.21-7.15 (m, 1H), 7.10-7.02 (m, 1H), 4.03 (s, 2H), 3.28-3.15 (m, 2H), 2.97-2.76 (m, 2H), 1.96-1.79 (m, 2H). LCMS [M+H⁺] 221.1

2-(7-Chloro-4,5-dihydroazepino[3,4-b]indol-2(1H,3H,10H)-yl)-1-(3,4-dichlorophenyl)ethanol

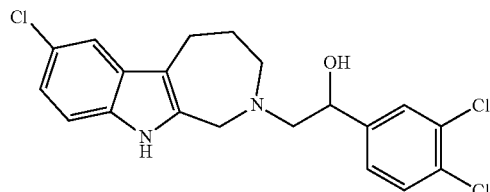

¹HNMR (300 MHz, CDCl₃) δ 7.76 (s, 1H), 7.45 (t, J=2.4 Hz, 2H), 7.45 (t, J=2.4 Hz, 1H), 7.27 (d, J=8.4 Hz, 1H), 7.20 (d, J=8.7 Hz, 1H), 7.13 (dd, J=8.1, 2.1 Hz 1H), 7.08 (dd, J=8.7, 2.1 Hz, 1H), 4.66 (dd, J=10.2, 3.6 Hz, 1H), 4.02 (d, J=2.7 Hz, 1H), 3.31-3.21 (m, 2H), 2.90-2.78 (m, 3H), 2.39-2.31 (m, 1H), 2.39-2.31 (m, 1H), 1.94-1.70 (m, 4H). LCMS: [M+H⁺] 409.0

2-(7-Chloro-4,5-dihydroazepino[3,4-b]indol-2(1H,3H,10H)-yl)-N-(5-chloro-6-methylpyridin-2-yl)acetamide

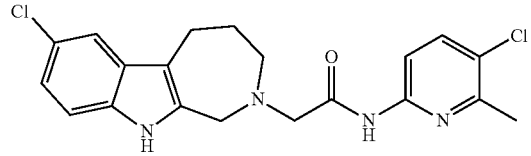 [SMILES: Cc1nc(NC(=O)CN2CCCc3c([nH]c4ccc(Cl)cc34)C2)ccc1Cl]

¹HNMR (300 MHz, CDCl₃) δ 9.59 (s, 1H), 8.11 (s, 1H), 8.02 (d, J=8.7 Hz, 1H), 7.63 (d, J=8.7 Hz, 1H), 7.46 (d, J=1.8 Hz, 1H), 7.21-7.11 (m, 1H), 7.11-7.01 (m, 1H), 4.01 (s, 2H), 3.37-3.26 (m, 2H), 3.23 (s, 2H), 2.96-2.81 (m, 2H), 2.52 (s, 3H), 1.92-1.76 (m, 2H).

5-Chloro-N-(2-(7-chloro-4,5-dihydroazepino[3,4-b]indol-2(1H,3H,10H)-yl)ethyl)-6-methylpyridin-2-amine

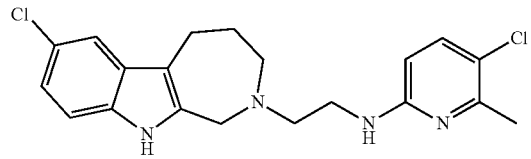 [SMILES: Cc1nc(NCCN2CCCc3c([nH]c4ccc(Cl)cc34)C2)ccc1Cl]

¹H NMR (300 MHz, CDCl₃) δ 7.94 (s, 1H), 7.45 (d, J=1.8 Hz, 1H), 7.31 (d, J=8.7 Hz, 1H), 7.21-7.15 (m, 1H), 7.09-7.03 (m, 1H), 6.18 (d, J=8.7 Hz, 1H), 3.97 (s, 2H), 3.83-3.59 (m, 2H), 3.31-3.18 (m, 4H), 2.92-2.63 (m, 4H), 2.44 (s, 3H). LCMS: [M+H⁺] 389.1

General Scheme 39

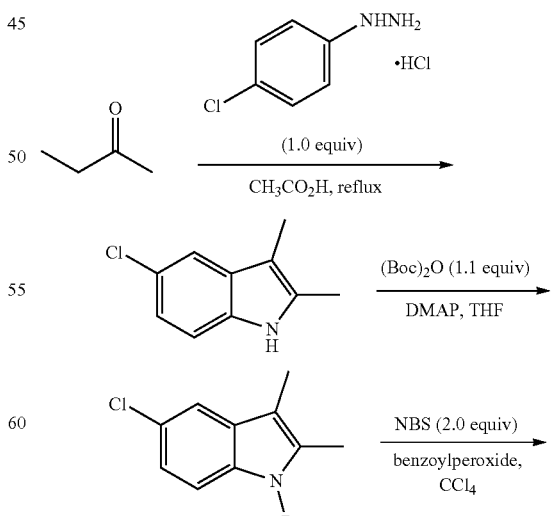

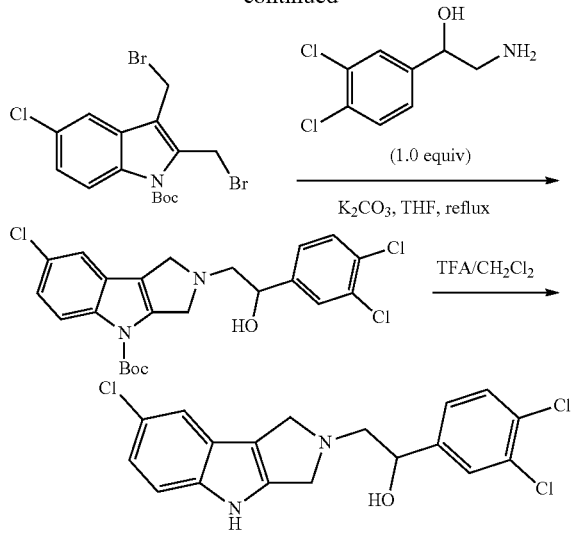

5-Chloro-2,3-dimethyl-1H-indole 4-Chlorophenylhydrazine hydrochloride (1.79 g, 10 mmol) and ethyl methylketone (0.89 mL, 10 mmol) were added in acetic acid (8 mL), and reaction mixture was heated to refluxing temperature. The reaction was then cooled to room temperature and poured into ice water. The crude product was extracted with water, dried over $Na_2SO_4$ and concentrated in vacuo to afford the product as a brown solid. The residue was further purified by silica gel column chromatography to afford 5-chloro-2,3-dimethyl-1H-indole (0.77 g, 4.3 mmol, 43% yield). $^1$HNMR (300 MHz, $CDCl_3$) δ 7.65 (s, 1H), 7.44 (d, J=1.9 Hz, 1H), 7.14 (dd, J=8.5, 0.6 Hz, 1H), 7.06 (dd, J=8.5, 2.0 Hz, 1H), 2.35 (s, 3H), 2.19 (s, 3H).

tert-Butyl 5-chloro-2,3-dimethyl-1H-indole-1-carboxylate 5-Chloro-2,3-dimethyl-1H-indole (0.77 g, 4.3 mmol) was dissolved in THF, followed by the addition of DMAP (52.5 mg, 0.43 mmol) and (Boc)$_2$O. The reaction mixture was stirred at room temperature for 16 h. The reaction mixture was then concentrated, and purified via silica gel column chromatography using Hexane/EtOAc=9:1 to give tert-butyl 5-chloro-2,3-dimethyl-1H-indole-1-carboxylate (1.16 g, 4.1 mmol, 97% yield).

tert-Butyl 2,3-bis(bromomethyl)-5-chloro-1H-indole-1-carboxylate A solution of tert-butyl 5-chloro-2,3-dimethyl-1H-indole-1-carboxylate (0.56 g, 2 mmol), NBS (0.71 g, 4 mmol), and benzoylperoxide (10 mg) in dry $CCl_4$ was refluxed for 2 h. The suspension was cooled to room temperature, filtered and the filtrate was concentrated in vacuo. The crude product was purified by silica gel column chromatography to afford tert-butyl 2,3-bis(bromomethyl)-5-chloro-1H-indole-1-carboxylate (0.53 g, 1.2 mmol, 60% yield). $^1$HNMR (300 MHz, $CDCl_3$) δ 8.11 (d, J=9.0 Hz, 1H), 7.64-7.56 (m, 1H), 7.33 (dd, J=9.0, 2.1 Hz, 1H), 5.00 (s, 2H), 4.64 (s, 2H), 1.73 (s, 9H) ppm.

tert-Butyl 7-chloro-2-(2-(3,4-dichlorophenyl)-2-hydroxyethyl)-2,3-dihydropyrrolo[3,4-b]indole-4(1H)-carboxylate A mixture of tert-butyl 2,3-bis(bromomethyl)-5-chloro-1H-indole-1-carboxylate (85.5 mg, 0.2 mmol), 2-amino-1-(3,4-dichlorophenyl)ethan-1-ol (41.2 mg, 0.2 mmol), and $K_2CO_3$ (0.11 g, 0.8 mmol) in THF was heated to reflux for 10 h. Then the mixture was concentrated. The crude product was purified by silica gel column chromatography to afford tert-butyl 7-chloro-2-(2-(3,4-dichlorophenyl)-2-hydroxyethyl)-2,3-dihydropyrrolo[3,4-b]indole-4(1H)-carboxylate (33.7 mg, 0.07 mmol, 35% yield). $^1$H NMR (300 MHz, $CDCl_3$) δ 8.08 (d, J=8.7 Hz, 1H), 7.55 (d, J=1.8 Hz, 1H), 7.43 (d, J=8.4 Hz, 1H), 7.31 (d, J=2.1 Hz, 1H), 7.27-7.20 (m, 2H), 5.22-4.88 (m, 1H), 4.72 (dd, J=9.6, 3.3 Hz, 1H), 4.28-4.18 (m, 2H), 4.06-3.88 (m, 2H), 3.16-3.03 (m, 1H), 2.98-2.84 (m, 1H), 1.62 (s, 9H) ppm. LCMS: [M+H$^+$] 481.1.

2-(7-Chloropyrrolo [3,4-b]indol-2 (1H,3H,4H)-yl)-1-(3,4-dichlorophenyl)ethanol A mixture of tert-butyl 7-chloro-2-(2-(3,4-dichlorophenyl)-2-hydroxyethyl)-2,3-dihydropyrrolo[3,4-b]indole-4(1H)-carboxylate (52.5 mg, 0.12 mmol), TFA (1 mL), and $CH_2Cl_2$ (1 mL) was stirred at room temperature until the starting material disappeared. Then the mixture was concentrated and treated with aq. NaOH solution (2N), extracted with $CH_2Cl_2$. The organic layer was concentrated under reduced pressure, and the residue was purified by silica gel column chromatography to afford 2-(7-chloropyrrolo[3,4-b]indol-2(1H,3H,4H)-yl)-1-(3,4-dichlorophenyl)ethanol (1.2 mg, 16% yield). $^1$HNMR (300 MHz, $CDCl_3$) δ 8.00 (s, 1H), 7.56 (d, J=2.1 Hz, 1H), 7.44 (d, J=8.4 Hz, 1H), 7.40 (d, J=2.1 Hz, 1H), 7.30-7.27 (m, 1H), 7.26-7.23 (m, 1H), 7.11 (dd, J=8.7, 2.1 Hz, 1H), 4.74 (dd, J=9.6, 3.3 Hz, 1H), 4.34-3.83 (m, 5H), 3.11 (dd, J=12.3, 3.6 Hz, 1H), 2.90 (dd, J=12.3, 9.9 Hz, 1H) ppm. LCMS: [M+H$^+$] 381.0.

tert-Butyl 7-chloro-2-(2-((5-chloro-6-(trifluoromethyl)pyridin-2-yl)amino)-2-oxoethyl)-2,3-dihydropyrrolo[3,4-b]indole-4(1H)-carboxylate

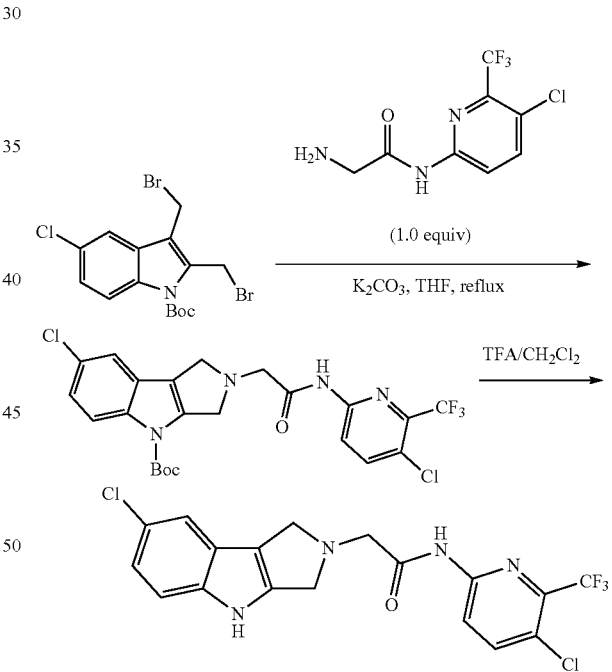

A mixture of tert-butyl 2,3-bis(bromomethyl)-5-chloro-1H-indole-1-carboxylate (52.5 mg, 0.12 mmol), 2-amino-N-(5-chloro-6-(trifluoromethyl)pyridin-2-yl)acetamide (30.9 mg, 0.12 mmol), and $K_2CO_3$ (66.2 mg, 0.48 mmol) in THF was heated to reflux for 10 h. Then the mixture was concentrated and the crude product was purified via silica gel column chromatography to afford tert-butyl 7-chloro-2-(2-((5-chloro-6-(trifluoromethyl)pyridin-2-yl)amino)-2-oxoethyl)-2,3-dihydropyrrolo[3,4-b]indole-4(1H)-carboxylate (3.3 mg, 0.006 mmol, 5% yield). $^1$HNMR (300 MHz, $CDCl_3$) δ 9.74 (s, 1H), 8.48 (d, J=8.9 Hz, 1H), 8.08 (d, J=8.8

Hz, 1H), 7.86 (d, J=8.8 Hz, 1H), 7.33 (d, J=2.1 Hz, 1H), 7.23 (d, J=2.2 Hz, 1H), 4.37 (t, J=3.5 Hz, 2H), 4.16 (t, J=3.5 Hz, 2H), 3.72 (s, 2H), 1.64 (s, 9H). LCMS: [M+H$^+$] 529.1

N-(5-chloro-6-(trifluoromethyl)pyridin-2-yl)-2-(7-chloropyrrolo[3,4-b]indol-2(1H,3H,4H)-yl)acetamide A mixture of tert-butyl 7-chloro-2-(2-((5-chloro-6-(trifluoromethyl)pyridin-2-yl)amino)-2-oxoethyl)-2,3-dihydropyrrolo[3,4-b]indol-4(1H)-carboxylate (3.3 mg, 0.006 mmol), TFA (2 mL), and CH$_2$Cl$_2$ (2 mL) was stirred at room temperature for 1.5 h. Then the mixture was concentrated and neutralized with aq. NaOH solution (2N), extracted with CH$_2$Cl$_2$. The organic layer was concentrated under reduced pressure, and the residue was purified by silica gel column chromatography to afford N-(5-chloro-6-(trifluoromethyl)pyridin-2-yl)-2-(7-chloropyrrolo[3,4-b]indol-2(1H,3H,4H)-yl)acetamide (1.4 mg, 0.003 mmol, 54% yield). $^1$HNMR (300 MHz, CDCl$_3$) δ 9.78 (s, 1H), 8.47 (d, J=8.9 Hz, 1H), 8.06 (s, 1H), 7.85 (d, J=8.9 Hz, 1H), 7.39 (d, J=2.0 Hz, 1H), 7.30-7.27 (m, 1H), 7.13 (dd, J=8.7, 2.1 Hz, 1H), 4.22 (d, J=4.6 Hz, 4H), 3.75 (s, 2H). LCMS: [M+H$^+$] 429.0

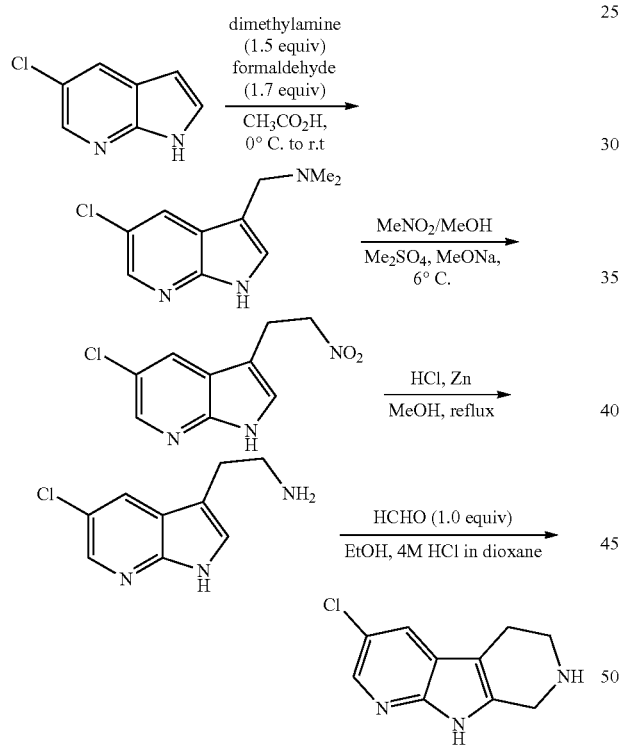

1-(5-Chloro-1H-pyrrolo[2,3-b]pyridin-3-yl)-N,N-dimethylmethanamine A mixture of 5-chloro-1H-pyrrolo[2,3-b]pyridin-3-yl (3.05 g, 20 mmol), 40% aqueous dimethylamine (3.8 mL, 30 mmol), and CH$_3$CO$_2$H is stirred at 0° C., then 36% aqueous formaldehyde solution is added dropwise. The mixture is allowed to warm up to room temperature. After stirring overnight, TLC show the absence of starting material. 10% Aqueous NaOH (60 mL) is added, and the mixture is stirred at room temperature for another 2 h. It is then extracted with DCM, dried over sodium sulfate and concentrated The residue is purified by silica gel column chromatography to give 1-(5-chloro-1H-pyrrolo[2,3-b]pyridin-3-yl)-N,N-dimethylmethanamine (1.22 g, 36% yield).

5-Chloro-3-(2-nitroethyl)-1H-pyrrolo[2,3-b]pyridine 1-(5-Chloro-1H-pyrrolo[2,3-b]pyridin-3-yl)-N,N-dimethylmethanamine (1.45 g, 6.9 mmol) was dissolved in a mixed solvent of methanol (10 mL) and nitromethane (10 mL). The solution was cooled to 0° C. Me$_2$SO$_4$ (0.78 mL, 8.3 mmol) was added, followed by the slow addition of sodium methoxide (0.53 g, 9.8 mmol) over 15 minutes. The ice bath was removed, and the mixture was stirred overnight. The reaction mixture is diluted with EtOAc (20 mL) and saturated aqueous NH$_4$Cl solution (20 mL). The aqueous layer is extracted with ethyl acetate (2*20 mL). The combined organic layer is dried over Na$_2$SO$_4$ and concentrated in vacuo. The crude product 5-chloro-3-(2-nitroethyl)-1H-pyrrolo[2,3-b]pyridine was used directly in the next step without further purification.

2-(5-Chloro-1H-pyrrolo[2,3-b]pyridin-3-yl)ethanamine 5-Chloro-3-(2-nitroethyl)-1H-pyrrolo[2,3-b]pyridine was dissolved in methanol (100 mL) and aqueous HCl (2M, 100 mL). Zinc powder (5.885 g, 90 mmol) was added in portions over 15 minutes. The suspension was then heated at refluxing temperature for 3 h. After cooling down to room temperature, the reaction mixture was filtered, and the solid cake was washed with methanol. The filtrate was concentrated under reduced pressure. A cooled aqueous solution of NaOH (15% w/w, 20 mL) was added, and the resulting aqueous solution was then extracted with DCM. The organic extracts were combined and dried with MgSO$_4$ and concentrated to give a crude product 2-(5-chloro-1H-pyrrolo[2,3-b]pyridin-3-yl)ethanamine, which was used directly in the next step. LCMS: [M+H$^+$] 196.1

3-Chloro-6,7,8,9-tetrahydro-5H-pyrrolo[2,3-b:5,4-c']pyridine 2-(5-Chloro-1H-pyrrolo[2,3-b]pyridin-3-yl)ethanamine (44.3 mg, 0.23 mmol) was dissolved in EtOH (0.3 mL). HCl (58 μL, 4M in dioxane) was added, followed by HCHO solution (37%). The reaction was stirred at 150° C. for 2 d. The reaction mixture was then concentrated. The crude product was purified by silica gel column chromatography to give 3-chloro-6,7,8,9-tetrahydro-5H-pyrrolo[2,3-b:5,4-c']dipyridine (22.3 mg, 47% yield). $^1$HNMR (300 MHz, CD$_3$OD) δ 8.04 (d, J=2.3 Hz, 1H), 7.81 (d, J=2.2 Hz, 1H), 3.99 (d, J=1.6 Hz, 2H), 3.13 (t, J=5.8 Hz, 2H), 2.78-2.55 (m, 2H). LCMS: [M+H$^+$] 208.1

2-(3-Chloro-5H-pyrrolo[2,3-b:5,4-c']dipyridin-7(6H,8H,9H)-yl)-1-(3,4-dichlorophenyl)ethanol

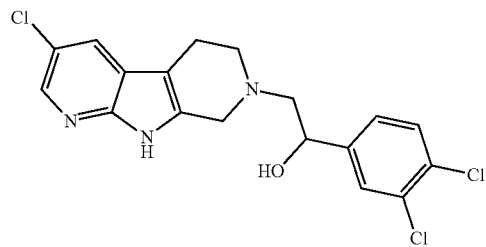 [SMILES: OC(CN1CCc2c([nH]c3ncc(Cl)cc23)C1)c1ccc(Cl)c(Cl)c1]

$^1$H NMR (300 MHz, CDCl$_3$) δ 9.26 (s, 1H), 8.24-8.12 (m, 1H), 7.81-7.73 (m, 1H), 7.56-7.46 (m, 1H), 7.46-7.36 (m, 1H), 7.25-7.11 (m, 1H), 4.87-4.68 (m, 1H), 4.08-3.68 (m, 3H), 3.21-2.89 (m, 2H), 2.88-2.78 (m, 3H), 2.68-2.57 (m, 1H) ppm. LCMS: [M+H$^+$] 396.0

2-(3-Chloro-5H-pyrrolo[2,3-b:5,4-c']dipyridin-7(6H,8H,9H)-yl)-N-(5-chloro-6-(trifluoromethyl)pyridin-2-yl)acetamide

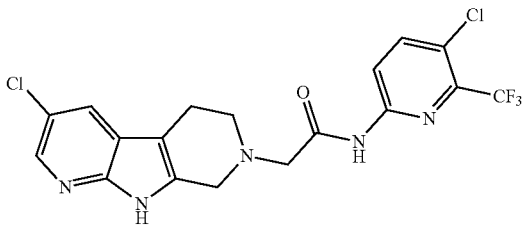 [SMILES: O=C(CN1CCc2c([nH]c3ncc(Cl)cc23)C1)Nc1ccc(Cl)c(C(F)(F)F)n1]

$^1$HNMR (300 MHz, CDCl$_3$) δ 9.77 (s, 1H), 9.27 (s, 1H), 8.48 (dd, J=8.9, 0.6 Hz, 1H), 8.20 (s, 1H), 7.98-7.84 (m, 1H), 7.81 (d, J=2.0 Hz, 1H), 3.97 (s, 2H), 3.48 (s, 2H), 3.07 (t, J=5.7 Hz, 2H), 2.88 (t, J=5.8 Hz, 2H). LCMS: [M+H$^+$] 444.0

5-Chloro-N-(2-(3-chloro-5H-pyrrolo[2,3-b:5,4-c']dipyridin-7(6H,8H,9H)-yl)ethyl)-6-(trifluoromethyl)pyridin-2-amine

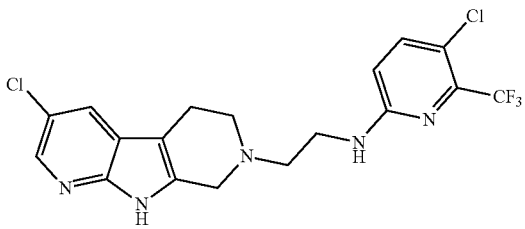 [SMILES: FC(F)(F)c1nc(NCCN2CCc3c([nH]c4ncc(Cl)cc34)C2)ccc1Cl]

$^1$HNMR (300 MHz, CDCl$_3$) δ 8.79 (s, 1H), 8.14 (s, 1H), 7.74 (d, J=2.1 Hz, 1H), 7.51-7.40 (m, 1H), 6.50 (d, J=8.9 Hz, 1H), 5.34 (s, 1H), 3.76 (s, 2H), 3.53 (q, J=5.6 Hz, 2H), 2.90 (dt, J=14.5, 5.8 Hz, 4H), 2.77 (t, J=5.7 Hz, 2H). LCMS: [M+H$^+$] 430.0

(Z)-3-(2-(5-chloro-6-methylpyridin-3-yl)hydrazono)piperidin-2-one

Step 1: A round-bottomed flask was charged with 18 mL water, ethyl 2-oxopiperidine-3-carboxylate (1.37 g, 8 mmol), and solid KOH (1.88 g, 33.6 mmol). The mixture was stirred at room temperature for 30 min and quenched by dropwise addition of concentrated HCl (3.2 mL, 38.4 mmol). NaCl (5.8 g) was then added to the solution and the resulting saturated mixture was extracted with an 85:15 solution of CHCl$_3$/i-PrOH (5*20 mL). The combined organics were dried over Na$_2$SO$_4$ and concentrated in vacuo to give 2-oxopiperidine-3-carboxylic acid. Step 2: 5-Chloro-6-methylpyridin-3-amine (0.285 g, 2 mmol) was dissolved in conc. HCl (0.67 mL, 8 mmol) and the mixture was cooled to −10° C., whereupon a solution of NaNO$_2$ (0.151 g, 2.2 mmol) in water (5 mL) was added dropwise to form the diazonium salt 5-chloro-6-methylpyridine-3-diazonium chloride.

Step 3: 2-oxopiperidine-3-carboxylic acid (0.342 g, 2 mmol) was dissolved in water and cooled in ice bath. Then the cooled solution was added directly to the reaction mixture of diazonium salt 5-chloro-6-methylpyridine-3-diazonium chloride prepared in step 2. The reaction mixture was stirred at 0° C. overnight to form hydrazone. The reaction was neutralized with 2N aq. NaOH solution, concentrated, and the crude product was purified by silica gel column chromatography to give (Z)-3-(2-(5-chloro-6-methylpyridin-3-yl)hydrazono)piperidin-2-one (0.284 g, 57% yield).

3-Chloro-2-methyl-8,9-dihydro-5H-pyrrolo[3,2-b:5,4-c']dipyridin-6(7H)-one (Z)-3-(2-(5-chloro-6-methylpyridin-3-yl)hydrazono)piperidin-2-one (0.284 g, 1.13 mmol) and HCO$_2$H (4 mL) was added to a pressurized pipe reactor and the reaction was heated at 145° C. for 8 h (or until the signal of starting material was disappeared). Then the reaction was concentrated, and neutralized with aq. NaOH solution (2N). The crude product was purified by silica gel column chro- General Scheme 41

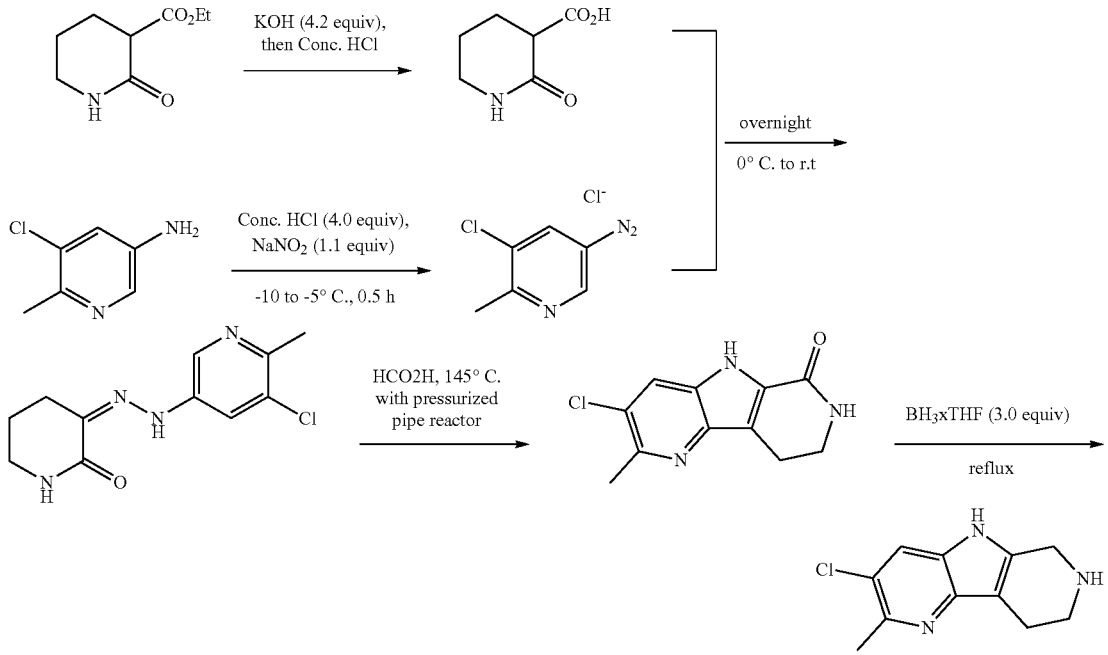

matography to give pure 3-chloro-2-methyl-8,9-dihydro-5H-pyrrolo[3,2-b:5,4-c']dipyridin-6(7H)-one (87 mg, 33% yield).

3-Chloro-2-methyl-6,7,8,9-tetrahydro-5H-pyrrolo[3,2-b:5,4-c']dipyridine A stirred mixture of 3-chloro-2-methyl-8,9-dihydro-5H-pyrrolo[3,2-b:5,4-c']dipyridin-6(7H)-one (44.7 mg, 0.19 mmol) and $BH_3 \cdot THF$ (0.57 mL, 0.57 mmol) in 2 mL THF was heated to reflux. After the reaction was completed, the solvent was removed under reduced pressure. Then MeOH was added and the mixture was concentrated again. The crude product was purified by silica gel column chromatography to give 3-chloro-2-methyl-6,7,8,9-tetrahydro-5H-pyrrolo[3,2-b:5,4-c']dipyridine (13.7 mg, 33% yield).

5-Chloro-N-(2-(3-chloro-2-methyl-8,9-dihydro-5H-pyrrolo[3,2-b:5,4-c']pyridin-7(6H)-yl)ethyl)-6-(trifluoromethyl)pyridin-2-amine

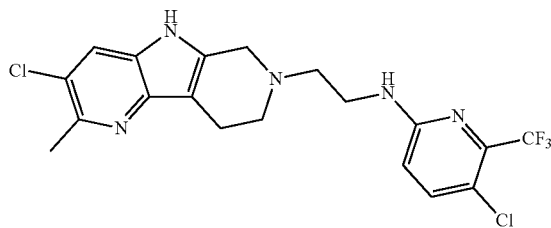 [SMILES: Cc1nc2c3c([nH]c2cc1Cl)CN(CCNc1ccc(Cl)c(C(F)(F)F)n1)CC3]

$^1$HNMR (300 MHz, $CDCl_3$) δ 7.75 (s, 1H), 7.58 (s, 2H), 7.48 (s, 1H), 7.45 (s, 1H), 3.91-3.86 (m, 2H), 3.77 (s, 2H), 3.73 (d, J=6.0 Hz, 2H), 2.95 (s, 2H), 2.91 (d, J=7.2 Hz, 2H), 2.72 (s, 3H). LCMS: [M+H$^+$] 444.2

Biological Assay Protocols

Bacterial strains representing pathogenic species of clinical concern, the so called ESKAPE pathogens, were selected for MIC studies using compounds A and B. The results are shown in Table A. These species are from the families or genera Enterococcus, Staphylococcus, Klebsiella, Acinetobacter, Pseudomonas, and Enterobacteriaceae. Specifically, Enterococcus faecium HM-204 and HM-460, Staphylococcus aureus strains NRS384 and COL, Klebsiella pneumoniae strains NR-48976 and NR-48977, Acinetobacter baumannii strains NR-17783 and NR-19299, Pseudomonas aeruginosa strain NR-48982 and Salmonella enterica strains NR-22067 and NR-22068 were purchased from BEI resources. Escherichia coli strain ATCC 25922, and the Staphylococcus aureus (S. aureus) strains ATCC 25923 (MSSA) and ATCC BAA-44 (MRSA) were purchased from the American Type Culture Collection (ATCC).

General Procedure for Minimal inhibitory concentration (MIC) determination. The minimal inhibitory concentrations (MICS) of antimicrobial compounds A, B, and C were determined by the broth microdilution method detailed in the Clinical and Laboratory Standards Institute handbook (Cockerill and Clinical and Laboratory Standards Institute, Methods for Dilution Antimicrobial Susceptibility Tests for Bacteria That Grow Aerobically). All antimicrobial compounds were purchased from Sigma-Aldrich. The growth media used for all MIC experiments, except those for Enterococcus faecium, was Mueller Hinton Broth (MHB) purchased from HIMEDIA through VWR (cat: 95039-356). For experiments using Enterococcus faecium, the growth and susceptibility medium was BD Bacto™ Brain Heart Infusion (BHI) Broth purchased from VWR (cat: 90003-040). USA Scientific CytoOne 96-well Clear Tissue Culture assay plates (cat: CC7682-7596) were used for all MIC and MRC experiments. MIC assay plates were prepared by diluting the antibiotic to be tested in a 2-fold series down the assay plate. A total of 8 concentrations of each compound were tested in triplicate. Compounds were prepared in 180 μL at 2× the intended final concentrations in MHB or BHI and 2% DMSO.

The bacterial inoculum was prepared by selecting 5-7 colonies from an agar plate to make a day culture in BHI of the bacterial species to be assayed. This was grown at 37° C. for 2-4 hours. After having reached the mid-logarithmic growth phase ($OD_{600}$ 0.15-0.4), the day culture was diluted in the appropriate assay medium (MHB or BHI) to $OD_{600}$ 0.002. 100 μL of this inoculum was added to each experimental well of the 96-well assay plate resulting in an additional two-fold dilution of the bacterial culture and an initial $OD_{600}$ of 0.001 in the assay plate, a final volume of 200 μL and the intended compound concentrations in 1% DMSO. MIC assay plates were then incubated at 37° C. with shaking for 18 hours.

The MICs were determined as defined in the Clinical and Laboratory Standards Institute handbook. After overnight growth, Plates were read by eye and 600 nm absorbance read using a BioTek Epoch2 Microplate Spectrophotometer (BioTek). The MIC was interpreted as the concentration of antibiotic at which no bacterial growth was visible by eye, or the concentration at which the 600 nm absorbance did not exceed 0.1 (the approximate absorbance of the blank control).

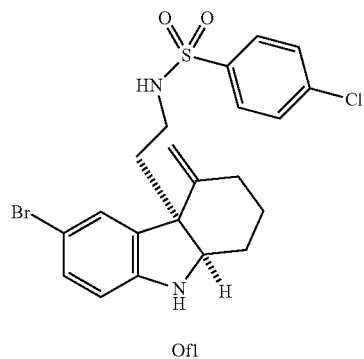

Ofl

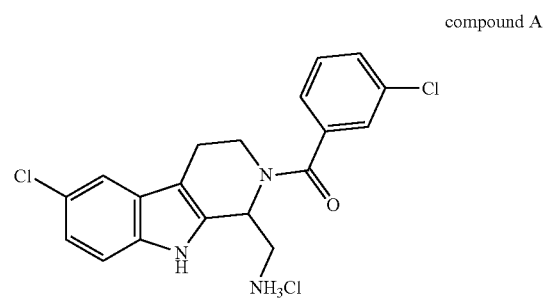

compound A

-continued compound B

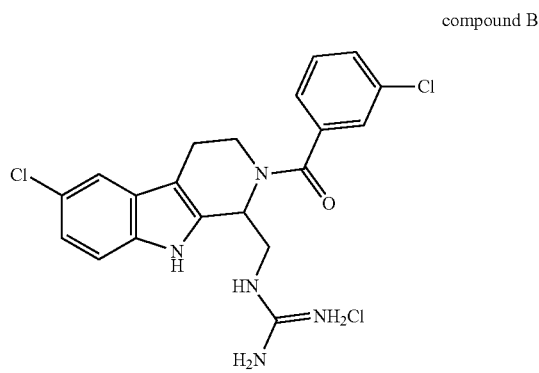

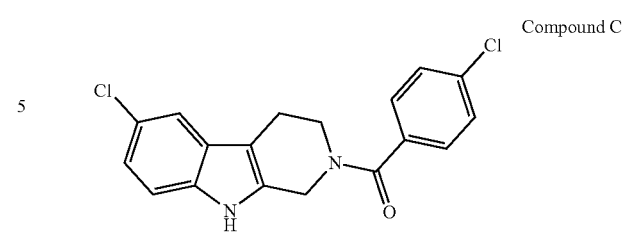

Compound C

TABLE A

Minimum inhibitory concentrations (MICs) of compounds A and B against a panel of pathogenic bacterial strains.

| Species (strain) | Compound A MIC (mg/L) | Compound B MIC (mg/L) |
| --- | --- | --- |
| Enterococcus faecium (HM-460) | 2 | 4 |
| Enterococcus (HM-204) | 2 | 2 |
| Pseudomonas aeruginosa (NR-48982) | >32 | 16 |
| Klebsiella pneumoniae (NR-48977) | 16 | 16 |
| Klebsiella pneumoniae (NR-48977) | 8 | 16 |
| Acinetobacter baumannii (NR-17783) | 32 | 16 |
| Acinetobacter baumannii (NR-19299) | 32 | 16 |
| Staphylococcus aureus (MRSA, NRS384) | 2 | 2 |
| Escherichia coli (ATCC 25922) | 8 | 8 |
| Salmonella enterica (NR-22067) | 16 | 8 |
| Salmonella enterica (NR-22068) | 16 | 8 |

Determination of Antibiotic MICs in the Presence of Compound C against MRSA and MSSA. Methicillin-resistant S. aureus (MRSA) strain ATCC BAA-44 and the methicillin-sensitive S. aureus (MSSA) strain ATCC 25923 were used to determine the MIC values of various antimicrobial compounds in the presence of 5 µg/mL Compound C. The experiment was conducted similarly to the CLSI MIC determination described previously; with the exception that the assay medium (MHB) was initially supplemented with 10 µg/mL Compound C prior to set up and inoculation. The test antibiotics were then diluted into assay plates as described earlier. The final concentration of Compound C after inoculation with BAA-44 was 5 µg/mL. MIC values were determined by the methods described above.

Minimal re-sensitizing concentration (MRC) determination. Antibiotic MIC breakpoint values where S. aureus is considered susceptible were determined from the CLSI handbook supplement. MHB was supplemented with the antibiotic at a concentration two-fold greater than the CLSI susceptible MIC value. Two-fold serial dilutions of Compound C were prepared in antibiotic supplemented media in 96-well microplates. These were inoculated with MRSA diluted to $OD_{600}$ 0.002 and incubated at 37° C. with shaking for 18 hours before results were interpreted. The concentration of Ofl in antibiotic supplemented media at which there was no observable growth was considered the minimum re-sensitizing concentration (MRC).

TABLE B

Minimum inhibitory concentrations (MICs) of antibiotics in the absence and presence of 5 mg/L Compound C against MRSA strains BAA-44 and NRS-384, respectively.

| Antibiotic | MIC mg/L (BAA-44) | MIC (BAA-44) (+5 mg/L Compound C) | MIC mg/L (NRS-384) | MIC (NRS-384) (+5 mg/L Compound C) |
| --- | --- | --- | --- | --- |
| Methicillin | >256 | 4 | 256 | 8 |
| Vancomycin | 1 | 0.5 | 1 | 0.5 |
| Meropenem | 16 | <0.25 | 8 | <0.25 |
| Clindamycin | >4 | >4 | 0.125 | <0.03125 |
| Linezolid | 1 | 0.5 | 2 | 1 |
| Rifampicin | 1 | 0.125 | <0.03125 | <0.03125 |
| Streptomycin | >32 | >32 | 8 | 1 |
| Tetracycline | 16 | 4 | 8 | 4 |
| Oxacillin | 64 | <2 | 64 | <2 |
| Cefazolin | 128 | <2 | 64 | <2 |
| Amox/clav | 16 | 0.5 | 8 | 1 |
| Compound C | >100 | | >100 | |

TABLE C

Minimum inhibitory concentrations (MICs) and minimum re-sensitizing concentrations (MRCs) of Compound C in various MRSA strains.

| MRSA Strain | MIC | MRC to Cefazolin | MRC to Amox/clav |
| --- | --- | --- | --- |
| BAA-44 | 64 | 4 | 4 |
| NRS-384 | >64 | 4 | 2 |
| ATCC 700789 | >64 | 4 | 4 |
| ATCC-33592 | 4 | 2 | 2 |

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A method for treating a β-lactam antibiotic resistant bacterial infection in a subject, said method comprising administering to the subject in need of such a treatment a therapeutically effective amount a β-lactam antibiotic and a β-lactam re-sensitizing agent selected from the group consisting of

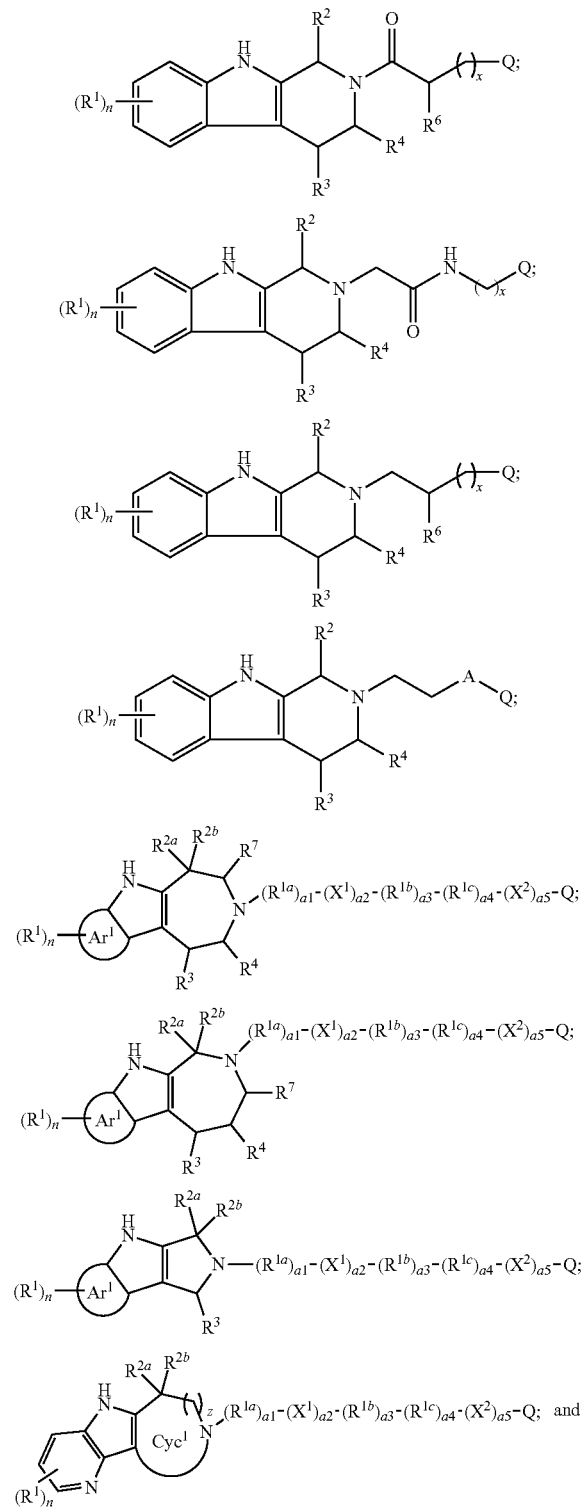

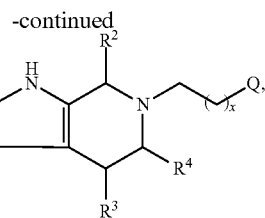

wherein
n is an integer from 0-4;
x is an integer from 0 to 3;
each of z, a1, a2, a3, a4, and a5 is independently 0 or 1, provided at least one of a1-a5 is 1;
$Ar^1$ is phenyl or a nitrogen atom containing 6-membered heteroaryl;
$Cyc^1$ is 5, 6, or 7-membered nitrogen atom containing heterocyclyl optionally containing one to three additional substituents in addition to $R^{2a}$ and $R^{2b}$;
$X^1$ is —C(=O)—, —C(=O)—$NR^6$—, or —$SO_2$—NH—;
each of $R^{1a}$ and $R^{1c}$ is independently $C_1$-$C_6$ alkylene;
$R^{1b}$ is optionally substituted $C_1$-$C_6$ alkylene or heteroaryl of the formula

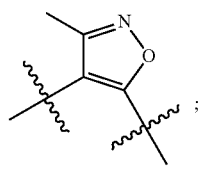 [SMILES: *c1onc(C)c1*]

$X^2$ is O or $NR^6$;
each $R^1$ is independently halogen, optionally substituted $C_1$-$C_6$ alkyl, optionally substituted $C_1$-$C_6$ haloalkyl, optionally substituted cycloalkyl, optionally substituted heterocyclyl, —$OR^a$, or —$NR^bR^c$, where $R^a$ hydrogen, $C_1$-$C_6$ alkyl, $C_1$-$C_6$ haloalkyl, or a hydroxyl protecting group, and wherein each of $R^b$ and $R^c$ is independently hydrogen, $C_1$-$C_6$ alkyl, $C_1$-$C_6$ haloalkyl, optionally substituted cycloalkyl, optionally substituted heterocyclyl, or a nitrogen protecting group;
each of $R^2$, $R^{2a}$ and $R^{2b}$ is independently hydrogen, halogen, optionally substituted $C_1$-$C_6$ haloalkyl, optionally substituted cycloalkyl, optionally substituted heterocyclyl, —($C_{1-6}$ alkylene)-heterocyclyl, —$OR^a$, or —$NR^bR^c$, where $R^a$ hydrogen, $C_1$-$C_6$ alkyl, $C_1$-$C_6$ haloalkyl, or a hydroxyl protecting group, and wherein each of $R^b$ and $R^c$ is independently hydrogen, $C_1$-$C_6$ alkyl, $C_1$-$C_6$ haloalkyl, optionally substituted cycloalkyl, optionally substituted heterocyclyl, or a nitrogen protecting group, or $R^{2a}$ and $R^{2b}$ together with the carbon atom to which they are attached to form a cycloalkyl group;
each of $R^3$, $R^4$, and $R^7$ is independently hydrogen, halogen, optionally substituted $C_1$-$C_6$ alkyl, optionally substituted $C_1$-$C_6$ haloalkyl, optionally substituted cycloalkyl, optionally substituted heterocyclyl, —$OR^a$, or —$NR^bR^c$, where $R^a$ hydrogen, $C_1$-$C_6$ alkyl, $C_1$-$C_6$ haloalkyl, or a hydroxyl protecting group, and wherein each of $R^b$ and $R^c$ is independently hydrogen, $C_1$-$C_6$ alkyl, $C_1$-$C_6$ haloalkyl, optionally substituted cycloalkyl, optionally substituted heterocyclyl, or a nitrogen protecting group;

R⁶ is $C_1$-$C_6$ alkyl, optionally substituted cycloalkyl, heterocyclyl, —OR$^a$, and —NR$^b$R$^c$;

A is O or NH; and

Q is an optionally substituted aryl, optionally substituted heteroaryl, optionally substituted $C_3$-$C_8$ cycloalkyl, or optionally substituted heterocycloalkyl.

2. The method of claim 1, wherein said β-lactam antibiotic comprises a penicillin, a cephalosporin, a penem, a monobactam, Amoxicillin/clavulanic acid, Imipenem/cilastatin, Ampicillin/flucloxacillin, Piperacillin/tazobactam, Piperacillin/sulbactam, Amoxicillin/sulbactam, Ampicillin/sulbactam (Sultamicillin), Amoxicillin/pivsulbactam, Ceftolozane/tazobactam, Cefoperazone/sulbactam, Cefoperazone/tazobactam, Ceftriaxone/tazobactam, Meropenem/vaborbactam, and Ceftazidime/avibactam, or a combination thereof.

3. The method of claim 2, wherein said cephalosporin comprises Cefathiamidine, Cefamandole, Cefacetrile (cephacetrile), Cefadroxil (cefadroxyl; Duricef), Cefadroxil/Trimethoprim, Cefalexin (cephalexin; Keflex), Cefalexin/Trimethoprim, Cefaloglycin (cephaloglycin), Cefalonium (cephalonium), Cefaloridine (cephaloradine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole, Cefaclor (Ceclor, Distaclor, Keflor, Raniclor), Cefonicid (Monocid), Cefprozil (cefproxil; Cefzil), Cefuroxime (Zefu, Zinnat, Zinacef, Ceftin, Biofuroksym, [19]Xorimax), Cefuzonam, Cefmetazole, Cefotetan, Loracarbef (Lorabid), Cefbuperazone, Cefmetazole (Zefazone), Cefminox, Cefotetan (Cefotan), Cefoxitin (Mefoxin), Cefotiam (Pansporin), Cefcapene, Cefdaloxime, Cefdinir (Sefdin, Zinir, Omnicef, Kefnir), Cefditoren, Cefetamet, Cefixime (Fixx, Zifi, Suprax), Cefmenoxime, Cefodizime, Cefotaxime (Claforan), Cefovecin (Convenia), Cefpimizole, Cefpodoxime (Vantin, PECEF, Simplicef), Cefteram, Ceftamere (Enshort), Ceftibuten (Cedax), Ceftiofur (Naxcel, Excenel), Ceftiolene, Ceftizoxime (Cefizox), Ceftriaxone (Rocephin), Cefoperazone (Cefobid), Ceftazidime (Meezat, Fortum, Fortaz), Latamoxef (moxalactam), Cefclidine, Cefepime (Maxipime), Cefluprenam, Cefoselis, Cefozopran, Cefpirome (Cefrom), Cefquinome, Flomoxef, Ceftobiprole, Ceftaroline, Ceftolozane, or a mixture thereof.

4. The method of claim 1, wherein said β-lactam resensitizing agent is selected from the group consisting of

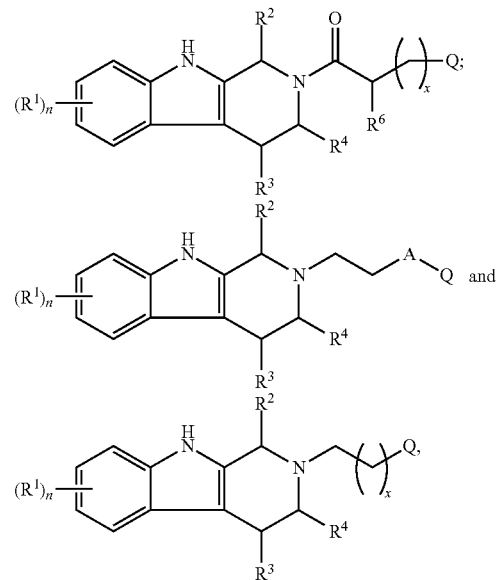

wherein x, A, R⁶, n, R¹, R², R³, R⁴, R$^a$, R$^b$, R$^c$ and Q are as defined in claim 1.

5. The method of claim 1, wherein said β-lactam antibiotic resistant bacterial infection is methicillin-resistant *Staphylococcus aureus* (MRSA) infection.

* * * * *